United States Patent
Desroy et al.

(10) Patent No.: US 11,072,611 B2
(45) Date of Patent: *Jul. 27, 2021

(54) COMPOUNDS AND PHARMACEUTICAL COMPOSITIONS THEREOF FOR THE TREATMENT OF INFLAMMATORY DISORDERS

(71) Applicant: Galapagos NV, Mechelen (BE)

(72) Inventors: Nicolas Desroy, Romainville (FR); Bertrand Heckmann, Romainville (FR); Reginald Christophe Xavier Brys, Mechelen (BE); Agnès Marie Joncour, Romainville (FR); Christophe Peixoto, Romainville (FR); Xavier Marie Bock, Romainville (FR)

(73) Assignee: GALAPAGOS NV, Mechelen (BE)

( * ) Notice: Subject to any disclaimer, the term of this patent is extended or adjusted under 35 U.S.C. 154(b) by 0 days.

This patent is subject to a terminal disclaimer.

(21) Appl. No.: 16/682,553

(22) Filed: Nov. 13, 2019

(65) Prior Publication Data

US 2020/0239466 A1    Jul. 30, 2020

Related U.S. Application Data

(60) Division of application No. 16/146,450, filed on Sep. 28, 2018, now Pat. No. 10,526,329, which is a
(Continued)

(51) Int. Cl.
| | |
|---|---|
| C07D 401/14 | (2006.01) |
| A61K 31/437 | (2006.01) |
| C07D 471/04 | (2006.01) |
| A61K 31/496 | (2006.01) |
| A61K 31/506 | (2006.01) |
| A61K 31/5377 | (2006.01) |
| A61K 31/541 | (2006.01) |

(Continued)

(52) U.S. Cl.
CPC .......... *C07D 471/04* (2013.01); *A61K 31/437* (2013.01); *A61K 31/444* (2013.01); *A61K 31/4545* (2013.01); *A61K 31/496* (2013.01); *A61K 31/506* (2013.01); *A61K 31/5377* (2013.01); *A61K 31/541* (2013.01); *A61K 45/06* (2013.01)

(58) Field of Classification Search
CPC ............................ C07D 401/14; A61K 31/437
USPC ............................................ 546/119; 514/303
See application file for complete search history.

(56) References Cited

U.S. PATENT DOCUMENTS

| | | | |
|---|---|---|---|
| 8,227,603 B2 | 7/2012 | Russell et al. | |
| 8,993,590 B2 * | 3/2015 | Desroy | A61P 11/00 514/300 |

(Continued)

FOREIGN PATENT DOCUMENTS

| | | |
|---|---|---|
| DE | 102008059578 A1 | 6/2010 |
| WO | 2008/138842 A1 | 11/2008 |

(Continued)

OTHER PUBLICATIONS

Bandoh, K., Aoki, J., Taira, A., Tsujimoto, M., Arai, H., and Inoue, K. (2000). Lysophosphatidic acid (LPA) receptors of the EDG family are differentially activated by LPA species. Structure-activity relationship of cloned LPA receptors. FEBS Lett. 478, 159-165.

Baumforth, K.R.N., Flavell, J.R., Reynolds, G.M., Davies, G., Pettit, T.R., Wei, W., Morgan, S., Stankovic, T., Kishi, Y., Arai, H., et al. (2005). Induction of autotaxin by the Epstein-Barr virus promotes the growth and survival of Hodgkin lymphoma cells. Blood 106, 2138-2146.

Bozinovski, S., Hutchinson, A., Thompson, M., Macgregor, L., Black, J., Giannakis, E., Karlsson, A.-S., Silvestrini, R., Smallwood, D., Vlahos, R., et al. (2008). Serum amyloid a is a biomarker of acute exacerbations of chronic obstructive pulmonary disease. Am. J. Respir. Crit. Care Med. 177, 269-278.

Braddock, D.T. (2010). Autotaxin and lipid signaling pathways as anticancer targets. Curr Opin Investig Drugs 11, 629-637.

(Continued)

*Primary Examiner* — Niloofar Rahmani
(74) *Attorney, Agent, or Firm* — Heslin Rothenberg Farley & Mesiti P.C.

(57) ABSTRACT

The present invention discloses compounds according to Formula I:

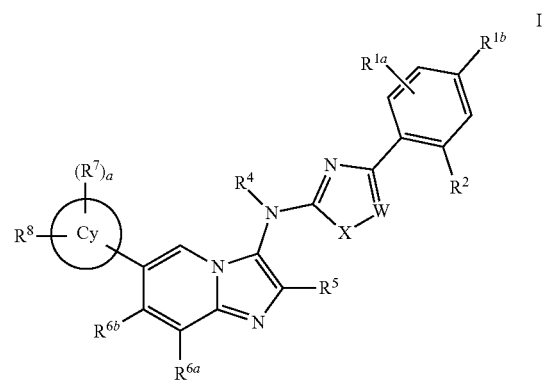

Wherein $R^{1a}$, $R^{1b}$, $R^2$, $R^4$, $R^5$, $R^{6a}$, $R^{6b}$, $R^8$, W, X, Cy, and the subscript a are as defined herein. The present invention relates to compounds inhibiting autotaxin (NPP2 or ENPP2), methods for their production, pharmaceutical compositions comprising the same, and methods of treatment using the same, for the prophylaxis and/or treatment of diseases involving fibrotic diseases, proliferative diseases, inflammatory diseases, autoimmune diseases, respiratory diseases, cardiovascular diseases, neurodegenerative diseases, dermatological disorders, and/or abnormal angiogenesis associated diseases by administering the compound of the invention.

15 Claims, No Drawings

Related U.S. Application Data continuation of application No. 15/583,161, filed on May 1, 2017, now Pat. No. 10,125,132, which is a continuation of application No. 14/977,918, filed on Dec. 22, 2015, now Pat. No. 9,670,204, which is a continuation of application No. 14/572,870, filed on Dec. 17, 2014, now Pat. No. 9,249,141, which is a continuation of application No. 14/205,885, filed on Mar. 12, 2014, now Pat. No. 8,993,590.

(60) Provisional application No. 61/781,174, filed on Mar. 14, 2013.

(51) Int. Cl.
*A61K 31/444* (2006.01)
*A61K 31/4545* (2006.01)
*A61K 45/06* (2006.01)

(56) References Cited

U.S. PATENT DOCUMENTS

| | | | |
|---|---|---|---|
| 9,249,141 B2* | 2/2016 | Desroy | A61K 31/541 |
| 9,670,204 B2* | 6/2017 | Desroy | A61P 9/10 |
| 10,125,132 B2* | 11/2018 | Desroy | A61K 31/496 |
| 10,526,329 B2 | 1/2020 | Desroy et al. | |
| 2013/0023556 A1 | 1/2013 | Schultz et al. | |
| 2014/0303140 A1 | 10/2014 | Desroy et al. | |
| 2015/0111872 A1 | 4/2015 | Desroy et al. | |
| 2016/0244443 A1 | 8/2016 | Desroy et al. | |
| 2019/0169184 A1 | 6/2019 | Desroy et al. | |

FOREIGN PATENT DOCUMENTS

| | | |
|---|---|---|
| WO | 2010/063352 A1 | 6/2010 |
| WO | 2011/054922 A1 | 5/2011 |
| WO | 2012/166415 A1 | 12/2012 |

OTHER PUBLICATIONS

Bush, K.A., Farmer, K.M., Walker, J.S., and Kirkham, B.W. (2002). Reduction of joint inflammation and bone erosion in rat adjuvant arthritis by treatment with interleukin-17 receptor IgG1 Fc fusion protein. Arthritis & Rheumatism 46, 802-805.
Castelino, F.V., Seiders, J., Bain, G., Brooks, S.F., King, C., Swaney, J.S., Lorrain, D.S., Chun, J., Luster, A.D., and Tager, A.M. (2011). Genetic deletion or pharmacologic antagonism of LPA1 ameliorates dermal fibrosis in a scleroderma mouse model. Arthritis Rheum 63, 1405-1415.
Corley, E.G., Conrad, K., Murry, J.A., Savarin, C., Holko, J., and Boice, G. (2004). Direct Synthesis of 4-Arylpiperidines via Palladium/Copper(I)-Cocatalyzed Negishi Coupling of a 4-Piperidylzinc Iodide with Aromatic Halides and Triflates. J. Org. Chem. 69, 5120-5123.
David, M., Wannecq, E., Descotes, F., Jansen, S., Deux, B., Ribeiro, J., Serre, C.-M., Gres, S., Bendriss-Vermare, N., Bollen, M., et al. (2010). Cancer Cell Expression of Autotaxin Controls Bone Metastasis Formation in Mouse through Lysophosphatidic Acid-Dependent Activation of Osteoclasts. PLoS One 5(3), e9741.
Demedts, I.K., Morel-Montero, A., Lebecque, S., Pacheco, Y., Cataldo, D., Joos, G.F., Pauwels, R.A., and Brusselle, G.G. (2006). Elevated MMP-12 protein levels in induced sputum from patients with COPD. Thorax 61, 196-201.
Eagan, T.M., Damås, J.L., Ueland, T., Voll-Aanerud, M., Mollnes, T.E., Hardie, J.A., Bakke, P.S., and Aukrust, P. (2010). Neutrophil gelatinase-associated lipocalin: A biomarker in copd. Chest 138(4), 888-895.
Emo, J., Meednu, N., Chapman, T.J. Rezaee, F., Balys, M., Randall, T., Rangasamy, T., and Georas, S.N. (2012). Lpa2 is a negative regulator of dendritic cell activation and murine models of allergic lung inflammation. J Immunol 188(8), 3784-3790.

Federico, L., Ren, H., Mueller, P.A., Wu, T., Liu, S., Popovic, J., Blalock, E.M., Sunkara, M., Ovaa, H., Albers, H.M., et al. (2012). Autotaxin and Its Product Lysophosphatidic Acid Suppress Brown Adipose Differentiation and Promote Diet-Induced Obesity in Mice. Molecular Endocrinology 26, 786-797.
Ferry, G., Tellier, E., Try, A., Grés, S., Naime, I., Simon, M.F., Rodriguez, M., Boucher, J., Tack, I., Gesta, S., et al. (2003). Autotaxin Is Released from Adipocytes, Catalyzes Lysophosphatidic Acid Synthesis, and Activates Preadipocyte Proliferation Up-Regulated Expression With Adipocyte Differentiation and Obesity. J. Biol. Chem. 278, 18162-18169.
Gaetano, C.G., Samadi, N., Tomsig, J.L., Macdonald, T.L., Lynch, K.R., and Brindley, D.N. (2009). Inhibition of autotaxin production or activity blocks lysophosphatidylcholine-induced migration of human breast cancer and melanoma cells. Mol. Carcinog. 48(9), 801-809.
Ganguly, K., Stoeger, T., Wesselkamper, S.C., Reinhard, C., Sartor, M.A., Medvedovic, M., Tomlinson, C.R., Bolle, I., Mason, J.M., Leikauf, G.D., et al. (2007). Candidate genes controlling pulmonary function in mice: transcript profiling and predicted protein structure. Physiol. Genomics 31, 410-421.
Gardell, S.E., Dubin, A.E., and Chun, J. (2006). Emerging medicinal roles for lysophospholipid signaling. Trends in Molecular Medicine 12(2), 65-75.
Gennero, I., Laurencin-Dalicieux, S., Conte-Auriol, F., Briand-Mésange, F., Laurencin, D., Rue, J., Beton, N., Malet, N., Mus, M., Tokumura, A., et al. (2011). Absence of the lysophatidic acid receptor LPA1 results in abnormal bone development and decreased bone mass. Bone 49, 395-403.
Georas, S.N., Berdyshev, E., Hubbard, W., Gorshkova, I.A., Usatyuk, P.V., Saatian, B., Myers, A.C., Williams, M.A., Xiao, H.Q., Liu, M., et al. (2006). Lysophosphatidic acid is detectable in human bronchoalveolar lavage fluids at baseline and increased after segmental allergen challenge. Clinical & Experimental Allergy 37, 311-322.
Gierse, J., Thorarensen, A., Beltey, K., Bradshaw-Pierce, E., Cortes-Burgos, L., Hall, T., Johnston, A., Murphy, M., Nemirovskiy, O., Ogawa, S., et al. (2010). A Novel Autotaxin Inhibitor Reduces Lysophosphatidic Acid Levels in Plasma and the Site of Inflammation J Pharmacol Exp Ther 334(1), 310-317.
Hausmann, J., Kamtekar, S., Christodoulou, E., Day, J.E., Wu, T., Fulkerson, Z., Albers, H.M.H.G., van Meeteren, L.A., Houben, A., van Zeijl, L., et al. (2011). Structural basis for substrate discrimination and integrin binding by autotaxin. Nat Struct Mol Biol 18(2), 198-204.
Inoue, M., Xie, W., Matsushita, Y., Chun, J., Aoki, J., and Ueda, H. (2008). Lysophosphatidylcholine induces neuropathic pain through an action of autotaxin to generate lysophosphatidic acid. Neuroscience 152, 296-298.
Iyer, P., Lalane, R., Morris, C., Challa, P., Vann, R., and Rao, P.V. (2012). Autotaxin-Lysophosphatidic Acid Axis Is a Novel Molecular Target for Lowering Intraocular Pressure. PLoS One 7(8), e42627.
Jou, I.-M., Shiau, A.-L., Chen, S.-Y., Wang, C.-R., Shieh, D.-B., Tsai, C.-S., and Wu, C.-L. (2005). Thrombospondin 1 as an effective gene therapeutic strategy in collagen-induced arthritis. Arthritis & Rheumatism 52(1), 339-344.
Kanda, H., Newton, R., Klein, R., Morita, Y., Gunn, M.D., and Rosen, S.D. (2008). Autotaxin, a lysophosphatidic acid-producing ectoenzyme, promotes lymphocyte entry into secondary lymphoid organs. Nat Immunol 9(4), 415-423.
Khachigian, L.M. (2006). Collagen antibody-induced arthritis. Nat. Protocols 1(5), 2512-2516.
Kishi, Y., Okudaira, S., Tanaka, M., Hama, K., Shida, D., Kitayama, J., Yamori, T., Aoki, J., Fujimaki, T., and Arai, H. (2006). Autotaxin Is Overexpressed in Glioblastoma Multiforme and Contributes to Cell Motility of Glioblastoma by Converting Lysophosphatidylcholine to Lysophosphatidic Acid. J. Biol. Chem. 281, 17492-17500.
Kolonko, K.J., and Reich, H.J. (2008). Stabilization of Ketone and Aldehyde Enols by Formation of Hydrogen Bonds to Phosphazene Enolates and Their Aldol Products. J. Am. Chem. Soc. 130, 9668-9669.
Kremer, A.E., Martens, J.J.W.W., Kulik, W., Ruëff, F., Kuiper, E.M.M., van Buuren, H.R., van Erpecum, K.J., Kondrackiene, J.,

(56) References Cited

OTHER PUBLICATIONS

Prieto, J., Rust, C., et al. (2010). Lysophosphatidic Acid Is a Potential Mediator of Cholestatic Pruritus. Gastroenterology 139(3), 1008-1018.e1.
Lin, H.-S., C.-Y., Chan, H.-Y., Liew, Y.-Y., Huang, H.-P., Lepescheux, L., Bastianelli, E., Baron, R., Rawadi, G., and Clément-Lacroix, P. (2007). Anti-rheumatic activities of histone deacetylase (HDAC) inhibitors rodents. British Journal of Pharmacology 150, 862-872.
Lin, M.-E., Herr, D.R., and Chun, J. (2010). Lysophosphatidic acid (LPA) receptors: signaling properties and disease relevance. Prostaglandins Other Lipid Mediat 91(3-4), 130-138.
Llinàs, L., Peñaido, V.I., Ramon Goñi, J., Rabinovich, R., Pizarro, S., Rodriguez-Roisin, R., Barberà, J.A., and Batos, R. (2011). Similar gene expression profiles in smokers and patients with moderate COPD. Pulmonary Pharmacology & Therapeutics 24, 32-41.
Matas-Rico, E., Garcia-Diaz, B., Llebrezy-Zayas, P., Lopez-Barroso, D., Santin, L., Pedraza, C., Smith-Fernandez, A., Fernandez, A., Fernandez-Llebrez, P., Tellez, T., Redondo, R. et al. (2008). Deletion of lysophosphatidic acid receptor LPA1 reduces neurogenesis in the mouse dentate gyrus. Mol Cell Neurosci 39(3), 342-355.
Van Meeteren, L.A., Ruurs, P., Stortelers, C., Bouwman, P., van Rooijen, M.A., Pradere, J.P., Pettit, T.R., Wakelam, M.J.O., Saulnier-Blache, J.S., Mummery, C.L., et al. (2006). Autotaxin, a Secreted Lysophospholipase D, Is Essential for Blood Vessel Formation during Development. Mol Cell Biol 26(13), 5015-5022.
Murph, M., Nguyen, G., Radhakrishna, H., and Mills, G.B. (2008). Sharpening the edges of understanding the structure/function of the LPA1 receptor. Biochim Biophys Acta 1781(9), 547-557.
Nakao, I., Kanaji, S., Ohta, S., Matsushita, H., Arima, K., Yuyama, N., Yamaya, M., Nakayama, K., Kubo, H., Watanabe, M., et al. (2008). Identification of Pendrin as a Common Mediator for Mucus Production in Bronchial Asthma and Chronic Obstructive Pulmonary Disease. J Immunol 180, 6262-6269.
Nakasaki, T., Tanaka, T., Okudaira, S., Hirosawa, M., Umemoto, E., Otani, K., Jin, S., Bai, Z., Hayasaka, H., Fukui, Y., et al. (2008). Involvement of the Lysophosphatidic Acid-Generating Enzyme Autotaxin in Lymphocyte-Endothelial Cell Interactions. Am J Pathol 173(5), 1566-1576.
Nikitopoulou, I., Oikonomou, N., Karouzakis, E., Sevastou, I., Nikolaidou-Katsaridou, N., Zhao, Z., Mersinias, V., Armaka, M., Xu, Y., Masu, M., et al. (2012). Autotaxin expression from synovial fibroblasts is essential for the pathogenesis of modeled arthritis. J Exp Med 209(5), 925-933.
Nishida, K., Komiyama, T., Miyazawa, S., Shen, Z.-N., Furumatsu, T., Doi, H., Yoshida, A., Yamana, J., Yamamura, M., Ninomiya, Y., et al. (2004). Histone deacetylase inhibitor suppression of autoantibody-mediated arthritis in mice via regulation of P16INK4a and p21WAFI/Cip1 expression. Arthritis & Rheumatism 50(10), 3365-3376.
Nouh, M.A.A.M., Wu, X.-X., Okazoe, H., Tsunemori, H., Haba, R., Abou-Zeid, A.M.M., Saleem, M.D., Inui, M., Sugimoto, M., Aoki, J., et al. (2009). Expression of Autotaxin and Acylglycerol kinase in prostate cancer: Association with cancer development and progression. Cancer Science 100(9), 1631-1638.
Oikonomou, N., Mouratis, M.-A., Tzouvelekis, A., Kaffe, E., Valavanis, C., Vilaras, G., Karameris, A., Prestwich, G.D., Bouros, D., and Aidinis, V. (2012). Pulmonary Autotaxin Expression Contributes to the Pathogenesis of Pulmonary Fibrosis. American Journal of Respiratory Cell and Molecular Biology 47(5), 566-574.
Oste, L., Salmon, P., Dixon, G., and van Rompaey, L. (2007). A high throughput method of measuring bone architectural disturbance in a murine CIA model by micro-CT morphometry (Copenhagen).
Panupinthu, N., Lee, H.Y., and Mills, G.B. (2010). Lysophosphatidic acid production and action: critical new players in breast cancer initiation and progression. Br J Cancer 102, 941-946.
Pradère, J.-P., Klein, J., Grès, S., Guigné, C., Neau, E., Valet, P., Calise, D., Chun, J., Bascands, J.-L., Saulnier-Blache, J.-S., et al. (2007). LPA1 Receptor Activation Promotes Renal Interstitial Fibrosis. JASN 18, 3110-3118.

Rall, L.C., and Roubenoff, R. (2004). Rheumatoid cachexia: metabolic abnormalities, mechanisms and interventions. Rheumatology 43, 1219-1223.
Salvemini, D., Mazzon, E., Dugo, L., Serraino, I., De Sarro, A., Caputi, A.P., and Cuzzocrea, S. (2001). Amelioration of joint disease in a rat model of collagen-induced arthritis by M40403, a superoxide dismutase mimetic. Arthritis Rheum. 44(12), 2909-2921.
Shelton, D.L., Zeller, J., Ho, W.-Ha., Pons, J., and Rodenthal, A. (2005). Nerve growth factor mediates hyperalfesia and cachexia in auto-immune arthritis. Pain 116, 8-16.
Sims, N.A., Green, J.R., Glatt, M., Schlict, S., Martin, T.J., Gillespie, M.T., and Romas, E. (2004). Targeting osteoclasts with zoledronic acid prevents bone destruction in collagen-induced arthritis. Arthritis & Rheumatism 50(7), 2338-2346.
Stassar, M.J.J.G., Devitt, G., Brosius, M., Rinnab, L., Prang, J., Schradin, T., Simon, J., Petersen, S., Kopp-Schneider, A., and Zoller, M. (2001). Identification of human renal cell carcinoma associated genes by suppresion subtractive hybridization. Br J Cancer 85(9), 1372-1382.
Sumida, H., Noguchi, L., Kihara, Y., Abe, M., Yanagida, K., Hamano, F., Sato, S., Tamaki, K., Morishita, Y., Kano, M.R., et al. (2010). LPA4 regulates blood and lymphatic vessel formation during mouse embryogenesis. Blood 116, 5060-5070.
Tager, A.M., LaCamera, P., Shea, B.S., Campanellam G.S., Selman, M., Zhao, Z., Polosukhin, V., Wain, J., Karimi-Shah, B.A., Kim, N.D., et al. (2008). The lysophosphatidic acid receptor LPA1 links pulmonary fibrosis to lung injury by mediating fibroblast recruitment and vascular leak. Nat Med 14(1), 45-54.
Tamaka, M., Okudaira, S., Kishi, Y., Ohkawa, R., Iseki, S., Ota, M., Noji, S., Yatomi, Y., Aoki, J., and Arai, H. (2006). Autotaxin Stabilizes Blood Vessels and Is Required for Embryonic Vasculature by Producing Lysophosphatidic Acid. J. Biol. Chem. 281, 25822-25830.
Tania, M., Khan, M.A., Zhang, H., Li, J., and Song, Y. (2010). Autotaxin: A protein with two faces. Biochemical and Biophysical Research Communications 401, 493-497.
Tilley, A.E., O'Connor, T.P., Hackett, N.R., Strulovici-Barel, Y., Salit, J., Amoroso, N., Zhou, X.K., Raman, T., Omberg, L., Clark, A., et al. (2001). Biologic Phenotyping of the Human Small Airway Epithelial Response to Cigarette Smoking. PLoS One 6(7), e22798.
Vidot, S., Withim, J., Agarwal, R., Greenhough, S., Bamrah, H.S., Tigyi, G.J., Kaye, S.B., and Richardson, A. (2010). Autotaxin delays apoptosis induced by carboplatin in ovarian cancer cells. Cellular Signalling 22, 926-935.
Walsmith, J., Abad, L., Kehayias, J., and Roubenoff, R. (2004). Tumor necrosis factor-alpha production is associated with less body cell mass in women with rheumatoid arthritis. J. Rheumatol. 31, 23-29.
Walters, D.M., and Kleeberger, S.R. (2001). Mouse Models of Bleomycin-Induced Pulmonary Fibrosis. In Current Protocols in Pharmacology, 40, 5.46.1-5.46.17.
Wirtz, S., and Neurath, M.F. (2007). Mouse models of inflammatory bowel disease. Advanced Drug Delivery Reviews 59, 1073-1083.
Wu, J.-M., Xu, Y., Skill, N.J., Sheng, H., Zhao, Z., Yu, M., Saxena, R., and Maluccio, M.A. (2010). Autotaxin expression and its connection with the TNF-alpha-NF-$_\kappa$B axis in human hepatocellular carcinoma. Mol Cancer 9, 71.
Xu, X., and Prestwich, G.D. (2010). Inhibition of Tumor Growth and Angiogenesis by a Lysophosphatidic Acid Antagonist in a Engineered Three-dimensional Lung Cancer Xenograft Model. Cancer 116(7), 1739-1750.
Xu, M.Y., Porte, J., Knox, A.J., Weinreb, P.H., Maher, T.M., Violette, S.M., McAnulty, R.J., Sheppard, D., and Jenkins, G. (2009). Lysophosphatidic Acid Induces $\alpha v \beta 6$ Integrin-Mediated TGF-$\beta$ Activation via the LPA2 Receptor and the Small G Protein G$\alpha$q. The American Journal of Pathology 174(4), 1264-1279.
Ye. X., Hama, K., Contos, J.J.A., Anliker, B., Inoue, A., Skinner, M.K., Suzuki, H., Amano, T., Kennedy, G., Arai, H., et al. (2005). LPA3-mediated lysophosphatidic acid signalling in implantation and embryo spacing. Nature 435(7038), 104-108.
Zhang, H., Xu, X., Gajewiak, J., Tsukahara, R., Fujiwara, Y., Liu, J., Fells, J.I., Perygin, D., Parrill, A.L., Tigyi, G., et al. (2009). Dual

(56) References Cited

OTHER PUBLICATIONS

Activity Lysophosphatidic Acid Receptor Pan-Antagonist/Autotaxin Inhibitor Reduces Breast Cancer Cell Migration In vitro and Causes Tumor Regression In vivo. Cancer Res 69(13), 5441-5449.

Zhao, Y., and Natarajan, V. (2()13). Inflammation and Remodeling. Biochim Lysophosphatidic acid (LPA) and as Receptors: Role in Airway Biophys Acta 1831(1), 86-92.

Zhao, J., He, D., Berdyshev, E., Zhong, M., Salgia, R., Morris, A.J., Smyth, S.S., Natarajan, V., and Zhao, Y. (2011). Autotaxin induces lung epithelial cell migration through lysoPLD activity-dependent and -independent pathways. Biochem J 439(1), 45-55.

Zhao, Y., Tong, J., He, D., Pendyala, S., Evgeny, B., Chun, J., Sperling, A.I., and Natarajan, V. (2009). Role of lysophosphatidic acid receptor LPA2 in the development of allergic airway inflammation in a murine model of asthma. Respir Res 10, 114.

De Alba, J., et al., "House Dust Mite Induces Direct Airway Inflammation In Vivo: Implications for Future Disease Therapy?", *European Respiratory Journal*, vol. 35(6), pp. 1377-1387 (2010).

Grimm, Scott W., et al., "The Conduct of in Vitro Studies to Address Time-Dependent Inhibition of Drug-Metabolizing Enzymes: A Perspective of the Pharmaceutical Research and Manufacturers of America", *Drug Metabolism and Disposition*, vol. 37(7), pp. 1355-1370 (2009).

Kudlacz, Elizabeth, et al., "The JAK-3 Inhibitor CP-690550 is a Potent Anti-Inflammatory Agent in a Murine Model of Pulmonary Eosinophilia", *European Journal of Pharmacology*, vol. 582, pp. 154-161 (2008).

McGinnity, Dermot F., et al, "Evaluation of Fresh and Cryopreserved Hepatocytes as In Vitro Drug Metabolism Tools for the Prediction of Metabolic Clearance", *Drug Metabolism and Disposition*, vol. 32(11), pp. 1247-1253 (2004).

Nials Anthony T., et al., "Mouse Models of Allergic Asthma: Acute and Chronic Allergen Challenge", *Disease Models & Mechanisms*, vol. 1, pp. 213-220 (2008).

Park Gye Y., et al, "Autotaxin Production of Lysophosphatidic Acid Mediates Allergic Asthmatic Inflammation", *The American Thoracic Society*, pp. 1-92 (2013).

Sina, Christian, et al., "G Protein-Coupled Receptor 43 Is Essential for Neutrophil Recruitment during Intestinal Inflammation", *The Journal of Immunology*, vol. 183, pp. 7514-7522 (2009).

Wirtz, Stefan, et al, Chemically Induced Mouse Models of Intestinal Inflammation, *Nature Protocols*, vol. 2(3), pp. 541-546 (2007).

International Search Report for International Application PCT/EP2014/054440 dated Jun. 17, 2014.

Hongrui Lei et al., "Catalyst-Free Cyclization- and Curtius Rearrangement-Induced Functional Group Transformation: An Improved Synthetic Strategy of First-in-Class ATX Inhibitor Ziritaxestat (GLPG-1690)," Org. Process Res. Dev., 2020, 24, pp. 997-1005.

\* cited by examiner

COMPOUNDS AND PHARMACEUTICAL COMPOSITIONS THEREOF FOR THE TREATMENT OF INFLAMMATORY DISORDERS

CROSS REFERENCE TO RELATED APPLICATIONS

This application is a divisional of U.S. patent application Ser. No. 16/146,450, filed Sep. 28, 2018, which is a continuation of U.S. patent application Ser. No. 15/583,161, filed May 1, 2017 (which issued as U.S. Pat. No. 10,125,132 on Nov. 13, 2018), which is a continuation of U.S. patent application Ser. No. 14/977,918, filed on Dec. 22, 2015 (which issued as U.S. Pat. No. 9,670,204 on Jun. 6, 2017), which is a continuation of U.S. patent application Ser. No. 14/572,870, filed on Dec. 17, 2014 (which issued as U.S. Pat. No. 9,249,141 on Feb. 2, 2016), which is a continuation of U.S. patent application Ser. No. 14/205,885, filed on Mar. 12, 2014 (which issued as U.S. Pat. No. 8,993,590 on Mar. 31, 2015), and claims priority to U.S. Provisional Application No. 61/781,174, filed on Mar. 14, 2013. The entire contents of each of the prior applications are hereby incorporated herein by reference.

FIELD OF THE INVENTION

The present invention relates to compounds that are inhibitors of autotaxin, also known as ectonucleotide pyrophosphatase/phosphodiesterase 2 (NPP2 or ENPP2), that is involved in fibrotic diseases, proliferative diseases, inflammatory diseases, autoimmune diseases, respiratory diseases, cardiovascular diseases, neurodegenerative diseases, dermatological disorders, and/or abnormal angiogenesis associated diseases. The present invention also provides methods for the production of a compound of the invention, pharmaceutical compositions comprising a compound of the invention, methods for the prophylaxis and/or treatment of diseases involving fibrotic diseases, proliferative diseases, inflammatory diseases, autoimmune diseases, respiratory diseases, cardiovascular diseases, neurodegenerative diseases, dermatological disorders, and/or abnormal angiogenesis associated diseases by administering a compound of the invention.

BACKGROUND OF THE INVENTION

Autotaxin (ATX; also known as ENPP2 (ectonucleotide pyrophosphatase/phosphodiesterase 2) or lysophospholipase D) is a ~120 kDa protein that belongs to the ENPP family of enzymes which is composed of seven members, out of which ENPP1 and ENPP3 are the closest to ATX. Whereas ENPP1 and ENPP3 are active in converting ATP into pyrophosphate (a regulator of mineralization and calcification processes in bone), ATX is the only ENPP enzyme with lysophospholipase D (lysoPLD) activity and is responsible for the hydrolysis of lysophosphatidylcholine (LPC) to produce the bioactive lipid lysophosphatidic acid (LPA). Several pieces of evidence have established ATX as the main source of LPA in blood. For example, blood LPA and ATX levels have been shown to be strongly correlated in humans. In addition, LPA levels are reduced by 50% in mice carrying a heterozygous null mutation of ATX (Tanaka, et al., 2006).

Due to the importance of LPA as a biological mediator, the levels of bio-active LPA are expected to be strictly spatially and temporally controlled. The relatively short half life of circulating LPA (~3 min) in mice is in line with this expectation. In the circulation, where LPC levels are very high (100-200 µM, mainly albumin-bound), ATX is constitutively active but newly produced LPA is rapidly degraded by membrane-bound phosphatases and levels of plasma LPA are thereby kept low (in the low µM range). This is confirmed by the fact that in cell-free plasma ex vivo, LPA levels increase at a steady rate. In addition, LPA in blood is bound to serum albumin, which might further reduce the levels of bio-active LPA. Besides this first level of control of LPA levels, the spatial control of LPA production is ensured by the capacity of ATX to bind to cell surface molecules such as integrins and heparan sulphate proteoglycans (HSPs) to facilitate LPA release near to its cognate receptors. Several pieces of evidence support this hypothesis. First, the structural studies of ATX are supporting the fact that the ATX structure is compatible with such a process (Hausmann, J, 2011). In addition, several reports indicated how ATX is involved in lymphocyte homing through the interaction with cell surface integrins (Kanda, 2008). It was shown, for example, that ATX can be induced on high endothelial venules (HEVs) on sites of inflammation. This ATX expressed by HEVs acts on HEVs in situ to facilitate lymphocyte binding to endothelial cells (Nakasaki, et al., 2008). As such, ATX not only drives the formation of LPA but, through these cellular interactions, also ensures specificity in LPA signaling.

ATX is widely expressed, with highest mRNA levels detected in brain, lymph nodes, kidney, and testis. Originally discovered as 'autocrine motility factor' in melanoma cells, ATX has emerged as the key LPA-producing enzyme in plasma and tissues. Unfortunately, embryonic lethality has hampered studies of the importance of ATX in adult life. This embryonic lethality reflects the key role of LPA in various developmental processes, vasculogenesis in particular. Knock-out studies of the LPA receptors have been more informative in terms of unraveling the physiological role of LPA. LPA acts through at least six distinct (G protein)-coupled receptors (LPA1-6) found on the surface of different cell types, three of which belong to the edg receptor family and three to the non-edg receptor family. LPA interacts with specific G protein-coupled receptors (GPCRs), namely LPA1 (also known as EDG2), LPA2 (also known as EDG4), LPA3 (also known as EDG7), LPA4 (also known as GPR23/p2y9), LPA5 (also known as GPR92/93), LPA6 (also known as p2y5). LPA has also been described to interact with three other GPCRs (GPR87, p2y10, GPR35). In addition, a preference of LPA receptors for specific LPA species has been demonstrated (Bandoh, et al., 2000). As such, the specificity of the LPA activities is controlled by the expression pattern of the LPA receptors and their downstream signaling route.

The main part of the LPA responses are mediated through trimeric G-proteins and include but are not limited to mitogen-activated protein kinase (MAPK) activation, adenylyl cyclase (AC) inhibition/activation, phospholipase C (PLC) activation/$Ca^{2+}$ mobilization, arachidonic acid release, Akt/PKB activation, and the activation of small GTPases, Rho, ROCK, Rac, and Ras. Other pathways that are affected by LPA receptor activation include cell division cycle 42/GTP-binding protein (Cdc42), proto-oncogene serine/threonine-protein kinase Raf (c-RAF), proto-oncogene tyrosine-protein kinase Src (c-src), extracellular signal-regulated kinase (ERK), focal adhesion kinase (FAK), guanine nucleotide exchange factor (GEF), glycogen synthase kinase 3b (GSK3b), c-jun amino-terminal kinase (INK), MEK, myosin light chain II (MLC II), nuclear factor kB (NF-kB), N-methyl-D-aspartate (NMDA) receptor activation, phosphatidylinositol3-kinase (PI3K), protein kinase A (PKA), protein kinase C (PKC), and ras-related C3 botulinum toxin substrate 1 (RAC1). The actual pathway is influenced by cell type, expression level of a receptor or signaling protein, receptor usage, and LPA concentration (Tania, Khan, Zhang, Li, & Song, 2010). LPA has a broad range of physiological actions and various cellular effects (for example blood pressure regulation, platelet activation, smooth muscle contraction, cell growth, cell rounding, neurite retraction, actin stress fiber formation and cell migration), In addition, a preference of LPA receptors for specific LPA species has been demonstrated (Bandoh, et al., 2000). The knock-out studies for these receptors indicated a role in bone development (Gennero, et al., 2011), and neurogenesis (Matas-Rico, et al., 2008), embryo implantation (Ye, et al., 2005) and the formation of blood and lymphatic vessels (Sumida, et al., 2010).

With regard to pathophysiology, a role for LPA and LPA receptors has been claimed in various patho-physiological conditions such as proliferative diseases, neuropathic pain, inflammation, autoimmune diseases, fibrosis, lymphocyte tracking in lymph nodes, obesity, diabetes, or embryonic blood vessel formation.

The role of LPA in lung fibrosis has been well described in literature and also an involvement in asthma has been claimed. The present inventors however are the first to report a link to chronic obstructive pulmonary disease (COPD).

Several lines of evidence suggest a role for ATX in the control of lung function in disease through effects on lung epithelial cells, fibroblasts and smooth muscle cells. In general, inflammatory conditions in the lung are often described as associated with increased ATX and LPA levels. Instillation of LPS in mice, for example, induces increased ATX and LPA levels in the broncho-alveolar lavage (BAL) fluid (Zhao, et al., 2011). Also in humans, a segmental LPS challenge led to increased LPA levels (Georas, et al., 2007). Overall, the role of LPA in activating lung epithelial cells, the first line of defense to inhaled noxious stimuli, towards increased cytokine and chemokine production and migration have been extensively described (Zhao & Natarajan, 2013). Exogenous LPA promotes inflammatory responses by regulating the expression of chemokines, cytokines, and cytokine receptors in lung epithelial cells. In addition to the modulation of inflammatory responses, LPA regulates cytoskeleton rearrangement and confers protection against lung injury by enhancing lung epithelial cell barrier integrity and remodeling.

In the asthmatic individual, the release of normal repair mediators, including LPA, is exaggerated or the actions of the repair mediators are inappropriately prolonged leading to inappropriate airway remodeling. Major structural features of the remodeled airway observed in asthma include a thickened lamina reticularis (the basement membrane-like structure just beneath the airway epithelial cells), increased numbers and activation of myofibroblasts, thickening of the smooth muscle layer, increased numbers of mucus glands and mucus secretions, and alterations in the connective tissue and capillary bed throughout the airway wall. ATX and/or LPA may contribute to these structural changes in the airway, for example ATX and/or LPA are involved in acute airway hyperresponsiveness in asthma. The lumen of the remodeled asthmatic airway is narrower due to the thickening of the airway wall, thus decreasing airflow. Additionally, LPA contributes to the long-term structural remodeling and the acute hyperresponsiveness of the asthmatic airway, for example LPA contributes to the hyper-responsiveness that is a primary feature of acute exacerbations of asthma. Reports describing the role of LPA in asthma generated different conclusions, ranging from a protective role (Zhao, et al., 2009) to a negative role (Emo, et al., 2012). The testing of autotaxin inhibitors in models for airway diseases as described herein allows for the clarification of the potential of this enzyme as a drug target.

Fibroblast proliferation and contraction and extracellular matrix secretion stimulated by LPA contributes to the fibroproliferative features of other airway diseases, such as the peribronchiolar fibrosis present in chronic bronchitis, and interstitial lung diseases and severe asthma. LPA plays a role in the fibrotic interstitial lung diseases and obliterative bronchiolitis, where both collagen and myofibroblasts are increased. Studies related to IPF (idiopathic pulmonary fibrosis) indicated an increase in LPA levels in the BAL fluid of patients (Tager, et al., 2008). Further LPA1 knock-out and inhibitor studies revealed a key role for LPA in fibrotic processes in lung and were complemented by studies using cell-specific knock-out mice lacking ATX in bronchial epithelial cells and macrophages. These mice were shown to be less sensitive to models of lung fibrosis (Oikonomou, et al., 2012). A role for LPA in other fibrotic diseases (kidney and skin) was based on similar types of observations (Pradère, et al., 2007), (Castelino, et al., 2011). The role of LPA in lung remodeling relates to the effects of LPA on both lung fibroblasts (through LPA1) and epithelial cells (through LPA2) (Xu, et al., 2009) have demonstrated that LPA2 plays a key role in the activation of TGFβ in epithelial cells under fibrotic conditions. The role of LPA in remodeling and fibrosis is relevant to COPD, IPF and asthma, diseases in which lung remodeling as a long term outcome will limit lung function. Finally, of interest towards lung diseases, in mice, ATX is one of the three main QTLs that appear to be associated with differences in lung function (Ganguly, et al., 2007).

One prominent area of research interest is the role of ATXLPA signaling in cancer (Braddock, 2010). Although cancer-specific mutations in ATX have not been identified so far, overexpression of ATX or individual LPA receptors in xenografted and transgenic mice promotes tumour formation, angiogenesis and metastasis. Conversely, ATX knockdown in mammary carcinoma cells reduces their metastatic spread to bone. Several human cancers show elevated ATX and/or aberrant LPA receptor expression patterns, as revealed by microarray analyses. Autotaxin is viewed as a pro-metastatic enzyme. It has initially been isolated from the conditioned medium of human melanoma cells that stimulates a myriad of biological activities, including angiogenesis and the promotion of cell growth, migration, survival, and differentiation through the production of LPA (Lin M. E., 2010). LPA contributes to tumorigenesis by increasing motility and invasiveness of cells. The initiation, progression and metastasis of cancer involve several concurrent and sequential processes including cell proliferation and growth, survival and anti-apoptosis, migration of cells, penetration of foreign cells into defined tissues and/or organs, and promotion of angiogenesis.

Therefore, the control of each of these processes by LPA signaling in physiological and pathophysiological conditions underscores the potential therapeutic usefulness of modulating LPA signaling pathways for the treatment of cancer. In particular, LPA has been implicated in the initiation or progression of ovarian cancer, prostate cancer, breast cancer, melanoma, head and neck cancer, bowel cancer (colorectal cancer), thyroid cancer, glioblastoma, follicular lymphoma and other cancers (Gardell, 2006) (Murph, Nguyen, Radhakrishna, & Mills, 2008) (Kishi, 2006).

Furthermore, autotaxin is implicated in the invasive and metastatic process of tumor cells, since ectopic overexpression of autotaxin is frequently observed in malignant tumor tissues such as ovarian cancer (Vidot, et al., 2010), breast cancer (Panupinthu, Lee, & Mills, 2010) (Zhang, et al., 2009), prostate cancer (Nouh, et al., 2009), renal cancer, Hodgkin lymphoma (Baumforth, 2005), hepatocellular carcinoma (Wu, et al., 2010), lung cancer (Xu & Prestwich, 2010), and glioblastoma (Kishi, 2006). Autotaxin overexpression has also been found in a variety of tumors such as malignant melanoma, teratocarcinoma, neuroblastoma, non-small-cell lung cancer, renal cell carcinoma (Stassar, et al., 2001).

Furthermore, expression of autotaxin by cancer cells controls osteolytic bone metastasis formation. In particular, LPA stimulates directly cancer growth and metastasis, and osteoclast differentiation. Therefore, targeting the autotaxin/LPA signaling route has also been found to be beneficial in patients with bone metastases (David, 2010). Finally, the inhibition of autotaxin seems to provide a beneficial adjuvant to chemotherapy for preventing tumor growth and metastasis in patients with high autotaxin expression in their tumors (Gaetano, 2009).

Upregulation of the autotaxin-LPA signaling pathway has been observed in a variety of inflammatory conditions. For example, pro-inflammatory effects of LPA include degranulation of mast cells, contraction of smooth-muscle cells and release of cytokines from dendritic cells. As an indication for its general role in inflammation, LPA and autotaxin activity have been shown to be induced by carageenan injection into the mouse air pouch model, which is used to develop anti-inflammatory drugs, including cyclooxygenase inhibitors for arthritis. Furthermore, a reduction in plasma and air pouch LPA has been observed in this rat air pouch model using an autotaxin inhibitor, confirming the role of autotaxin during inflammation as a major source of LPA (Gierse, 2010). It has been observed that autotaxin inhibitors reduce LPA and PGE2 and also reduce inflammatory pain.

As another general role in inflammatory diseases, LPA has been shown to induce chemokinesis in T-cells. Intravenous injection of enzymatically inactive autotaxin has been shown to attenuate the homing of T-cells to lymphoid tissues, likely by competing with endogenous autotaxin and exerting a dominant-negative effect. In certain instances, autotaxin facilitates lymphocyte entry into lymphoid organs (Kanda, 2008). Therefore an autotaxin inhibitor may block lymphocyte migration into secondary lymphoid organs and be of benefit in autoimmune diseases.

Specifically in rheumatoid arthritis, an increased expression of ATX in synovial fibroblasts from RA patients was demonstrated and ablation of ATX expression in mesenchymal cells (including synovial fibroblasts) resulted in attenuated symptoms in mouse models for rheumatoid arthritis (Nikitopoulou, et al., 2012). As such, the role of autotaxin in rheumatoid arthritis has been strongly established.

Several lines of evidence suggest a role for LPA in vascular injury and atherosclerosis. These relate to the role of LPA in modulating endothelial barrier function and the phenotype of vascular smooth muscle cells and the action of LPA as a weak platelet agonist. Platelets have been identified as important participants in LPA production in the circulation in some settings, mainly by providing sufficient LPC amounts. Plasma autotaxin associates with platelets during aggregation and concentrates in arterial thrombus, and activated but not resting platelets bind recombinant autotaxin in an integrin-dependent manner. Experimental induction of thrombocytopenia in rats, using an anti-platelet antibody, decreases the production of LPA in serum by almost 50%, which suggests a role for LPA during clotting. In some instances, transgenic overexpression of autotaxin elevates circulating LPA levels and induces a bleeding diathesis and attenuation of thrombosis in mice. Intravascular administration of exogenous LPA recapitulates the prolonged bleeding time observed in autotaxin-Tg mice. Finally, autotaxin mice, which have ~50% normal plasma LPA levels, are more prone to thrombosis.

In addition to a role in blood clotting, LPA has multiple effects on the endothelial monolayer permeability increase, and endothelial cells, in particular in critical aspects of angiogenesis such as cell migration stimulation and invasion. Furthermore, LPA also exerts migratory and contractile effects on vascular smooth muscle cells: autotaxin-mediated LPA production and subsequent LPA signaling contributes to vascular development by stimulating endothelial cell migration and invasion as well as regulating adhesive interactions with the extracellular matrix and smooth muscle cells. For example, similar vascular defects have been observed in autotaxin-deficient mice and in mice lacking genes involved in cell migration and adhesion (Van Meeteren, et al., 2006). Therefore an autotaxin inhibitor may have benefit in some diseases involving dysregulated angiogenesis.

LPA induces neuropathic pain as well as demyelination and pain-related protein expression changes via LPA1 (Inoue, et al., 2008). ATX heterozygous knockout mice show about 50% recovery of nerve injury-induced neuropathic pain compared to wild type mice. Lysophosphatidylcholine (LPC), also known as lyso-lecithin, is known to induce neuropathic pain. It has been observed that LPC-induced neuropathic pain is partially reduced in ATX heterozygous knockout mice. These results support the idea that LPA is produced by autotaxin resulting in neuropathic pain (Lin M. E., 2010).

Autotaxin is also implicated in metabolic diseases, in particular obesity and diabetes (Federico, et al., 2012). In some instances, autotaxin is responsible for the lysoPLD activity released by adipocytes and exerts a paracrine control on preadipocyte growth via an LPA-dependent mechanism. In addition, autotaxin is upregulated during adipocyte differentiation and in genetic obesity. In certain instances, autotaxin mRNA is upregulated in adipocytes from db/db mice suggesting that the upregulation of autotaxin is related to the severe type 2 diabetes phenotype and adipocyte insuline resistance. In some instances, upregulation of adipocyte autotaxin is associated with type 2 diabetes in human (Ferry, 2003). The relationship between adipocyte and autotaxin biology suggests the use of an autotaxin inhibitor for the treatment of metabolic diseases.

Finally, two other conditions clearly related to autotaxin biology are cholestatic pruritus (Kremer, et al., 2010) and regulation of ocular pressure (Iyer, et al., 2012).

The current therapies are not satisfactory and therefore there remains a need to identify further compounds that may be of use in the treatment of fibrotic diseases, proliferative diseases, inflammatory diseases, autoimmune diseases, respiratory diseases, cardiovascular diseases, neurodegenerative diseases, dermatological disorders, and/or abnormal angiogenesis associated diseases. The present invention therefore provides compounds, methods for their manufacture and pharmaceutical compositions comprising a compound of the invention together with a suitable pharmaceutical carrier. The present invention also provides for the use of a compound of the invention in the preparation of a medicament for the treatment of fibrotic diseases, proliferative diseases, inflammatory diseases, autoimmune diseases, respiratory diseases, cardiovascular diseases, neurodegenerative diseases, dermatological disorders, and/or abnormal angiogenesis associated diseases.

SUMMARY OF THE INVENTION

The present invention is based on the identification of novel compounds, and their ability to act as inhibitors of autotaxin and that they may be useful for the treatment of fibrotic diseases, proliferative diseases, inflammatory diseases, autoimmune diseases, respiratory diseases, cardiovascular diseases, neurodegenerative diseases, dermatological disorders, and/or abnormal angiogenesis associated diseases. The present invention also provides methods for the production of these compounds, pharmaceutical compositions comprising these compounds and methods of treatment for fibrotic diseases, proliferative diseases, inflammatory diseases, autoimmune diseases, respiratory diseases, cardiovascular diseases, neurodegenerative diseases, dermatological disorders, and/or abnormal angiogenesis associated diseases by administering the compounds of the invention.

Accordingly, in a first aspect of the invention, the compounds of the invention are provided having a Formula (I):

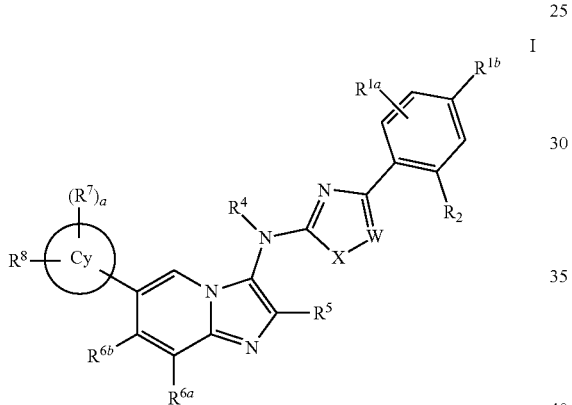

wherein
$R^{1a}$ is H, halo or $C_{1-4}$ alkyl;
$R^{1b}$ is:
  halo,
  $C_{1-4}$ alkyl (which alkyl is optionally substituted with one or more independently selected halo), or
  $C_{1-4}$ alkoxy (which alkoxy is optionally substituted with one or more independently selected halo);
X is —S—, —O—, —N=CH—, —CH=N— or CH=CH—;
W is N, or $CR^3$
when W is N, $R^2$ is:
  H,
  —CN,
  halo,
  $C_{1-4}$ alkyl (which alkyl is optionally substituted with one or more independently selected OH, or CN),
  —C(=O)CH$_3$,
  —C(=O)CF$_3$,
  —C(=O)OCH$_3$,
  —C(=O)NH$_2$, or
  —NHC(=O)CH$_3$, or
when W is $CR^3$, one of $R^2$ or $R^3$ is:
  H,
  —CN,
  halo,
  $C_{1-4}$ alkyl (which alkyl is optionally substituted with one or more independently selected OH, or CN),
  —C(=O)CH$_3$,
  —C(=O)CF$_3$,
  —C(=O)OCH$_3$,
  —C(=O)NH$_2$, or
  —NHC(=O)CH$_3$,
  and the other is H, or $C_{1-4}$ alkyl;
$R^4$ is $C_{1-4}$ alkyl;
$R^5$ is $C_{1-4}$ alkyl optionally substituted with one or more independently selected CN, OH, halo, or —C(=O)NH$_2$;
one of $R^{6a}$ or $R^{6b}$ is selected from H, —CH$_3$, and halo, and the other is H;
Cy is:
  $C_{4-10}$ cycloalkyl,
  4-10 membered mono or bicyclic heterocycloalkyl containing one or more heteroatoms independently selected from O, N, and S, or
  4-7 membered heterocycloalkenyl containing 1 double bond, containing one or more heteroatoms independently selected from O, N, and S;
each $R^7$ is independently selected from:
  OH,
  oxo,
  halo, and
  $C_{1-4}$ alkyl (which alkyl is optionally substituted with one or more independently selected OH, or $C_{1-4}$ alkoxy);
the subscript a is 0, 1 or 2;
$R^8$ is -(L$_1$-W$_1$)$_m$-L$_2$-G$_1$,
  wherein
  L$_1$ is absent, or is —O—, —C(=O)—, —NR$^i$, —NR$^h$C(=O)—, or —SO$_2$—;
  W$_1$ is $C_{1-4}$ alkylene;
  the subscript m is 0, or 1;
  L$_2$ is absent, or is —O—, —C(=O)—, —C(=O)O—, —OC(=O)—, —C(=O)—C(=O)—, —C(=O)—C(=O)NR$^a$—, —NR$^b$—, —C(=O)NR$^c$—, —NR$^d$C(=O)—, —NR$^j$C(=O)O—, —SO$_2$—, —SO$_2$NR$^e$— or —NR$^f$SO$_2$—;
  G$_1$ is
    H,
    —CN,
    $C_{1-4}$ alkyl (which alkyl is optionally substituted with one or more independently selected —CN, OH, halo or phenyl),
    $C_{3-7}$ cycloalkyl (which cycloalkyl is optionally substituted with —NH$_2$),
    5-6 membered heterocycloalkenyl containing 1 double bond containing one or more heteroatoms independently selected from O, N, and S (which heterocycloalkenyl is optionally substituted with one or more independently selected $R^9$ groups),
    4-10 membered mono, bi or spirocyclic heterocycloalkyl containing one or more heteroatoms independently selected from O, N, and S (which heterocycloalkyl is optionally substituted with one or more independently selected $R^9$ groups), or
    5-6 membered heteroaryl containing one or more heteroatoms independently selected from O, N, and S (which heteroaryl is optionally substituted with one or more independently selected $R^{10}$ groups), each $R^9$ is oxo, or $R^{10}$;
each $R^{10}$ is:
—OH,
halo,
—CN,
$C_{1-4}$ alkyl (which alkyl is optionally substituted with one or more independently selected OH, halo, or phenyl),
$C_{1-4}$ alkoxy,
$C_{3-7}$ cycloalkyl,
phenyl,
—SO$_2$CH$_3$,
—C(=O)$C_{1-4}$ alkoxy,
—C(=O)$C_{1-4}$ alkyl, or
—NR$^g$C(=O)$C_{1-4}$ alkyl; and
each $R^a$, $R^b$, $R^c$, $R^d$, $R^e$, $R^f$, $R^g$, $R^h$, $R^i$, and $R^j$ is independently selected from H and $C_{1-4}$ alkyl.

In one aspect, the compounds of the invention are inhibitors of autotaxin. Furthermore, the compounds of the invention may exhibit low clearance, possibly resulting in low therapeutic dose levels.

In a more particular aspect, the compounds of the invention are active in vivo against IPF and/or COPD.

In a particular aspect, the compounds of the invention are provided for use in the prophylaxis and/or treatment of fibrotic diseases, proliferative diseases, inflammatory diseases, autoimmune diseases, respiratory diseases, cardiovascular diseases, neurodegenerative diseases, dermatological disorders, and/or abnormal angiogenesis associated diseases.

In a further aspect, the present invention provides pharmaceutical compositions comprising a compound of the invention, and a pharmaceutical carrier, excipient or diluent. In a particular aspect, the pharmaceutical composition may additionally comprise further therapeutically active ingredients suitable for use in combination with the compounds of the invention. In a more particular aspect, the further therapeutically active ingredient is an agent for the treatment of fibrotic diseases, proliferative diseases, inflammatory diseases, autoimmune diseases, respiratory diseases, cardiovascular diseases, neurodegenerative diseases, dermatological disorders, and/or abnormal angiogenesis associated diseases.

Moreover, the compounds of the invention, useful in the pharmaceutical compositions and treatment methods disclosed herein, are pharmaceutically acceptable as prepared and used.

In a further aspect of the invention, this invention provides a method of treating a mammal, in particular humans, afflicted with a condition selected from among those listed herein, and particularly fibrotic diseases, proliferative diseases, inflammatory diseases, autoimmune diseases, respiratory diseases, cardiovascular diseases, neurodegenerative diseases, dermatological disorders, and/or abnormal angiogenesis associated diseases, which method comprises administering an effective amount of the pharmaceutical composition or compounds of the invention as described herein.

The present invention also provides pharmaceutical compositions comprising a compound of the invention, and a suitable pharmaceutical carrier, excipient or diluent for use in medicine. In a particular aspect, the pharmaceutical composition is for use in the prophylaxis and/or treatment of fibrotic diseases, proliferative diseases, inflammatory diseases, autoimmune diseases, respiratory diseases, cardiovascular diseases, neurodegenerative diseases, dermatological disorders, and/or abnormal angiogenesis associated diseases.

In additional aspects, this invention provides methods for synthesizing the compounds of the invention, with representative synthetic protocols and pathways disclosed later on herein.

Other objects and advantages will become apparent to those skilled in the art from a consideration of the ensuing detailed description.

It will be appreciated that compounds of the invention may be metabolized to yield biologically active metabolites.

DETAILED DESCRIPTION OF THE INVENTION

Definitions

The following terms are intended to have the meanings presented therewith below and are useful in understanding the description and intended scope of the present invention.

When describing the invention, which may include compounds, pharmaceutical compositions containing such compounds and methods of using such compounds and compositions, the following terms, if present, have the following meanings unless otherwise indicated. It should also be understood that when described herein any of the moieties defined forth below may be substituted with a variety of substituents, and that the respective definitions are intended to include such substituted moieties within their scope as set out below. Unless otherwise stated, the term 'substituted' is to be defined as set out below. It should be further understood that the terms 'groups' and 'radicals' can be considered interchangeable when used herein.

The articles 'a' and 'an' may be used herein to refer to one or to more than one (i.e. at least one) of the grammatical objects of the article. By way of example 'an analogue' means one analogue or more than one analogue.

As used herein the term 'IPA' relates to lysophosphatidic acid which is a member of the membrane-derived bioactive lipid mediators, further comprising sphingosine-1-phosphate (S1P), lysophosphatidylcholine (LPC), and sphingosylphosphorylcholine (SPC). LPA interacts with specific G protein-coupled receptors (GPCRs), namely LPA$_1$, LPA$_2$, LPA$_3$, LPA$_4$, LPA$_5$, LPA$_6$, LPA$_7$, LPA$_8$, in an autocrine and paracrine fashion, to activate intracellular signaling pathways, and in turn produce a variety of biological responses.

'Alkyl' means straight or branched aliphatic hydrocarbon with the number of carbon atoms specified. Particular alkyl groups have 1 to 8 carbon atoms. More particular is lower alkyl which has 1 to 6 carbon atoms. A further particular group has 1 to 4 carbon atoms. Exemplary straight chained groups include methyl, ethyl n-propyl, and n-butyl. Branched means that one or more lower alkyl groups such as methyl, ethyl, propyl or butyl is attached to a linear alkyl chain, exemplary branched chain groups include isopropyl, iso-butyl, t-butyl and isoamyl.

'Alkoxy' refers to the group —OR$^{26}$ where R$^{26}$ is alkyl with the number of carbon atoms specified. Particular alkoxy groups are methoxy, ethoxy, n-propoxy, isopropoxy, n-butoxy, tert-butoxy, sec-butoxy, n-pentoxy, n-hexoxy, and 1,2-dimethylbutoxy. Particular alkoxy groups are lower alkoxy, i.e. with between 1 and 6 carbon atoms. Further particular alkoxy groups have between 1 and 4 carbon atoms.

'Alkylene' refers to divalent alkene radical groups having the number of carbon atoms specified, in particular having 1 to 6 carbon atoms and more particularly 1 to 4 carbon atoms which can be straight-chained or branched. This term is exemplified by groups such as methylene (—$CH_2$—), ethylene (—$CH_2$—$CH_2$—), or —$CH(CH_3)$— and the like.

'Alkenyl' refers to monovalent olefinically (unsaturated) hydrocarbon groups with the number of carbon atoms specified. Particular alkenyl has 2 to 8 carbon atoms, and more particularly, from 2 to 6 carbon atoms, which can be straight-chained or branched and having at least 1 and particularly from 1 to 2 sites of olefinic unsaturation. Particular alkenyl groups include ethenyl (—CH=$CH_2$), n-propenyl (—$CH_2$CH=$CH_2$), isopropenyl (—$C(CH_3)$=$CH_2$) and the like.

'Amino' refers to the radical —$NH_2$.

'Aryl' refers to a monovalent aromatic hydrocarbon group derived by the removal of one hydrogen atom from a single carbon atom of a parent aromatic ring system. In particular aryl refers to an aromatic ring structure, monocyclic or polycyclic, with the number of ring atoms specified. Specifically, the term includes groups that include from 6 to 10 ring members. Where the aryl group is a monocyclic ring system it preferentially contains 6 carbon atoms. Particularly aryl groups include phenyl, naphthyl, indenyl, and tetrahydronaphthyl.

'Cycloalkyl' refers to a non-aromatic hydrocarbyl ring structure, monocyclic or polycyclic, with the number of ring atoms specified. A cycloalkyl may have from 3 to 10 carbon atoms, and in particular from 3 to 7 carbon atoms. Such cycloalkyl groups include, by way of example, single ring structures such as cyclopropyl, cyclobutyl, cyclopentyl, cyclohexyl, and cycloheptyl.

'Cyano' refers to the radical —CN.

'Halo' or 'halogen' refers to fluoro (F), chloro (Cl), bromo (Br) and iodo (I). Particular halo groups are either fluoro or chloro.

'Hetero' when used to describe a compound or a group present on a compound means that one or more carbon atoms in the compound or group have been replaced by a nitrogen, oxygen, or sulfur heteroatom. Hetero may be applied to any of the hydrocarbyl groups described above such as alkyl, e.g. heteroalkyl, cycloalkyl, e.g. heterocycloalkyl, aryl, e.g. heteroaryl, and the like having from 1 to 4, and particularly from 1 to 3 heteroatoms, more typically 1 or 2 heteroatoms, for example a single heteroatom.

'Heteroaryl' means an aromatic ring structure, monocyclic or polycyclic, that includes one or more heteroatoms independently selected from O, N and S and the number of ring atoms specified. In particular, the aromatic ring structure may have from 5 to 10 ring members. The heteroaryl group can be, for example, a five membered or six membered monocyclic ring or a bicyclic structure formed from fused five and six membered rings or two fused six membered rings or, by way of a further example, two fused five membered rings. Each ring may contain up to four heteroatoms typically selected from nitrogen, sulphur and oxygen. Typically the heteroaryl ring will contain up to 4 heteroatoms, more typically up to 3 heteroatoms, more usually up to 2, for example a single heteroatom. In one embodiment, the heteroaryl ring contains at least one ring nitrogen atom. The nitrogen atoms in the heteroaryl rings can be basic, as in the case of an imidazole or pyridine, or essentially non-basic as in the case of an indole or pyrrole nitrogen. In general the number of basic nitrogen atoms present in the heteroaryl group, including any amino group substituents of the ring, will be less than five. Examples of five membered monocyclic heteroaryl groups include but are not limited to pyrrole, furan, thiophene, imidazole, furazan, oxazole, oxadiazole, oxatriazole, isoxazole, thiazole, isothiazole, thiadiazole, pyrazole, triazole and tetrazole groups. Examples of six membered monocyclic heteroaryl groups include but are not limited to pyridine, pyrazine, pyridazine, pyrimidine and triazine. Particular examples of bicyclic heteroaryl groups containing a five membered ring fused to another five membered ring include but are not limited to imidazothiazole and imidazoimidazole. Particular examples of bicyclic heteroaryl groups containing a six membered ring fused to a five membered ring include but are not limited to benzofuran, benzothiophene, benzoimidazole, benzoxazole, isobenzoxazole, benzisoxazole, benzthiazole, benzisothiazole, isobenzofuran, indole, isoindole, isoindolone, indolizine, indoline, isoindoline, purine (e.g. adenine, guanine), indazole, imidazopyridines, imidazopyrimidines, imidazopyrazines, pyrazolopyrimidine, triazolopyrimidine, benzodioxole and pyrazolopyridine groups. Particular examples of bicyclic heteroaryl groups containing two fused six membered rings include but are not limited to quinoline, isoquinoline, chroman, thiochroman, chromene, isochromene, chroman, isochroman, benzodioxan, quinolizine, benzoxazine, benzodiazine, pyridopyridine, quinoxaline, quinazoline, cinnoline, phthalazine, naphthyridine and pteridine groups. Particular heteroaryl groups are those derived from thiophene, pyrrole, benzothiophene, benzofuran, indole, pyridine, quinoline, imidazole, thiazole, oxazole and pyrazine.

Examples of representative heteroaryls include the following:

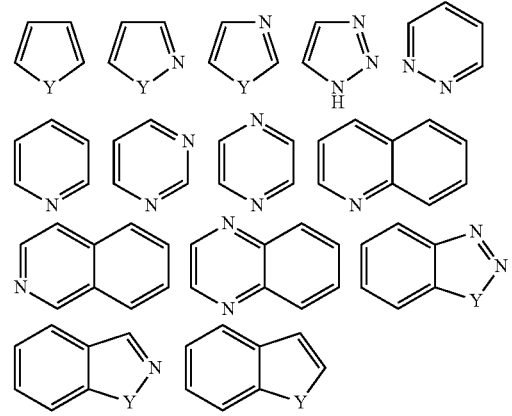

wherein each Y is selected from >C(=O), NH, O and S.

As used herein, the term 'heterocycloalkyl' means a stable non-aromatic ring structure, mono-cyclic or polycyclic, that includes one or more heteroatoms independently selected from O, N and S and the number of ring atoms specified. The non-aromatic ring structure may have from 4 to 10 ring members, and in particular from 4 to 7 ring members. A fused heterocyclic ring system may include carbocyclic rings and need only to include one heterocyclic ring. Examples of heterocyclic rings include, but are not limited to, morpholine, piperidine (e.g. 1-piperidinyl, 2-piperidinyl, 3-piperidinyl and 4-piperidinyl), pyrrolidine (e.g. 1-pyrrolidinyl, 2-pyrrolidinyl and 3-pyrrolidinyl), pyrrolidone, pyran tetrahydrofuran, tetrahydrothiophene, dioxane, tetrahydropyran (e.g. 4-tetrahydro pyranyl), imidazoline, imidazolidinone, oxazoline, thiazoline, 2-pyrazoline, pyrazolidine, piperazine, and N-alkyl piperazines such as N-methyl piperazine. Further examples include thiomorpholine and its S-oxide and S,S-dioxide (particularly thiomorpholine). Still further examples include azetidine, piperidone, piperazone, and N-alkyl piperidines such as N-methyl piperidine. Particular examples of heterocycloalkyl groups are shown in the following illustrative examples:

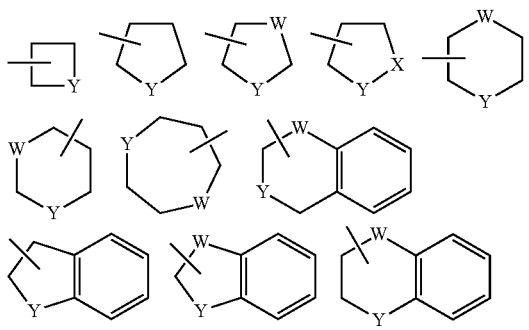

wherein each W is selected from $CH_2$, NH, O and S; and each Y is selected from NH, O, C(=O), $SO_2$, and S.

As used herein, the term 'heterocycloalkenyl' means a 'heterocycloalkyl', which comprises at least one double bond. Particular examples of heterocycloalkenyl groups are shown in the following illustrative examples:

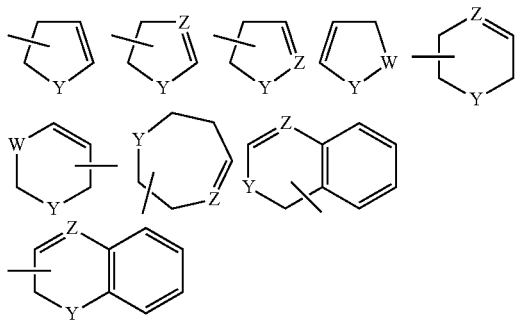

wherein each W is selected from $CH_2$, NH, O and S; each Y is selected from NH, O, C(=O), $SO_2$, and S; and each Z is selected from N or CH.

'Hydroxyl' refers to the radical —OH.

'Oxo' refers to the radical =O.

'Substituted' refers to a group in which one or more hydrogen atoms are each independently replaced with the same or different substituent(s).

'Sulfo' or 'sulfonic acid' refers to a radical such as —$SO_3H$.

'Thiol' refers to the group —SH.

As used herein, term 'substituted with one or more' refers to one to four substituents. In one embodiment it refers to one to three substituents. In further embodiments it refers to one or two substituents. In a yet further embodiment it refers to one substituent.

'Thioalkoxy' refers to the group —$SR^{26}$ where $R^{26}$ is alkyl with the number of carbon atoms specified. Particular thioalkoxy groups are thiomethoxy, thioethoxy, n-thiopropoxy, isothiopropoxy, n-thiobutoxy, tert-thiobutoxy, sec-thiobutoxy, n-thiopentoxy, n-thiohexoxy, and 1,2-dimethylthiobutoxy. More particular thioalkoxy groups are lower thioalkoxy, i.e. with between 1 and 6 carbon atoms. Further particular alkoxy groups have between 1 and 4 carbon atoms.

One having ordinary skill in the art of organic synthesis will recognize that the maximum number of heteroatoms in a stable, chemically feasible heterocyclic ring, whether it is aromatic or non aromatic, is determined by the size of the ring, the degree of unsaturation and the valence of the heteroatoms. In general, a heterocyclic ring may have one to four heteroatoms so long as the heteroaromatic ring is chemically feasible and stable.

'Pharmaceutically acceptable' means approved or approvable by a regulatory agency of the Federal or a state government or the corresponding agency in countries other than the United States, or that is listed in the U.S. Pharmacopoeia or other generally recognized pharmacopoeia for use in animals, and more particularly, in humans.

'Pharmaceutically acceptable salt' refers to a salt of a compound of the invention that is pharmaceutically acceptable and that possesses the desired pharmacological activity of the parent compound. In particular, such salts are non-toxic may be inorganic or organic acid addition salts and base addition salts. Specifically, such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl) benzoic acid, cinnamic acid, mandelic acid, methanesulfonic acid, ethanesulfonic acid, 1,2-ethanedisulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound either is replaced by a metal ion, e.g. an alkali metal ion, an alkaline earth ion, or an aluminum ion; or coordinates with an organic base such as ethanolamine, diethanolamine, triethanolamine, N-methylglucamine and the like. Salts further include, by way of example only, sodium, potassium, calcium, magnesium, ammonium, tetraalkylammonium, and the like; and when the compound contains a basic functionality, salts of non toxic organic or inorganic acids, such as hydrochloride, hydrobromide, tartrate, mesylate, acetate, maleate, oxalate and the like. The term 'pharmaceutically acceptable cation' refers to an acceptable cationic counter-ion of an acidic functional group. Such cations are exemplified by sodium, potassium, calcium, magnesium, ammonium, tetraalkylammonium cations, and the like.

'Pharmaceutically acceptable vehicle' refers to a diluent, adjuvant, excipient or carrier with which a compound of the invention is administered.

'Prodrugs' refers to compounds, including derivatives of the compounds of the invention, which have cleavable groups and become by solvolysis or under physiological conditions the compounds of the invention which are pharmaceutically active in vivo. Such examples include, but are not limited to, choline ester derivatives and the like, N-alkylmorpholine esters and the like.

'Solvate' refers to forms of the compound that are associated with a solvent, usually by a solvolysis reaction. This physical association includes hydrogen bonding. Conventional solvents include water, ethanol, acetic acid and the like. The compounds of the invention may be prepared e.g.

in crystalline form and may be solvated or hydrated. Suitable solvates include pharmaceutically acceptable solvates, such as hydrates, and further include both stoichiometric solvates and non-stoichiometric solvates. In certain instances the solvate will be capable of isolation, for example when one or more solvent molecules are incorporated in the crystal lattice of the crystalline solid. 'Solvate' encompasses both solution-phase and isolable solvates. Representative solvates include hydrates, ethanolates and methanolates.

'Subject' includes humans. The terms 'human', 'patient' and 'subject' are used interchangeably herein.

'Effective amount' means the amount of a compound of the invention that, when administered to a subject for treating a disease, is sufficient to effect such treatment for the disease. The 'effective amount' can vary depending on the compound, the disease and its severity, and the age, weight, etc., of the subject to be treated.

'Preventing' or 'prevention' refers to a reduction in risk of acquiring or developing a disease or disorder (i.e. causing at least one of the clinical symptoms of the disease not to develop in a subject that may be exposed to a disease-causing agent, or predisposed to the disease in advance of disease onset).

The term 'prophylaxis' is related to 'prevention', and refers to a measure or procedure the purpose of which is to prevent, rather than to treat or cure a disease. Non-limiting examples of prophylactic measures may include the administration of vaccines; the administration of low molecular weight heparin to hospital patients at risk for thrombosis due, for example, to immobilization; and the administration of an anti-malarial agent such as chloroquine, in advance of a visit to a geographical region where malaria is endemic or the risk of contracting malaria is high.

'Treating' or 'treatment' of any disease or disorder refers, in one embodiment, to ameliorating the disease or disorder (i.e. arresting the disease or reducing the manifestation, extent or severity of at least one of the clinical symptoms thereof). In another embodiment 'treating' or 'treatment' refers to ameliorating at least one physical parameter, which may not be discernible by the subject. In yet another embodiment, 'treating' or 'treatment' refers to modulating the disease or disorder, either physically (e.g. stabilization of a discernible symptom), physiologically (e.g. stabilization of a physical parameter), or both. In a further embodiment, 'treating' or 'treatment' relates to slowing the progression of the disease.

As used herein the term 'fibrotic diseases' refers to diseases characterized by excessive scarring due to excessive production, deposition, and contraction of extracellular matrix, and are that are associated with the abnormal accumulation of cells and/or fibronectin and/or collagen and/or increased fibroblast recruitment and include but are not limited to fibrosis of individual organs or tissues such as the heart, kidney, liver, joints, lung, pleural tissue, peritoneal tissue, skin, cornea, retina, musculoskeletal and digestive tract. In particular, the term fibrotic diseases refers to idiopathic pulmonary fibrosis (IPF); cystic fibrosis, other diffuse parenchymal lung diseases of different etiologies including iatrogenic drug-induced fibrosis, occupational and/or environmental induced fibrosis, granulomatous diseases (sarcoidosis, hypersensitivity pneumonia), collagen vascular disease, alveolar proteinosis, langerhans cell granulomatosis, lymphangioleiomyomatosis, inherited diseases (Hermansky-Pudlak Syndrome, tuberous sclerosis, neurofibromatosis, metabolic storage disorders, familial interstitial lung disease); radiation induced fibrosis; chronic obstructive pulmonary disease (COPD); scleroderma; bleomycin induced pulmonary fibrosis; chronic asthma; silicosis; asbestos induced pulmonary fibrosis; acute respiratory distress syndrome (ARDS); kidney fibrosis; tubulointerstitium fibrosis; glomerular nephritis; focal segmental glomerular sclerosis; IgA nephropathy; hypertension; Alport; gut fibrosis; liver fibrosis; cirrhosis; alcohol induced liver fibrosis; toxic/drug induced liver fibrosis; hemochromatosis; nonalcoholic steatohepatitis (NASH); biliary duct injury; primary biliary cirrhosis; infection induced liver fibrosis; viral induced liver fibrosis; and autoimmune hepatitis; corneal scarring; hypertrophic scarring; Dupuytren disease, keloids, cutaneous fibrosis; cutaneous scleroderma; systemic sclerosis, spinal cord injury/fibrosis; myelofibrosis; vascular restenosis; atherosclerosis; arteriosclerosis; Wegener's granulomatosis; Peyronie's disease, or chronic lymphocytic. More particularly, the term 'fibrotic diseases' refers to idiopathic pulmonary fibrosis (IPF).

As used herein the term 'proliferative disease(s)' refers to conditions such as cancer (e.g. uterine leiomyosarcoma or prostate cancer), myeloproliferative disorders (e.g. polycythemia vera, essential thrombocytosis and myelofibrosis), leukemia (e.g. acute myeloid leukaemia, acute and chronic lymphoblastic leukemia), multiple myeloma, psoriasis, restenosis, scleroderma or fibrosis. In particular the term refers to cancer, leukemia, multiple myeloma and psoriasis.

As used herein, the term 'cancer' refers to a malignant or benign growth of cells in skin or in body organs, for example but without limitation, breast, prostate, lung, kidney, pancreas, stomach or bowel. A cancer tends to infiltrate into adjacent tissue and spread (metastasise) to distant organs, for example to bone, liver, lung or the brain. As used herein the term cancer includes both metastatic tumour cell types (such as but not limited to, melanoma, lymphoma, leukaemia, fibrosarcoma, rhabdomyosarcoma, and mastocytoma) and types of tissue carcinoma (such as but not limited to, colorectal cancer, prostate cancer, small cell lung cancer and non-small cell lung cancer, breast cancer, pancreatic cancer, bladder cancer, renal cancer, gastric cancer, glioblastoma, primary liver cancer, ovarian cancer, prostate cancer and uterine leiomyosarcoma). In particular, the term "cancer' refers to acute lymphoblastic leukemia, acute myeloidleukemia, adrenocortical carcinoma, anal cancer, appendix cancer, astrocytomas, atypical teratoid/rhabdoid tumor, basal cell carcinoma, bile duct cancer, bladder cancer, bone cancer (osteosarcoma and malignant fibrous histiocytoma), brain stem glioma, brain tumors, brain and spinal cord tumors, breast cancer, bronchial tumors, Burkitt lymphoma, cervical cancer, chronic lymphocytic leukemia, chronic myelogenous leukemia, colon cancer, colorectal cancer, craniopharyngioma, cutaneous T-Cell lymphoma, embryonal tumors, endometrial cancer, ependymoblastoma, ependymoma, esophageal cancer, ewing sarcoma family of tumors, eye cancer, retinoblastoma, gallbladder cancer, gastric (stomach) cancer, gastrointestinal carcinoid tumor, gastrointestinal stromal tumor (GIST), gastrointestinal stromal cell tumor, germ cell tumor, glioma, hairy cell leukemia, head and neck cancer, hepatocellular (liver) cancer, hodgkin lymphoma, hypopharyngeal cancer, intraocular melanoma, islet cell tumors (endocrine pancreas), Kaposi sarcoma, kidney cancer, Langerhans cell histiocytosis, laryngeal cancer, leukemia, Acute lymphoblastic leukemia, acute myeloid leukemia, chronic lymphocytic leukemia, chronic myelogenous leukemia, hairy cell leukemia, liver cancer, non-small cell lung cancer, small cell lung cancer, Burkitt lymphoma, cutaneous T-celllymphoma, Hodgkin lymphoma, non-Hodgkin lymphoma, lymphoma, Waldenstrom macroglobulinemia, medulloblastoma, medulloepithelioma, melanoma, mesothelioma, mouth cancer, chronic myelogenous leukemia, myeloid leukemia, multiple myeloma, asopharyngeal cancer, neuroblastoma, non-small cell lung cancer, oral cancer, oropharyngeal cancer, osteosarcoma, malignant fibrous histiocytoma of bone, ovarian cancer, ovarian epithelial cancer, ovarian germ cell tumor, ovarian low malignant potential tumor, pancreatic cancer, papillomatosis, parathyroid cancer, penile cancer, pharyngeal cancer, pineal parenchymal tumors of intermediate differentiation, pineoblastoma and supratentorial primitive neuroectodermal tumors, pituitary tumor, plasma cell neoplasm/multiple myeloma, pleuropulmonary blastoma, primary central nervous system lymphoma, prostate cancer, rectal cancer, renal cell (kidney) cancer, retinoblastoma, rhabdomyosarcoma, salivary gland cancer, sarcoma, Ewing sarcoma family of tumors, sarcoma, kaposi, Sezary syndrome, skin cancer, small cell Lung cancer, small intestine cancer, soft tissue sarcoma, squamous cell carcinoma, stomach (gastric) cancer, supratentorial primitive neuroectodermal tumors, T-cell lymphoma, testicular cancer, throat cancer, thymoma and thymic carcinoma, thyroid cancer, urethral cancer, uterine cancer, uterine sarcoma, vaginal cancer, vulvar cancer, Waldenstrom macroglobulinemia, and Wilms tumor As used herein the term 'leukemia' refers to neoplastic diseases of the blood and blood forming organs. Such diseases can cause bone marrow and immune system dysfunction, which renders the host highly susceptible to infection and bleeding. In particular the term leukemia refers to acute myeloid leukaemia (AML), and acute lymphoblastic leukemia (ALL) and chronic lymphoblastic leukaemia (CLL).

As used herein the term 'inflammatory diseases' refers to the group of conditions including, rheumatoid arthritis, osteoarthritis, juvenile idiopathic arthritis, psoriasis, psoriatic arthritis, allergic airway disease (e.g. asthma, rhinitis), chronic obstructive pulmonary disease (COPD), inflammatory bowel diseases (e.g. Crohn's disease, ulcerative colitis), endotoxin-driven disease states (e.g. complications after bypass surgery or chronic endotoxin states contributing to e.g. chronic cardiac failure), and related diseases involving cartilage, such as that of the joints. Particularly the term refers to rheumatoid arthritis, osteoarthritis, allergic airway disease (e.g. asthma), chronic obstructive pulmonary disease (COPD) and inflammatory bowel diseases (e.g. Crohn's disease and ulcerative colitis). More particularly the term refers to rheumatoid arthritis, and chronic obstructive pulmonary disease (COPD).

As used herein the term 'autoimmune disease(s)' refers to the group of diseases including obstructive airways disease, including conditions such as COPD, asthma (e.g intrinsic asthma, extrinsic asthma, dust asthma, infantile asthma) particularly chronic or inveterate asthma (for example late asthma and airway hyperreponsiveness), bronchitis, including bronchial asthma, systemic lupus erythematosus (SLE), cutaneous lupus erythrematosis, lupus nephritis, dermatomyositis, Sjogren's syndrome, multiple sclerosis, psoriasis, dry eye disease, type I diabetes mellitus and complications associated therewith, atopic eczema (atopic dermatitis), thyroiditis (Hashimoto's and autoimmune thyroiditis), contact dermatitis and further eczematous dermatitis, inflammatory bowel disease (e.g. Crohn's disease and ulcerative colitis), atherosclerosis and amyotrophic lateral sclerosis. Particularly the term refers to COPD, asthma, systemic lupus erythematosus, type I diabetes mellitus and inflammatory bowel disease.

As used herein, the term 'respiratory disease' refers to diseases affecting the organs that are involved in breathing, such as the nose, throat, larynx, eustachian tubes, trachea, bronchi, lungs, related muscles (e.g., diaphram and intercostals), and nerves. In particular, examples of respiratory diseases include asthma, adult respiratory distress syndrome and allergic (extrinsic) asthma, non-allergic (intrinsic) asthma, acute severe asthma, chronic asthma, clinical asthma, nocturnal asthma, allerGen-induced asthma, aspirin-sensitive asthma, exercise-induced asthma, isocapnic hyperventilation, child onset asthma, adult-onset asthma, cough-variant asthma, occupational asthma, steroid-resistant asthma, seasonal asthma, seasonal allergic rhinitis, perennial allergic rhinitis, chronic obstructive pulmonary disease, including chronic bronchitis or emphysema, pulmonary hypertension, interstitial lung fibrosis and/or airway inflammation, cystic fibrosis, and hypoxia.

As used herein the term 'allergy' refers to the group of conditions characterized by a hypersensitivity disorder of the immune system including, allergic airway disease (e.g. asthma, rhinitis), sinusitis, eczema and hives, as well as food allergies or allergies to insect venom.

As used herein the term 'asthma' as used herein refers to any disorder of the lungs characterized by variations in pulmonary gas flow associated with airway constriction of whatever cause (intrinsic, extrinsic, or both; allergic or non-allergic). The term asthma may be used with one or more adjectives to indicate the cause.

As used herein the term 'cardiovascular disease' refers to diseases affecting the heart or blood vessels or both. In particular, cardiovascular disease includes arrhythmia (atrial or ventricular or both); atherosclerosis and its sequelae; angina; cardiac rhythm disturbances; myocardial ischemia; myocardial infarction; cardiac or vascular aneurysm; vasculitis, stroke; peripheral obstructive arteriopathy of a limb, an organ, or a tissue; reperfusion injury following ischemia of the brain, heart, kidney or other organ or tissue; endotoxic, surgical, or traumatic shock; hypertension, valvular heart disease, heart failure, abnormal blood pressure, vasoconstriction (including that associated with migraines); vascular abnormality, inflammation, insufficiency limited to a single organ or tissue.

As used herein the term 'neurodegenerative diseases' refers to disorders that are associated with atrophy of the affected central or peripheral structures of the nervous system. In particular, the term 'neurodegenerative diseases' refers to diseases such as Alzheimer's disease and other dementias, degenerative nerve diseases, encephalitis, epilepsy, genetic brain disorders, head and brain malformations, hydrocephalus, stroke, Parkinson's disease, multiple sclerosis, amyotrophic lateral sclerosis (ALS or Lou Gehrig's Disease), Huntington's disease, and prion diseases.

As used herein the term 'dermatological disorder' refers to a skin disorder. In particular, dermatological disorders include proliferative or inflammatory disorders of the skin such as, atopic dermatitis, bullous disorders, collagenoses, psoriasis, psoriatic lesions, dermatitis, contact dermatitis, eczema, pruritus, urticaria, rosacea, scleroderma, wound healing, scarring, hypertrophic scarring, keloids, Kawasaki Disease, rosacea, Sjogren-Larsso Syndrome, or urticaria.

As used herein the term 'abnormal angiogenesis associated disease' refers to diseases caused by the dysregulation of the processes mediating angiogenesis. In particular, abnormal angiogenesis associated disease refers to atherosclerosis, hypertension, tumor growth, inflammation, rheumatoid arthritis, wet-form macular degeneration, choroidal neovascularization, retinal neovascularization, and diabetic retinopathy.

'Compound(s) of the invention', and equivalent expressions, are meant to embrace compounds of the Formula(e) as herein described, which expression includes the pharmaceutically acceptable salts, and the solvates, e.g. hydrates, and the solvates of the pharmaceutically acceptable salts where the context so permits. Similarly, reference to intermediates, whether or not they themselves are claimed, is meant to embrace their salts, and solvates, where the context so permits.

When ranges are referred to herein, for example but without limitation, $C_{1-8}$ alkyl, the citation of a range should be considered a representation of each member of said range.

Other derivatives of the compounds of this invention have activity in both their acid and acid derivative forms, but in the acid sensitive form often offers advantages of solubility, tissue compatibility, or delayed release in the mammalian organism (Bundgard, H, 1985). Prodrugs include acid derivatives well know to practitioners of the art, such as, for example, esters prepared by reaction of the parent acid with a suitable alcohol, or amides prepared by reaction of the parent acid compound with a substituted or unsubstituted amine, or acid anhydrides, or mixed anhydrides. Simple aliphatic or aromatic esters, amides and anhydrides derived from acidic groups pendant on the compounds of this invention are particularly useful prodrugs. In some cases it is desirable to prepare double ester type prodrugs such as (acyloxy)alkyl esters or ((alkoxycarbonyl)oxy)alkylesters. Particular such prodrugs are the $C_{1-8}$ alkyl, $C_{2-8}$ alkenyl, $C_{6-10}$ optionally substituted aryl, and $(C_{6-10}$ aryl)-$(C_{1-4}$ alkyl) esters of the compounds of the invention.

As used herein, the term 'isotopic variant' refers to a compound that contains unnatural proportions of isotopes at one or more of the atoms that constitute such compound. For example, an 'isotopic variant' of a compound can contain one or more non-radioactive isotopes, such as for example, deuterium ($^2$H or D), carbon-13 ($^{13}$C), nitroGen-15 ($^{15}$N), or the like. It will be understood that, in a compound where such isotopic substitution is made, the following atoms, where present, may vary, so that for example, any hydrogen may be $^2$H/D, any carbon may be $^{13}$C, or any nitrogen may be $^{15}$N, and that the presence and placement of such atoms may be determined within the skill of the art. Likewise, the invention may include the preparation of isotopic variants with radioisotopes, in the instance for example, where the resulting compounds may be used for drug and/or substrate tissue distribution studies. The radioactive isotopes tritium, i.e. $^3$H, and carbon-14, i.e. $_{14}$C, are particularly useful for this purpose in view of their ease of incorporation and ready means of detection. Further, compounds may be prepared that are substituted with positron emitting isotopes, such as $^{11}$C, $^{18}$F, $^{15}$O and $^{13}$N, and would be useful in Positron Emission Topography (PET) studies for examining substrate receptor occupancy.

All isotopic variants of the compounds provided herein, radioactive or not, are intended to be encompassed within the scope of the invention.

It is also to be understood that compounds that have the same molecular formula but differ in the nature or sequence of bonding of their atoms or the arrangement of their atoms in space are termed 'isomers'. Isomers that differ in the arrangement of their atoms in space are termed 'stereoisomers'.

Stereoisomers that are not mirror images of one another are termed 'diastereomers' and those that are non-superimposable mirror images of each other are termed 'enantiomers'. When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e. as (+) or (−)-isomers respectively). A chiral compound can exist as either individual enantiomer or as a mixture thereof. A mixture containing equal proportions of the enantiomers is called a 'racemic mixture'.

'Tautomers' refer to compounds that are interchangeable forms of a particular compound structure, and that vary in the displacement of hydrogen atoms and electrons. Thus, two structures may be in equilibrium through the movement of 7E electrons and an atom (usually H). For example, enols and ketones are tautomers because they are rapidly interconverted by treatment with either acid or base. Another example of tautomerism is the aci- and nitro-forms of phenylnitromethane, that are likewise formed by treatment with acid or base.

Tautomeric forms may be relevant to the attainment of the optimal chemical reactivity and biological activity of a compound of interest.

The compounds of the invention may possess one or more asymmetric centers; such compounds can therefore be produced as individual (R)- or (S)-stereoisomers or as mixtures thereof.

Unless indicated otherwise, the description or naming of a particular compound in the specification and claims is intended to include both individual enantiomers and mixtures, racemic or otherwise, thereof. The methods for the determination of stereochemistry and the separation of stereoisomers are well-known in the art.

It will be appreciated that compounds of the invention may be metabolized to yield biologically active metabolites.

The Invention

The present invention is based on the identification of novel compounds, and their ability to act as inhibitors of autotaxin and that they may be useful for the treatment of fibrotic diseases, proliferative diseases, inflammatory diseases, autoimmune diseases, respiratory diseases, cardiovascular diseases, neurodegenerative diseases, dermatological disorders, and/or abnormal angiogenesis associated diseases.

The present invention also provides methods for the production of these compounds, pharmaceutical compositions comprising these compounds and methods of treatment for fibrotic diseases, proliferative diseases, inflammatory diseases, autoimmune diseases, respiratory diseases, cardiovascular diseases, neurodegenerative diseases, dermatological disorders, and/or abnormal angiogenesis associated diseases by administering the compounds of the invention.

Accordingly, in a first aspect of the invention, the compounds of the invention are provided having a Formula (I):

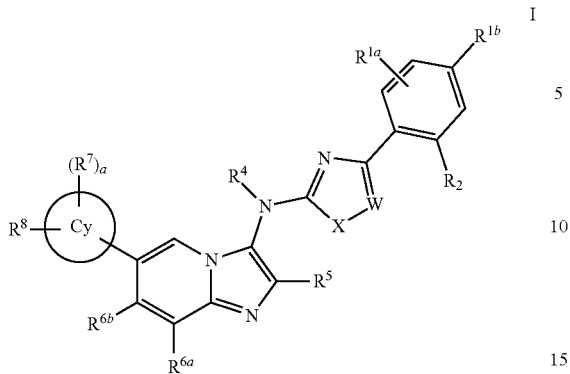

wherein
R$^{1a}$ is H, halo or C$_{1-4}$ alkyl;
R$^{1b}$ is:
  halo,
  C$_{1-4}$ alkyl (which alkyl is optionally substituted with one or more independently selected halo), or
  C$_{1-4}$ alkoxy (which alkoxy is optionally substituted with one or more independently selected halo);
X is —S—, —O—, —N=CH—, —CH=N— or —CH=CH—;
W is N, or CR$^3$
when W is N, R$^2$ is:
  H,
  —CN,
  halo,
  C$_{1-4}$ alkyl (which alkyl is optionally substituted with one or more independently selected OH, or CN),
  —C(=O)CH$_3$,
  —C(=O)CF$_3$,
  —C(=O)OCH$_3$,
  —C(=O)NH$_2$, or
  —NHC(=O)CH$_3$, or
when W is CR$^3$, one of R$^2$ or R$^3$ is:
  H,
  —CN,
  halo,
  C$_{1-4}$ alkyl (which alkyl is optionally substituted with one or more independently selected OH, or CN)
  —C(=O)CH$_3$,
  —C(=O)CF$_3$,
  —C(=O)OCH$_3$,
  —C(=O)NH$_2$, or
  —NHC(=O)CH$_3$,
  and the other is H, or C$_{1-4}$ alkyl;
R$^4$ is C$_{1-4}$ alkyl;
R$^5$ is C$_{1-4}$ alkyl optionally substituted with one or more independently selected CN, OH, halo, or —C(=O)NH$_2$;
one of R$^{6a}$ or R$^{6b}$ is selected from H, —CH$_3$, and halo, and the other is H;
Cy is:
  C$_{4-10}$ cycloalkyl,
  4-10 membered mono or bicyclic heterocycloalkyl containing one or more heteroatoms independently selected from O, N, and S, or
  4-7 membered heterocycloalkenyl containing 1 double bond, containing one or more heteroatoms independently selected from O, N, and S;

each R$^7$ is independently selected from:
  OH,
  oxo,
  halo, and
  C$_{1-4}$ alkyl (which alkyl is optionally substituted with one or more independently selected OH, or C$_{1-4}$ alkoxy);
the subscript a is 0, 1 or 2;
R$^8$ is -(L$_1$-W$_1$)$_m$-L$_2$-G$_1$,
  wherein
  L$_1$ is absent, or is —O—, —C(=O)—, —NR$^i$, —NR$^h$C(=O)—, or —SO$_2$—;
  W$_1$ is C$_{1-4}$ alkylene;
  the subscript m is 0, or 1;
  L$_2$ is absent, or is —O—, —C(=O)—, —C(=O)O—, —OC(=O) —C(=O)—C(=O)—, —C(=O)—C(=O)NR$^a$—, —NR$^b$—, —C(=O)NR$^c$—, —NR$^d$C(=O)—, —NR$^j$C(=O)O—, —SO$_2$—, —SO$_2$NR$^e$— or NR$^f$SO$_2$—;
  G$_1$ is
    H,
    —CN,
    C$_{1-4}$ alkyl (which alkyl is optionally substituted with one or more independently selected CN, OH, halo or phenyl),
    C$_{3-7}$ cycloalkyl (which cycloalkyl is optionally substituted with NH$_2$),
    5-6 membered heterocycloalkenyl containing 1 double bond containing one or more heteroatoms independently selected from O, N, and S (which heterocycloalkenyl is optionally substituted with one or more independently selected R$^9$ groups),
    4-10 membered mono, bi or spirocyclic heterocycloalkyl containing one or more heteroatoms independently selected from O, N, and S (which heterocycloalkyl is optionally substituted with one or more independently selected R$^9$ groups), or
    5-6 membered heteroaryl containing one or more heteroatoms independently selected from O, N, and S (which heteroaryl is optionally substituted with one or more independently selected R$^{10}$ groups),
  each R$^9$ is oxo, or R$^{10}$;
  each R$^{10}$ is:
    —OH,
    halo,
    —CN,
    C$_{1-4}$ alkyl (which alkyl is optionally substituted with one or more independently selected OH, halo, or phenyl),
    C$_{1-4}$ alkoxy,
    C$_{3-7}$ cycloalkyl,
    phenyl,
    —SO$_2$CH$_3$,
    —C(=O)C$_{1-4}$ alkoxy,
    —C(=O)C$_{1-4}$ alkyl, or
    —NR$^g$C(=O)C$_{1-4}$ alkyl; and
  each R$^a$, R$^b$, R$^c$, R$^d$, R$^e$, R$^f$, R$^g$, R$^h$, R$^i$, and R$^j$ is independently selected from H and C$_{1-4}$ alkyl.

In one embodiment, a compound of the invention is according to Formula I, wherein R$^{1a}$ is H.

In one embodiment, a compound of the invention is according to Formula I, wherein R$^{1a}$ is halo. In a particular embodiment, R$^{1a}$ is F, Cl, or Br. In a more particular embodiment, R$^{1a}$ is F, or Cl. In a most particular embodiment, R$^{1a}$ is F.

In one embodiment, a compound of the invention is according to Formula I, wherein R$^{1a}$ is C$_{1-4}$ alkyl. In a particular embodiment, R$^{1a}$ is —CH$_3$, —CH$_2$—CH$_3$, —$CH_2$—$CH_2$—$CH_3$, —$CH(CH_3)_2$. In a more particular embodiment, $R^{1a}$ is —$CH_3$, or —$CH_2$—$CH_3$.

In one embodiment, a compound of the invention is according to Formula I, wherein $R^{1b}$ is halo. In a particular embodiment, $R^{1b}$ is F, Cl, or Br. In a more particular embodiment, $R^{1b}$ is F, or Cl. In a most particular embodiment, $R^{1b}$ is F.

In one embodiment, a compound of the invention is according to Formula I, wherein $R^{1b}$ is $C_{1-4}$ alkyl. In a particular embodiment, $R^{1b}$ is —$CH_3$, —$CH_2$—$CH_3$, —$CH_2$—$CH_2$—$CH_3$, —$CH(CH_3)_2$. In a more particular embodiment, $R^{1b}$ is —$CH_3$, or —$CH_2$—$CH_3$.

In one embodiment, a compound of the invention is according to Formula I, wherein $R^{1b}$ is $C_{1-4}$ alkyl substituted with one or more independently selected halo. In a particular embodiment, $R^{1b}$ is —$CF_3$, or —$CH_2$—$CF_3$. In a more particular embodiment, $R^{1b}$ is —$CF_3$.

In one embodiment, a compound of the invention is according to Formula I, wherein $R^{1b}$ is $C_{1-4}$ alkoxy. In a particular embodiment, $R^{1b}$ is —$OCH_3$, —$OCH_2$—$CH_3$, —$OCH_2$—$CH_2$—$CH_3$, —$OCH(CH_3)_2$. In a more particular embodiment, $R^{1b}$ is —$OCH_3$, or —$OCH_2$—$CH_3$. In a most particular embodiment, $R^{1b}$ is —$OCH_3$.

In one embodiment, a compound of the invention is according to Formula I, wherein $R^{1b}$ is $C_{1-4}$ alkoxy substituted with one or more independently selected halo. In a more particular embodiment, $R^{1b}$ is —$OCF_3$, —$OCH_2$—$CHF_2$ or —$OCH_2$—$CF_3$. In a most particular embodiment, $R^{1b}$ is —$OCF_3$.

In one embodiment, a compound of the invention is according to Formula I, wherein X is —S—, —O—, —N=CH—, —CH=N— or —CH=CH—. In a particular embodiment, X is —S—, or —O—. In another particular embodiment, X is —N=CH—.

In one embodiment, a compound of the invention is according to Formula I, wherein W is N, and $R^2$ is as previously defined. In a particular embodiment, $R^2$ is H, —CN, —C(=O)$CH_3$, —C(=O)$CF_3$, —C(=O)$OCH_3$, —C(=O)$NH_2$, or —NHC(=O)$CH_3$. In a more particular embodiment, $R^2$ is —CN.

In one embodiment, a compound of the invention is according to Formula I, wherein W is N, and $R^2$ is as previously defined. In a particular embodiment, $R^2$ is halo. In a more particular embodiment, $R^2$ is F, Cl, or Br. In a most particular embodiment, $R^2$ is F, or Cl.

In one embodiment, a compound of the invention is according to Formula I, wherein W is N, and $R^2$ is as previously defined. In a particular embodiment, $R^2$ is $C_{1-4}$ alkyl. In another particular embodiment, $R^2$ is $C_{1-4}$ alkyl substituted with one or more independently selected OH, and CN. In yet another particular embodiment, $R^2$ is $C_{1-4}$ alkyl substituted with one OH, or CN. In a more particular embodiment, $R^2$ is —$CH_3$, —$CH_2$—$CH_3$, —$CH_2$—OH, or —$CH_2$—CN. In a most particular embodiment, $R^2$ is —$CH_2$—OH, or —$CH_2$—CN.

In another embodiment, a compound of the invention is according to Formula I, wherein W is $CR^3$, and $R^2$ and $R^3$ are as previously defined. In a particular embodiment, $R^2$ is H, —CN, —C(=O)$CH_3$, —C(=O)$CF_3$, —C(=O)$OCH_3$, —C(=O)$NH_2$, or —NHC(=O)$CH_3$, and $R^3$ is H, or $C_{1-4}$ alkyl. In another particular embodiment, $R^2$ is H, or $C_{1-4}$ alkyl, and $R^3$ is H, —CN, —C(=O)$CH_3$, —C(=O)$CF_3$, —C(=O)$OCH_3$, —C(=O)$NH_2$, or —NHC(=O)$CH_3$. In a more particular embodiment, $R^2$ is H, —CN, —C(=O)$CH_3$, —C(=O)$CF_3$, —C(=O)$OCH_3$, —C(=O)$NH_2$, or —NHC(=O)$CH_3$, and $R^3$ is H, —$CH_3$, or —$CH_2$—$CH_3$. In another more particular embodiment, $R^2$ is H, —$CH_3$, or —$CH_2$—$CH_3$, and $R^3$ is H, —CN, —C(=O)$CH_3$, —C(=O)$CF_3$, —C(=O)$OCH_3$, —C(=O)$NH_2$, or —NHC(=O)$CH_3$. In a most particular embodiment, $R^2$ is —CN, and $R^3$ is H, —$CH_3$, or —$CH_2$—$CH_3$. In another most particular embodiment, $R^2$ is H, —$CH_3$, or —$CH_2$—$CH_3$, and $R^3$ is —CN.

In another embodiment, a compound of the invention is according to Formula I, wherein W is $CR^3$, and $R^2$ and $R^3$ are as previously defined. In a particular embodiment, $R^2$ is halo, and $R^3$ is H, or $C_{1-4}$ alkyl. In another particular embodiment, $R^2$ is H, or $C_{1-4}$ alkyl, and $R^3$ is halo. In a more particular embodiment, $R^2$ is F, Cl, or Br, and $R^3$ is H, —$CH_3$, or —$CH_2$—$CH_3$. In another more particular embodiment, $R^2$ is H, —$CH_3$, or —$CH_2$—$CH_3$, and $R^3$ is F, Cl, or Br. In a most particular embodiment, $R^2$ is F, or Cl, and $R^3$ is H, —$CH_3$, or —$CH_2$—$CH_3$. In another most particular embodiment, $R^2$ is H, —$CH_3$, or —$CH_2$—$CH_3$, and $R^3$ is F, or Cl.

In another embodiment, a compound of the invention is according to Formula I, wherein W is $CR^3$, and $R^2$ and $R^3$ are as previously defined. In a particular embodiment, $R^2$ is $C_{1-4}$ alkyl, and $R^3$ is H, or $C_{1-4}$ alkyl. In another particular embodiment, $R^2$ is H, or $C_{1-4}$ alkyl, and $R^3$ is $C_{1-4}$ alkyl. In a more particular embodiment, $R^2$ is —$CH_3$, or —$CH_2$—$CH_3$, and $R^3$ is H, —$CH_3$, or —$CH_2$—$CH_3$. In another more particular embodiment, $R^2$ is H, —$CH_3$, or —$CH_2$—$CH_3$, and $R^3$ is —$CH_3$, or —$CH_2$—$CH_3$.

In another embodiment, a compound of the invention is according to Formula I, wherein W is $CR^3$, and $R^2$ and $R^3$ are as previously defined. In a particular embodiment, $R^2$ is $C_{1-4}$ alkyl substituted with OH, or CN, and $R^3$ is H, or $C_{1-4}$ alkyl. In another particular embodiment, $R^2$ is H, or $C_{1-4}$ alkyl, and $R^3$ is $C_{1-4}$ alkyl substituted with OH, or CN. In a more particular embodiment, $R^2$ is —$CH_2$—OH, or —$CH_2$—CN, and $R^3$ is H, —$CH_3$, or —$CH_2$—$CH_3$. In another more particular embodiment, $R^2$ is H, —$CH_3$, or —$CH_2$—$CH_3$, and $R^3$ is —$CH_2$—OH, or —$CH_2$—CN.

In one embodiment, a compound of the invention is according to Formula II:

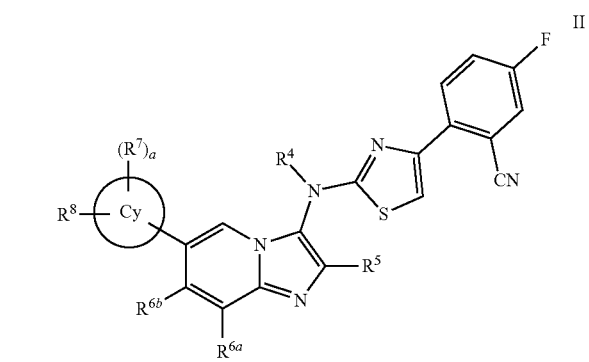

wherein the subscript a, $R^4$, $R^5$, $R^{6a}$, $R^{6b}$, $R^7$ and $R^8$ are as described above.

In another embodiment, a compound of the invention is according to Formula III:

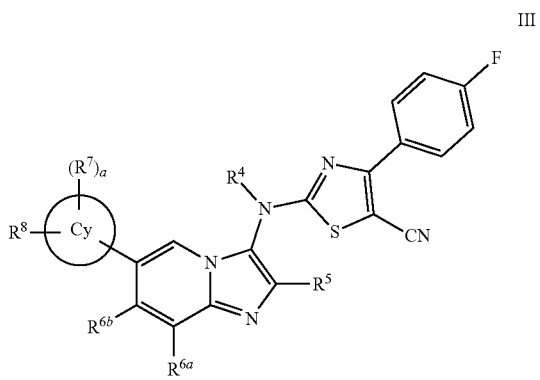

wherein the subscript a, $R^4$, $R^5$, $R^{6a}$, $R^{6b}$, $R^7$ and $R^8$ are as described above.

In one embodiment, a compound of the invention is according to Formula I, II or III, wherein $R^4$ is $C_{1-4}$ alkyl. In a particular embodiment, $R^4$ is —$CH_3$, or —$CH_2$—$CH_3$. In a more particular embodiment, $R^4$ is —$CH_3$.

In one embodiment, a compound of the invention is according to Formula I, II or III, wherein $R^5$ is $C_{1-4}$ alkyl. In a particular embodiment, $R^5$ is —$CH_3$, —$CH_2$—$CH_3$ or —$CH_2$—$CH_2$—$CH_3$. In a more particular embodiment, $R^5$ is —$CH_3$, or —$CH_2$—$CH_3$. In a most particular embodiment, $R^5$ is —$CH_2$—$CH_3$.

In one embodiment, a compound of the invention is according to Formula I, II or III, wherein $R^5$ is $C_{1-4}$ alkyl substituted with one or more independently selected CN, OH, halo, and —C(=O)$NH_2$. In a particular embodiment, $R^5$ is $C_{1-4}$ alkyl substituted with one CN, OH, halo, or —C(=O)$NH_2$. In a more particular embodiment, $R^5$ is —$CH_3$, —$CH_2$—$CH_3$, —$CH_2$—$CH_2$—$CH_3$, —$CH_2$—$CH_2$—$CH_2$—$CH_3$, —$CH(CH_3)_2$, or —$CH_2$—$CH(CH_3)_2$, each of which is substituted with one CN, OH, halo, or —C(=O)$NH_2$. In another more particular embodiment, $R^5$ is —$CH_3$, —$CH_2$—$CH_3$, —$CH_2$—$CH_2$—$CH_3$, —$CH_2$—$CH_2$—$CH_2$—$CH_3$, or —$CH_2$, —$CH(CH_3)_2$, each of which is substituted with one —CN, OH, F, or —C(=O)$NH_2$. In a most particular embodiment, $R^5$ is —$CH_2$—$CH_2$—CN, —$CH_2$—$CH_2$—OH, —$CH_2$—$CF_3$, or —$CH_2$—$CH_2$—C(=O)$NH_2$.

In one embodiment, a compound of the invention is according to Formula I, II or III, wherein Cy is $C_{3-10}$ cycloalkyl. In a particular embodiment, Cy is cyclobutyl, cyclopentyl or cyclohexyl. In a more particular embodiment, Cy is cyclohexyl.

In one embodiment, a compound of the invention is according to Formula I, II or III, wherein Cy is 4-10 membered mono or bicyclic heterocycloalkyl containing one or more heteroatoms independently selected from O, N, and S. In a particular embodiment, Cy is oxetanyl, azetidinyl, tetrahydrofuranyl, pyrrolidinyl, tetrahydropyranyl, piperidinyl, piperazinyl, morpholinyl, or thiomorpholinyl. In a more particular embodiment, Cy is piperidinyl. In another more particular embodiment, Cy is piperazinyl.

In one embodiment, a compound of the invention is according to Formula I, II or III, wherein Cy is 4-7 membered heterocycloalkenyl containing 1 double bond, containing one or more heteroatoms independently selected from O, N, and S. In a particular embodiment, Cy is dihydropyranyl, dihydrothiazolyl, dihydrooxazolyl, dihydropyranyl, tetrahydropyridinyl, or dihydrothiopyranyl. In a more particular embodiment, Cy is dihydrooxazolyl.

In one embodiment, a compound of the invention is according to Formula I, II or III, wherein the subscript a is 1 or 2, and $R^7$ is OH, oxo, or halo. In a particular embodiment, $R^7$ is OH, oxo, F, or Cl.

In one embodiment, a compound of the invention is according to Formula I, II or III, wherein the subscript a is 1 or 2, and $R^7$ is $C_{1-4}$ alkyl. In a particular embodiment, $R^7$ is —$CH_3$, —$CH_2$—$CH_3$, or —$CH(CH_3)_2$. In a more particular embodiment, $R^7$ is —$CH_3$.

In one embodiment, a compound of the invention is according to Formula I, II or III, wherein the subscript a is 1 or 2, and $R^7$ is $C_{1-4}$ alkyl substituted with OH, or $C_{1-4}$ alkoxy. In a particular embodiment, $R^7$ is —$CH_3$, —$CH_2$—$CH_3$, or —$CH(CH_3)_2$, each of which is substituted with OH, or $C_{1-4}$ alkoxy. In a more particular embodiment, $R^7$ is —$CH_2$—OH, or —$CH_2$—$OCH_3$.

In one embodiment, a compound of the invention is according to Formula I, II or III, wherein the subscript a is 0.

In one embodiment, a compound of the invention is according to Formula IVa, IVb, IVc or IVd:

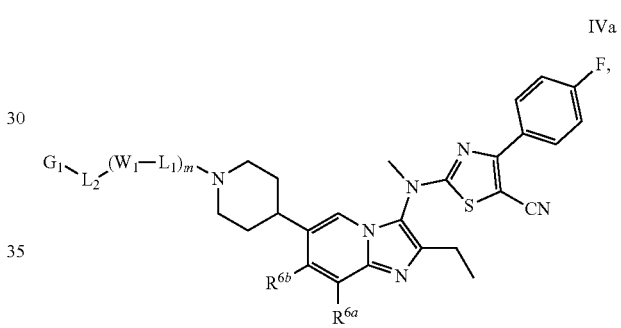

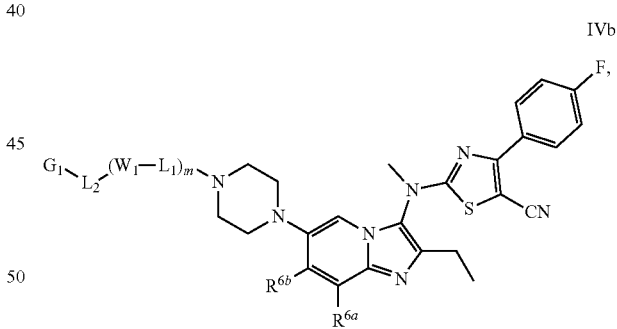

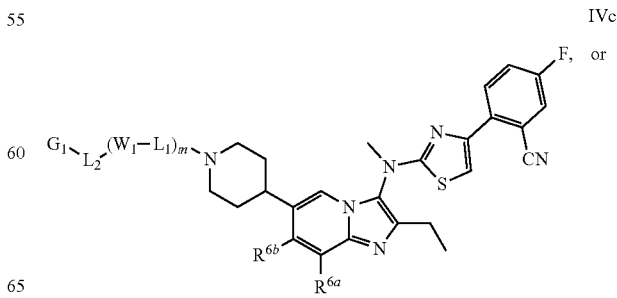

-continued

IVd

[Chemical structure: G₁—L₂—(W₁—L₁)ₘ—N(piperazine)—fused imidazopyridine with R⁶ᵃ, R⁶ᵇ substituents, N-methyl linked thiazole bearing 4-fluoro-2-cyanophenyl, and ethyl group]

wherein R⁶ᵃ, R⁶ᵇ, L₁, W₁, L₂, G₁ and the subscript m are as previously described.

In one embodiment, a compound of the invention is according to Formula I-IVd, wherein the subscript m is 1, and L₁ is absent.

In one embodiment, a compound of the invention is according to Formula I-IVd, wherein the subscript m is 1, L₁ is —NR$^i$—, and R$^i$ is as previously described. In a particular embodiment, R$^i$ is H. In another particular embodiment, R$^i$ is —CH₃, —CH₂—CH₃, or —CH(CH₃)₂.

In one embodiment, a compound of the invention is according to Formula I-IVd, wherein the subscript m is 1, L₁ is —NR$^h$C(=O)—, and R$^h$ is as previously described. In a particular embodiment, R$^h$ is H. In another particular embodiment, R$^h$ is —CH₃, —CH₂—CH₃, or —CH(CH₃)₂.

In one embodiment, a compound of the invention is according to Formula I-IVd, wherein the subscript m is 1, and L₁ is —C(=O)—, or —SO₂—.

In one embodiment, a compound of the invention is according to Formula I-IVd, wherein the subscript m is 1, and W1 is C₁₋₄ alkylene. In a particular embodiment, W₁ is —CH₂—, —CH₂—CH₂—, —C(CH₃)H—, —CH₂—CH₂—CH₂— or —CH₂—C(CH₃)H—. In a more particular embodiment, W₁ is —CH₂—, or —C(CH₃)H—.

In one embodiment, a compound of the invention is according to Formula I-IVd, wherein the subscript m is 0.

In one embodiment, a compound of the invention is according to Formula I-IVd, wherein L₂ is absent.

In one embodiment, a compound of the invention is according to Formula I-IVd, wherein L₂ is —O—.

In one embodiment, a compound of the invention is according to Formula I-IVd, wherein L₂ is —O—, —C(=O)—, —C(=O)O—, —OC(=O)—, —C(=O)—C(=O)—, or —SO₂—.

In one embodiment, a compound of the invention is according to Formula I-IVd, wherein L₂ is —C(=O)—C(=O)NR$^a$—, and R$^a$ is as previously described. In a particular embodiment, R$^a$ is H. In another particular embodiment, R$^a$ is —CH₃, —CH₂—CH₃, or —CH(CH₃)₂.

In one embodiment, a compound of the invention is according to Formula I-IVd, wherein L₂ is —NR$^b$—, and R$^b$ is as previously described. In a particular embodiment, R$^b$ is H. In another particular embodiment, R$^b$ is —CH₃, —CH₂—CH₃, or —CH(CH₃)₂.

In one embodiment, a compound of the invention is according to Formula I-IVd, wherein L₂ is —C(=O)NR$^c$—, and R$^c$ is as previously described. In a particular embodiment, R$^c$ is H. In another particular embodiment, R$^c$ is —CH₃, —CH₂—CH₃, or —CH(CH₃)₂.

In one embodiment, a compound of the invention is according to Formula I-IVd, wherein L₂ is —NR$^d$C(=O)—, and R$^d$ is as previously described. In a particular embodiment, R$^d$ is H. In another particular embodiment, R$^d$ is —CH₃, —CH₂—CH₃, or —CH(CH₃)₂.

In one embodiment, a compound of the invention is according to Formula I-IVd, wherein L₂ is —NR$^j$C(=O)O—, and R$^j$ is as previously described. In a particular embodiment, R$^j$ is H. In another particular embodiment, R$^j$ is —CH₃, —CH₂—CH₃, or —CH(CH₃)₂.

In one embodiment, a compound of the invention is according to Formula I-IVd, wherein L₂ is —SO₂NR$^e$—, and R$^e$ is as previously described. In a particular embodiment, R$^e$ is H. In another particular embodiment, R$^e$ is —CH₃, —CH₂—CH₃, or —CH(CH₃)₂.

In one embodiment, a compound of the invention is according to Formula I-IVd, wherein L₂ is —NR$^f$SO₂—, and R$^f$ is as previously described. In a particular embodiment, R$^f$ is H. In another particular embodiment, R$^f$ is —CH₃, —CH₂—CH₃, or —CH(CH₃)₂.

In one embodiment, a compound of the invention is according to Formula I-IVd, wherein G₁ is H, or CN.

In one embodiment, a compound of the invention is according to Formula I-IVd, wherein G₁ is C₁₋₄ alkyl. In a particular embodiment, G₁ is —CH₃, or —CH₂—CH₃.

In one embodiment, a compound of the invention is according to Formula I-IVd, wherein G₁ is C₁₋₄ alkyl substituted with CN, OH, halo or phenyl. In a particular embodiment, G₁ is —CH₃, —CH₂—CH₃, or —CH(CH₃)₂, each of which is substituted with —CN, OH, halo or phenyl. In a more particular embodiment, G₁ is —CF₃, —CH₂—Cl, —CH₂—CN, —CH₂—OH or —CH₂-Ph.

In one embodiment, a compound of the invention is according to Formula I-IVd, wherein G₁ is C₃₋₇ cycloalkyl. In a particular embodiment, G₁ is cyclopropyl, cyclobutyl, cyclopropyl, or cyclohexyl.

In one embodiment, a compound of the invention is according to Formula I-IVd, wherein G₁ is C₃₋₇ cycloalkyl substituted with —NH₂. In a particular embodiment, G₁ is cyclopropyl, cyclobutyl, cyclopropyl, or cyclohexyl, each of which is substituted with —NH₂.

In one embodiment, a compound of the invention is according to Formula I-IVd, wherein G₁ is 5-6 membered heterocycloalkenyl containing 1 double bond, containing one to three heteroatoms independently selected from O, N, and S. In a particular embodiment, G₁ is dihydrofuranyl, dihydrothiazolyl, dihydrooxazolyl, dihydropyranyl, or dihydrothiopyranyl.

In one embodiment, a compound of the invention is according to Formula I-IVd, wherein G₁ is 5-6 membered heterocycloalkenyl containing 1 double bond, containing one to three heteroatoms independently selected from O, N, and S, substituted with one or more independently selected R⁹, and R⁹ is as previously defined. In another embodiment, G₁ is 5-6 membered heterocycloalkenyl containing 1 double bond, containing one to three heteroatoms independently selected from O, N, and S, substituted with one or two independently selected R⁹, and R⁹ is as previously defined. In a particular embodiment, G₁ is dihydrofuranyl, dihydrothiazolyl, dihydrooxazolyl, dihydropyranyl, or dihydrothiopyranyl, each of which is substituted with one or two independently selected R⁹, and R⁹ is as previously defined.

In one embodiment, a compound of the invention is according to Formula I-IVd, wherein G₁ is 4-10 membered mono, bi or spirocyclic heterocycloalkyl containing one to three heteroatoms independently selected from O, N, and S. In a particular embodiment, G₁ is oxetanyl, azetidinyl, tetrahydrofuranyl, pyrolidinyl, tetrahydropyranyl, piperidinyl, piperazinyl, morpholinyl, thiomorpholinyl, or 2,6-diaza-spiro[3.3]heptane.

In one embodiment, a compound of the invention is according to Formula I-IVd, wherein $G_1$ is 4-10 membered mono, bi or spirocyclic heterocycloalkyl containing one to three heteroatoms independently selected from O, N, and S, substituted with one or more independently selected $R^9$, and $R^9$ is as previously defined. In another embodiment, $G_1$ is 4-10 membered mono, bi or spirocyclic heterocycloalkyl containing one to three heteroatoms independently selected from O, N, and S, substituted with one or two independently selected $R^9$, and $R^9$ is as previously defined. In a particular embodiment, $G_1$ is oxetanyl, azetidinyl, tetrahydrofuranyl, pyrolidinyl, tetrahydropyranyl, piperidinyl, piperazinyl, morpholinyl, thiomorpholinyl, or 2,6-diaza-spiro[3.3]heptanes, each of which is substituted with one or two independently selected $R^9$, and $R^9$ is as previously defined.

In one embodiment, a compound of the invention is according to Formula I-IVd, wherein $R^9$ is oxo.

In another embodiment, a compound of the invention is according to Formula I-IVd, wherein $R^9$ is $R^{10}$.

In one embodiment, a compound of the invention is according to Formula I-IVd, wherein $R^{10}$ is selected from OH, F, Cl, and —CN.

In one embodiment, a compound of the invention is according to Formula I-IVd, wherein $R^{10}$ is $C_{1-4}$ alkyl. In a particular embodiment, $R^{10}$ is selected from —$CH_3$, —$CH_2$—$CH_3$, and —$CH(CH_3)_2$. In a more particular embodiment, $R^{10}$ is selected from —$CH_3$, and —$CH_2$—$CH_3$.

In one embodiment, a compound of the invention is according to Formula I-IVd, wherein $R^{10}$ is $C_{1-4}$ alkyl substituted with one or more independently selected OH, halo, phenyl. In a further embodiment, $R^{10}$ is $C_{1-4}$ alkyl substituted with one to three independently selected OH, halo, and phenyl. In a more particular embodiment, $R^{10}$ is —$CH_3$, —$CH_2$—$CH_3$, and —$CH(CH_3)_2$, each of which is substituted with one to three independently selected OH, halo, and phenyl. In a most particular embodiment, $R^{10}$ is —$CF_3$, —$CH_2$—$CH_2$—OH, and —$CH_2$-phenyl.

In one embodiment, a compound of the invention is according to Formula I-IVd, wherein $R^{10}$ is $C_{1-4}$ alkoxy. In a particular embodiment, $R^{10}$ is selected from —$OCH_3$, —$OCH_2$—$CH_3$, and —$OC(CH_3)_3$. In a particular embodiment, $R^{10}$ is —$OCH_3$.

In one embodiment, a compound of the invention is according to Formula I-IVd, wherein $R^{10}$ is selected from —$SO_2CH_3$, —$C(=O)C_{1-4}$ alkoxy, and —$C(=O)C_{1-4}$ alkyl. In a particular embodiment, $R^{10}$ is selected from —$SO_2CH_3$, —$C(=O)OCH_3$, —$C(=O)OCH_2CH_3$, —$C(=O)OCH(CH_3)_2$, —$C(=O)CH_3$, —$C(=O)CH_2CH_3$, and —$C(=O)OCH(CH_3)_2$. In a most particular embodiment, $R^{10}$ is selected from —$SO_2CH_3$, —$C(=O)OCH_3$, and —$C(=O)CH_3$.

In one embodiment, a compound of the invention is according to Formula I-IVd, wherein $R^{10}$ is —$NR^gC(=O)$ $C_{1-4}$ alkyl, and $R^g$ is as described previously. In a particular embodiment, $R^{10}$ is —$NR^gC(=O)CH_3$, or $NR^gC(=O)$ $CH_2CH_3$, and $R^g$ is as described previously. In a more particular embodiment, $R^{10}$ is $NR^gC(=O)CH_3$, or $NR^gC(=O)CH_2CH_3$, and $R^g$ is H, —$CH_3$, or —$CH_2CH_3$. In a most particular embodiment, $R^{10}$ is —$NHC(=O)CH_3$, or —$NHC(=O)CH_2CH_3$.

In one embodiment, a compound of the invention is according to Formula I-IVd, wherein $G_1$ is 4-7 membered heterocycloalkyl containing one or more heteroatoms independently selected from O, N, and S, each of which is substituted with one or two independently selected $R^9$ groups, and $R^9$ is oxo. In a further particular embodiment, $G_1$ is oxetanyl, azetidinyl, tetrahydrofuranyl, pyrolidinyl, tetrahydropyranyl, piperidinyl, piperazinyl, morpholinyl, thiomorpholinyl, or 2,6-diaza-spiro[3.3]heptane, each of which is substituted with one or two independently selected $R^9$ groups, and $R^9$ is oxo.

In one embodiment, a compound of the invention is according to Formula I-IVd, wherein $G_1$ is 4-7 membered heterocycloalkyl containing one or more heteroatoms independently selected from O, N, and S, each of which is substituted with one or two independently selected $R^9$ groups, $R^9$ is $R^{10}$, and $R^{10}$ is as previously described. In a further embodiment, $G_1$ is oxetanyl, azetidinyl, tetrahydrofuranyl, pyrolidinyl, tetrahydropyranyl, piperidinyl, piperazinyl, morpholinyl, thiomorpholinyl, or 2,6-diaza-spiro [3.3]heptane, each of which is substituted with one or two independently selected $R^9$ groups, $R^9$ is $R^{10}$, and $R^{10}$ is as previously described. In a particular embodiment, $R^{10}$ is selected from OH, F, Cl, and —CN.

In one embodiment, a compound of the invention is according to Formula I-IVd, wherein $G_1$ is 4-7 membered heterocycloalkyl containing one or more heteroatoms independently selected from O, N, and S, each of which is substituted with one or two independently selected $R^9$ groups, $R^9$ is $R^{10}$, and $R^{10}$ is as previously described. In a further embodiment, $G_1$ is oxetanyl, azetidinyl, tetrahydrofuranyl, pyrolidinyl, tetrahydropyranyl, piperidinyl, piperazinyl, morpholinyl, thiomorpholinyl, or 2,6-diaza-spiro [3.3]heptane, each of which is substituted with one or two independently selected $R^9$ groups, $R^9$ is $R^{10}$, and $R^{10}$ is as previously described. In a particular embodiment, $R^{10}$ is selected $C_{1-4}$ alkyl. In a more particular embodiment, $R^{10}$ is selected from —$CH_3$, —$CH_2$—$CH_3$, and —$CH(CH_3)_2$. In a most particular embodiment, $R^{10}$ is selected from —$CH_3$, and —$CH_2$—$CH_3$.

In one embodiment, a compound of the invention is according to Formula I-IVd, wherein $G_1$ is 4-7 membered heterocycloalkyl containing one or more heteroatoms independently selected from O, N, and S, each of which is substituted with one or two independently selected $R^9$ groups, $R^9$ is $R^{10}$, and $R^{10}$ is as previously described. In a further embodiment, $G_1$ is oxetanyl, azetidinyl, tetrahydrofuranyl, pyrolidinyl, tetrahydropyranyl, piperidinyl, piperazinyl, morpholinyl, thiomorpholinyl, or 2,6-Diaza-spiro [3.3]heptane, each of which is substituted with one or two independently selected $R^9$ groups, $R^9$ is $R^{10}$, and $R^{10}$ is as previously described. In a particular embodiment, $R^{10}$ is $C_{1-4}$ alkyl substituted with one or more independently selected OH, halo, or phenyl. In a further embodiment, $R^{10}$ is $C_{1-4}$ alkyl substituted with one to three independently selected OH, halo, or phenyl. In a more particular embodiment, $R^{10}$ is —$CH_3$, —$CH_2$—$CH_3$, or —$CH(CH_3)_2$, each of which is substituted with one to three independently selected OH, halo, or phenyl. In a most particular embodiment, $R^{10}$ is —$CF_3$, —$CH_2$—$CH_2$—OH, or —$CH_2$-phenyl.

In one embodiment, a compound of the invention is according to Formula I-IVd, wherein $G_1$ is 4-7 membered heterocycloalkyl containing one or more heteroatoms independently selected from O, N, and S, each of which is substituted with one or two independently selected $R^9$ groups, $R^9$ is $R^{10}$, and $R^{10}$ is as previously described. In a further embodiment, $G_1$ is oxetanyl, azetidinyl, tetrahydrofuranyl, pyrolidinyl, tetrahydropyranyl, piperidinyl, piperazinyl, morpholinyl, thiomorpholinyl, or 2,6-diaza-spiro [3.3]heptane, each of which is substituted with one or two independently selected $R^9$ groups, $R^9$ is $R^{10}$, and $R^{10}$ is as previously described. In a particular embodiment, $R^{10}$ is $C_{1-4}$ alkoxy. In a more particular embodiment, $R^{10}$ is selected from —OCH$_3$, —OCH$_2$—CH$_3$, and —OC(CH$_3$)$_3$. In a most particular embodiment, R$^{10}$ is —OCH$_3$.

In one embodiment, a compound of the invention is according to Formula I-IVd, wherein G$_1$ is 4-7 membered heterocycloalkyl containing one or more heteroatoms independently selected from O, N, and S, each of which is substituted with one or two independently selected R$^9$ groups, R$^9$ is R$^{10}$, and R$^{10}$ is as previously described. In a further embodiment, G$_1$ is oxetanyl, azetidinyl, tetrahydrofuranyl, pyrolidinyl, tetrahydropyranyl, piperidinyl, piperazinyl, morpholinyl, thiomorpholinyl, or 2,6-Diaza-spiro[3.3]heptane, each of which is substituted with one or two independently selected R$^9$ groups, R$^9$ is R$^{10}$, and R$^{10}$ is as previously described. In a particular embodiment, R$^{10}$ is selected from —SO$_2$CH$_3$, —C(=O)C$_{1-4}$ alkoxy, and —C(=O)C$_{1-4}$ alkyl. In a more particular embodiment, R$^{10}$ is selected from —SO$_2$CH$_3$, —C(=O)OCH$_3$, —C(=O)OCH$_2$CH$_3$, —C(=O)OCH(CH$_3$)$_2$, —C(=O)CH$_3$, —C(=O)CH$_2$CH$_3$, and —C(=O)OCH(CH$_3$)$_2$. In a most particular embodiment, R$^{10}$ is selected from —SO$_2$CH$_3$, —C(=O)OCH$_3$, and —C(=O)CH$_3$.

In one embodiment, a compound of the invention is according to Formula I-IVd, wherein G$_1$ is 4-7 membered heterocycloalkyl containing one or more heteroatoms independently selected from O, N, and S, each of which is substituted with one or two independently selected R$^9$ groups, R$^9$ is R$^{10}$, and R$^{10}$ is as previously described. In a further embodiment, G$_1$ is oxetanyl, azetidinyl, tetrahydrofuranyl, pyrolidinyl, tetrahydropyranyl, piperidinyl, piperazinyl, morpholinyl, thiomorpholinyl, or 2,6-Diaza-spiro[3.3]heptane, each of which is substituted with one or two independently selected R$^9$ groups, R$^9$ is R$^{10}$, and R$^{10}$ is as previously described. In a particular embodiment, R$^{10}$ is NR$^g$C(=O)C$_{1-4}$ alkyl, and R$^g$ is as described previously. In a particular embodiment, R$^{10}$ is NR$^g$C(=O)CH$_3$, or NR$^g$C(=O)CH$_2$CH$_3$, and R$^g$ is as described previously. In a more particular embodiment, R$^{10}$ is NR$^g$C(=O)CH$_3$, or NR$^g$C(=O)CH$_2$CH$_3$, and R$^g$ is H, —CH$_3$, or —CH$_2$CH$_3$. In a most particular embodiment, R$^{10}$ is NHC(=O)CH$_3$, or NHC(=O)CH$_2$CH$_3$.

In one embodiment, a compound of the invention is according to Formula Va, Vb, Vc, or Vd:

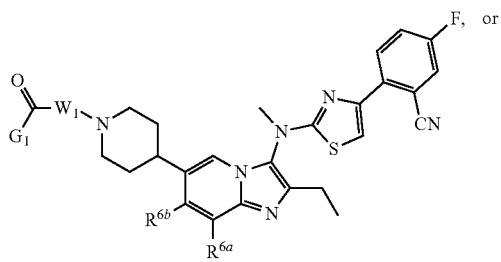

Va

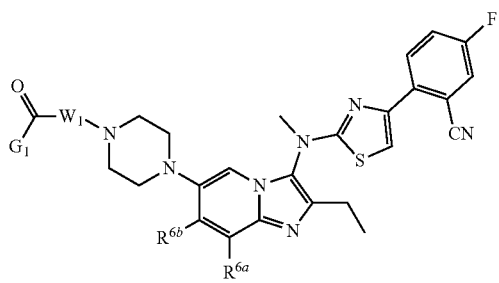

Vb

Vc

Vd wherein R$^{6a}$, R$^{6b}$, W$_1$, and G$_1$ are as described above.

In one embodiment, a compound of the invention is according to Formula Va-Vd, wherein W$_1$ is C$_{1-4}$ alkylene. In a particular embodiment, W$_1$ is —CH$_2$—, —CH$_2$—CH$_2$—, —C(CH$_3$)H—, —CH$_2$—CH$_2$—CH$_2$— or —CH$_2$—C(CH$_3$)H—. In a more particular embodiment, W$_1$ is —CH$_2$—, or —C(CH$_3$)H—. In a most particular embodiment, W$_1$ is —CH$_2$—.

In one embodiment, a compound of the invention is according to Formula VIa, VIb, VIc, or VId:

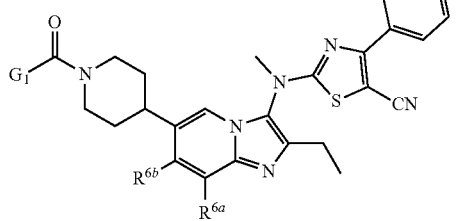

VIa

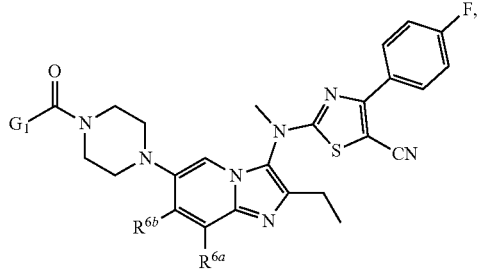

VIb

-continued

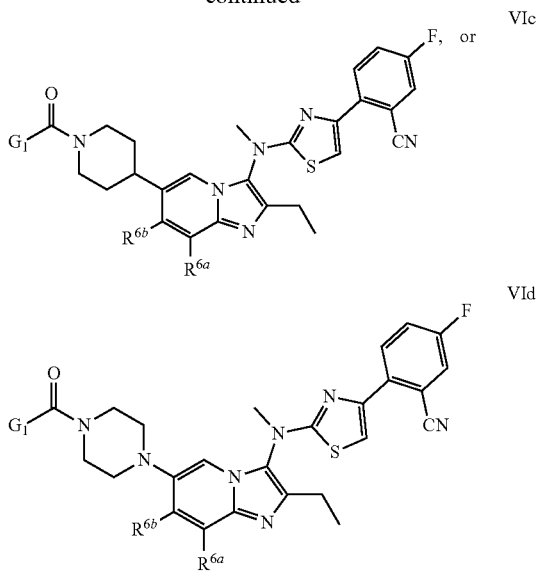

wherein R⁶ᵃ, R⁶ᵇ, and G₁ are as described above.

In one embodiment, a compound of the invention is according to Formula Va-VId, wherein G₁ is 4-7 membered heterocycloalkyl containing one or more heteroatoms independently selected from O, N, and S. In a particular embodiment, G₁ is oxetanyl, azetidinyl, tetrahydrofuranyl, pyrolidinyl, tetrahydropyranyl, piperidinyl, piperazinyl, morpholinyl, or thiomorpholinyl. In a more particular embodiment, G₁ is azetidinyl.

In one embodiment, a compound of the invention is according to Formula Va-VId, wherein G₁ is 4-7 membered heterocycloalkyl containing one or more heteroatoms independently selected from O, N, and S, which heterocycle is substituted with one or more independently selected R⁹ groups. In a further embodiment, G₁ is 4-7 membered heterocycloalkyl containing one or more heteroatoms independently selected from O, N, and S, which heterocycle is substituted with one or two independently selected R⁹ groups. In a particular embodiment, G₁ is oxetanyl, azetidinyl, tetrahydrofuranyl, pyrolidinyl, tetrahydropyranyl, piperidinyl, piperazinyl, morpholinyl, or thiomorpholinyl, each of which is substituted with one or two independently selected R⁹ groups. In a more particular embodiment, G₁ is azetidinyl substituted with one or two independently selected R⁹ groups.

In one embodiment, a compound of the invention is according to Formula Va-VId, wherein G₁ is 4-7 membered heterocycloalkyl containing one or more heteroatoms independently selected from O, N, and S, each of which is substituted with one or two independently selected R⁹ groups, and R⁹ is oxo. In a further particular embodiment, G₁ is oxetanyl, azetidinyl, tetrahydrofuranyl, pyrolidinyl, tetrahydropyranyl, piperidinyl, piperazinyl, morpholinyl, or thiomorpholinyl, each of which is substituted with one or two independently selected R⁹ groups, and R⁹ is oxo.

In one embodiment, a compound of the invention is according to Formula Va-VId, wherein G₁ is 4-7 membered heterocycloalkyl containing one or more heteroatoms independently selected from O, N, and S, each of which is substituted with one or two independently selected R⁹ groups, R⁹ is R¹⁰, and R¹⁰ is as previously described. In a further embodiment, G₁ is oxetanyl, azetidinyl, tetrahydrofuranyl, pyrolidinyl, tetrahydropyranyl, piperidinyl, piperazinyl, morpholinyl, or thiomorpholinyl, each of which is substituted with one or two independently selected R⁹ groups, R⁹ is R¹⁰, and R¹⁰ is as previously described. In a particular embodiment, R¹⁰ is selected from OH, F, Cl, and —CN. In a more particular embodiment, G₁ is azetidinyl substituted with one or two independently selected R⁹ groups, R⁹ is R¹⁰, and R¹⁰ as previously described. In a most particular embodiment, R¹⁰ is selected from OH, F, Cl, and —CN.

In one embodiment, a compound of the invention is according to Formula Va-VId, wherein G₁ is 4-7 membered heterocycloalkyl containing one or more heteroatoms independently selected from O, N, and S, each of which is substituted with one or two independently selected R⁹ groups, R⁹ is R¹⁰, and R¹⁰ is as previously described. In a further embodiment, G₁ is oxetanyl, azetidinyl, tetrahydrofuranyl, pyrolidinyl, tetrahydropyranyl, piperidinyl, piperazinyl, morpholinyl, or thiomorpholinyl, each of which is substituted with one or two independently selected R⁹ groups, R⁹ is R¹⁰, and R¹⁰ is as previously described. In a particular embodiment, R¹⁰ is selected C₁₋₄ alkyl. In a more particular embodiment, R¹⁰ is selected from —CH₃, —CH₂—CH₃, and —CH(CH₃)₂. In a most particular embodiment, R¹⁰ is selected from —CH₃, and —CH₂—CH₃.

In one embodiment, a compound of the invention is according to Formula Va-VId, wherein G₁ is 4-7 membered heterocycloalkyl containing one or more heteroatoms independently selected from O, N, and S, each of which is substituted with one or two independently selected R⁹ groups, R⁹ is R¹⁰, and R¹⁰ is as previously described. In a further embodiment, G₁ is oxetanyl, azetidinyl, tetrahydrofuranyl, pyrolidinyl, tetrahydropyranyl, piperidinyl, piperazinyl, morpholinyl, or thiomorpholinyl, each of which is substituted with one or two independently selected R⁹ groups, R⁹ is R¹⁰, and R¹⁰ is as previously described. In a particular embodiment, R¹⁰ is C₁₋₄ alkyl substituted with one or more independently selected OH, halo, phenyl. In a further embodiment, R¹⁰ is C₁₋₄ alkyl substituted with one to three independently selected OH, halo, and phenyl. In a more particular embodiment, R¹⁰ is —CH₃, —CH₂—CH₃, and —CH(CH₃)₂, each of which is substituted with one to three independently selected OH, halo, and phenyl. In a most particular embodiment, R¹⁰ is —CF₃, —CH₂—CH₂—OH, and —CH₂-phenyl.

In one embodiment, a compound of the invention is according to Formula Va-VId, wherein G₁ is 4-7 membered heterocycloalkyl containing one or more heteroatoms independently selected from O, N, and S, each of which is substituted with one or two independently selected R⁹ groups, R⁹ is R¹⁰, and R¹⁰ is as previously described. In a further embodiment, G₁ is oxetanyl, azetidinyl, tetrahydrofuranyl, pyrolidinyl, tetrahydropyranyl, piperidinyl, piperazinyl, morpholinyl, or thiomorpholinyl, each of which is substituted with one or two independently selected R⁹ groups, R⁹ is R¹⁰, and R¹⁰ is as previously described. In a particular embodiment, R¹⁰ is C₁₋₄ alkoxy. In a more particular embodiment, R¹⁰ is selected from —OCH₃, —OCH₂—CH₃, and —OC(CH₃)₃. In a most particular embodiment, R¹⁰ is —OCH₃.

In one embodiment, a compound of the invention is according to Formula Va-VId, wherein G₁ is 4-7 membered heterocycloalkyl containing one or more heteroatoms independently selected from O, N, and S, each of which is substituted with one or two independently selected R⁹ groups, R⁹ is R¹⁰, and R¹⁰ is as previously described. In a further embodiment, G₁ is oxetanyl, azetidinyl, tetrahydrofuranyl, pyrolidinyl, tetrahydropyranyl, piperidinyl, piperazinyl, morpholinyl, or thiomorpholinyl, each of which is substituted with one or two independently selected $R^9$ groups, $R^9$ is $R^{10}$, and $R^{10}$ is as previously described. In a particular embodiment, $R^{10}$ is selected from —$SO_2CH_3$, —C(=O)Ch4 alkoxy, and —C(=O)$C_{1-4}$ alkyl. In a more particular embodiment, $R^{10}$ is selected from —$SO_2CH_3$, —C(=O)$OCH_3$, —C(=O)$OCH_2CH_3$, —C(=O)OCH$(CH_3)_2$, —C(=O)$CH_3$, —C(=O)$CH_2CH_3$, and —C(=O)OCH$(CH_3)_2$. In a most particular embodiment, $R^{10}$ is selected from —$SO_2CH_3$, —C(=O)$OCH_3$, and —C(=O)$CH_3$.

In one embodiment, a compound of the invention is according to Formula Va-VId, wherein $G_1$ is 4-7 membered heterocycloalkyl containing one or more heteroatoms independently selected from O, N, and S, each of which is substituted with one or two independently selected $R^9$ groups, $R^9$ is $R^{10}$, and $R^{10}$ is as previously described. In a further embodiment, $G_1$ is oxetanyl, azetidinyl, tetrahydrofuranyl, pyrolidinyl, tetrahydropyranyl, piperidinyl, piperazinyl, morpholinyl, or thiomorpholinyl, each of which is substituted with one or two independently selected $R^9$ groups, $R^9$ is $R^{10}$, and $R^{10}$ is as previously described. In a particular embodiment, $R^{10}$ is —$NR^gC$(=O)$C_{1-4}$ alkyl, and $R^g$ is as described previously. In a particular embodiment, $R^{10}$ is —$NR^gC$(=O)$CH_3$, or —$NR^gC$(=O)$CH_2CH_3$, and $R^g$ is as described previously. In a more particular embodiment, $R^{10}$ is —$NR^gC$(=O)$CH_3$, or —$NR^gC$(=O)$CH_2CH_3$, and $R^g$ is H, —$CH_3$, or —$CH_2CH_3$. In a most particular embodiment, $R^{10}$ is —NHC(=O)$CH_3$, or —NHC(=O)$CH_2CH_3$.

In one embodiment, a compound of the invention is according to Formula I-VId, wherein $R^{6a}$ is H, —$CH_3$ or halo, and $R^{6b}$ is H. In a particular embodiment, $R^{6a}$ is H, —$CH_3$, F, or Cl, and $R^{6b}$ is H. In a more particular embodiment, $R^{6a}$ is H, —$CH_3$, or F, and $R^{6b}$ is H.

In one embodiment, a compound of the invention is according to Formula I-VId, wherein $R^{6a}$ is H, and $R^{6b}$ is H, —$CH_3$ or halo. In a particular embodiment, $R^{6a}$ is H, and $R^{6b}$ is H, —$CH_3$, F, or Cl. In a more particular embodiment, $R^{6a}$ is H, and $R^{6b}$ is H, —$CH_3$, or F.

In another embodiment, $R^{6a}$ and $R^{6b}$ are both H.

In one embodiment, a compound of the invention according to Formula I is selected from:
2-((2-ethyl-8-methyl-6-(piperazin-1-yl)imidazo[1,2-a]pyridin-3-yl)(methyl)amino)-4-(4-fluorophenyl)thiazole-5-carbonitrile,
2-((2-ethyl-6-(4-(2-(3-hydroxyazetidin-1-yl)-2-oxoethyl)piperazin-1-yl)-8-methylimidazo[1,2-a]pyridin-3-yl)(methyl)amino)-4-(4-fluorophenyl)thiazole-5-carbonitrile,
2-((2-ethyl-6-(4-(2-(3-hydroxy-3-methylazetidin-1-yl)-2-oxoethyl)piperazin-1-yl)-8-methylimidazo[1,2-a]pyridin-3-yl)(methyl)amino)-4-(4-fluorophenyl)thiazole-5-carbonitrile,
(R)-2-((2-ethyl-6-(4-(2-(3-hydroxypyrrolidin-1-yl)-2-oxoethyl)piperazin-1-yl)-8-methylimidazo[1,2-a]pyridin-3-yl)(methyl)amino)-4-(4-fluorophenyl)thiazole-5-carbonitrile,
(S)-2-((2-ethyl-6-(4-(2-(3-hydroxypyrrolidin-1-yl)-2-oxoethyl)piperazin-1-yl)-8-methylimidazo[1,2-a]pyridin-3-yl)(methyl)amino)-4-(4-fluorophenyl)thiazole-5-carbonitrile,
2-((2-ethyl-6-(4-(2-(3-hydroxyazetidin-1-yl)-2-oxoethyl)-3,3-dimethylpiperazin-1-yl)-8-methylimidazo[1,2-a]pyridin-3-yl)(methyl)amino)-4-(4-fluorophenyl)thiazole-5-carbonitrile,
2-(4-(2-ethyl-3-((4-(4-fluorophenyl)thiazol-2-yl)(methyl)amino)-8-methylimidazo[1,2-a]pyridin-6-yl)piperazin-1-yl)-1-(3-hydroxyazetidin-1-yl)ethanone,
(R)-2-(4-(2-ethyl-3-((4-(4-fluorophenyl)thiazol-2-yl)(methyl)amino)-8-methylimidazo[1,2-a]pyridin-6-yl)piperazin-1-yl)-1-(3-hydroxypyrrolidin-1-yl)ethanone,
(S)-2-(4-(2-ethyl-3-((4-(4-fluorophenyl)thiazol-2-yl)(methyl)amino)-8-methylimidazo[1,2-a]pyridin-6-yl)piperazin-1-yl)-1-(3-hydroxypyrrolidin-1-yl)ethanone,
2-((2-ethyl-6-(1-(2-(3-hydroxyazetidin-1-yl)-2-oxoethyl)piperidin-4-yl)-8-methylimidazo[1,2-a]pyridin-3-yl)(methyl)amino)-4-(4-fluorophenyl)thiazole-5-carbonitrile,
2-(ethyl(2-ethyl-8-methyl-6-(1-(methylsulfonyl)-1,2,3,6-tetrahydropyridin-4-yl)imidazo[1,2-a]pyridin-3-yl)amino)-4-(4-fluorophenyl)thiazole-5-carbonitrile,
2-((2-ethyl-8-fluoro-6-(4-(2-(3-hydroxyazetidin-1-yl)-2-oxoethyl)piperazin-1-yl)imidazo[1,2-a]pyridin-3-yl)(methyl)amino)-4-(4-fluorophenyl)thiazole-5-carbonitrile,
2-(4-(3-((5-cyano-4-(4-fluorophenyl)thiazol-2-yl)(methyl)amino)-2-ethyl-8-fluoroimidazo[1,2-a]pyridin-6-yl)piperazin-1-yl)-N-methylacetamide,
2-(4-(2-ethyl-8-fluoro-3-((4-(4-fluorophenyl)thiazol-2-yl)(methyl)amino)imidazo[1,2-a]pyridin-6-yl)piperazin-1-yl)-1-(3-hydroxyazetidin-1-yl)ethanone,
(S)-2-(4-(2-ethyl-8-fluoro-3-((4-(4-fluorophenyl)thiazol-2-yl)(methyl)amino)imidazo[1,2-a]pyridin-6-yl)piperazin-1-yl)-1-(3-hydroxypyrrolidin-1-yl)ethanone,
(R)-2-(4-(2-ethyl-8-fluoro-3-((4-(4-fluorophenyl)thiazol-2-yl)(methyl)amino)imidazo[1,2-a]pyridin-6-yl)piperazin-1-yl)-1-(3-hydroxypyrrolidin-1-yl)ethanone,
2-(4-(2-ethyl-3-((4-(4-fluorophenyl)thiazol-2-yl)(methyl)amino)-7-methylimidazo[1,2-a]pyridin-6-yl)piperidin-1-yl)-1-(3-hydroxyazetidin-1-yl)ethanone,
2-[(2-Ethyl-7-fluoro-6-{4-[2-(3-hydroxy-azetidin-1-yl)-2-oxo-ethyl]-piperazin-1-yl}-imidazo[1,2-a]pyridin-3-yl)-methyl-amino]-4-(4-fluoro-phenyl)-thiazole-5-carbonitrile,
2-[4-(2-Ethyl-7-fluoro-3-{[4-(4-fluoro-phenyl)-thiazol-2-yl]-methyl-amino}-imidazo[1,2-a]pyridin-6-yl)-piperazin-1-yl]-1-(3-hydroxy-azetidin-1-yl)-ethanone,
2-[4-(2-Ethyl-7-fluoro-3-{[4-(4-fluoro-phenyl)-thiazol-2-yl]-methyl-amino}-imidazo[1,2-a]pyridin-6-yl)-piperazin-1-yl]-1-(3-hydroxy-pyrrolidin-1-yl)-ethanone,
2-[4-(2-Ethyl-7-fluoro-3-{[4-(4-fluoro-phenyl)-thiazol-2-yl]-methyl-amino}-imidazo[1,2-a]pyridin-6-yl)-piperazin-1-yl]-1-(3-hydroxy-pyrrolidin-1-yl)-ethanone,
2-(4-(3-((5-cyano-4-(4-fluorophenyl)thiazol-2-yl)(methyl)amino)-2-ethylimidazo[1,2-a]pyridin-6-yl)piperazin-1-yl)-N-methylacetamide,
tert-butyl 4-(2-ethyl-3-((4-(4-fluorophenyl)thiazol-2-yl)(methyl)amino)imidazo[1,2-a]pyridin-6-yl)piperazine-1-carboxylate,
2-(4-(2-ethyl-3-((4-(4-fluorophenyl)thiazol-2-yl)(methyl)amino)imidazo[1,2-a]pyridin-6-yl)piperazin-1-yl)-1-(3-hydroxyazetidin-1-yl)ethanone,
(S)-2-(4-(2-ethyl-3-((4-(4-fluorophenyl)thiazol-2-yl)(methyl)amino)imidazo[1,2-a]pyridin-6-yl)piperazin-1-yl)-1-(3-hydroxypyrrolidin-1-yl)ethanone,
(R)-2-(4-(2-ethyl-3-((4-(4-fluorophenyl)thiazol-2-yl)(methyl)amino)imidazo[1,2-a]pyridin-6-yl)piperazin-1-yl)-1-(3-hydroxypyrrolidin-1-yl)ethanone,
N-(1-(2-(4-(2-ethyl-3-((4-(4-fluorophenyl)thiazol-2-yl)(methyl)amino)imidazo[1,2-a]pyridin-6-yl)piperazin-1-yl)acetoyl)pyrrolidin-3-yl)acetamide, 2-(4-(2-ethyl-3-((4-(4-fluorophenyl)thiazol-2-yl)(methyl) amino)imidazo[1,2-a]pyridin-6-yl)piperazin-1-yl)-1-(3-fluoroazetidin-1-yl)ethanone, 1-(3,3-difluoroazetidin-1-yl)-2-(4-(2-ethyl-3-((4-(4-fluorophenyl)thiazol-2-yl)(methyl)amino)imidazo[1,2-a]pyridin-6-yl)piperazin-1-yl)ethanone, 1-(azetidin-1-yl)-2-(4-(2-ethyl-3-((4-(4-fluorophenyl)thiazol-2-yl)(methyl)amino)imidazo[1,2-a]pyridin-6-yl)piperazin-1-yl)ethanone, 2-(4-(2-ethyl-3-((4-(4-fluorophenyl)thiazol-2-yl)(methyl) amino)imidazo[1,2-a]pyridin-6-yl)piperazin-1-yl)-1-(pyrrolidin-1-yl)ethanone, 2-(4-(2-ethyl-3-((4-(4-fluorophenyl)thiazol-2-yl)(methyl) amino)imidazo[1,2-a]pyridin-6-yl)piperazin-1-yl)-1-morpholinoethanone, 2-(4-(2-ethyl-3-((4-(4-fluorophenyl)thiazol-2-yl)(methyl) amino)imidazo[1,2-a]pyridin-6-yl)piperazin-1-yl)acetamide, 2-(4-(2-ethyl-3-((4-(4-fluorophenyl)thiazol-2-yl)(methyl) amino)imidazo[1,2-a]pyridin-6-yl)piperazin-1-yl)-1-(3-(hydroxymethyl)azetidin-1-yl)ethanone, 2-(4-(2-ethyl-3-((4-(4-fluorophenyl)thiazol-2-yl)(methyl) amino)imidazo[1,2-a]pyridin-6-yl)piperazin-1-yl)-N,N-dimethylacetamide, ethyl 2-(4-(2-ethyl-3-((4-(4-fluorophenyl)thiazol-2-yl) (methyl)amino)imidazo[1,2-a]pyridin-6-yl)piperazin-1-yl)acetate, ethyl 2-(4-(2-ethyl-3-((4-(4-fluorophenyl)thiazol-2-yl) (methyl)amino)imidazo[1,2-a]pyridin-6-yl)piperazin-1-yl)propanoate, 2-(4-(2-ethyl-3-((4-(4-fluorophenyl)thiazol-2-yl)(methyl) amino)imidazo[1,2-a]pyridin-6-yl)piperazin-1-yl)acetonitrile, N-(6-(4-((1-cyclopropyl-1H-tetrazol-5-yl)methyl)piperazin-1-yl)-2-ethylimidazo[1,2-a]pyridin-3-yl)-4-(4-fluorophenyl)-N-methylthiazol-2-amine, N-(2-ethyl-6-(4-(oxazol-2-ylmethyl)piperazin-1-yl)imidazo [1,2-a]pyridin-3-yl)-4-(4-fluorophenyl)-N-methylthiazol-2-amine, N-(6-(4-((1,2,4-oxadiazol-3-yl)methyl)piperazin-1-yl)-2-ethylimidazo[1,2-a]pyridin-3-yl)-4-(4-fluorophenyl)-N-methylthiazol-2-amine, 2-(4-(2-ethyl-3-((4-(4-fluorophenyl)thiazol-2-yl)(methyl) amino)imidazo[1,2-a]pyridin-6-yl)piperazin-1-yl)acetic acid, 2-hydroxyethyl 4-(2-ethyl-3-((4-(4-fluorophenyl)thiazol-2-yl)(methyl)amino)imidazo[1,2-a]pyridin-6-yl)piperazine-1-carboxylate, tert-butyl 2-(4-(2-ethyl-3-((4-(4-fluorophenyl)thiazol-2-yl) (methyl)amino)imidazo[1,2-a]pyridin-6-yl)piperazine-1-carbonyl)pyrrolidine-1-carboxylate, tert-butyl 3-(4-(2-ethyl-3-((4-(4-fluorophenyl)thiazol-2-yl) (methyl)amino)imidazo[1,2-a]pyridin-6-yl)piperazine-1-carbonyl)pyrrolidine-1-carboxylate, (4-(2-ethyl-3-((4-(4-fluorophenyl)thiazol-2-yl)(methyl) amino)imidazo[1,2-a]pyridin-6-yl)piperazin-1-yl)(pyrrolidin-2-yl)methanone, (4-(2-ethyl-3-((4-(4-fluorophenyl)thiazol-2-yl)(methyl) amino)imidazo[1,2-a]pyridin-6-yl)piperazin-1-yl)(pyrrolidin-3-yl)methanone, 1-(3-(4-(2-ethyl-3-((4-(4-fluorophenyl)thiazol-2-yl) (methyl)amino)imidazo[1,2-a]pyridin-6-yl)piperazine-1-carbonyl)pyrrolidin-1-yl)ethanone, (4-(2-ethyl-3-((4-(4-fluorophenyl)thiazol-2-yl)(methyl) amino)imidazo[1,2-a]pyridin-6-yl)piperazin-1-yl)(1-(methylsulfonyl)pyrrolidin-3-yl)methanone, 1-(4-(2-ethyl-3-((4-(4-fluorophenyl)thiazol-2-yl)(methyl) amino)imidazo[1,2-a]pyridin-6-yl)piperazin-1-yl)-2-hydroxyethanone, 1-(4-(2-ethyl-3-((4-(4-fluorophenyl)thiazol-2-yl)(methyl) amino)imidazo[1,2-a]pyridin-6-yl)piperazin-1-yl)propan-1-one, 1-(4-(2-ethyl-3-((4-(4-fluorophenyl)thiazol-2-yl)(methyl) amino)imidazo[1,2-a]pyridin-6-yl)piperazin-1-yl)-4-hydroxybutan-1-one, 4-(dimethylamino)-1-(4-(2-ethyl-3-((4-(4-fluorophenyl)thiazol-2-yl)(methyl)amino)imidazo[1,2-a]pyridin-6-yl)piperazin-1-yl)butan-1-one, N-(2-ethyl-6-(4-(methylsulfonyl)piperazin-1-yl)imidazo[1, 2-a]pyridin-3-yl)-4-(4-fluorophenyl)-N-methylthiazol-2-amine, N-(6-(4-(3-chloropropylsulfonyl)piperazin-1-yl)-2-ethylimidazo[1,2-a]pyridin-3-yl)-4-(4-fluorophenyl)-N-methylthiazol-2-amine, N-(6-(4-(3-(dimethylamino)propylsulfonyl)piperazin-1-yl)-2-ethylimidazo[1,2-a]pyridin-3-yl)-4-(4-fluorophenyl)-N-methylthiazol-2-amine, N-(2-ethyl-6-(4-(3-(pyrrolidin-1-yl)propylsulfonyl)piperazin-1-yl)imidazo[1,2-a]pyridin-3-yl)-4-(4-fluorophenyl)-N-methylthiazol-2-amine, 3-(4-(2-ethyl-3-((4-(4-fluorophenyl)thiazol-2-yl)(methyl) amino)imidazo[1,2-a]pyridin-6-yl)piperazin-1-ylsulfonyl)propan-1-ol, methyl 2-(4-(2-ethyl-3-((4-(4-fluorophenyl)thiazol-2-yl) (methyl)amino)imidazo[1,2-a]pyridin-6-yl)piperazin-1-ylsulfonyl)acetate, 2-(4-(2-ethyl-3-((4-(4-fluorophenyl)thiazol-2-yl)(methyl) amino)imidazo[1,2-a]pyridin-6-yl)piperazin-1-ylsulfonyl)acetic acid, 2-(4-(2-ethyl-3-((4-(4-fluorophenyl)thiazol-2-yl)(methyl) amino)imidazo[1,2-a]pyridin-6-yl)piperazin-1-ylsulfonyl)acetamide, tert-butyl 4-(2-ethyl-3-((4-(4-fluorophenyl)thiazol-2-yl) (methyl)amino)imidazo[1,2-a]pyridin-6-yl)-3-oxopiperazine-1-carboxylate, tert-butyl 4-(3-((4-(4-chlorophenyl)thiazol-2-yl)(methyl) amino)-2-ethylimidazo[1,2-a]pyridin-6-yl)-3-oxopiperazine-1-carboxylate, ethyl 2-(4-(2-ethyl-3-((4-(4-fluorophenyl)thiazol-2-yl) (methyl)amino)imidazo[1,2-a]pyridin-6-yl)-3-oxopiperazin-1-yl)acetate, 1-(2-ethyl-3-((4-(4-fluorophenyl)thiazol-2-yl)(methyl) amino)imidazo[1,2-a]pyridin-6-yl)-4-(methylsulfonyl) piperazin-2-one, N-(2-ethyl-6-(1-(methylsulfonyl)-1,2,3,6-tetrahydropyridin-4-yl)imidazo[1,2-a]pyridin-3-yl)-4-(4-fluorophenyl)-N-methylthiazol-2-amine, N-(6-(1-(chloromethylsulfonyl)-1,2,3,6-tetrahydropyridin-4-yl)-2-ethylimidazo[1,2-a]pyridin-3-yl)-4-(4-fluorophenyl)-N-methylthiazol-2-amine, 4-(4-chlorophenyl)-N-(2-ethyl-6-(1-(methylsulfonyl)-2,5-dihydro-1H-pyrrol-3-yl)imidazo[1,2-a]pyridin-3-yl)-N-methylthiazol-2-amine, 4-(4-chlorophenyl)-N-(2-ethyl-6-(1-(methylsulfonyl)-1,4,5, 6-tetrahydropyridin-3-yl)imidazo[1,2-a]pyridin-3-yl)-N-methylthiazol-2-amine, 4-(4-tert-butylphenyl)-N-(2-ethyl-6-(1-(methylsulfonyl)-1, 2,3,6-tetrahydropyridin-4-yl)imidazo[1,2-a]pyridin-3-yl)-N-methylthiazol-2-amine, N-(2-ethyl-6-(1-(methylsulfonyl)-1,2,3,6-tetrahydropyridin-4-yl)imidazo[1,2-a]pyridin-3-yl)-4-(4-methoxyphenyl)-N-methylthiazol-2-amine, N-(2-ethyl-6-(1-(methylsulfonyl)-1,2,3,6-tetrahydropyridin-4-yl)imidazo[1,2-a]pyridin-3-yl)-N-methyl-4-(4-(trifluoromethoxy)phenyl)thiazol-2-amine, 4-(3,4-difluorophenyl)-N-(2-ethyl-6-(1-(methylsulfonyl)-1,2,3,6-tetrahydropyridin-4-yl)imidazo[1,2-a]pyridin-3-yl)-N-methylthiazol-2-amine, 3-(4-(2-ethyl-3-((4-(4-fluorophenyl)thiazol-2-yl)(methyl)amino)imidazo[1,2-a]pyridin-6-yl)-5,6-dihydropyridin-1(2H)-yl sulfonyl)propyl acetate, 3-(4-(2-ethyl-3-((4-(4-fluorophenyl)thiazol-2-yl)(methyl)amino)imidazo[1,2-a]pyridin-6-yl)-5,6-dihydropyridin-1(2H)-ylsulfonyl)propan-1-ol, 4-(2-ethyl-3-((4-(4-chlorophenyl)thiazol-2-yl)(methyl)amino)imidazo[1,2-a]pyridin-6-yl)-3,6-dihydro-2H-thiopyran 1,1-dioxide, N-(2-ethyl-6-(1-(methylsulfonyl)-1,2,3,6-tetrahydropyridin-4-yl)imidazo[1,2-a]pyridin-3-yl)-5-fluoro-4-(4-fluorophenyl)-N-methylthiazol-2-amine, tert-butyl 4-(2-ethyl-3-((4-(4-fluorophenyl)thiazol-2-yl)(methyl)amino)imidazo[1,2-a]pyridin-6-yl)-3-hydroxypiperidine-1-carboxylate, 4-(2-ethyl-3-((4-(4-fluorophenyl)thiazol-2-yl)(methyl)amino)imidazo[1,2-a]pyridin-6-yl)-1-(methylsulfonyl)piperidin-3-ol, N-(2-ethyl-6-(1-(methylsulfonyl)piperidin-4-yl)imidazo[1,2-a]pyridin-3-yl)-4-(4-fluorophenyl)-N-methylthiazol-2-amine, 4-(4-tert-butylphenyl)-N-(2-ethyl-6-(1-(methylsulfonyl)piperidin-4-yl)imidazo[1,2-a]pyridin-3-yl)-N-methylthiazol-2-amine, N-(2-ethyl-6-(1-(methylsulfonyl)piperidin-4-yl)imidazo[1,2-a]pyridin-3-yl)-4-(4-methoxyphenyl)-N-methylthiazol-2-amine, 4-(3,4-difluorophenyl)-N-(2-ethyl-6-(1-(methylsulfonyl)piperidin-4-yl)imidazo[1,2-a]pyridin-3-yl)-N-methylthiazol-2-amine, N-(2-ethyl-6-(1-(methylsulfonyl)piperidin-4-yl)imidazo[1,2-a]pyridin-3-yl)-N-methyl-4-(4-(trifluoromethyl)phenyl)thiazol-2-amine, N-(2-ethyl-6-(1-(methylsulfonyl)piperidin-4-yl)imidazo[1,2-a]pyridin-3-yl)-N-methyl-4-(4-(trifluoromethoxy)phenyl)thiazol-2-amine, N-(6-(1-(3-chloropropylsulfonyl)piperidin-4-yl)-2-ethylimidazo[1,2-a]pyridin-3-yl)-4-(4-fluorophenyl)-N-methylthiazol-2-amine, N-(6-(1-(3-(dimethylamino)propylsulfonyl)piperidin-4-yl)-2-ethylimidazo[1,2-a]pyridin-3-yl)-4-(4-fluorophenyl)-N-methylthiazol-2-amine, N-(2-ethyl-6-(1-(3-morpholinopropylsulfonyl)piperidin-4-yl)imidazo[1,2-a]pyridin-3-yl)-4-(4-fluorophenyl)-N-methylthiazol-2-amine, N-(2-ethyl-6-(1-(3-(pyrrolidin-1-yl)propylsulfonyl)piperidin-4-yl)imidazo[1,2-a]pyridin-3-yl)-4-(4-fluorophenyl)-N-methylthiazol-2-amine, N-(6-(1-(3-aminopropylsulfonyl)piperidin-4-yl)-2-ethylimidazo[1,2-a]pyridin-3-yl)-4-(4-fluorophenyl)-N-methylthiazol-2-amine, N-(2-ethyl-6-(1-(2-morpholinoe thylsulfonyl)piperidin-4-yl)imidazo[1,2-a]pyridin-3-yl)-4-(4-fluorophenyl)-N-methylthiazol-2-amine, 4-(2-ethyl-3-((4-(4-fluorophenyl)thiazol-2-yl)(methyl)amino)imidazo[1,2-a]pyridin-6-yl)piperidine-1-sulfonamide, 3-(4-(2-ethyl-3-((4-(4-fluorophenyl)thiazol-2-yl)(methyl)amino)imidazo[1,2-a]pyridin-6-yl)piperidin-1-ylsulfonyl)propyl acetate, 3-(4-(2-ethyl-3-((4-(4-fluorophenyl)thiazol-2-yl)(methyl)amino)imidazo[1,2-a]pyridin-6-yl)piperidin-1-ylsulfonyl)propan-1-ol, 3-(4-(2-ethyl-3-((5-fluoro-4-(4-fluorophenyl)thiazol-2-yl)(methyl)amino)imidazo[1,2-a]pyridin-6-yl)piperidin-1-ylsulfonyl)propan-1-ol, 2-(2-((2-ethyl-6-(1-(methylsulfonyl)piperidin-4-yl)imidazo[1,2-a]pyridin-3-yl)(methyl)amino)thiazol-4-yl)-5-fluorobenzonitrile, 2-(2-((2-ethyl-6-(1-(methylsulfonyl)piperidin-4-yl)imidazo[1,2-a]pyridin-3-yl)(methyl)amino)-5-methylthiazol-4-yl)-5-fluorobenzonitrile, N-(2-ethyl-6-(1-(methylsulfonyl)piperidin-4-yl)imidazo[1,2-a]pyridin-3-yl)-4-(4-fluoro-2-methylphenyl)-N-methylthiazol-2-amine, 4-(2-chloro-4-fluorophenyl)-N-(2-ethyl-6-(1-(methylsulfonyl)piperidin-4-yl)imidazo[1,2-a]pyridin-3-yl)-N-methylthiazol-2-amine, 4-(2,4-difluorophenyl)-N-(2-ethyl-6-(1-(methylsulfonyl)piperidin-4-yl)imidazo[1,2-a]pyridin-3-yl)-N-methylthiazol-2-amine, N-(2-ethyl-6-(1-(methylsulfonyl)piperidin-4-yl)imidazo[1,2-a]pyridin-3-yl)-4-(4-fluorophenyl)-N,5-dimethylthiazol-2-amine, 4-(4-fluorophenyl)-N-(2-ethyl-6-(1-(methylsulfonyl)piperidin-4-yl)imidazo[1,2-a]pyridin-3-yl)-N-(d3-methypthiazol-2-amine, 4-(4-fluorophenyl)-N-(2-ethyl-6-(1-(methylsulfonyl)piperidin-4-yl)imidazo[1,2-a]pyridin-3-yl)-N-(d3-methyl)-(d-thiazol-2)-amine, methyl 2-((2-ethyl-6-(1-(methylsulfonyl)piperidin-4-yl)imidazo[1,2-a]pyridin-3-yl)(methyl)amino)-4-(4-fluorophenyl)thiazole-5-carboxylate, 1-(2-((2-ethyl-6-(1-(methylsulfonyl)piperidin-4-yl)imidazo[1,2-a]pyridin-3-yl)(methyl)amino)-4-(4-fluorophenyl)thiazol-5-yl)ethanone, N-(2-(2-((2-ethyl-6-(1-(methylsulfonyl)piperidin-4-yl)imidazo[1,2-a]pyridin-3-yl)(methyl)amino)thiazol-4-yl)-5-fluorophenypacetamide, (2-(2-((2-ethyl-6-(1-(methylsulfonyl)piperidin-4-yl)imidazo[1,2-a]pyridin-3-yl)(methyl)amino)thiazol-4-yl)-5-fluorophenyl)methanol, ethyl 2-(4-(2-ethyl-3-((4-(4-fluorophenyl)thiazol-2-yl)(methyl)amino)imidazo[1,2-a]pyridin-6-yl)-5,6-dihydropyridin-1(2H)-yl)acetate, ethyl 2-(4-(2-ethyl-3-((4-(4-fluorophenyl)thiazol-2-yl)(methyl)amino)imidazo[1,2-a]pyridin-6-yl)piperidin-1-yl)acetate, 2-(4-(2-ethyl-3-((4-(4-fluorophenyl)thiazol-2-yl)(methyl)amino)imidazo[1,2-a]pyridin-6-yl)piperidin-1-yl)-1-(3-hydroxyazetidin-1-yl)ethanone, (R)-2-(4-(2-ethyl-3-((4-(4-fluorophenyl)thiazol-2-yl)(methyl)amino)imidazo[1,2-a]pyridin-6-yl)piperidin-1-yl)-1-(3-hydroxypyrrolidin-1-yl)ethanone, (S)-2-(4-(2-ethyl-3-((4-(4-fluorophenyl)thiazol-2-yl)(methyl)amino)imidazo[1,2-a]pyridin-6-yl)piperidin-1-yl)-1-(3-hydroxypyrrolidin-1-yl)ethanone, 2-(4-(2-ethyl-3-((4-(4-fluorophenyl)thiazol-2-yl)(methyl)amino)imidazo[1,2-a]pyridin-6-yl)piperidin-1-yl)-1-(3-(hydroxymethyl)azetidin-1-yl)ethanone, 2-(4-(2-ethyl-3-((4-(4-fluorophenyl)thiazol-2-yl)(methyl)amino)imidazo[1,2-a]pyridin-6-yl)piperidin-1-yl)-N,N-dimethylacetamide, 2-(4-(2-ethyl-3-((4-(4-fluorophenyl)thiazol-2-yl)(methyl)amino)imidazo[1,2-a]pyridin-6-yl)piperidin-1-yl)-1-(pyrrolidin-1-yl)ethanone, (S)-1-(2-(4-(2-ethyl-3-((4-(4-fluorophenyl)thiazol-2-yl)(methyl)amino)imidazo[1,2-a]pyridin-6-yl)piperidin-1-yl)acetoyl)pyrrolidine-3-carbonitrile, 2-(4-(2-ethyl-3-((4-(4-fluorophenyl)thiazol-2-yl)(methyl)amino)imidazo[1,2-a]pyridin-6-yl)piperidin-1-yl)-1-(3-(hydroxymethyl)pyrrolidin-1-yl)ethanone, 4-((4-(2-ethyl-3-((4-(4-fluorophenyl)thiazol-2-yl)(methyl)amino)imidazo[1,2-a]pyridin-6-yl)piperidin-1-yl)methyl)-1,3-dioxolan-2-one, 2-(4-(2-ethyl-3-((4-(4-fluorophenyl)thiazol-2-yl)(methyl)amino)imidazo[1,2-a]pyridin-6-yl)piperidin-1-yl)-N-(2-hydroxyethyl)-N-methylacetamide, 2-(4-(2-ethyl-3-((4-(4-fluorophenyl)thiazol-2-yl)(methyl)amino)imidazo[1,2-a]pyridin-6-yl)piperidin-1-yl)-N-methoxy-N-methylacetamide, N-(cyanomethyl)-2-(4-(2-ethyl-3-((4-(4-fluorophenyl)thiazol-2-yl)(methyl)amino)imidazo[1,2-a]pyridin-6-yl)piperidin-1-yl)-N-methylacetamide, 5-((4-(2-ethyl-3-((4-(4-fluorophenyl)thiazol-2-yl)(methyl)amino)imidazo[1,2-a]pyridin-6-yl)piperidin-1-yl)methyl)oxazolidin-2-one, 2-(4-(2-ethyl-3-((4-(4-fluorophenyl)thiazol-2-yl)(methyl)amino)imidazo[1,2-a]pyridin-6-yl)piperidin-1-yl)-N-(3-hydroxypropyl)acetamide, 1-(3,3-difluoroazetidin-1-yl)-2-(4-(2-ethyl-3-((4-(4-fluorophenyl)thiazol-2-yl)(methyl)amino)imidazo[1,2-a]pyridin-6-yl)piperidin-1-yl)ethanone, 2-(4-(2-ethyl-3-((4-(4-fluorophenyl)thiazol-2-yl)(methyl)amino)imidazo[1,2-a]pyridin-6-yl)piperidin-1-yl)acetamide, 1-(4-(2-ethyl-3-((4-(4-fluorophenyl)thiazol-2-yl)(methyl)amino)imidazo[1,2-a]pyridin-6-yl)piperidin-1-yl)-2-(pyrrolidin-1-yl)ethanone, 1-(4-(2-ethyl-3-((4-(4-fluorophenyl)thiazol-2-yl)(methyl)amino)imidazo[1,2-a]pyridin-6-yl)piperidin-1-yl)-2-(methylamino)ethanone, 1-(4-(2-ethyl-3-((4-(4-fluorophenyl)thiazol-2-yl)(methyl)amino)imidazo[1,2-a]pyridin-6-yl)piperidin-1-yl)-2-(3-hydroxyazetidin-1-yl)ethanone, 2-(dimethylamino)-1-(4-(2-ethyl-3-((4-(4-fluorophenyl)thiazol-2-yl)(methyl)amino)imidazo[1,2-a]pyridin-6-yl)piperidin-1-yl)ethanone, 3-(dimethylamino)-1-(4-(2-ethyl-3-((4-(4-fluorophenyl)thiazol-2-yl)(methyl)amino)imidazo[1,2-a]pyridin-6-yl)piperidin-1-yl)propan-1-one, 2-(3,3-difluoroazetidin-1-yl)-1-(4-(2-ethyl-3-((4-(4-fluorophenyl)thiazol-2-yl)(methyl)amino)imidazo[1,2-a]pyridin-6-yl)piperidin-1-yl)ethanone, 1-(4-(2-ethyl-3-((4-(4-fluorophenyl)thiazol-2-yl)(methyl)amino)imidazo[1,2-a]pyridin-6-yl)piperidin-1-yl)-3-(methylamino)propan-1-one, 1-(4-(2-ethyl-3-((4-(4-fluorophenyl)thiazol-2-yl)(methyl)amino)imidazo[1,2-a]pyridin-6-yl)piperidin-1-yl)-2-(3-fluoroazetidin-1-yl)ethanone, 1-(3-(4-(2-ethyl-3-((4-(4-fluorophenyl)thiazol-2-yl)(methyl)amino)imidazo[1,2-a]pyridin-6-yl)piperidin-1-yl)azetidin-1-yl)ethanone, 5-bromo-N-(2-ethyl-6-(1-(methylsulfonyl)piperidin-4-yl)imidazo[1,2-a]pyridin-3-yl)-4-(4-fluorophenyl)-N-methylthiazol-2-amine, 2-((2-ethyl-6-(1-(methylsulfonyl)piperidin-4-yl)imidazo[1,2-a]pyridin-3-yl)(methyl)amino)-4-(4-fluorophenyl)thiazole-5-carbonitrile, 2-((2-ethyl-6-(1-(methylsulfonyl)piperidin-4-yl)imidazo[1,2-a]pyridin-3-yl)(methyl)amino)-4-(4-fluorophenyl)thiazole-5-carboxamide, 2-((2-ethyl-6-(4-(2-(3-hydroxyazetidin-1-yl)-2-oxoethyl)piperazin-1-yl)imidazo[1,2-a]pyridin-3-yl)(methyl)amino)-4-(4-fluorophenyl)thiazole-5-carbonitrile, 2-((2-ethyl-6-(4-(2-(3-(hydroxymethyl)azetidin-1-yl)-2-oxoethyl)piperazin-1-yl)imidazo[1,2-a]pyridin-3-yl)(methyl)amino)-4-(4-fluorophenyl)thiazole-5-carbonitrile, 2-(4-(3-((5-cyano-4-(4-fluorophenyl)thiazol-2-yl)(methyl)amino)-2-ethylimidazo[1,2-a]pyridin-6-yl)piperazin-1-yl)-N,N-dimethylacetamide, 2-((2-ethyl-6-(1-(2-(3-hydroxyazetidin-1-yl)-2-oxoethyl)piperidin-4-yl)imidazo[1,2-a]pyridin-3-yl)(methyl)amino)-4-(4-fluorophenyl)thiazole-5-carbonitrile, (R)-2-((2-ethyl-6-(1-(2-(3-hydroxypyrrolidin-1-yl)-2-oxoethyl)piperidin-4-yl)imidazo[1,2-a]pyridin-3-yl)(methyl)amino)-4-(4-fluorophenyl)thiazole-5-carbonitrile, (S)-2-((2-ethyl-6-(1-(2-(3-hydroxypyrrolidin-1-yl)-2-oxoethyl)piperidin-4-yl)imidazo[1,2-a]pyridin-3-yl)(methyl)amino)-4-(4-fluorophenyl)thiazole-5-carbonitrile, 2-((2-ethyl-6-(1-(2-(3-(hydroxymethyl)azetidin-1-yl)-2-oxoethyl)piperidin-4-yl)imidazo[1,2-a]pyridin-3-yl)(methyl)amino)-4-(4-fluorophenyl)thiazole-5-carbonitrile, 2-(4-(3-((5-cyano-4-(4-fluorophenyl)thiazol-2-yl)(methyl)amino)-2-ethylimidazo[1,2-a]pyridin-6-yl)piperidin-1-yl)-N,N-dimethylacetamide, 2-(4-(2-ethyl-3-((4-(4-fluorophenyl)-5-(hydroxymethyl)thiazol-2-yl)(methyl)amino)imidazo[1,2-a]pyridin-6-yl)piperazin-1-yl)-1-(3-(hydroxymethyl)azetidin-1-yl)ethanone, (2-((2-ethyl-6-(1-(methylsulfonyl)piperidin-4-yl)imidazo[1,2-a]pyridin-3-yl)(methyl)amino)-4-(4-fluorophenyl)thiazol-5-yl)methanol, (2-((2-ethyl-6-(1-(methylsulfonyl)piperidin-4-yl)imidazo[1,2-a]pyridin-3-yl)(methyl)amino)-4-(4-(trifluoromethoxy)phenyl)thiazol-5-yl)methanol, (2-((6-(1-(3-(dimethylamino)propylsulfonyl)piperidin-4-yl)-2-ethylimidazo[1,2-a]pyridin-3-yl)(methyl)amino)-4-(4-fluorophenyl)thiazol-5-yl), (2-((2-ethyl-6-(1-(methylsulfonyl)piperidin-4-yl)imidazo[1,2-a]pyridin-3-yl)(methyl)amino)-4-(4-(trifluoromethyl)phenyl)thiazol-5-yl)methanol, 2-(4-(2-ethyl-3-((4-(4-fluorophenyl)-5-(hydroxymethyl)thiazol-2-yl)(methyl)amino)imidazo[1,2-a]pyridin-6-yl)piperidin-1-yl)-1-(pyrrolidin-1-yl)ethanone, 2-(4-(2-ethyl-3-((4-(4-fluorophenyl)-5-(hydroxymethyl)thiazol-2-yl)(methyl)amino)imidazo[1,2-a]pyridin-6-yl)piperidin-1-yl)-1-(3-(hydroxymethyl)azetidin-1-yl)ethanone, 2-(dimethylamino)-1-(4-(2-ethyl-3-((4-(4-fluorophenyl)-5-(hydroxymethypthiazol-2-yl)(methyl)amino)imidazo[1,2-a]pyridin-6-yl)piperidin-1-yl)ethanone, 1-(4-(2-ethyl-3-((4-(4-fluorophenyl)-5-(hydroxymethyl)thiazol-2-yl)(methyl)amino)imidazo[1,2-a]pyridin-6-yl)piperidin-1-yl)propan-1-one, 2-(4-(2-ethyl-3-((4-(4-fluorophenyl)-5-(hydroxymethyl)thiazol-2-yl)(methyl)amino)imidazo[1,2-a]pyridin-6-yl)piperazin-1-yl)-N,N-dimethylacetamide, 2-(4-(2-ethyl-3-((4-(4-fluorophenyl)-5-(hydroxymethyl)thiazol-2-yl)(methyl)amino)imidazo[1,2-a]pyridin-6-yl)piperidin-1-yl)-1-(3-hydroxyazetidin-1-yl)ethanone, 2-(4-(2-ethyl-3-((4-(4-fluorophenyl)-5-(hydroxymethyl)thiazol-2-yl)(methyl)amino)imidazo[1,2-a]pyridin-6-yl)piperidin-1-yl)-N,N-dimethylacetamide, 2-(4-(2-ethyl-3-((4-(4-fluorophenyl)-5-(2,2,2-trifluoroacetoyl)thiazol-2-yl)(methyl)amino)imidazo[1,2-a]pyridin-6-yl)piperazin-1-yl)-N,N-dimethylacetamide, 1-(2-((2-ethyl-6-(1-(2-(3-hydroxyazetidin-1-yl)-2-oxoethyl) piperidin-4-yl)imidazo[1,2-a]pyridin-3-yl)(methyl) amino)-4-(4-fluorophenyl)thiazol-5-yl)-2,2,2-trifluoroethanone, 1-(2-((2-ethyl-6-(1-(methylsulfonyl)piperidin-4-yl)imidazo [1,2-a]pyridin-3-yl)(methyl)amino)-4-(4-fluorophenyl) thiazol-5-yl)-2,2,2-trifluoroethanone, 2-(2-((2-ethyl-6-(piperazin-1-yl)imidazo[1,2-a]pyridin-3-yl)(methyl)amino)-5-methylthiazol-4-yl)-5-fluorobenzonitrile, 2-(2-((2-ethyl-6-(4-(2-(3-hydroxyazetidin-1-yl)-2-oxoethyl) piperazin-1-yl)imidazo[1,2-a]pyridin-3-yl)(methyl) amino)-5-methylthiazol-4-yl)-5-fluorobenzonitrile, 2-(4-(3-((4-(2-cyano-4-fluorophenyl)-5-methylthiazol-2-yl) (methyl)amino)-2-ethylimidazo[1,2-a]pyridin-6-yl)piperazin-1-yl)-N-methylacetamide, 2-(2-((2-ethyl-6-(4-(2-(3-fluoroazetidin-1-yl)-2-oxoethyl) piperazin-1-yl)imidazo[1,2-a]pyridin-3-yl)(methyl) amino)thiazol-4-yl)-5-fluorobenzonitrile, 2-(2-((6-(4-(2-(3,3-difluoroazetidin-1-yl)-2-oxoethyl)piperazin-1-yl)-2-ethylimidazo[1,2-a]pyridin-3-yl)(methyl) amino)thiazol-4-yl)-5-fluorobenzonitrile, 2-(2-((2-ethyl-6-(4-(2-(3-hydroxyazetidin-1-yl)-2-oxoethyl) piperazin-1-yl)imidazo[1,2-a]pyridin-3-yl)(methyl) amino)thiazol-4-yl)-5-fluorobenzonitrile, 2-(2-((6-(4-(2-(azetidin-1-yl)-2-oxoethyl)piperazin-1-yl)-2-ethylimidazo[1,2-a]pyridin-3-yl)(methyl)amino)thiazol-4-yl)-5-fluorobenzonitrile, 2-(4-(3-((4-(2-cyano-4-fluorophenyl)thiazol-2-yl)(methyl) amino)-2-ethylimidazo[1,2-a]pyridin-6-yl)piperazin-1-yl)-N,N-dimethylacetamide, 2-(4-(3-((4-(2-cyano-4-fluorophenyl)thiazol-2-yl)(methyl) amino)-2-ethylimidazo[1,2-a]pyridin-6-yl)piperazin-1-yl)-N-methylacetamide, 2-(2-((2-ethyl-6-(1-(2-(3-hydroxyazetidin-1-yl)-2-oxoethyl) piperidin-4-yl)imidazo[1,2-a]pyridin-3-yl)(methyl) amino)thiazol-4-yl)-5-fluorobenzonitrile, 2-(4-(3-((4-(2-cyano-4-fluorophenyl)thiazol-2-yl)(methyl) amino)-2-ethylimidazo[1,2-a]pyridin-6-yl)piperidin-1-yl)-N,N-dimethylacetamide, 2-(2-((2-ethyl-6-(1-(2-(3-hydroxyazetidin-1-yl)-2-oxoethyl) piperidin-4-yl)imidazo[1,2-a]pyridin-3-yl)(methyl) amino)-5-methylthiazol-4-yl)-5-fluorobenzonitrile, 2-(5-((2-ethyl-6-(1-(2-(3-hydroxyazetidin-1-yl)-2-oxoethyl) piperidin-4-yl)imidazo[1,2-a]pyridin-3-yl)(methyl) amino)-1,2,4-thiadiazol-3-yl)-5-fluorobenzonitrile, 2-(4-(2-(2-cyanoethyl)-3-((4-(4-fluorophenyl)thiazol-2-yl) (methyl)amino)imidazo[1,2-a]pyridin-6-yl)piperidin-1-yl)-N,N-dimethylacetamide, 3-(3-((4-(4-fluorophenyl)-5-(hydroxymethyl)thiazol-2-yl) (methyl)amino)-6-(1-(methylsulfonyl)piperidin-4-yl)imidazo[1,2-a]pyridin-2-yl)propanenitrile, 3-(6-(1-(2-(dimethylamino)-2-oxoethyl)piperidin-4-yl)-3-((4-(4-fluorophenyl)thiazol-2-yl)(methyl)amino)imidazo [1,2-a]pyridin-2-yl)propanamide, N-(6-(3-aminoazetidin-1-yl)-2-ethylimidazo[1,2-a]pyridin-3-yl)-4-(4-fluorophenyl)-N-methylthiazol-2-amine, 2-(1-(2-ethyl-3-((4-(4-fluorophenyl)thiazol-2-yl)(methyl) amino)imidazo[1,2-a]pyridin-6-yl)azetidin-3-ylamino)-1-(3-hydroxyazetidin-1-yl)ethanone, N-(1-(2-ethyl-3-((4-(4-fluorophenyl)thiazol-2-yl)(methyl) amino)imidazo[1,2-a]pyridin-6-yl)azetidin-3-yl)-2-(3-hydroxyazetidin-1-yl)acetamide, 2-(4-(2-ethyl-3-((4-(4-fluorophenyl)thiazol-2-yl)(methyl) amino)imidazo[1,2-a]pyridin-6-yl)piperazin-1-yl)ethanol, N-(2-ethyl-6-morpholinoimidazo[1,2-a]pyridin-3-yl)-4-(4-fluorophenyl)-N-methylthiazol-2-amine, 4-(2-ethyl-3-((4-(4-fluorophenyl)thiazol-2-yl)(methyl) amino)imidazo[1,2-a]pyridin-6-yl)-thiomorpholine 1,1-dioxide, 1-(3-((4-(4-chlorophenyl)thiazol-2-yl)(methyl)amino)-2-ethylimidazo[1,2-a]pyridin-6-yl)imidazolidin-2-one, ethyl 2-(3-(3-((4-(4-chlorophenyl)thiazol-2-yl)(methyl) amino)-2-ethylimidazo[1,2-a]pyridin-6-yl)-2-oxoimidazolidin-1-yl)acetate, 4-(4-chlorophenyl)-N-methyl-N-(6-(1-(methylsulfonyl)-1, 2,3,6-tetrahydropyridin-4-yl)-2-(2,2,2-trifluoroethyl)imidazo[1,2-a]pyridin-3-yl)thiazol-2-amine, 2-(2-((2-ethyl-6-(1-(methylsulfonyl)piperidin-4-yl)imidazo [1,2-a]pyridin-3-yl)(methyl)amino)-4-(4-fluorophenyl) thiazol-5-yl)acetonitrile, 2-ethyl-N-(4-(4-fluorophenyl)pyrimidin-2-yl)-N-methyl-6-(1-(methylsulfonyl)-1,2,3,6-tetrahydropyridin-4-yl)imidazo[1,2-a]pyridin-3-amine, 3-(4-chlorophenyl)-N-(2-ethyl-6-(4-(methylsulfonyl)piperazin-1-yl)imidazo[1,2-a]pyridin-3-yl)-N-methyl-1,2,4-thiadiazol-5-amine, N-(2-ethyl-6-(1-(methylsulfonyl)-1,2,3,6-tetrahydropyridin-4-yl)imidazo[1,2-a]pyridin-3-yl)-3-(4-fluorophenyl)-N-methyl-1,2,4-oxadiazol-5-amine, 2-(4-(2-ethyl-3-((3-(4-fluorophenyl)-1,2,4-thiadiazol-5-yl) (methyl)amino)imidazo[1,2-a]pyridin-6-yl)-5,6-dihydropyridin-1 (2H)-yl)-N,N-dimethylacetamide, 2-(4-(2-ethyl-3-((3-(4-fluorophenyl)-1,2,4-thiadiazol-5-yl) (methyl)amino)imidazo[1,2-a]pyridin-6-yl)piperidin-1-yl)-N,N-dimethylacetamide, N-(6-(4-((1H-imidazol-5-yl)methyl)piperazin-1-yl)-2-ethylimidazo[1,2-a]pyridin-3-yl)-4-(4-fluorophenyl)-N-methylthiazol-2-amine, N-(2-ethyl-6-(1-(methylsulfonyl)-1,2,3,6-tetrahydropyridin-4-yl)imidazo[1,2-a]pyridin-3-yl)-N-methyl-4-(4-(trifluoromethyl)phenyl)thiazol-2-amine, N-cyclopropyl-2-(4-(2-ethyl-3-((4-(4-fluorophenyl)thiazol-2-yl)(methyl)amino)imidazo[1,2-a]pyridin-6-yl)piperidin-1-yl)acetamide, 5-((4-(2-ethyl-3-((4-(4-fluorophenyl)thiazol-2-yl)(methyl) amino)imidazo[1,2-a]pyridin-6-yl)piperidin-1-yl) methyl)-3-methyloxazolidin-2-one, (R)-5-((4-(2-ethyl-3-((4-(4-fluorophenyl)thiazol-2-yl) (methyl)amino)imidazo[1,2-a]pyridin-6-yl)piperidin-1-yl)methyl)oxazolidin-2-one, (S)-5-((4-(2-ethyl-3-((4-(4-fluorophenyl)thiazol-2-yl) (methyl)amino)imidazo[1,2-a]pyridin-6-yl)piperidin-1-yl)methyl)oxazolidin-2-one, 4-((4-(2-ethyl-3-((4-(4-fluorophenyl)thiazol-2-yl)(methyl) amino)imidazo[1,2-a]pyridin-6-yl)piperidin-1-yl)methyl) oxazolidin-2-one, N-(2-ethyl-6-(1-(methylsulfonyl)-1,2,3,6-tetrahydropyridin-4-yl)imidazo[1,2-a]pyridin-3-yl)-3-(4-fluorophenyl)-N-methyl-1,2,4-thiadiazol-5-amine, 1-(4-(2-ethyl-3-((4-(4-fluorophenyl)thiazol-2-yl)(methyl) amino)imidazo[1,2-a]pyridin-6-yl)piperazin-1-yl)propane-1,2-dione, 5-(4-(2-ethyl-3-((4-(4-fluorophenyl)thiazol-2-yl)(methyl) amino)imidazo[1,2-a]pyridin-6-yl)piperazine-1-carbonyl)pyrrolidin-2-one, (1-aminocyclopropyl)(4-(2-ethyl-3-((4-(4-fluorophenyl)thiazol-2-yl)(methyl)amino)imidazo[1,2-a]pyridin-6-yl)piperazin-1-yl)methanone, (S)-1-(4-(2-ethyl-3-((4-(4-fluorophenyl)thiazol-2-yl) (methyl)amino)imidazo[1,2-a]pyridin-6-yl)piperazin-1-yl)-2-hydroxypropan-1-one, 2-(4-(2-ethyl-3-((4-(4-fluorophenyl)thiazol-2-yl)(methyl) amino)imidazo[1,2-a]pyridin-6-yl)piperazin-1-yl)-2-oxoacetamide, 1-benzyl-4-(4-(2-ethyl-3-((4-(4-fluorophenyl)thiazol-2-yl) (methyl)amino)imidazo[1,2-a]pyridin-6-yl)piperazine-1-carbonyl)pyrrolidin-2-one, 3-(3-((4-(4-chlorophenyl)thiazol-2-yl)(methyl)amino)-2-ethylimidazo[1,2-a]pyridin-6-yl)oxazolidin-2-one, 2-(2-ethyl-3-((4-(4-chlorophenyl)thiazol-2-yl)(methyl) amino)imidazo[1,2-a]pyridin-6-yl)-1-[1,2]thiazinane-1,1-dioxide, 4-(2-ethyl-3-((4-(4-fluorophenyl)thiazol-2-yl)(methyl) amino)imidazo[1,2-a]pyridin-6-yl)-N-(thiophen-2-yl)-5,6-dihydropyridine-1(2H)-carboxamide, 4-(4-chlorophenyl)-N-(2-ethyl-6-(1-(methylsulfonyl)-1,2,3,6-tetrahydropyridin-4-yl)imidazo[1,2-a]pyridin-3-yl)-N-methylthiazol-2-amine, 4-(4-chlorophenyl)-N-(2-ethyl-6-(1-(trifluoromethylsulfonyl)-1,2,3,6-tetrahydropyridin-4-yl)imidazo[1,2-a]pyridin-3-yl)-N-methylthiazol-2-amine, 1-(2-ethyl-3-((4-(4-fluorophenyl)thiazol-2-yl)(methyl) amino)imidazo[1,2-a]pyridin-6-yl)piperidin-4-ol, 2-(4-(3-((4-(4-chlorophenyl)thiazol-2-yl)(methyl)amino)-2-ethylimidazo[1,2-a]pyridin-6-yl)piperazin-1-yl)ethanol, 4-(2-ethyl-3-((4-(4-chlorophenyl)thiazol-2-yl)(methyl) amino)imidazo[1,2-a]pyridin-6-yl)-thiomorpholine-1,1-dioxide, tert-butyl 4-(2-ethyl-3-((4-(4-fluorophenyl)thiazol-2-yl) (methyl)amino)imidazo[1,2-a]pyridin-6-yl)-5,6-dihydropyridine-1(2H)-carboxylate, 1-(4-(2-ethyl-3-((4-(4-fluorophenyl)thiazol-2-yl)(methyl) amino)imidazo[1,2-a]pyridin-6-yl)piperidin-1-yl)propan-1-one, N-(2-ethyl-6-(piperidin-4-yl)imidazo[1,2-a]pyridin-3-yl)-4-(4-fluorophenyl)-N-methylthiazol-2-amine, N-(6-(1-benzylpiperidin-4-yl)-2-ethylimidazo[1,2-a]pyridin-3-yl)-4-(4-fluorophenyl)-N-methylthiazol-2-amine, N-(2-ethyl-6-(1-isopropylpiperidin-4-yl)imidazo[1,2-a]pyridin-3-yl)-4-(4-fluorophenyl)-N-methylthiazol-2-amine, tert-butyl 4-(2-ethyl-3-((4-(4-fluorophenyl)thiazol-2-yl) (methyl)amino)imidazo[1,2-a]pyridin-6-yl)piperidine-1-carboxylate, N-(6-(3,6-dihydro-2H-pyran-4-yl)-2-ethylimidazo[1,2-a]pyridin-3-yl)-4-(4-fluorophenyl)-N-methylthiazol-2-amine, 4-(4-chlorophenyl)-N-(6-(3,6-dihydro-2H-pyran-4-yl)-2-ethylimidazo[1,2-a]pyridin-3-yl)-N-methylthiazol-2-amine, (2-(4-(2-ethyl-3-((4-(4-fluorophenyl)thiazol-2-yl)(methyl) amino)imidazo[1,2-a]pyridin-6-yl)piperidin-1-yl)-4,5-dihydrooxazol-5-yl)methanol, 2-(4-(2-ethyl-3-((4-(4-fluorophenyl)thiazol-2-yl)(methyl) amino)imidazo[1,2-a]pyridin-6-yl)piperidin-1-yl)-1-(3-hydroxypyrrolidin-1-yl)ethanone, 2-(2-((2-ethyl-6-(1-(methylsulfonyl)piperidin-4-yl)imidazo [1,2-a]pyridin-3-yl)(methyl)amino)thiazol-4-yl)-5-fluorophenol, tert-butyl 4-(3-((3-(4-chlorophenyl)-1,2,4-thiadiazol-5-yl) (methyl)amino)-2-ethylimidazo[1,2-a]pyridin-6-yl)piperazine-1-carboxylate, N-(6-(4-((1H-imidazol-2-yl)methyl)piperazin-1-yl)-2-ethylimidazo[1,2-a]pyridin-3-yl)-4-(4-fluorophenyl)-N-methylthiazol-2-amine, cyclopropyl(4-(2-ethyl-3-((4-(4-fluorophenyl)thiazol-2-yl) (methyl)amino)imidazo[1,2-a]pyridin-6-yl)piperazin-1-yl)methanone, ethyl 2-(4-(2-ethyl-3-((4-(4-fluorophenyl)thiazol-2-yl) (methyl)amino)imidazo[1,2-a]pyridin-6-yl)piperazin-1-yl)-2-oxoacetate,

[6-(1,1-Dioxo-isothiazolidin-2-yl)-2-ethyl-imidazo[1,2-a] pyridin-3-yl]-[4-(4-fluoro-phenyl)-thiazol-2-yl]-methyl-amine, tert-butyl 4-(3-((4-(4-chlorophenyl)thiazol-2-yl)(methyl) amino)-2-ethylimidazo[1,2-a]pyridin-6-yl)-5,6-dihydropyridine-1(2H)-carboxylate, 4-(4-chlorophenyl)-N-(6-(3,6-dihydro-2H-thiopyran-4-yl)-2-ethylimidazo[1,2-a]pyridin-3-yl)-N-methylthiazol-2-amine, N-(6-(4,4-difluoropiperidin-1-yl)-2-ethylimidazo[1,2-a] pyridin-3-yl)-4-(4-fluorophenyl)-N-methylthiazol-2-amine, N-(6-(1-(3-chloropropylsulfonyl)-1,2,3,6-tetrahydropyridin-4-yl)-2-ethylimidazo[1,2-a]pyridin-3-yl)-4-(4-fluorophenyl)-N-methylthiazol-2-amine, tert-butyl 4-(3-((4-(4-chlorophenyl)thiazol-2-yl)(methyl) amino)-2-ethylimidazo[1,2-a]pyridin-6-yl)piperazine-1-carboxylate, N-(6-(1-(cyclohexylmethyl)piperidin-4-yl)-2-ethylimidazo [1,2-a]pyridin-3-yl)-4-(4-fluorophenyl)-N-methylthiazol-2-amine, N-(2-ethyl-6-(5-methyl-4,5-dihydrooxazol-2-yl)imidazo[1,2-a]pyridin-3-yl)-4-(4-fluorophenyl)-N-methylthiazol-2-amine, N-(2-ethyl-6-(4-methyl-4,5-dihydrooxazol-2-yl)imidazo[1,2-a]pyridin-3-yl)-4-(4-fluorophenyl)-N-methylthiazol-2-amine, 2-(2-ethyl-3-((4-(4-fluorophenyl)thiazol-2-yl)(methyl) amino)imidazo[1,2-a]pyridin-6-yl)-4,5-dihydrooxazole-4-carboxylic acid, (2-(2-ethyl-3-((4-(4-fluorophenyl)thiazol-2-yl)(methyl) amino)imidazo[1,2-a]pyridin-6-yl)-4,5-dihydrooxazol-4-yl)methanol, and 4-(4-chlorophenyl)-N-(6-(4,5-dihydrooxazol-2-yl)-2-ethylimidazo[1,2-a]pyridin-3-yl)-N-methylthiazol-2-amine.

In one embodiment, a compound of the invention according to Formula I is 2-((2-ethyl-6-(4-(2-(3-hydroxyazetidin-1-yl)-2-oxoethyl)piperazin-1-yl)-8-methylimidazo[1,2-a] pyridin-3-yl)(methyl)amino)-4-(4-fluorophenyl)thiazole-5-carbonitrile.

In another embodiment, a compound of the invention according to Formula I is not 2-((2-ethyl-6-(4-(2-(3-hydroxyazetidin-1-yl)-2-oxoethyl)piperazin-1-yl)-8-methylimidazo[1,2-a]pyridin-3-yl)(methyl)amino)-4-(4-fluorophenyl)thiazole-5-carbonitrile.

In one embodiment a compound of the invention is not an isotopic variant.

In one aspect a compound of the invention according to any one of the embodiments herein described is present as the free base.

In one aspect a compound of the invention according to any one of the embodiments herein described is a pharmaceutically acceptable salt.

In one aspect a compound of the invention according to any one of the embodiments herein described is a solvate of the compound.

In one aspect a compound of the invention according to any one of the embodiments herein described is a solvate of a pharmaceutically acceptable salt of a compound.

While specified groups for each embodiment have generally been listed above separately, a compound of the invention includes one in which several or each embodiment in the above Formula, as well as other formulae presented herein, is selected from one or more of particular members or groups designated respectively, for each variable. Therefore, this invention is intended to include all combinations of such embodiments within its scope.

While specified groups for each embodiment have generally been listed above separately, a compound of the invention may be one for which one or more variables (for example, R groups) is selected from one or more embodiments according to any of the Formula(e) listed above. Therefore, the present invention is intended to include all combinations of variables from any of the disclosed embodiments within its scope.

Alternatively, the exclusion of one or more of the specified variables from a group or an embodiment, or combinations thereof is also contemplated by the present invention.

In certain aspects, the present invention provides prodrugs and derivatives of the compounds according to the formulae above. Prodrugs are derivatives of the compounds of the invention, which have metabolically cleavable groups and become by solvolysis or under physiological conditions the compounds of the invention, which are pharmaceutically active, in vivo. Such examples include, but are not limited to, choline ester derivatives and the like, N-alkylmorpholine esters and the like.

Other derivatives of the compounds of this invention have activity in both their acid and acid derivative forms, but the acid sensitive form often offers advantages of solubility, tissue compatibility, or delayed release in the mammalian organism (Bundgard, H, 1985). Prodrugs include acid derivatives well know to practitioners of the art, such as, for example, esters prepared by reaction of the parent acid with a suitable alcohol, or amides prepared by reaction of the parent acid compound with a substituted or unsubstituted amine, or acid anhydrides, or mixed anhydrides. Simple aliphatic or aromatic esters, amides and anhydrides derived from acidic groups pendant on the compounds of this invention are preferred prodrugs. In some cases it is desirable to prepare double ester type prodrugs such as (acyloxy) alkyl esters or ((alkoxycarbonyl)oxy)alkylesters. Particularly useful are the $C_1$ to $C_8$ alkyl, $C_2$-$C_8$ alkenyl, aryl, $C_7$-$C_{12}$ substituted aryl, and $C_7$-$C_{12}$ arylalkyl esters of the compounds of the invention.

Clauses

1) A compound according to Formula I:

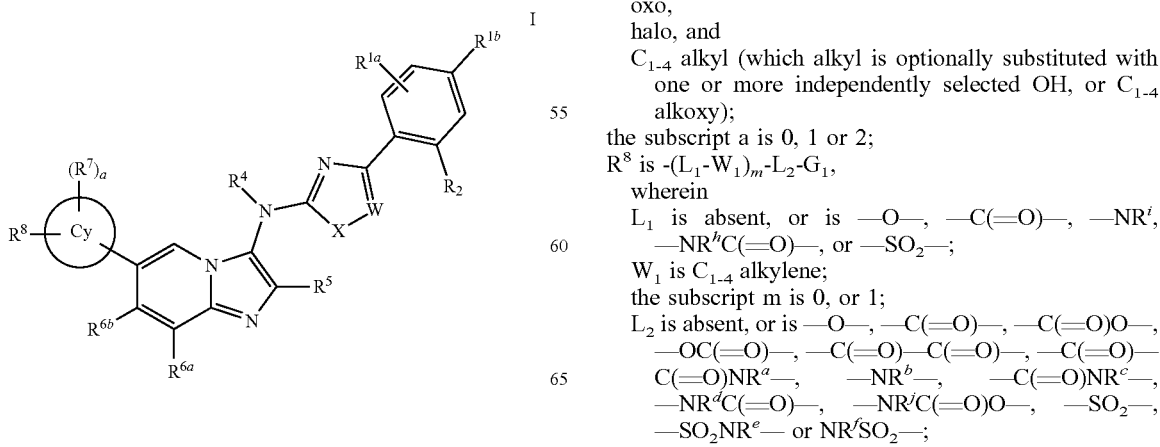

I wherein
$R^{1a}$ is H, halo or $C_{1-4}$ alkyl;
$R^{1b}$ is:
  halo,
  $C_{1-4}$ alkyl (which alkyl is optionally substituted with one or more independently selected halo), or
  $C_{1-4}$ alkoxy (which alkoxy is optionally substituted with one or more independently selected halo);
X is —S—, —O—, —N=CH—, —CH=N— or —CH=CH—;
W is N, or $CR^3$
when W is N, $R^2$ is:
  H,
  —CN,
  halo,
  $C_{1-4}$ alkyl (which alkyl is optionally substituted with one or more independently selected OH, or CN)
  —C(=O)CH$_3$,
  —C(=O)CF$_3$,
  —C(=O)OCH$_3$,
  —C(=O)NH$_2$,
  —NHC(=O)CH$_3$, or
when W is $CR^3$, one of $R^2$ or $R^3$ is:
  H,
  —CN,
  halo,
  $C_{1-4}$ alkyl (which alkyl is optionally substituted with one or more independently selected OH, or CN)
  —C(=O)CH$_3$,
  —C(=O)CF$_3$,
  —C(=O)OCH$_3$,
  —C(=O)NH$_2$,
  —NHC(=O)CH$_3$,
and the other is H, or $C_{1-4}$ alkyl;
$R^4$ is $C_{1-4}$ alkyl;
$R^5$ is $C_{1-4}$ alkyl optionally substituted with one or more independently selected CN, OH, halo, or —C(=O)NH$_2$;
one of $R^{6a}$ or $R^{6b}$ is selected from H, —CH$_3$, and halo, and the other is H;
Cy is:
  $C_{4-10}$ cycloalkyl,
  4-10 membered mono or bicyclic heterocycloalkyl containing one or more heteroatoms independently selected from O, N, and S, or
  4-7 membered heterocycloalkenyl containing 1 double bond, containing one or more heteroatoms independently selected from O, N, and S;
each $R^7$ is independently selected from:
  OH,
  oxo,
  halo, and
  $C_{1-4}$ alkyl (which alkyl is optionally substituted with one or more independently selected OH, or $C_{1-4}$ alkoxy);
the subscript a is 0, 1 or 2;
$R^8$ is -(L$_1$-W$_1$)$_m$-L$_2$-G$_1$,
  wherein
  L$_1$ is absent, or is —O—, —C(=O)—, —NR$^i$, —NR$^h$C(=O)—, or —SO$_2$—;
  W$_1$ is $C_{1-4}$ alkylene;
  the subscript m is 0, or 1;
  L$_2$ is absent, or is —O—, —C(=O)—, —C(=O)O—, —OC(=O)—, —C(=O)—C(=O)—, —C(=O)C(=O)NR$^a$—, —NR$^b$—, —C(=O)NR$^c$—, —NR$^d$C(=O)—, —NR$^j$C(=O)O—, —SO$_2$—, —SO$_2$NR$^e$— or NR$^f$SO$_2$—;

G₁ is
H,
—CN,
C₁₋₄ alkyl (which alkyl is optionally substituted with one or more independently selected —CN, OH, halo or phenyl),
C₃₋₇ cycloalkyl (which cycloalkyl is optionally substituted with —NH₂),
5-6 membered heterocycloalkenyl containing 1 double bond containing one or more heteroatoms independently selected from O, N, and S (which heterocycloalkenyl is optionally substituted with one or more independently selected $R^9$ groups),
4-10 membered mono, bi or spirocyclic heterocycloalkyl containing one or more heteroatoms independently selected from O, N, and S (which heterocycloalkyl is optionally substituted with one or more independently selected $R^9$ groups), or
5-6 membered heteroaryl containing one or more heteroatoms independently selected from O, N, and S (which heteroaryl is optionally substituted with one or more independently selected $R^{10}$ groups),
each $R^9$ is oxo, or $R^{10}$;
each $R^{10}$ is:
—OH,
halo,
—CN,
C₁₋₄ alkyl (which alkyl is optionally substituted with one or more independently selected OH, halo, or phenyl),
C₁₋₄ alkoxy,
C₃₋₇ cycloalkyl,
phenyl,
—SO₂CH₃,
—C(=O)C₁₋₄ alkoxy,
—C(=O)C₁₋₄ alkyl, or
—NR$^g$C(=O)C₁₋₄ alkyl; and
each $R^a$, $R^b$, $R^c$, $R^d$, $R^e$, $R^f$, $R^g$, $R^h$, $R^i$, and $R^j$ is independently selected from H and C₁₋₄ alkyl; or a pharmaceutically acceptable salt, or a solvate, or a pharmaceutically acceptable salt of a solvate thereof; or a biologically active metabolite thereof.

2) A compound or pharmaceutically acceptable salt thereof, according to clause 1, wherein $R^{1a}$ is F, Cl, —CH₃ or —C₂H₅.

3) A compound or pharmaceutically acceptable salt thereof, according to clause 1, wherein $R^{1a}$ is H.

4) A compound or pharmaceutically acceptable salt thereof, according to any one of clauses 1-3, wherein $R^{1b}$ is F, Cl, —CH₃, —C₂H₅, —CF₃, —OCH₃, or —OCF₃.

5) A compound or pharmaceutically acceptable salt thereof, according to any one of clauses 1-3, wherein $R^{1b}$ is F.

6) A compound or pharmaceutically acceptable salt thereof, according to any one of clauses 1-5, wherein X is —S— or —O—.

7) A compound or pharmaceutically acceptable salt thereof, according to any one of clauses 1-5, wherein X is —S—.

8) A compound or pharmaceutically acceptable salt thereof, according to any one of clauses 1-5, wherein W is N.

9) A compound or pharmaceutically acceptable salt thereof, according to any one of clauses 1-5, wherein W is CR³.

10) A compound or pharmaceutically acceptable salt thereof, according to clause 9, wherein R³ is H, CN, F, or Cl.

11) A compound or pharmaceutically acceptable salt thereof, according to clause 1, wherein the compound is according to Formula II:

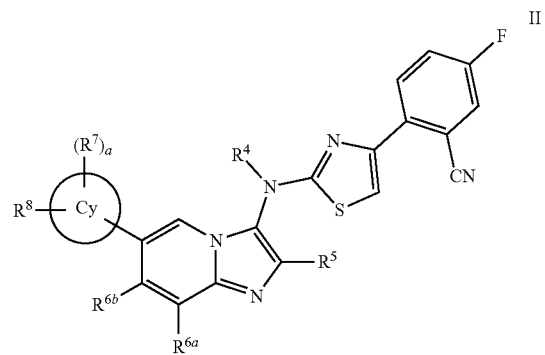

wherein R₄, R⁵, $R^{6a}$, $R^{6b}$, R⁷, R⁸ and the subscript a are according to clause 1.

12) A compound or pharmaceutically acceptable salt thereof, according to clause 1, wherein the compound is according to Formula III:

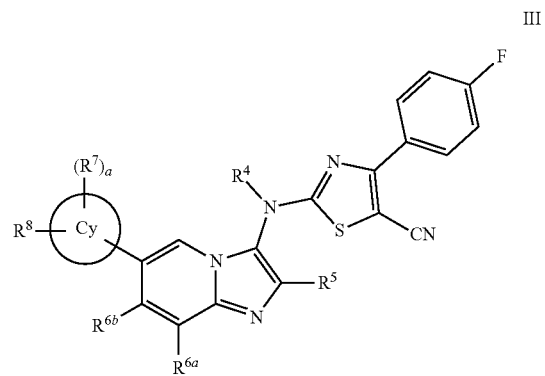

wherein R₄, R⁵, $R^{6a}$, $R^{6b}$, R⁷, R⁸ and the subscript a are according to clause 1.

13) A compound or pharmaceutically acceptable salt thereof, according to any one of clauses 1-12, wherein R⁴ is —CH₃, or —C₂H₅.

14) A compound or pharmaceutically acceptable salt thereof, according to any one of clauses 1-12, wherein R⁴ is —CH₃.

15) A compound or pharmaceutically acceptable salt thereof, according to any one of clauses 1-14, wherein R⁵ is C₁₋₄ alkyl.

16) A compound or pharmaceutically acceptable salt thereof, according to any one of clauses 1-14, wherein R⁵ is —CH₃, or —C₂H₅.

17) A compound or pharmaceutically acceptable salt thereof, according to any one of clauses 1-14, wherein R⁵ is C₁₋₄ alkyl substituted with one CN, OH, halo, or —C(=O)NH₂.

18) A compound or pharmaceutically acceptable salt thereof, according to clause 17, wherein R⁵ is —CH₃, —C₂H₅ or —C₃H₇ substituted with one CN, OH, halo, or —C(=O)NH₂.

19) A compound or pharmaceutically acceptable salt thereof, according to clause 17, wherein R⁵ is —CH₂—CH₂—CN, —CH₂—CH₂—OH, —CH₂—CF₃, or —CH₂—CH₂—C(=O)NH₂.

20) A compound or pharmaceutically acceptable salt thereof, according to any one of clauses 1-19, wherein Cy is $C^{4-10}$ cycloalkyl.

21) A compound or pharmaceutically acceptable salt thereof, according to clause 20, wherein Cy is cyclobutyl, cyclopentyl or cyclohexyl.

22) A compound or pharmaceutically acceptable salt thereof, according to any one of clauses 1-19, wherein Cy is 4-10 membered mono or bicyclic heterocycloalkyl containing one or more heteroatoms independently selected from O, N, and S.

23) A compound or pharmaceutically acceptable salt thereof, according to clause 22, wherein Cy is oxetanyl, azetidinyl, tetrahydrofuranyl, pyrrolidinyl, tetrahydropyranyl, piperidinyl, piperazinyl, morpholinyl, or thiomorpholinyl.

24) A compound or pharmaceutically acceptable salt thereof, according to any one of clauses 1-19, wherein Cy is 4-7 membered heterocycloalkenyl containing 1 double bond, containing one or more heteroatoms independently selected from O, N, and S.

25) A compound or pharmaceutically acceptable salt thereof, according to clause 24, wherein Cy is dihydrofuranyl, dihydrothiazolyl, dihydrooxazolyl, dihydropyranyl, tetrahydropyridinyl, or dihydrothiopyranyl.

26) A compound or pharmaceutically acceptable salt thereof, according to any one of clauses 1-25, wherein the subscript a is 1 or 2, and $R^7$ is OH, oxo, F, Cl, or —$CH_3$.

27) A compound or pharmaceutically acceptable salt thereof, according to any one of clauses 1-25, wherein the subscript a is 0.

28) A compound or pharmaceutically acceptable salt thereof, according to any one of clauses 1-27, wherein $R^8$ is -($L_1$-$W_1$)$_m$-$L_2$-$G_1$.

29) A compound according to Formula I, II, or III, wherein the compound is according to Formula IVa, IVb, IVc or IVd:

IVa

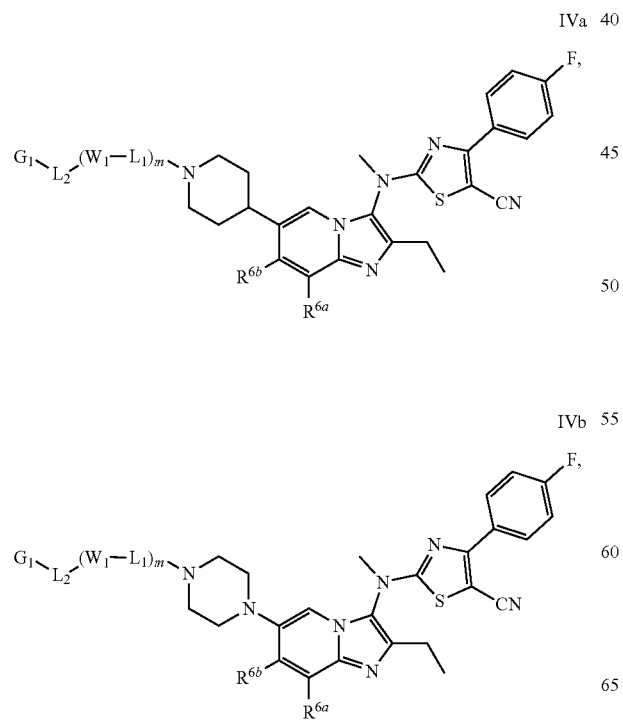

IVb

IVc

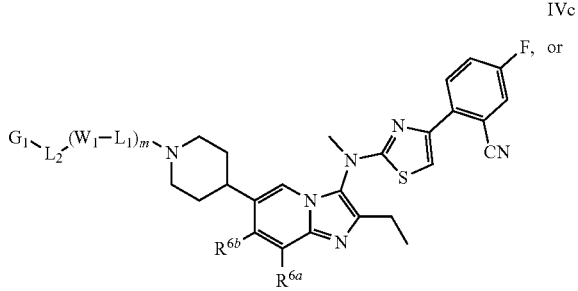

IVd

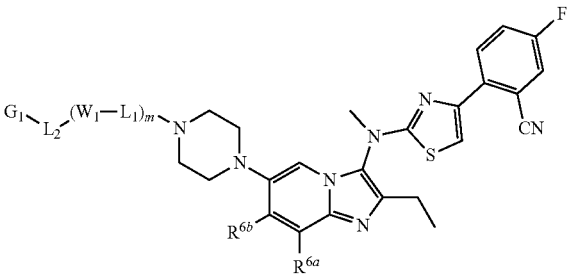

wherein $R^{6a}$, $R^{6b}$, $L_1$, $W_1$, $L_2$, $G_1$ and the subscript m are according to clause 1.

30) A compound or pharmaceutically acceptable salt thereof, according to clause 28, or 29, wherein the subscript m is 1, $L_1$ is absent.

31) A compound or pharmaceutically acceptable salt thereof, according to clause 28, or 29, wherein the subscript m is 1, $L_1$ is —C(=O)—, or —$SO_2$—.

32) A compound or pharmaceutically acceptable salt thereof, according to any one of clauses 28-31, wherein the subscript m is 1, and W1 is $C_{1-4}$ alkylene.

33) A compound or pharmaceutically acceptable salt thereof, according to clause 32, wherein the subscript m is 1, $L_1$ is as defined above and W1 is —$CH_2$—, —$CH_2$—$CH_2$—, —$C(CH_3)H$—, —$CH_2$—$CH_2$—$CH_2$— or —$CH_2$—$C(CH_3)H$—.

34) A compound or pharmaceutically acceptable salt thereof, according to clause 28, or 29, wherein the subscript m is 0.

35) A compound or pharmaceutically acceptable salt thereof, according to any one of clauses 28-34, wherein $L_2$ is absent.

36) A compound or pharmaceutically acceptable salt thereof, according to any one of clauses 28-34, wherein $L_2$ is —O—.

37) A compound or pharmaceutically acceptable salt thereof, according to any one of clauses 28-34, wherein $L_2$ is —C(=O)—.

38) A compound or pharmaceutically acceptable salt thereof, according to any one of clauses 28-34, wherein $L_2$ is —C(=O)O— or —OC(=O)—.

39) A compound or pharmaceutically acceptable salt thereof, according to any one of clauses 28-34, wherein $L_2$ is —C(=O)—C(=O)$NR^a$—.

40) A compound or pharmaceutically acceptable salt thereof, according to clause 39, wherein $R^a$ is H.

41) A compound or pharmaceutically acceptable salt thereof, according to any one of clauses 28-34, wherein $L_2$ is —$NR^b$—.

42) A compound or pharmaceutically acceptable salt thereof, according to clause 41, wherein $R^b$ is H.

43) A compound or pharmaceutically acceptable salt thereof, according to any one of clauses 28-34, wherein $L_2$ is —C(=O)NR$^c$—.

44) A compound or pharmaceutically acceptable salt thereof, according to clause 41, wherein R$^c$ is H, —CH$_3$, or —CH$_2$—CH$_3$.

45) A compound or pharmaceutically acceptable salt thereof, according to any one of clauses 28-34, wherein $L_2$ is —NR$^d$C(=O)—.

46) A compound or pharmaceutically acceptable salt thereof, according to clause 45, wherein R$^d$ is H, —CH$_3$, or —CH$_2$—CH$_3$.

47) A compound or pharmaceutically acceptable salt thereof, according to any one of clauses 28-34, wherein $L_2$ is —SO$_2$—.

48) A compound or pharmaceutically acceptable salt thereof, according to any one of clauses 28-34, wherein $L_2$ is —SO$_2$NR$^e$—.

49) A compound or pharmaceutically acceptable salt thereof, according to clause 48, wherein R$^e$ is H, —CH$_3$, or —CH$_2$—CH$_3$.

50) A compound or pharmaceutically acceptable salt thereof, according to any one of clauses 28-34, wherein $L_2$ is —NR$^f$SO$_2$—.

51) A compound or pharmaceutically acceptable salt thereof, according to clause 50, wherein R$^f$ is H, —CH$_3$, or —CH$_2$—CH$_3$.

52) A compound or pharmaceutically acceptable salt thereof, according to any one of clauses 28-51, wherein $G_1$ is H, or CN.

53) A compound or pharmaceutically acceptable salt thereof, according to any one of clauses 28-51, wherein $G_1$ is $C_{1-4}$ alkyl.

54) A compound or pharmaceutically acceptable salt thereof, according to clause 53, wherein $G_1$ is —CH$_3$, or —CH$_2$—CH$_3$.

55) A compound or pharmaceutically acceptable salt thereof, according to any one of clauses 28-51, wherein $G_1$ is $C_{1-4}$ alkyl substituted with —CN, OH, halo or phenyl.

56) A compound or pharmaceutically acceptable salt thereof, according to clause 55, wherein $G_1$ is —CF$_3$, —CH$_2$—Cl, —CH$_2$—CN, —CH$_2$—OH or —CH$_2$-Ph.

57) A compound or pharmaceutically acceptable salt thereof, according to any one of clauses 28-51, wherein $G_1$ is $C_{3-7}$ cycloalkyl.

58) A compound or pharmaceutically acceptable salt thereof, according to clause 57, wherein $G_1$ is cyclopropyl, cyclobutyl, cyclopropyl, or cyclohexyl.

59) A compound or pharmaceutically acceptable salt thereof, according to any one of clauses 28-51, wherein $G_1$ is $C_{3-7}$ cycloalkyl substituted with NH$_2$.

60) A compound or pharmaceutically acceptable salt thereof, according to clause 59, wherein $G_1$ is cyclopropyl, cyclobutyl, cyclopropyl, or cyclohexyl, each of which is substituted with NH$_2$.

61) A compound or pharmaceutically acceptable salt thereof, according to any one of clauses 28-51, wherein $G_1$ is 5-6 membered heterocycloalkenyl containing 1 double bond containing one to three heteroatoms independently selected from O, N, and S.

62) A compound or pharmaceutically acceptable salt thereof, according to clause 61, wherein $G_1$ is dihydrofuranyl, dihydrothiazolyl, dihydrooxazolyl, dihydropyranyl, or dihydrothiopyranyl.

63) A compound or pharmaceutically acceptable salt thereof, according to any one of clauses 28-51, wherein $G_1$ is 4-10 membered mono, bi or spirocyclic heterocycloalkyl containing one to three heteroatoms independently selected from O, N, and S.

64) A compound or pharmaceutically acceptable salt thereof, according to clause 63, wherein $G_1$ is oxetanyl, azetidinyl, tetrahydrofuranyl, pyrolidinyl, tetrahydropyranyl, piperidinyl, piperazinyl, morpholinyl, thiomorpholinyl, or 2,6-Diaza-spiro[3.3]heptane.

65) A compound or pharmaceutically acceptable salt thereof, according to any one of clauses 28-51, wherein $G_1$ is 4-10 membered mono, bi or spirocyclic heterocycloalkyl containing one to three heteroatoms independently selected from O, N, and S, substituted with one or two independently selected R$^9$.

66) A compound or pharmaceutically acceptable salt thereof, according to clause 65, wherein $G_1$ is oxetanyl, azetidinyl, tetrahydrofuranyl, pyrolidinyl, tetrahydropyranyl, piperidinyl, piperazinyl, morpholinyl, thiomorpholinyl, or 2,6-Diaza-spiro[3.3]heptane, each of which is substituted with one or two independently selected R$^9$.

67) A compound or pharmaceutically acceptable salt thereof, according to clause 65 or 66, wherein R$^9$ is oxo.

68) A compound or pharmaceutically acceptable salt thereof, according to clause 65 or 66, wherein R$^9$ is R$^{10}$ and R$^{10}$ is selected from OH, F, Cl, and —CN.

69) A compound or pharmaceutically acceptable salt thereof, according to clause 65 or 66, wherein R$^9$ is R$^{10}$ and R$^{10}$ is selected from —CH$_3$, —CH$_2$—CH$_3$, —CF$_3$, —CH$_2$—CH$_2$—OH, —CH$_2$-phenyl, 70) A compound or pharmaceutically acceptable salt thereof, according to clause 65 or 66, wherein R$^9$ is R$^{10}$ and R$^{10}$ is selected from —OCH$_3$, —OCH$_2$—CH$_3$, and —OC(CH$_3$)$_3$.

71) A compound or pharmaceutically acceptable salt thereof, according to clause 65 or 66, wherein R$^9$ is R$^{10}$ and R$^{10}$ is selected from —SO$_2$CH$_3$, —C(=O)OCH$_3$, and —C(=O)CH$_3$.

72) A compound or pharmaceutically acceptable salt thereof, according to clause 65 or 66, wherein each R$^9$ is R$^{10}$ and R$^{10}$ is —NR$^g$C(=O)CH$_3$, or —NR$^g$C(=O)CH$_2$CH$_3$.

73) A compound or pharmaceutically acceptable salt thereof, according to clause 72, wherein each R$^g$ is H, —CH$_3$, or —CH$_2$CH$_3$.

74) A compound or pharmaceutically acceptable salt thereof, according to any one of clauses 28-51, wherein $G_1$ is 5-6 membered heteroaryl containing one to three heteroatoms independently selected from O, N, and S.

75) A compound or pharmaceutically acceptable salt thereof, according to clause 74, wherein $G_1$ is furanyl, thienyl, pyrrolyl, pyrazolyl, imidazolyl, triazolyl, oxazolyl, oxadiazolyl, thiazolyl, thiadiazolyl, pyridyl, pyrazinyl, or pyrimidyl.

76) A compound or pharmaceutically acceptable salt thereof, according to any one of clauses 28-51, wherein $G_1$ is 5-6 membered heteroaryl containing one to three heteroatoms independently selected from O, N, and S, substituted with one or two independently selected R$^{10}$.

77) A compound or pharmaceutically acceptable salt thereof, according to clause 76, wherein $G_1$ is furanyl, thienyl, pyrolyl, pyrazolyl, imidazolyl, triazolyl, oxazolyl, oxadiazolyl, thiazolyl, thiadiazolyl, pyridyl, pyrazinyl, or pyrimidyl, each of which is substituted with one or two independently selected R$^{10}$.

78) A compound or pharmaceutically acceptable salt thereof, according to clause 77, wherein R$^{10}$ is selected from OH, F, Cl, and —CN.

79) A compound or pharmaceutically acceptable salt thereof, according to clause 77, wherein $R^{10}$ is selected from —$CH_3$, —$CH_2$—$CH_3$, —$CF_3$, —$CH_2$—$CH_2$—OH, and —$CH_2$-phenyl.
80) A compound or pharmaceutically acceptable salt thereof, according to clause 77, wherein $R^{10}$ is selected from —$OCH_3$, —$OCH_2$—$CH_3$, and —$OC(CH_3)_3$.
81) A compound or pharmaceutically acceptable salt thereof, according to clause 77, wherein $R^{10}$ is selected from —$SO_2CH_3$, —$C(=O)OCH_3$, and —$C(=O)CH_3$.
82) A compound or pharmaceutically acceptable salt thereof, according to clause 77, wherein each $R^{10}$ is —$NR^gC(=O)CH_3$, or —$NR^gC(=O)CH_2CH_3$.
83) A compound or pharmaceutically acceptable salt thereof, according to clause 82, wherein each $R^g$ is H, —$CH_3$, or —$CH_2CH_3$.
84) A compound according to clause 1, wherein the compound is according to Formula Va, Vb, Vc, or Vd:

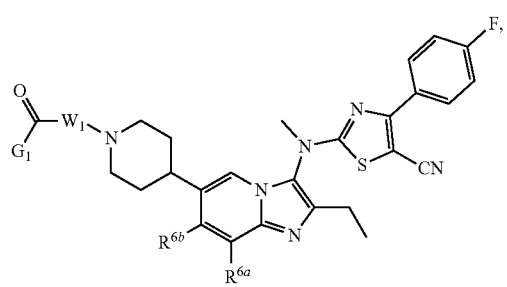

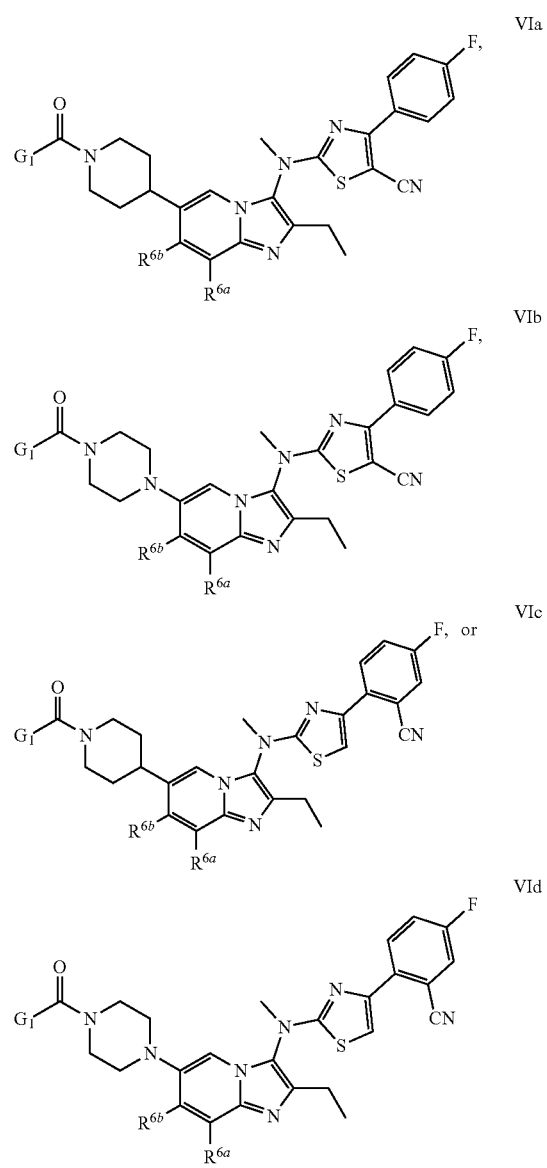

wherein $R^{6a}$, $R^{6b}$, $W_1$ and $G_1$ are according to clause 1.
85) A compound or pharmaceutically acceptable salt thereof, according to clause 84, wherein $W_1$ is $C_{1-4}$ alkylene.
86) A compound or pharmaceutically acceptable salt thereof, according to clause 85, wherein W1 is —$CH_2$—, —$CH_2$—$CH_2$—, —$C(CH_3)H$—, —$CH_2$—$CH_2$—$CH_2$— or —$CH_2$—$C(CH_3)H$—.
87) A compound according to clause 1, wherein the compound is according to Formula VIa, VIb, VIc, or VId:

wherein $R^{6a}$, $R^{6b}$ and $G_1$ are according to clause 1.
88) A compound or pharmaceutically acceptable salt thereof, according to any one of clauses 84-87, wherein $G_1$ is 4-7 membered heterocycloalkyl containing one or more heteroatoms independently selected from O, N, and S.
89) A compound or pharmaceutically acceptable salt thereof, according to clause 88, wherein $G_1$ is oxetanyl, azetidinyl, tetrahydrofuranyl, pyrolidinyl, tetrahydropyranyl, piperidinyl, piperazinyl, morpholinyl, or thiomorpholinyl.
90) A compound or pharmaceutically acceptable salt thereof, according to any one of clauses 84-87, wherein $G_1$ is 4-7

91) A compound or pharmaceutically acceptable salt thereof, according to clause 90, wherein $G_1$ is oxetanyl, azetidinyl, tetrahydrofuranyl, pyrolidinyl, tetrahydropyranyl, piperidinyl, piperazinyl, morpholinyl, or thiomorpholinyl, each of which is substituted with one or two independently selected $R^9$ groups.
92) A compound or pharmaceutically acceptable salt thereof, according to clause 90 or 91, wherein $R^9$ is oxo.
93) A compound or pharmaceutically acceptable salt thereof, according to clause 90 or 91, wherein $R^9$ is $R^{10}$ and $R^{10}$ is selected from OH, F, Cl, and —CN.
94) A compound or pharmaceutically acceptable salt thereof, according to clause 90 or 91, wherein $R^9$ is $R^{10}$ and $R^{10}$ is selected from —$CH_3$, —$CH_2$—$CH_3$, —$CF_3$, —$CH_2$—$CH_2$—OH, and —$CH_2$-phenyl.
95) A compound or pharmaceutically acceptable salt thereof, according to clause 90 or 91, wherein $R^9$ is $R^{10}$ and $R^{10}$ is selected from —$OCH_3$, —$OCH_2$—$CH_3$, and —$OC(CH_3)_3$.
96) A compound or pharmaceutically acceptable salt thereof, according to clause 90 or 91, wherein $R^9$ is $R^{10}$ and $R^{10}$ is selected from —$SO_2CH_3$, —$C(=O)OCH_3$, and —$C(=O)CH_3$.
97) A compound or pharmaceutically acceptable salt thereof, according to clause 90 or 91, wherein $R^9$ is $R^{10}$ and $R^{10}$ is —$NR^gC(=O)CH_3$, or —$NR^gC(=O)CH_2CH_3$.
98) A compound or pharmaceutically acceptable salt thereof, according to clause 90 or 91, wherein each $R^g$ is H, —$CH_3$, or —$CH_2CH_3$.
99) A compound or pharmaceutically acceptable salt thereof, according to any one of clauses 1-98, wherein $R^{6a}$ is H, —$CH_3$ or F, and $R^{6b}$ is H.
100) A compound or pharmaceutically acceptable salt thereof, according to any one of clauses 1-98, wherein $R^{6a}$ is $CH_3$, and $R^{6b}$ is H.
101) A compound or pharmaceutically acceptable salt thereof, according to any one of clauses 1-98, wherein $R^{6a}$ is H, and $R^{6b}$ is H, —$CH_3$ or F.
102) A compound or pharmaceutically acceptable salt thereof, according to any one of clauses 1-98, wherein $R^{6a}$ and $R^{6b}$ are H.
103) A compound or pharmaceutically acceptable salt thereof, wherein the compound is selected from the compounds of Table III.
104) A compound or pharmaceutically acceptable salt thereof, wherein the compound is 2-((2-ethyl-6-(4-(2-(3-hydroxyazetidin-1-yl)-2-oxoethyl)piperazin-1-yl)-8-methylimidazo[1,2-a]pyridin-3-yl)(methyl)amino)-4-(4-fluorophenyl)thiazole-5-carbonitrile.
105) A pharmaceutical composition comprising a pharmaceutically acceptable carrier and a pharmaceutically effective amount of a compound according to any one of clauses 1-104.
106) A pharmaceutical composition according to clause 105, comprising a further therapeutic agent.
107) A compound or pharmaceutically acceptable salt thereof, according to any one of clauses 1-104, or a pharmaceutical composition according to clause 105 or 106, for use in medicine.
108) A compound or pharmaceutically acceptable salt thereof, according to any one of clauses 1-104, or a pharmaceutical composition according to clause 105 or 106, for use in the treatment of fibrotic diseases, proliferative diseases, inflammatory diseases, autoimmune diseases, respiratory diseases, cardiovascular diseases, neurodegenerative diseases, dermatological disorders, and/or abnormal angiogenesis associated diseases.
109) A compound or pharmaceutically acceptable salt thereof, according to any one of clauses 1-104, or a pharmaceutical composition according to clause 105 or 106, for use in the treatment of idiopathic pulmonary fibrosis.
110) The use of a compound or pharmaceutically acceptable salt thereof or the pharmaceutical composition according to clause 108 or 109, wherein said compound or pharmaceutical composition is administered in combination with a further therapeutic agent.
111) A method for the treatment, or prevention of diseases or conditions selected from fibrotic diseases, proliferative diseases, inflammatory diseases, autoimmune diseases, respiratory diseases, cardiovascular diseases, neurodegenerative diseases, dermatological disorders, and/or abnormal angiogenesis associated diseases, comprising administering an amount of compound according to any one of clauses 1-104, or the pharmaceutical composition according any one of clauses 105 or 106, sufficient to effect said treatment, or prevention.
112) A method for the treatment, or prevention of diseases or conditions selected from idiopathic pulmonary fibrosis, comprising administering an amount of compound according to any one of clauses 1-104, or the pharmaceutical composition according any one of clauses 105 or 106, sufficient to effect said treatment, or prevention.
113) The method according to clause 111 or 112, wherein the compound, or the pharmaceutical composition, is administered in combination with a further therapeutic agent.
114) The pharmaceutical composition according to clause 106, or the use according to clause 110, or the method according to clause 113, wherein the further therapeutic agent is for the treatment of fibrotic diseases, proliferative diseases, inflammatory diseases, autoimmune diseases, respiratory diseases, cardiovascular diseases, neurodegenerative diseases, dermatological disorders, and/or abnormal angiogenesis associated diseases.
115) The pharmaceutical composition according to clause 106, or the use according to clause 110, or the method according to clause 113, wherein the further therapeutic agent is for the treatment of idiopathic pulmonary fibrosis.

Pharmaceutical Compositions

When employed as a pharmaceutical, a compound of the invention is typically administered in the form of a pharmaceutical composition. Such compositions can be prepared in a manner well known in the pharmaceutical art and comprise at least one active compound of the invention according to Formula I. Generally, a compound of the invention is administered in a pharmaceutically effective amount. The amount of compound of the invention actually administered will typically be determined by a physician, in the light of the relevant circumstances, including the condition to be treated, the chosen route of administration, the actual compound of the invention administered, the age, weight, and response of the individual patient, the severity of the patient's symptoms, and the like.

The pharmaceutical compositions of this invention can be administered by a variety of routes including oral, rectal, transdermal, subcutaneous, intra-articular, intravenous, intramuscular, and intranasal. Depending on the intended route of delivery, a compound of the invention is preferably formulated as either injectable or oral compositions or as salves, as lotions or as patches all for transdermal administration.

The compositions for oral administration can take the form of bulk liquid solutions or suspensions, or bulk powders. More commonly, however, the compositions are presented in unit dosage forms to facilitate accurate dosing. The term 'unit dosage forms' refers to physically discrete units suitable as unitary dosages for human subjects and other mammals, each unit containing a predetermined quantity of active material calculated to produce the desired therapeutic effect, in association with a suitable pharmaceutical excipient, vehicle or carrier. Typical unit dosage forms include prefilled, premeasured ampules or syringes of the liquid compositions or pills, tablets, capsules or the like in the case of solid compositions. In such compositions, the compound of the invention according to Formula I is usually a minor component (from about 0.1 to about 50% by weight or preferably from about 1 to about 40% by weight) with the remainder being various vehicles or carriers and processing aids helpful for forming the desired dosing form.

Liquid forms suitable for oral administration may include a suitable aqueous or non-aqueous vehicle with buffers, suspending and dispensing agents, colorants, flavors and the like. Solid forms may include, for example, any of the following ingredients, or compound of the inventions of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate; a glidant such as colloidal silicon dioxide; a sweetening agent such as sucrose or saccharin; or a flavoring agent such as peppermint or orange flavoring.

Injectable compositions are typically based upon injectable sterile saline or phosphate-buffered saline or other injectable carriers known in the art. As before, the active compound of the invention according to Formula I in such compositions is typically a minor component, often being from about 0.05 to 10% by weight with the remainder being the injectable carrier and the like.

Transdermal compositions are typically formulated as a topical ointment or cream containing the active ingredient(s), generally in an amount ranging from about 0.01 to about 20% by weight, preferably from about 0.1 to about 20% by weight, preferably from about 0.1 to about 10% by weight, and more preferably from about 0.5 to about 15% by weight. When formulated as an ointment, the active ingredients will typically be combined with either a paraffinic or a water-miscible ointment base. Alternatively, the active ingredients may be formulated in a cream with, for example an oil-in-water cream base. Such transdermal formulations are well-known in the art and generally include additional ingredients to enhance the dermal penetration of stability of the active ingredients or the formulation. All such known transdermal formulations and ingredients are included within the scope of this invention.

A compound of the invention can also be administered by a transdermal device. Accordingly, transdermal administration can be accomplished using a patch either of the reservoir or porous membrane type, or of a solid matrix variety.

The above-described components for orally administrable, injectable or topically administrable compositions are merely representative. Other materials as well as processing techniques and the like are set forth in Part 8 of Remington's Pharmaceutical Sciences, 17$^{th}$ edition, 1985, Mack Publishing Company, Easton, Pa., which is incorporated herein by reference.

A compound of the invention can also be administered in sustained release forms or from sustained release drug delivery systems. A description of representative sustained release materials can be found in Remington's Pharmaceutical Sciences.

The following formulation examples illustrate representative pharmaceutical compositions that may be prepared in accordance with this invention. The present invention, however, is not limited to the following pharmaceutical compositions.

Formulation 1—Tablets

A compound of the invention according to Formula I may be admixed as a dry powder with a dry gelatin binder in an approximate 1:2 weight ratio. A minor amount of magnesium stearate may be added as a lubricant. The mixture may be formed into 240-270 mg tablets (80-90 mg of active compound of the invention according to Formula I per tablet) in a tablet press.

Formulation 2—Capsules

A compound of the invention according to Formula I may be admixed as a dry powder with a starch diluent in an approximate 1:1 weight ratio. The mixture may be filled into 250 mg capsules (125 mg of active compound of the invention according to Formula I per capsule).

Formulation 3—Liquid

A compound of the invention according to Formula I (125 mg), may be admixed with sucrose (1.75 g) and xanthan gum (4 mg) and the resultant mixture may be blended, passed through a No. 10 mesh U.S. sieve, and then mixed with a previously made solution of microcrystalline cellulose and sodium carboxymethyl cellulose (11:89, 50 mg) in water. Sodium benzoate (10 mg), flavor, and color may be diluted with water and added with stirring. Sufficient water may then be added with stirring. Further sufficient water may be then added to produce a total volume of 5 mL.

Formulation 4—Tablets

A compound of the invention according to Formula I may be admixed as a dry powder with a dry gelatin binder in an approximate 1:2 weight ratio. A minor amount of magnesium stearate may be added as a lubricant. The mixture may be formed into 450-900 mg tablets (150-300 mg of active compound of the invention according to Formula I) in a tablet press.

Formulation 5—Injection

A compound of the invention according to Formula I may be dissolved or suspended in a buffered sterile saline injectable aqueous medium to a concentration of approximately 5 mg/mL.

Formulation 6—Topical

Stearyl alcohol (250 g) and a white petrolatum (250 g) may be melted at about 75° C. and then a mixture of A compound of the invention according to Formula I (50 g) methylparaben (0.25 g), propylparaben (0.15 g), sodium lauryl sulfate (10 g), and propylene glycol (120 g) dissolved in water (about 370 g) may be added and the resulting mixture may be stirred until it congeals.

Methods of Treatment

In one embodiment, the present invention provides compounds of the invention, or pharmaceutical compositions comprising a compound of the invention, for use in medicine. In a particular embodiment, the present invention provides compounds of the invention or pharmaceutical compositions comprising a compound of the invention, for use in the prophylaxis and/or treatment of fibrotic diseases, proliferative diseases, inflammatory diseases, autoimmune diseases, respiratory diseases, cardiovascular diseases, neurodegenerative diseases, dermatological disorders, and/or abnormal angiogenesis associated diseases.

In another embodiment, the present invention provides compounds of the invention, or pharmaceutical compositions comprising a compound of the invention for use in the manufacture of a medicament for use in the prophylaxis and/or treatment of fibrotic diseases, proliferative diseases, inflammatory diseases, autoimmune diseases, respiratory diseases, cardiovascular diseases, neurodegenerative diseases, dermatological disorders, and/or abnormal angiogenesis associated diseases.

In one embodiment, the present invention provides pharmaceutical compositions comprising a compound of the invention, and another therapeutic agent. In a particular embodiment, the other therapeutic agent is a fibrotic diseases, proliferative diseases, inflammatory diseases, autoimmune diseases, respiratory diseases, cardiovascular diseases, neurodegenerative diseases, dermatological disorders, and/or abnormal angiogenesis associated diseases treatment agent.

In additional method of treatment aspects, this invention provides methods of prophylaxis and/or treatment of a mammal afflicted with fibrotic diseases, proliferative diseases, inflammatory diseases, autoimmune diseases, respiratory diseases, cardiovascular diseases, neurodegenerative diseases, dermatological disorders, and/or abnormal angiogenesis associated diseases, which methods comprise the administration of an effective amount of a compound of the invention or one or more of the pharmaceutical compositions herein described for the treatment or prophylaxis of said condition.

In one embodiment, the present invention provides compounds of the invention or pharmaceutical compositions comprising a compound of the invention, for use in the prophylaxis and/or treatment of fibrotic diseases. In a particular embodiment, the fibrotic disease is selected from idiopathic pulmonary fibrosis (IPF), cystic fibrosis, other diffuse parenchymal lung diseases of different etiologies including iatrogenic drug-induced fibrosis, occupational and/or environmental induced fibrosis, granulomatous diseases (sarcoidosis, hypersensitivity pneumonia), collagen vascular disease, alveolar proteinosis, langerhans cell granulomatosis, lymphangioleiomyomatosis, inherited diseases (Hermansky-Pudlak Syndrome, tuberous sclerosis, neurofibromatosis, metabolic storage disorders, familial interstitial lung disease), radiation induced fibrosis, chronic obstructive pulmonary disease (COPD), scleroderma, bleomycin induced pulmonary fibrosis, chronic asthma, silicosis, asbestos induced pulmonary fibrosis, acute respiratory distress syndrome (ARDS), kidney fibrosis, tubulointerstitium fibrosis, glomerular nephritis, focal segmental glomerular sclerosis, IgA nephropathy, hypertension, Alport, gut fibrosis, liver fibrosis, cirrhosis, alcohol induced liver fibrosis, toxic/drug induced liver fibrosis, hemochromatosis, nonalcoholic steatohepatitis (NASH), biliary duct injury, primary biliary cirrhosis, infection induced liver fibrosis, viral induced liver fibrosis, and autoimmune hepatitis, corneal scarring, hypertrophic scarring, Dupuytren disease, keloids, cutaneous fibrosis, cutaneous scleroderma, systemic sclerosis, spinal cord injury/fibrosis, myelofibrosis, vascular restenosis, atherosclerosis, arteriosclerosis, Wegener's granulomatosis, Peyronie's disease, or chronic lymphocytic. More particularly, the fibrotic diseases is idiopathic pulmonary fibrosis (IPF).

In another embodiment, the present invention provides compounds of the invention, or pharmaceutical compositions comprising a compound of the invention for use in the manufacture of a medicament for use in the prophylaxis and/or treatment of fibrotic diseases. In a particular embodiment, the fibrotic disease is selected from idiopathic pulmonary fibrosis (IPF), cystic fibrosis, other diffuse parenchymal lung diseases of different etiologies including iatrogenic drug-induced fibrosis, occupational and/or environmental induced fibrosis, granulomatous diseases (sarcoidosis, hypersensitivity pneumonia), collagen vascular disease, alveolar proteinosis, langerhans cell granulomatosis, lymphangioleiomyomatosis, inherited diseases (Hermansky-Pudlak Syndrome, tuberous sclerosis, neurofibromatosis, metabolic storage disorders, familial interstitial lung disease), radiation induced fibrosis, chronic obstructive pulmonary disease (COPD), scleroderma, bleomycin induced pulmonary fibrosis, chronic asthma, silicosis, asbestos induced pulmonary fibrosis, acute respiratory distress syndrome (ARDS), kidney fibrosis, tubulointerstitium fibrosis, glomerular nephritis, focal segmental glomerular sclerosis, IgA nephropathy, hypertension, Alport, gut fibrosis, liver fibrosis, cirrhosis, alcohol induced liver fibrosis, toxic/drug induced liver fibrosis, hemochromatosis, nonalcoholic steatohepatitis (NASH), biliary duct injury, primary biliary cirrhosis, infection induced liver fibrosis, viral induced liver fibrosis, and autoimmune hepatitis, corneal scarring, hypertrophic scarring, Dupuytren disease, keloids, cutaneous fibrosis, cutaneous scleroderma, systemic sclerosis, spinal cord injury/fibrosis, myelofibrosis, vascular restenosis, atherosclerosis, arteriosclerosis, Wegener's granulomatosis, Peyronie's disease, or chronic lymphocytic. More particularly, the fibrotic disease is idiopathic pulmonary fibrosis (IPF).

In additional method of treatment aspects, this invention provides methods of prophylaxis and/or treatment of a mammal afflicted with fibrotic diseases, which methods comprise the administration of an effective amount of a compound of the invention or one or more of the pharmaceutical compositions herein described for the treatment or prophylaxis of said condition. In a particular embodiment, the fibrotic disease is selected from idiopathic pulmonary fibrosis (IPF), cystic fibrosis, other diffuse parenchymal lung diseases of different etiologies including iatrogenic drug-induced fibrosis, occupational and/or environmental induced fibrosis, granulomatous diseases (sarcoidosis, hypersensitivity pneumonia), collagen vascular disease, alveolar proteinosis, langerhans cell granulomatosis, lymphangioleiomyomatosis, inherited diseases (Hermansky-Pudlak Syndrome, tuberous sclerosis, neurofibromatosis, metabolic storage disorders, familial interstitial lung disease), radiation induced fibrosis, chronic obstructive pulmonary disease (COPD), scleroderma, bleomycin induced pulmonary fibrosis, chronic asthma, silicosis, asbestos induced pulmonary fibrosis, acute respiratory distress syndrome (ARDS), kidney fibrosis, tubulointerstitium fibrosis, glomerular nephritis, focal segmental glomerular sclerosis, IgA nephropathy, hypertension, Alport, gut fibrosis, liver fibrosis, cirrhosis, alcohol induced liver fibrosis, toxic/drug induced liver fibrosis, hemochromatosis, nonalcoholic steatohepatitis (NASH), biliary duct injury, primary biliary cirrhosis, infection induced liver fibrosis, viral induced liver fibrosis, and autoimmune hepatitis, corneal scarring, hypertrophic scarring, Dupuytren disease, keloids, cutaneous fibrosis, cutaneous scleroderma, systemic sclerosis, spinal cord injury/fibrosis, myelofibrosis, vascular restenosis, atherosclerosis, arteriosclerosis, Wegener's granulomatosis, Peyronie's disease, or chronic lymphocytic. More particularly, the fibrotic disease is idiopathic pulmonary fibrosis (IPF).

A particular regimen of the present method comprises the administration to a subject suffering from a fibrotic disease of an effective amount of a compound of the invention according to Formula I for a period of time sufficient to reduce the level of fibrosis in the subject, and preferably terminate the processes responsible for said fibrosis. A special embodiment of the method comprises administering of an effective amount of a compound of the invention according to Formula I to a subject patient suffering from to the development of idiopathic pulmonary fibrosis, for a period of time sufficient to reduce or prevent idiopathic pulmonary fibrosis of said patient, and preferably terminate, the processes responsible for said idiopathic pulmonary fibrosis.

In one embodiment, the present invention provides compounds of the invention or pharmaceutical compositions comprising a compound of the invention, for use in the prophylaxis and/or treatment of proliferative diseases. In a particular embodiment, the proliferative disease is selected from cancer, leukemia, multiple myeloma and psoriasis.

In another embodiment, the present invention provides compounds of the invention, or pharmaceutical compositions comprising a compound of the invention for use in the manufacture of a medicament for use in the prophylaxis and/or treatment of proliferative diseases. In a particular embodiment, the proliferative disease is selected from cancer, leukemia, multiple myeloma and psoriasis.

In additional method of treatment aspects, this invention provides methods of prophylaxis and/or treatment of a mammal afflicted with proliferative diseases, which methods comprise the administration of an effective amount of a compound of the invention or one or more of the pharmaceutical compositions herein described for the treatment or prophylaxis of said condition. In a particular embodiment, the proliferative disease is selected from cancer, leukemia, multiple myeloma and psoriasis.

In one embodiment, the present invention provides compounds of the invention or pharmaceutical compositions comprising a compound of the invention, for use in the prophylaxis and/or treatment of inflammatory diseases. In a particular embodiment, the inflammatory disease is selected from rheumatoid arthritis, osteoarthritis, allergic airway disease (e.g. asthma), chronic obstructive pulmonary disease (COPD) and inflammatory bowel diseases (e.g. Crohn's disease and ulcerative colitis). More particularly, the inflammatory disease is selected from rheumatoid arthritis, and chronic obstructive pulmonary disease (COPD).

In another embodiment, the present invention provides compounds of the invention, or pharmaceutical compositions comprising a compound of the invention for use in the manufacture of a medicament for use in the prophylaxis and/or treatment of inflammatory diseases. In a particular embodiment, the inflammatory disease is selected from rheumatoid arthritis, osteoarthritis, allergic airway disease (e.g. asthma), chronic obstructive pulmonary disease (COPD) and inflammatory bowel diseases (e.g. Crohn's disease and ulcerative colitis). More particularly, the inflammatory disease is selected from rheumatoid arthritis, and chronic obstructive pulmonary disease (COPD).

In additional method of treatment aspects, this invention provides methods of prophylaxis and/or treatment of a mammal afflicted with inflammatory diseases, which methods comprise the administration of an effective amount of a compound of the invention or one or more of the pharmaceutical compositions herein described for the treatment or prophylaxis of said condition. In a particular embodiment, the inflammatory disease is selected from rheumatoid arthritis, osteoarthritis, allergic airway disease (e.g. asthma), chronic obstructive pulmonary disease (COPD) and inflammatory bowel diseases (e.g. Crohn's disease and ulcerative colitis). More particularly the inflammatory disease is selected from rheumatoid arthritis, and chronic obstructive pulmonary disease (COPD).

In one embodiment, the present invention provides compounds of the invention or pharmaceutical compositions comprising a compound of the invention, for use in the prophylaxis and/or treatment of autoimmune diseases. In a particular embodiment, the autoimmune disease is selected from COPD, asthma (e.g intrinsic asthma, extrinsic asthma, dust asthma, infantily asthma) particularly chronic or inveterate asthma (for example late asthma and airway hyperreponsiveness), bronchitis, including bronchial asthma, systemic lupus erythematosus (SLE), cutaneous lupus erythrematosis, lupus nephritis, dermatomyositis, Sjogren's syndrome, multiple sclerosis, psoriasis, dry eye disease, type I diabetes mellitus and complications associated therewith, atopic eczema (atopic dermatitis), thyroiditis (Hashimoto's and autoimmune thyroiditis), contact dermatitis and further eczematous dermatitis, inflammatory bowel disease (e.g. Crohn's disease and ulcerative colitis), atherosclerosis and amyotrophic lateral sclerosis. Particularly, the autoimmune disease is selected from COPD, asthma, systemic lupus erythematosis, type I diabetes mellitus and inflammatory bowel disease.

In another embodiment, the present invention provides compounds of the invention, or pharmaceutical compositions comprising a compound of the invention for use in the manufacture of a medicament for use in the prophylaxis and/or treatment of autoimmune diseases. In a particular embodiment, the autoimmune disease is selected from COPD, asthma (e.g intrinsic asthma, extrinsic asthma, dust asthma, infantily asthma) particularly chronic or inveterate asthma (for example late asthma and airway hyperreponsiveness), bronchitis, including bronchial asthma, systemic lupus erythematosus (SLE), cutaneous lupus erythrematosis, lupus nephritis, dermatomyositis, Sjogren's syndrome, multiple sclerosis, psoriasis, dry eye disease, type I diabetes mellitus and complications associated therewith, atopic eczema (atopic dermatitis), thyroiditis (Hashimoto's and autoimmune thyroiditis), contact dermatitis and further eczematous dermatitis, inflammatory bowel disease (e.g. Crohn's disease and ulcerative colitis), atherosclerosis and amyotrophic lateral sclerosis. Particularly, the autoimmune disease is selected from COPD, asthma, systemic lupus erythematosis, type I diabetes mellitus and inflammatory bowel disease.

In additional method of treatment aspects, this invention provides methods of prophylaxis and/or treatment of a mammal afflicted with autoimmune diseases, which methods comprise the administration of an effective amount of a compound of the invention or one or more of the pharmaceutical compositions herein described for the treatment or prophylaxis of said condition. In a particular embodiment, the autoimmune disease is selected from COPD, asthma (e.g intrinsic asthma, extrinsic asthma, dust asthma, infantily asthma) particularly chronic or inveterate asthma (for example late asthma and airway hyperreponsiveness), bronchitis, including bronchial asthma, systemic lupus erythematosus (SLE), cutaneous lupus erythrematosis, lupus nephritis, dermatomyositis, Sjogren's syndrome, multiple sclerosis, psoriasis, dry eye disease, type I diabetes mellitus and complications associated therewith, atopic eczema (atopic dermatitis), thyroiditis (Hashimoto's and autoimmune thyroiditis), contact dermatitis and further eczematous dermatitis, inflammatory bowel disease (e.g. Crohn's disease and ulcerative colitis), atherosclerosis and amyotrophic lateral sclerosis. Particularly, the autoimmune disease is selected from COPD, asthma, systemic lupus erythematosis, type I diabetes mellitus and inflammatory bowel disease.

In one embodiment, the present invention provides compounds of the invention or pharmaceutical compositions comprising a compound of the invention, for use in the prophylaxis and/or treatment of respiratory diseases. In a particular embodiment, the respiratory disease is selected from asthma, adult respiratory distress syndrome and allergic (extrinsic) asthma, non-allergic (intrinsic) asthma, acute severe asthma, chronic asthma, clinical asthma, nocturnal asthma, allergen-induced asthma, aspirin-sensitive asthma, exercise-induced asthma, isocapnic hyperventilation, child onset asthma, adult-onset asthma, cough-variant asthma, occupational asthma, steroid-resistant asthma, seasonal asthma, seasonal allergic rhinitis, perennial allergic rhinitis, chronic obstructive pulmonary disease, including chronic bronchitis or emphysema, pulmonary hypertension, interstitial lung fibrosis and/or airway inflammation and cystic fibrosis, and hypoxia.

In another embodiment, the present invention provides compounds of the invention, or pharmaceutical compositions comprising a compound of the invention for use in the manufacture of a medicament for use in the prophylaxis and/or treatment of respiratory diseases. In a particular embodiment, the respiratory disease is selected from asthma, adult respiratory distress syndrome and allergic (extrinsic) asthma, non-allergic (intrinsic) asthma, acute severe asthma, chronic asthma, clinical asthma, nocturnal asthma, allergen-induced asthma, aspirin-sensitive asthma, exercise-induced asthma, isocapnic hyperventilation, child onset asthma, adult-onset asthma, cough-variant asthma, occupational asthma, steroid-resistant asthma, seasonal asthma, seasonal allergic rhinitis, perennial allergic rhinitis, chronic obstructive pulmonary disease, including chronic bronchitis or emphysema, pulmonary hypertension, interstitial lung fibrosis and/or airway inflammation and cystic fibrosis, and hypoxia.

In additional method of treatment aspects, this invention provides methods of prophylaxis and/or treatment of a mammal afflicted with respiratory diseases, which methods comprise the administration of an effective amount of a compound of the invention or one or more of the pharmaceutical compositions herein described for the treatment or prophylaxis of said condition. In a particular embodiment, the respiratory disease is selected from asthma, adult respiratory distress syndrome and allergic (extrinsic) asthma, non-allergic (intrinsic) asthma, acute severe asthma, chronic asthma, clinical asthma, nocturnal asthma, allergen-induced asthma, aspirin-sensitive asthma, exercise-induced asthma, isocapnic hyperventilation, child onset asthma, adult-onset asthma, cough-variant asthma, occupational asthma, steroid-resistant asthma, seasonal asthma, seasonal allergic rhinitis, perennial allergic rhinitis, chronic obstructive pulmonary disease, including chronic bronchitis or emphysema, pulmonary hypertension, interstitial lung fibrosis and/or airway inflammation and cystic fibrosis, and hypoxia.

In one embodiment, the present invention provides compounds of the invention or pharmaceutical compositions comprising a compound of the invention, for use in the prophylaxis and/or treatment of cardiovascular diseases. In a particular embodiment, the cardiovascular disease is selected from arrhythmia (atrial or ventricular or both), atherosclerosis and its sequelae, angina, cardiac rhythm disturbances, myocardial ischemia, myocardial infarction, cardiac or vascular aneurysm, vasculitis, stroke, peripheral obstructive arteriopathy of a limb, an organ, or a tissue, reperfusion injury following ischemia of the brain, heart, kidney or other organ or tissue, endotoxic, surgical, or traumatic shock, hypertension, valvular heart disease, heart failure, abnormal blood pressure, shock, vasoconstriction (including that associated with migraines), vascular abnormality, inflammation, insufficiency limited to a single organ or tissue.

In another embodiment, the present invention provides compounds of the invention, or pharmaceutical compositions comprising a compound of the invention for use in the manufacture of a medicament for use in the prophylaxis and/or treatment of cardiovascular diseases. In a particular embodiment, the cardiovascular disease is selected from arrhythmia (atrial or ventricular or both), atherosclerosis and its sequelae, angina, cardiac rhythm disturbances, myocardial ischemia, myocardial infarction, cardiac or vascular aneurysm, vasculitis, stroke, peripheral obstructive arteriopathy of a limb, an organ, or a tissue, reperfusion injury following ischemia of the brain, heart, kidney or other organ or tissue, endotoxic, surgical, or traumatic shock, hypertension, valvular heart disease, heart failure, abnormal blood pressure, shock, vasoconstriction (including that associated with migraines), vascular abnormality, inflammation, insufficiency limited to a single organ or tissue.

In additional method of treatment aspects, this invention provides methods of prophylaxis and/or treatment of a mammal afflicted with cardiovascular diseases, which methods comprise the administration of an effective amount of a compound of the invention or one or more of the pharmaceutical compositions herein described for the treatment or prophylaxis of said condition. In a particular embodiment, the cardiovascular disease is selected from arrhythmia (atrial or ventricular or both), atherosclerosis and its sequelae, angina, cardiac rhythm disturbances, myocardial ischemia, myocardial infarction, cardiac or vascular aneurysm, vasculitis, stroke, peripheral obstructive arteriopathy of a limb, an organ, or a tissue, reperfusion injury following ischemia of the brain, heart, kidney or other organ or tissue, endotoxic, surgical, or traumatic shock, hypertension, valvular heart disease, heart failure, abnormal blood pressure, shock, vasoconstriction (including that associated with migraines), vascular abnormality, inflammation, insufficiency limited to a single organ or tissue.

In one embodiment, the present invention provides compounds of the invention or pharmaceutical compositions comprising a compound of the invention, for use in the prophylaxis and/or treatment of neurodegenerative diseases. In a particular embodiment, the neurodegenerative disease is selected from Alzheimer's disease and other dementias, brain cancer, degenerative nerve diseases, encephalitis, epilepsy, genetic brain disorders, head and brain malformations, hydrocephalus, stroke, Parkinson's disease, multiple sclerosis, amyotrophic lateral sclerosis (ALS or Lou Gehrig's Disease), Huntington's disease, and prion diseases.

In another embodiment, the present invention provides compounds of the invention, or pharmaceutical compositions comprising a compound of the invention for use in the manufacture of a medicament for use in the prophylaxis and/or treatment of neurodegenerative diseases. In a particular embodiment, the neurodegenerative disease is selected from Alzheimer's disease and other dementias, brain cancer, degenerative nerve diseases, encephalitis, epilepsy, genetic brain disorders, head and brain malformations, hydrocephalus, stroke, Parkinson's disease, multiple sclerosis, amyotrophic lateral sclerosis (ALS or Lou Gehrig's Disease), Huntington's disease, and prion diseases.

In additional method of treatment aspects, this invention provides methods of prophylaxis and/or treatment of a mammal afflicted with neurodegenerative diseases, which methods comprise the administration of an effective amount of a compound of the invention or one or more of the pharmaceutical compositions herein described for the treatment or prophylaxis of said condition. In a particular embodiment, the neurodegenerative disease is selected from Alzheimer's disease and other dementias, brain cancer, degenerative nerve diseases, encephalitis, epilepsy, genetic brain disorders, head and brain malformations, hydrocephalus, stroke, Parkinson's disease, multiple sclerosis, amyotrophic lateral sclerosis (ALS or Lou Gehrig's Disease), Huntington's disease, and prion diseases.

In one embodiment, the present invention provides compounds of the invention or pharmaceutical compositions comprising a compound of the invention, for use in the prophylaxis and/or treatment of dermatological disorders. In a particular embodiment, the dermatological disease is selected from atopic dermatitis, bullous disorders, collagenoses, psoriasis, psoriatic lesions, dermatitis, contact dermatitis, eczema, pruritus, urticaria, rosacea, scleroderma, wound healing, scarring, hypertrophic scarring, keloids, Kawasaki Disease, rosacea, or Sjogren-Larsso Syndrome.

In another embodiment, the present invention provides compounds of the invention, or pharmaceutical compositions comprising a compound of the invention for use in the manufacture of a medicament for use in the prophylaxis and/or treatment of dermatological disorders. In a particular embodiment, the dermatological disease is selected from atopic dermatitis, bullous disorders, collagenoses, psoriasis, psoriatic lesions, dermatitis, contact dermatitis, eczema, pruritus, urticaria, rosacea, scleroderma, wound healing, scarring, hypertrophic scarring, keloids, Kawasaki Disease, rosacea, or Sjogren-Larsso Syndrome.

In additional method of treatment aspects, this invention provides methods of prophylaxis and/or treatment of a mammal afflicted with dermatological disorders, which methods comprise the administration of an effective amount of a compound of the invention or one or more of the pharmaceutical compositions herein described for the treatment or prophylaxis of said condition. In a particular embodiment, the dermatological disease is selected from atopic dermatitis, bullous disorders, collagenoses, psoriasis, psoriatic lesions, dermatitis, contact dermatitis, eczema, pruritus, urticaria, rosacea, scleroderma, wound healing, scarring, hypertrophic scarring, keloids, Kawasaki Disease, rosacea, or Sjogren-Larsso Syndrome.

In one embodiment, the present invention provides compounds of the invention or pharmaceutical compositions comprising a compound of the invention, for use in the prophylaxis and/or treatment of abnormal angiogenesis associated diseases. In a particular embodiment, the abnormal angiogenesis associated disease is selected from atherosclerosis, hypertension, tumor growth, inflammation, rheumatoid arthritis, wet-form macular degeneration, choroidal neovascularization, retinal neovascularization, diabetic retinopathy, and glioblastoma multiforma.

In another embodiment, the present invention provides compounds of the invention, or pharmaceutical compositions comprising a compound of the invention for use in the manufacture of a medicament for use in the prophylaxis and/or treatment of abnormal angiogenesis associated diseases. In a particular embodiment, the abnormal angiogenesis associated disease is selected from atherosclerosis, hypertension, tumor growth, inflammation, rheumatoid arthritis, wet-form macular degeneration, choroidal neovascularization, retinal neovascularization, diabetic retinopathy, and glioblastoma multiforma.

In additional method of treatment aspects, this invention provides methods of prophylaxis and/or treatment of a mammal afflicted with abnormal angiogenesis associated diseases, which methods comprise the administration of an effective amount of a compound of the invention or one or more of the pharmaceutical compositions herein described for the treatment or prophylaxis of said condition. In a particular embodiment, the abnormal angiogenesis associated disease is selected from atherosclerosis, hypertension, tumor growth, inflammation, rheumatoid arthritis, wet-form macular degeneration, choroidal neovascularization, retinal neovascularization, diabetic retinopathy, and glioblastoma multiforma.

Injection dose levels range from about 0.1 mg/kg/h to at least 10 mg/kg/h, all for from about 1 to about 120 h and especially 24 to 96 h. A preloading bolus of from about 0.1 mg/kg to about 10 mg/kg or more may also be administered to achieve adequate steady state levels. The maximum total dose is not expected to exceed about 1 g/day for a 40 to 80 kg human patient.

For the prophylaxis and/or treatment of long-term conditions, such as degenerative conditions, the regimen for treatment usually stretches over many months or years so oral dosing is preferred for patient convenience and tolerance. With oral dosing, one to four (1-4) regular doses daily, especially one to three (1-3) regular doses daily, typically one to two (1-2) regular doses daily, and most typically one (1) regular dose daily are representative regimens. Alternatively for long lasting effect drugs, with oral dosing, once every other week, once weekly, and once a day are representative regimens. In particular, dosage regimen can be every 1-14 days, more particularly 1-10 days, even more particularly 1-7 days, and most particularly 1-3 days.

Using these dosing patterns, each dose provides from about 1 to about 1000 mg of a compound of the invention, with particular doses each providing from about 10 to about 500 mg and especially about 30 to about 250 mg.

Transdermal doses are generally selected to provide similar or lower blood levels than are achieved using injection doses.

When used to prevent the onset of a condition, a compound of the invention will be administered to a patient at risk for developing the condition, typically on the advice and under the supervision of a physician, at the dosage levels described above. Patients at risk for developing a particular condition generally include those that have a family history of the condition, or those who have been identified by genetic testing or screening to be particularly susceptible to developing the condition.

A compound of the invention can be administered as the sole active agent or it can be administered in combination with other therapeutic agents, including other compound of the inventions that demonstrate the same or a similar therapeutic activity and that are determined to be safe and efficacious for such combined administration. In a specific embodiment, co-administration of two (or more) agents allows for significantly lower doses of each to be used, thereby reducing the side effects seen.

In one embodiment, a compound of the invention or a pharmaceutical composition comprising a compound of the invention is administered as a medicament. In a specific embodiment, said pharmaceutical composition additionally comprises a further active ingredient.

In one embodiment, a compound of the invention is co-administered with another therapeutic agent for the treatment and/or prophylaxis of a disease involving inflammation, particular agents include, but are not limited to, immunoregulatory agents e.g. azathioprine, corticosteroids (e.g. prednisolone or dexamethasone), cyclophosphamide, cyclosporin A, tacrolimus, mycophenolate, mofetil, muromonab-CD3 (OKT3, e.g. Orthocolone®), ATG, aspirin, acetaminophen, ibuprofen, naproxen, and piroxicam.

In one embodiment, a compound of the invention is co-administered with another therapeutic agent for the treatment and/or prophylaxis of arthritis (e.g. rheumatoid arthritis), particular agents include but are not limited to analgesics, non-steroidal anti-inflammatory drugs (NSAIDS), steroids, synthetic DMARDS (for example but without limitation methotrexate, leflunomide, sulfasalazine, auranofin, sodium aurothiomalate, penicillamine, chloroquine, hydroxychloroquine, azathioprine, tofacitinib, baricitinib, fostamatinib, and cyclosporin), and biological DMARDS (for example but without limitation infliximab, etanercept, adalimumab, rituximab, and abatacept).

In one embodiment, a compound of the invention is co-administered with another therapeutic agent for the treatment and/or prophylaxis of proliferative disorders, particular agents include but are not limited to: methotrexate, leukovorin, adriamycin, prednisone, bleomycin, cyclophosphamide, 5-fluorouracil, paclitaxel, docetaxel, vincristine, vinblastine, vinorelbine, doxorubicin, tamoxifen, toremifene, megestrol acetate, anastrozole, goserelin, anti-HER2 monoclonal antibody (e.g. Herceptin™), capecitabine, raloxifene hydrochloride, EGFR inhibitors (e.g. Lressa®, Tarceva™, Erbitux™), VEGF inhibitors (e.g. Avastin™), proteasome inhibitors (e.g. Velcade™), Glivec® and hsp90 inhibitors (e.g. 17-AAG). Additionally, the compound of the invention according to Formula I may be administered in combination with other therapies including, but not limited to, radiotherapy or surgery. In a specific embodiment the proliferative disorder is selected from cancer, myeloproliferative disease or leukaemia.

In one embodiment, a compound of the invention is co-administered with another therapeutic agent for the treatment and/or prophylaxis of autoimmune diseases, particular agents include but are not limited to: glucocorticoids, cytostatic agents (e.g. purine analogs), alkylating agents (e.g nitrogen mustards (cyclophosphamide), nitrosoureas, platinum compound of the inventions, and others), antimetabolites (e.g. methotrexate, azathioprine and mercaptopurine), cytotoxic antibiotics (e.g. dactinomycin anthracyclines, mitomycin C, bleomycin, and mithramycin), antibodies (e.g. anti-CD20, anti-CD25 or anti-CD3 (OTK3) monoclonal antibodies, Atgam® and Thymoglobuline®), cyclosporin, tacrolimus, rapamycin (sirolimus), interferons (e.g. IFN-β), TNF binding proteins (e.g. infliximab, etanercept, or adalimumab), mycophenolate, fingolimod and myriocin.

In one embodiment, a compound of the invention is co-administered with another therapeutic agent for the treatment and/or prophylaxis of transplant rejection, particular agents include but are not limited to: calcineurin inhibitors (e.g. cyclosporin or tacrolimus (FK506)), mTOR inhibitors (e.g. sirolimus, everolimus), anti-proliferatives (e.g. azathioprine, mycophenolic acid), corticosteroids (e.g. prednisolone, hydrocortisone), antibodies (e.g. monoclonal anti-IL-2Ra receptor antibodies, basiliximab, daclizumab), polyclonal anti-T-cell antibodies (e.g. anti-thymocyte globulin (ATG), anti-lymphocyte globulin (ALG)).

In one embodiment, a compound of the invention is co-administered with another therapeutic agent for the treatment and/or prophylaxis of asthma and/or rhinitis and/or COPD, particular agents include but are not limited to: beta2-adrenoceptor agonists (e.g. salbutamol, levalbuterol, terbutaline and bitolterol), epinephrine (inhaled or tablets), anticholinergics (e.g. ipratropium bromide), glucocorticoids (oral or inhaled). Long-acting β2-agonists (e.g. salmeterol, formoterol, bambuterol, and sustained-release oral albuterol), combinations of inhaled steroids and long-acting bronchodilators (e.g. fluticasone/salmeterol, budesonide/formoterol), leukotriene antagonists and synthesis inhibitors (e.g. montelukast, zafirlukast and zileuton), inhibitors of mediator release (e.g. cromoglycate and ketotifen), biological regulators of IgE response (e.g. omalizumab), antihistamines (e.g. ceterizine, cinnarizine, fexofenadine) and vasoconstrictors (e.g. oxymethazoline, xylomethazoline, nafazoline and tramazoline).

Additionally, a compound of the invention may be administered in combination with emergency therapies for asthma and/or COPD, such therapies include oxygen or heliox administration, nebulized salbutamol or terbutaline (optionally combined with an anticholinergic (e.g. ipratropium), systemic steroids (oral or intravenous, e.g. prednisone, prednisolone, methylprednisolone, dexamethasone, or hydrocortisone), intravenous salbutamol, non-specific beta-agonists, injected or inhaled (e.g. epinephrine, isoetharine, isoproterenol, metaproterenol), anticholinergics (IV or nebulized, e.g. glycopyrrolate, atropine, ipratropium), methylxanthines (theophylline, aminophylline, bamiphylline), inhalation anesthetics that have a bronchodilatory effect (e.g. isoflurane, halothane, enflurane), ketamine and intravenous magnesium sulfate.

In one embodiment, a compound of the invention is co-administered with another therapeutic agent for the treatment and/or prophylaxis of inflammatory bowel disease (IBD), particular agents include but are not limited to: glucocorticoids (e.g. prednisone, budesonide) synthetic disease modifying, immunomodulatory agents (e.g. methotrexate, leflunomide, sulfasalazine, mesalazine, azathioprine, 6-mercaptopurine and cyclosporin) and biological disease modifying, immunomodulatory agents (infliximab, adalimumab, rituximab, and abatacept).

In one embodiment, a compound of the invention is co-administered with another therapeutic agent for the treatment and/or prophylaxis of SLE, particular agents include but are not limited to: human monoclonal antibodies (belimumab (Benlysta)), Disease-modifying antirheumatic drugs (DMARDs) such as antimalarials (e.g. plaquenil, hydroxychloroquine), immunosuppressants (e.g. methotrexate and azathioprine), cyclophosphamide and mycophenolic acid, immunosuppressive drugs and analgesics, such as nonsteroidal anti-inflammatory drugs, opiates (e.g. dextropropoxyphene and co-codamol), opioids (e.g. hydrocodone, oxycodone, MS Contin, or methadone) and the fentanyl duragesic transdermal patch.

In one embodiment, a compound of the invention is co-administered with another therapeutic agent for the treatment and/or prophylaxis of psoriasis, particular agents include but are not limited to: topical treatments such as bath solutions, moisturizers, medicated creams and ointments containing coal tar, dithranol (anthralin), corticosteroids like desoximetasone (Topicort™), fluocinonide, vitamin D3 analogues (for example, calcipotriol), argan oil and retinoids (etretinate, acitretin, tazarotene), systemic treatments such as methotrexate, cyclosporine, retinoids, tioguanine, hydroxyurea, sulfasalazine, mycophenolate mofetil, azathioprine, tacrolimus, fumaric acid esters or biologics such as Amevive™, Enbrel™, Humira™, Remicade™, Raptiva™ and ustekinumab (a IL-12 and IL-23 blocker). Additionally, a compound of the invention may be administered in combination with other therapies including, but not limited to phototherapy, or photochemotherapy (e.g. psoralen and ultraviolet A phototherapy (PUVA)).

In one embodiment, a compound of the invention is co-administered with another therapeutic agent for the treatment and/or prophylaxis of allergic reaction, particular agents include but are not limited to: antihistamines (e.g. cetirizine, diphenhydramine, fexofenadine, levocetirizine), glucocorticoids (e.g. prednisone, betamethasone, beclomethasone, dexamethasone), epinephrine, theophylline or anti-leukotrienes (e.g. montelukast or zafirlukast), anti-cholinergics and decongestants.

By co-administration is included any means of delivering two or more therapeutic agents to the patient as part of the same treatment regime, as will be apparent to the skilled person. Whilst the two or more agents may be administered simultaneously in a single formulation, i.e. as a single pharmaceutical composition, this is not essential. The agents may be administered in different formulations and at different times.

Chemical Synthetic Procedures

General

The compound of the invention can be prepared from readily available starting materials using the following general methods and procedures. It will be appreciated that where typical or preferred process conditions (i.e. reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures.

Additionally, as will be apparent to those skilled in the art, conventional protecting groups may be necessary to prevent certain functional groups from undergoing undesired reactions. The choice of a suitable protecting group for a particular functional group as well as suitable conditions for protection and deprotection are well known in the art (Greene, T W; Wuts, P G M; 1991).

The following methods are presented with details as to the preparation of a compound of the invention as defined hereinabove and the comparative examples. A compound of the invention may be prepared from known or commercially available starting materials and reagents by one skilled in the art of organic synthesis.

All reagents were of commercial grade and were used as received without further purification, unless otherwise stated. Commercially available anhydrous solvents were used for reactions conducted under inert atmosphere. Reagent grade solvents were used in all other cases, unless otherwise specified. Column chromatography was performed on silica gel 60 (35-70 μm). Thin layer chromatography was carried out using pre-coated silica gel F-254 plates (thickness 0.25 mm). $^1$H NMR spectra were recorded on a Bruker DPX 400 NMR spectrometer (400 MHz or a Bruker Advance 300 NMR spectrometer (300 MHz). Chemical shifts (δ) for 1H NMR spectra are reported in parts per million (ppm) relative to tetramethylsilane (δ 0.00) or the appropriate residual solvent peak, i.e. $CHCl_3$ (δ 7.27), as internal reference. Multiplicities are given as singlet (s), doublet (d), triplet (t), quartet (q), quintuplet (quin), multiplet (m) and broad (br). Electrospray MS spectra were obtained on a Waters platform LC/MS spectrometer or with Waters Acquity UPLC with Waters Acquity PDA detector and SQD mass spectrometer. Columns used: UPLC BEH C18 1.7 μm 2.1×5 mm VanGuard Pre-column with Acquity UPLC BEH C18 1.7 μm 2.1×30 mm Column or Acquity UPLC BEH C18 1.7 μm 2.1×50 mm Column. All the methods are using MeCN/$H_2O$ gradients. MeCN and $H_2O$ contain either 0.1% Formic Acid or $NH_3$ (10 mM). LC-MS columns used: Waters XBridge Prep OBD C18 5 μm 30 mm ID×100 mm L (preparative column) and Waters XBridge BEH C18 5 μm 4.6 mm ID×100 mm L (analytical column). All the methods are using either MeOH/$H_2O$ or MeCN/$H_2O$ gradients. MeOH, MeCN and $H_2O$ contain either 0.1% Formic Acid or 0.1% Diethylamine. Microwave heating was performed with a Biotage Initiator. Celpure® P65 is a filtration aid, commercial product (cas number 61790-53-2).

List of abbreviations used in the experimental section:

| | |
|---|---|
| μL | microliter |
| APMA | 4-aminophenylmercuric acetate |
| app t | Apparent triplet |
| AUC | Area Under the Curve |
| BAL | Broncho-alveolar lavage |
| BALF | Broncho-alveolar lavage fluid |
| bd | Broad doublet |
| Boc | tert-Butyloxy-carbonyl |
| bs | Broad singlet |
| BSA | Bovine serum albumine |
| bt | Broad triplet |
| Cat. | Catalytic amount |
| cDNA | copy deoxyribonucleic acid |
| d | doublet |
| DavePhos | 2-Dicyclohexylphosphino-2'-(N,N-dimethylamino)biphenyl |
| DCM | Dichloromethane |
| DDQ | 2,3-Dichloro-5,6-dicyano-1,4-benzoquinone |
| DEAD | diethyl azodicarboxylate |
| Desc'd | Described in details |
| DIAD | Diisopropyl azodicarboxylate |
| DIPE | Diisopropylether |
| DIPEA | N,N-diisopropylethylamine |
| DMA | Dimethylacetamide |
| DMF | N,N-dimethylformamide |
| DMSO | Dimethylsulfoxide |
| dppf | 1,1'-Bis(diphenylphosphino) ferrocene |
| EDC | 1-ethyl-3-(3-dimethylaminopropyl)carbodiimide) |
| EDC•HCl | N-(3-Dimethylaminopropyl)-N'-ethylcarbodiimide hydrochloride |
| eq. | Equivalent |
| $Et_2O$ | Diethyl ether |
| EtOAc | Ethyl acetate |
| EtOH | Ethanol |
| FBS | Fetal bovine serum |
| FITC | Fluorescein Isothiocyanate |
| Fmoc | 9-Fluorenylmethoxycarbonyl |
| g | gram |
| h | hour |
| HOBt | Hydroxybenzotriazole |
| HPLC | High pressure liquid chromatography |
| HRP | horseradish peroxydase |
| Int | Intermediate |

| | |
|---|---|
| JohnPhos | (2-Biphenyl)di-tert-butylphosphine |
| kg | kilogram |
| L | liter |
| LC-MS | Liquid Chromatography-Mass Spectrometry |
| LPC | lysophosphatidylcholine |
| m | multiplet |
| MeCN | Acetonitrile |
| MeOH | Methanol |
| mg | milligram |
| min | minute |
| mL | milliliter |
| mmol | millimoles |
| MMP | Matrix Metallo Proteinase |
| MS Ms'd | Mass measured by LC-MS |
| MW | Molecular weight |
| N.A. | Not available |
| NBS | N-Bromosuccinimide |
| nBuOH | n-Butanol |
| NMR | Nuclear Magnetic Resonance |
| PBF | phosphate buffered formalin |
| PBS | Phosphate buffered saline |
| PCR | Polymerase chain reaction |
| Pd(PPh$_3$)$_4$ | Tetrakis(triphenylphosphine)palladium(0) |
| Pd/C | Palladium on Carbon 10% |
| Pd$_2$(dba)$_3$ | Tris(dibenzylideneacetone)dipalladium(0) |
| PdCl$_2$dppf | [1,1'-Bis(diphenylphosphino)ferrocene]dichloropalladium(II) |
| PEG | Polyethylene glycol |
| ppm | part-per-million |
| q | quartet |
| QrtPCR | quantitative real-time PCR |
| QTL | quantitative trait loci |
| r.t. | Room temperature |
| RNA | Ribonucleic acid |
| Rt | retention time |
| s | singlet |
| sept | septuplet |
| t | triplet |
| TEA | Triethylamine |
| TFA | Trifluoroacetic acid |
| THF | Tetrahydrofuran |
| TOOS | (N-ethyl-N-(2-hydroxy-3-sulfopropyl)-3-methylaniline, sodium salt dihydrate |
| TS | Tobacco smoke |
| XantPhos | 4,5-Bis(diphenylphosphino)-9,9-dimethylxanthene |

Synthetic Preparation of the Compounds of the Invention

Example 1

General Synthetic Methods 1.1. Synthetic Methods Overview

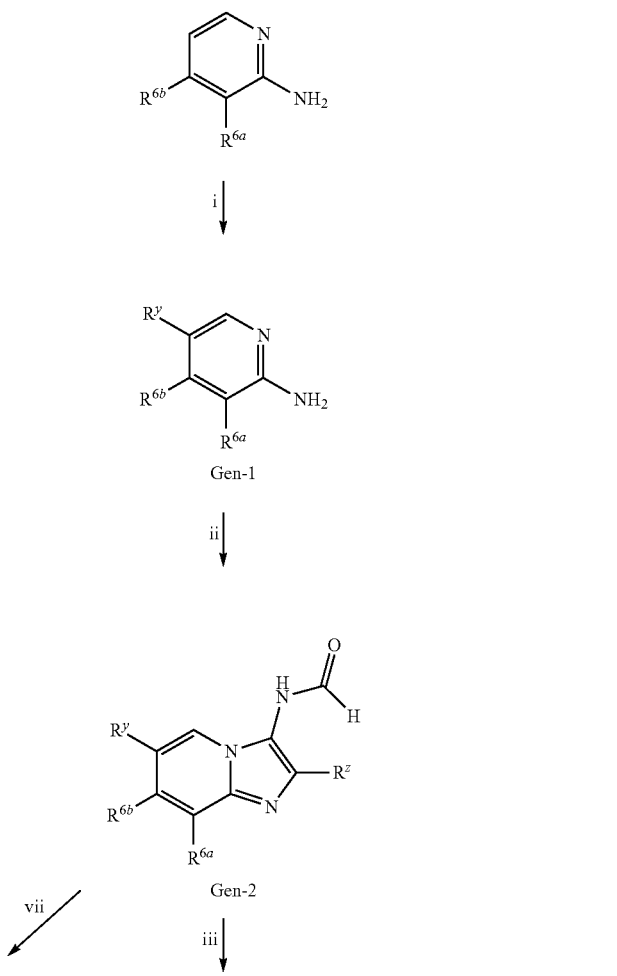

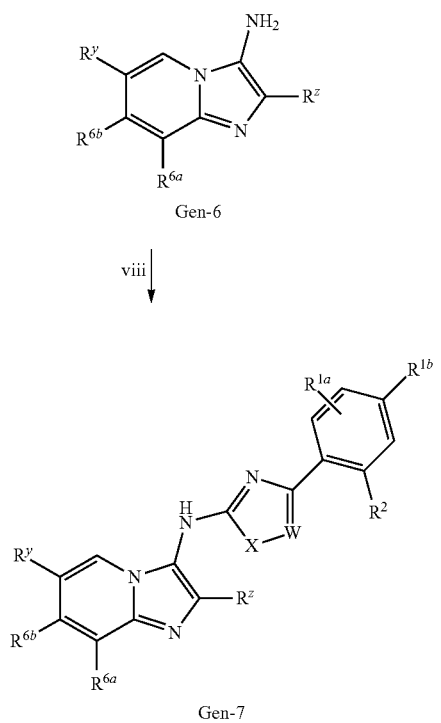

Gen-6

Gen-7

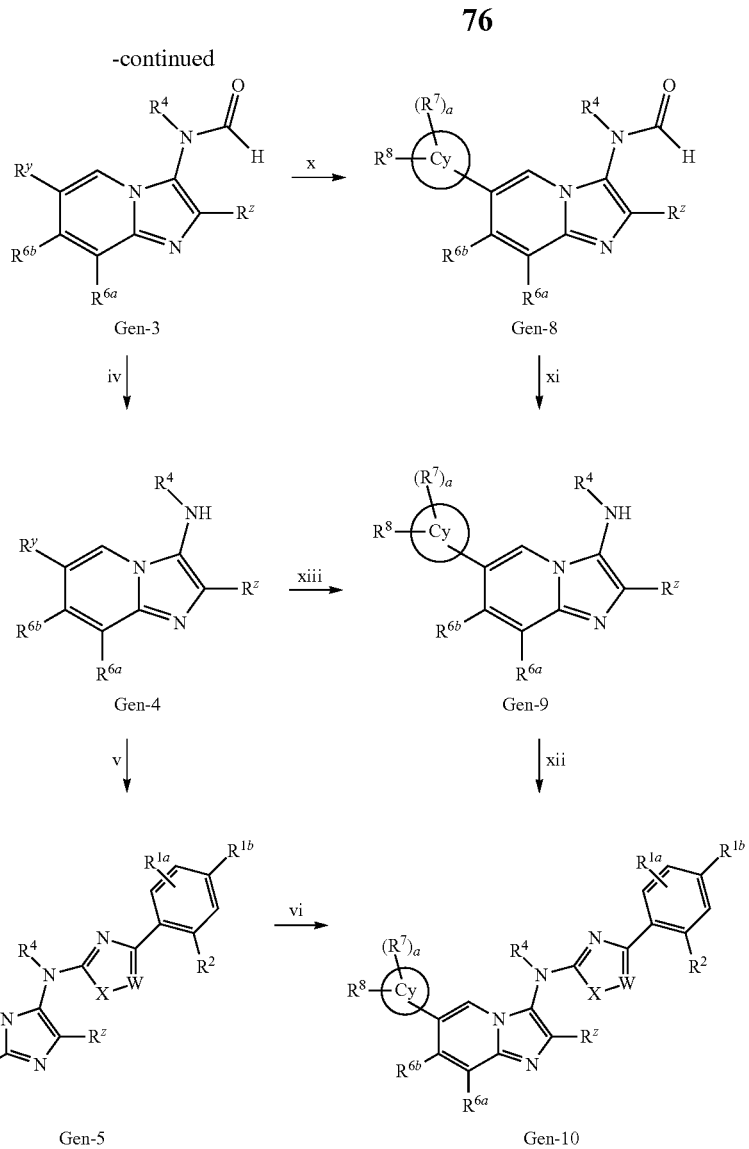

-continued

Gen-3

Gen-8

Gen-4

Gen-9

Gen-5

Gen-10

Where $R^y$ is halo, $NO_2$, or —C(=O)Oalkyl, $R^z$ is $R^5$ or an alkyl, alkenyl or carbonyl group optionally substituted.
Step i: Method A
Step ii: consists in one of the following methods
 B1 (2 steps): Route using isonitrile reagent then reaction with HCOOH
 B2 (2 steps): Route using KCN then reaction with HCOOH
Step iii: consists in one of the following methods
 C1: Alkylation with NaH as base in DMF
 C2: Alkylation with $K_2CO_3$ as base in acetone
Step iv: consists in one of the following methods
 D1: Deformylation under acid conditions
 D2: Deformylation under basic conditions
Step v: consists in one of the following methods
 E1 (2 steps): formation of thiourea then cyclisation to give thiazole derivative
 E2: Aromatic or heteroaromatic nucleophilic substitution
 E3 (3 steps): formation of thiourea, methylation, then cyclisation to give oxadiazole derivative
 C1: NaH, DMF Step vi: consists in one of several of the following methods
 F1: Buchwald coupling
 F2: Suzuki coupling
 F3: Negishi coupling
 F4: Copper mediated coupling
 F5: Boc deprotection
 F6: Reduction with ($H_2$) in presence of transition metal catalyst
 F7: Boc protection
 F8: Alkylation
 F9a and F9b: Amide bond forming reaction
 F10: Reductive amination
 F11: Sulfonylation
 F12a and F12b: Nucleophilic substitution
 F13: Saponification
 F14: Introduction of hydroxymethyl group
 F15: Introduction of trifluoroacetyl group
 F16a and F16b: Halogenation
 F17: Copper mediated cyanation
 F18: Reduction with lithium borohydride
 F19: Synthesis of oxazoline
Step vii: consists in one of methods D
Step viii: consists in one of methods E or method H Step ix: consists in one of methods C Step x: consists in one or several methods F Step xi: consists in one of methods D Step xii: consists in one or several methods E and F E1 (2 steps): formation of thiourea then cyclisation to give thiazole derivative E4: Buchwald coupling E5 (2 steps): SNAr then Suzuki coupling Step xiii: consists in one or several methods F

1.2. General Methods

1.2.1. General Method A: Synthesis of Intermediate Gen-1

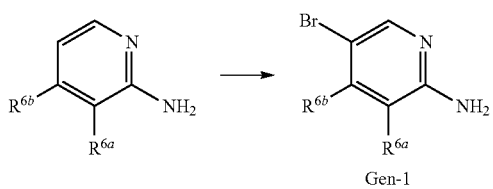

Gen-1

To a solution of amino-pyridine derivative (1 eq.) in MeCN under argon at 0° C. is added NBS (0.5 eq.). The reaction mixture is stirred at r.t. for 1 h then cooled to 0° C. before introducing additional NBS (0.5 eq.). The reaction mixture is stirred at r.t. for 1 h then diluted in EtOAc. The organic layer is washed with a saturated NaHCO$_3$ solution, dried over Na$_2$SO$_4$, filtered and concentrated in vacuo. The residue is diluted in DCM, washed with a 1 M NaOH solution. The organic phase is dried over Na$_2$SO$_4$, filtered and concentrated in vacuo to give Intermediate Gen-1.

1.2.2. Illustrative Synthesis of Intermediate Gen-1-a: 2-amino-5-bromo-3-fluoropyridine

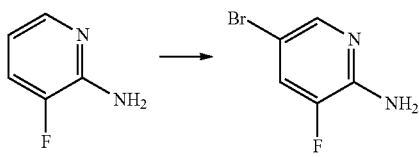 [SMILES: Nc1ncccc1F ; Nc1ncc(Br)cc1F]

To a solution of 2-amino-3-fluoro-pyridine (9.4 g, 83.1 mmol, 1 eq.) in MeCN (470 mL) under argon at 0° C. was added NBS (7.4 g, 41.5 mmol, 0.5 eq.). The reaction mixture was stirred at r.t. for 1 h then cooled to 0° C. before introducing additional NBS (7.39 g, 41.5 mmol, 0.5 eq.). The reaction mixture was stirred at r.t. for 1 h then diluted in EtOAc. The organic layer was washed with a saturated NaHCO$_3$ solution, dried over Na$_2$SO$_4$, filtered and concentrated in vacuo. The residue was diluted in DCM, washed with a 1 N NaOH solution. The organic phase was dried over Na$_2$SO$_4$, filtered and concentrated in vacuo to afford Intermediate Gen-1-a (2-amino-5-bromo-3-fluoropyridine).

LC-MS: MW (calcd): 190 ($^{79}$Br), 192 ($^{81}$Br); m/z MW (obsd): 191 ($^{79}$Br M+1), 193 ($^{81}$Br M+1)

1.2.3. General Methods B1 and B2: Synthesis of Intermediate Gen-2

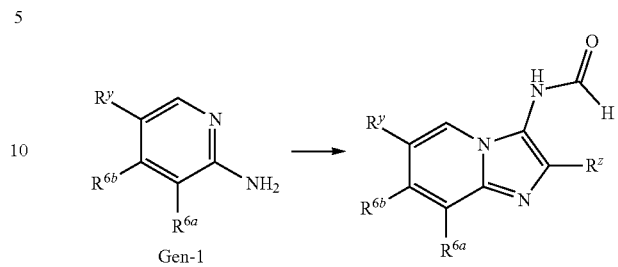

1.2.3.1. General Method B1

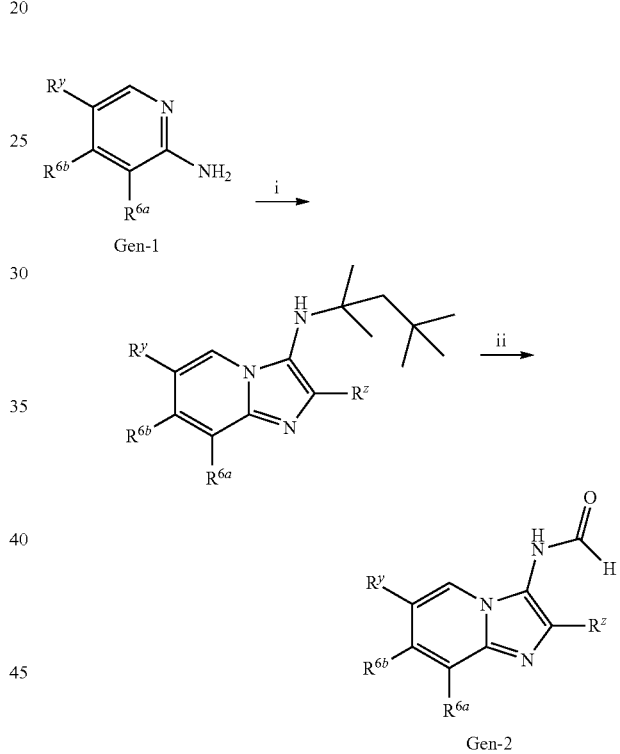

Step i)

To a solution of amino-pyridine derivative Gen-1 (1 eq.) in nBuOH under argon are added successively the aldehyde R$^z$CHO (2.5 eq.), MgCl$_2$ (0.04 eq.) and 1,1,3,3-tetramethylbutyl isocyanide (1.15 eq.). The reaction mixture is heated at 130° C. for 3.5 h, and then concentrated in vacuo. The residue is partitioned between heptane and water, stirred for 15 min and filtered on Celpure® P65. The resulting solid is then dissolved with DCM, dried over Na$_2$SO$_4$, filtered and concentrated in vacuo to afford the expected amine.

Step ii)

A solution of the above prepared compound (1 eq.) in formic acid is heated at 80° C. for 1 h. The reaction mixture is concentrated in vacuo. The residue is then triturated in Et$_2$O. The formed precipitate is filtered, rinsed and dried to afford Intermediate Gen-2.

1.2.3.2. Illustrative Synthesis of Intermediate Gen-2-a: N-(6-Bromo-2-ethyl-8-fluoro-imidazo[1,2-a]pyridin-3-yl)-formamide

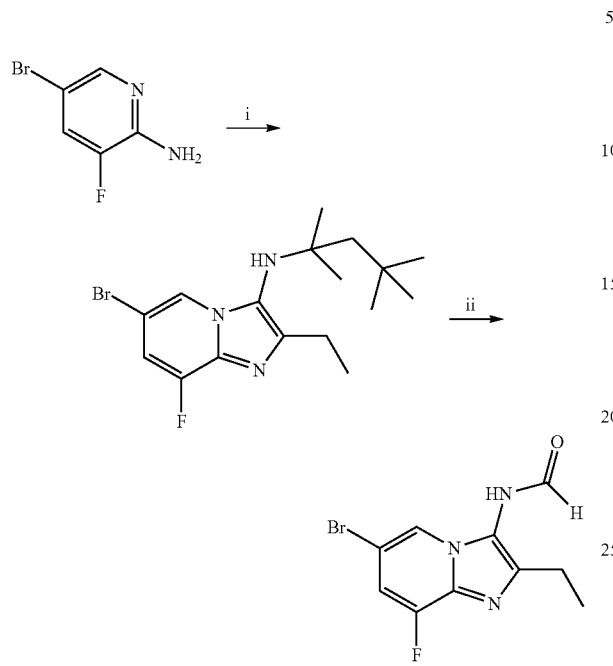

Step i)

To a solution of 2-amino-3-Fluoro-4-bromo-pyridine (Gen-1-a) (2 g, 10.5 mmol, 1 eq.) in nBuOH (12 mL) under argon were added successively propionaldehyde (1.9 mL, 26.2 mmol, 2.5 eq.), $MgCl_2$ (40 mg, 0.42 mmol, 0.04 eq.) and 1,1,3,3-tetramethylbutyl isocyanide (2.1 mL, 12 mmol, 1.15 eq.). The reaction mixture was heated at 130° C. for 3.5 h, then concentrated in vacuo.

The residue was partitioned between heptane (10 mL) and water (20 mL), stirred for 15 min and filtered on Celpure® P65. The resulting solid was then dissolved with DCM, dried over $Na_2SO_4$, filtered and concentrated in vacuo to afford the corresponding amine. The filtrate was further extracted with DCM, the combined organic layers were washed with water, a 1 M NaOH solution, and brine dried over $Na_2SO_4$, filtered and concentrated in vacuo to deliver a second batch of the expected amine.

$^1$H NMR δ (ppm) (400 MHz, $CDCl_3$): 8.11 (1H, s), 6.90 (1H, d), 2.85-2.80 (1H, m), 2.76 (2H, q), 1.67 (2H, s), 1.37 (3H, t), 1.16 (6H, s), 1.11 (9H, s).

LC-MS: MW (calcd): 369 ($^{79}$Br), 371 ($^{81}$Br); m/z MW (obsd): 370 ($^{79}$Br M+1), 372 ($^{81}$Br M+1)

Step ii)

A solution of amine (2.9 g, 7.83 mmol, 1 eq.) in formic acid (23 mL) was heated at 80° C. for 1 h. The reaction mixture was then concentrated in vacuo. The residue was triturated in toluene and evaporated twice. The resulting solid was taken up in $Et_2O$, stirred for 45 min, then filtered, rinsed and dried to afford Intermediate Gen-2-a.

$^1$H NMR δ (ppm) (400 MHz, $CDCl_3$): 2 rotamers 8.55 (1H, s), 8.15 (1H, d), 7.95 (1H, s), 7.76 (1H, s), 7.54-7.44 (1H, m), 7.13-6.96 (3H, m), 2.80 (2H, q), 2.74 (2H, q), 1.33 (3H, t), 1.31 (3H, t).

LC-MS: MW (calcd): 285 ($^{79}$Br), 287 ($^{81}$Br); m/z MW (obsd): 286 ($^{79}$Br M+1), 288 ($^{81}$Br M+1)

1.2.3.3. General Method B2

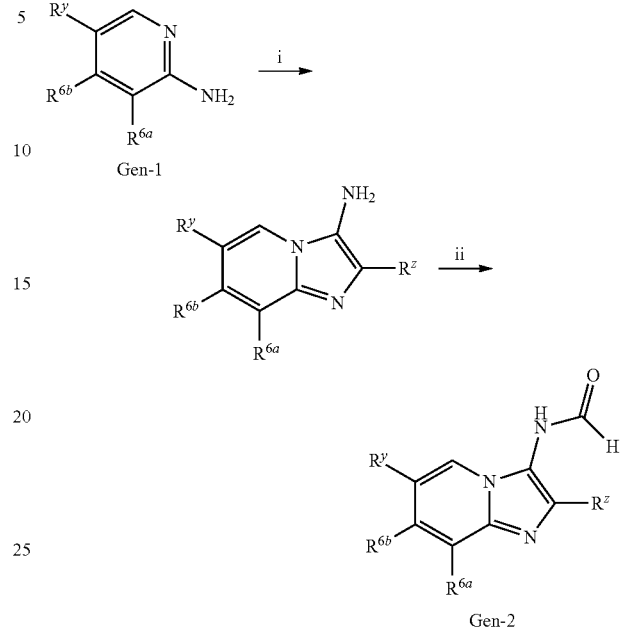

Step i)

To a suspension of amino-pyridine derivative Gen-1 (1 eq.) in toluene are added the aldehyde $R^z$CHO (1 eq.) and benzotriazole (1 eq.). The mixture is stirred at r.t. overnight. Additional aldehyde reagent (0.06 eq.) and benzotriazole (0.06 eq.) are added. After 4 h stirring, potassium cyanide (1.2 eq.) is added, followed by EtOH. The reaction mixture is stirred at r.t. for 5 days. The crude product mixture is then quenched with a 3 M NaOH solution. Solvents are evaporated carefully in vacuo. The residue is diluted with water and EtOAc. The aqueous layer is extracted with EtOAc. The combined organic layers are washed with water and brine, dried over $Na_2SO_4$ and concentrated in vacuo. The crude product mixture is dissolved in EtOH and carefully added to a solution of acetyl chloride (2.1 eq.) in EtOH at 0° C. The resulting reaction mixture is stirred at r.t. overnight and then concentrated to dryness to afford the corresponding imidazo[1,2-a]pyridin-3-ylamine as hydrochloride salt.

Step ii)

A solution of the above prepared imidazo[1,2-a]pyridin-3-ylamine hydrochloride salt (1 eq.) in formic acid is heated at 90° C. for 2 h. Solvents are evaporated in vacuo. The residue is dissolved in water. The mixture is carefully basified with a saturated $NaHCO_3$ solution until pH 8-9 is reached. The formed solid is filtered, washed with water and DIPE and dried to afford Intermediate Gen-2.

1.2.3.4. Illustrative Synthesis of Intermediate Gen-2-d: N-(6-Bromo-2-ethyl-8-methyl-imidazo[1,2-a]pyridin-3-yl)-formamide

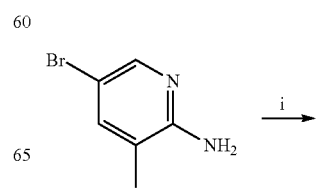

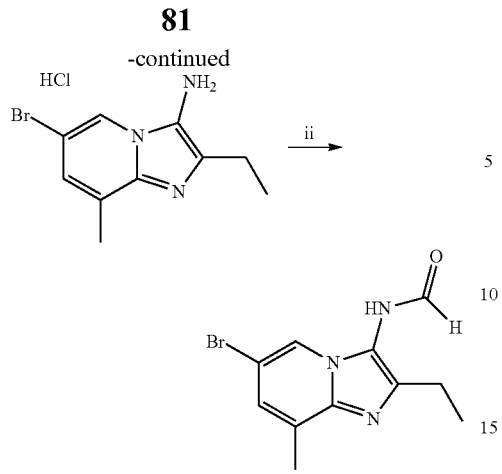

Step i)
To a suspension of 2-amino-5-bromo-3-methylpyridine (420 g, 2.24 mol, 1 eq.) previously washed with a saturated NaHCO₃ solution before use in 1.5 L of toluene under nitrogen were added propionaldehyde (248 mL, 3.36 mol, 1.5 eq.) and 1H-benzotriazole (281 g, 2.36 mol, 1.05 eq.). The resulting mixture was stirred 4 h at r.t. before adding 3.5 L of EtOH and potassium cyanide (175 g, 2.70 mol, 1.2 eq.). The reaction mixture was further stirred overnight at r.t. and 2 h at 78° C. After cooling to r.t., the mixture was quenched by addition of a 2.5 M NaOH solution (3 L).

This experiment was performed in four batches with the same quantities of reagents, the crude mixture were then pooled together and concentrated in vacuo. The remaining oil was diluted with EtOAc (15 L) and washed with a 2 M NaOH solution (2×2 L). The aqueous layer was extracted twice with EtOAc (2×1 L). The combined organic layers were then dried over Na₂SO₄, filtered and concentrated in vacuo. The crude mixture was dissolved in EtOH (2 L) and carefully added to a solution of acetyl chloride (1 L, 14.0 mol, 1.6 eq.) in EtOH (6 L). The resulting reaction mixture was stirred at r.t. overnight and then concentrated to dryness. The residue was triturated in DCM (7 L) for 3 days, the precipitate formed was collected, washed with DCM (2×500 mL) and dried to afford 6-Bromo-2-ethyl-8-methyl-imidazo[1,2-a]pyridin-3-ylamine as a hydrochloride salt.

¹H NMR δ (ppm) (400 MHz, DMSO): 8.70 (1H, s), 7.75 (1H, s), 4.86 (3H, bs), 2.81 (2H, q), 2.56 (3H, s), 1.56 (3H, s).

LC-MS: MW (calcd): 253 (⁷⁹Br), 255 (⁸¹Br); m/z MW (obsd): 254 (⁷⁹Br M+1), 256 (⁸¹Br M+1)

Step ii)
A suspension of the above prepared 6-bromo-2-ethyl-8-methyl-imidazo[1,2-a]pyridin-3-ylamine hydrochloride (785 g, 2.70 mol, 1 eq.) in formic acid (713 mL, 18.9 mol, 7 eq.) was heated to 80° C. for 2 h. The crude mixture was concentrated in vacuo to low volume (about 400 mL). The residue was brought up in water (1 L) and a 3 M solution of NaOH (2 L), and further basified with a saturated NaHCO₃ solution until foaming ceased and pH reached 8-9. After homogenization for 1 h, the precipitate was filtered and washed with water (2×300 mL). Purification was achieved by dissolution in a mixture of toluene and MeOH 3:1 (4 L) followed by concentration in vacuo. Trituration of the residue in a mixture of 200 mL of MeOH and 5 L of DIPE, decantation and filtration of the resulting suspension afforded N-(6-bromo-2-ethyl-8-methylimidazo[1,2-a]pyridin-3-yl)formamide (Intermediate Gen-2-d).

Rotamer A: ¹H NMR δ (ppm) (400 MHz, DMSO): 10.2 (1H, bs), 8.36 (1H, s), 8.11 (1H, s), 7.21 (1H, s), 2.63-2.60 (2H, m), 2.56 (3H, s), 1.24-1.17 (3H, m)

Rotamer B: ¹H NMR δ (ppm) (400 MHz, DMSO): 8.51 (1H, s), 8.23 (1H, s), 8.11 (1H, s), 7.23 (1H, s), 2.63-2.60 (2H, m), 2.58 (3H, s), 1.24-1.17 (3H, m)

LC-MS: MW (calcd): 281 (⁷⁹Br), 283 (⁸¹Br); m/z MW (obsd): 282 (⁷⁹Br M+1), 284 (⁸¹Br M+1)

1.2.4. General Methods C1 and C2: Synthesis of Intermediate Gen-3

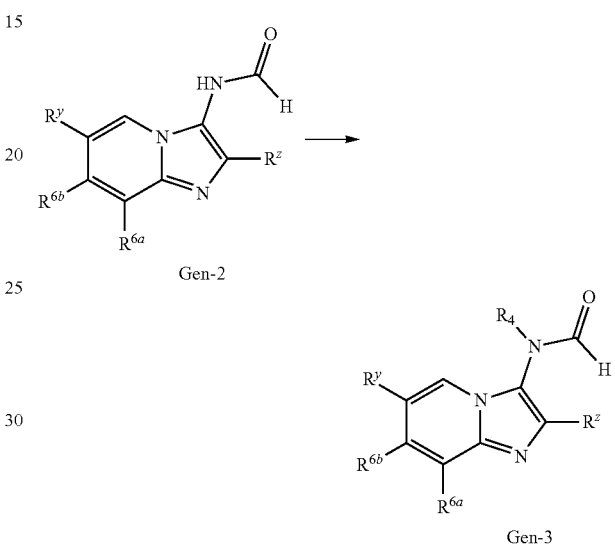

1.2.4.1. General Method C1

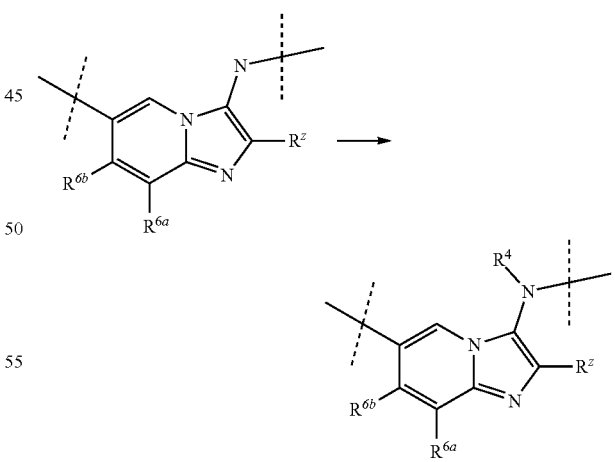

To a solution of imidazo[1,2-a]pyridine-3-ylamine derivative (1 eq.) in DMF is added NaH (1.5 eq.) portionwise, then alkyl iodide (1.4 eq.). The reaction mixture is stirred for 1 h then quenched with water and diluted with EtOAc. The aqueous layer is extracted with EtOAc. The combined organic layers are washed with water and brine, dried over Na₂SO₄ and concentrated in vacuo. The residue is triturated with DIPE. The solid is filtered, rinsed with DIPE and dried to give the expected intermediate.

1.2.4.2. Illustrative Synthesis of Intermediate Gen3-b: N-(6-bromo-2-ethylimidazo[1,2-a]pyridin-3-yl)-N-methylformamide

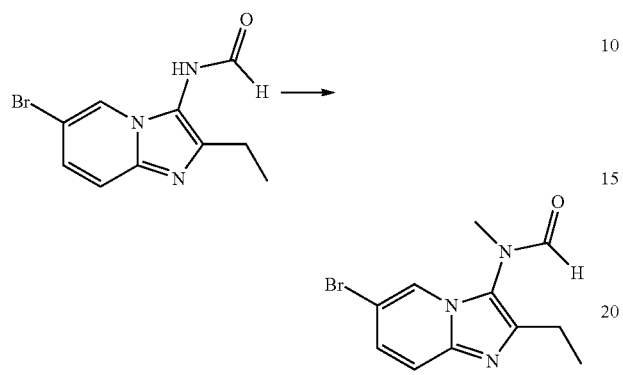

NaH (60% suspension in oil, 151 g, 3.76 mol, 1.5 eq.) was added portionwise at r.t. over a period of 30 min. to a solution of Intermediate Gen-2-b (673 g, 2.51 mol, 1 eq.) in DMF (6 L). The internal temperature increased to 35° C. during the addition and the reaction mixture was directly cooled to 15° C. Methyl iodide (502 g, 3.53 mol, 1.4 eq.) was added dropwise over a period of 1 h. The reaction mixture was kept below 20° C., stirred for 1 h then quenched with water (220 mL). Solvents were evaporated in vacuo. The residue was diluted with water (3 L) and EtOAc (4 L). The aqueous layer was extracted with EtOAc (3×1 L). The combined organic layers were washed with water (2×3 L) and brine (1.5 L), dried over $Na_2SO_4$ and concentrated in vacuo. The residue was triturated with DIPE (2 L). The solids were filtered, rinsed with DIPE (2×1 L) and dried to give Intermediate Gen3-b.

$^1$H NMR δ (ppm) (400 MHz, $CDCl_3$): 7.92 (1H, s), 7.78 (1H, s), 7.33 (1H, d), 7.30 (1H, d), 3.25 (3H, s), 2.72 (2H, q), 1.35 (3H, t).

LC-MS: MW (calcd): 281 ($^{79}$Br), 283 ($^{81}$Br); m/z MW (obsd): 284 ($^{81}$Br M+1)

1.2.4.3. General Method C2

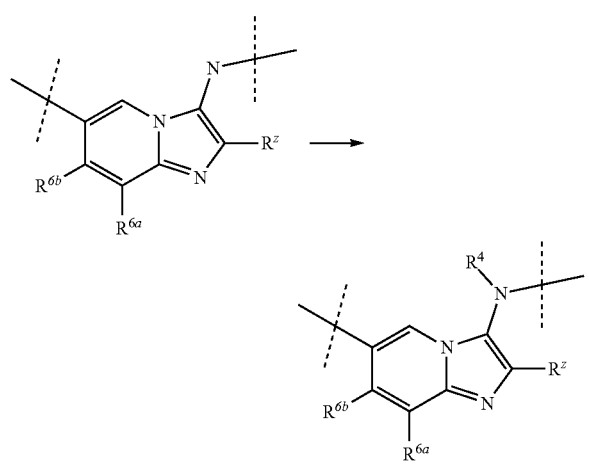

To a suspension of imidazo[1,2-a]pyridine-3-ylamine derivative (1 eq.) in acetone are added potassium carbonate (3 eq.) and alkyl iodide (1.5 eq. to 1.9 eq.). The reaction mixture is stirred at a temperature comprised between r.t. and refluxing temperature. If after stirring overnight, the reaction is not complete, additional alkyl iodide (0.07 eq.) is then introduced and stirring is continued for 1 h. The reaction mixture is filtered and washed with acetone and DCM. The filtrate is concentrated in vacuo and the residue is partitioned between DCM and water. The aqueous layer is further extracted with DCM. The combined organic layers are then washed with brine, dried over $Na_2SO_4$, filtered and concentrated in vacuo. The solid is triturated with $Et_2O$ at r.t. for 1 h, filtered off and dried to afford the expected Intermediate.

1.2.4.4. Illustrative Synthesis of Intermediate Gen-3-e: N-(6-bromo-2-ethyl-8-methylimidazo[1,2-a]pyridin-3-yl)-N-methylformamide

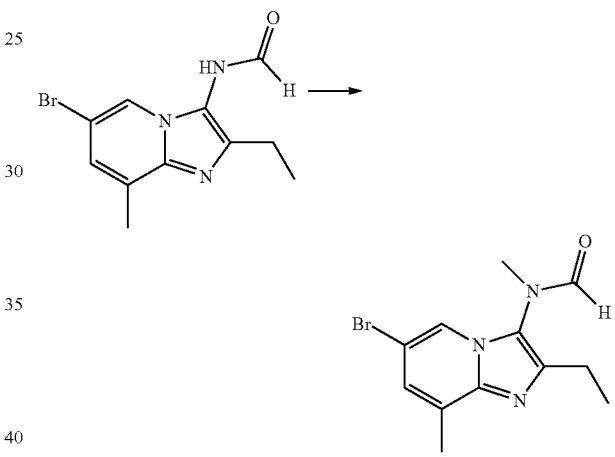

To a suspension of formamide Gen-2-d (720 g, 2.55 mol, 1 eq.) in 5 L of acetone were added potassium carbonate (1 kg, 7.66 mol, 3 eq.) and methyl iodide (700 g, 4.93 mol, 1.9 eq.). The reaction mixture was heated to 40° C. overnight. Additional methyl iodide (25 g, 0.18 mol, 0.07 eq.) was then introduced and stirring continued for 1 h at 40° C. The reaction mixture was filtered and washed with acetone (2×300 mL) and DCM (2×300 mL). The filtrate was concentrated in vacuo and the residue was partitioned between DCM (3 L) and water (1 L). The aqueous layer was further extracted with DCM. The combined organic layers were then washed with brine, dried over $Na_2SO_4$, filtered and concentrated in vacuo. The solid was triturated with $Et_2O$ (1 L) at r.t. for 1 h, filtered off and dried to afford Intermediate Gen-3-e.

Rotamer A (Major): $^1$H NMR δ (ppm) (400 MHz, $CDCl_3$): 8.19 (1H, s), 7.78 (1H, s), 7.15 (1H, s), 3.24 (3H, s), 2.72 (2H, q), 2.59 (3H, s), 1.31 (3H, t)

Rotamer B (Minor): $^1$H NMR δ (ppm) (400 MHz, $CDCl_3$): 8.49 (1H, s), 7.65 (1H, s), 7.08 (1H, s), 3.36 (3H, s), 2.72 (2H, q), 2.59 (3H, s), 1.31 (3H, t)

LC-MS: MW (calcd): 295 ($^{79}$Br), 297 ($^{81}$Br); m/z MW (obsd): 296 ($^{79}$Br M+1), 298 ($^{81}$Br M+1)

1.2.5. General Methods D1 and D2: Synthesis of Intermediate Gen-4

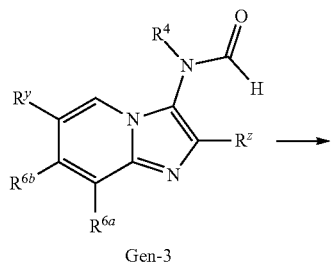

Gen-3

1.2.5.2. Illustrative Synthesis of Intermediate Gen-4-d: (6-Bromo-2-ethyl-8-methyl-imidazo[1,2-a]pyridin-3-yl)-methyl-amine

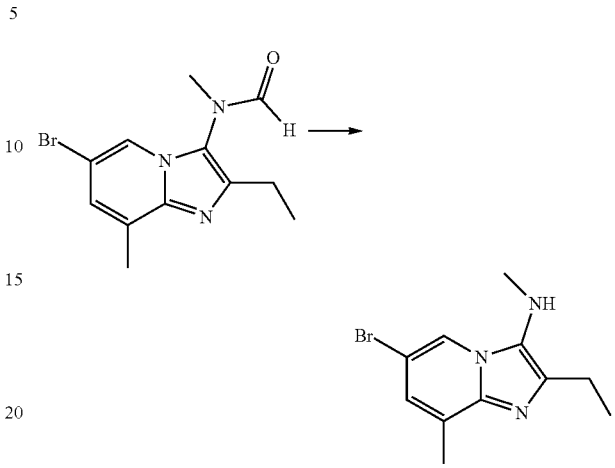

Intermediate Gen-3-e (80 g, 270 mmol, 1 eq.) was dissolved in a 1.25 M HCl solution in MeOH (540 mL, 2.5 eq.) and the resulting mixture was refluxed overnight. 270 mL of 1.25 M HCl solution in MeOH were added and heating continued overnight. After 48 h, additional 70 mL of the 1.25 M HCl solution in MeOH were introduced in the reaction mixture. Heating was maintained overnight until conversion was complete. The crude mixture was then concentrated in vacuo and the residue was partitioned between EtOAc (300 mL) and water (700 mL). A saturated NaHCO$_3$ solution was added until pH reached 8-9. The aqueous layer was extracted twice with EtOAc (2×300 mL). The combined organic layers were then washed with brine (200 mL), dried over Na$_2$SO$_4$, filtered and concentrated in vacuo to give Intermediate Gen-4-d (6-bromo-2-ethyl-8-methyl-imidazo[1,2-a]pyridin-3-yl)-methyl-amine as a free base.

$^1$H NMR δ (ppm) (400 MHz, CDCl$_3$): 8.05 (1H, s), 7.04 (1H, s), 2.84-2.78 (5H, m), 2.60 (3H, s), 1.35 (3H, t)

LC-MS: MW (calcd): 267 ($^{79}$Br), 269 ($^{81}$Br); m/z MW (obsd): 268 ($^{79}$Br M+1), 270 ($^{81}$Br M+1)

1.2.5.1. General Method D1

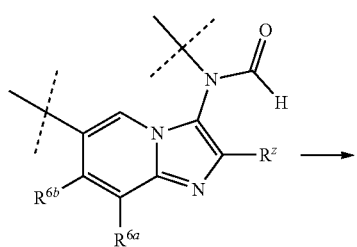

A 4 M HCl solution in dioxane or 1.25 M HCl solution in MeOH (9 eq.) is added to a solution of imidazo[1,2-a]pyridine-3-yl formamide derivative (1 eq.) in MeOH. The reaction mixture is stirred at a room temperature or refluxed for 3 h. Additional 4 M HCl solution (1.5 eq.) is added and stirring is continued until completion of the reaction. The reaction mixture is then concentrated in vacuo to afford the expected intermediate.

1.2.5.3. General Method D2

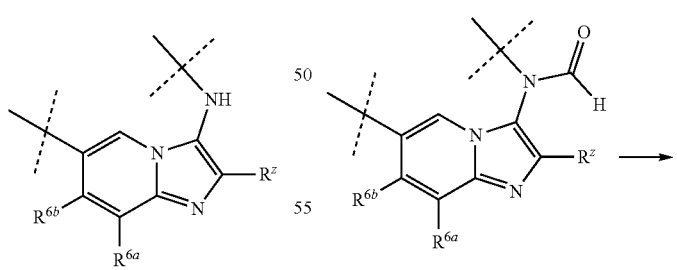

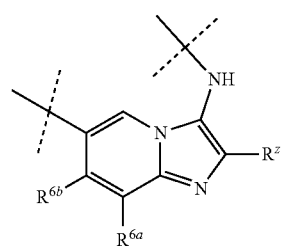

A 10 M aqueous KOH solution (15 eq.) is added to a solution of imidazo[1,2-a]pyridine-3-yl formamide derivative (1 eq.) in MeOH. The reaction mixture is stirred at r.t. for 3 h, then quenched with brine and MeOH is removed in vacuo. The remaining aqueous phase is extracted with DCM three times. The combined organic layers are washed with brine, dried over MgSO$_4$, filtered and concentrated in vacuo to afford the expected intermediate as a free base.

1.2.5.4. Illustrative Synthesis of Intermediate Gen-4-a: (6-Bromo-2-ethyl-8-fluoro-imidazo[1,2-a]pyridin-3-yl)-methyl-amine

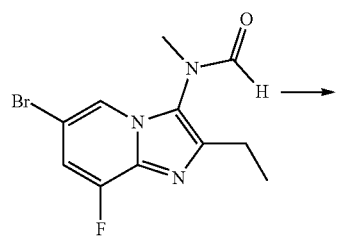

A 10 M aqueous KOH solution (25 mL, 250 mmol, 15 eq.) was added to a solution of imidazo-pyridine Intermediate Gen-3-a (5 g, 16.67 mmol, 1 eq.) in 25 mL of MeOH. The reaction mixture was stirred at r.t. for 3 h, then quenched with brine and MeOH was removed in vacuo. The remaining aqueous phase was extracted with DCM three times. The combined organic layers were washed with brine, dried over MgSO$_4$, filtered and concentrated in vacuo to afford Intermediate Gen-4-a as a free base.

LC-MS: MW (calcd): 271 ($^{79}$Br), 273 ($^{81}$Br); m/z (obsd): 272 ($^{79}$Br M+1), 274 ($^{81}$Br M+1)

1.2.6. General Methods E1, E2, E3 and C: Synthesis of Intermediate Gen-5

1.2.6.1. General Method E1

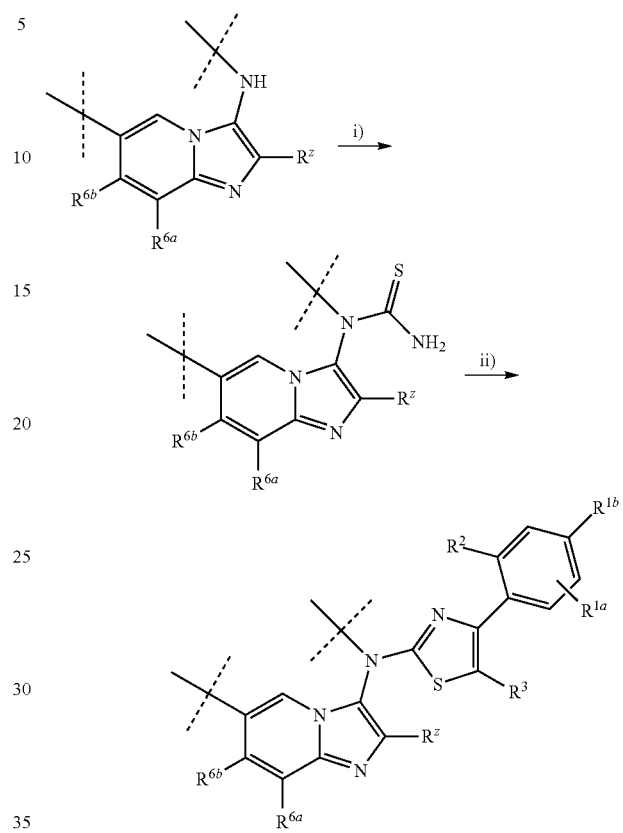

Step i)

To a suspension of imidazo[1,2-a]pyridine-3-ylamine derivative (1 eq.) in DCM is added TEA (4.5 eq.). The mixture is stirred for 30 min at r.t. then Fmoc-isothiocyanate (1.3 eq.) is added. The resulting solution is stirred at r.t. for 3 h. Piperidine (3.2 eq.) is then introduced and the reaction mixture is stirred at r.t. overnight. Water is added to the solution and the layers are separated. The aqueous layer is extracted with DCM/MeOH. The combined organic layers are washed with brine, dried over Na$_2$SO$_4$ and concentrated in vacuo. The expected product is obtained either by chromatography on silica gel or crystallization to afford the corresponding thiourea.

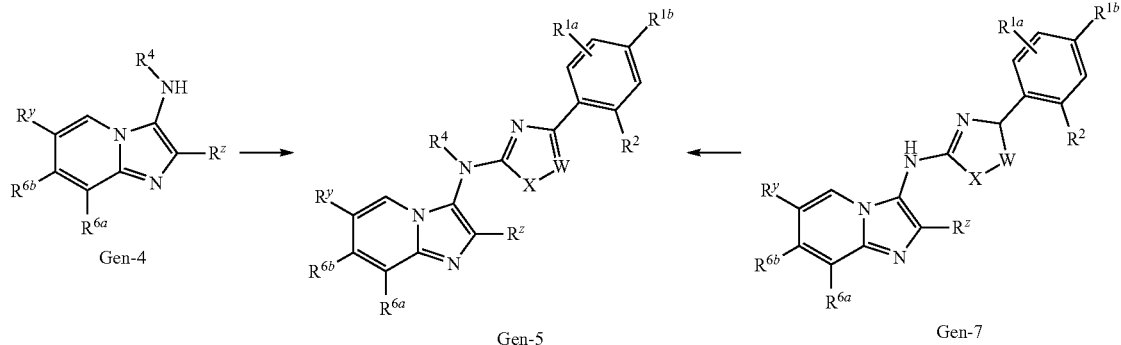

Step ii)

The above prepared thiourea (1 eq.) is added to a solution of the corresponding bromo acetophenone Gen-11 or commercial product (1.3 eq.) in EtOH. The reaction mixture is stirred at reflux for 3 h then concentrated in vacuo. The crude product is triturated in hot EtOAc and stirred for 30 min, allowed to cool to r.t., filtered off and rinsed with EtOAc to afford the expected Intermediate Gen-5.

1.2.6.2. Illustrative Synthesis of Intermediate Gen-5-b: (6-Bromo-2-ethyl-imidazo[1,2-a]pyridin-3-yl)-[4-(4,fluoro-phenyl)-thiazol-2-yl]-methyl-amine

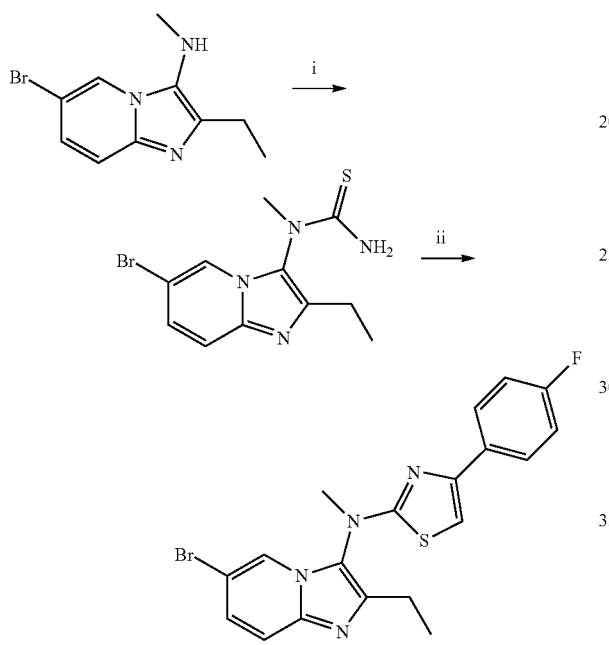

Step i)

To a suspension of Intermediate Gen-4-b (170 g, 520 mmol, 1 eq.) in DCM (3 L), was added triethylamine (325 mL, 2.34 mol, 4.5 eq.). The mixture was stirred for 30 min at r.t. then Fmoc-isothiocyanate (190 g, 676 mmol, 1.3 eq.) was added. The formed solution was stirred at r.t. for 3 h. Piperidine (164 mL, 1.66 mol, 3.2 eq.) was added to the solution and the reaction mixture was stirred at r.t. overnight. Water (1.5 L) was added to the solution and the layers were separated. The aqueous layer was extracted with DCM/MeOH. The combined organic layers were washed with brine, dried over $Na_2SO_4$ and concentrated in vacuo. The residue was triturated with MeCN, filtered and rinsed with MeCN and $Et_2O$ to afford the corresponding thiourea.

$^1$H NMR δ (ppm) (400 MHz, $CDCl_3$): 7.88 (1H, s), 7.32 (1H, d), 7.30 (1H, d), 3.67 (3H, s), 2.75 (2H, q), 1.33 (3H, t).

LC-MS: MW (calcd): 312 ($^{79}$Br), 314 ($^{81}$Br); m/z MW (obsd): 313 ($^{79}$Br M+1), 315 ($^{81}$Br M+1)

Step ii)

The above prepared thiourea (62.5 g, 180 mmol, 1 eq.) was added to a solution of 2-bromo-4'-fluoroacetophenone (50.7 g, 233 mmol, 1.3 eq.) in EtOH (1.5 L). The reaction mixture was stirred at reflux for 3 h then concentrated in vacuo. The crude product was triturated in hot EtOAc and stirred for 30 min, allowed to cool to r.t., filtered off and rinsed with EtOAc to afford Intermediate Gen-5-b.

$^1$H NMR δ (ppm) (400 MHz, MeOD): 8.75 (1H, s), 7.98 (2H, dd), 7.83-7.75 (3H, m), 7.14-7.03 (3H, m), 3.63 (3H, s), 2.86 (2H, q), 1.36 (3H, t).

LC-MS: MW (calcd): 430 ($^{79}$Br), 432 ($^{81}$Br); m/z MW (obsd): 431 ($^{79}$Br M+1), 433 ($^{81}$Br M+1)

1.2.6.3. General Method E2

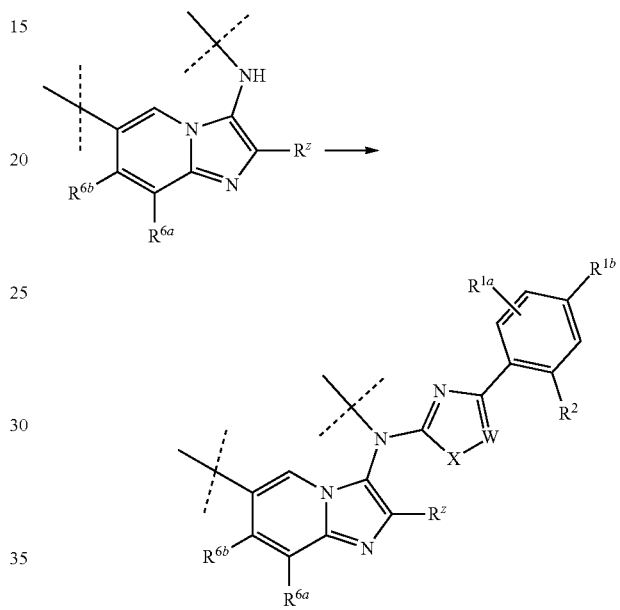

To a solution of imidazo[1,2-a]pyridine-3-ylamine derivative (1 eq.) and the halogeno heteroaryl derivative (1.2 eq.) in THF under argon is added NaH (3 eq.). The reaction mixture is heated at 90° C. overnight. After cooling to r.t. the mixture is slowly quenched by addition of water and then diluted with EtOAc. The organic layer is separated and the aqueous layer extracted with EtOAc. The combined organic layers are washed with water and brine, dried over $Na_2SO_4$, filtered and concentrated in vacuo. The residue is purified either by chromatography on silica gel or by crystallization to deliver the expected intermediate.

1.2.6.4. Illustrative Synthesis of Intermediate Gen-5-t: 2-[(6-Bromo-2-ethyl-8-methyl-imidazo[1,2-a]pyridin-3-A-methyl-amino]-4-(4-fluoro-phenyl)-thiazole-5-carbonitrile

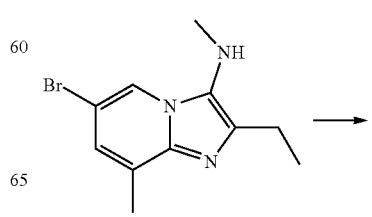

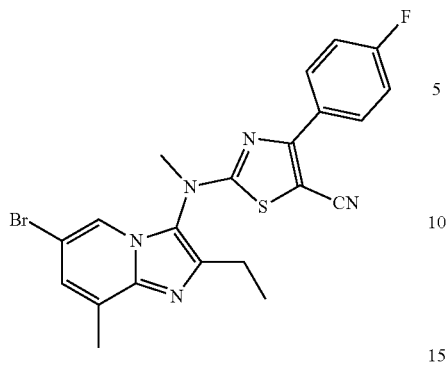

To a solution of amine Gen-4-d (4.4 g, 16.6 mmol, 1 eq.) in THF (44 mL) under argon was slowly added NaH (60% in oil suspension, 2.0 g, 50.0 mmol, 3 eq.). The reaction mixture was heated at 90° C. for 30 min then cooled to 40° C. before adding the chlorothiazole Gen-12-a (4.74 g, 19.9 mmol, 1.2 eq.). The reaction mixture was stirred at 90° C. overnight. After cooling to r.t. the mixture was slowly quenched by addition of water and then diluted with EtOAc. The organic layer was separated and the aqueous layer extracted with EtOAc. The combined organic layers were then washed with water and brine, dried over $Na_2SO_4$, filtered and concentrated in vacuo. The residue was triturated in $Et_2O$, filtered and washed with $Et_2O$ and MeCN. Recrystallization was performed in MeCN (180 mL) to afford Intermediate Gen-5-t (2-[(6-Bromo-2-ethyl-8-methyl-imidazo[1,2-a]pyridin-3-yl)-methyl-amino]-4-(4-fluoro-phenyl)-thiazole-5-carbonitrile).

$^1$H NMR δ (ppm) (400 MHz, $CDCl_3$): 8.15 (2H, dd), 7.80 (1H, s), 7.22-7.14 (3H, m), 3.62 (3H, s), 2.77 (2H, q), 2.64 (3H, s), 1.35 (3H, t)

LC-MS: MW (calcd): 469 ($^{79}$Br), 471 ($^{81}$Br); m/z MW (obsd): 470 ($^{79}$Br M+1), 472 ($^{81}$Br M+1)

1.2.6.5. General Method E3

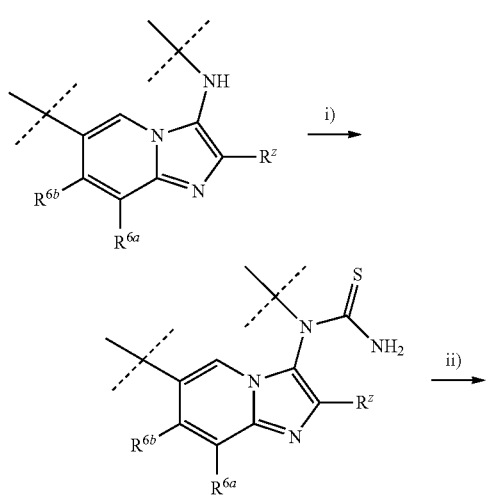

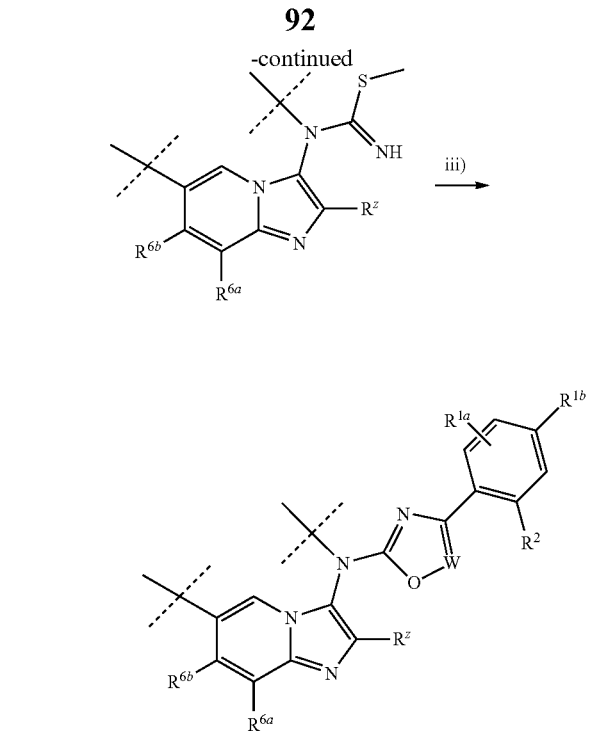

Step i)

To a suspension of imidazo[1,2-a]pyridin-3-ylamine derivative (1 eq.) in DCM is added TEA (4.5 eq.). The mixture is stirred until dissolved at r.t. then Fmoc-isothiocyanate (2.2 eq.) is added. The resulting solution is stirred at r.t. overnight. Piperidine (5 eq.) is then introduced and the reaction mixture is stirred at r.t. for 4 h. Water is added to the solution and the layers are separated. The aqueous layer is extracted with DCM. The combined organic layers are washed with brine, dried over $Na_2SO_4$ and concentrated in vacuo to give the expected thiourea.

Step ii)

The above prepared thiourea (1 eq.) is dissolved in acetone and MeOH, $NaHCO_3$ (1 eq.) and MeI (6 eq.) are added, the reaction mixture is stirred at 60° C. for 3 h. Then the reaction mixture is stirred at r.t. over 2 d. Then the reaction mixture is concentrated in vacuo, the residue is dissolved in a mixture of DCM and MeOH. Solids are filtered off, and the filtrate is concentrated in vacuo. The residue is purified by chromatography on silica gel (elution with DCM/MeOH: 100/0 to 90/10) to afford the expected methylthiourea.

Step iii)

TEA (3 eq.) is added to a solution of the above prepared methylthiourea (1 eq.) in EtOH, followed by the arylamidoxime derivative (2 eq.), then the reaction mixture is stirred at 80° C. over 2 d. The reaction mixture is quenched by addition of a saturated $NaHCO_3$ solution and extracted with DCM three times. The organic phases are combined, dried over $Na_2SO_4$ and concentrated in vacuo. The residue is purified by chromatography on silica gel to afford the expected intermediate.

1.2.6.6. Illustrative Synthesis of Intermediate Gen-5-ae: (6-Bromo-2-ethyl-imidazo[1,2-a]pyridin-3-yl)-[3-(4-fluoro-phenyl)-[1,2,4]oxadiazol-5-yl]-methyl-amine

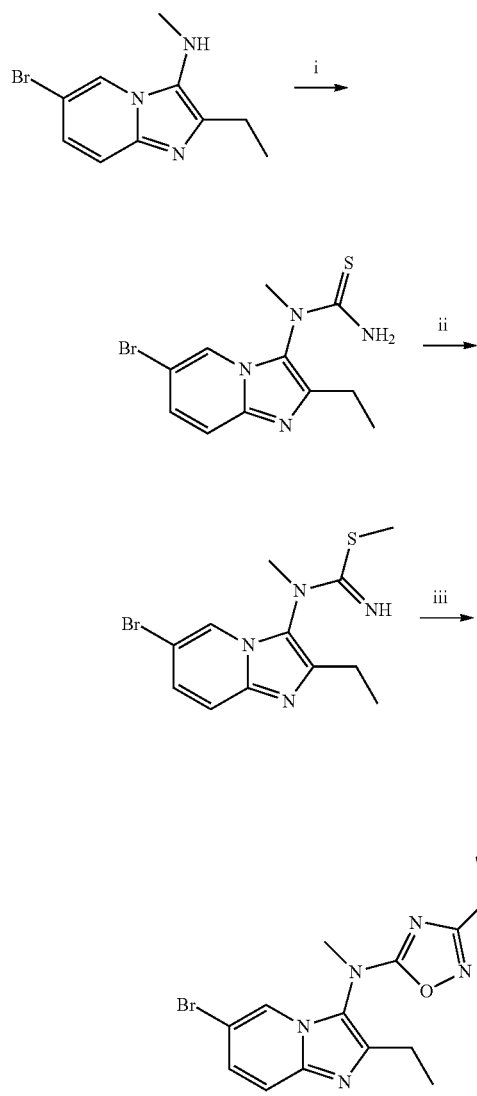

Step i)

To a suspension of the hydrochloride salt of Gen-4-b (11.6 g, 35.5 mmol, 1 eq.) in 250 mL of DCM was added TEA (20.49 mL, 147.1 mmol, 4.5 eq.). The mixture was stirred at r.t. until full dissolution occurred, then Fmoc-isothiocyanate (21.95 g, 74.5 mmol, 2.2 eq.) was added. The resulting solution was stirred at r.t. overnight. Piperidine (17.52 mL, 177.0 mmol, 5 eq.) was then introduced and the reaction mixture was stirred at r.t. for 4 h. Water was added to the solution and the layers were separated. The aqueous layer was extracted with DCM. The combined organic layers were washed with brine, dried over $Na_2SO_4$ and concentrated in vacuo to give the expected thiourea.

Step ii)

The above prepared thiourea (500 mg, 1.59 mmol, 1 eq.) was dissolved in 150 mL of acetone and 30 mL of MeOH, $NaHCO_3$ (134 mg, 1.59 mmol, 1 eq.) and MeI (1.36 g, 9.58 mmol, 6 eq.) were added, the reaction mixture is stirred at 60° C. for 3 h. Then the reaction mixture was stirred at r.t. over 2 d. The reaction mixture was then concentrated in vacuo, and the residue was dissolved in a mixture of DCM and MeOH (9/1). Solids were filtered off, and the filtrate was concentrated in vacuo. The residue was purified by chromatography on silica gel (elution with DCM/MeOH: 100/0 to 90/10) to afford the expected methylthiourea.

LC-MS: MW (calcd): 326 ($^{79}$Br), 328 ($^{81}$Br); m/z (obsd): 327 ($^{79}$Br M+1), 329 ($^{81}$Br M+1)

Step iii)

TEA (0.383 mL, 2.75 mmol, 3 eq.) was added to a solution of the above prepared methylthiourea (300 mg, 0.917 mmol, 1 eq.) in 10 mL of EtOH, followed by 4-fluorobenzamidoxime (283 mg, 1.833 mmol, 2 eq.), then the reaction mixture was stirred at 80° C. over 2 days. The reaction mixture was quenched by addition of a saturated $NaHCO_3$ solution (100 mL) and extracted with 20 mL of DCM three times. The organic phases were combined, dried over $Na_2SO_4$ and concentrated in vacuo. The residue was purified by chromatography on silica gel (elution with DCM/MeOH: 100/0 to 95/5) to afford Intermediate Gen-5-ae.

LC-MS: MW (calcd): 415 ($^{79}$Br), 417 ($^{81}$Br); m/z (obsd): 416 ($^{79}$Br M+1), 418 ($^{81}$Br M+1)

1.2.6.7. General Method C1

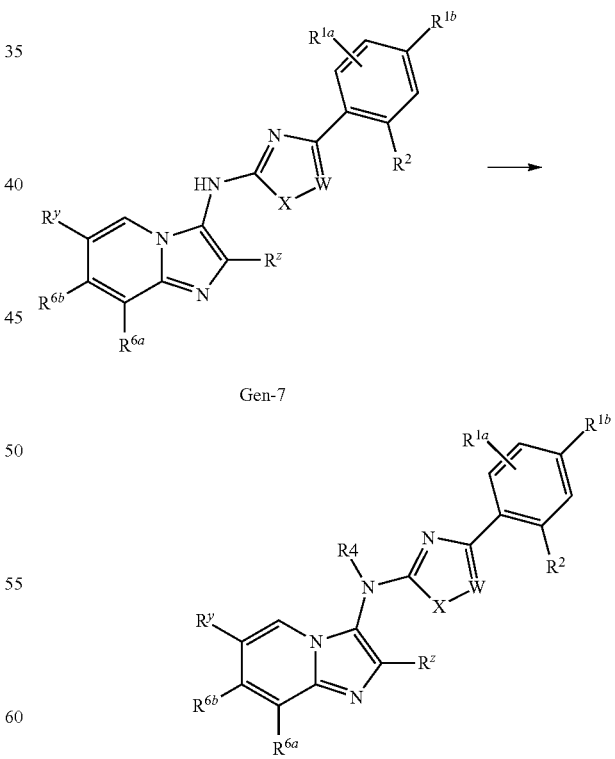

Intermediates Gen-5 are prepared from intermediates Gen-7 according to general method C1 described previously 1.2.7. General Methods F, E1, E4 and E5: Synthesis of Intermediate Gen-10

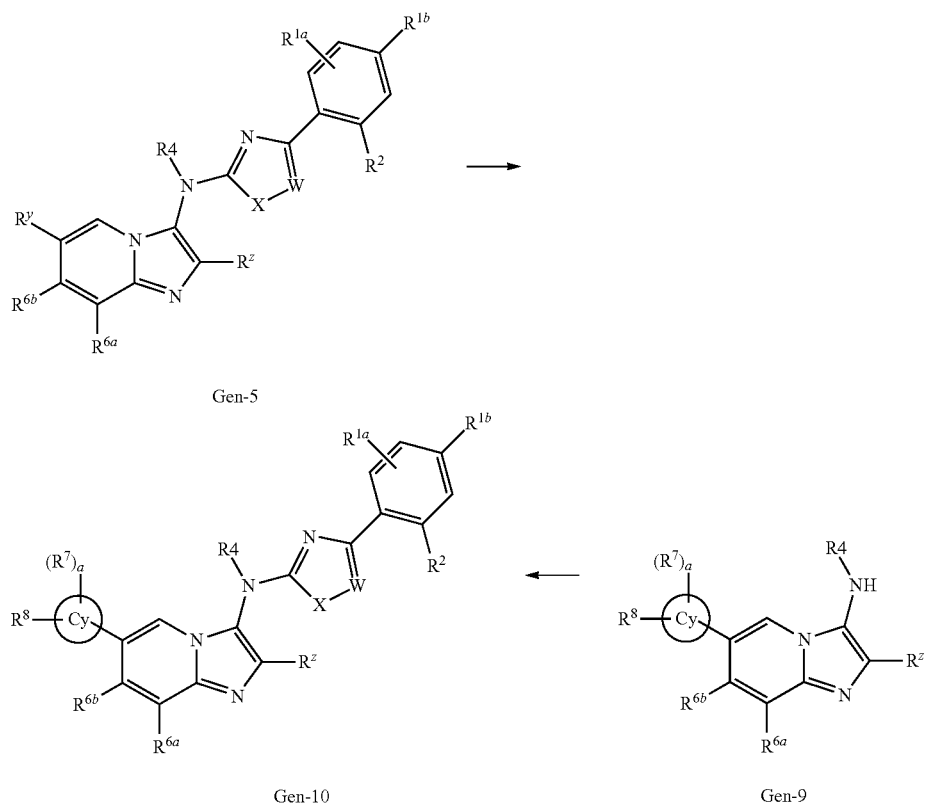

Gen-5

Gen-10

Gen-9

1.2.7.1. General methods F1

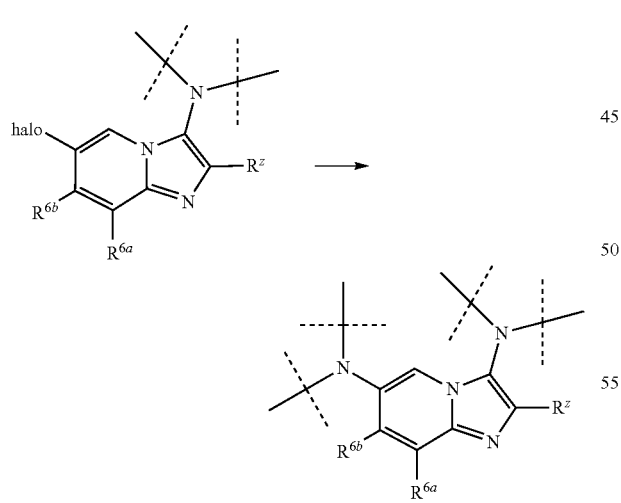

1.2.7.1.1. General Method F1a

To a solution of the 6-halo-imidazo[1,2-a]pyridine-3-ylamine derivative (1 eq.) in toluene under argon are successively added the corresponding amine (5 eq.), sodium tert-butoxide (2 eq.), and then ligand (0.13 eq.) and palladium catalyst (0.1 eq.). The reaction mixture is heated at 115° C. until completion. After cooling to r.t., the crude product is filtered on Celpure® P65, the residue is washed with EtOAc and the filtrate is then concentrated in vacuo. The crude product is purified by chromatography on silica gel to afford the expected intermediate.

1.2.7.1.2. Illustrative Synthesis of Intermediate Gen-10-i: 2-((2-ethyl-6-(piperazin-1-yl)imidazo[1,2-a]pyridine-3-yl)(methyl)amino-4-(4-fluorophenyl) thiazole-5-carbonitrile

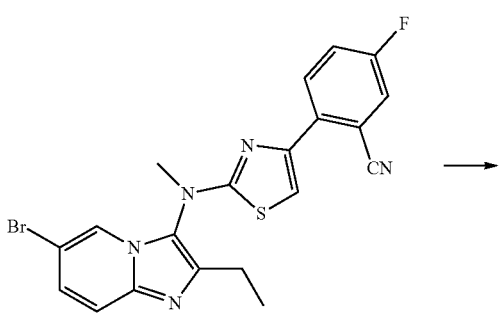

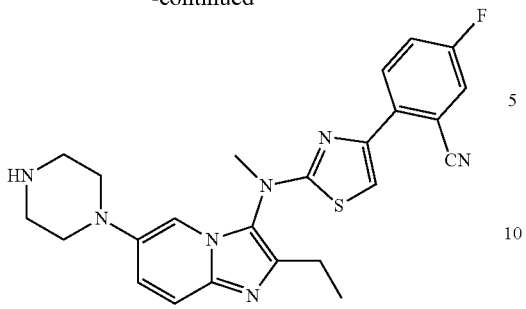

To a solution of bromide Gen-5-e (300 mg, 0.66 mmol, 1 eq.) in toluene (6 mL) under argon were successively added piperazine (283 mg, 3.28 mmol, 5 eq.), sodium tert-butoxide (126 mg, 1.31 mmol, 2 eq.), and then JohnPhos (26 mg, 0.085 mmol, 0.13 eq.) and Pd$_2$(dba)$_3$ (60 mg, 0.065 mmol, 0.1 eq.). The reaction mixture was heated at 115° C. for 45 min. After cooling to r.t., the crude product was filtered on Celpure® P65, the residue was washed with EtOAc and the filtrate was then concentrated in vacuo. The crude product was purified by chromatography on silica gel (elution with DCM/MeOH/7 N NH$_3$ in MeOH: 100/0/0 to 100/8/1) to afford Intermediate Gen-10-i.

$^1$H NMR δ (ppm) (400 MHz, CDCl$_3$): 8.08 (1H, dd), 7.50 (1H, d), 7.46-7.31 (2H, m), 7.21-7.11 (3H, m), 3.61(3H, s), 3.06(8H, bs), 2.73 (2H, q), 1.33 (3H, t).

LC-MS: MW (calcd): 461; m/z MW (obsd): 462 (M+1)

1.2.7.1.3. General Method F1b

To a solution of the 6-halo-imidazo[1,2-a]pyridine-3-ylamine derivative (1 eq.) in toluene under argon are successively added the corresponding amine (1.1 to 1.5 eq.), sodium tert-butoxide (1.18 to 2 eq.), and then JohnPhos, XantPhos or DavePhos (0.06 to 0.1 eq.) and Pd$_2$(dba)$_3$ (0.02 to 0.05 eq.). The reaction mixture is heated at 115° C. until completion. After cooling to r.t., the crude product is filtered on Celpure® P65, the residue is washed with EtOAc and the filtrate concentrated in vacuo. The crude product is purified by chromatography on silica gel to afford the expected intermediate.

1.2.7.1.4. Illustrative Synthesis of 4-(3-{[5-Cyano-4-(4-fluoro-phenyl)-thiazol-2-yl]-methyl-amino}-2-ethyl-8-methyl-imidazo[1,2-a]pyridin-6-yl)-ppera-zine-1-carboxylic acid tert-butyl ester

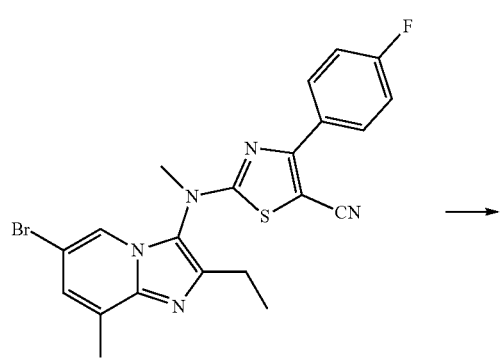

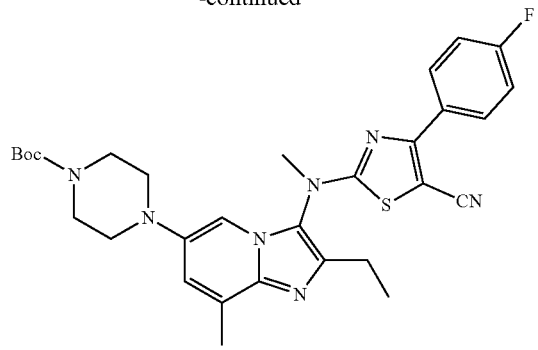

To a solution of Intermediate Gen-5-t (24.2 g, 51.5 mmol, 1 eq.) in toluene under argon were successively added N-Boc piperazine (14.4 g, 77.3 mmol, 1.5 eq.), sodium tert-butoxide (9.9 g, 103 mmol, 2 eq.), JohnPhos (1.54 g, 5.15 mmol, 0.1 eq.) and Pd$_2$(dba)$_3$ (2.36 g, 2.58 mmol, 0.05 eq.). The reaction mixture was heated at 115° C. for 1 h. After cooling to r.t., the crude product was filtered on Celpure® P65 and the residue dissolved in EtOAc and washed with water. The organic layer was further washed with brine, dried over Na$_2$SO$_4$, filtered and concentrated in vacuo. The crude product was purified by chromatography on silica gel (elution with heptane/EtOAc: 90/10 to 20/80) to afford the expected product.

$^1$H NMR δ (ppm) (400 MHz, CDCl$_3$): 8.16 (2H, dd), 7.17 (2H, app t), 6.99 (2H, bs), 3.62-3.53 (4H, m), 3.60 (3H, s), 3.04-2.93 (4H, m), 2.74 (2H, q), 2.62 (3H, s), 1.47 (9H, s), 1.33 (3H, t).

LC-MS: MW (calcd): 575; m/z MW (obsd): 576 (M+1)

1.2.7.2. General Method F2

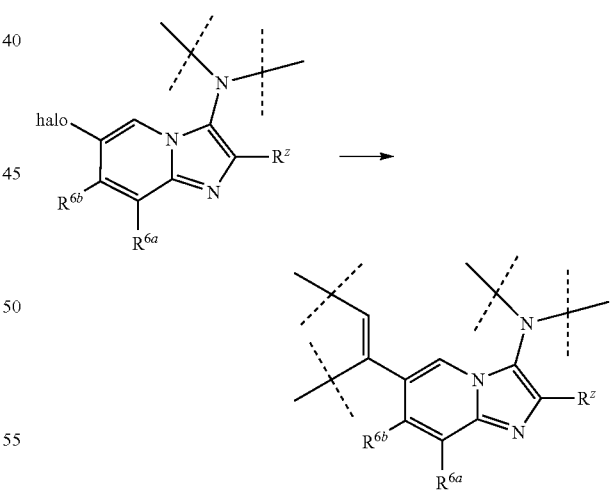

To a solution of the bromide Gen-5-b (21.6 g, 45.1 mmol, 1 eq.) in a mixture dioxane/water (300 mL/75 mL) under argon were successively added sodium carbonate (14.3 g, 135 mmol, 3 eq.), tert-butyl 4-(4,4,5,5-tetramethyl-1,3,2-dioxaborol an-2-yl)-5,6-dihydropyridine-1(2H)-carboxylate (18.1 g, 58.6 mmol, 1.3 eq.), and then Pd(PPh$_3$)$_4$ (3.91 g, 3.38 mmol, 0.075 eq.). The reaction mixture was heated at 85° C. for 3 h. After cooling to r.t., the crude product is filtered on Clarcel and the filtrate is concentrated in vacuo.

The residue is purified by chromatography on silica gel to afford the expected intermediate.

1.2.7.3. Illustrative Synthesis of 4-(2-Ethyl-3-{[4-(4-fluoro-phenyl)-thiazol-2-yl]-methyl-amino}-imidazo[1,2-a]pyridin-6-yl)-3,6-dihydro-2H-pyridine-1-carboxylic acid tert-butyl ester

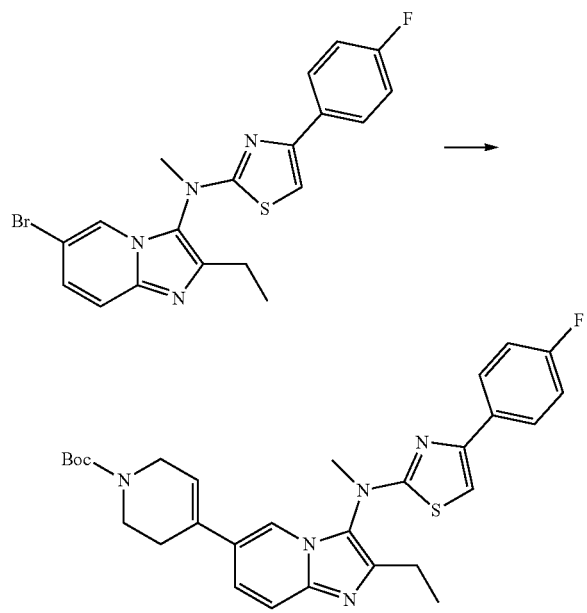

To a solution of the bromide Gen-5-b (21.6 g, 45.1 mmol, 1 eq.) in a dioxane/water (300 mL/75 mL) mixture under argon were successively added sodium carbonate (14.3 g, 135 mmol, 3 eq.), the corresponding boronic ester (18.1 g, 58.6 mmol, 1.3 eq.), and then Pd(PPh$_3$)$_4$ (3.91 g, 3.38 mmol, 0.075 eq.). The reaction mixture was heated at 85° C. for 3 h until completion. After cooling to r.t., the reaction mixture was concentrated in vacuo. The crude product was partitioned between EtOAc and water. The aqueous layer was extracted twice with EtOAc. The combined organic layers were then washed with brine, dried over Na$_2$SO$_4$, filtered and concentrated in vacuo. The residue was then purified by chromatography on silica gel (elution with DCM/MeOH 100/0 to 97/3) to afford the expected compound.

LC-MS: MW (calcd): 533; m/z MW (obsd): 534 (M+1)

1.2.7.4. General Method F3

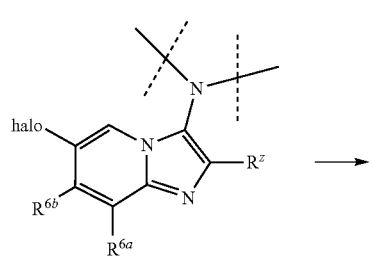

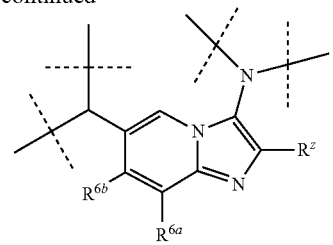

To a solution of the 6-halo-imidazo[1,2-a]pyridine-3-ylamine derivative (1 eq.) in DMA under argon are successively added the copper iodide (0.25 eq.), PdCl$_2$dppf (0.1 eq.), and a solution of the corresponding organozinc compound (1.3 eq.) in DMA. The reaction mixture is heated at 80° C. for 3 h then additional solution of the corresponding organozinc compound (0.6 eq.) in DMA is added. Stirring at 80° C. is continued overnight. After cooling to r.t., the crude product is filtered on Celpure® P65, the residue is washed with EtOAc and the filtrate is washed with water and brine, dried over Na$_2$SO$_4$, filtered and concentrated in vacuo. The crude product is purified by chromatography on silica gel to afford the expected intermediate.

1.2.7.5. Illustrative Synthesis of 4-(3-{[5-Cyano-4-(4-fluoro-phenyl)-thiazol-2-yl]-methyl-amino}-2-ethyl-8-methyl-imidazo[1,2-a]pyridin-6-yl)-piperidine-1-carboxylic acid tert-butyl ester

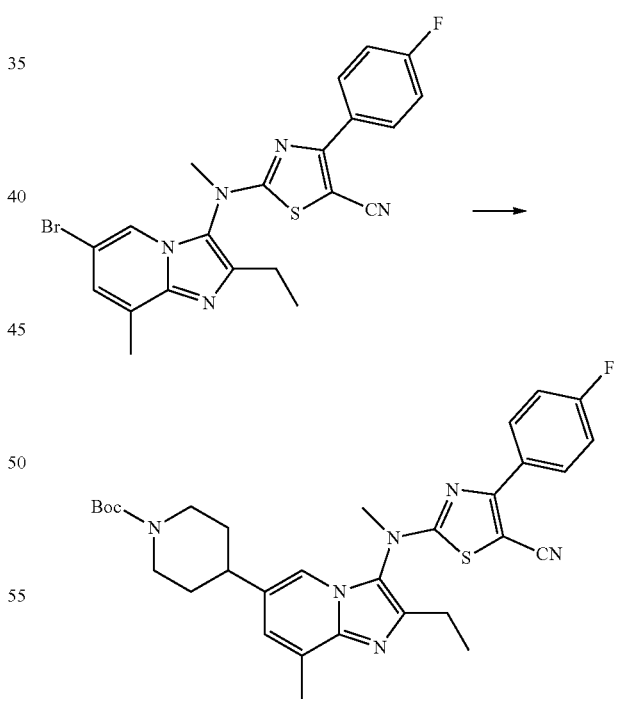

To a solution of the bromide Gen-5-t (600 mg, 1.28 mmol, 1 eq.) in DMA (4.4 mL) under argon were successively added the copper iodide (61 mg, 0.32 mmol, 0.25 eq.), PdCl$_2$dppf (93 mg, 0.13 mmol, 0.1 eq.), and a solution of the corresponding organozinc compound (prepared from 4-iodo-Boc-piperidine (Corley, et al., 2004)) in DMA (1 M in DMA, 1.66 mL, 1.66 mmol, 1.3 eq.). The reaction mixture was heated at 80° C. for 3 h then additional solution of the corresponding organozinc compound (0.5 mL, 0.5 mmol, 0.6 eq.) in DMA was added. Stirring at 80° C. was continued overnight. After cooling to r.t., the crude product was filtered on Celpure® P65, the residue was washed with EtOAc and the filtrate washed with water and brine, dried over $Na_2SO_4$ and concentrated in vacuo. The crude product was purified by chromatography on silica gel (elution heptanes/EtOAc 100/0 to 50/50) to deliver the expected compound.

LC-MS: MW (calcd): 574; m/z MW (obsd): 575 (M+1)

1.2.7.6. General Method F4

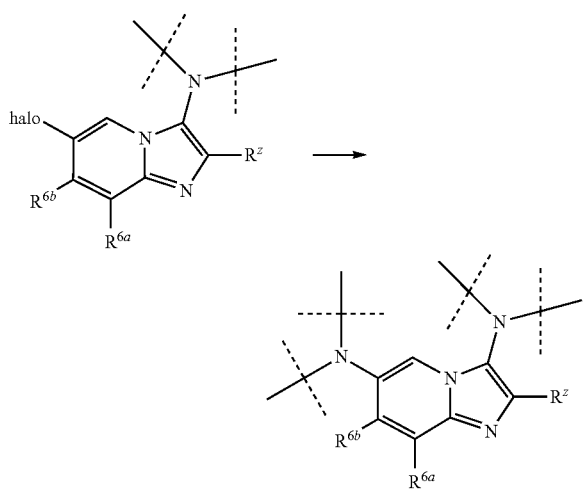

To a suspension of 6-halo-imidazo[1,2-a]pyridine-3-ylamine derivative (1 eq.), potassium carbonate (2 to 3 eq.), the corresponding amine (1.2 to 2 eq.), and CuI (0.1 to 0.2 eq.) in DMF under argon, is added the trans-1,2-diaminocyclohexane (0.2 to 0.4 eq.), and then the reaction mixture is heated between 85° C. and 100° C. overnight. After cooling to r.t., the crude product is filtered on Celite, and the residue is washed with EtOAc. The filtrate is washed with a saturated $NaHCO_3$ solution, the two phases are separated, and the aqueous phase is washed twice with EtOAc. The combined organic layers are washed with brine, dried over $Na_2SO_4$, filtered and concentrated in vacuo. The crude product is purified by chromatography on silica gel to afford the expected intermediate.

1.2.7.7. Illustrative Synthesis of Compound 62: 4-(2-Ethyl-3-{[4-(4-fluoro-phenyl)-thiazol-2-yl]-methyl-amino}-imidazo[1,2-a]pyridin-6-yl)-3-oxo-pperazine-1-carboxylic acid tert-butyl est

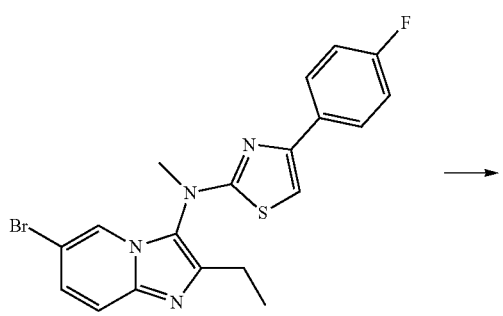

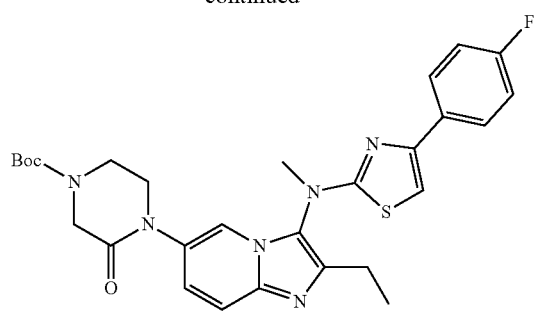

To a suspension of Gen-5-b (600 mg, 1.391 mmol, 1 eq.), potassium carbonate (577 mg, 4.173 mmol, 3 eq.), 3-oxo-piperazine-1-carboxylic acid tert-butyl ester (557 mg, 2.78 mmol, 2 eq.), and CuI (53 mg, 0.278 mmol, 0.2 eq.) in DMF (4 mL) under argon, was added the 1,2-diaminocyclohexane (67 μL, 0.56 mmol, 0.4 eq.), and then the reaction mixture was heated at 100° C. overnight. After cooling to r.t., the crude product was filtered on Celite, and the residue was washed with EtOAc. The filtrate was washed with a saturated $NaHCO_3$ solution, the two phases were separated, and the aqueous phase was washed twice with EtOAc. The combined organic layers were washed with brine, dried over $Na_2SO_4$, filtered and concentrated in vacuo. The crude product was purified by chromatography on silica gel to afford the expected compound.

LC-MS: MW (calcd): 550; m/z MW (obsd): 551 (M+1)

1.2.7.8. General Method F5 (Boc Removal)

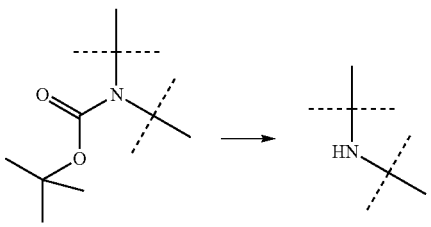

1.2.7.8.1. General Method F5a

To a solution of the boc protected amine (1 eq.) in DCM is added TFA (10 eq.). The reaction mixture is stirred at r.t. until completion. Then the reaction mixture is partitioned between DCM and water. The aqueous layer is washed twice with DCM. A saturated $Na_2CO_3$ solution is added to the aqueous layer until pH reached 8-9 and is extracted with DCM twice. The combined organic layers are then washed with brine, dried over $Na_2SO_4$, filtered and concentrated in vacuo to afford the expected intermediate

1.2.7.8.2. Illustrative Synthesis of Compound 177: [6-(3-Amino-azetidin-1-yl)-2-ethyl-imidazo[1,2-a]pyridin-3-yl]-[4-(4-fluoro-phenyl)-thiazol-2-yl]-methyl-amine

1.2.7.8.4. Illustrative Synthesis of Compound 1: 2-[(2-Ethyl-8-methyl-6-piperazin-1-yl-imidazo[1,2-a]pyridin-3-yl)-methyl-amino]-4-(4-fluoro-phenyl)-thiazole-5-carbonitrile

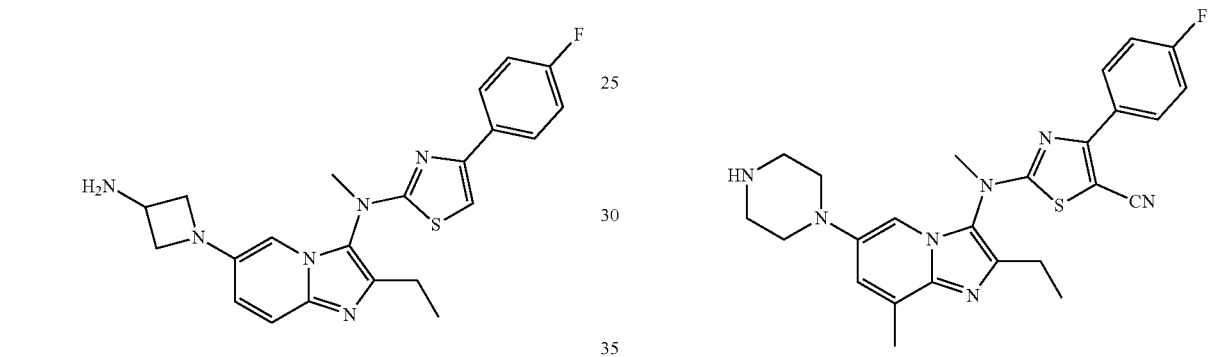

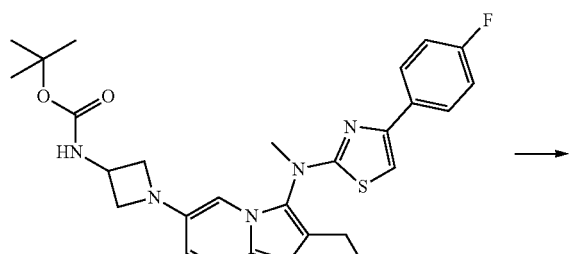

[1-(2-Ethyl-3-{[4-(4-fluoro-phenyl)-thiazol-2-yl]-methyl-amino}-imidazo[1,2-a]pyridin-6-yl)-azetidin-3-yl]-carbamic acid tert-butyl ester was prepared from intermediate Gen-5-b and 3-N-Boc-amino-azetidine using method F1b. To a solution of this compound [(200 mg, 0.383 mmol, 1 eq.) in DCM (3 mL) was added TFA (291 µL, 3.827 mmol, 10 eq.). The reaction mixture was stirred at r.t. for 2.5 days, then the reaction mixture was partitioned between DCM and water. The aqueous layer was washed twice with DCM. A saturated $Na_2CO_3$ solution was added to the aqueous layer until pH reached 8-9 and was extracted with DCM twice. The combined organic layers were then washed with brine, dried over $Na_2SO_4$, filtered and concentrated in vacuo to afford the expected compound.

LC-MS: MW (calcd): 422; m/z MW (obsd): 423 (M+1)

1.2.7.8.3. General Method F5b

To a solution of the boc protected amine (1 eq.) in MeOH is added a 2 N HCl solution in $Et_2O$ or 4 M HCl solution in dioxane or 1.25 M HCl solution in MeOH (6 eq.). The reaction mixture is stirred at r.t. until completion then concentrated in vacuo. The residue is partitioned between EtOAc and water. The aqueous layer is extracted twice with EtOAc. A 2 N NaOH solution is added to the aqueous layer until pH reached 8-9 and further extraction with EtOAc is performed. The combined organic layers are then washed with brine, dried over $Na_2SO_4$, filtered and concentrated in vacuo to afford the Intermediate Gen-10.

4-(3-{[5-Cyano-4-(4-fluoro-phenyl)-thiazol-2-yl]-methyl-amino}-2-ethyl-8-methyl-imidazo[1,2-a]pyridin-6-yl)-piperazine-1-carboxylic acid tert-butyl ester was prepared from intermediate Gen-5-t using Boc-piperazine and method F1b.

To a solution of 4-(3-{[5-Cyano-4-(4-fluoro-phenyl)-thiazol-2-yl]-methyl-amino}-2-ethyl-8-methyl-imidazo[1,2-a]pyridin-6-yl)-piperazine-1-carboxylic acid tert-butyl ester (24.4 g, 42 mmol, 1 eq.) in MeOH (100 mL) was added a 2 M HCl solution in $Et_2O$ (127 mL, 254 mmol, 6 eq.). The reaction mixture was stirred at r.t. for 3.5 h then concentrated in vacuo. The residue was partitioned between EtOAc and water. The aqueous layer was extracted twice with EtOAc. A 2 M NaOH solution was added to the aqueous layer until pH reached 8-9 and further extraction with EtOAc was performed. The combined organic layers were then washed with brine, dried over $Na_2SO_4$, filtered and concentrated in vacuo. The solid was triturated with heptane (100 mL) at r.t. overnight, filtered off, washed with heptane and $Et_2O$, and dried to afford the expected compound.

$^1$H NMR δ (ppm) (400 MHz, $CDCl_3$): 8.17 (2H, dd), 7.18 (2H, app t), 6.99 (2H, bs), 3.61 (3H, s), 3.09-2.98 (8H, m), 2.75 (2H, q), 2.61 (3H, s), 1.34 (3H, t).

LC-MS: MW (calcd): 475; m/z MW (obsd): 476 (M+1)

1.2.7.9. General Method F6

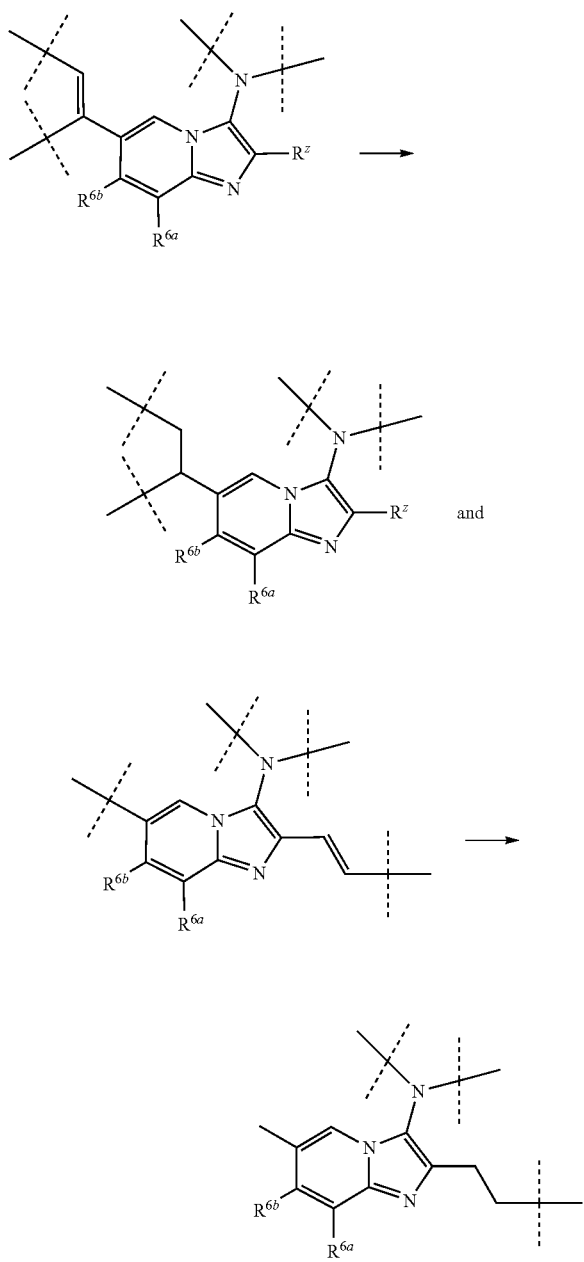

To a solution of the imidazo[1,2-a]pyridine-3-ylamine derivative (1 eq.) in a mixture THF/MeOH with AcOH (0 to 0.05 eq.) is added PtO$_2$ (15%) or Pd/C (10%). The flask is evacuated and backfilled with argon. Then the reaction is evacuated and backfilled with H$_2$ and stirred at r.t. under atmospheric pressure until completion. The crude product is filtered through a pad of Clarcel and washed with MeOH. The filtrate is concentrated under reduced pressure. The residue is purified to chromatography on silica gel to afford the expected compound.

1.2.7.10. Illustrative Synthesis of 4-(2-Ethyl-3-{[4-(4-fluoro-phenyl)-thiazol-2-yl]-methyl-amino}-imidazol[2-a]pyridin-6-yl)-piperidine-1-carboxylic acid tert-butyl ester

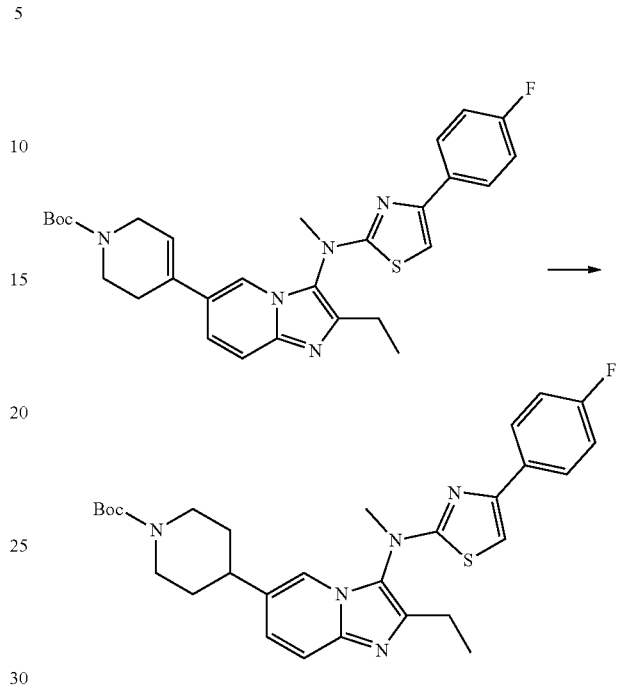

4-(2-Ethyl-3-{[4-(4-fluoro-phenyl)-thiazol-2-yl]-methyl-amino}-imidazo[1,2-a]pyridin-6-yl)-3,6-dihydro-2H-pyridine-1-carboxylic acid tert-butyl ester was prepared from Intermediate Gen-5-b and tert-butyl 4-(4,4,5,5-tetramethyl-1,3,2-dioxaborolan-2-yl)-5,6-dihydropyridine-1(2H)-carboxylate using method F2.

To a solution of 4-(2-Ethyl-3-{[4-(4-fluoro-phenyl)-thiazol-2-yl]-methyl-amino}-imidazo[1,2-a]pyridin-6-yl)-3,6-dihydro-2H-pyridine-1-carboxylic acid tert-butyl ester (60.0 g, 97 mmol, 1 eq.) in a mixture of THF (750 mL) and MeOH (750 mL) with AcOH (0.279 mL, 4.83 mmol, 0.05 eq.) was added Pd/C (10.3 g, 9.67 mmol, 0.1 eq.). The flask was evacuated and backfilled with argon. Then the reaction was evacuated and backfilled with H$_2$ and stirred at r.t. under atmospheric pressure overnight. The crude product was filtered through a pad of Clarcel and washed with MeOH. The filtrate was concentrated under reduced pressure. The residue was purified to chromatography on silica gel to afford the expected compound.

LC-MS: MW (calcd): 535; m/z MW (obsd): 536 (M+1)

1.2.7.11. General Method F7

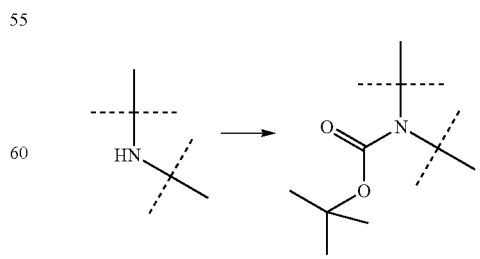

To a solution of the amino derivative in DCM are added TEA (5 eq.) then Boc$_2$O (0.9 eq.). The reaction mixture is stirred at r.t. for 1.5 h then diluted with DCM. The organic layer is separated and the aqueous layer extracted with DCM. The combined organic layers are washed with water and brine, dried over $Na_2SO_4$, filtered and concentrated in vacuo to afford the corresponding intermediate.

1.2.7.12. Illustrative Synthesis of: 4-(2-Ethyl-3-methylamino-imidazo[1,2-a]pyridin-6-yl)-piperidine-1-carboxylic acid tert-butyl ester

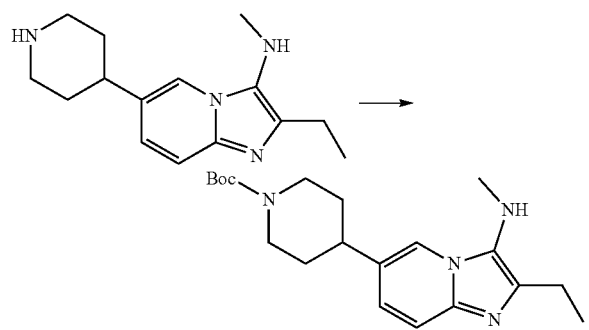

(2-Ethyl-6-piperidin-4-yl-imidazo[1,2-a]pyridin-3-yl)-methyl-amine is prepared from intermediate Gen-3-b through successive methods F2 (with tert-butyl 4-(4,4,5,5-tetramethyl-1,3,2-dioxaborol an-2-yl)-5,6-dihydropyridine-1(2H)-carboxylate), F6 and D1.

To a solution of (2-Ethyl-6-piperidin-4-yl-imidazo[1,2-a]pyridin-3-yl)-methyl-amine (1.67 g, 4.15 mmol, 1 eq.) in DCM (35 mL) were added TEA (2.9 mL, 20.7 mmol, 5 eq.) then $Boc_2O$ (815 mg, 3.74 mmol, 0.9 eq.). The reaction mixture was stirred at r.t. for 1.5 h then diluted with DCM. The organic layer was separated and the aqueous layer extracted with DCM. The combined organic layers were washed with water and brine, dried over $Na_2SO_4$, filtered and concentrated in vacuo to afford the expected compound.

LC-MS: MW (calcd): 358; m/z MW (obsd): 359 (M+1)

1.2.7.13. General Method F8

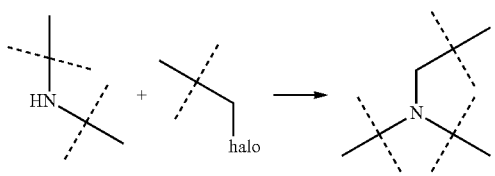

To a solution of amino derivative (1 eq.) in MeCN are added potassium carbonate (2 eq.) or TEA (5 eq.) and halogenated derivative Gen-13 (or commercially available products) (1.5 eq.). The reaction mixture is heated between 70° C. and reflux for 1.5 h to 6 h then cooled to r.t. The reaction mixture is quenched with water and diluted with EtOAc. The aqueous layer is extracted with EtOAc. The combined organic layers are washed with water and brine, dried over $Na_2SO_4$ and concentrated in vacuo. The residue is purified by chromatography on silica gel to deliver the expected compound. If the product is precipitated in the reaction mixture the following work up is used: after cooling to r.t., the reaction mixture is filtered. The solid is washed with MeCN, water and dried in vacuo to afford the expected product.

1.2.7.14. Illustrative Synthesis of Compound 2: 2-((2-ethyl-6-(4-(2-(3-hydroxyazetidin-1-yl)-2-oxo-ethyl)piperazin-1-yl)-8-methylimidazo[1,2-a]pyridin-3-yl)(methyl)amino)-4-(4-fluorophenyl)thiazole-5-carbonitrile

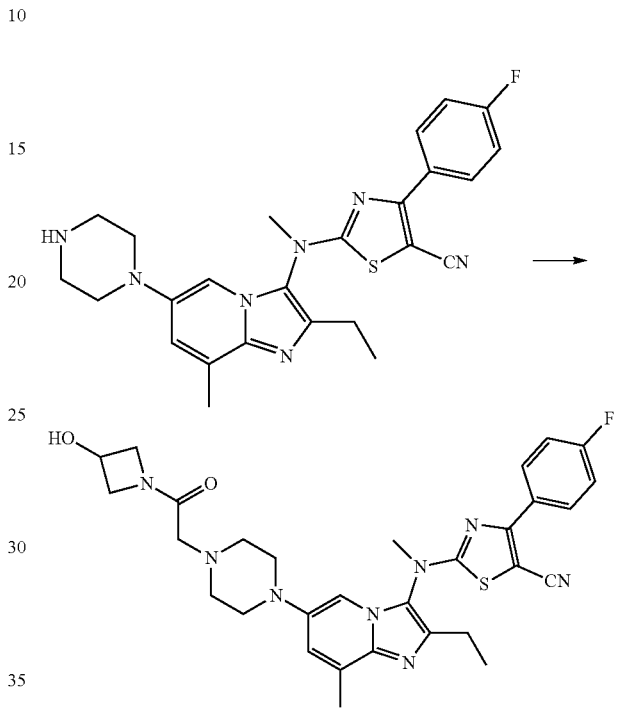

To a solution of amine compound 1 (12.6 g, 27 mmol, 1 eq.) in 100 mL of MeCN were added potassium carbonate (7.3 g, 53 mmol, 2 eq.) and Gen13-a (5.2 g, 34 mmol, 1.3 eq.). The reaction mixture was refluxed for 5.5 h then cooled to r.t. and stirred for 40 h. The crude product was filtered and washed with MeCN. The collected precipitate was then suspended in 300 mL of water, stirred for 1 h, filtered, and finally washed with water and MeCN. The solid obtained was dried in vacuo for 48 h to afford Compound 2.

$^1$H NMR (400 MHz, $CDCl_3$) δ ppm 8.20-8.12 (2H, m), 7.22-7.13 (2H, m), 6.99 (2H, s), 4.68 (1H, m), 4.43 (1H, dd), 4.26 (1H, dd), 4.14-4.05 (1H, m), 3.88 (1H, dd), 3.61 (3H, s), 3.58-3.52 (1H, m), 3.14-3.02 (6H, m), 2.74 (2H, q), 2.70-2.62 (4H, m), 2.59 (3H, s), 1.33 (3H, t)

LC-MS: MW (calcd): 588; m/z MW (obsd): 589 (M+1)

1.2.7.15. General Methods F9

1.2.7.15.1. General Method F9a

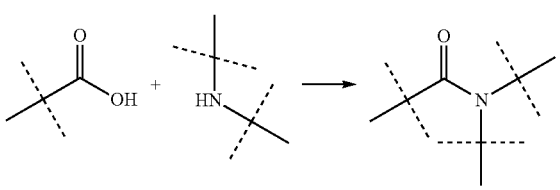

To a solution of acid (1.1 eq.) in DCM are added HOBT (1.2 eq.) and EDC.HCl (1.2 eq.). The reaction mixture is stirred at r.t. for 45 min then prepared solution of amine (1 eq.) in DCM with TEA (3 eq.) is added. The reaction mixture is stirred at r.t. until completion, then water and a solution of HCl 1 M are added, the aqueous layer is extracted with DCM, the organic layer is washed with a saturated Na₂CO₃ solution, and brine, dried over Na₂SO₄, filtered and concentrated in vacuo. The residue is purified by chromatography on silica gel to afford the expected compound.

1.2.7.15.2. Illustrative Synthesis of Compound 205: 1-Benzyl-4-[4-(2-ethyl-3-{[4-(4-fluoro-phenyl)-thiazol-2-yl]-methyl-amino}-imidazo[1,2-a]pyridin-6-yl)-piperazine-1-carbonyl]-pyrrolidin-2-one

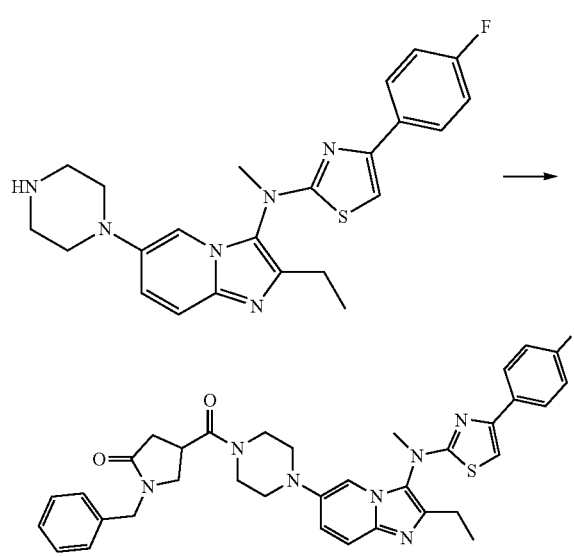

To a solution of 1-benzyl-5-oxo-pyrrolidine-3-carboxylic acid (38 mg, 0.173 mmol, 1.1 eq.) in DCM (3 mL) were added HOBT (25 mg, 0.188 mmol, 1.2 eq.) and EDC.HCl (36 mg, 0.188 mmol, 1.2 eq.). The reaction mixture was stirred at r.t. for 45 min then Gen-10-e (80 mg, 0.157 mmol, 1 eq.) dissolved in DCM (1 mL) with TEA (65 μL, 0.471 mmol, 3 eq.) was added. The reaction mixture was stirred at r.t overnight, then water and a solution of HCl 1 M were added, the aqueous layer was extracted with DCM, the organic layer was washed with a saturated Na₂CO₃ solution, and brine, dried over Na₂SO₄, filtered and concentrated in vacuo. The residue was purified by chromatography on silica gel to afford the Compound 205

LC-MS: MW (calcd): 637; m/z MW (obsd): 638 (M+1)

1.2.7.15.3. General Method F9b

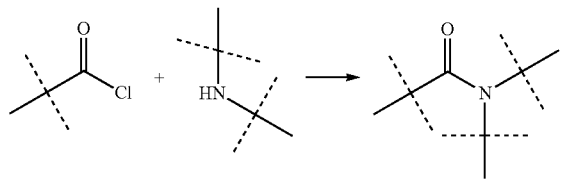

To a solution of amine (1 eq.) in DCM are added TEA (4 to 5 eq.) followed by acyl chloride derivative (1.2 to 2 eq.). The reaction mixture is stirred at r.t. until completion, then is quenched with water and the aqueous layer is extracted with DCM twice. The organic layer is washed with water, and brine, dried over Na₂SO₄, filtered and concentrated in vacuo. The residue is purified by chromatography on silica gel to afford the expected compound.

1.2.7.15.4. Illustrative Synthesis of Compound 48: 1-{3-[4-(2-Ethyl-3-{[4-(4-fluoro-phenyl)-thiazol-2-yl]-methyl-amino}-imidazo[1,2-a]pyridin-6-yl)-piperazine-1-carbonyl]-pyrrolidin-1-yl}-ethanone

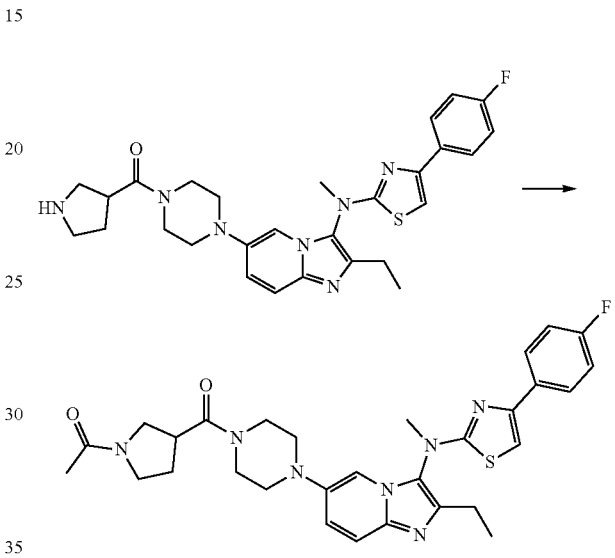

To a solution of compound 47 (30 mg, 0.049 mmol, 1 eq.) in DCM (2 mL) were added TEA (34 μL, 0.247 mmol, 5 eq.) followed by the acetyl chloride (7 μL, 0.099 mmol, 2 eq.). The reaction mixture was stirred at r.t. for 2 h, then quenched with water and the aqueous layer was extracted with DCM twice. The organic layer was washed with water, and brine, dried over Na₂SO₄, filtered and concentrated in vacuo. The residue was purified by chromatography on silica gel to afford Compound 48

LC-MS: MW (calcd): 575; m/z MW (obsd): 576 (M+1)

1.2.7.16. General Method F10

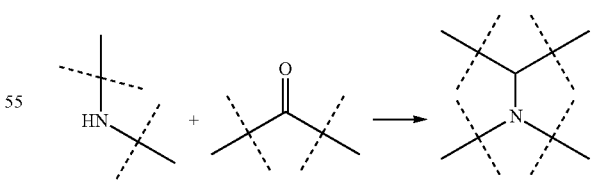

To a solution of the appropriate amine (1.0 eq.) in MeOH are added TEA (0 to 3 eq.), acetic acid if needed (0 to 3 eq.) and the aldehyde or ketone (1.5 to 2 eq.). The reaction mixture is stirred at r.t. for 10 min then NaBH₃CN (1.5 to 3 eq.) is added. The reaction mixture is stirred at r.t. overnight, then concentrated in vacuo. The residue is dissolved in a mixture of DCM and water, the two phases are separated and the aqueous phase is extracted with DCM. The combined organic layers are washed with a saturated Na$_2$CO$_3$ solution, and brine, dried over Na$_2$SO$_4$, filtered and concentrated in vacuo. The residue was purified by chromatography on silica gel to afford the expected compound.

1.2.7.17. Illustrative Synthesis of Compound 217: [6-(1-Benzyl-piperidin-4-yl)-2-ethyl-imidazo[1,2-a]pyridin-3-yl]-[4-(4-fluoro-phenyl)-thiazol-2-yl]-methyl-amine DCM, the aqueous layer is extracted with DCM. The combined organic layers are washed with water and brine, dried over Na$_2$SO$_4$, filtered and concentrated in vacuo. The residue is purified by chromatography on silica gel to afford the expected compound.

1.2.7.19. Illustrative Synthesis of Compound 80: N-(2-ethyl-6-(1-(methylsulfonyl)piperidin-4-yl)imidazo[1,2-a]pyridin-3-yl)-4-(4-fluorophenyl)-N-methylthiazol-2-amine

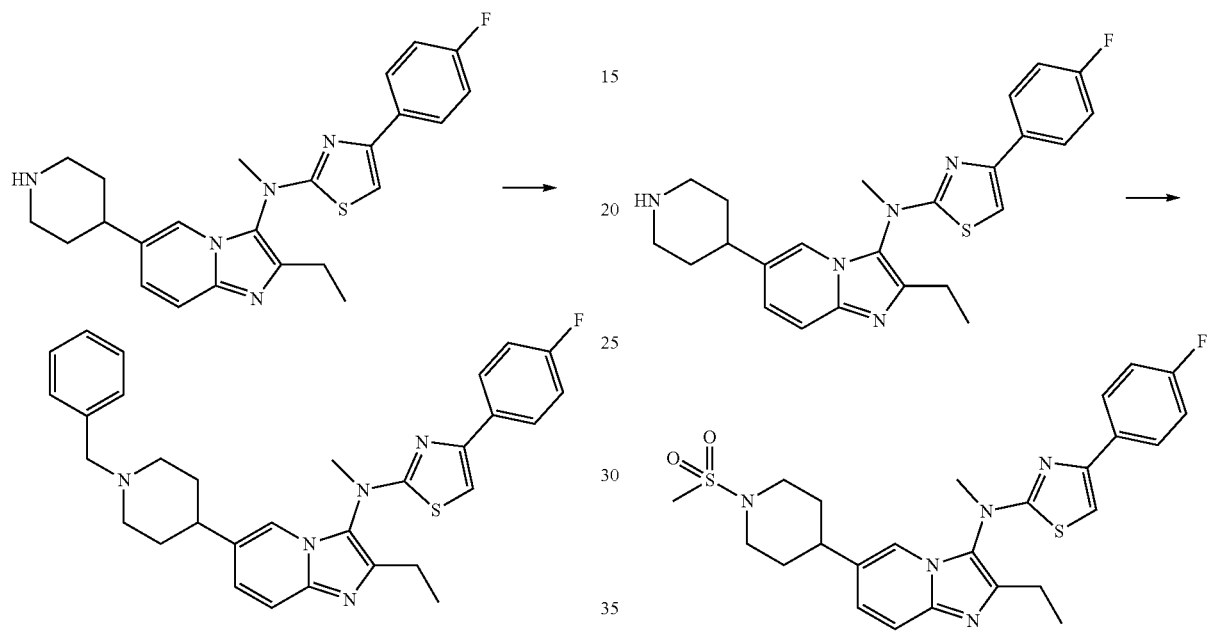

To a solution of amine Gen-10-c (40 mg, 0.085 mmol, 1.0 eq.) in MeOH (2 mL) were added TEA (35 μL, 0.254 mmol, 3 eq.) and the benzaldehyde (17 μL, 0.169 mmol, 2 eq.). The reaction mixture was stirred at r.t. for 10 min then NaBH$_3$CN (158 mg, 0.254 mmol, 3 eq.) was added. The reaction mixture was stirred at r.t. overnight, then concentrated in vacuo. The residue was dissolved in a mixture of DCM and water, the two phases were separated and the aqueous phase is extracted with DCM. The combined organic layers were washed with a saturated Na$_2$CO$_3$ solution, and brine, dried over Na$_2$SO$_4$, filtered and concentrated in vacuo. The residue was purified by chromatography on silica gel to afford Compound 217.

LC-MS: MW (calcd): 525; m/z MW (obsd): 526 (M+1)

1.2.7.18. General Method F11

To a solution of the previously prepared amine Gen-10-c (2.9 g, 6.7 mmol, 1 eq.) in DCM at 0° C. were added TEA (2.8 mL, 20.1 mmol, 3 eq.) and mesyl chloride (1.03 mL, 13.3 mmol, 2 eq.). The reaction mixture was stirred at r.t. for 3 h. The crude product was quenched with water and diluted with DCM, the aqueous layer was extracted with DCM. The combined organic layers were washed with water and brine, dried over Na$_2$SO$_4$, filtered and concentrated in vacuo. The residue was purified by chromatography on silica gel (elution DCM/MeOH 90/10) to afford Compound 80.

LC-MS: MW (calcd): 513; m/z MW (obsd): 514 (M+1)

1.2.7.20. General Methods F12

1.2.7.20.1. General Methods F12a

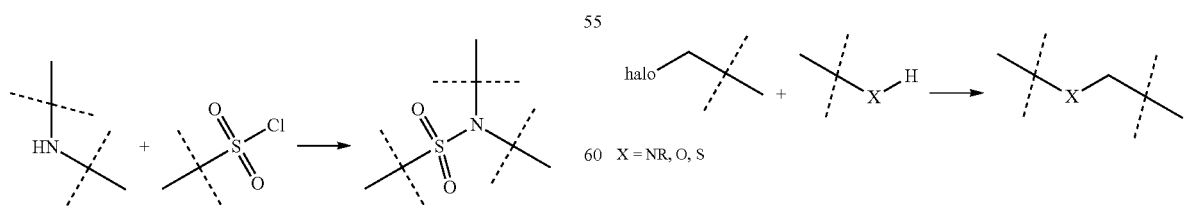

To a solution of the appropriate amine (1 eq.) in DCM at 0° C. are added TEA (3 eq.) and sulfonyl chloride (1.3 to 2 eq.). The reaction mixture is stirred at r.t. until completion. The crude product is quenched with water and diluted with To a solution of the corresponding nucleophile (2 to 6 eq.) in THF or DMF are added NaI or KI (cat) and halogenoalkyl group containing imidazo[1,2-a]pyridine-3-ylamine derivative Gen-10 (1 eq.). When the nucleophile amine corresponding as a hydrochloride, the amine is premixed with K$_2$CO$_3$ (5 to 6 eq.) in the solvent for 10 min before the addition of the catalyst and the halogenoalkyl group containing imidazo[1,2-a]pyridine-3-ylamine derivative. The reaction mixture is heated between 80° C. and 150° C. under microwave irradiation or in thermic conditions for 1.5 to 3 h. After cooling, water and EtOAc are added to the reaction mixture, the aqueous layer is extracted with EtOAc twice. The combined organic layers are washed with water and brine, dried over Na$_2$SO$_4$, filtered and concentrated in vacuo. The residue is purified by chromatography on silica gel to afford the expected compound.

1.2.7.20.2. Illustrative Synthesis of Compound 89: {2-Ethyl-6-[1-(3-pyrrolidin-1-yl-propane-1-sulfonyl)-piperidin-4-yl]-imidazo[1,2-a]pyridin-3-yl}-[4-(4-fluoro-phenyl)-thiazol-2-yl]-methyl-amine

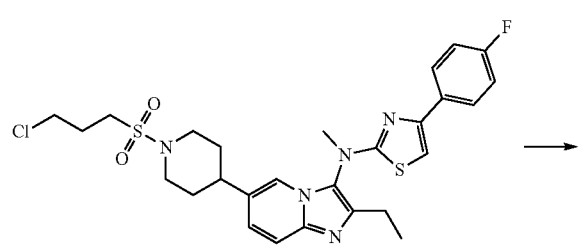

To a solution of the pyrrolidine (36 µL, 0.434 mmol, 5 eq.) in THF (3 mL) were added NaI (2 mg, cat) and Compound 86 (50 mg, 0.087 mmol, 1 eq.). The reaction mixture was heated at 150° C. under microwave irradiation for 2 h. After cooling, water and EtOAc were added to the reaction mixture, the aqueous layer was extracted with EtOAc twice. The combined organic layers were washed with water and brine, dried over Na$_2$SO$_4$, filtered and concentrated in vacuo. The residue was purified by chromatography on silica gel to afford Compound 89.

LC-MS: MW (calcd): 610; m/z MW (obsd): 611 (M+1)

1.2.7.20.3. Illustrative Synthesis of Compound 131: {2-(3,3-Difluoro-azetidin-1-yl)-1-[4-(2-ethyl-3-{[4-(4-fluoro-phenyl)-thiazol-2-yl]-methyl-amino}-imidazo[1,2-a]pyridin-6-yl)-piperidin-1-yl]-ethanone

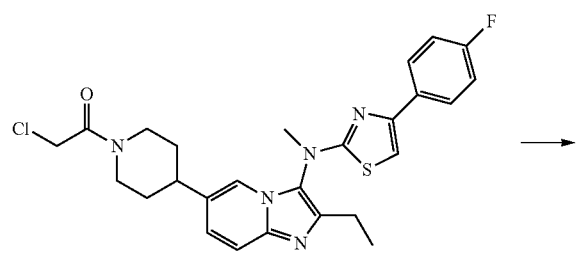

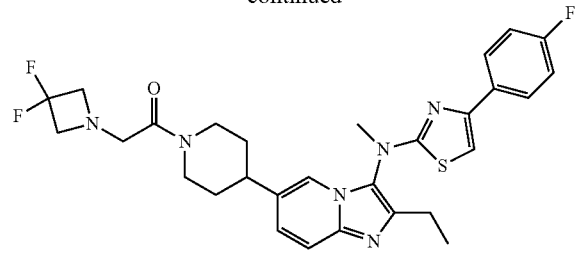

To a solution of the 3,3-difluoroazetidine hydrochloride (40 mg, 0.31 mmol, 2 eq.) in DMF (1.5 mL) was added K$_2$CO$_3$ (111 mg, 0.80 mmol, 5 eq.), the reaction mixture was stirred at r.t. for 10 min., then KI (4 mg, cat) and the 2-Chloro-1-[4-(2-ethyl-3-{[4-(4-fluoro-phenyl)-thiazol-2-yl]-methyl-amino}-imidazo[1,2-a]pyridin-6-yl)-piperidin-1-yl]-ethanone (1 eq.) were added. The reaction mixture is heated at 80° C. in thermic conditions for 2 h. After cooling, water and EtOAc were added to the reaction mixture, the aqueous layer was extracted with EtOAc twice. The combined organic layers were washed with water and brine, dried over Na$_2$SO$_4$, filtered and concentrated in vacuo. The residue was purified by chromatography on silica gel to afford Compound 131.

LC-MS: MW (calcd): 568; m/z MW (obsd): 569 (M+1)

1.2.7.20.4. General Methods F12b

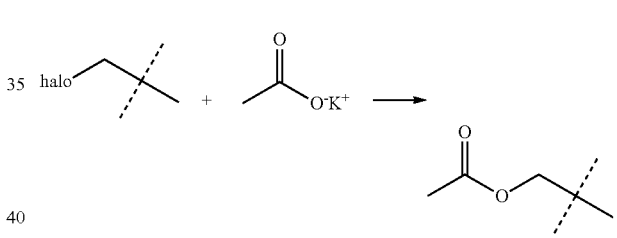

To a solution of the halogenoalkyl group containing imidazo[1,2-a]pyridine-3-ylamine derivative (1 eq.) in DMF is added potassium acetate (3 eq.), the reaction mixture is heated at 90° C. for 4 h to overnight. After cooling, water and EtOAc are added to the reaction mixture, the aqueous layer is extracted with EtOAc twice. The combined organic layers are washed with water and brine, dried over Na$_2$SO$_4$, filtered and concentrated in vacuo. The residue is purified by chromatography on silica gel to afford the expected compound.

1.2.7.20.5. Illustrative Synthesis of Compound 74: Acetic acid 3-[4-(2-ethyl-3-{[4-(4-fluoro-phenyl)-thiazol-2-yl]-methyl-amino}-imidazo[1,2-a]pyridin-6-yl)-3,6-dihydro-2H-pyridine-1-sulfonyl]-propyl ester

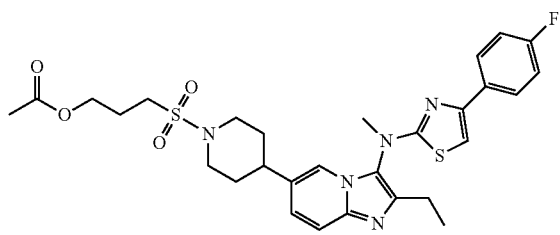

To a solution of the {6-[1-(3-Chloro-propane-1-sulfonyl)-1,2,3,6-tetrahydro-pyridin-4-yl]-2-ethyl-imidazo[1,2-a]pyridin-3-yl}-[4-(4-fluoro-phenyl)-thiazol-2-yl]-methyl-amine (105 mg, 0.183 mmol, 1 eq.) in DMF (3 mL) was added potassium acetate (54 mg, 0.549 mmol, 3 eq.), the reaction mixture was heated at 90° C. for 4 h. After cooling, water and EtOAc were added to the reaction mixture, the aqueous layer was extracted with EtOAc twice. The combined organic layers were washed with water and brine, dried over Na₂SO₄, filtered and concentrated in vacuo. The residue was purified by chromatography on silica gel to afford Compound 74.

LC-MS: MW (calcd): 597; m/z MW (obsd): 598 (M+1)

1.2.7.21. General Method F13

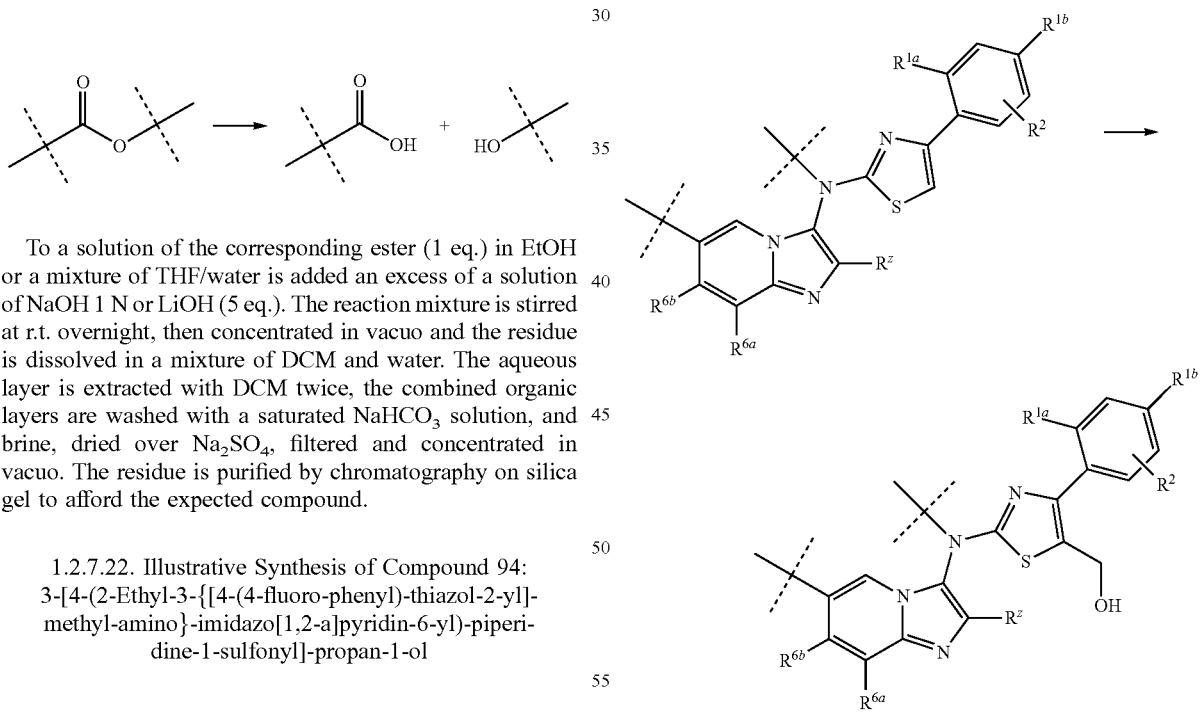

To a solution of the corresponding ester (1 eq.) in EtOH or a mixture of THF/water is added an excess of a solution of NaOH 1 N or LiOH (5 eq.). The reaction mixture is stirred at r.t. overnight, then concentrated in vacuo and the residue is dissolved in a mixture of DCM and water. The aqueous layer is extracted with DCM twice, the combined organic layers are washed with a saturated NaHCO₃ solution, and brine, dried over Na₂SO₄, filtered and concentrated in vacuo. The residue is purified by chromatography on silica gel to afford the expected compound.

1.2.7.22. Illustrative Synthesis of Compound 94: 3-[4-(2-Ethyl-3-{[4-(4-fluoro-phenyl)-thiazol-2-yl]-methyl-amino}-imidazo[1,2-a]pyridin-6-yl)-piperidine-1-sulfonyl]-propan-1-ol

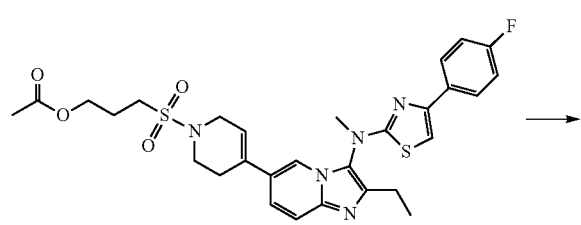

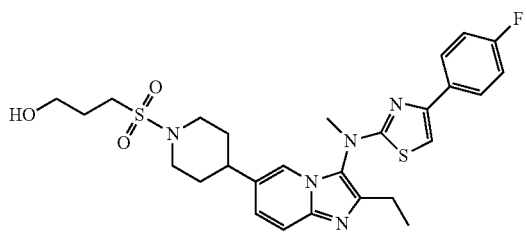

To a solution of the compound 93 (1.14 g, 1.901 mmol, 1 eq.) in EtOH (15 mL) was added an excess of a solution of NaOH 1 N (10 mL). The reaction mixture was stirred at r.t. overnight, then concentrated in vacuo and the residue was dissolved in a mixture of DCM and water. The aqueous layer was extracted with DCM twice, the combined organic layers were washed with a saturated NaHCO₃ solution, and brine, dried over Na₂SO₄, filtered and concentrated in vacuo. The residue was purified by chromatography on silica gel to afford Compound 94.

LC-MS: MW (calcd): 557; m/z MW (obsd): 558 (M+1)

1.2.7.23. General Method F14

To a solution of thiazole derivative (1 eq.) in THF are added formaldehyde (48 eq.), TEA (5.9 eq.) and water. The reaction mixture is heated to 140° C. under microwave irradiation for 2.5 h. The crude product mixture is quenched with water and a NH₃ aqueous solution. The aqueous layer is extracted with EtOAc. The combined organic layers are washed with water and brine, dried over Na₂SO₄, filtered and concentrated in vacuo. The residue is purified by chromatography on silica gel to deliver the expected compound.

1.2.7.24. Illustrative Synthesis of Compound 147: (2-((2-ethyl-6-(1-(methylsulfonyl)piperidin-4-yl)imidazo[1,2-a]pyridin-3-yl)(methyl)amino)-4-(4-fluorophenyl)thiazol-5-yl)methanol

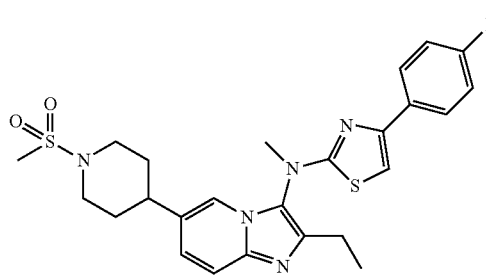

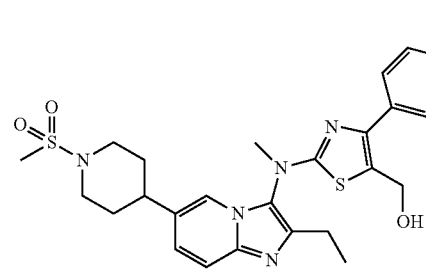

To a solution of compound 80 (500 mg, 0.97 mmol, 1 eq.) in THF (3.5 mL) were added formaldehyde (37% in water, 3.5 mL, 47 mmol, 48 eq.), TEA (800 µL, 5.75 mmol, 5.9 eq.) and water (3.5 mL). The reaction mixture was heated to 140° C. under microwave irradiation for 2.5 h. The crude mixture was quenched with water and a NH₃ aqueous solution. The aqueous layer was extracted with EtOAc. The combined organic layers were washed with water and brine, dried over Na₂SO₄, filtered and concentrated in vacuo. The residue was purified by chromatography on silica gel (elution with DCM/MeOH: 100/0 to 97/3) to afford Compound 147.

LC-MS: MW (calcd): 543; m/z MW (obsd): 544 (M+1)

1.2.7.25. General Method F15

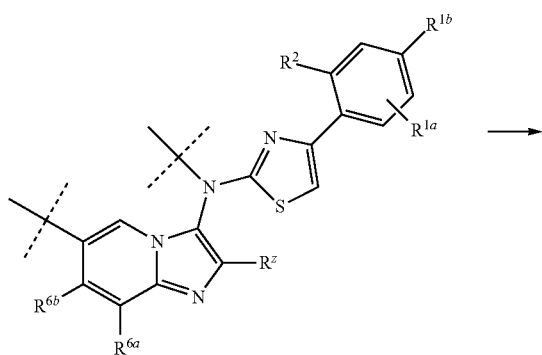

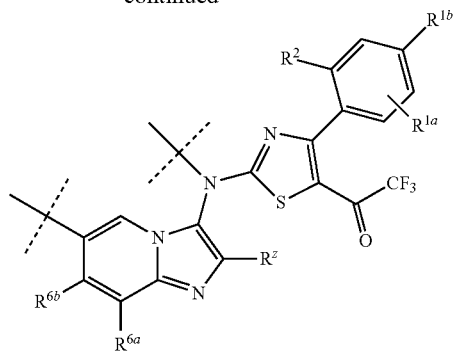

To a solution of thiazole derivative (1 eq.) in pyridine at 0° C. is slowly added trifluoroacetic anhydride (6 eq.). The reaction mixture is stirred at 0° C. for 1 h then partitioned between DCM and water. The organic phase is separated. The aqueous layer is extracted with DCM. The combined organic layers are washed with water and brine, dried over MgSO₄, filtered and concentrated in vacuo. The residue is purified by chromatography on silica gel to afford the expected compound.

1.2.7.26. Illustrative Synthesis of Compound 160: 1-(2-((2-ethyl-6-(1-(methylsulfonyl)piperidin-4-yl)imidazo[1,2-a]pyridin-3-yl)(methyl)amino)-4-(4-fluorophenyl)thiazol-5-yl)-2,2,2-trifluoroethanone

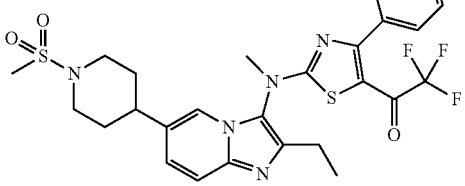

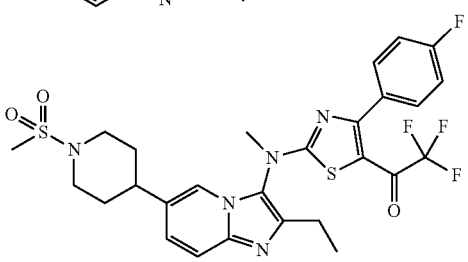

To a solution of compound 80 (80 mg, 0.16 mmol, 1 eq.) in pyridine (5 mL) at 0° C. was slowly added trifluoroacetic anhydride (150 µL, 0.93 mmol, 6 eq.). The reaction mixture was stirred at 0° C. for 1 h then partitioned between DCM and water. The organic phase was separated. The aqueous layer was extracted with DCM. The combined organic layers were washed with water and brine, dried over MgSO₄, filtered and concentrated in vacuo. The residue was purified by chromatography on silica gel (elution with DCM/MeOH: 100/0 to 95/5) to afford Compound 160.

LC-MS: MW (calcd): 609; m/z MW (obsd): 610 (M+1)

1.2.7.27. General Methods F16

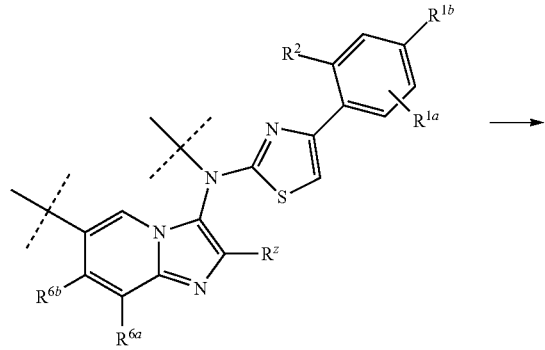

1.2.7.27.1. General Method F16a

To a solution of thiazole derivative (1 eq.) in DCM is added polymer-supported bromide (1.1 eq.). The mixture is stirred vigorously at r.t. for 4 h. The crude mixture is filtered, the residue is washed with DCM and MeOH. The filtrate is concentrated in vacuo, then diluted with DCM, washed with a saturated NaHCO$_3$ solution, water and brine, dried over Na$_2$SO$_4$ and concentrated in vacuo to afford the expected compound.

1.2.7.27.2. Illustrative Synthesis of 2-[4-(3-{[5-Bromo-4-(4-fluoro-phenyl)-thiazol-2-yl]-methyl-amino}-2-ethyl-imidazo[1,2-a]pyridin-6-yl)-piperazin-1-yl]-1-(3-hydroxymethyl-cyclobutyl)-ethanone

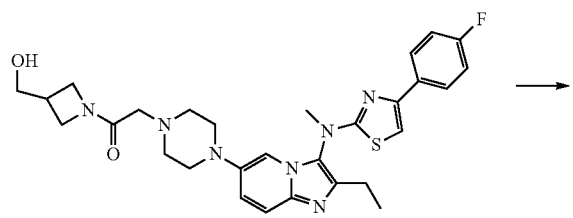

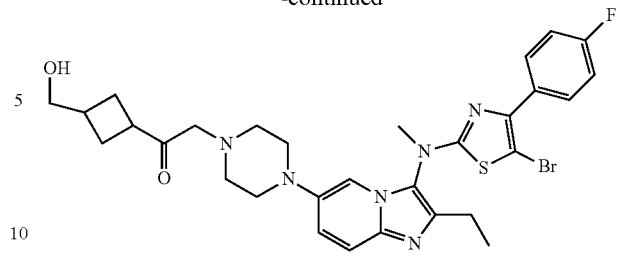

To a solution of compound 34 (200 mg, 0.36 mmol, 1 eq.) in DCM (7.5 mL), was added polymer-supported bromide (1.2-1.8 mmol/g, 244 mg, 0.39 mmol, 1.1 eq.). The mixture was stirred vigorously at r.t. for 4 h. The crude mixture was filtered; the residue was washed with DCM and MeOH. The filtrate was concentrated in vacuo, then diluted with DCM, washed with a saturated NaHCO$_3$ solution, water and brine, dried over Na$_2$SO$_4$ and concentrated in vacuo to afford the expected compound.

LC-MS: MW (calcd): 641 ($^{79}$Br), 643 ($^{81}$Br); m/z MW (obsd): 642 ($^{79}$Br M+1), 644 ($^{81}$Br M+1)

1.2.7.27.3. General Method F16b

To a solution of thiazole derivative (1 eq.) in MeCN is added selectfluor (1.2 eq.) portionwise. The mixture is stirred at r.t. for 20 h to 2 days. The crude mixture is concentrated in vacuo, the residue is dissolved in mixture of EtOAc and water. The aqueous layer is extracted with EtOAc twice, the combined organic layers are washed with water, then brine, dried over Na$_2$SO$_4$, filtered and concentrated in vacuo. The residue is purified by chromatography on silica gel to afford the expected compound.

1.2.7.27.4. Illustrative Synthesis of Compound 95: 3-[4-(2-Ethyl-3-{[5-fluoro-4-(4-fluoro-phenyl)-thiazol-2-yl]-methyl-amino}-imidazo[1,2-a]pyridin-6-yl)-piperidine-1-sulfonyl]-propan-1-ol

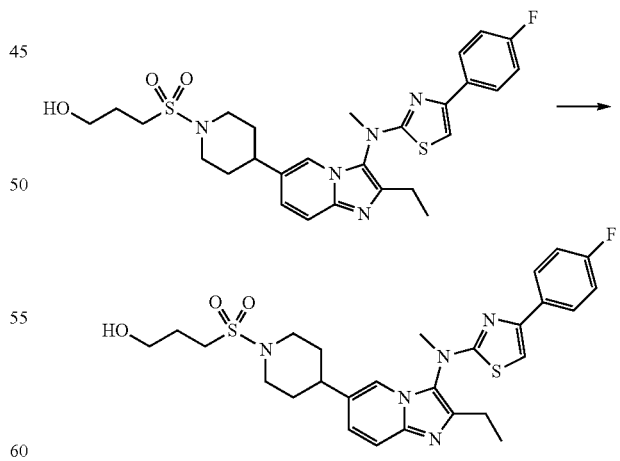

To a solution of compound 94 (90 mg, 0.161 mmol, 1 eq.) in MeCN (5 mL) was added selectfluor (69 mg, 0.194 mmol, 1.2 eq.) portionwise. The mixture was stirred at r.t. for 2 days. The crude mixture is concentrated in vacuo, the residue was dissolved in mixture of EtOAc and water. The aqueous layer was extracted with EtOAc twice, the combined organic layers were washed with water, and brine, dried over Na₂SO₄, filtered and concentrated in vacuo. The residue was purified by chromatography on silica gel to afford Compound 95.

LC-MS: MW (calcd): 575; m/z MW (obsd): 576 (M+1)

1.2.7.28. General Method F17

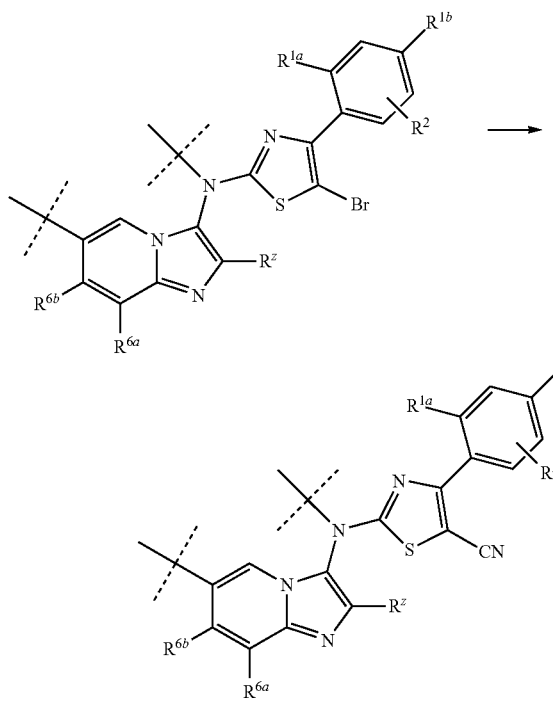

To a solution of the above prepared bromide (1 eq.) in pyridine is added copper cyanide (5 eq.). The mixture is heated to 160° C. under microwave irradiation for 2 h. The crude mixture is quenched with water and a NH₃ aqueous solution, and diluted in EtOAc. The organic layer is separated, the aqueous layer is extracted with EtOAc. The combined organic layers are washed with water and brine, dried over Na₂SO₄ and concentrated in vacuo. The residue is purified by chromatography on silica gel or preparative LC-MS to afford the expected compound.

1.2.7.29. Illustrative Synthesis of Compound 139:
2-((2-ethyl-6-(4-(2-(3-(hydroxymethyl)azetidin-1-yl)-2-oxoethyl)piperazin-1-yl)imidazo[1,2-a]pyridin-3-yl)(methyl)amino)-4-(4-fluorophenyl)thiazole-5-carbonitrile

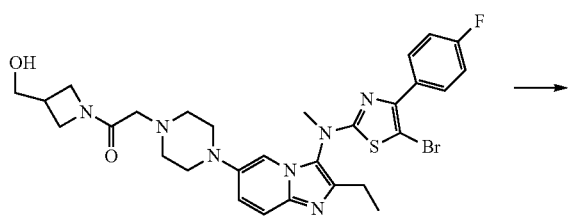

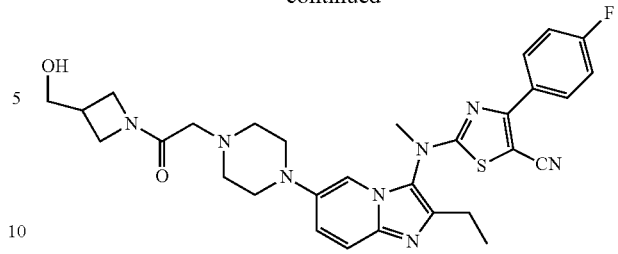

The bromo derivative (128 mg, 0.20 mmol, 1 eq.), obtained by bromination of compound 34 by the general method F16a, was dissolved in pyridine (3 mL), then copper cyanide (89 mg, 1 mmol, 5 eq.) was added. The mixture was heated to 160° C. under microwave irradiation for 2 h. The crude mixture was quenched with water and a NH₃ aqueous solution, and diluted in EtOAc. The organic layer was separated; the aqueous layer was extracted with EtOAc. The combined organic layers were washed with water and brine, dried over Na₂SO₄ and concentrated in vacuo. The residue was purified by preparative LC-MS to afford Compound 139.

LC-MS: MW (calcd): 588; m/z MW (obsd): 589 (M+1)

1.2.7.30. General Method F18

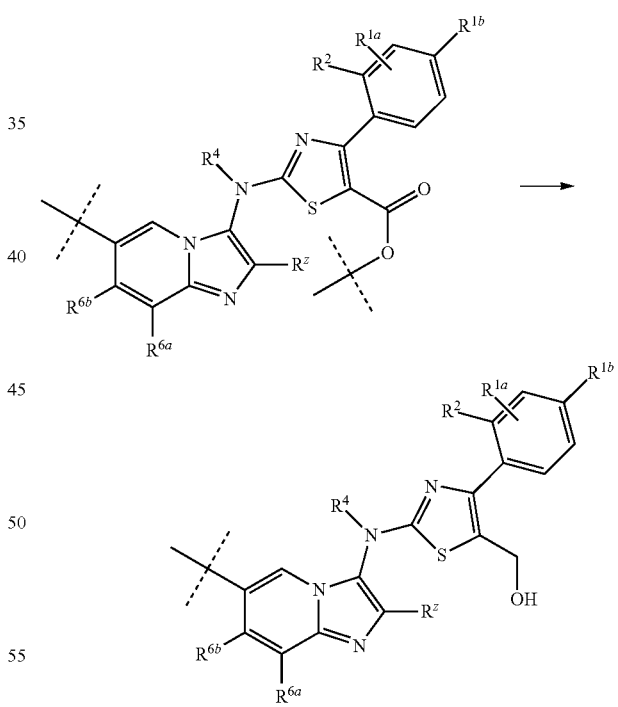

To a solution of ester derivative (1 eq.) in anhydrous THF at 0° C. is added LiBH₄ (2 M in THF, 5 eq.). The reaction mixture is allowed to warm to r.t. then stirred overnight at 80° C. Solid sodium sulfate hydrate is added and the mixture is kept stirring for 10 min. The reaction mixture is then filtered and the solid is rinsed with THF. The filtrate is concentrated to give the hydroxymethyl derivative that can be used as such in the next step or purified by chromatography.

1.2.7.31. Illustrative Synthesis of 4-(2-Ethyl-3-{[4-(4-fluoro-phenyl)-5-hydroxymethyl-thiazol-2-yl]-methyl-amino}-imidazo[1,2-a]pyridin-6-yl)-ppera-zine-1-carboxylic acid tert-butyl ester

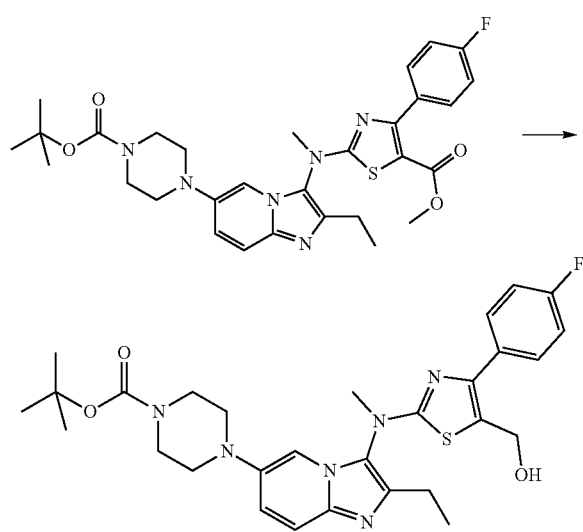

To a solution of Intermediate Gen-10-ag (723 mg, 1.22 mmol, 1 eq.) in anhydrous THF (12 mL) at 0° C. was added LiBH$_4$ (2 M in THF, 3 mL, 6.1 mmol, 5 eq.). The reaction mixture was allowed to warm to r.t. then stirred overnight at 80° C. Solid sodium sulfate hydrate was added and the mixture was kept stirring for 10 min. The reaction mixture was then filtered and the solid rinsed with THF. The filtrate was concentrated to give the expected compound used as such in the next step.
LC-MS: MW (calcd): 566; m/z (obsd): 567 (M+1)

1.2.7.32. General Method F19: General Synthesis of Oxazoline Derivative

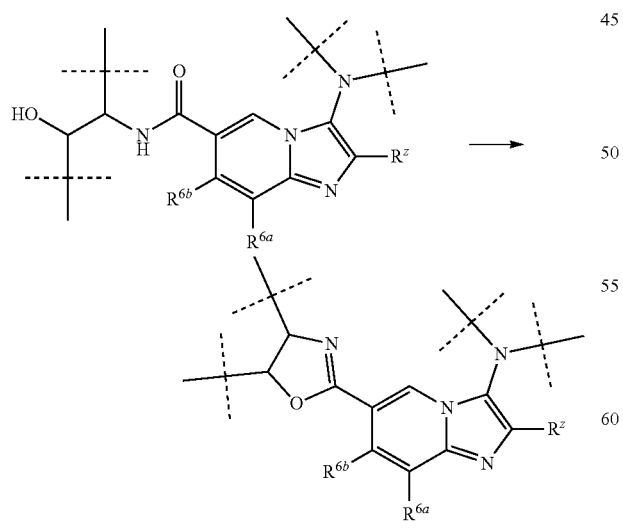

3-Amino-imidazo[1,2-a]pyridine-6-carboxylic acid (2-hydroxy-ethyl)-amide derivative is prepared from Intermediate Gen-5 (with R$^y$=CO$_2$R) and 2-ethanolamine derivative via successive general synthetic methods F13 and F9a. To the 3-amino-imidazo[1,2-a]pyridine-6-carboxylic acid (2-hydroxy-ethyl)-amidederivative prepared from Intermediate Gen-5-aa with the desired amine via successive general synthetic methods F13 and F9a (1 eq.) in anhydrous DCM are added triphenylphosphine (1.5 eq.) and DDQ (1.5 eq.). The reaction mixture is stirred at r.t. for 0.5 h then the solvent is evaporated. The crude product is purified by chromatography to give the expected compound.

1.2.7.33. Illustrative Synthesis of Compound 240: [6-(4,5-Dihydro-oxazol-2-yl)-2-ethyl-imidazo[1,2-a]pyridin-3-yl]-[4-(4-fluoro-phenyl)-thiazol-2-yl]-methyl-amine

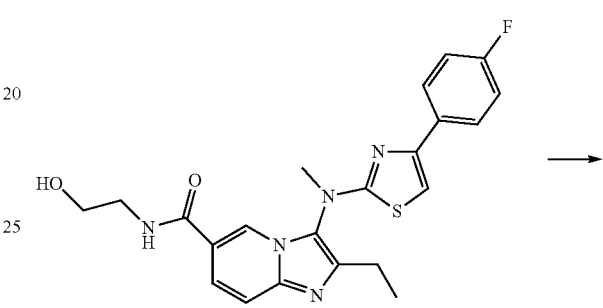

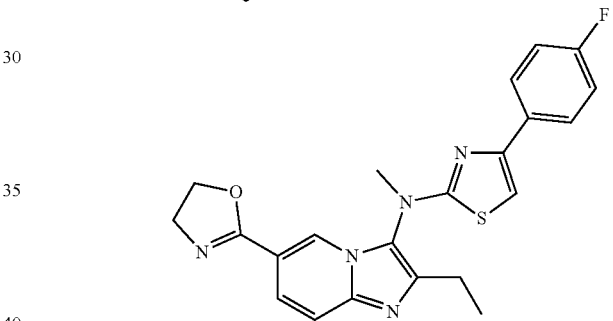

To a solution of 3-((4-(4-chlorophenyl)thiazol-2-yl)(methyl)amino)-2-ethyl-N-(2-hydroxyethypimidazo[1,2-a]pyridine-6-carboxamide (40 mg, 0.09 mmol, 1 eq.), prepared from Intermediate Gen-5-aa and ethanolamine via successive general synthetic methods F13 and F9a) in DCM (1.5 mL), were added triphenylphosphine (35 mg, 0.13 mmol, 1.5 eq.) and DDQ (30 mg, 0.13 mmol, 1.5 eq.). The reaction mixture was stirred at room temperature for 0.5 h and then concentrated. The crude product was purified by chromatography on silica gel (eluent DCM/MeOH 100/0 to 97/3) to give Compound 240.
LC-MS: MW (calcd): 437; m/z (obsd): 438 (M+1)

1.2.7.34. General Method E1

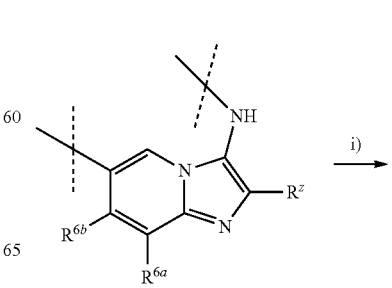

125
-continued

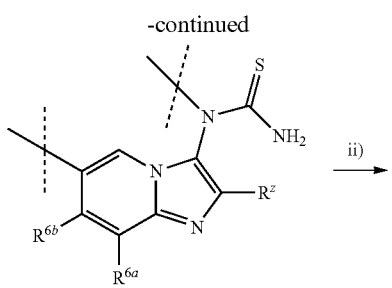

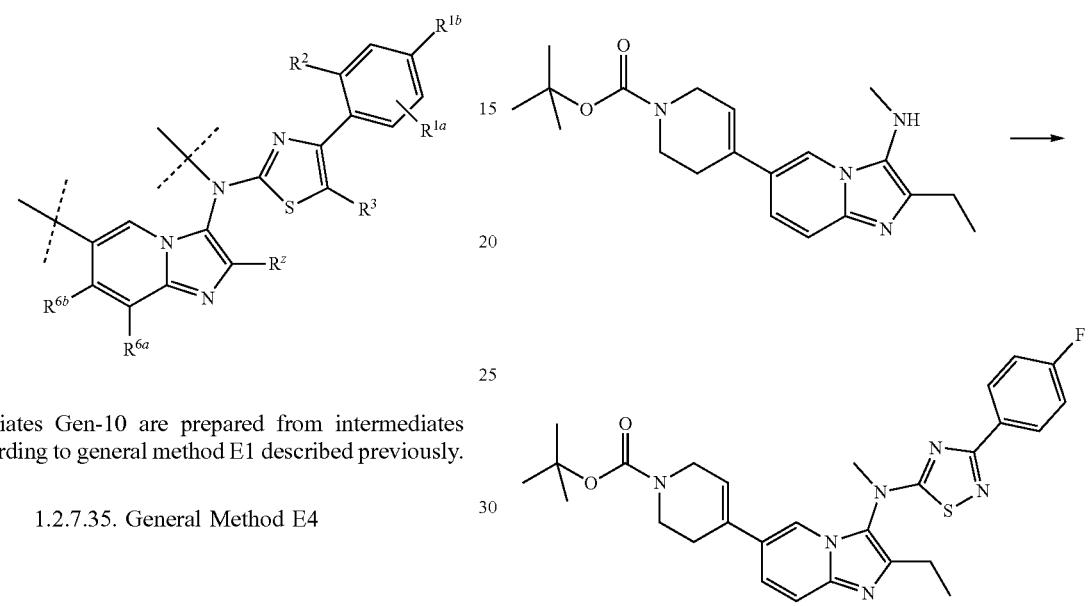

Intermediates Gen-10 are prepared from intermediates Gen-9 according to general method E1 described previously.

1.2.7.35. General Method E4

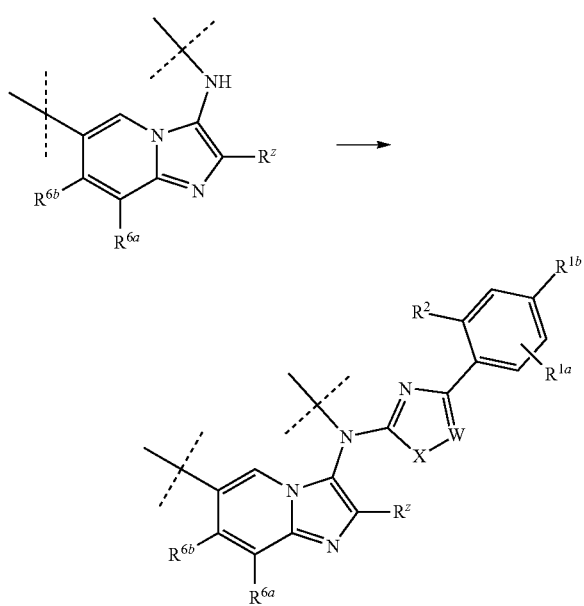

To a previously degassed solution of halogeno heteroaryl derivative (1 eq.), the imidazo[1,2-a]pyridine-3-ylamine derivative (1.2 eq.), cesium carbonate (3 eq.), and Xantphos (0.15 eq.) in dioxane under argon is added Pd(OAc)$_2$ (0.2 eq.). The reaction mixture is heated to reflux until completion. After cooling to r.t., the reaction mixture is partitioned between water and EtOAc and the layers separated. The aqueous layer is extracted with EtOAc. The combined organic layers are washed with water and brine, dried Na$_2$SO$_4$, filtered and concentrated in vacuo. The crude product is purified by chromatography on silica gel to afford the expected intermediate.

1.2.7.36. Illustrative Synthesis of 4-(2-Ethyl-3-{[3-(4-fluoro-phenyl)-[1,2,4]thiadiazol-5-yl]-methyl-amino}-imidazo[1,2-a]pyridin-6-yl)-3,6-dihydro-2H-pyridine-1-carboxylic acid tert-butyl ester To a previously degassed solution of 5-chloro-3-(4-fluorophenyl)-1,2,4-thiadiazole (800 mg, 3.73 mmol, 1 eq.), amine Gen-9-c (1.57 g, 4.41 mmol, 1.2 eq.), cesium carbonate (3.64 g, 11.2 mmol, 3 eq.), and Xantphos (323 mg, 0.56 mmol, 0.15 eq.) in dioxane (20 mL) under argon was added Pd(OAc)$_2$ (167 mg, 0.74 mmol, 0.2 eq.). The reaction mixture was heated to reflux for 3 h. After cooling to r.t., the reaction mixture was partitioned between water and EtOAc and the layers separated. The aqueous layer was extracted twice with EtOAc. The combined organic layers were washed with water and brine, dried Na$_2$SO$_4$, filtered and concentrated in vacuo. The crude product was purified by chromatography on silica gel (elution with heptane/EtOAc: 80/20 to 40/60) to afford the expected compound.

LC-MS: MW (calcd): 534; m/z MW (obsd): 535 (M+1)

1.2.7.37. General Method E5

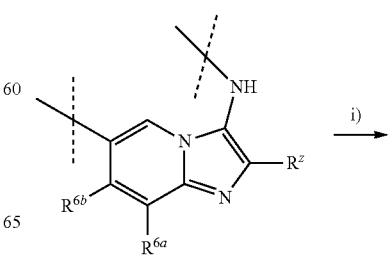

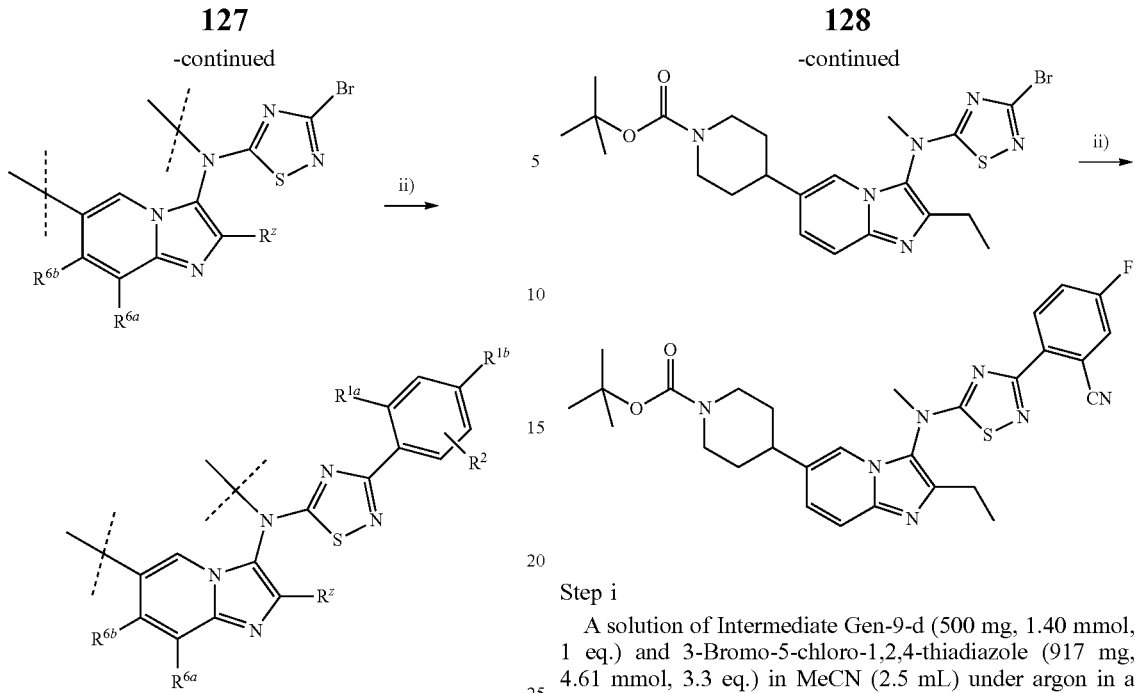

Step i

A solution of imidazo[1,2-a]pyridine-3-ylamine derivative (1 eq.) and 3-Bromo-5-chloro-1,2,4-thiadiazole (3.3 eq.) in MeCN (2.5 mL) under argon in a sealed tube is heated at 90° C. overnight. After cooling to r.t. the mixture is concentrated in vacuo. The residue is purified by chromatography on silica gel.

Step ii

To a solution of the above prepared bromo derivative (1 eq.) in a mixture dioxane/water under argon are added cesium fluoride (2.1 eq.), the corresponding aryl boronic acid derivative (1.2 eq.), and then $PdCl_2(P\text{-}tBu_2(p\text{-}NMe_2Ph))_2$ (0.1 eq.). The reaction mixture is heated at 80° C. for 48 h. After cooling to r.t., the reaction mixture is partitioned between water and EtOAc and the layers separated. The aqueous layer is extracted twice with EtOAc. The combined organic layers are washed with water and brine, dried $Na_2SO_4$, filtered and concentrated in vacuo. The crude product is purified by chromatography on silica gel to afford the expected intermediate.

1.2.7.38. Illustrative Synthesis of 4-(3-{[3-(2-Cyano-4-fluoro-phenyl)-[1,2,4]thiadiazol-5-yl]-methyl-amino}-2-ethyl-imidazo[1,2-a]pyridin-6-yl)-piperidine-1-carboxylic acid tert-butyl ester

Step i

A solution of Intermediate Gen-9-d (500 mg, 1.40 mmol, 1 eq.) and 3-Bromo-5-chloro-1,2,4-thiadiazole (917 mg, 4.61 mmol, 3.3 eq.) in MeCN (2.5 mL) under argon in a sealed tube was heated at 90° C. overnight. After cooling to r.t. the mixture was concentrated in vacuo. The residue was purified by chromatography on silica gel (elution with DCM/MeOH: 100/0 to 96/4) to afford the expected compound.

LC-MS: MW (calcd): 520 ($^{79}$Br), 522 ($^{81}$Br); m/z MW (obsd): 521 ($^{79}$Br M+1), 523 ($^{81}$Br M+1)

Step ii

To a solution of bromide obtained previously in step i) (120 mg, 0.23 mmol, 1 eq.) in a mixture dioxane/water (1.1/0.68 mL) under argon were added cesium fluoride (73 mg, 0.48 mmol, 2.1 eq.), 2-Cyano-4-fluorobenzeneboronic acid, pinacol ester (69 mg, 0.28 mmol, 1.2 eq.), and then $Pd(P\text{-}tBu_2(p\text{-}NMe_2Ph))_2$ (16 mg, 0.022 mmol, 0.1 eq.). The reaction mixture was heated at 80° C. for 48 h. After cooling to r.t., the reaction mixture was partitioned between water and EtOAc and the layers separated. The aqueous layer was extracted twice with EtOAc. The combined organic layers were washed with water and brine, dried over $Na_2SO_4$, filtered and concentrated in vacuo. The crude product was purified by chromatography on silica gel (elution with DCM/MeOH: 100/0 to 96/4) to afford the expected compound.

LC-MS: MW (calcd): 561; m/z MW (obsd): 562 (M+1)

1.2.8. General Method D1: Synthesis of Intermediate Gen-6

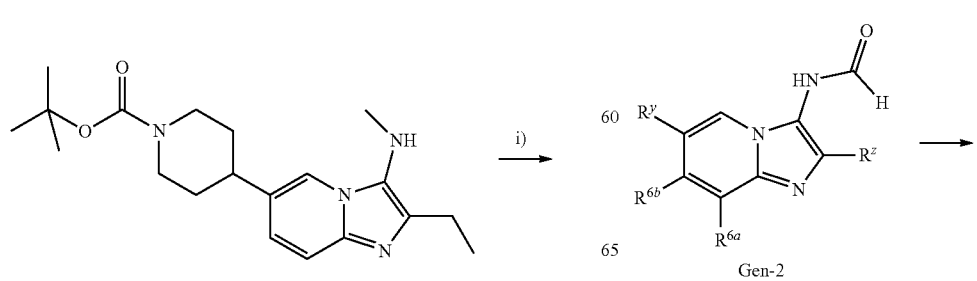

Gen-2

129
-continued

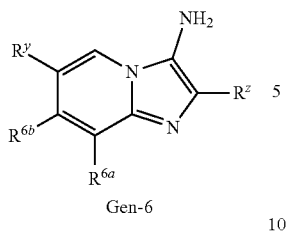

Gen-6

Intermediates Gen-6 are prepared from intermediates Gen-2 according to general method D1 described previously.

1.2.9. General Methods E1 or H1: Synthesis of Intermediate Gen-7

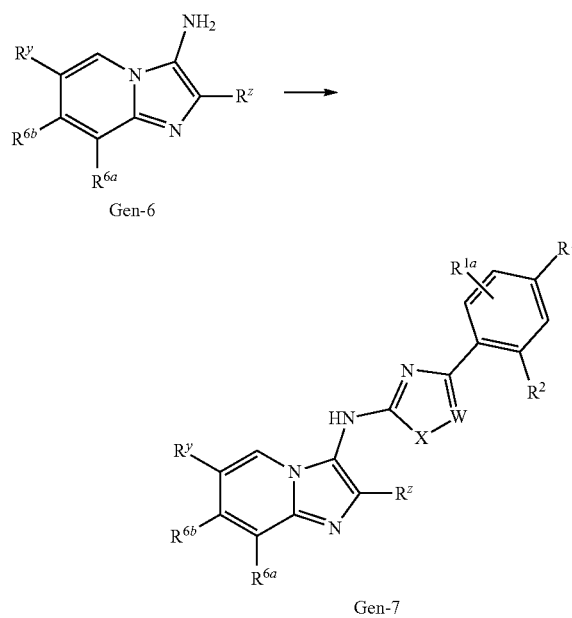

Gen-6

Gen-7

1.2.9.1. General Method E1

Intermediates Gen-7 are prepared from intermediates Gen-6 according to general method E1 described previously 1.2.9.2. General Method H1

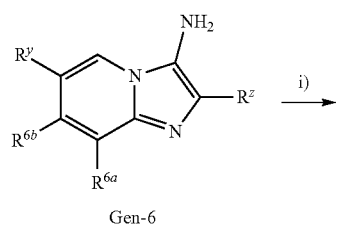

Gen-6

130
-continued

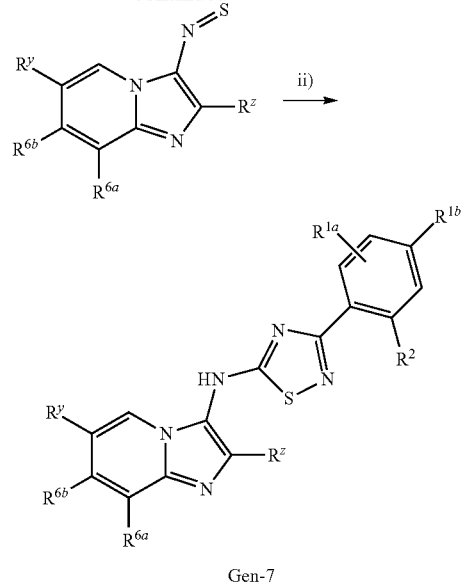

Gen-7

Step i

To a solution of the corresponding intermediate (1 eq.) in DCM at 0° C. are added calcium carbonate (3 eq.) and a few min later thiophosgene (1.2 eq.). The reaction mixture is stirred at 0° C. for 3.5 h then quenched with water. The layers are separated. The aqueous phase is extracted with DCM. The combined organic layers are washed with water and brine, dried over $Na_2SO_4$ and concentrated in vacuo to give the expected isothiocyanate.

Step ii

To a solution of the above prepared isothiocyanate (1 eq.) in DMF are added DIPEA (1.1 eq.) and then the corresponding benzamidine hydrochloride (1 eq.). The reaction mixture is stirred at r.t. overnight. DIAD (1.1 eq.) is added and the resulting mixture is heated at 80° C. for 45 min. Stirring is continued at r.t. for 3 h then water and EtOAc were added. The layers are separated. The aqueous phase is extracted with EtOAc. The combined organic layers are washed with water and brine, dried over $Na_2SO_4$ and concentrated in vacuo. The residue is purified by chromatography on silica gel and give Intermediate Gen-7

1.2.9.3. Illustrative Synthesis of Intermediate Gen-7-a: (6-Bromo-2-ethyl-imidazo[1,2-a]pyridin-3-yl)-[3-(4-chloro-phenyl)-[1,2,4]thiadiazol-5-yl]-amine

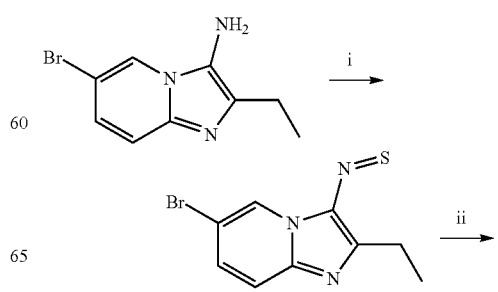

-continued

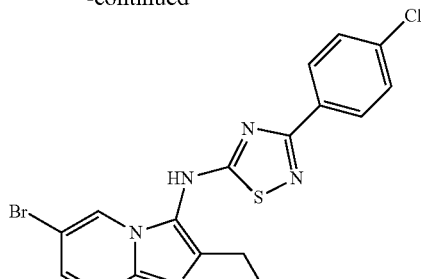

Step i

To a suspension of hydrochloride salt of Intermediate Gen-6-a_(530 mg,1.92 mmol, 1 eq.) in DCM (7 mL) at 0° C. were added calcium carbonate (799 mg, 5.75 mmol, 3 eq.) and a few min later thiophosgene (176 μL, 2.30 mmol, 1.2 eq.). The reaction mixture was stirred at 0° C. for 3.5 h then quenched with water. The layers were separated. The aqueous phase was extracted with DCM. The combined organic layers were washed with water and brine, dried over $Na_2SO_4$ and concentrated in vacuo to afford 6-Bromo-2-ethyl-3-isothiocyanato-imidazo[1,2-a]pyridine isothiocyanate.

LC-MS: MW (calcd): 281 ($^{79}Br$), 283 ($^{81}Br$); m/z MW (obsd): 282 ($^{79}Br$ M+1), 284 ($^{81}Br$ M+1)

Step ii

To a solution of the above prepared isothiocyanate (305 mg,1.08 mmol, 1 eq.) in DMF (6 mL) were added DIPEA (207 μL, 1.19 mmol, 1.1 eq.) and then 4-chloro-benzamidine hydrochloride (207 mg, 1.08 mmol, 1 eq.). The reaction mixture was stirred at r.t. overnight. DIAD (236 μL, 1.19 mmol, 1.1 eq.) was added and the resulting mixture was heated at 80° C. for 45 min. Stirring was continued at r.t. for 3 h then water and EtOAc were added. The layers were separated. The aqueous phase was extracted with EtOAc. The combined organic layers were washed with water and brine, dried over $Na_2SO_4$ and concentrated in vacuo. The residue was purified by chromatography on silica gel (elution with heptane/EtOAc: 100/0 to 50/50 then DCM/MeOH 98/2) to afford Intermediate Gen-7-a.

LC-MS: MW (calcd): 433 ($^{79}Br$), 435 ($^{81}Br$); m/z MW (obsd): 434 ($^{79}Br$), 436 ($^{81}Br$ M+1)

1.2.10. General Methods F: Synthesis of Intermediate Gen-8

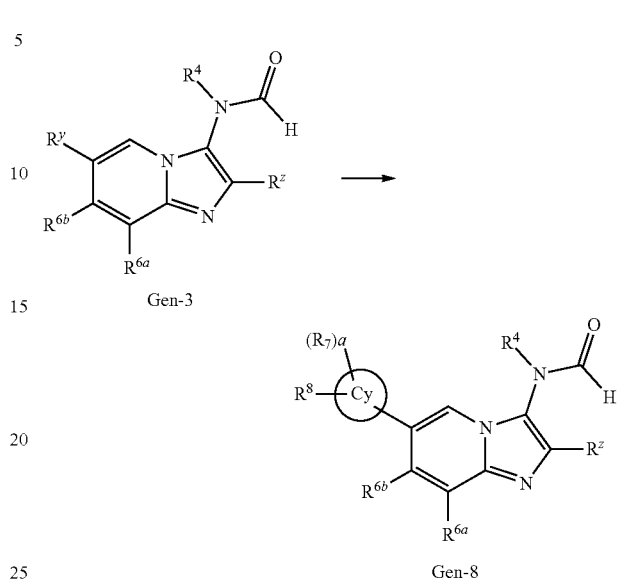

Intermediates Gen-8 are prepared from Intermediates Gen-3 according to one or several general methods F described previously

1.2.11. General Methods D and F: Synthesis of Intermediate Gen-9

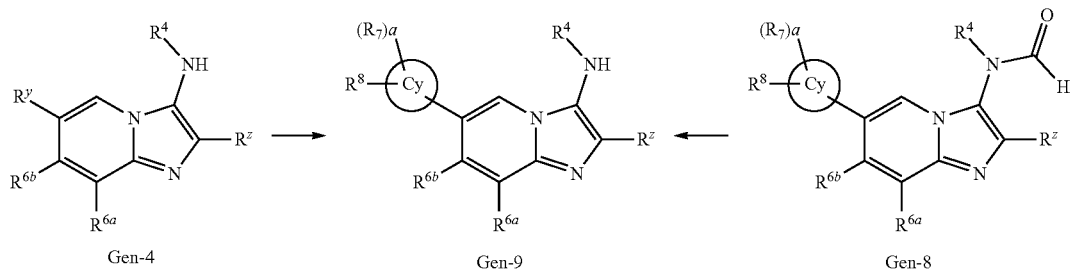

1.2.11.1. General Method D and F

Intermediates Gen-9 are prepared from Intermediates Gen-8 according to general method D1 and one or several general methods F described previously.

1.2.11.2. General Method F

Intermediates Gen-9 are prepared from Intermediate Gen-4 according to one or several general methods F described previously

1.2.12. General Method G1: General Synthesis of α-halogenoketones Gen-11

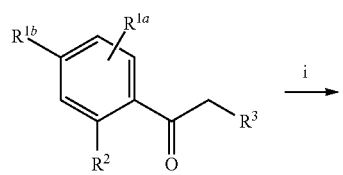

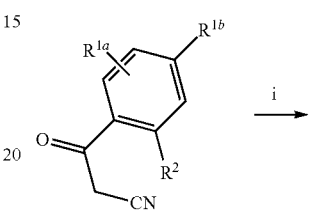

To a solution of ketone (1 eq.) in MeCN is added phenyltrimethylammonium tribromide (1 eq.). The resulting mixture is stirred at r.t. for 3 h, and then is concentrated in vacuo. The organic residue is dissolved in EtOAc and the organic layer is washed with water, with brine, dried over $Na_2SO_4$, filtered and concentrated in vacuo to give the Intermediate Gen-11. The crude product is used directly for the next step without purification

1.2.13. Illustrative Synthesis of Intermediate Gen-11-a: 2-(2-Bromo-acetyl)-5-fluoro-benzonitrile

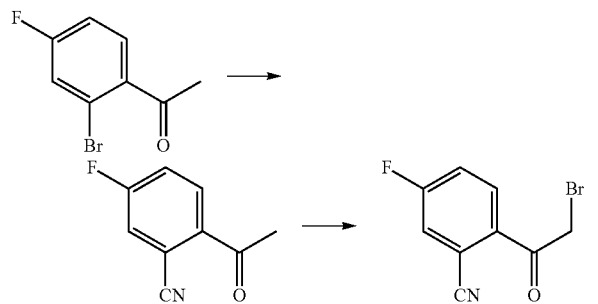

Step i

To a solution of 1-(2-Bromo-4-fluoro-phenyl)-ethanone (3.0 g, 13.82 mmol, 1 eq.) in DMA (150 mL) under argon was added $Zn(CN)_2$ (1.6 g, 13.82 mmol, 1 eq.), $Pd_2(dba)_3$ (1.26 g, 1.38 mmol, 0.1 eq.), dppf (1.53 g, 2.76 mmol, 0.2 eq.) and Zn dust (107.8 mg, 1.65 mmol, 0.12 eq.). The reaction mixture was heated at 100° C. for 1.4 h, after cooling to r.t. the mixture was slowly quenched by addition of water and then diluted with EtOAc. The organic layer was separated and the aqueous layer extracted with EtOAc twice. The combined organic layers were washed with water, dried over $Na_2SO_4$, filtered and concentrated in vacuo. The residue was purified either by chromatography on silica gel to deliver Intermediate 2-acetyl-5-fluoro-benzonitrile LC-MS: MW (calcd): 163; m/z MW (obsd): 164 (M+1)

Step ii

To a solution of 2-acetyl-5-fluoro-benzonitrile (1.52 g, 9.33 mmol, 1 eq.) in MeCN (40 mL) was added phenyltrimethylammonium tribromide (3.51 g, 1 eq.). The resulting mixture was stirred at r.t. for 3 h, and then is concentrated in vacuo. The organic residue was dissolved in EtOAc and the organic layer was washed with water, with brine, dried over $Na_2SO_4$, filtered and concentrated in vacuo to give the Intermediate Gen-11-a. The crude was used directly for the next step without purification LC-MS: MW (calcd): 241 ($^{79}Br$), 243 ($^{81}Br$); m/z MW (obsd): 242 ($^{79}Br$ M+1), 244 ($^{81}Br$ M+1)

1.2.14. General Method G2: General Synthesis of Chlorothiazoles Gen-12

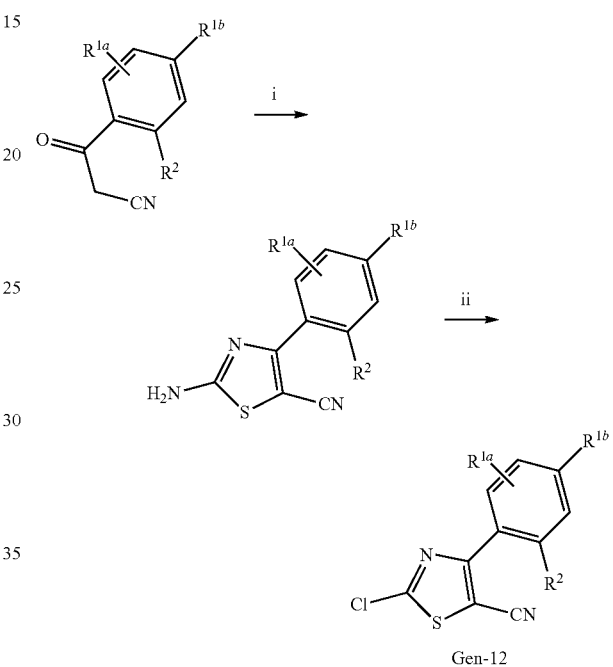

Step i

To a solution of benzoylacetonitrile derivative (1 eq.) in EtOH is added pyridine (1 eq.). The resulting mixture is stirred at 70° C. for 15 min then cooled at r.t. A previously stirred suspension of thiourea (2 eq.) and iodine (1 eq.) in EtOH is then slowly added. After 1 h at r.t. a cold 1 M $Na_2S_2O_3$ solution is added under stirring. The resulting precipitate is filtered, washed with water, and finally dried under vacuo to afford the amino-4-phenyl-thiazole-5-carbonitrile derivative.

Step ii

To a solution of copper (II) chloride (1.2 eq.) in MeCN is added dropwise tert-butyl nitrite (1.5 eq.). After stirring at r.t. for 30 min, the amino-4-phenyl-thiazole-5-carbonitrile (1 eq.) is introduced portionwise and stirring is continued for 1 h. The reaction mixture is then carefully quenched by addition of a 1 N HCl solution. After 15 min stirring, the organic phase is separated; the aqueous phase is further extracted with EtOAc. The combined organic layers are washed with brine, dried over $Na_2SO_4$, filtered and concentrated in vacuo. The crude product is filtered on a silica plug and eluted with DCM. Solvents are evaporated and the residue is finally triturated in heptane, filtered and dried to give Intermediate Gen-12.

1.2.15. Illustrative Synthesis of Intermediate Gen-12-a 2-Chloro-4-(4-fluoro-phenyl)-thiazole-5-carbonitrile

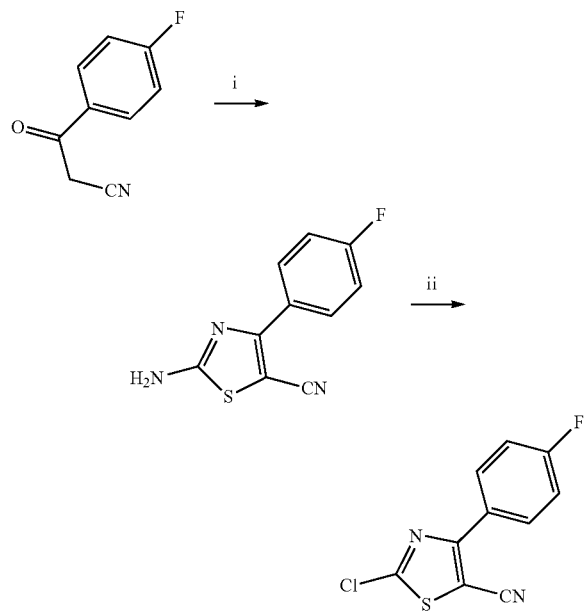

Step i

To a solution of 4-fluorobenzoylacetonitrile (50 g, 306 mmol, 1 eq.) in EtOH (600 mL) was added pyridine (24.7 mL, 306 mmol, 1 eq.). The resulting mixture was stirred at 70° C. for 15 min then cooled to r.t. A previously stirred suspension of thiourea (46.7 g, 613 mmol, 2 eq.) and iodine (77.8 g, 306 mmol, 1 eq.) in EtOH (300 mL) was then slowly added. After 1 h at r.t. a cold 1 M $Na_2S_2O_3$ solution (360 mL) was added under stirring. The resulting precipitate was filtered, washed with water, and finally dried under vacuo to afford 2-Amino-4-(4-fluoro-phenyl)-thiazole-5-carbonitrile.

$^1$H NMR δ (ppm) (400 MHz, DMSO): 8.26 (2H, s), 7.97 (2H, dd), 7.36 (2H, t)

Step ii

To a solution of copper (II) chloride (36.8 g, 273 mmol, 1.2 eq.) in MeCN (500 mL) was added dropwise tert-butyl nitrite (40.7 mL, 342 mmol, 1.5 eq.). After stirring at r.t. for 30 min, amine previously obtained in step i (50 g, 228 mmol, 1 eq.) was introduced portionwise and stirring was continued for 1 h. The reaction mixture was then carefully quenched by addition of a 1 N HCl solution (750 mL). After 15 min stirring, the organic phase was separated; the aqueous phase was further extracted with EtOAc. The combined organic layers were washed with brine, dried over $Na_2SO_4$, filtered and concentrated in vacuo. The crude product was filtered on a silica plug (250 g) and eluted with DCM. Solvents were evaporated and the residue was finally triturated in heptane, filtered and dried to afford 2-Chloro-4-(4-fluoro-phenyl)-thiazole-5-carbonitrile (Intermediate Gen-12-a).

$^1$H NMR δ (ppm) (400 MHz, DMSO): 8.06 (2H, dd), 7.46 (2H, dd)

1.2.16. General Method G3: General Synthesis of intermediaire Gen-13

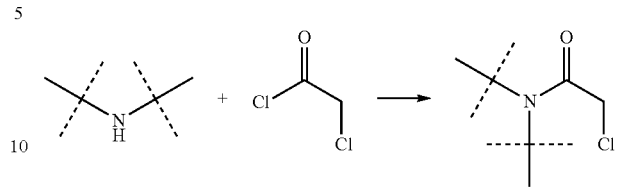

1.2.16.1. General Method G3a

To a suspension of potassium carbonate (2.2 eq.) in water is added the amine derivative (1 eq.). The reaction mixture is stirred at r.t. until complete dissolution, then diluted with DCM and cooled to 0° C. prior to the dropwise introduction of chloroacetyl chloride (1.2 eq.) over 30 min. After 2 h stirring at r.t., the reaction mixture is filtered, the organic layer and the aqueous phase are separated, and the aqueous phase is extracted either with DCM or with a mixture of EtOAc/nBuOH 1:1. The combined organic layers are dried over $Na_2SO_4$, filtered and concentrated in vacuo. The residue is suspended in acetone and stirred vigorously for 20 min, filtered and the filtrate was concentrated in vacuo to afford Intermediate Gen-13

1.2.16.2. Illustrative Synthesis of Intermediate Gen-13-a: 2-Chloro-1-(3-hydroxy-azetidin-1-yl)-ethanone

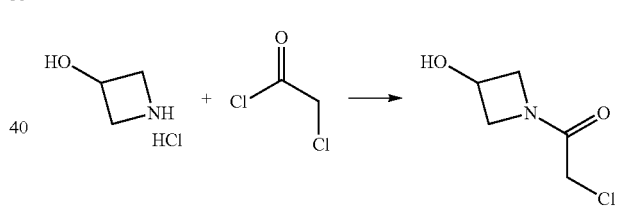

To a suspension of potassium carbonate (13.9 g, 100 mmol, 2.2 eq.) in water (33.5 mL) was added hydroxyazetidine hydrochloride (5 g, 45.6 mmol, 1 eq.). The reaction mixture was stirred at r.t. until complete dissolution, then diluted with 33.5 mL of DCM and cooled to 0° C. prior to the dropwise introduction of chloroacetyl chloride (4.4 mL, 54.8 mmol, 1.2 eq.) over 30 min After 2 h stirring at r.t., the reaction mixture was filtered, the organic layer was separated, and the aqueous phase was extracted with a mixture EtOAc/nBuOH 1:1 (6×16 mL). The combined organic layers were dried over $Na_2SO_4$, filtered and concentrated in vacuo. The residue was suspended in acetone (48 mL) and stirred vigorously for 20 min, filtered and the filtrate was concentrated in vacuo to afford Intermediate Gen-13-a.

$^1$H NMR δ (ppm) (400 MHz, $CDCl_3$): 4.77-4.68 (1H, m), 4.50 (1H, dd), 4.50 (1H, dd), 4.32 (1H, dd), 4.16 (1H, dd), 3.89 (2H, s), 2.55 (1H, d).

1.2.17. General Method G3b

To a solution of chloroacetyl chloride (1 eq.) and TEA (1.5 eq.) in DCM at 0° C. is added the amine derivative (1.1 eq.). The reaction mixture is stirred overnight at r.t., then concentrated in vacuo. The residue is suspended in acetone and stirred vigorously for 20 min, filtered and the filtrate is concentrated in vacuo to afford Intermediate Gen-13 which is used directly without further purification.

1.2.17.1. Illustrative Synthesis of Intermediate Gen-13-o: 2-Chloro-N-methoxy-N-methylacetamide

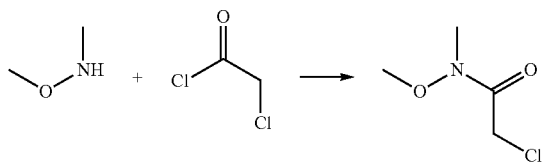

To a solution of chloroacetyl chloride (0.195 mL, 1.21 mmol, 1 eq.) and TEA (0.253 mL, 1.81 mmol, 1.5 eq.) in 3 mL of DCM at 0° C. was added the N,O-dimethylhydroxylamine (0.081 g, 1.33 mmol, 1.1 eq.). The reaction mixture was stirred overnight at r.t., then concentrated in vacuo. The residue was suspended in acetone and stirred vigorously for 20 min, filtered and the filtrate was concentrated in vacuo to afford Intermediate Gen-13-o which was used directly without further purification.

LC-MS: MW (calcd): 137 ($^{35}$Cl) 139 ($^{37}$Cl); m/z MW (obsd): 138 ($^{35}$Cl M+1), 140 ($^{37}$Cl M+1)

Example 2

Preparation of the Compounds of the Invention 2.1. Compound 1: 2-((2-ethyl-8-methyl-6-(piperazin-1-yl)imidazo[1,2-a]pyridin-3-yl)(methyl)amino)-4-(4-fluorophenyl)thiazole-5-carbonitrile

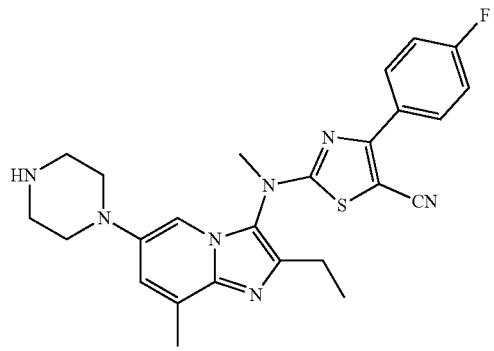

Step i: 6-Bromo-2-ethyl-8-methyl-imidazo[1,2-a]pyridin-3-ylamine

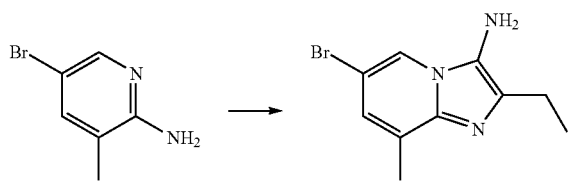

To a suspension of 2-amino-5-bromo-3-methylpyridine (420 g, 2.24 mol, 1 eq.) previously washed before use with a saturated NaHCO$_3$ solution in 1.5 L of toluene under nitrogen were added propionaldehyde (248 mL, 3.36 mol, 1.5 eq.) and 1H-benzotriazole (281 g, 2.36 mol, 1.05 eq.). The resulting mixture was stirred 4 h at r.t. before adding 3.5 L of EtOH and potassium cyanide (175 g, 2.70 mol, 1.2 eq.). The reaction mixture was further stirred overnight at r.t. and 2 h at 78° C. After cooling to r.t., the mixture was quenched by addition of a 2.5 M NaOH solution (3 L).

This experiment was performed in four batches with the same quantities of reagents, the crude mixture were then pooled together and concentrated in vacuo to low volume. The remaining oil was diluted with EtOAc (15 L) and washed with a 2 M NaOH solution (2×2 L). The aqueous layer was extracted twice with EtOAc (2×1 L). The combined organic layers were then dried over Na$_2$SO$_4$, filtered and concentrated in vacuo. The crude mixture was dissolved in EtOH (2 L) and carefully added to a solution of acetyl chloride (1 L, 14.0 mol, 1.6 eq.) in EtOH (6 L). The resulting reaction mixture was stirred at r.t. overnight and then concentrated to dryness. The residue was triturated in DCM (7 L) for 3 days, the precipitate formed was collected, washed with DCM (2×500 mL) and dried to afford 6-bromo-2-ethyl-8-methylimidazo[1,2-a]pyridin-3-amine as a hydrochloride salt.

$^1$H NMR δ (ppm) (400 MHz, DMSO): 8.70 (1H, s), 7.75 (1H, s), 4.86 (3H, bs), 2.81 (2H, q), 2.56(3H, s), 1.56 (3H, t).

LC-MS: MW (calcd): 253 ($^{79}$Br) and 255 ($^{81}$Br); m/z (obsd): 254 ($^{79}$Br M+1) and 256 ($^{81}$Br M+1)

Step ii: N-(6-Bromo-2-ethyl-8-methyl-imidazo[1,2-a]pyridin-3-yl)-formamide (Gen-2-d)

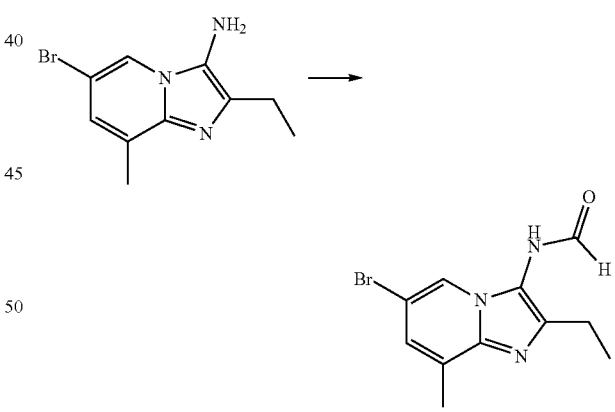

A suspension of the latter compound (785 g, 2.70 mol, 1 eq.) in formic acid (713 mL, 18.9 mol, 7 eq.) was heated to 80° C. for 2 h. The crude mixture was concentrated in vacuo to low volume (about 400 mL). The residue was brought up in water (1 L) and a 3 M solution of NaOH (2 L), and further basified with a saturated NaHCO$_3$ solution until foaming ceased and pH reached 8-9. After homogenization for 1 h, the precipitate was filtered and washed with water (2×300 mL). Purification was achieved by dissolution in a mixture of toluene and MeOH 3:1 (4 L) followed by concentration in vacuo. Trituration of the residue in a mixture of 200 mL of MeOH and 5 L of DIPE, decantation and filtration of the resulting suspension afforded Intermediate Gen-2-d N-(6-bromo-2-ethyl-8-methylimidazo[1,2-a]pyridin-3-yl)formamide.

¹H NMR δ (ppm) (400 MHz, DMSO): presence of 2 rotamers 10.2 (1H, bs, one rotamer), 8.51 (1H, s, one rotamer), 8.36 (1H, s, one rotamer), 8.23 (1H, s, one rotamer), 8.11 (1H, s, both rotamers), 7.23 (1H, s, one rotamer), 7.21 (1H, s, one rotamer), 2.63-2.60 (2H, m, both rotamers), 2.58 (3H, s, one rotamer), 2.56 (3H, s, one rotamer), 1.24-1.17 (3H, m, both rotamers)

LC-MS: MW (calcd): 281 (⁷⁹Br) and 283 (⁸¹Br); m/z (obsd; m/z (obsd): 282 (⁷⁹Br M+1) and 284 (⁸¹Br M+1)

Step iii: N-(6-Bromo-2-ethyl-8-methyl-imidazo[1,2-a]pyridin-3-yl)-N-methyl-formamide (Gen-3-e)

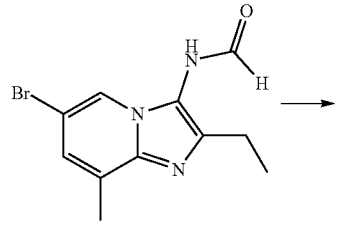

To a suspension of formamide Gen-2-d (720 g, 2.55 mol, 1 eq.) in 5 L of acetone were added potassium carbonate (1 kg, 7.66 mol, 3 eq.) and methyl iodide (700 g, 4.93 mol, 1.9 eq.). The reaction mixture was heated to 40° C. overnight. Additional methyl iodide (25 g, 0.18 mol, 0.07 eq.) was then introduced and stirring continued for 1 h at 40° C. The reaction mixture was filtered and washed with acetone (2×300 mL) and DCM (2×300 mL). The filtrate was concentrated in vacuo and the residue was partitioned between DCM (3 L) and water (1 L). The aqueous layer was further extracted with DCM. The combined organic layers were then washed with brine, dried over Na₂SO₄, filtered and concentrated in vacuo. The solid was triturated with Et₂O (1 L) at r.t. for 1 h, filtered off and dried to afford the Intermediate Gen-3-e.

¹H NMR δ (ppm) (400 MHz, CDCl₃), presence of 2 rotamers, major rotamer: 8.19 (1H, s), 7.78 (1H, s), 7.15 (1H, s), 3.24 (3H, s), 2.72 (2H, q), 2.59 (3H, s), 1.31 (3H, t)

¹H NMR δ (ppm) (400 MHz, CDCl₃), minor rotamer: 8.49 (1H, s), 7.65 (1H, s), 7.08 (1H, s), 3.36 (3H, s), 2.72 (2H, q), 2.59 (3H, s), 1.31 (3H, t)

LC-MS: MW (calcd): 295 (⁷⁹Br) and 297 (⁸¹Br); m/z (obsd): 296 (⁷⁹Br M+1) and 298 (⁸¹Br M+1)

Step iv: (6-Bromo-2-ethyl-8-methyl-imidazo[1,2-a]pyridin-3-yl)-methyl-amine

The above prepared formamide Gen-3-e (80 g, 270 mmol, 1 eq.) was dissolved in a 1.25 M HCl solution in MeOH (540 mL, 2.5 eq.) and the resulting mixture was heated at 110° C. overnight. 270 mL of the 1.25 M HCl solution in MeOH were added and heating continued overnight. After 48 h, additional 70 mL of the 1.25 M HCl solution in MeOH were introduced in the reaction mixture. Heating was maintained overnight until conversion was complete. The crude mixture was then concentrated in vacuo and the residue was partitioned between EtOAc (300 mL) and water (700 mL). A saturated NaHCO₃ solution was added until pH reached 8-9. The aqueous layer was extracted twice with EtOAc (2×300 mL). The combined organic layers were then washed with brine (200 mL), dried over Na₂SO₄, filtered and concentrated in vacuo to give (6-bromo-2-ethyl-8-methyl-imidazo[1,2-a]pyridin-3-yl)-methyl-amine Gen-4-d as a free base.

¹H NMR δ (ppm) (400 MHz, CDCl₃): 8.05 (1H, s), 7.04 (1H, s), 2.84-2.78 (5H, m), 2.60 (3H, s), 1.35 (3H, t)

LC-MS: MW (calcd): 267 (⁷⁹Br) and 269 (⁸¹Br); m/z (obsd): 268 (⁷⁹Br M+1) and 270 (⁸¹Br M+1)

Step v: 2-[(6-Bromo-2-ethyl-8-methyl-imidazo[1,2-a]pyridin-3-yl)-methyl-amino]-4-(4-fluoro-phenyl)-thiazole-5-carbonitrile

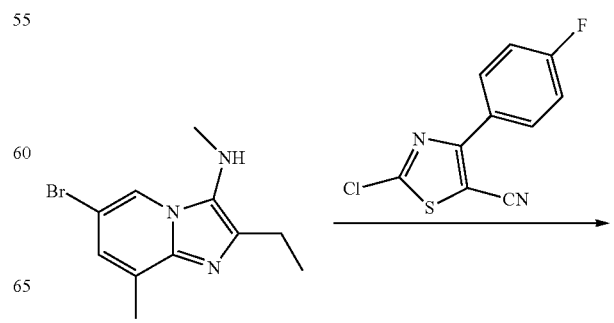

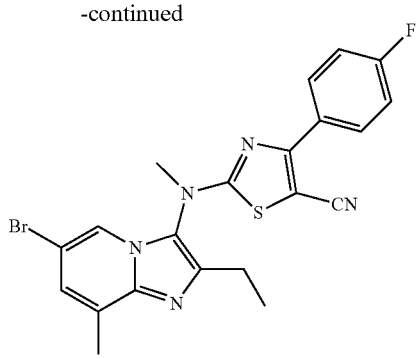

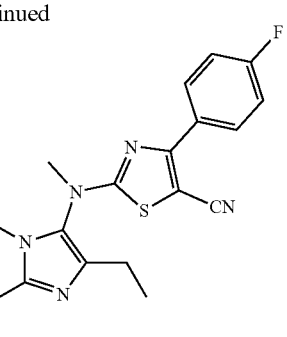

To a solution of amine Gen-4-d (4.4 g, 16.6 mmol, 1 eq.) in THF (44 mL) under argon was slowly added NaH (60% in oil suspension, 2.0 g, 50.0 mmol, 3 eq.). The reaction mixture was heated at 90° C. for 30 min then cooled to 40° C. before adding the chlorothiazole Gen-12-a (4.74 g, 19.9 mmol, 1.2 eq.). The reaction mixture was stirred at 90° C. overnight. After cooling to r.t. the mixture was slowly quenched by addition of water and then diluted with EtOAc. The organic layer was separated and the aqueous layer extracted with EtOAc. The combined organic layers were then washed with water and brine, dried over Na$_2$SO$_4$, filtered and concentrated in vacuo. The residue was triturated in Et$_2$O, filtered and washed with Et$_2$O and MeCN. Recrystallization was performed in MeCN (180 mL) to afford 2-[(6-Bromo-2-ethyl-8-methyl-imidazo[1,2-a]pyridin-3-yl)-methyl-amino]-4-(4-fluoro-phenyl)-thiazole-5-carbonitrile (Intermediate Gen-5-t).

$^1$H NMR δ (ppm) (400 MHz, CDCl$_3$): 8.15 (2H, dd), 7.80 (1H, s), 7.22-7.14 (3H, m), 3.62 (3H, s), 2.77 (2H, q), 2.64 (3H, s), 1.35 (3H, t)

LC-MS: MW (calcd): 469 ($^{79}$Br), 471 ($^{81}$Br); m/z (obsd): 470 ($^{79}$Br M+1), 472 ($^{81}$Br M+1)

Step vi: 4-(3-{[5-Cyano-4-(4-fluoro-phenyl)-thiazol-2-yl]-methyl-amino}-2-ethyl-8-methyl-imidazo[1,2-a]pyridin-6-yl)-pperazine-1-carboxylic acid tert-butyl ester

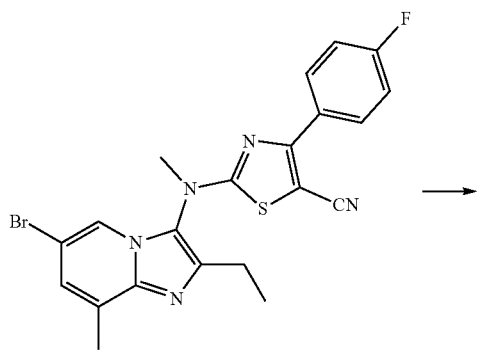

To a solution of the above prepared bromide Gen-5-t (24.2 g, 51.5 mmol, 1 eq.) in toluene (345 mL) under argon were successively added N-Boc piperazine (14.4 g, 77.3 mmol, 1.5 eq.), sodium tert-butoxide (9.9 g, 103 mmol, 2 eq.) and then JohnPhos (1.54 g, 5.15 mmol, 0.1 eq.) and Pd$_2$(dba)$_3$ (2.36 g, 2.58 mmol, 0.05 eq.). The reaction mixture was heated at 115° C. for 1 h. After cooling to r.t., the crude product was filtered on Celpure® P65 and the residue washed with water and EtOAc. The organic layer of the filtrate was washed with brine, dried over Na$_2$SO$_4$, filtered and concentrated in vacuo. The crude product was purified by chromatography on silica gel (elution with heptane/EtOAc: 90/10 to 20/80) to afford the expected compound.

$^1$H NMR δ (ppm) (400 MHz, CDCl$_3$): 8.16 (2H, dd), 7.17 (2H, app t), 6.99 (2H, bs), 3.62-3.53 (4H, m) 3.60 (3H, s), 3.04-2.93 (4H, m), 2.74 (2H, q), 2.62 (3H, s), 1.47 (9H, s), 1.33 (3H, t)

LC-MS: MW (calcd): 575; m/z (obsd): 576 (M+1)

Step vii: 2-[(2-Ethyl-8-methyl-6-piperazin-1-yl-imidazo[1,2-a]pyridin-3-yl)-methyl-amino]-4-(4-fluoro-phenyl)-thiazole-5-carbonitrile

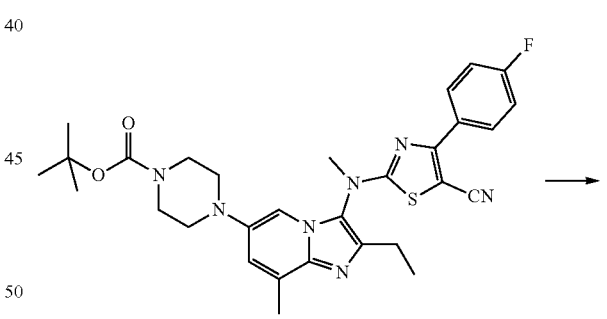

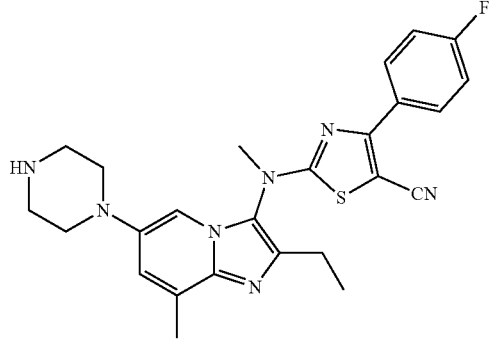 [SMILES: CCc1nc2c(C)cc(N3CCNCC3)cn2c1N(C)c1nc(-c2ccc(F)cc2)c(C#N)s1]

To a solution of 4-(3-{[5-Cyano-4-(4-fluoro-phenyl)-thiazol-2-yl]-methyl-amino}-2-ethyl-8-methyl-imidazo[1,2-a]

pyridin-6-yl)-piperazine-1-carboxylic acid tert-butyl ester (24.4 g, 42 mmol, 1 eq.) in MeOH (100 mL) was added a 2 M HCl solution in Et₂O (127 mL, 254 mmol, 6 eq.). The reaction mixture was stirred at r.t. for 3.5 h then concentrated in vacuo. The residue was partitioned between EtOAc and water. The aqueous layer was extracted twice with EtOAc. A 2 M NaOH solution was added to the aqueous layer until pH reached 8-9 and further extraction with EtOAc was performed. The combined organic layers were then washed with brine, dried over Na₂SO₄, filtered and concentrated in vacuo. The solid was triturated with heptane (100 mL) at r.t. overnight, filtered off, washed with heptane and Et₂O, and dried to afford Compound 1.

¹H NMR δ (ppm) (400 MHz, CDCl₃): 8.17 (2H, dd), 7.18 (2H, app t), 6.99 (2H, bs), 3.61 (3H, s), 3.09-2.98 (8H, m), 2.75 (2H, q), 2.61 (3H, s), 1.34 (3H, t)

LC-MS: MW (calcd): 475; m/z (obsd): 476 (M+1)

2.2. Compound 2: 2-((2-ethyl-6-(4-(2-(3-hydroxyazetidin-1-yl)-2-oxoethyl)piperazin-1-yl)-8-methylimidazo[1,2-a]pyridin-3-yl)(methyl)amino)-4-(4-fluorophenyl)thiazole-5-carbonitrile 2.3. Compounds 3-5

Compounds 3-5 listed in the table of compounds were prepared similarly as compound 2 following general synthetic method F8 using Compound 1 and Intermediates Gen-13-b, Gen-13-g, Gen-13-h listed in the table of synthetic intermediates. Analytical details for these compounds and the following compounds are provided in the table of analytical details. Analytical details for synthetic intermediates are provided in the table of synthetic intermediates.

2.4. Compound 6: 2-((2-ethyl-6-(4-(2-(3-hydroxyazetidin-1-yl)-2-oxoethyl)-3,3-dimethylpiperazin-1-yl)-8-methylimidazo[1,2-a]pyridin-3-yl)(methyl)amino)-4-(4-fluorophenyl)thiazole-5-carbonitrile Step i: 2-{[6-(3,3-Dimethyl-piperazin-1-yl)-2-ethyl-8-methyl-imidazo[1,2-a]pyridin-3-yl]-methyl-amino}-4-(4-fluoro-phenyl)-thiazole-5-carbonitrile

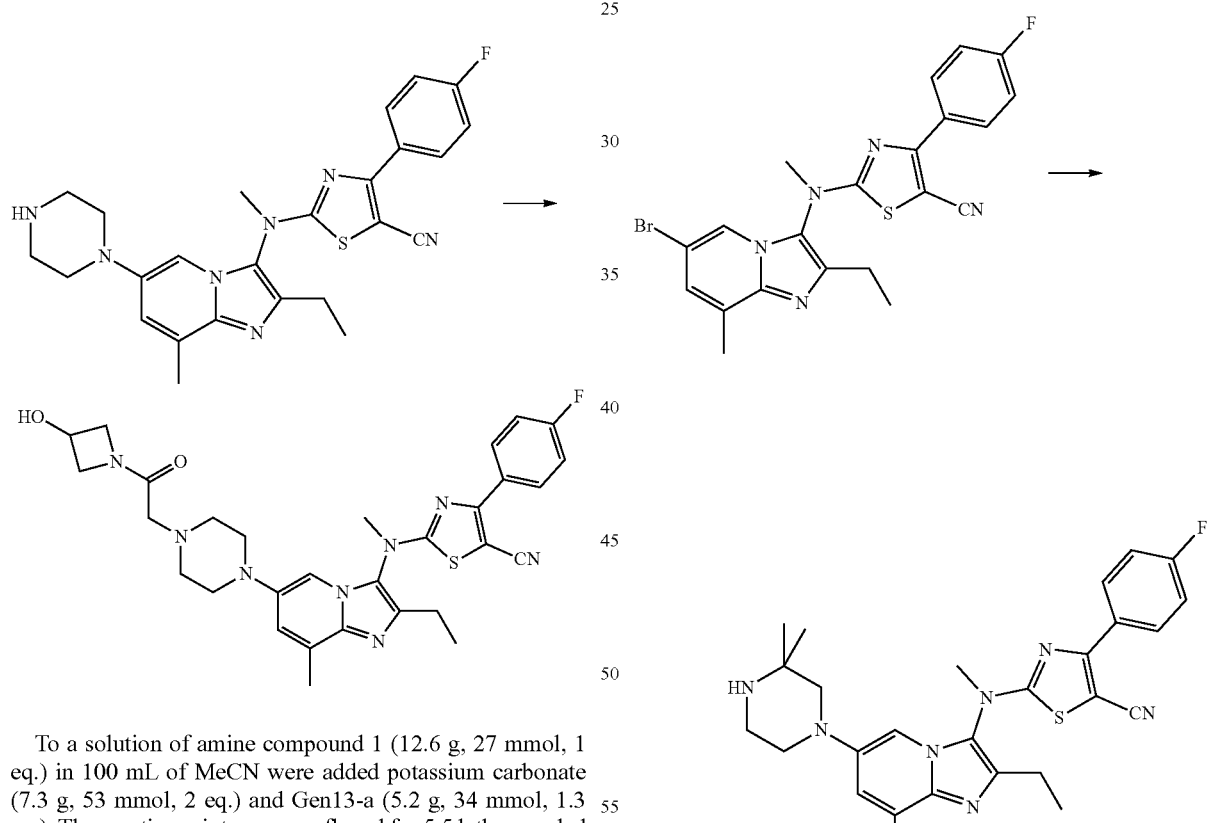

To a solution of amine compound 1 (12.6 g, 27 mmol, 1 eq.) in 100 mL of MeCN were added potassium carbonate (7.3 g, 53 mmol, 2 eq.) and Gen13-a (5.2 g, 34 mmol, 1.3 eq.). The reaction mixture was refluxed for 5.5 h then cooled to r.t. and stirred for 40 h. The crude product was filtered and washed with MeCN. The collected precipitate was then suspended in 300 mL of water, stirred for 1 h, filtered, and finally washed with water and MeCN. The solid obtained was dried in vacuo for 48 h to afford Compound 2.

¹H NMR (400 MHz, CDCl₃) δ ppm 8.20-8.12 (2H, m), 7.22-7.13 (2H, m), 6.99 (2H, s), 4.68 (1H, m), 4.43 (1H, dd), 4.26 (1H, dd), 4.14-4.05 (1H, m), 3.88 (1H, dd), 3.61 (3H, s), 3.58-3.52 (1H, m), 3.14-3.02 (6H, m), 2.74 (2H, q), 2.70-2.62 (4H, m), 2.59 (3H, s), 1.33 (3H, t)

LC-MS: MW (calcd): 588; m/z (obsd): 589 (M+1)

Intermediate Gen-10-x 2-{[6-(3,3-Dimethyl-piperazin-1-yl)-2-ethyl-8-methyl-imidazo[1,2-a]pyridin-3-yl]-methyl-amino}-4-(4-fluoro-phenyl)-thiazole-5-carbonitrile is prepared from Intermediate Gen-5-t and 2,2-dimethylpiperazine following general synthetic method F1a.

Step ii: 2-[(2-Ethyl-6-{4-[2-(3-hydroxy-azetidin-1-yl)-2-oxo-ethyl]-3,3-dimethyl-piperazin-1-yl}-8-methyl-imidazo[1,2-a]pyridin-3-yl)-methyl-amino]-4-(4-fluoro-phenyl)-thiazole-5-carbonitrile Step i: (6-bromo-2-ethyl-8-methyl-imidazo[1,2-a]pyridin-3-yl)-[4-(4-fluoro-phenyl)-thiazol-2-yl]-methyl-amine

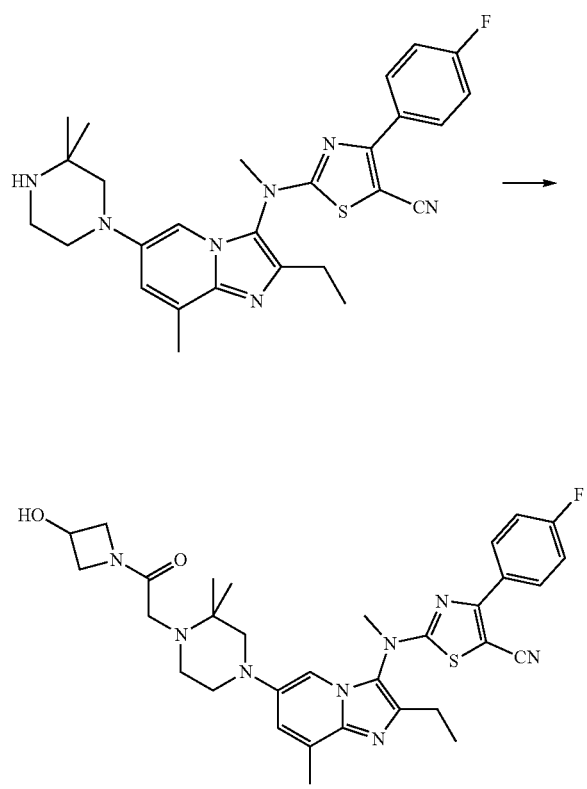

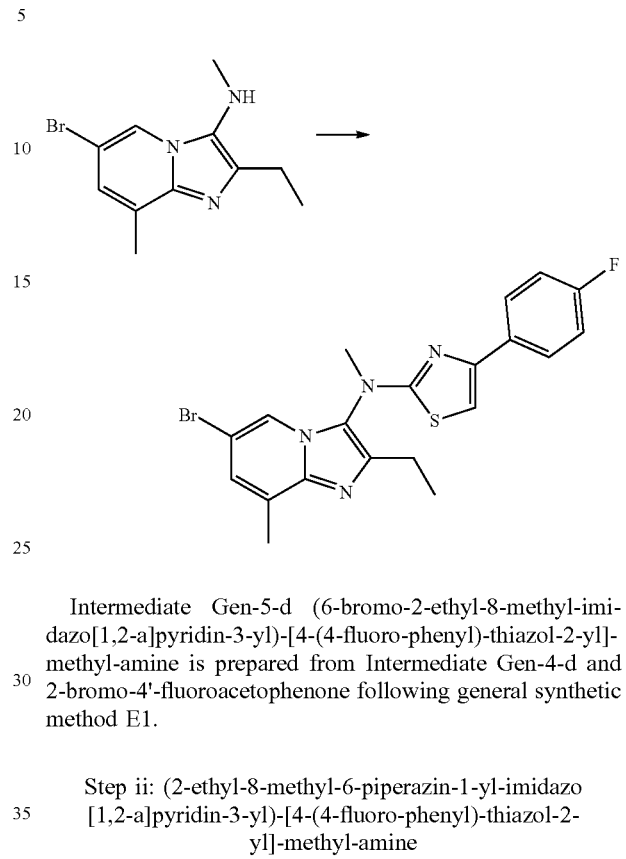

Intermediate Gen-5-d (6-bromo-2-ethyl-8-methyl-imidazo[1,2-a]pyridin-3-yl)-[4-(4-fluoro-phenyl)-thiazol-2-yl]-methyl-amine is prepared from Intermediate Gen-4-d and 2-bromo-4'-fluoroacetophenone following general synthetic method E1.

Step ii: (2-ethyl-8-methyl-6-piperazin-1-yl-imidazo[1,2-a]pyridin-3-yl)-[4-(4-fluoro-phenyl)-thiazol-2-yl]-methyl-amine Compound 6 is obtained from Intermediate Gen-10-x by alkylation with Intermediate Gen-13-a following general synthetic method F8.

2.5. Compound 7: 2-(4-(2-ethyl-3-((4-(4-fluorophenyl)thiazol-2-yl)(methyl)amino)-8-methylimidazo[1,2-a]pyridin-6-yl)piperazin-1-yl)-1-(3-hydroxyazetidin-1-yl)ethanone

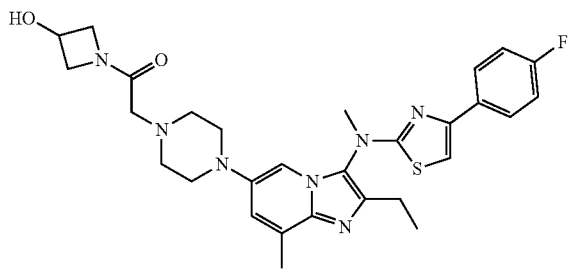 [SMILES: CCc1nc2c(C)cc(N3CCN(CC(=O)N4CC(O)C4)CC3)cn2c1N(C)c1nc(-c2ccc(F)cc2)cs1]

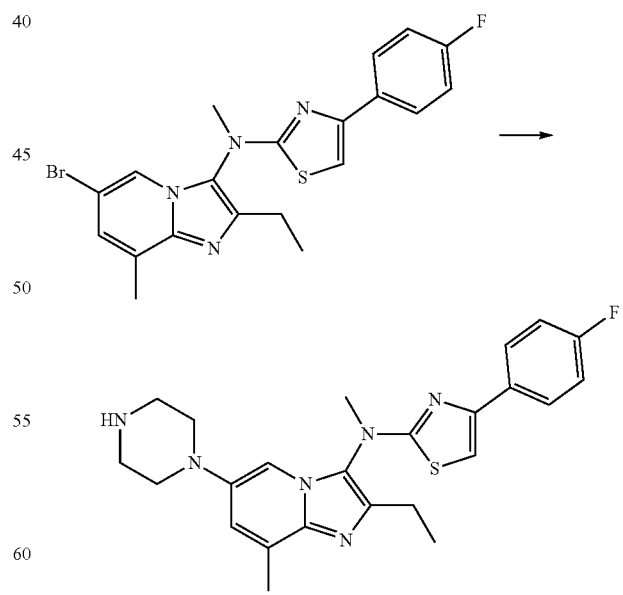

Intermediate Gen-10-n (2-ethyl-8-methyl-6-piperazin-1-yl-imidazo[1,2-a]pyridin-3-yl)-[4-(4-fluoro-phenyl)-thiazol-2-yl]-methyl-amine is prepared from Intermediate Gen-5-d and piperazine following general synthetic method F1a.

Step iii: 2-(4-(2-ethyl-3-((4-(4-fluorophenyl)thiazol-2-yl)(methyl)amino)-8-methylimidazo[1,2-a]pyridin-6-yl)piperazin-1-yl)-1-(3-hydroxyazetidin-1-yl)ethanone Step i) 2-[(2-ethyl-8-methyl-6-piperidin-4-yl-imidazo[1,2-a]pyridin-3-yl)-methyl-amino]-4-(4-fluoro-phenyl)-thiazole-5-carbonitrile

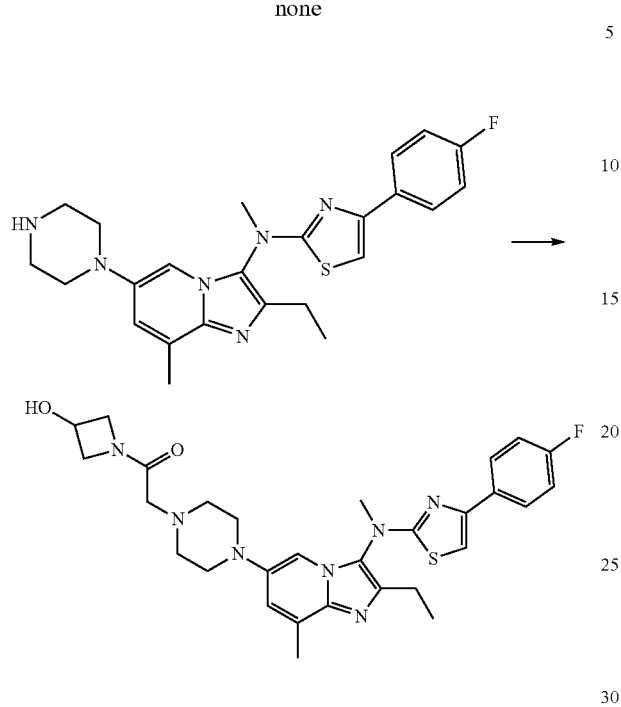

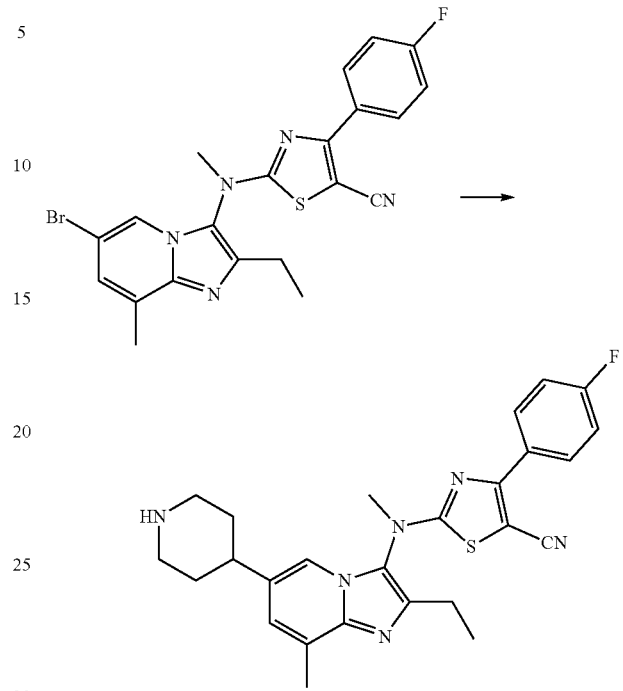

Compound 7 is obtained by alkylation of Intermediate Gen-10-n with Intermediate Gen-13-a following general synthetic method F8.

2.6. Compounds 8 and 9

Compounds 8-9 listed in the table of compounds are prepared similarly as compound 7 following general synthetic method F8 using Intermediates Gen-10-n, Gen-13-g, Gen-13-h listed in the table of synthetic intermediates.

2.7. Compound 10: 2-((2-ethyl-6-(1-(2-(3-hydroxyazetidin-1-yl)-2-oxoethyl)piperidin-4-yl)-8-methylimidazo[1,2-a]pyridin-3-yl)(methyl)amino)-4-(4-fluorophenyl)thiazole-5-carbonitrile Synthetic Intermediate Gen-10-o 2-[(2-ethyl-8-methyl-6-piperidin-4-yl-imidazo[1,2-a]pyridin-3-yl)-methyl-amino]-4-(4-fluoro-phenyl)-thiazole-5-carbonitrile is obtained from Intermediate Gen-5-t using general synthetic methods F3 followed by F5b.

Step ii) 2-((2-ethyl-6-(1-(2-(3-hydroxyazetidin-1-yl)-2-oxoethyl)piperidin-4-yl)-8-methylimidazo[1,2-a]pyridin-3-yl)(methyl)amino)-4-(4-fluorophenyl)thiazole-5-carbonitrile Compound 10 is then obtained by alkylation of Intermediate Gen-10-o with Intermediate Gen-13-a using general synthetic method F8.

2.8. Compound 11: 2-(ethyl(2-ethyl-8-methyl-6-(1-(methylsulfonyl)-1,2,3,6-tetrahydropyridin-4-yl)imidazo[1,2-a]pyridin-3-yl)amino)-4-(4-fluorophenyl)thiazole-5-carbonitrile

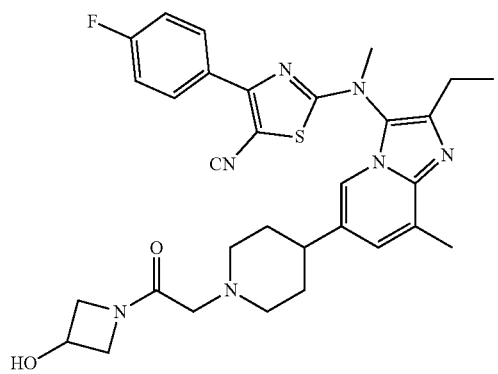

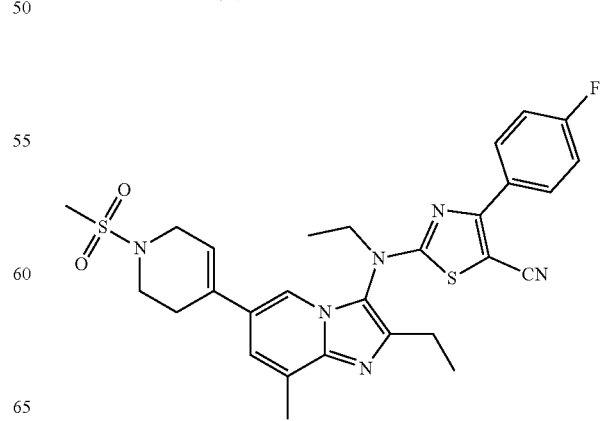

Step i) N-(6-bromo-2-ethyl-8-methylimidazo[1,2-a]pyridin-3-yl)-N-ethylformamide

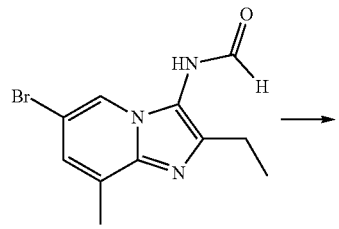

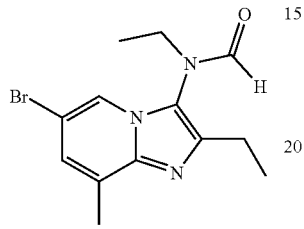

Intermediate Gen-3-h N-(6-bromo-2-ethyl-8-methylimidazo[1,2-a]pyridin-3-yl)-N-ethylformamide is prepared from Intermediate Gen-2-d with iodoethane according to general synthetic method C2.

Step ii)

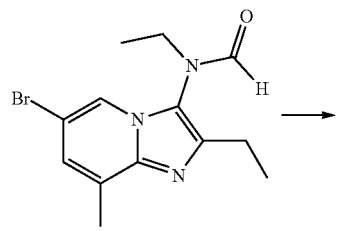

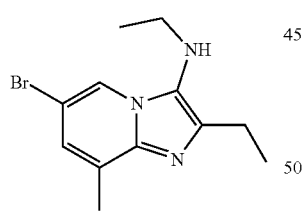

Reaction of Intermediate Gen-3-h following general synthetic method D1 affords Intermediate Gen-4-h.

Step iii)

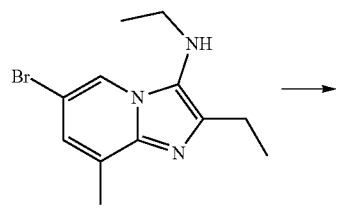

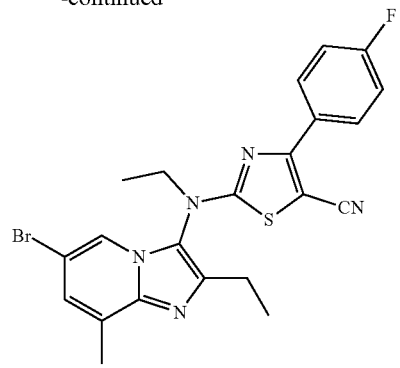

Reaction of Intermediate Gen-4-h with Intermediate Gen-12-a following general synthetic method E2 affords Intermediate Gen-5-h.

Step iv)

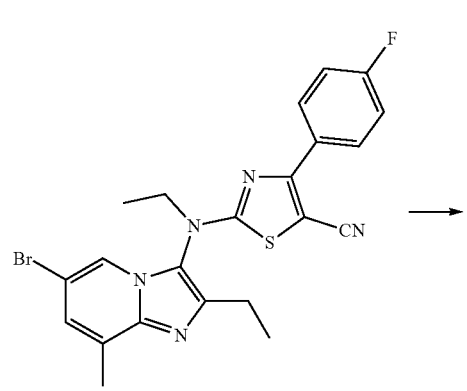

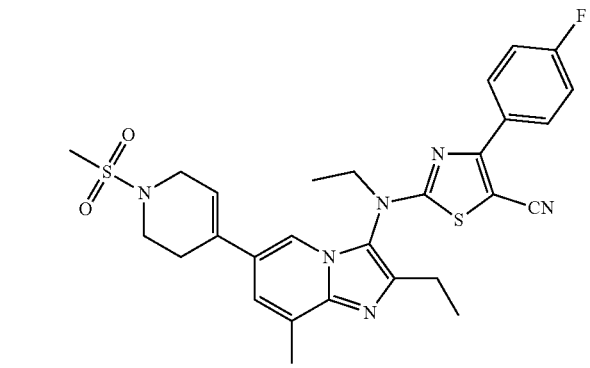

Suzuki coupling of Intermediate Gen-5-h with 1-(methylsulfonyl)-4-(4,4,5,5-tetramethyl-1,3,2-dioxaborolan-2-yl)-1,2,3,6-tetrahydropyridine following general synthetic method F2 afford compound 11.

2.9. Compound 12: 2-((2-ethyl-8-fluoro-6-(4-(2-(3-hydroxyazetidin-1-yl)-2-oxoethyl)piperazin-1-yl)imidazo[1,2-a]pyridin-3-yl)(methyl)amino)-4-(4-fluorophenyl)thiazole-5-carbonitrile

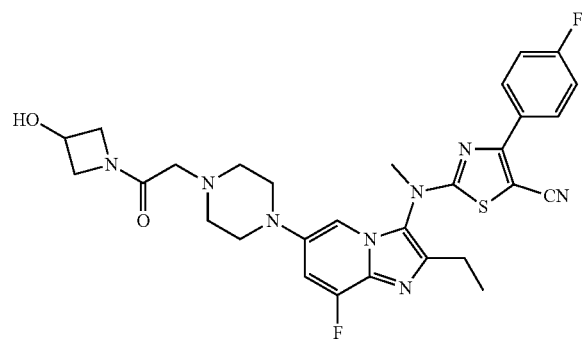 [SMILES: CCc1nc2c(F)cc(N3CCN(CC(=O)N4CC(O)C4)CC3)cn2c1N(C)c1nc(-c2ccc(F)cc2)c(C#N)s1]

Step i)

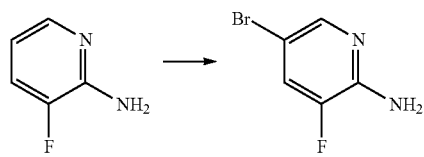 [SMILES: Nc1ncccc1F ; Nc1ncc(Br)cc1F]

Intermediate Gen-1-a 2-amino-5-bromo-3-fluoropyridine is prepared from 2-amino-3-fluoropyridine using general synthetic method A.

Step ii)

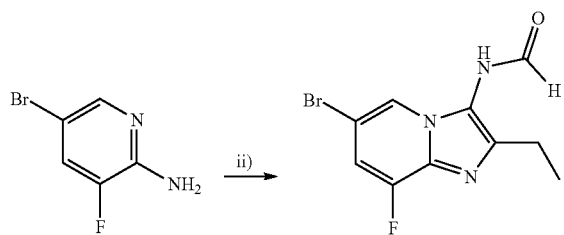 [SMILES: Nc1ncc(Br)cc1F ; CCc1nc2c(F)cc(Br)cn2c1NC=O]

Intermediate Gen-2-a N-(6-bromo-2-ethyl-8-fluoro-imidazo[1,2-a]pyridin-3-yl)-formamide is prepared from Intermediate Gen-1-a and propionaldehyde using general synthetic method B1.

Step iii)

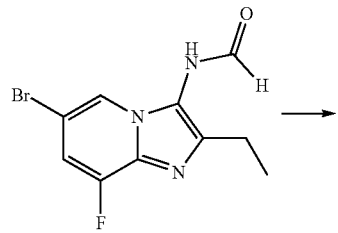

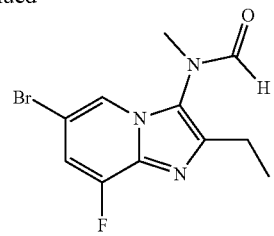

Intermediate Gen-2-a is methylated with iodomethane following general method C2 to give Intermediate Gen-3-a N-(6-bromo-2-ethyl-8-fluoro-imidazo[1,2-a]pyridin-3-yl)-N-methyl-formamide.

Step iv)

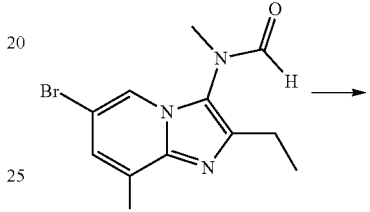

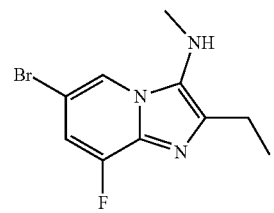

Formyl group of Intermediate Gen-3-a is removed under conditions of general synthetic method D1 to furnish Intermediate Gen-4-a (6-bromo-2-ethyl-8-fluoro-imidazo[1,2-a]pyridin-3-yl)-methyl-amine.

Step v)

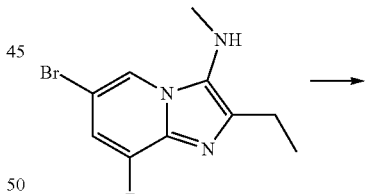

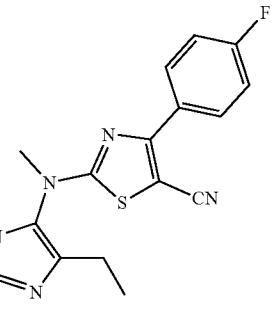

Reaction of Intermediate Gen-4-a with Intermediate Gen-12-a following general synthetic method E2 afforded Intermediate Gen-5-r 2-[(6-bromo-2-ethyl-8-fluoro-imidazo[1,2-a]pyridin-3-yl)-methyl-amino]-4-(4-fluoro-phenyl)-thiazole-5-carbonitrile.

Step vi)

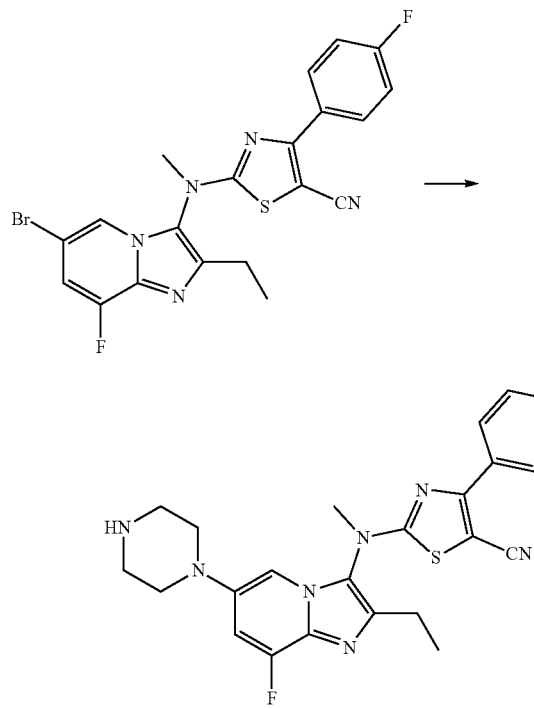

Reaction of Intermediate Gen-5-r with piperazine following general synthetic method F1a afforded Intermediate Gen-10-m 2-[(2-ethyl-8-fluoro-6-piperazin-1-yl-imidazo[1,2-a]pyridin-3-yl)-methyl-amino]-4-(4-fluoro-phenyl)-thiazole-5-carbonitrile.

Step vii)

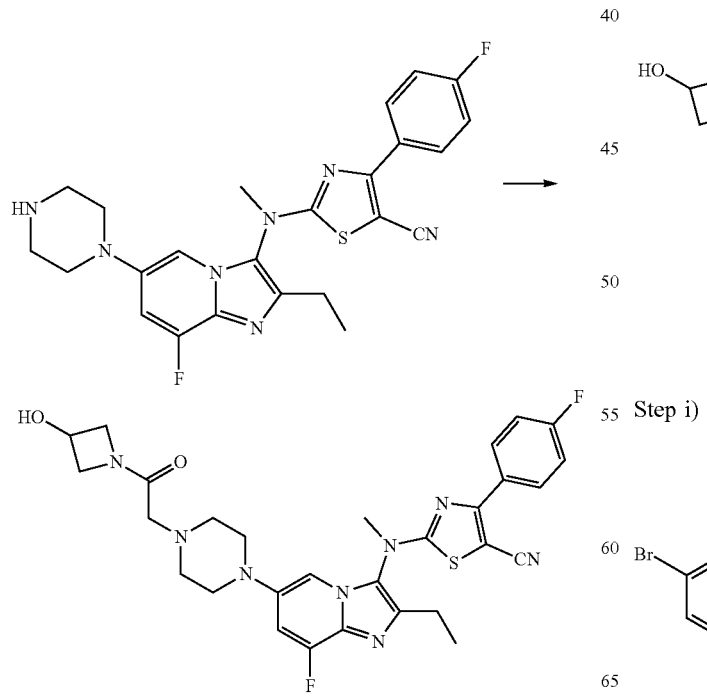

Alkylation of Intermediate Gen-10-m with Intermediate Gen-13-a following general synthetic method F8 gave compound 12.

2.10. Compound 13: 2-(4-(3-((5-cyano-4-(4-fluorophenyl)thiazol-2-yl)(methyl)amino)-2-ethyl-8-fluoroimidazo[1,2-a]pyridin-6-yl)piperazin-1-yl)-N-methylacetamide

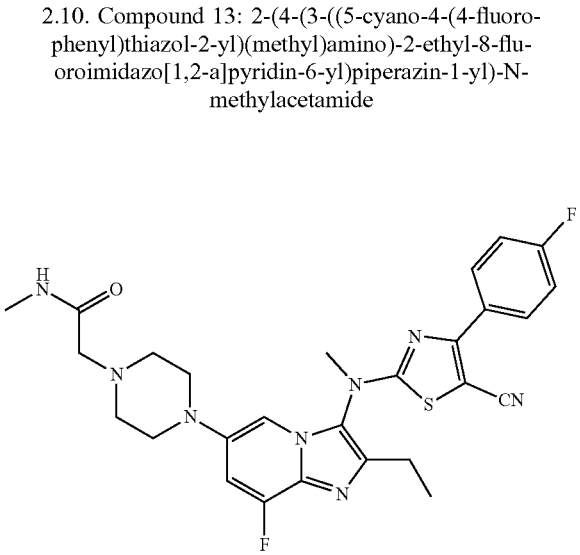

Compounds 13 listed in the table of compounds is prepared similarly as compound 12 following general synthetic method F8 using Intermediates Gen-10-m and 2-chloro-N-methylacetamide.

2.11. Compound 14: 2-(4-(2-ethyl-8-fluoro-3-((4-(4-fluorophenyl)thiazol-2-yl)(methyl)amino)imidazo[1,2-a]pyridin-6-yl)piperazin-1-yl)-1-(3-hydroxyazetidin-1-yl)ethanone

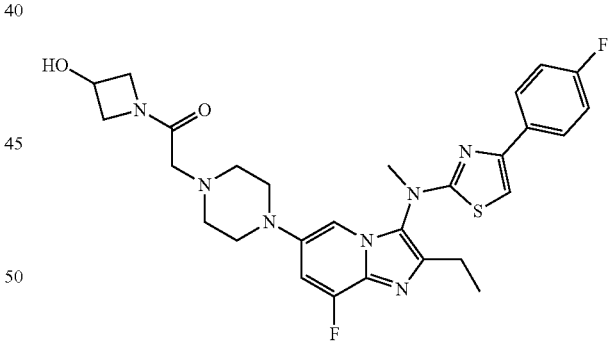

Step i)

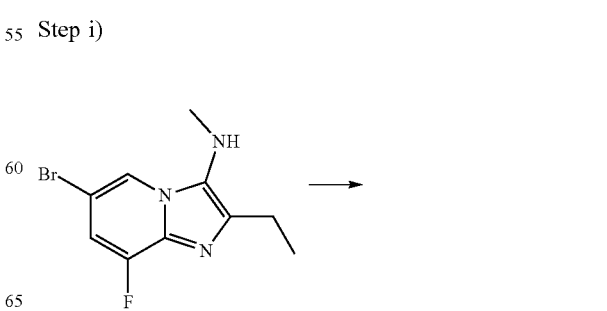

-continued

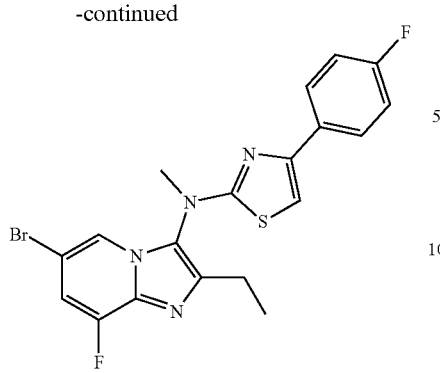

Intermediate Gen-5-a (6-bromo-2-ethyl-8-fluoro-imidazo[1,2-a]pyridin-3-yl)-[4-(4-fluoro-phenyl)-thiazol-2-yl]-methyl-amine is prepared from Intermediate Gen-4-a and 2-bromo-4'-fluoroacetophenone following general synthetic method E1.

Step ii)

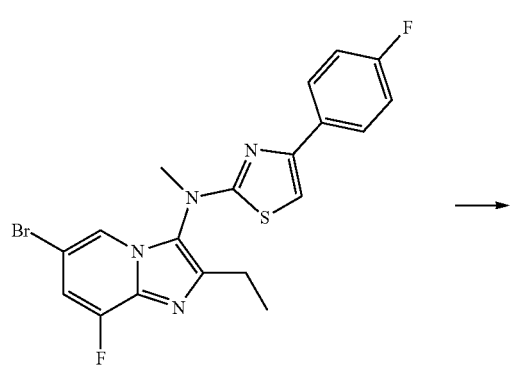

Intermediate Gen-10-1 (2-ethyl-8-fluoro-6-piperazin-1-yl-imidazo[1,2-a]pyridin-3-yl)-[4-(4-fluoro-phenyl)-thiazol-2-yl]-methyl-amine is prepared from Intermediate Gen-5-a and piperazine following general synthetic method F1a.

Step iii)

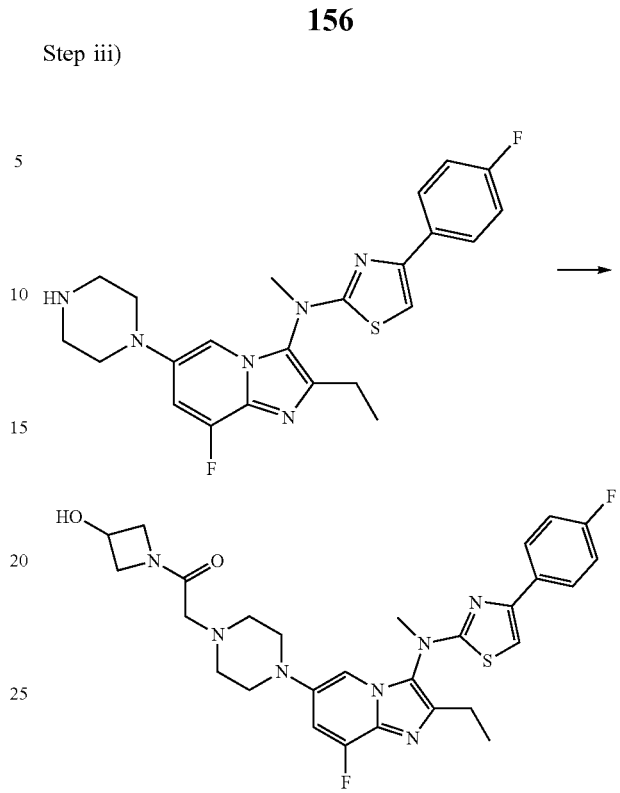

Compound 14 is obtained by alkylation of Intermediate Gen-10-1 with Intermediate Gen-13-a following general synthetic method F8.

2.12. Compounds 15-16

Compounds 15-16 listed in the table of compounds are prepared similarly as compound 7 following general synthetic method F8 using Intermediates Gen-10-1, Gen-13-g, Gen-13-h listed in the table of synthetic Intermediates.

2.13. Compound 17: 2-(4-(2-ethyl-3-((4-(4-fluoro-phenyl)thiazol-2-yl)(methyl)amino)-7-methylimidazo[1,2-a]pyridin-6-yl)piperidin-1-yl)-1-(3-hydroxyazetidin-1-yl)ethanone

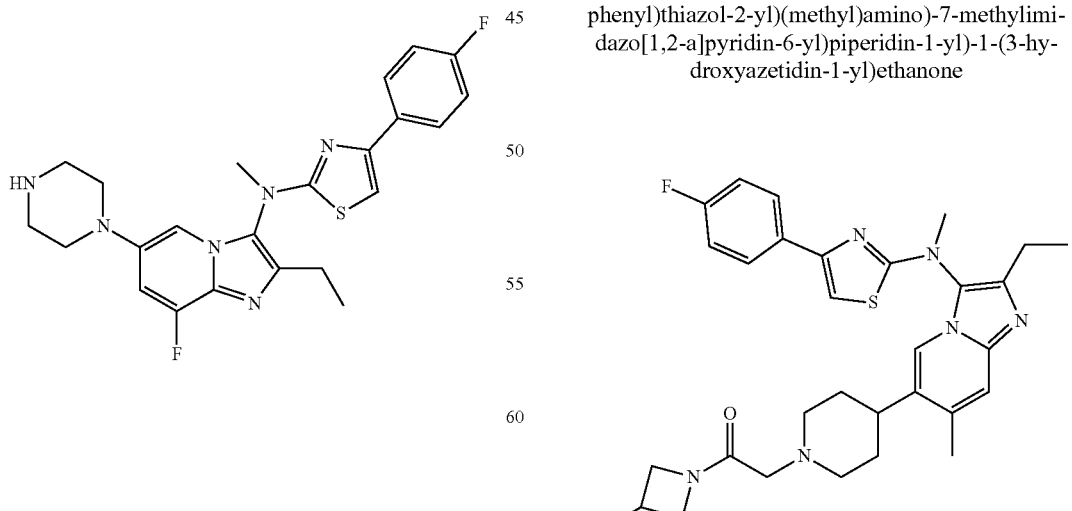

Step i) N-(6-Bromo-2-ethyl-7-methyl-imidazo[1,2-a]pyridin-3-yl)-formamide

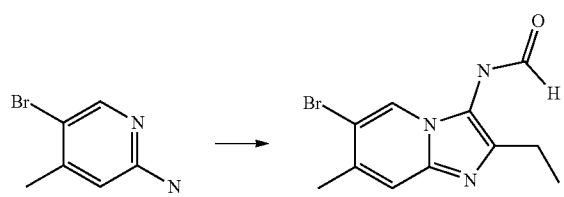

Intermediate Gen-2-h N-(6-Bromo-2-ethyl-7-methyl-imidazo[1,2-a]pyridin-3-yl)-formamide is prepared from 2-amino-4-bromo-5-methylpyridine and propionaldehyde following general synthetic method B1.

Step ii) N-(6-Bromo-2-ethyl-7-methyl-imidazo[1,2-a]pyridin-3-yl)-N-methyl-formamide

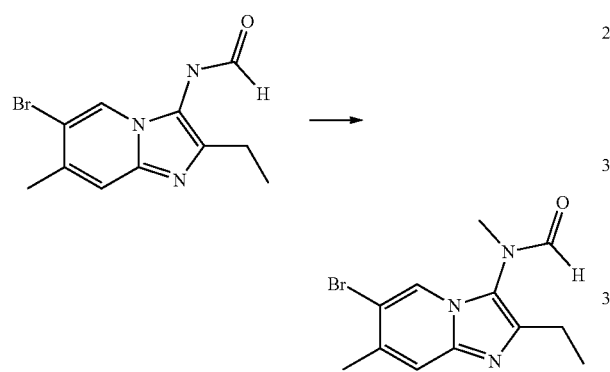

Intermediate Gen-2-h is methylated with iodomethane following general method C2 to give Intermediate Gen-3-i.

Step iii) 4-[2-Ethyl-3-(formyl-methyl-amino)-7-methyl-imidazo[1,2-a]pyridin-6-yl]-piperidine-1-carboxylic acid tert-butyl ester

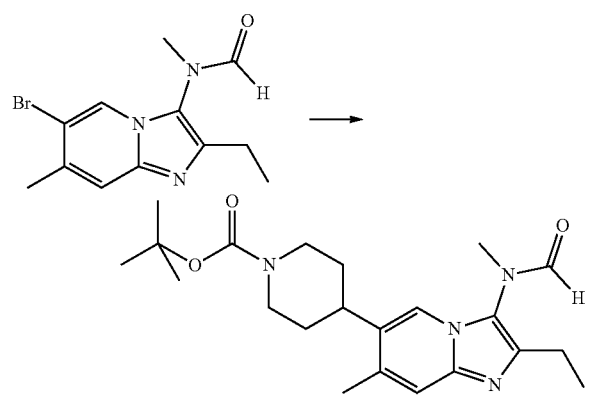

Negishi coupling of Gen-3-i with N-boc-4-iodopiperidine derived organozinc reagent following general synthetic method F3 afforded Intermediate Gen-8-f.

Step iv) 4-(2-Ethyl-7-methyl-3-methylamino-imidazo[1,2-a]pyridin-6-yl)-piperidine-1-carboxylic acid tert-butyl ester

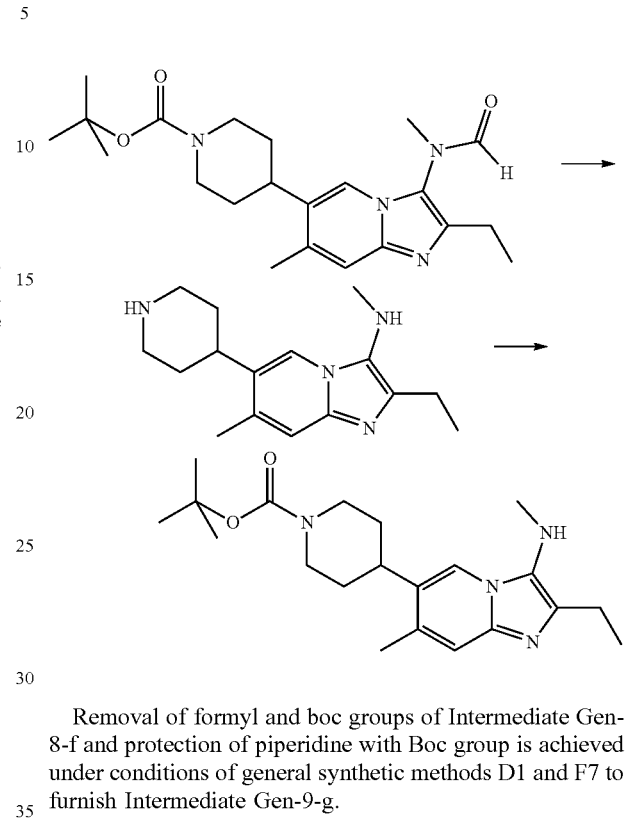

Removal of formyl and boc groups of Intermediate Gen-8-f and protection of piperidine with Boc group is achieved under conditions of general synthetic methods D1 and F7 to furnish Intermediate Gen-9-g.

Step v) (2-Ethyl-7-methyl-6-piperidin-4-yl-imidazo[1,2-a]pyridin-3-yl)-[4-(4-fluoro-phenyl)-thiazol-2-yl]-methyl-amine

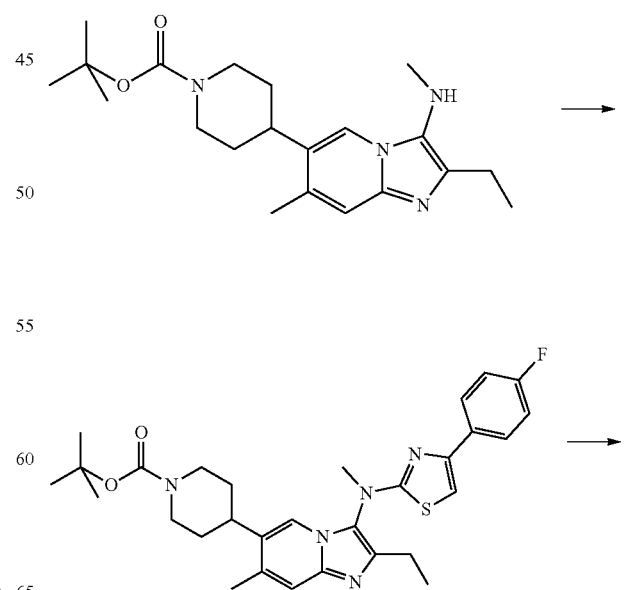

-continued

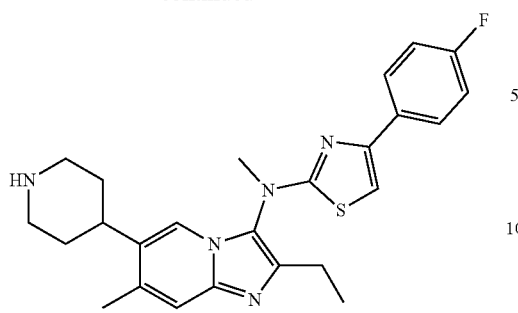

Intermediate Gen-10-s is prepared from Intermediate Gen-9-g and 2-bromo-4'-fluoroacetophenone under conditions of general synthetic method E1 followed by boc removal with general synthetic method F5b.

Step vi) 2-[4-(2-Ethyl-3-{[4-(4-fluoro-phenyl)-thiazol-2-yl]-methyl-amino}-7-methyl-imidazo[1,2-a]pyridin-6-yl)-piperidin-1-yl]-1-(3-hydroxy-azetidin-1-yl)-ethanone

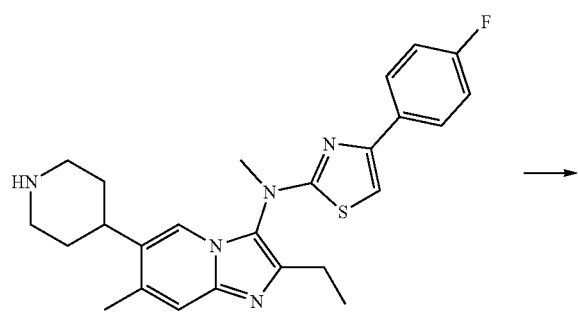

Alkylation of Intermediate Gen-10-s with Intermediate Gen-13-a following general synthetic method F8 gave compound 17.

2.14. Compound 18: 2-[(2-Ethyl-7-fluoro-6-{4-[2-(3-hydroxy-azetidin-1-yl)-2-oxo-ethyl]-piperazin-1-yl}-imidazo[1,2-a]pyridin-3-yl)-methyl-amino]-4-(4-fluoro-phenyl)-thiazole-5-carbonitrile

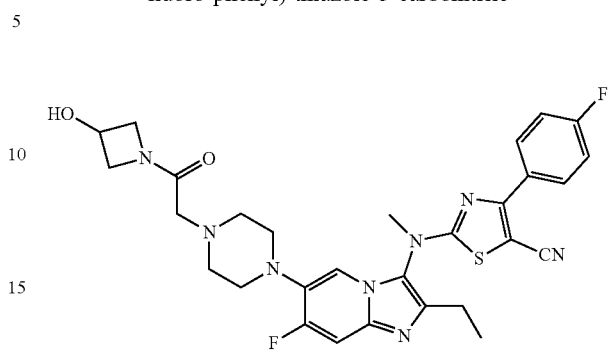

Step i)

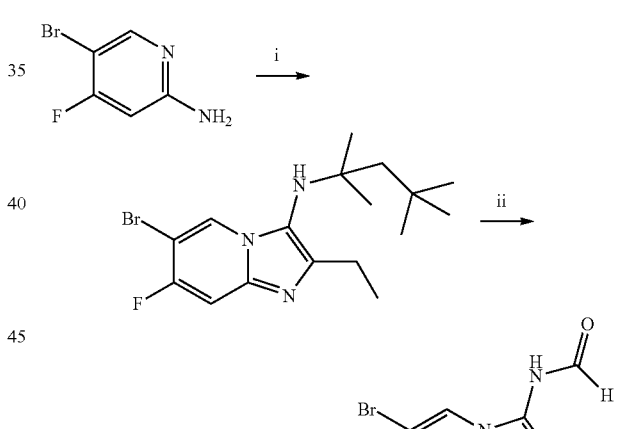

Intermediate Gen-1-b is prepared from 2-amino-4-fluoropyridine following general synthetic method A.

Step ii)

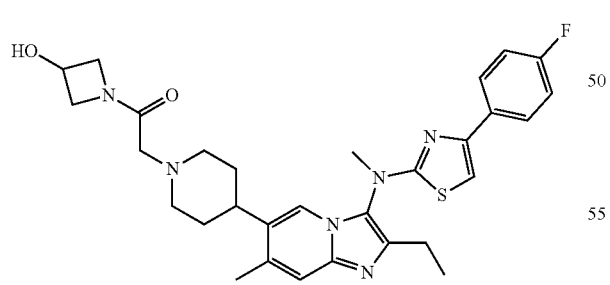

Intermediate Gen-2-i is prepared from Intermediate Gen-1-b and propionaldehyde following general synthetic method B1.

Step iii)

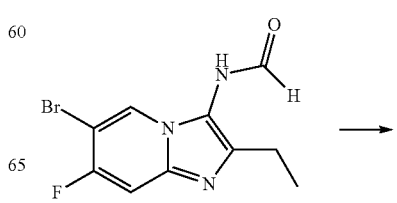

-continued

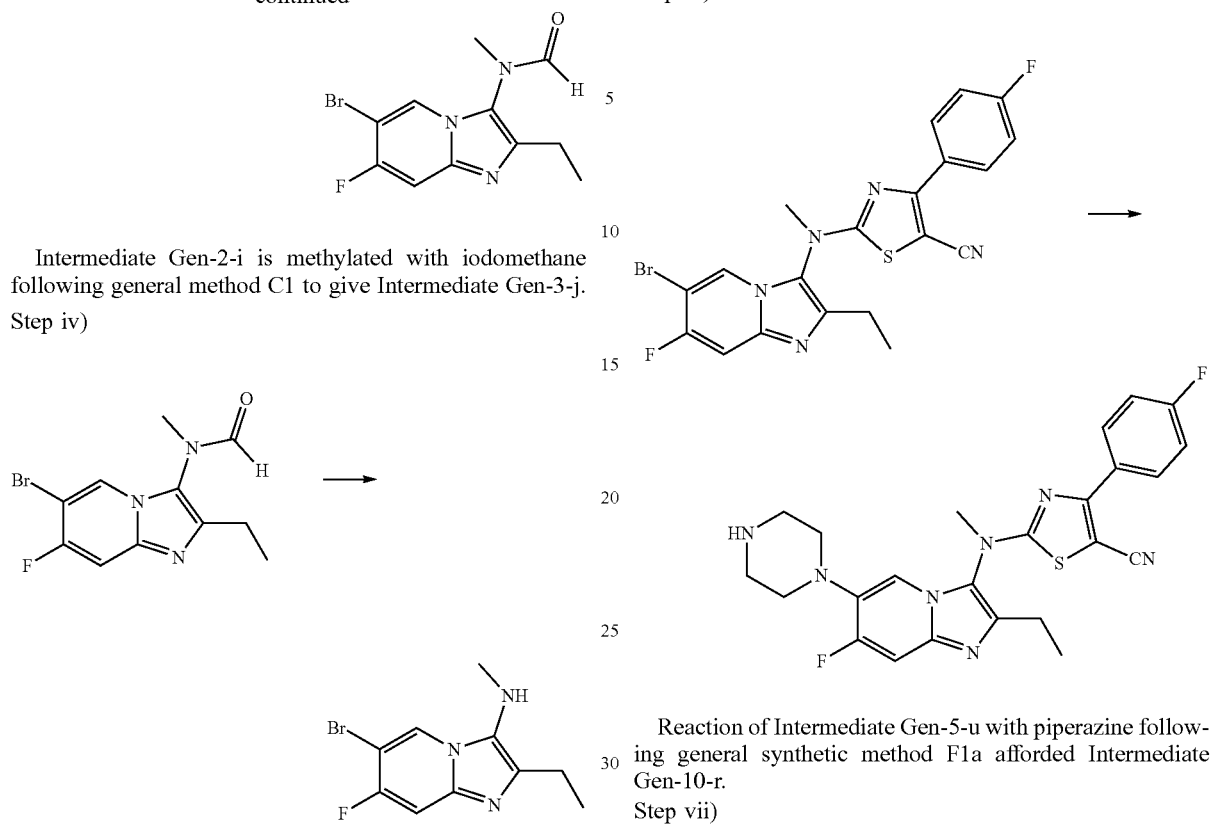

Intermediate Gen-2-i is methylated with iodomethane following general method C1 to give Intermediate Gen-3-j.

Step iv)

Formyl group of Intermediate Gen-3-j is removed under conditions of general synthetic method D2 to furnish Intermediate Gen-4-g.

Step v)

Reaction of Intermediate Gen-4-g with Intermediate Gen-12-a following general synthetic method E2 afforded Intermediate Gen-5-u.

Step vi)

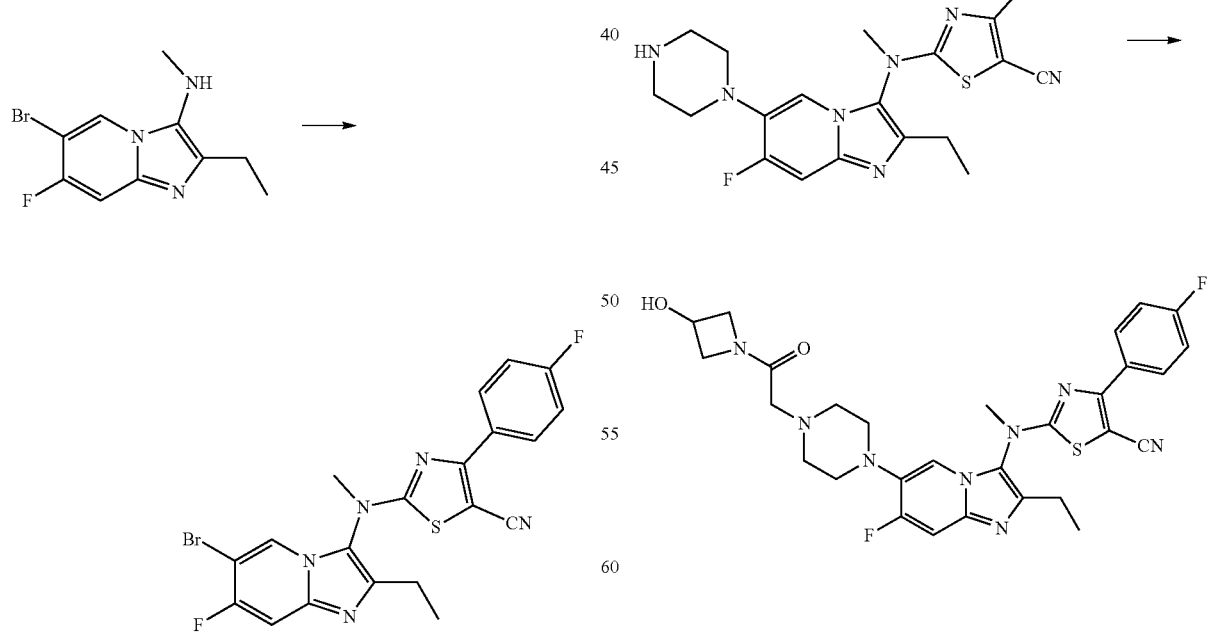

Reaction of Intermediate Gen-5-u with piperazine following general synthetic method F1a afforded Intermediate Gen-10-r.

Step vii)

Alkylation of Intermediate Gen-10-r with Intermediate Gen-13-a following general synthetic method F8 gave compound 18.

2.15. Compound 24: 2-(4-(2-ethyl-3-((4(4-(4-fluoro-phenyl)thiazol-2-yl)(methyl)amino)imidazo[1,2-a]pyridin-6-yl)piperazin-1-yl)-1-(3-hydroxyazetidin-1-yl)ethanone

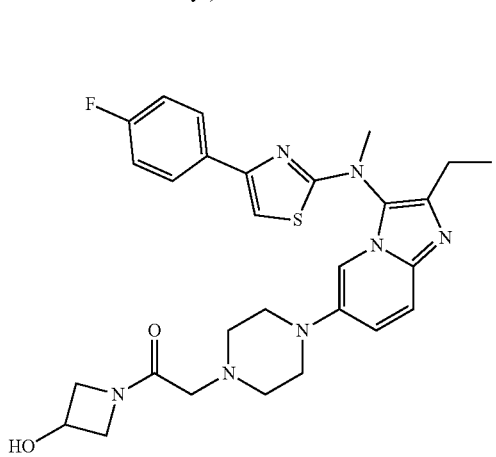

Step i)

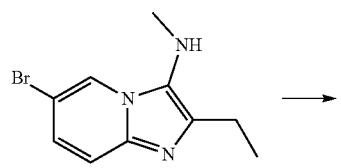

Intermediate Gen-5-b (6-Bromo-2-ethyl-imidazo[1,2-a]pyridin-3-yl)-[4-(4-fluoro-phenyl)-thiazol-2-yl]-methyl-amine is prepared from Gen-4-b (6-Bromo-2-ethyl-imidazo[1,2-a]pyridin-3-yl)-methyl-amine and 2-Bromo-4'-fluoroacetophenone following general synthetic method E1.

Step ii)

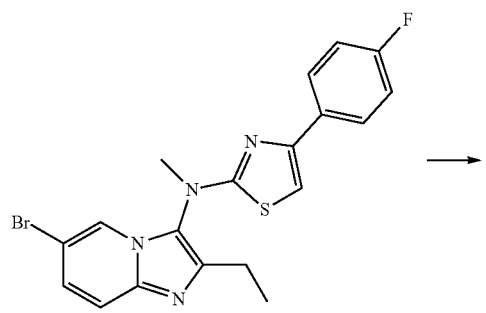

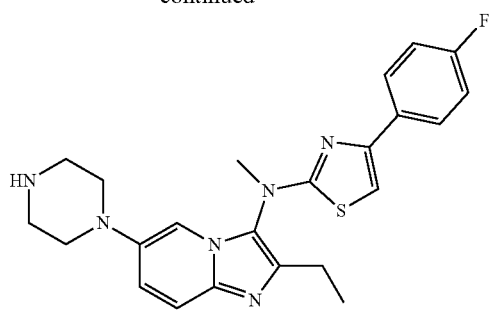

Reaction of Intermediate Gen-5-b with piperazine following general synthetic method F1a afforded Intermediate Gen-10-e 2-Ethyl-6-piperazin-1-yl-imidazo[1,2-a]pyridin-3-yl)-[4-(4-fluoro-phenyl)-thiazol-2-yl]-methyl-amine.

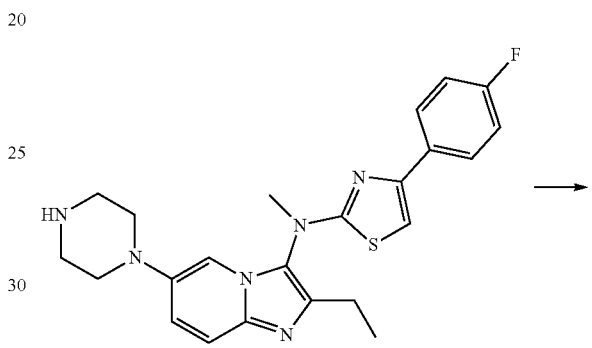

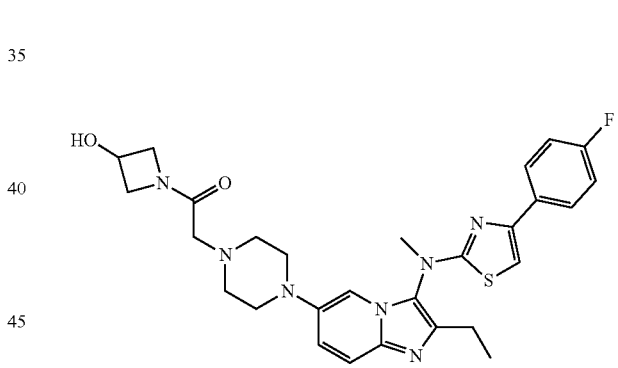

Step iii)

Alkylation of Intermediate Gen-10-e with Intermediate Gen-13-a following general synthetic method F8 give compound 24.

2.16. Compounds 25 to 41

These compounds listed in Table II are prepared similarly as compound 24 following general synthetic method F8 using Intermediates Gen-10-e and respectively Intermediates Gen-13-g, Gen-13-h, Gen-13-j, Gen-13-d, Gen-13-e, Gen-13-f, 1-(Chloroacetyl)pyrrolidine, Gen-13-l, 2-Chloroacetamide, Gen-13-c, 2-Chloro-N,N-dimethyl-acetamide, ethyl 2-chloroacetate, Ethyl 2-Chloropropionate, Chloroacetonitrile, 5-(chloromethyl)-1-cyclopropyl-1H-tetrazole, 2-Chloromethyl-oxazole, 3-(Chloromethyl)-1,2,4-oxadiazole.

2.17. Compound 43: 2-hydroxyethyl 4-(2-ethyl-3-((4-(4-fluorophenyl)thiazol-2-yl)(methyl)amino)imidazo[1,2-a]pyridin-6-yl)piperazine-1-carboxylate

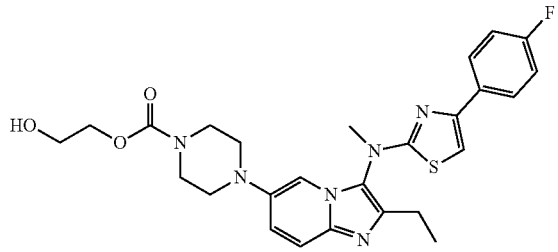 [SMILES: CCc1nc2ccc(N3CCN(C(=O)OCCO)CC3)cn2c1N(C)c1nc(-c2ccc(F)cc2)cs1]

The compound 43 is prepared similarly as compound 24 until the Intermediate Gen-10-e

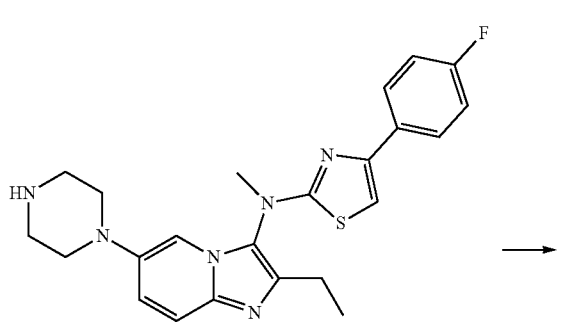

TEA (89 µL, 0.64 mmol, 3 eq.) and potassium carbonate (88 mg, 0.64 mmol, 3 eq.) were added to a solution of hydrochloride salt of Gen-10-e (100 mg, 0.21 mmol, 1 eq.) in DCM (3 mL) followed by ethylene carbonate (28 mg, 0.32 mmol, 1.5 eq.). The reaction mixture was stirred at r.t. for 18 h. Then DMF (1 mL) was added and the reaction was stirred at 80° C. for 15 h. The reaction was quenched by addition of water. The mixture was extracted with DCM, combined organic layers were dried over sodium sulfate, filtered and evaporated. The crude product was purified by chromatography on silica gel (elution with DCM/MeOH 100/0 to 98/2) to afford Compound 43.

¹H NMR (400 MHz, MeOD-d₄) δ ppm 7.89 (2H, dd), 7.50-7.34 (3H, m), 7.16-7.05 (2H, m), 6.94 (1H, s), 4.17-4.10 (2H, m), 3.74-3.67 (2H, m), 3.68-3.57 (7H, m), 3.14-2.98 (4H, m), 2.69(2H, q), 1.30(3H, t)

LC-MS: MW (calcd): 524; m/z MW (obsd): 525 (M+1)

2.18. Compound 61: 2-(4-(2-ethyl-3-((4-(4-fluorophenyl)thiazol-2-yl)(methyl)amino)imidazo[1,2-a]pyridin-6-yl)piperazin-1-ylsulfonyl)acetamide

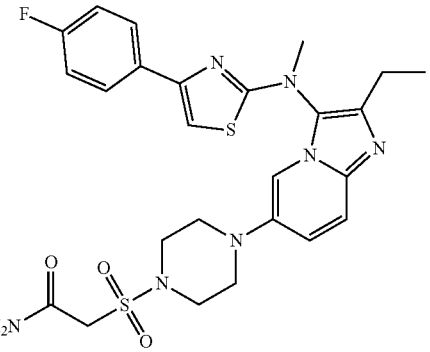

Step i)

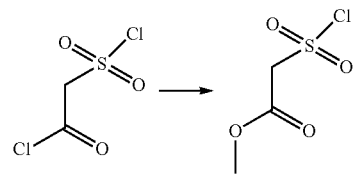

To a solution of chlorosulfonylacetyl chloride (419 µL, 3.955 mmol, 1 eq.) in Et₂O (4 mL), at 0° C. was added MeOH (160 µL, 3.955 mmol, 1 eq.). The reaction mixture is stirred at 0° C. for 3 h, then concentrated in vacuo to give chlorosulfonyl-acetic acid methyl ester.

Step ii)

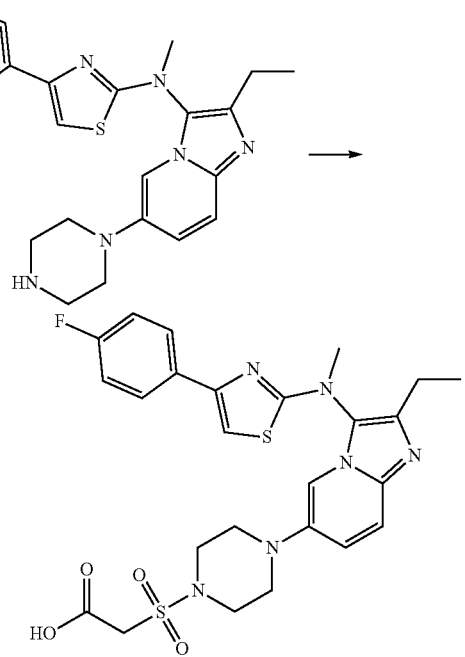

Compound 60 was obtained by reaction of intermediate Gen-10-e with chlorosulfonyl-acetic acid methyl ester following general synthetic methods F11 and F13.
Step iii)

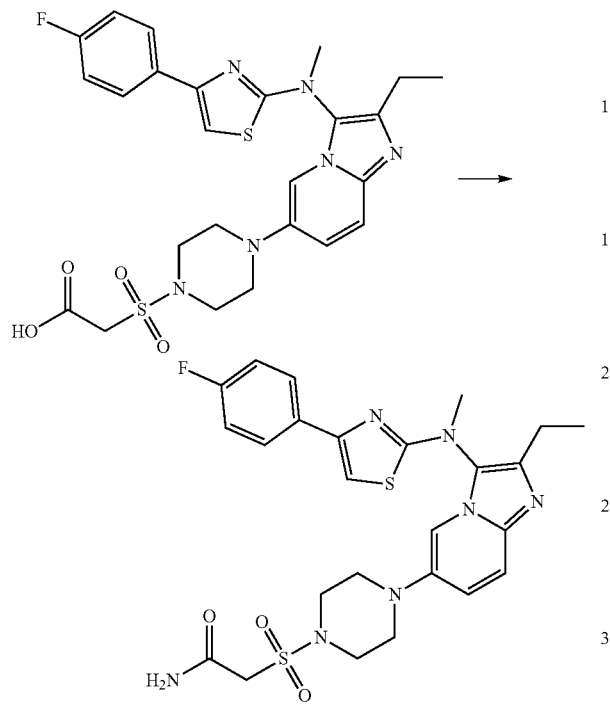

To a solution of compound 60 (38 mg, 0.068 mmol, 1 eq.) in DCM (3 mL) and THF (2 mL) were added HOBT (11 mg, 0.082 mmol, 1.2 eq.) and EDC.HCl (14 mg, 0.075 mmol, 1.1 eq.). The reaction mixture was stirred at r.t. for 1.25 h then a solution of ammoniac 7 M in MeOH (2 drops) was added. The reaction mixture was stirred at r.t. for 30 min., then filtered on celite and the filtrate was concentrated in vacuo. The residue was purified by preparative HPLC to afford the compound 61.

$^1$H NMR (400 MHz, CDCl$_3$) δ ppm 7.88-7.85 (2H, m), 7.62 (1H, d), 7.23 (1H, d), 7.17-7.07 (3H, m), 6.70 (1H, s), 6.51 (1H, bs)NH, 5.68 (1H, bs)NH, 3.90 (2H, s), 3.61 (3H, s), 3.56-3.51 (4H, m), 3.18-3.06 (4H, m), 2.75 (2H, q), 1.34 (3H, t)

LC-MS: MW (calcd): 557; m/z MW (obsd): 558 (M+1)

2.19. Compound 64: ethyl 2-(4-(2-ethyl-3-((4-(4-fluorophenyl)thiazol-2-yl)(methyl)amino)imidazo[1,2-a]pyridin-6-yl)-3-oxopiperazin-1-yl)acetate Compound 64 is prepared from Intermediate Gen-5-b and 3-Oxo-piperazine-1-carboxylic acid tert-butyl ester using the method F4, following by the method F5b to give 1-(2-Ethyl-3-{[4-(4-fluoro-phenyl)-thiazol-2-yl]-methyl-amino}-imidazo[1,2-a]pyridin-6-yl)-piperazin-2-one (Gen-10-d).

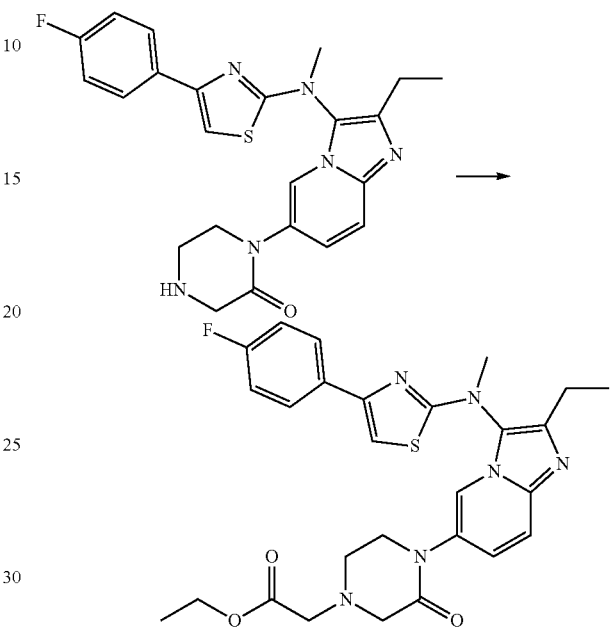

To a solution of Gen-10-d (60 mg, 0.133 mmol, 1 eq.) in 4 mL of DMF at r.t. was added NaH 60% in oil (8 mg, 0.199 mmol, 1.5 eq.). The reaction mixture was stirred for 1 h at r.t. then ethyl bromo acetate (0.018 mL, 0.159 mmol, 1.2 eq.) was added. The reaction mixture was stirred at r.t. for 2 h. The reaction mixture was quenched with a saturated solution of ammonium chloride. The aqueous phase was extracted with AcOEt. The combined organic layers were washed with a saturated solution of sodium carbonate, with brine, dried over Na$_2$SO$_4$, filtered and concentrated in vacuo. The crude product was purified by chromatography on silica gel to afford Compound 64.

LC-MS: MW (calcd): 536; m/z MW (obsd): 537 (M+1)

2.20. Compound 76: 4-(2-ethyl-3-((4-(4-chlorophenyl)thiazol-2-yl)(methyl)amino)imidazo[1,2-a]pyridin-6-yl)-3,6-dihydro-2H-thiopyran 1,1-dioxide

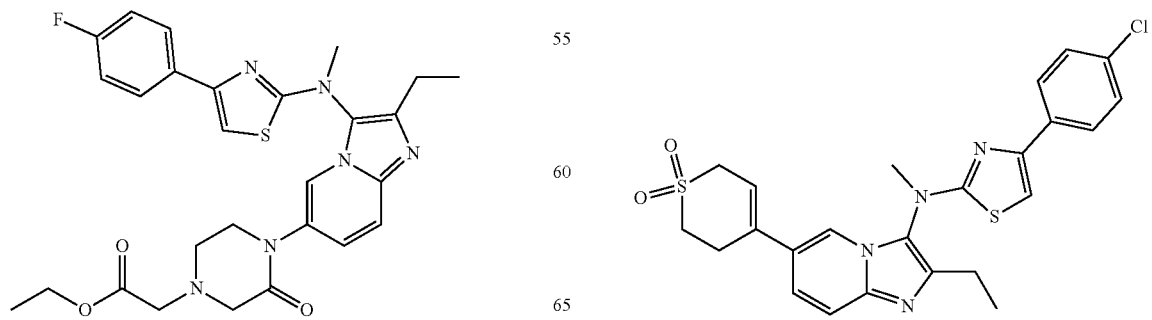

Compound 76 is prepared from Intermediate Gen-5-i and 2-(3,6-Dihydro-2H-thiopyran-4-yl)-4,4,5,5-tetramethyl-[1,3,2]dioxaborolane using method F2 to give 4-(2-ethyl-3-((4-(4-chlorophenyl)thiazol-2-yl)(methyl)amino)imidazo[1,2-a]pyridin-6-yl)-3,6-dihydro-2H-thiopyran (Gen-10-g).

Compound 78 is prepared from Intermediate Gen-5-c and 4-(4,4,5,5-tetramethyl-[1,3,2]dioxaborolan-2-yl)-piperidine-1-carboxylic acid tert-butyl ester using method F2 to give 4-(2-Ethyl-3-{[4-(4-fluoro-phenyl)-thiazol-2-yl]-methyl-amino}-imidazo[1,2-a]pyridin-6-yl)-3,6-dihydro-2H-pyridine-1-carboxylic acid tert-butyl ester.

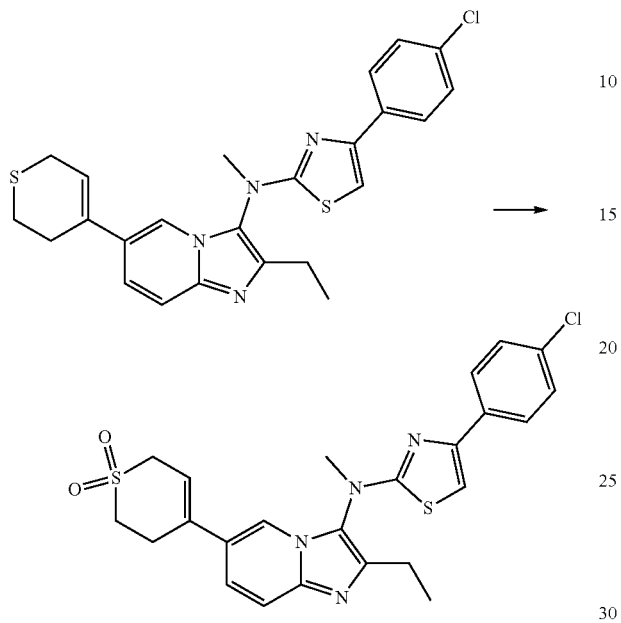

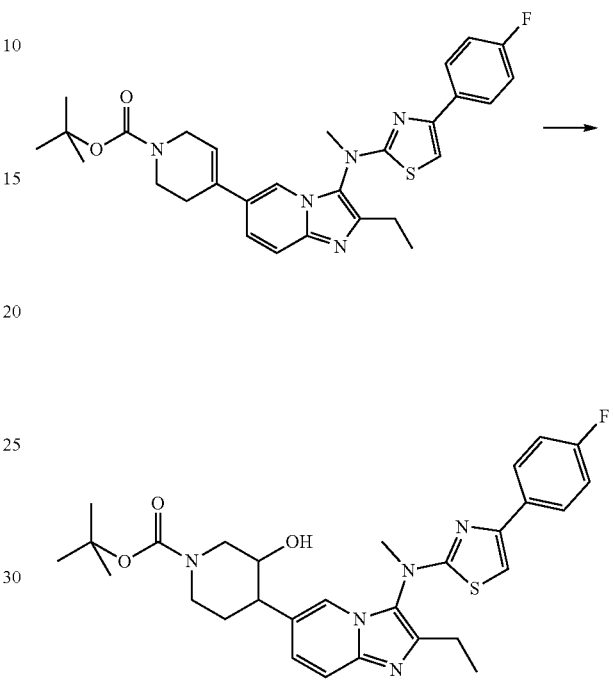

Oxone tetrabutylammonium salt (489 mg, 0.3 mmol, 1.5 eq.) was added to a solution of 4-(2-ethyl-3-((4-(4-chlorophenyl)thiazol-2-yl)(methyl)amino)imidazo[1,2-a]pyridin-6-yl)-3,6-dihydro-2H-thiopyran Gen-10-g (93.5 mg, 0.2 mmol, 1 eq.) in DCM (1.1 mL). The reaction mixture was stirred at r.t. for 4 h, then brine was added and layers were separated. The aqueous layer was extracted with dichloromethane, then combined organic layers were dried over sodium sulfate, filtered and evaporated. The crude product was purified by chromatography on silica gel (elution with DCM/MeOH 100/0 to 98/2) to afford Compound 76.

$^1$H NMR (400 MHz, CDCl$_3$) δ ppm 7.81 (2H, d), 7.77 (1H, bs), 7.61 (1H, d), 7.37 (2H, d), 7.29 (1H, d), 6.76 (1H, s), 5.90 (1H, t), 3.79 (2H, bs), 3.63 (3H, s), 3.26-3.20 (2H, m), 3.15-3.07 (2H, m), 2.77 (2H, q), 1.35 (3H, t)

LC-MS: MW (calcd): 498 ($^{35}$Cl), 500 ($^{37}$Cl); m/z MW (obsd): 499 ($^{35}$Cl M+1), 501 ($^{37}$Cl M+1)

2.21. Compound 78: tert-butyl 4-(2-ethyl-3-((4-(4-fluorophenyl)thiazol-2-yl)(methyl)amino)imidazo[1,2-a]pyridin-6-yl)-3-hydroxypiperidine-1-carboxylate

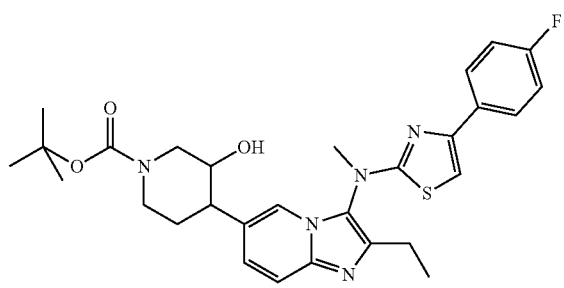 [SMILES: CCc1nc2ccc(C3CCN(C(=O)OC(C)(C)C)CC3O)cn2c1N(C)c1nc(-c2ccc(F)cc2)cs1]

To a solution of 4-(2-Ethyl-3-{[4-(4-fluoro-phenyl)-thiazol-2-yl]-methyl-amino}-imidazo[1,2-a]pyridin-6-yl)-3,6-dihydro-2H-pyridine-1-carboxylic acid tert-butyl ester (0.15 g, 0.28 mmol, 1 eq.) in 6 mL of THF at 0° C. under nitrogen was added BH$_3$.THF 1 M in THF (2.81 mL, 2.81 mmol, 10 eq.). The reaction mixture was stirred at 0° C. for 4 h, then at r.t. for 14 h. The reaction mixture was cooled to 0° C., then NaOH 2 M (6 mL) and H$_2$O$_2$ 30% aqueous (6 mL) were added. The reaction mixture was refluxed for 3 h then cooled to r.t. and THF was removed in vacuo. The remaining aqueous phase was extracted with DCM three times. The combined organic layers were washed with brine, dried over Na$_2$SO$_4$, filtered and concentrated in vacuo. The crude product was purified by chromatography on silica gel (elution with heptane/EtOAc: 100/0 to 40/60) to afford Compound 78.

$^1$H NMR (400 MHz, MeOD-d$_4$) δ ppm 8.04 (1H, d), 7.96-7.92 (2H, m), 7.65-7.61 (1H, m), 7.57-7.54 (1H, m), 7.10 (2H, t), 7.03 (1H, s), 4.37-4.33 (1H, m), 4.19-4.16 (1H, m), 3.75-3.61 (4H, m), 2.91-2.78 (3H, m), 2.73-2.60 (2H, m), 1.91-1.66 (2H, m), 1.52 (9H, d), 1.39 (3H, t)

LC-MS: MW (calcd): 551; m/z MW (obsd): 552 (M+1)

2.22. Compound 90: N-(6-(1-(3-aminopropylsulfonyl)piperidin-4-yl)-2-ethylimidazo[1,2-a]pyridin-3-yl)-4-(4-fluorophenyl)-N-methylthiazol-2-amine

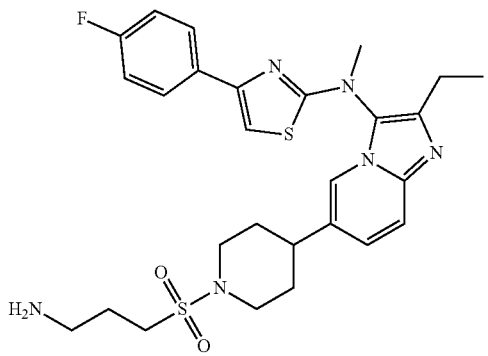 [SMILES: CCc1nc2ccc(C3CCN(S(=O)(=O)CCCN)CC3)cn2c1N(C)c1nc(-c2ccc(F)cc2)cs1]

Step i)
Reaction of Intermediate Gen-10-c and 3-chloro-propane-1-sulfonyl chloride following method F11 then general synthetic method F12a with phtalimide afforded Intermediate Gen-10-p.

Step ii) {6-[1-(3-Amino-propane-1-sulfonyl)-piperidin-4-yl]-2-ethyl-imidazo[1,2-a]pyridin-3-yl}-[4-(4-fluoro-phenyl)-thiazol-2-y]-methyl-amine

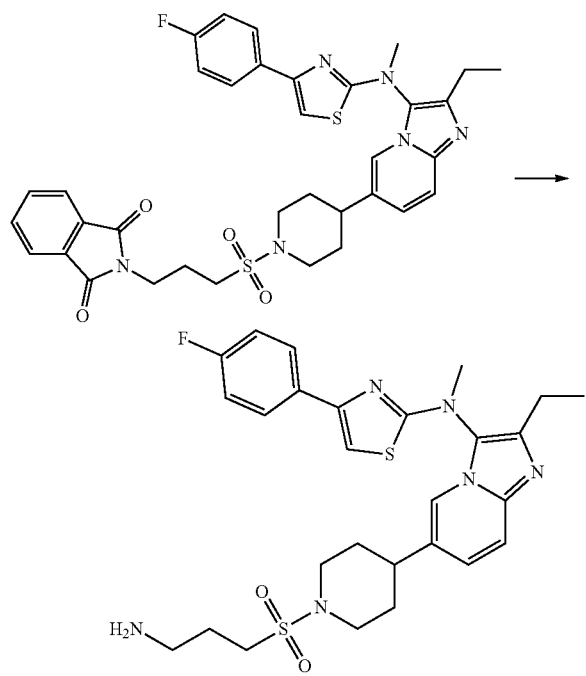

To a solution of Intermediate Gen-10-p (0.053 g, 0.077 mmol, 1 eq.) in 4 mL of EtOH at r.t. was added hydrazine hydrate (0.013 mL, 0.270 mmol, 3.5 eq.). The reaction mixture was stirred 2 h at 90° C. and at r.t. overnight. The reaction mixture was concentrated in vacuo. The residue was taken up with DCM and a saturated Na$_2$CO$_3$ solution. The aqueous phase was extracted with DCM. The combined organic layers were washed with brine, dried over Na$_2$SO$_4$, filtered and concentrated in vacuo. The crude product was purified by chromatography on silica gel (elution with DCM/MeOH) to afford Compound 90.

$^1$H NMR (300 MHz, CDCl$_3$) δ ppm 7.85 (2H, dd), 7.61 (1H, s), 7.57 (1H, d), 7.19-7.02 (3H, m), 6.67 (1H, s), 3.92 (2H, bd), 3.61 (3H, s), 3.16-3.02 (1H, m), 3.01-2.69 (7H, m), 2.68-2.51 (1H, m), 2.11-1.97(2H, m), 1.96-1.87 (2H, m), 1.86-1.66 (2H, m), 1.34(3H, t)

LC-MS: MW (calcd): 556; m/z MW (obsd): 557 (M+1)

2.23. Compound 91: N-(2-ethyl-6-(1-(2-morpholinoethylsulfonyOpperidin-4-yl)imidazo[1,2-a]pyridin-3-yl)-4-(4-fluorophenyl)-N-methylthiazol-2-amine

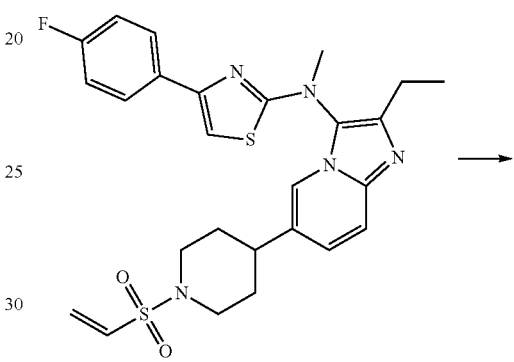

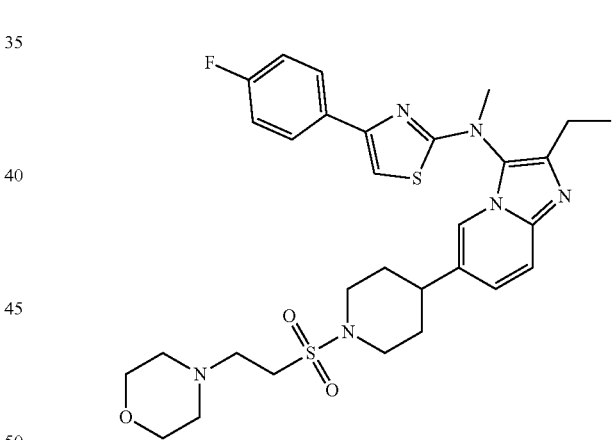

To a solution of Gen-10-y (0.026 g, 0.049 mmol, 1 eq.) in 2 mL of MeCN at r.t. was added morpholine (0.013 mL, 0.148 mmol, 3 eq.). The reaction mixture was stirred for 45 min at r.t. then ethyl bromo acetate (0.009 mL, 0.079 mmol, 1.2 eq.) was added. The reaction mixture was stirred at 90° C. for 4.5 h and at r.t. overnight. The reaction mixture was concentrated in vacuo. The crude product was purified by chromatography on silica gel (elution with DCM/MeOH: 100/0 to 98/2) to afford Compound 91.

$^1$H NMR (400 MHz, MeOD-d$_4$) δ ppm 7.99-7.81 (3H, m), 7.51 (2H, dd), 7.10 (2H, t), 6.96 (1H, s), 3.84 (2H, d), 3.75-3.58 (7H, m), 3.24 (2H, t), 2.95 (2H, t), 2.89-2.66 (5H, m), 2.55 (4H, bs), 1.92 (2H, d), 1.85-1.67 (2H, m), 1.32 (3H, t)

LC-MS: MW (calcd): 612; m/z MW (obsd): 613 (M+1)

2.24. Compound 92: 4-(2-ethyl-3-((4-(4-fluorophenyl)thiazol-2-yl)(methyl)amino)imidazo[1,2-a]pyridin-6-yl)piperidine-1-sulfonamide

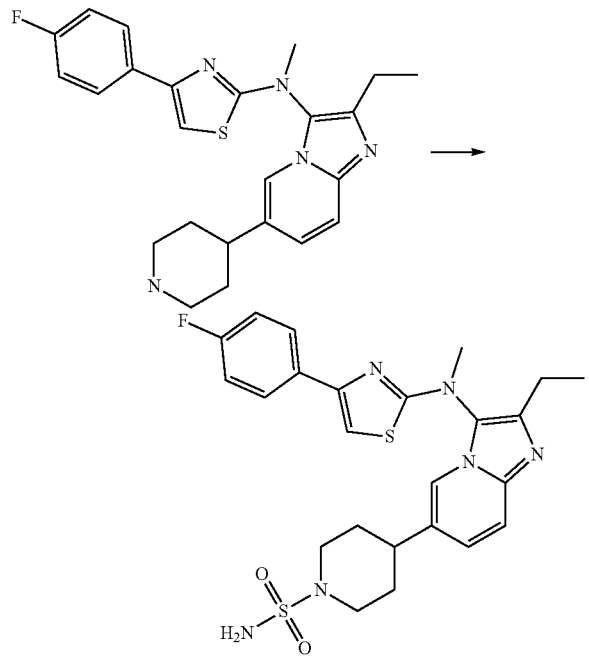

To a solution of Gen-10-c (0.05 g, 0.115 mmol, 1 eq.) in dioxane (2 mL) was added sulfamide (0.039 g, 0.402 mmol, 3.5 eq.). The reaction mixture was heated at 110° C. under microwave irradiation for 45 min. After cooling, water and EtOAc were added to the reaction mixture, the aqueous layer was extracted with EtOAc twice. The combined organic layers were washed with water and brine, dried over Na$_2$SO$_4$, filtered and concentrated in vacuo. The residue was purified by chromatography on silica gel to afford Compound 92.

$^1$H NMR (400 MHz, MeOD-d$_4$) δ ppm 7.93-7.84 (3H, m), 7.53 (1H, dd), 7.40 (1H, dd), 7.11 (2H, t), 6.94 (1H, s), 3.75 (2H, d), 3.62 (3H, s), 2.76-2.66 (5H, m), 1.90 (2H, bd), 1.83 (2H, qd), 1.32 (3H, t)

LC-MS: MW (calcd): 514; m/z MW (obsd): 515 (M+1)

2.25. Compound 105: 1-(2-((2-ethyl-6-(1-(methylsulfonyl)piperidin-4-yl)imidazo[1,2-a]pyridin-3-yl)(methyl)amino)-4-(4-fluorophenyl)thiazol-5-yl)ethanone

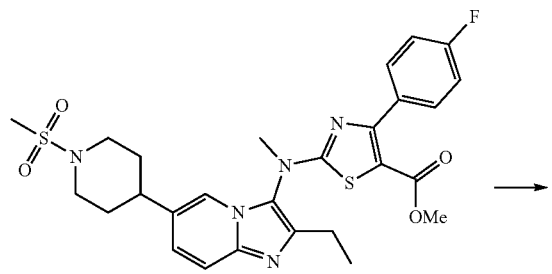

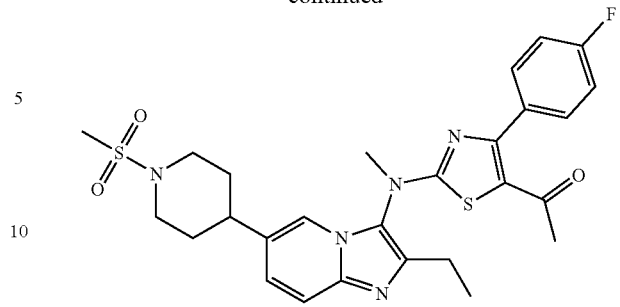

To a solution of Compound 104 (0.06 g, 0.11 mmol, 1 eq.) in 2 mL of THF at −78° C. under argon was added MeLi 1.6 M in Et$_2$O (0.1 mL, 0.16 mmol, 1.45 eq.) dropwise. The reaction mixture was stirred at-78° C. for 1 h, then warmed up to r.t. and stirred for 4 d. The reaction mixture was quenched with a saturated solution of ammonium chloride, the aqueous phase was extracted with AcOEt. The combined organic layers were washed with brine, dried over Na$_2$SO$_4$, filtered and concentrated in vacuo. The crude product was purified by preparative HPLC to afford Compound 105.

$^1$H NMR (400 MHz, MeOD-d$_4$) δ ppm 7.96 (1H, s), 7.69-7.60 (2H, m), 7.55 (1H, d), 7.44 (1H, dd), 7.23 (2H, t), 3.85 (2H, d), 3.59 (3H, s), 2.91-2.81 (5H, m), 2.80-2.68 (3H, m), 2.00 (3H, s), 1.99-1.92 (2H, m), 1.91-1.77 (2H, m), 1.33 (3H, t)

LC-MS: MW (calcd): 555; m/z MW (obsd): 556 (M+1)

2.26. Compound 106: N-(2-(2-((2-ethyl-6-(1-(methylsulfonyl)piperidin-4-yl)imidazo[1,2-a]pyridin-3-yl)(methyl)amino)thiazol-4-yl)-5-fluorophenyl)acetamide

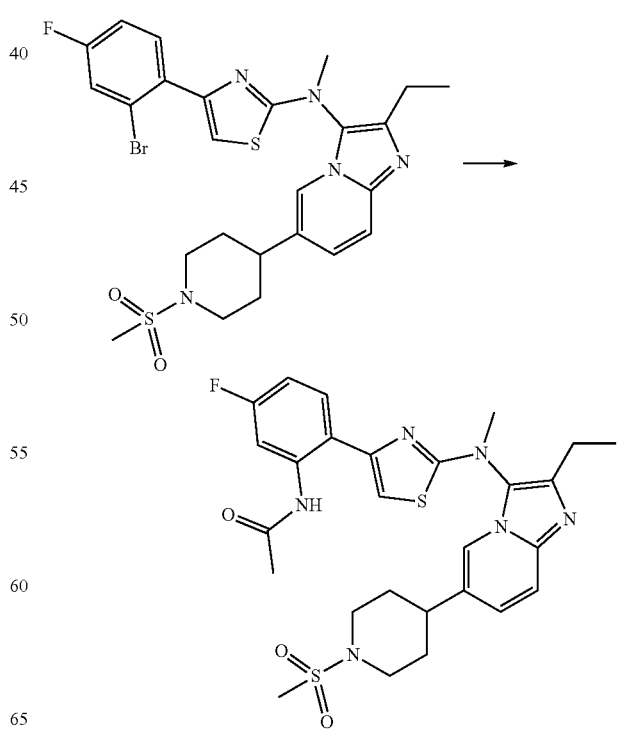

To Intermediate Gen-10-al (0.07 g, 0.118 mmol, 1 eq.), acetamide (0.009 g, 0.141 mmol, 1.2 eq.), cesium carbonate (0.054 g, 0.165 mmol, 1.4 eq.), Xantphos (0.010 g, 0.017 mmol, 0.15 eq.) and Pd$_2$(dba)$_3$ (0.006 g, 0.006 mmol, 0.05 eq.) in a sealed tube under argon was added degased dioxane. The reaction mixture was heated at 100° C. for 6 h. After cooling to r.t., the reaction mixture was filtered on Celpure® P65 and the residue is washed with EtOAc. The filtrate was concentrated in vacuo and the crude product was purified by chromatography on silica gel (elution with DCM/MeOH) to afford Compound 106.

$^1$H NMR (400 MHz, CDCl$_3$) δ ppm 11.56 (1H, bs), 8.43 (1H, d), 7.66 (1H, d), 7.61 (1H, s), 7.55 (1H, dd), 7.22 (1H, d), 6.84-6.73 (2H, m), 3.96 (2H, d), 3.63 (3H, s), 2.87-2.71 (7H, m), 2.71-2.54 (1H, m), 2.09 (3H, s), 2.02-1.92 (2H, m), 1.91-1.77(2H, m), 1.37(3H, t)

LC-MS: MW (calcd): 570; m/z MW (obsd): 571 (M+1)

2.27. Compound 107: (2-(2-((2-ethyl-6-(1-(methylsulfonyl)piperidin-4-yl)imidazo[1,2-a]pyridin-3-yl)(methyl)amino)thiazol-4-yl)-5-fluorophenyl)methanol

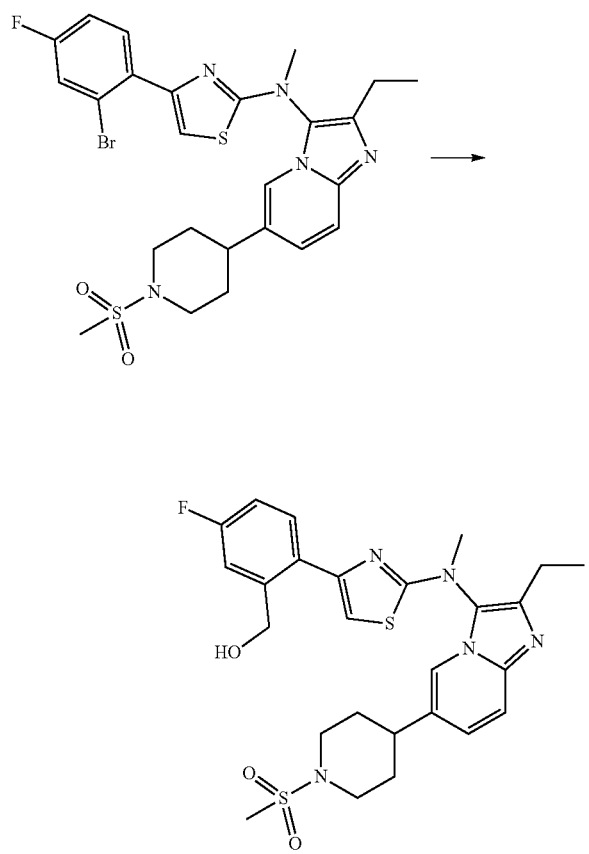

To a solution of Intermediate Gen-10-al (0.050 g, 0.084 mmol, 1 eq.) in 0.84 mL of THF at −78° C. under argon was added iPrMgCl.LiCl 1.3 M in THF (0.32 mL, 0.421 mmol, 5 eq.) dropwise. The reaction mixture was warmed up from −78° C. to 0° C. over 1 h, then was added iPrMgCl.LiCl 1.3 M in THF (0.32 mL, 0.421 mmol, 5 eq.). The reaction mixture was warmed up to r.t. and stirred for 1.5 h. At this point, paraformaldehyde (0.025 g, 0.843 mmol, 10 eq.) was added and the reaction mixture was left under stirring overnight. The reaction mixture was quenched with a saturated solution of ammonium chloride and then filtered on celite. The two phases of the filtrate were separated. The aqueous phase was extracted with EtOAc. The combined organic layers were washed with brine, dried over MgSO$_4$, filtered and concentrated in vacuo. The crude product was purified by preparative HPLC to afford Compound 107.

$^1$H NMR (300 MHz, CDCl$_3$) δ ppm 7.61 (2H, dd), 7.53 (1H, dd), 7.17 (2H, td), 7.05 (1H, td), 6.64 (1H, s), 4.60 (2H, d), 3.97 (2H, d), 3.58 (3H, s), 2.87-2.59 (8H, m), 2.05-1.76 (4H, m), 1.36 (3H, t)

LC-MS: MW (calcd): 543; m/z MW (obsd): 544 (M+1)

2.28. Compound 137: 2-((2-ethyl-6-(1-(methylsulfonyl)piperidin-4-yl)imidazo[1,2-a]pyridin-3-yl)(methyl)amino)-4-(4-fluorophenyl)thiazole-5-carboxamide

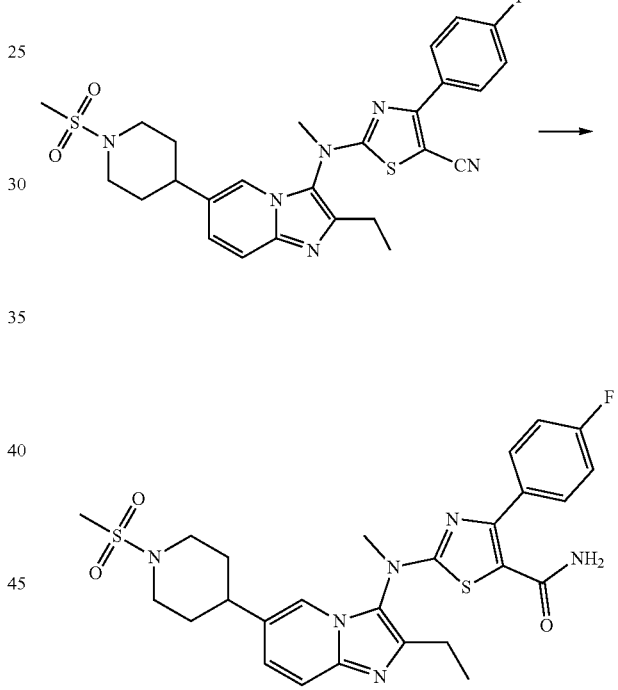

A solution of compound 136 (0.050 g, 0.093 mmol, 1 eq.) in H$_2$SO$_4$ (208 μL, 3.90 mmol, 42 eq.) was stirred at r.t. overnight. Then water was added to the reaction mixture water, and the reaction was neutralized with a saturated NaHCO$_3$ solution. The crude product was filtered and washed with water twice. The solid obtained was dried in vacuo for 48 h to afford Compound 137.

$^1$H NMR (400 MHz, DMSO-d$_6$) δ ppm 8.10 (1H, s), 7.75 (2H, t), 7.54 (1H, d), 7.36 (1H, d), 7.25 (2H, t), 3.68 (2H, d), 3.50 (3H, s), 3.30 (2H, s)NH$_2$, 2.89 (3H, s), 2.82-2.71 (3H, m), 2.63 (2H, q), 1.92-1.83 (2H, m), 1.81-1.71 (2H, m), 1.25 (3H, t)

LC-MS: MW (calcd): 556; m/z MW (obsd): 557 (M+1)

2.29. Compound 174: 2-(4-(2-(2-cyanoethyl)-3-((4-(4-fluorophenyl)thiazol-2-yl)(methyl)amino)imidazo[1,2-a]pyridin-6-yl)piperidin-1-yl)-N,N-dimethylacetamide

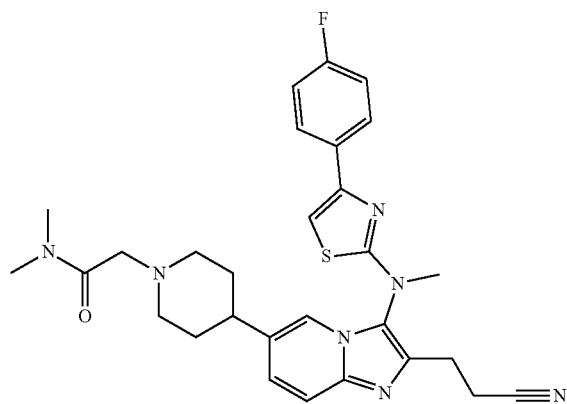 [SMILES: CN(C)C(=O)CN1CCC(c2ccc3nc(CCC#N)c(N(C)c4nc(-c5ccc(F)cc5)cs4)n3c2)CC1]

Step i)

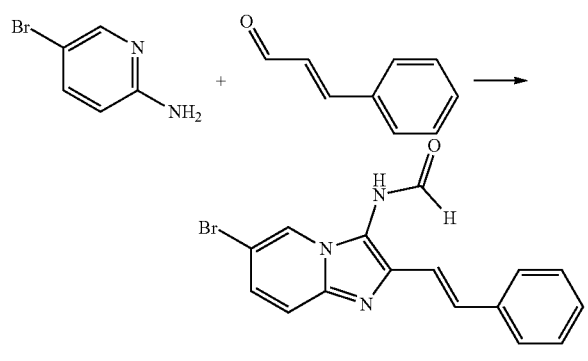

Reaction of 2-amino-5-bromo-pyridine with Z-cinnamaldehyde according to general method B1 afforded Intermediate Gen-2-g (E)-N-(6-bromo-2-styrylimidazo[1,2-a]pyridin-3-yl)-formamide.

Step ii)

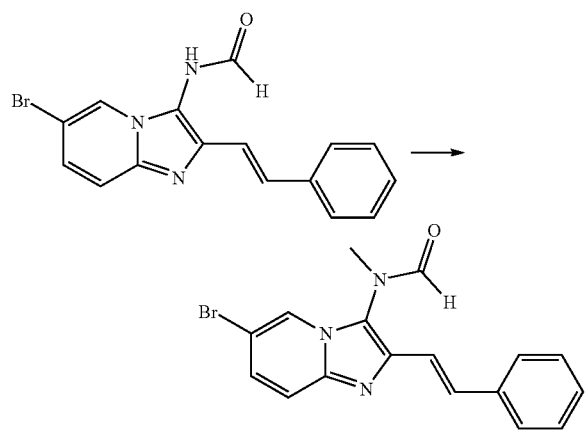

Methylation of Intermediate Gen-2-g following general method C1 led to Intermediate Gen-3-g (E)-N-(6-bromo-2-styrylimidazo[1,2-a]pyridin-3-yl)-N-methylformamide.

LC-MS: MW (calcd): 355 ($^{79}$Br), 357 ($^{81}$Br); m/z (obsd): 356 ($^{79}$Br M+1), 358 ($^{81}$Br M+1)

Step iii)

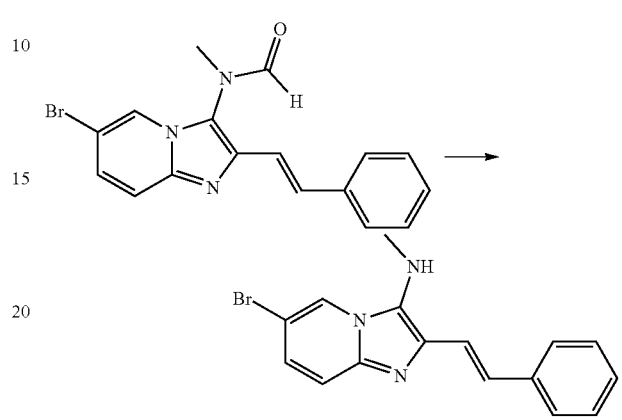

Deformylation of Intermediate Gen-3-g is performed according to method D1 to give Intermediate Gen-4-f (E)-6-bromo-N-methyl-2-styrylimidazo[1,2-a]pyridin-3-amine.

LC-MS: MW (calcd): 327 ($^{79}$Br), 329 ($^{81}$Br); m/z (obsd): 328 ($^{79}$Br M+1), 330 ($^{81}$Br M+1)

Step iv)

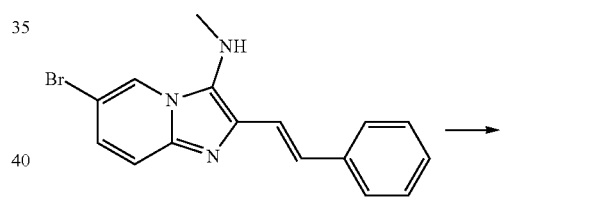

Intermediate Gen-4-f is reacted with 2-bromo-1-(4-fluorophenyl)ethanone according to general method E1 to lead to Intermediate Gen-5-p (E)-N-(6-bromo-2-styrylimidazo[1,2-a]pyridin-3-yl)-4-(4-fluorophenyl)-N-methylthiazol-2-amine.

LC-MS: MW (calcd): 504 ($^{79}$Br), 506 ($^{81}$Br); m/z (obsd): 505 ($^{79}$Br M+1), 507 ($^{81}$Br M+1)

Step v)

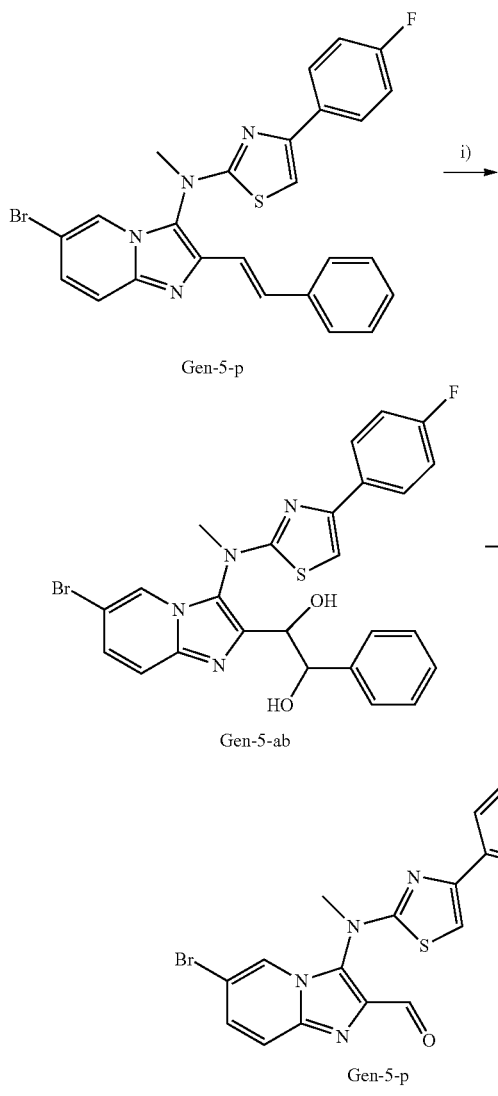

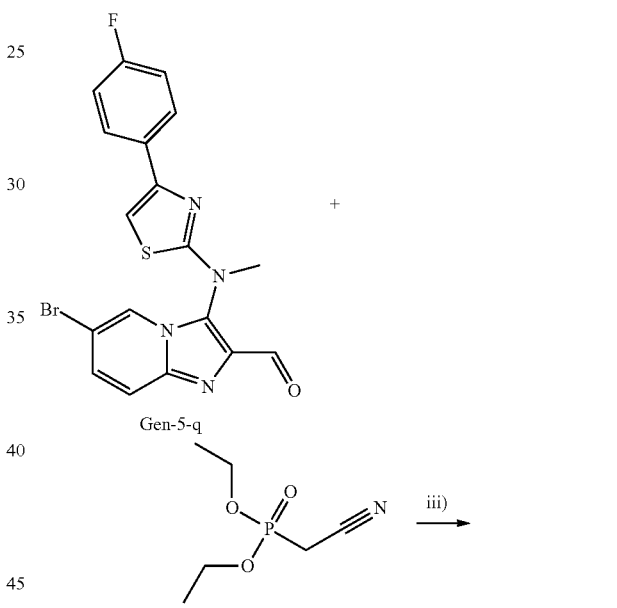

Step i)

To a solution of Intermediate Gen-5-p (16.2 g, 32.1 mmol, 1 eq.) in DCM (500 mL) cooled at 3° C. was added Osmium tetroxide (in t-BuOH, 14.6 g, 1.44 mmol, 0.045 eq.). N-methylmorpholine-4-oxide (8.6 g, 63.6 mmol, 2 eq.) was added and the reaction kept stirring. After 20 min an additional portion of N-methylmorpholine-4-oxide (4.3 g, 31.8 mmol, 1 eq.) was added, this operation was performed 7 times (until complete conversion of starting material was observed). The reaction was quenched by addition of water (500 mL). Layers were separated and the aqueous layer was extracted with DCM (2×100 mL). The combined organic layers were dried over sodium sulfate, filtered and concentrated. The crude product was purified by chromatography on silica gel (elution with DCM/MeOH 99.5/0.5 to 95/5) to give Intermediate Gen-5-q (6-bromo-3-((4-(4-fluorophenyl)thiazol-2-yl)(methyl)amino)imidazo[1,2-a]pyridine-2-carbaldehyde) and Gen-5-ab 1-(6-bromo-3-((4-(4-fluorophenyl)thiazol-2-yl)(methyl)amino)imidazo[1,2-a]pyridin-2-yl)-2-phenylethane-1,2-diol.

Gen-5-q LC-MS: MW (calcd): 430 ($^{79}$Br), 432 ($^{81}$Br); m/z (obsd): 431 ($^{79}$Br M+1), 433 ($^{81}$Br M+1)

Gen-5-ab LC-MS: MW (calcd): 538 ($^{79}$Br), 540 ($^{81}$Br); m/z (obsd): 539 ($^{79}$Br M+1), 541 ($^{81}$Br M+1)

Step ii)

A solution of 1-(6-bromo-3-((4-(4-fluorophenyl)thiazol-2-yl)(methyl)amino)imidazo[1,2-a]pyridin-2-yl)-2-phenylethane-1,2-diol (Gen-5-ab) (10.8 g, 20 mmol, 1 eq.) in DCM (500 mL) was cooled to-4° C. Lead tetraacetate (dried before use, 13.3 g, 30 mmol, 1.5 eq.) was added and stirred at −4° C. for 0.5 h. The reaction was quenched by addition of water (500 mL). The mixture was filtered and the layers in the filtrate were separated. The aqueous layer was extracted with DCM (2×200 mL). The combined organic layers were dried over sodium sulfate, filtered and concentrated. The crude product was purified by chromatography on silica gel (elution with heptane/EtOAc 100/0 to 50/50) to give an additional amount of Intermediate Gen-5-q 6-bromo-3-((4-(4-fluorophenyl)thiazol-2-yl)(methyl)amino)imidazo[1,2-a]pyridine-2-carbaldehyde.

LC-MS: MW (calcd): 430 ($^{79}$Br), 432 ($^{81}$Br); m/z (obsd): 431 ($^{79}$Br M+1), 433 ($^{81}$Br M+1)

Step iii)

Sodium hydride (60% in oil suspension, 55.2 mg, 1.38 mmol, 1.15 eq.) was added to a solution of diethyl cyanomethylphosphonate (234 mg, 1.32 mmol, 1.1 eq.) in anhydrous THF (5 mL). The resulting white suspension was stirred for 10 min at room temperature and then cooled to −78° C. Intermediate Gen-5-q (518 mg, 1.2 mmol, 1 eq.) dissolved in anhydrous THF (10 mL) was added with a syringe pump at a rate of 60 mL/h. The mixture was stirred for 0.5 h at −78° C., then allowed to warm to room temperature and stirred for additional 20 min. The reaction mixture was quenched by addition of water (100 mL) and extracted with EtOAc (3×30 mL). The organic layers were combined, dried over sodium sulfate, filtered and concentrated. The crude product was purified by chromatography on silica gel (elution with heptanes/EtOAc 70/30 to 65/35) to give 3-(6-bromo-3-((4-(4-fluorophenyl)thiazol-2-yl)(methyl)amino)imidazo[1,2-a]pyridine-2-yl)acrylonitrile (Gen-5-ac).

LC-MS: MW (calcd): 453 ($^{79}$Br), 455 ($^{81}$Br); m/z (obsd): 454 ($^{79}$Br M+1), 456 ($^{81}$Br M+1)

Step vii)

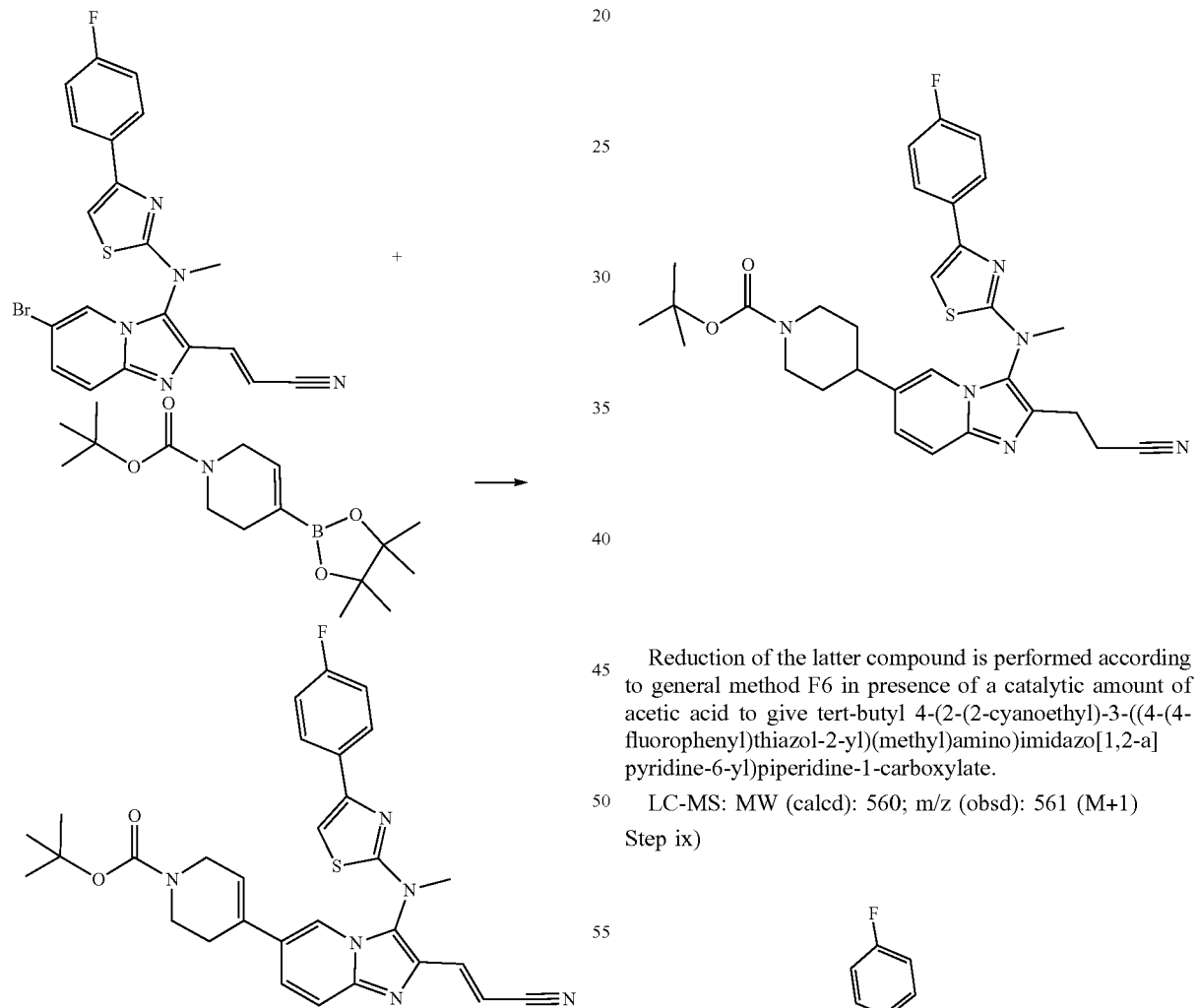

Suzuki coupling of 3-(6-bromo-3-((4-(4-fluorophenyl)thiazol-2-yl)(methyl)amino)imidazo[1,2-a]pyridine-2-yl)acrylonitrile (Gen-5-ac) with tert-butyl 4-(4,4,5,5-tetramethyl-1,3,2-dioxaborolan-2-yl)-5,6-dihydropyridine-1(2H)-carboxylate according to general method F2 afforded tert-butyl 4-(2-(2-cyanovinyl)-3-((4-(4-fluorophenyl)thiazol-2-yl)(methyl)amino)imidazo[1,2-a]pyridine-6-yl)-5,6-dihydropyridine-1(2H)-carboxylate.

LC-MS: MW (calcd): 556; MW (obsd): 557 (M+1)

Step viii)

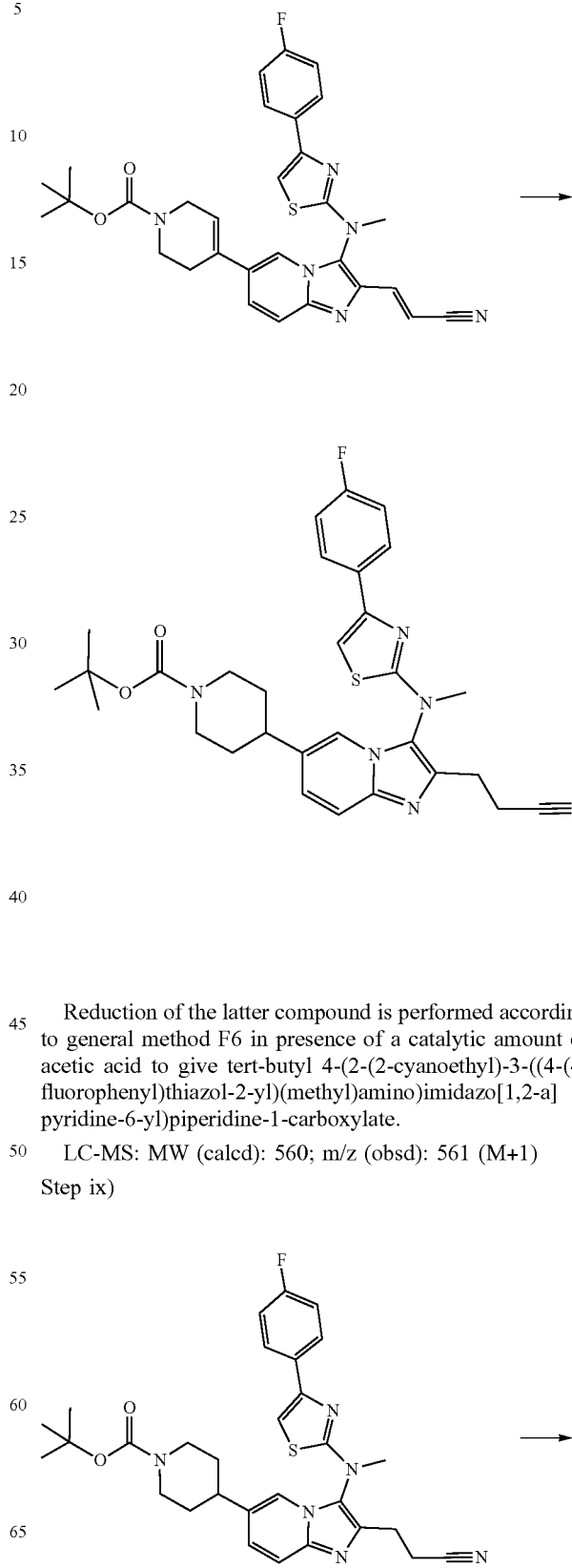

Reduction of the latter compound is performed according to general method F6 in presence of a catalytic amount of acetic acid to give tert-butyl 4-(2-(2-cyanoethyl)-3-((4-(4-fluorophenyl)thiazol-2-yl)(methyl)amino)imidazo[1,2-a]pyridine-6-yl)piperidine-1-carboxylate.

LC-MS: MW (calcd): 560; m/z (obsd): 561 (M+1)

Step ix)

-continued

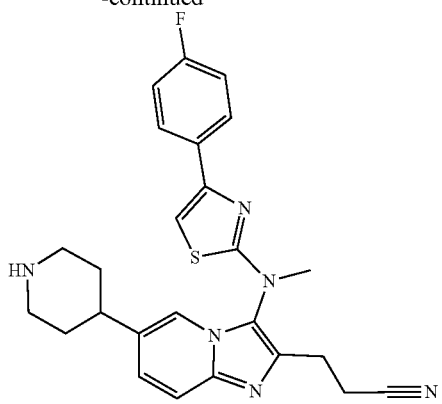

Boc deprotection of the latter compound is performed according to general method F5b to afford Intermediate Gen-10-aa.

LC-MS: MW (calcd): 460; m/z (obsd): 461 (M+1)

Step x)

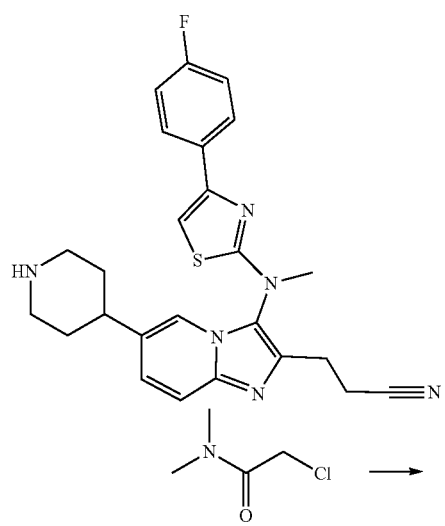

Intermediate Gen-10-aa is alkylated with 2-chloro-N,N-dimethylacetamide using general method F8 to give the expected compound 174.

2.30. Compound 175: 3-(3-((4-(4-fluorophenyl)-5-(hydroxymethyl)thiazol-2-yl)(methyl)amino)-6-(1-(methylsulfonyl)piperidin-4-yl)imidazo[1,2-a]pyridin-2-yl)propanenitrile Step i)

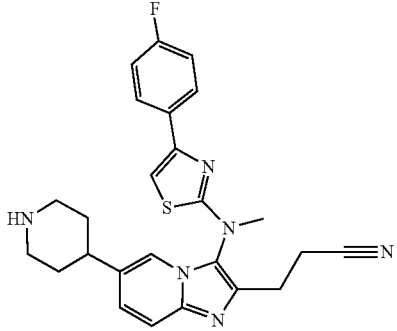
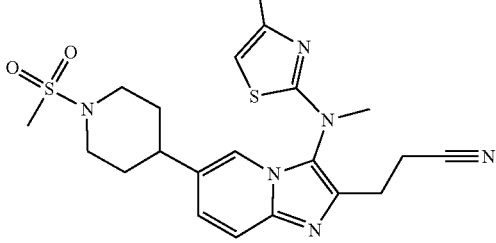

Intermediate Gen-10-aa is sulfonylated with methanesulfonyl chloride using general method F11 to give 3-(3-((4-(4-fluorophenyl)thiazol-2-yl)(methyl)amino)-6-(1-(methylsulfonyl)piperidin-4-yl)imidazo[1,2-a]pyridin-2-yl) propanenitrile.

LC-MS: MW (calcd): 538; m/z (obsd): 539 (M+1)

Step ii:

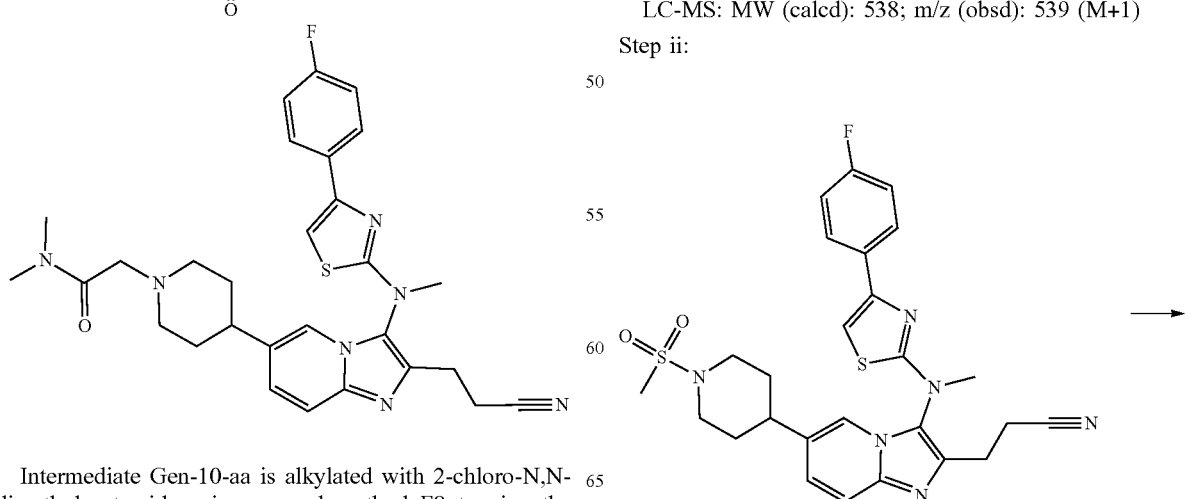

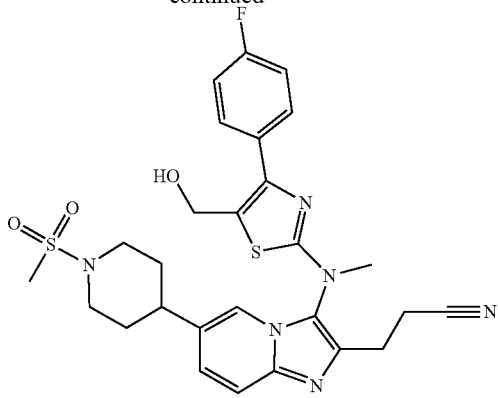

The latter compound is reacted under conditions of general method F14 to give the expected compound 175.

2.31. Compound 176: 3-(6-(1-(2-(dimethylamino)-2-oxoethyl)piperidin-4-yl)-3-((4-(4-fluorophenyl)thiazol-2-yl)(methyl)amino)imidazo[1,2-a]pyridin-2-yl)propanamide Step i)

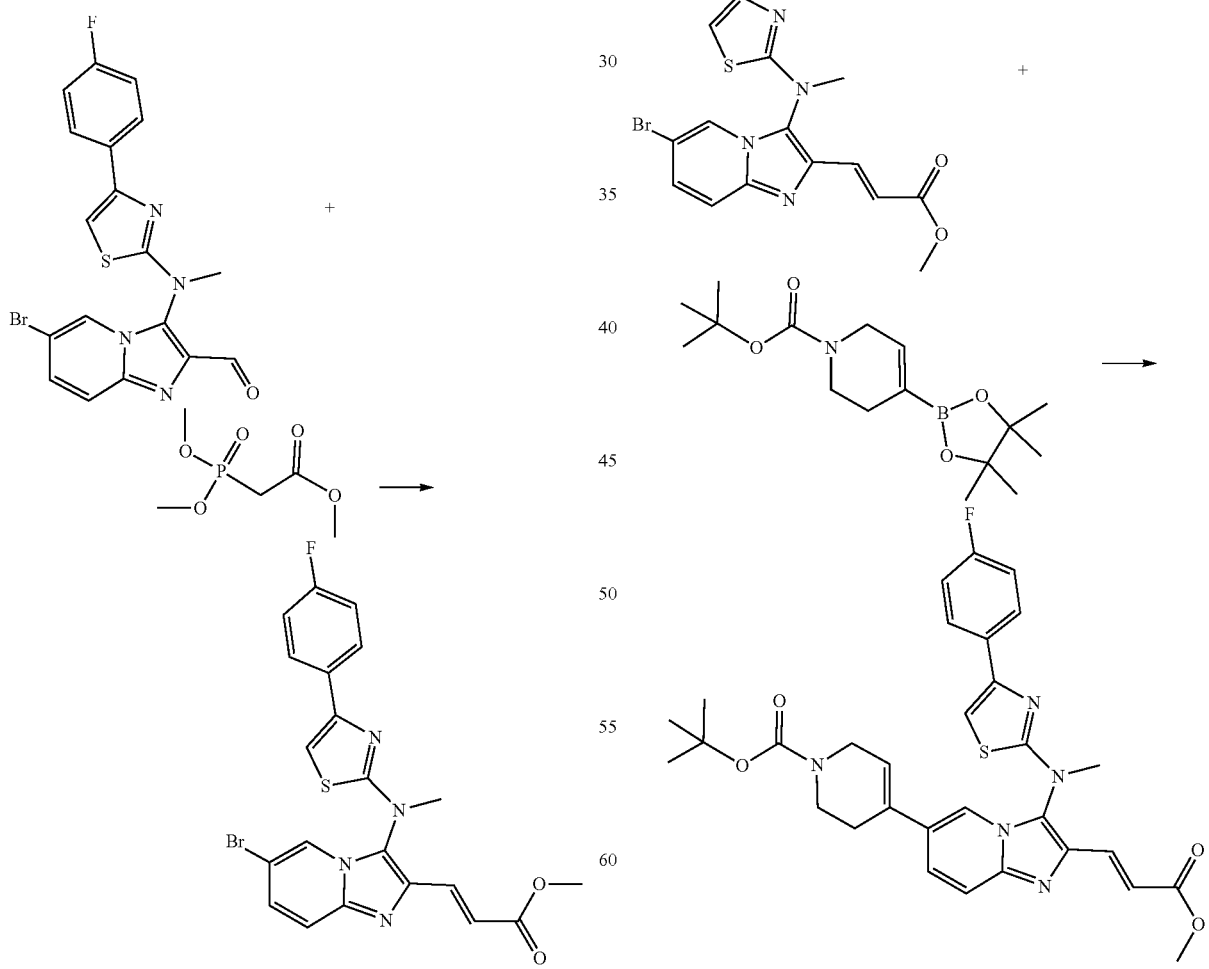

Sodium hydride (60% in oil suspension, 92 mg, 2.3 mmol, 1.15 eq.) was added to a solution of methyl 2-(dimethoxyphosphoryl)acetate (401 mg, 2.2 mmol, 1.1 eq.) in anhydrous THF (20 mL). The resulting white suspension was stirred for 20 min at room temperature and then cooled to −78° C. Intermediate Gen-5-q (863 mg, 2.0 mmol, 1 eq.) dissolved in anhydrous THF (15 mL) was added with a syringe pump at a rate of 45 mL/h. The mixture was stirred for 50 min at −78° C., then allowed to warm to room temperature and stirred for additional 40 min. The reaction mixture was evaporated. Brine (50 mL) was added to the crude product and the mixture was extracted with EtOAc (3×50 mL). The organic layers were combined, dried over sodium sulfate, filtered and concentrated. The crude product was purified by chromatography on silica gel (elution with heptanes/EtOAc 100/0 to 50/50) to give the Intermediate Gen-5-ad.

LC-MS: MW (calcd): 486 ($^{79}$Br), 488 ($^{81}$Br); m/z (obsd): 487 ($^{79}$Br M+1), 489 ($^{81}$Br M+1)

Step ii)

Suzuki coupling of methyl 3-(6-bromo-3-((4-(4-fluorophenyl)thiazol-2-yl)(methyl)amino)imidazo[1,2-a]pyridin-

187

2-yl)acrylate with tert-butyl 4-(4,4,5,5-tetramethyl-1,3,2-dioxaborolan-2-yl)-5,6-dihydropyridine-1(2H)-carboxylate according to general method F2 afforded tert-butyl 4-(3-((4-(4-fluorophenyl)thiazol-2-yl)(methyl)amino)-2-(3-methoxy-3-oxoprop-1-enyl)imidazo[1,2-a]pyridin-6-yl)-5,6-dihydropyridine-1(2H)-carboxylate.

LC-MS: MW (calcd): 589; MW (obsd): 590 (M+1)

Step iii)

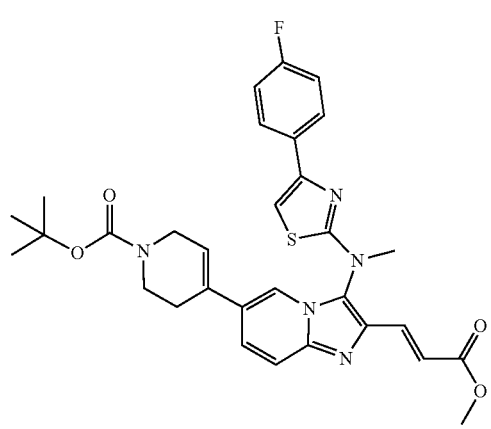

Reduction of the latter compound is performed according to general method F6 in presence of a catalytic amount of acetic acid to give tert-butyl 4-(3-((4-(4-fluorophenyl)thiazol-2-yl)(methyl)amino)-2-(3-methoxy-3-oxopropyl)imidazo[1,2-a]pyridin-6-yl)piperidine-1-carboxylate.

LC-MS: MW (calcd): 593; m/z (obsd): 594 (M+1)

188

Step iv)

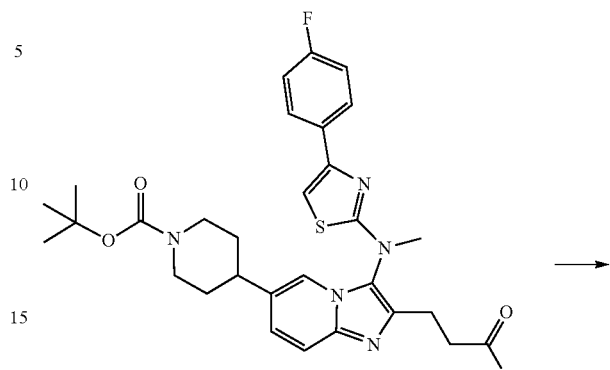

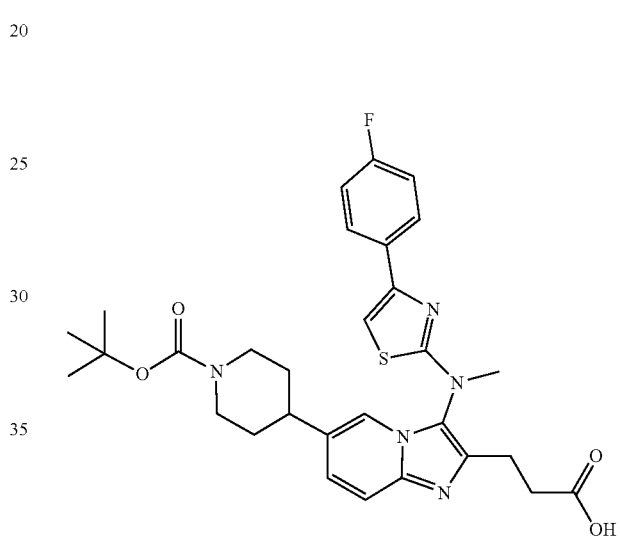

The latter compound is saponified according to general method F13 to afford 3-(6-(1-(tert-butoxycarbonyl)piperidin-4-yl)-3-((4-(4-fluorophenyl)thiazol-2-yl)(methyl)amino)imidazo[1,2-a]pyridin-2-yl)propanoic acid.

LC-MS: MW (calcd): 579; m/z (obsd): 580 (M+1)

Step v)

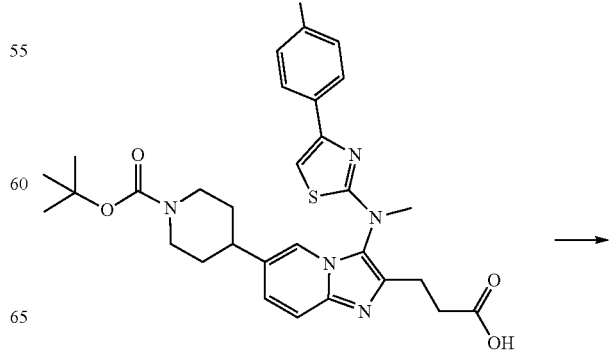

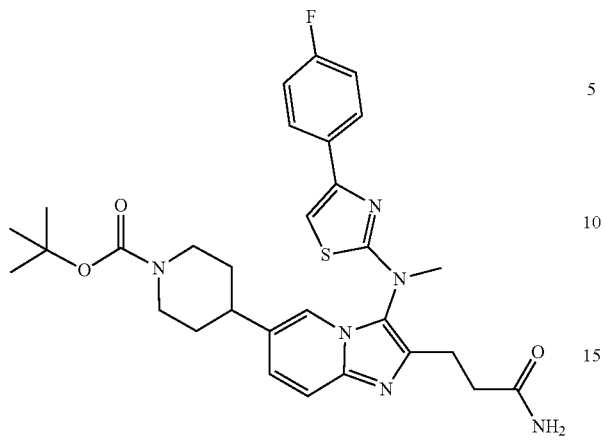

A solution of 3-(6-(1-(tert-butoxycarbonyl)piperidin-4-yl)-3-((4-(4-fluorophenyl)thiazol-2-yl)(methyl)amino)imidazo[1,2-a]pyridin-2-yl)propanoic acid (220 mg, 0.38 mmol, 1 eq.) and TEA (211 µL, 1.52 mmol, 4 eq.) in DMF (3 mL) was stirred for 10 min at r.t. Propane phosphonic acid anhydride (226 µL, 0.76 mmol, 2 eq.) followed by ammonium chloride (40.7 mg, 0.76 mmol, 2 eq.) were added and the resulting mixture was stirred at r.t. for 4 days. TEA (211 µL, 1.52 mmol, 4 eq.), propane phosphonic acid anhydride (226 µL, 0.76 mmol, 2 eq.) and ammonium chloride (40.7 mg, 0.76 mmol, 2 eq.) were added and the reaction mixture kept stirring for 2 h. Brine was added (100 mL) and the mixture was extracted with DCM (3×20 mL). The organic layers were combined, dried over sodium sulfate, filtered and concentrated. The crude product was purified by chromatography on silica gel (elution with DCM/MeOH 100/0 to 80/20) to give tert-butyl 4-(2-(3-amino-3-oxopropyl)-3-((4-(4-fluorophenyl)thiazol-2-yl)(methyl)amino)imidazo[1,2-a]pyridin-6-yl)piperidine-1-carboxylate (Gen-10-am).

LC-MS: MW (calcd): 578; m/z (obsd): 579 (M+1)

Step vi)

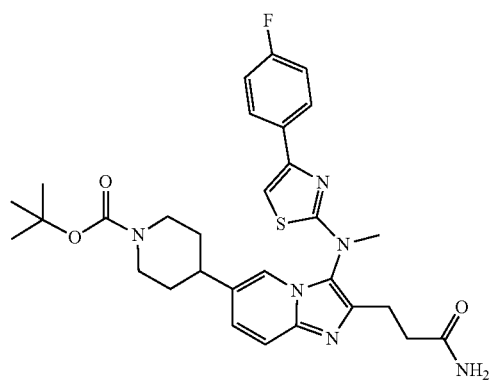

→

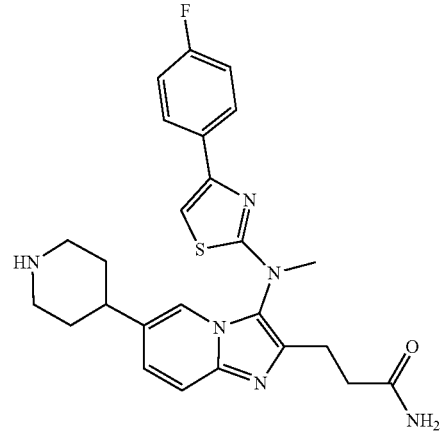

Boc deprotection of the latter compound is performed according to general method F5b to afford 3-(3-((4-(4-fluorophenyl)thiazol-2-yl)(methyl)amino)-6-(piperidin-4-yl)imidazo[1,2-a]pyridin-2-yl)propanamide.

LC-MS: MW (calcd): 478; m/z (obsd): 479 (M+1)

Step vii)

The latter compound was alkylated with 2-chloro-N,N-dimethylacetamide using general method F8 to give the expected compound 176.

2.32. Compound 184: ethyl 2-(3-((4-(4-chlorophenyl)thiazol-2-yl)(methyl)amino)-2-ethylimidazo[1,2-a]pyridin-6-yl)-2-oxoimidazolidin-1-yl)acetate

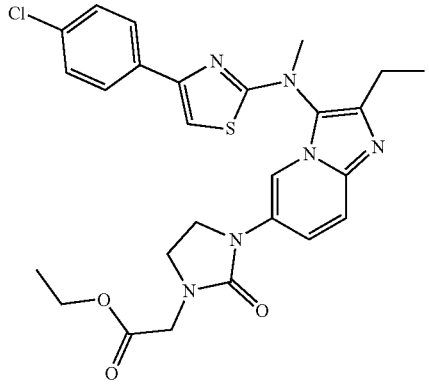 [SMILES: CCOC(=O)CN1CCN(c2ccc3nc(CC)c(N(C)c4nc(-c5ccc(Cl)cc5)cs4)n3c2)C1=O]

To a solution of Gen-10-a (0.30 g, 0.066 mmol, 1 eq.) in 3 mL of DMF at r.t. was added NaH 60% in oil (0.004 g, 0.099 mmol, 1.5 eq.). The reaction mixture was stirred 45 min at r.t. then ethyl bromo acetate (0.009 mL, 0.079 mmol, 1.2 eq.) was added. The reaction mixture was stirred at r.t. for 1 h. The reaction mixture was quenched with a saturated solution of ammonium chloride. The aqueous phase was extracted with AcOEt. The combined organic layers were washed with a saturated solution of sodium carbonate, with brine, dried over $Na_2SO_4$, filtered and concentrated in vacuo. The crude product was purified by chromatography on silica gel (elution with Heptane/AcOEt: 100/0 to 50/50) to afford Compound 184.

$^1$H NMR (400 MHz, MeOD) δ ppm 8.39-8.28 (1H, m), 7.84 (2H, d), 7.71 (1H, dd), 7.57 (1H, dd), 7.40-7.33 (2H, m), 7.00 (1H, s), 4.18 (2H, q), 4.01 (2H, s), 3.93-3.86 (2H, m), 3.67-3.57 (5H, m), 2.72 (2H, q), 1.31 (3H, t), 1.25 (3H, t)

LC-MS: MW (calcd): 538 ($^{35}$Cl), 540 ($^{37}$Cl); m/z MW (obsd): 539 ($^{35}$Cl M+1), 541 ($^{37}$Cl M+1)

2.33. Compound 186: 2-(2-((2-ethyl-6-(1-(methylsulfonyl)piperidin-4-yl)imidazo[1,2-a]pyridin-3-yl)(methyl)amino)-4-(4-fluorophenyl)thiazol-5-yl)acetonitrile

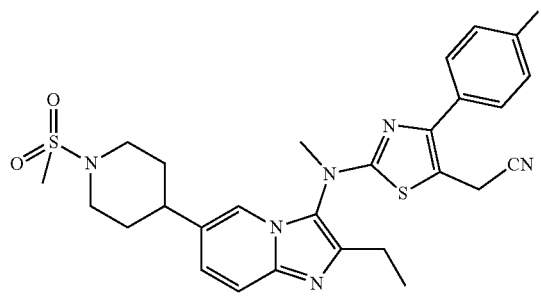

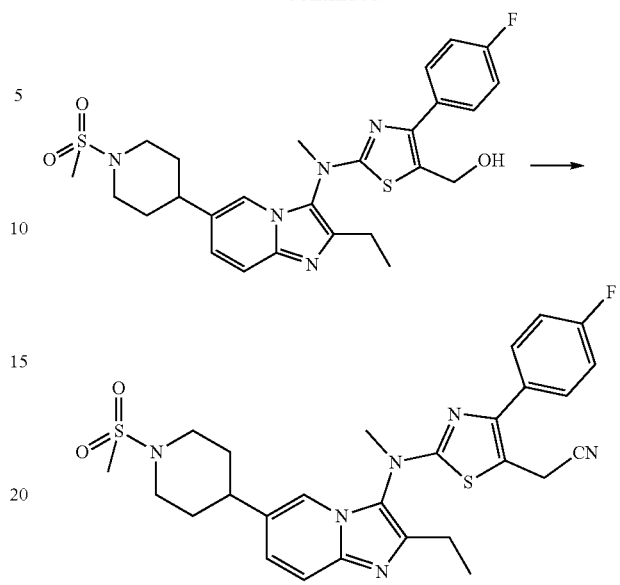

To a solution of compound 147 (50 mg, 0.092 mmol, 1 eq.) with triphenyl phosphine (60 mg, 0.23 mmol, 2.5 eq.) in THF (1.5 mL) at 0° C. were added acetone cyanohydrine (23 mg, 0.27 mmol, 3 eq.) and DEAD (40 mg, 0.23 mmol, 2.5 eq.). The reaction mixture was stirred at 0° C. for 3 h, then quenched by addition of a saturated $NaHCO_3$ solution and EtOAc. The organic layer was washed with a saturated $NaHCO_3$ soltution, water, and brine, dried over $Na_2SO_4$, filtered and concentrated in vacuo. The crude product was purified by preparative HPLC to afford Compound 186.

$^1$H NMR (400 MHz, CDCl$_3$) δ ppm 7.64-7.57 (4H, m), 7.22-7.14 (3H, m), 3.97 (2H, d), 3.72 (2H, d), 3.56 (3H, s), 2.85-2.72 (7H, m), 2.71-2.60 (1H, m), 2.06-1.95 (2H, m), 1.86 (2H, qd), 1.37 (3H, t)

LC-MS: MW (calcd): 552; m/z (obsd): 553 (M+1)

2.34. Compound 187: 2-ethyl-N-(4-(4-fluorophenyl)pyrimidin-2-yl)-N-methyl-6-(1-(methylsulfonyl)-1,2,3,6-tetrahydropyridin-4-yl)imidazo[1,2-a]pyridin-3-amine

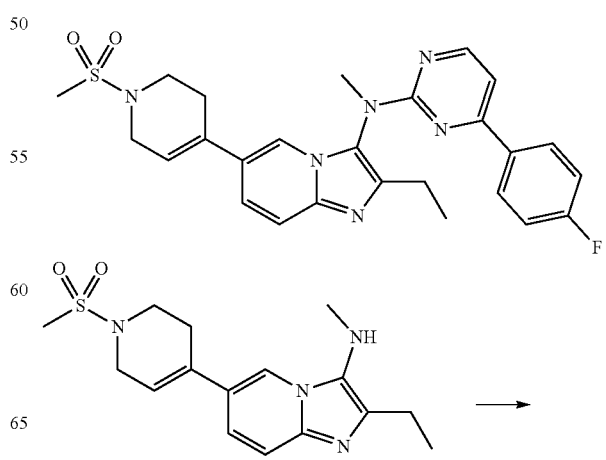

-continued

To Intermediate Gen-9-a (90 mg, 0.27 mmol, 1 eq.), 2-chloro-4-(4-fluorophenyl)-pyrimidine (63 mg, 0.30 mmol, 1.1 eq.), cesium carbonate (0.177 g, 0.54 mmol, 2 eq.), Xantphos (0.008 g, 0.014 mmol, 0.05 eq.) and palladium acetate (0.003 g, 0.009 mmol, 0.03 eq.) in a sealed tube under nitrogen was added degazed dioxane. The reaction mixture was heated at 130° C. overnight. After cooling to r.t., the reaction mixture was quenched with water. The aqueous phase was extracted with AcOEt three times. The combined organic layers were washed with brine, dried over $Na_2SO_4$, filtered and concentrated in vacuo. The crude product was purified by chromatography on silica gel (elution with DCM/MeOH: 100/0 to 95/5) to afford Compound 187.

$^1$H NMR (300 MHz, $CDCl_3$) δ ppm 8.41 (1H, d), 8.05-7.90 (2H, m), 7.65-7.42 (2H, m), 7.28 (1H, dd), 7.13 (3H, d), 6.03 (1H, t), 4.00-3.87 (2H, m), 3.62 (3H, s), 3.47 (2H, t), 2.82 (3H, s), 2.73 (2H, q), 2.64-2.43 (2H, m), 1.28 (3H, t)

LC-MS: MW (calcd): 506; m/z MW (obsd): 507 (M+1)

2.35. Compound 202: (1-aminocyclopropyl)(4-(2-ethyl-3-((4-(4-fluorophenyl)thiazol-2-yl)(methyl)amino)imidazo[1,2-a]pyridin-6-yl)piperazin-1-yl)methanone

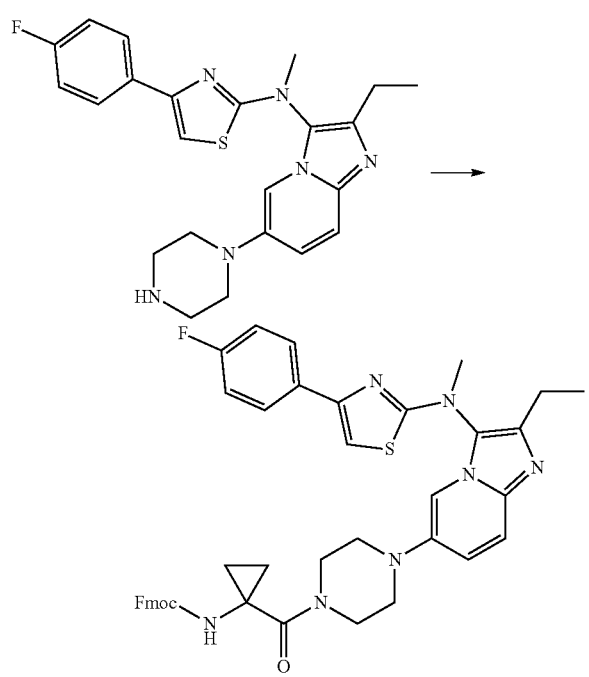

Step i)
Intermediate Gen-10-e was reacted with Fmoc-1-amino-1-cyclopropane carboxylic acid according to general synthetic method F9a to give Fmoc-protected derivative.

Step ii)

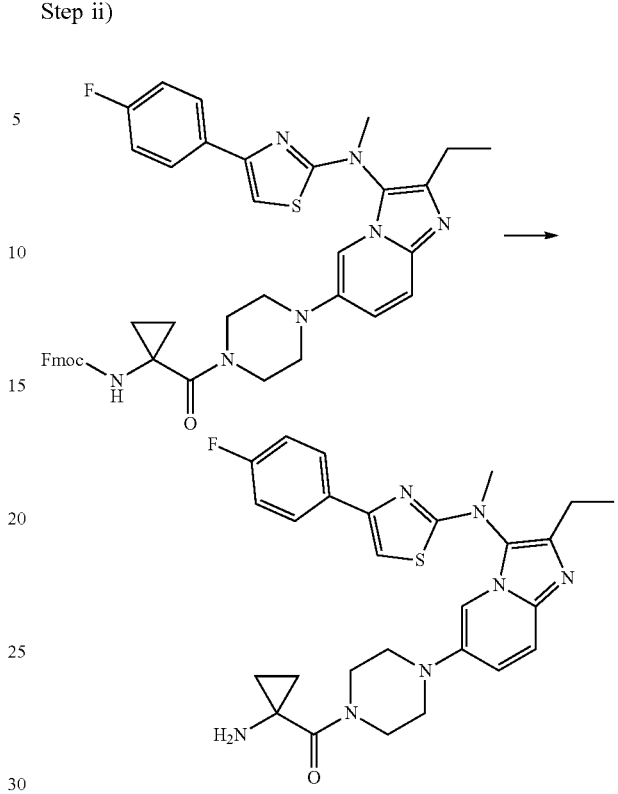

To a solution of Fmoc-protected derivative obtained in step i) above (66 mg, 0.089 mmol, 1 eq.) in a mixture of DCM/DMF (2/4 mL) were added pyridine (100 μL, excess.) then morpholine (78 μL, 0.89 mmol, 10 eq.). The reaction mixture was stirred at r.t. for 20 h, then diluted with water and EtOAc. The aqueous layer was extracted with EtOAc, then the organic layer was washed with water, and brine, dried over $Na_2SO_4$, filtered and concentrated in vacuo. The crude product was purified by chromatography on silica gel (elution with DCM/MeOH: 100/0 to 98/2) to afford Compound 202.

$^1$H NMR (300 MHz, $CDCl_3$) δ ppm 7.86 (2H, dd), 7.54 (1H, d), 7.24-7.04 (4H, m), 6.68 (1H, s), 3.84 (4H, bt), 3.61 (3H, s), 3.04 (4H, bt), 2.73 (2H, q), 1.33 (3H, t), 1.07-0.99 (2H, m), 0.86-0.77 (2H, m)

LC-MS: MW (calcd): 519; m/z (obsd): 520 (M+1)

2.36. Compound 204: 2-(4-(2-ethyl-3-((4-(4-fluorophenyl)thiazol-2-yl)(methyl)amino)imidazo[1,2-a]pyridin-6-yl)piperazin-1-yl)-2-oxoacetamide Step i)

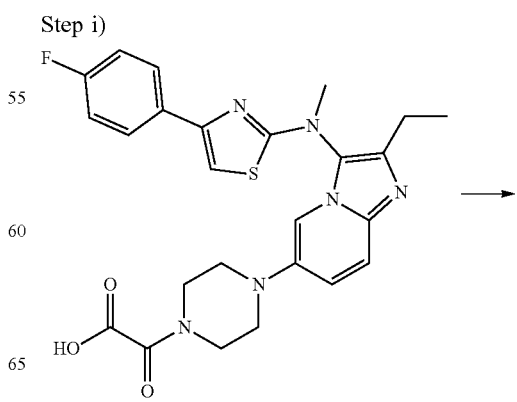

-continued

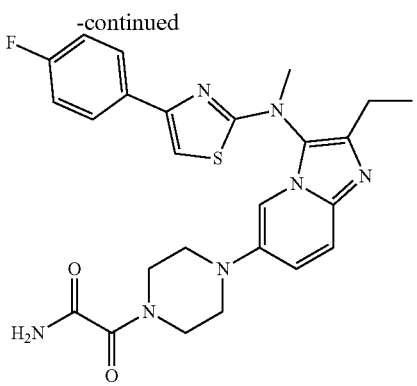

Intermediate Gen-10-e was reacted with chloro-oxo-acetic acid ethyl ester following successive general synthetic methods F9b and F13 to give [4-(2-ethyl-3-{[4-(4-fluoro-phenyl)-thiazol-2-yl]-methyl-amino}-imidazo[1,2-a]pyridin-6-yl)-piperazin-1-yl]-oxo-acetic acid (Intermediate Gen-10-an).

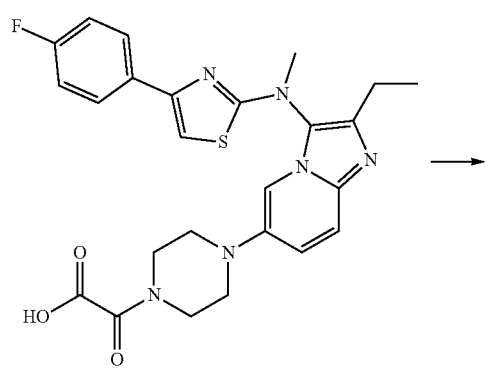

To a solution of Intermediate Gen-10-an (24 mg, 0.047 mmol, 1 eq.) in DCM (3 mL) and THF (2 mL) were added HOBT (8 mg, 0.057 mmol, 1.2 eq.) and EDC.HCl (10 mg, 0.075 mmol, 1.1 eq.). The reaction mixture was stirred at r.t. for 1 h then a solution of ammoniac 7 N in MeOH (3 drops) was added. The reaction mixture was stirred at r.t. for 3 h, then filtered on celite and the filtrate was concentrated in vacuo. The residue was purified by preparative HPLC to afford Compound 204.

$^1$H NMR (400 MHz, CDCl3) δ ppm 7.87-7.81 (2H, m), 7.53 (1H, dd), 7.20 (1H, d), 7.14-7.05 (3H, m), 7.04 (1H, bs) NH, 6.66 (1H, s), 5.59 (1H, bs) NH, 4.24 (2H, t), 3.80 (2H, t), 3.59 (3H, s), 2.72 (2H, q), 3.11-3.05 (4H, m), 1.33 (3H, t)

LC-MS: MW (calcd): 507; m/z MW (obsd): 508 (M+1)

2.37. Compound 211: 1-(2-ethyl-3-((4-(4-fluorophenyl)thiazol-2-yl)(methyl)amino)imidazo[1,2-a]pyridin-6-yl)piperidin-4-ol Step i)

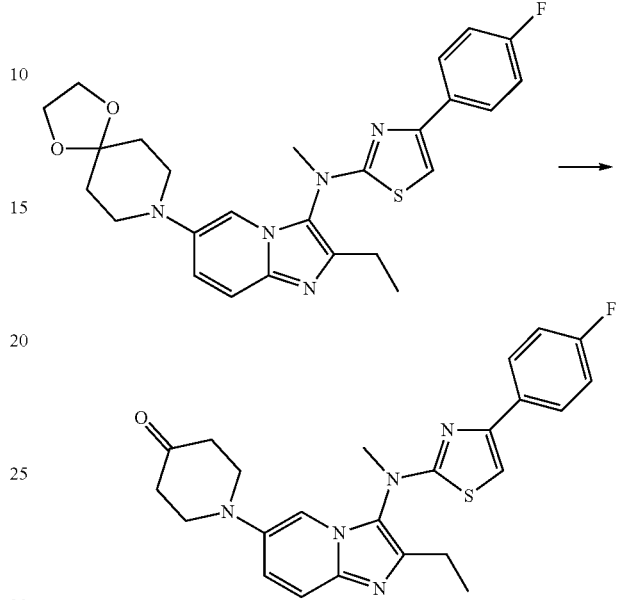

Intermediate Gen-5-c is reacted under conditions of general method F1b with 1,4-Dioxa-8-aza-spiro[4.5]decane to give the [6-(1,4-Dioxa-8-aza-spiro[4.5]dec-8-yl)-2-ethyl-imidazo[1,2-a]pyridin-3-yl]-[4-(4-fluoro-phenyl)-thiazol-2-yl]-methyl-amine (Intermediate Gen-10-ap)

Step ii)

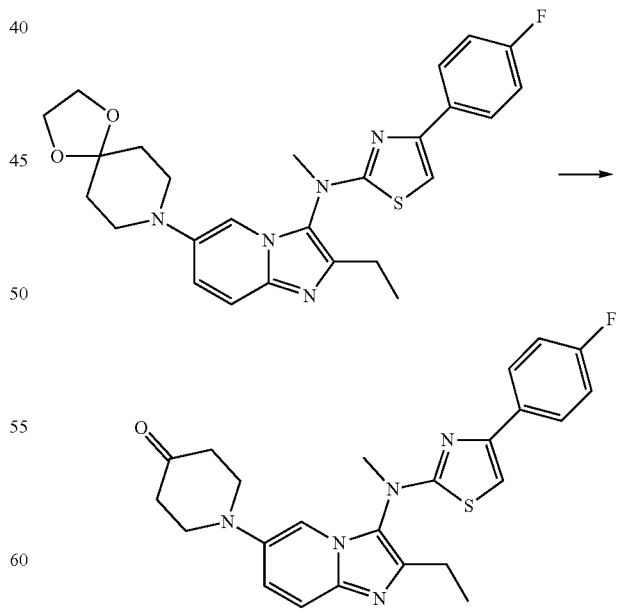

To as solution of Intermediate Gen-10-ap (162 mg, 0.33 mmol, 1 eq.) in a THF/water (1/1) mixture (1 mL) was added HCl (6 N in water, 1 mL). The reaction mixture was stirred at 60° C. overnight. Solvents were evaporated, then aqueous sodium carbonate was added and the mixture was extracted with ethyl acetate. Combined organic layers were washed with water, dried over Na$_2$SO$_4$, filtered and concentrated. The crude product was purified by chromatography on silica gel (elution with heptane/EtOAc: 100/0 to 0/100) to afford Intermediate Gen-10-aq LC-MS: MW (calcd): 449; m/z (obsd): 450 (M+1)

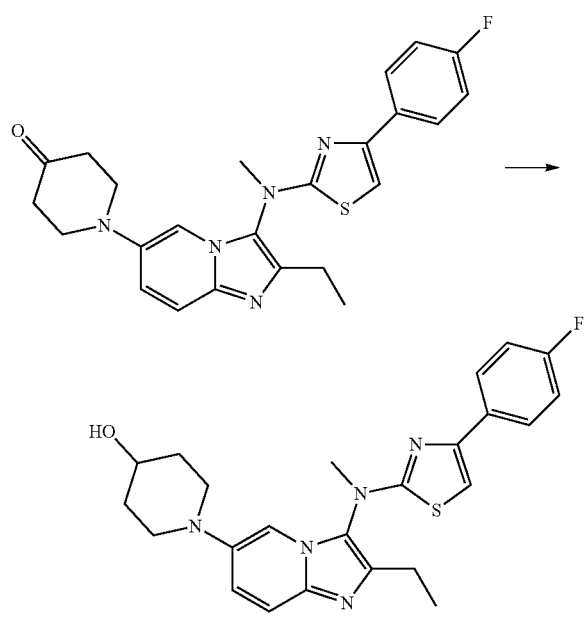

Step iii)

To a solution of Intermediate Gen-10-aq (70 mg, 0.16 mmol, 1 eq.) in ethanol (0.5 mL) stirred at 0° C. was added sodium borohydride (5 mg, 0.12 mmol, 0.8 eq.). The reaction was stirred overnight allowing the temperature to rise to room temperature. Solvent was evaporated, aqueous ammonium chloride was added and the mixture was extracted with ethyl acetate. The combined organic layers were dried over sodium sulfate, filtered and evaporated. Compound 211 was then obtained by purification by preparative LC-MS.

LC-MS: MW (calcd): 451; m/z (obsd): 452 (M+1)

2.38. Compound 222: {2-[4-(2-Ethyl-3-{[4-(4-fluoro-phenyl)-thiazol-2-yl]-methyl-amino}-imidazo[1,2-a]pyridin-6-yl)-piperazin-1-yl]-4,5-dihydro-oxazol-5-yl}-methanol

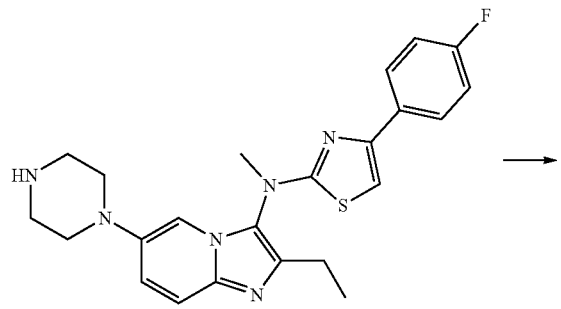

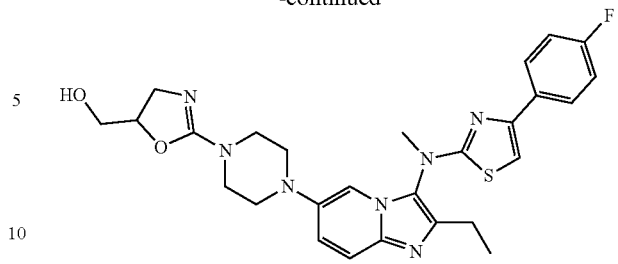

A solution of Intermediate Gen-10-c (300 mg, 0.69 mmol, 1 eq.), 4-(chloromethyl)-1,3-oxazolidin-2-one (103 mg, 0.76 mmol, 1.1 eq.), Cs$_2$CO$_3$ (450 mg, 1.38 mmol, 2 eq.) and NaI (103 mg, 0.69 mmol, 1 eq.) in DMF (3 mL) was stirred at 90° C. overnight. Water was added and the reaction mixture was extracted with EtOAc. The combined organic layers were dried over sodium sulfate, filtered and evaporated. The crude product was purified by chromatography on silica gel (elution with DCM/MeOH: 100/0 to 90/10) and preparative HPLC to give Compound 222.

LC-MS: MW (calcd): 534; m/z (obsd): 535 (M+1)

2.39. Compound 227: Cyclopropyl-[4-(2-ethyl-3-{[4-(4-fluoro-phenyl)-thiazol-2-yl]-methyl-amino}-imidazo[1,2-a]pyridin-6-yl)-piperazin-1 yl]-methasone

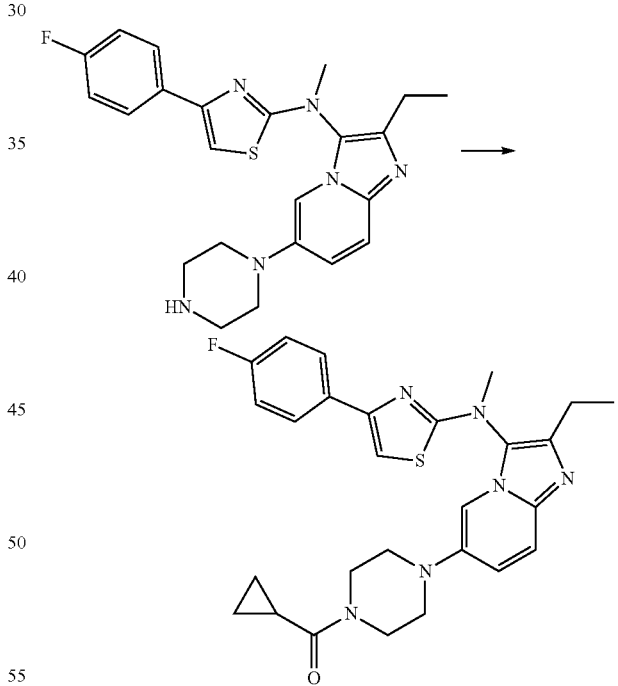

To a solution of Gen-10-e (200 mg, 0.423 mmol, 1 eq.) in DCM (3 mL) were added TEA (294 mg, 2.114 mmol, 5 eq.) followed by the 4-Bromo-butyryl chloride (73 µL, 0.634 mmol, 1.5 eq.). The reaction mixture was stirred at r.t. overnight, then was quenched with water and the aqueous layer was extracted with DCM twice. The organic layer was washed with water, and brine, dried over Na$_2$SO$_4$, filtered and concentrated in vacuo. The residue was purified by chromatography on silica gel (elution with DCM/MeOH: 100/0 to 97/3) to afford the Compound 227.

LC-MS: MW (calcd): 504; m/z MW (obsd): 505 (M+1)

2.40. Compound 229: [6-(1,1-Dioxo-isothiazolidin-2-yl)-2-ethyl-imidazo[1,2-a]pyridin-3-yl]-[4-(4-fluoro-phenyl)-thiazol-2-yl]-methyl-amine

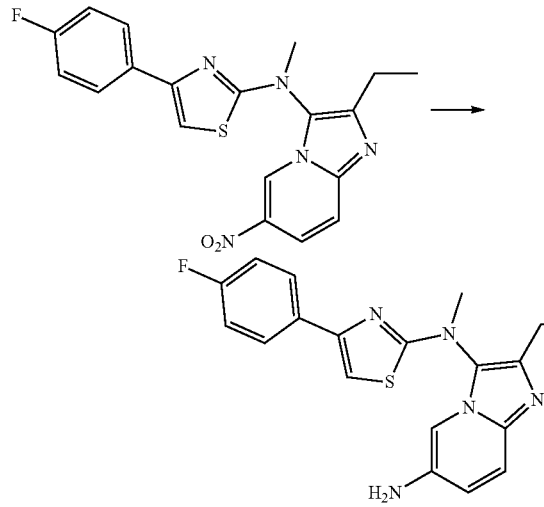

Step i)

To a a solution of ammonium chloride (440 mg, 8.23 mmol, 4 eq.) in water (10 mL) were added a solution of Gen-5-z (818 mg, 2.058 mmol, 1 eq.) in MeOH (5 mL) and THF (5 mL), followed by iron (460 mg, 8.23 mmol, 4 eq.). The reaction mixture was stirred at 70° C. for 3 h. The solvents were evaporated. The residue was resuspended/dissolved in EtOAc/water, this mixture was filtered over Celite prior to separation. The separated aqueous phase was extracted once more with EtOAc, The combined organic phases were dried over Na₂SO₄, filtered and concentrated in vacuo. The residue was purified by chromatography on silica gel (elution with DCM/MeOH: 100/0 to 95/5) to afford Intermediate Gen-5-af.

LC-MS: MW (calcd): 367; m/z MW (obsd): 368 (M+1)

Step ii)

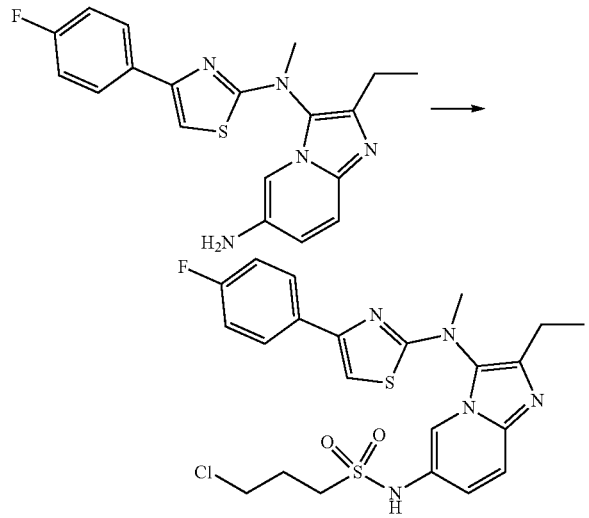

Intermediate Gen-5-af was reacted with 3-chloro-propane-1-sulfonyl chloride using general method F11 to give Intermediate 3-Chloro-propane-1-sulfonic acid (2-ethyl-3-{[4-(4-fluoro-phenyl)-thiazol-2-yl]-methyl-amino}-imidazo[1,2-a]pyridin-6-yl)-amide (Intermediate Gen-10-ao).

LC-MS: MW (calcd): 507 ($^{35}$Cl), 509 ($^{37}$Cl); m/z MW (obsd): 508 ($^{35}$Cl M+1), 510 ($^{37}$Cl M+1)

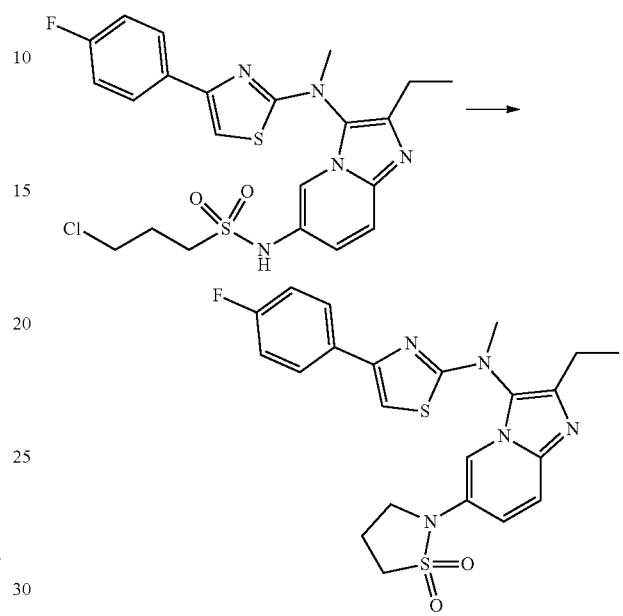

Step iii)

To a solution of the chlorine derivative Gen-10-ao (55 mg, 0.108 mmol, 1 eq.) in DMF (2 mL) was added potassium acetate (32 mg, 0.325 mmol, 3 eq.), the reaction mixture was heated at 90° C. for 1 h, then at 60° C. overnight. After cooling, water and EtOAc were added to the reaction mixture, the aqueous layer was extracted with EtOAc twice. The combined organic layers were washed with water and brine, dried over Na₂SO₄, filtered and concentrated in vacuo. The residue was purified by chromatography on silica gel (elution with DCM/MeOH: 100/0 to 95/5) to afford Compound 229.

LC-MS: MW (calcd): 471; m/z MW (obsd): 472 (M+1)

2.41. Intermediate Gen-13-j: N-[1-(2-Chloro-acetyl)-pyrrolidin-3-yl]-acetamide

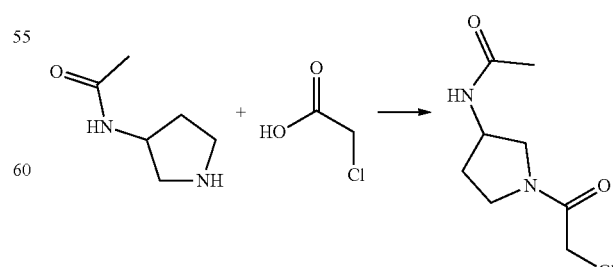

To a solution of chloroacetic acid (0.715 g, 7.56 mmol, 1 eq.) in DCM (15 mL) and THF (12 mL) at r.t. was added EDC.HCl (1.89 g, 9.83 mmol, 1.3 eq.) and HOBt (1.33 g, 9.83 mmol, 1.3 eq.). The reaction mixture was stirred at r.t. for 30 min and then 3-acetamidopyrrolidine (1.26 g, 9.83 mmol, 1.3 eq.) was added. After stirring two days at r.t., the reaction mixture was diluted with water, HCl 1 M, and DCM. The aqueous phase was extracted with DCM five times. The combined organic layers were washed with a saturated NaHCO$_3$ solution, with brine, dried over Na$_2$SO$_4$, filtered and concentrated in vacuo. The resulting crude oil was used as such in the next step.

$^1$H NMR (400 MHz, CDCl$_3$-d) δ ppm 5.33-5.01 (2H, m), 4.60-4.41 (1H, m), 3.79-3.65 (2H, m), 3.63-3.44 (2H, m), 1.97 (3H, d), 1.90-1.80 (2H, m)

2.42. Intermediate Gen-11-d:
2-Bromo-1-(4-fluoro-phenyl)-d$_2$ ethanone

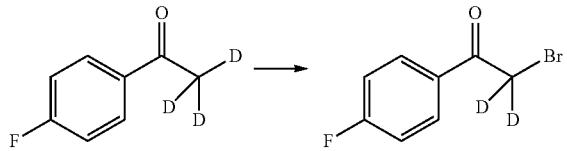 [SMILES: [2H]C([2H])([2H])C(=O)c1ccc(F)cc1 ; [2H]C([2H])(Br)C(=O)c1ccc(F)cc1]

A mixture of starting material (Kolonko & Reich, 2008) (1.04 g, 7.37 mmol, 1 eq.) and Br$_2$ immobilized on resin used in large excess in deuterated chloroform was shaken overnight at r.t. The resin was filtered off, washed with deuterated chloroform. The filtrate was concentrated in vacuo and the crude product was used directly in the next step.

TABLE I

Intermediates used towards the compounds of the invention.

| Int | Structures | Name | Int-Mtd | MW | MS Ms'd |
|---|---|---|---|---|---|
| Gen-1-a | 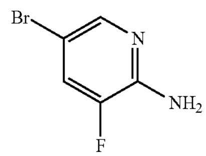 | 2-amino-5-Bromo-3-fluoropyridine | A | 190 ($^{79}$Br), 192 ($^{81}$Br) | 191 ($^{79}$Br M + 1), 193 ($^{81}$Br M + 1) |
| Gen-1-b | 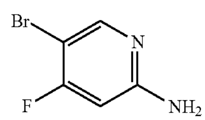 | 5-Bromo-4-fluoro-pyridin-2-ylamine | A | 190 ($^{79}$Br), 192 ($^{81}$Br) | N.A. |
| Gen-2-a | 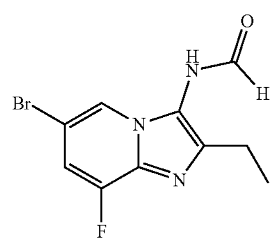 [SMILES: CCc1nc2c(F)cc(Br)cn2c1NC=O] | N-(6-Bromo-2-ethyl-8-fluoro-imidazo[1,2-a]pyridin-3-yl)-formamide | Gen-1-a B1 | 285 ($^{79}$Br), 287 ($^{81}$Br) | 286 ($^{79}$Br M + 1), 288 ($^{81}$Br M + 1) |
| Gen-2-b | 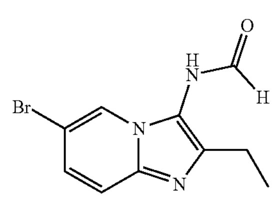 | N-(6-Bromo-2-ethyl-imidazo[1,2-a]pyridin-3-yl)-formamide | B1 | 267 ($^{79}$Br), 269 ($^{81}$Br) | 268 ($^{79}$Br M + 1), 270 ($^{81}$Br M + 1) |
| Gen-2-c | 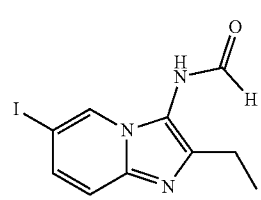 | N-(2-Ethyl-6-iodo-imidazo[1,2-a]pyridin-3-yl)-formamide | B1 | 315 | 316 (M + 1) |

TABLE I-continued

Intermediates used towards the compounds of the invention.

| Int | Structures | Name | Int-Mtd | MW | MS Ms'd |
|---|---|---|---|---|---|
| Gen-2-d | 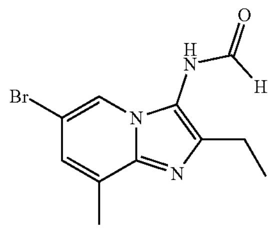 [SMILES: CCc1nc2c(C)cc(Br)cn2c1NC=O] | N-(6-Bromo-2-ethyl-8-methyl-imidazo[1,2-a]pyridin-3-yl)-formamide | B1 or B2 | 281 ($^{79}$Br), 283 ($^{81}$Br) | 284 ($^{81}$Br M + 1) |
| Gen-2-e | 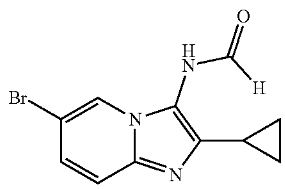 [SMILES: O=CNc1c(C2CC2)nc2ccc(Br)cn12] | N-(6-Bromo-2-cyclopropyl-imidazo[1,2-a]pyridin-3-yl)-formamide | B2 | 279 ($^{79}$Br), 281 ($^{81}$Br) | 280 ($^{79}$Br M + 1), 282 ($^{81}$Br M + 1) |
| Gen-2-f | 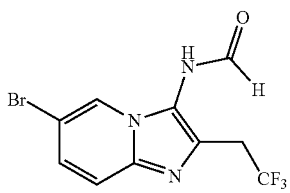 [SMILES: O=CNc1c(CC(F)(F)F)nc2ccc(Br)cn12] | N-[6-Bromo-2-(2,2,2-trifluoro-ethyl)-imidazo[1,2-a]pyridin-3-yl]-formamide | B1 | 321 ($^{79}$Br), 323 ($^{81}$Br) | N.A. |
| Gen-2-g | 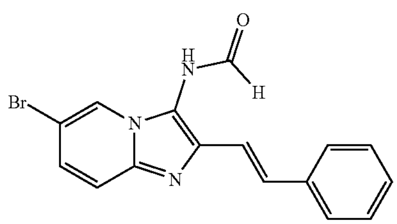 [SMILES: O=CNc1c(/C=C/c2ccccc2)nc2ccc(Br)cn12] | (E)-N-(6-bromo-2-styrylimidazo[1,2-a]pyridin-3-yl)-formamide | B1 | 341 ($^{79}$Br), 343 ($^{81}$Br) | N.A. |
| Gen-2-h | 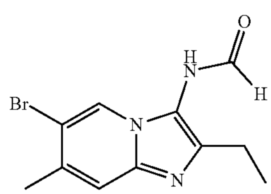 [SMILES: CCc1nc2cc(C)c(Br)cn2c1NC=O] | N-(6-Bromo-2-ethyl-7-methyl-imidazo[1,2-a]pyridin-3-yl)-formamide | B1 | 281 ($^{79}$Br), 283 ($^{81}$Br) | 282 ($^{79}$Br M + 1), 284 ($^{81}$Br M + 1) |
| Gen-2-i | 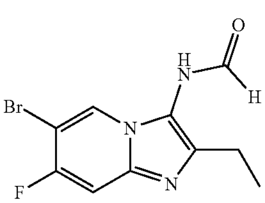 [SMILES: CCc1nc2cc(F)c(Br)cn2c1NC=O] | N-(6-Bromo-2-ethyl-7-fluoro-imidazo[1,2-a]pyridin-3-yl)-formamide | Gen-1-b B1 | 285 ($^{79}$Br), 287 ($^{81}$Br) | 286 ($^{79}$Br M + 1), 288 ($^{81}$Br M + 1) |
| Gen-2-j | 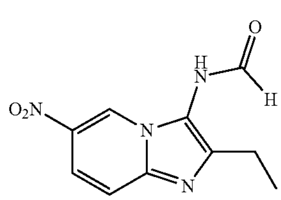 [SMILES: CCc1nc2ccc([N+](=O)[O-])cn2c1NC=O] | N-(2-Ethyl-6-nitro-imidazo[1,2-a]pyridin-3-yl)-formamide | B1 | 234 | 235 (M + 1) |

TABLE I-continued

Intermediates used towards the compounds of the invention.

| Int | Structures | Name | Int-Mtd | MW | MS Ms'd |
|---|---|---|---|---|---|
| Gen-2-k | 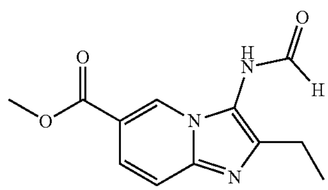 [SMILES: CCc1nc2ccc(C(=O)OC)cn2c1NC=O] | 2-Ethyl-3-formylamino-imidazo[1,2-a]pyridine-6-carboxylic acid methyl ester | B1 | 247 | No LC-MSNMR |
| Gen-3-a | 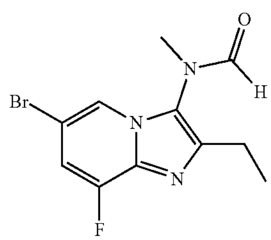 [SMILES: CCc1nc2c(F)cc(Br)cn2c1N(C)C=O] | N-(6-Bromo-2-ethyl-8-fluoro-imidazo[1,2-a]pyridin-3-yl)-N-methyl-formamide | Gen-2-a C2 | 299 ($^{79}$Br), 301 ($^{81}$Br) | 300 ($^{79}$Br M + 1), 302 ($^{81}$Br M + 1) |
| Gen-3-b | 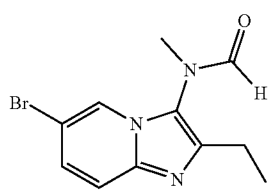 [SMILES: CCc1nc2ccc(Br)cn2c1N(C)C=O] | N-(6-Bromo-2-ethyl-imidazo[1,2-a]pyridin-3-yl)-N-methyl-formamide | Gen-2-b C1 | 281 ($^{79}$Br), 283 ($^{81}$Br) | 282 ($^{79}$Br M + 1), 284 ($^{81}$Br M + 1) |
| Gen-3-c | 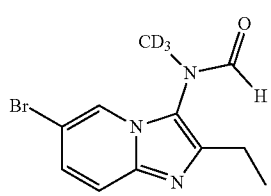 [SMILES: [2H]C([2H])([2H])N(C=O)c1c(CC)nc2ccc(Br)cn12] | N-(6-Bromo-2-ethyl-imidazo[1,2-a]pyridin-3-yl)-N-(d$_3$-methyl)-formamide | Gen-2-b C1 | 284 ($^{79}$Br), 286 ($^{81}$Br) | N.A. |
| Gen-3-d | 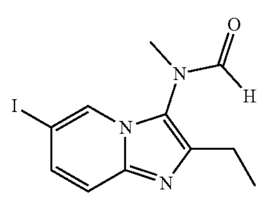 [SMILES: CCc1nc2ccc(I)cn2c1N(C)C=O] | N-(2-Ethyl-6-iodo-imidazo[1,2-a]pyridin-3-yl)-N-methyl-formamide | Gen-2-c C1 | 329 | 330 (M + 1) |
| Gen-3-e | 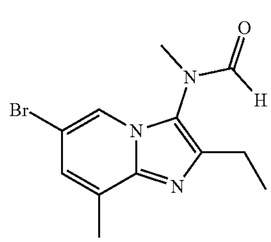 [SMILES: CCc1nc2c(C)cc(Br)cn2c1N(C)C=O] | N-(6-Bromo-2-ethyl-8-methyl-imidazo[1,2-a]pyridin-3-yl)-N-methyl-formamide | Gen-2-d C2 | 295 ($^{79}$Br), 297 ($^{81}$Br) | 296 ($^{79}$Br M + 1), 298 ($^{81}$Br M + 1) |
| Gen-3-f | 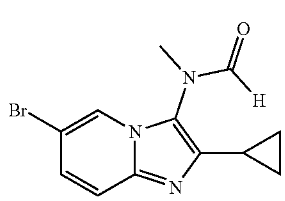 [SMILES: CN(C=O)c1c(C2CC2)nc2ccc(Br)cn12] | N-(6-Bromo-2-cyclopropyl-imidazo[1,2-a]pyridin-3-yl)-N-methyl-formamide | Gen-2-e C1 | 293 ($^{79}$Br), 295 ($^{81}$Br) | 294 ($^{79}$Br M + 1), 296 ($^{81}$Br M + 1) |

TABLE I-continued

Intermediates used towards the compounds of the invention.

| Int | Structures | Name | Int-Mtd | MW | MS Ms'd |
|---|---|---|---|---|---|
| Gen-3-g | 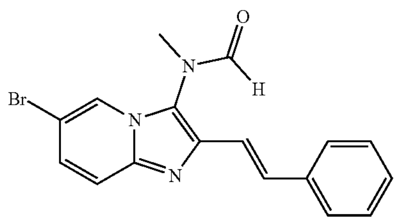 [SMILES: CN(C=O)c1c(/C=C/c2ccccc2)nc2ccc(Br)cn12] | (E)-N-(6-bromo-2-styrylimidazo[1,2-a]pyridin-3-yl)-N-methylformamide | Gen-2-g C1 | 355 ($^{79}$Br), 357 ($^{81}$Br) | 356 ($^{79}$Br M + 1), 358 ($^{81}$Br M + 1) |
| Gen-3-h | 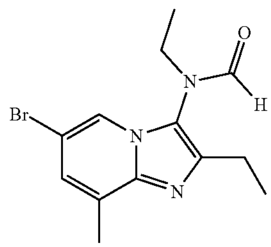 [SMILES: CCc1nc2c(C)cc(Br)cn2c1N(C=O)CC] | N-(6-Bromo-2-ethyl-8-methyl-imidazo[1,2-a]pyridin-3-yl)-N-ethyl-formamide | Gen-2-d C2 | 309 ($^{79}$Br), 311 ($^{81}$Br) | 310 ($^{79}$Br M + 1), 312 ($^{81}$Br M + 1) |
| Gen-3-i | 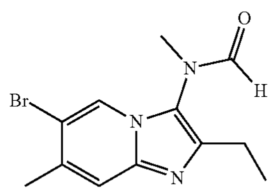 [SMILES: CCc1nc2cc(C)c(Br)cn2c1N(C)C=O] | N-(6-Bromo-2-ethyl-7-methyl-imidazo[1,2-a]pyridin-3-yl)-N-methyl-formamide | Gen-2-h C1 | 295 ($^{79}$Br), 297 ($^{81}$Br) | 296 ($^{79}$Br M + 1), 298 ($^{81}$Br M + 1) |
| Gen-3-j | 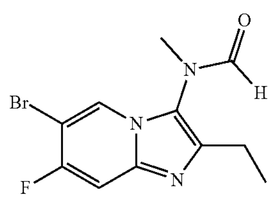 [SMILES: CCc1nc2cc(F)c(Br)cn2c1N(C)C=O] | N-(6-Bromo-2-ethyl-7-fluoro-imidazo[1,2-a]pyridin-3-yl)-N-methyl-formamide | Gen-2-i C1 | 299 ($^{79}$Br), 301 ($^{81}$Br) | 300 ($^{79}$Br M + 1), 302 ($^{81}$Br M + 1) |
| Gen-3-k | 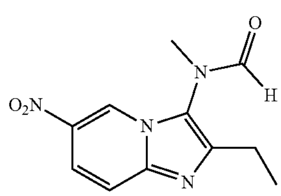 [SMILES: CCc1nc2ccc([N+](=O)[O-])cn2c1N(C)C=O] | N-(2-Ethyl-6-nitro-imidazo[1,2-a]pyridin-3-yl)-N-methyl-formamide | Gen-2-j C2 | 248 | 249 (M + 1) |
| Gen-3-l | 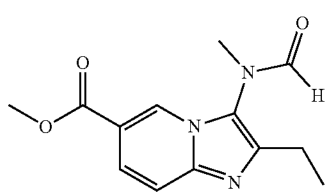 [SMILES: CCc1nc2ccc(C(=O)OC)cn2c1N(C)C=O] | 2-Ethyl-3-(formyl-methyl-amino)-imidazo[1,2-a]pyridine-6-carboxylic acid methyl ester | Gen-2-k C1 | 261 | 262 (M + 1 |
| Gen-4-a | 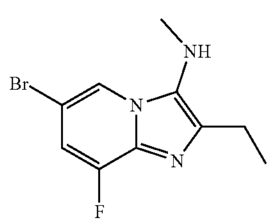 | (6-Bromo-2-ethyl-8-fluoro-imidazo[1,2-a]pyridin-3-yl)-methyl-amine | Gen-3-a D1 | 271 ($^{79}$Br), 273 ($^{81}$Br) | 272 ($^{79}$Br M + 1), 274 ($^{81}$Br M + 1) |

TABLE I-continued

Intermediates used towards the compounds of the invention.

| Int | Structures | Name | Int-Mtd | MW | MS Ms'd |
|---|---|---|---|---|---|
| Gen-4-b | 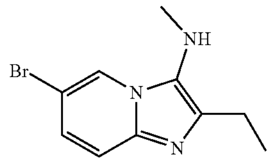 | (6-Bromo-2-ethyl-imidazo[1,2-a]pyridin-3-yl)-methyl-amine | Gen-3-b D1 | 253 ($^{79}$Br), 255 ($^{81}$Br) | 254 ($^{79}$Br M + 1), 256 ($^{81}$Br M + 1) |
| Gen-4-c | 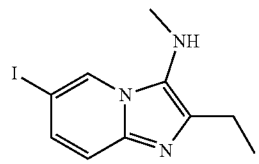 | (2-Ethyl-6-iodo-imidazo[1,2-a]pyridin-3-yl)-methyl-amine | Gen-3-d D1 | 301 | 302 (M + 1) |
| Gen-4-d | 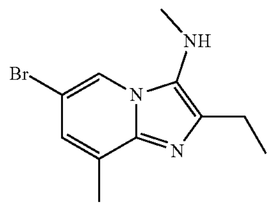 | (6-Bromo-2-ethyl-8-methyl-imidazo[1,2-a]pyridin-3-yl)-methyl-amine | Gen-3-e D1 | 267 ($^{79}$Br), 269 ($^{81}$Br) | 268 ($^{79}$Br M + 1), 270 ($^{81}$Br M + 1) |
| Gen-4-e | 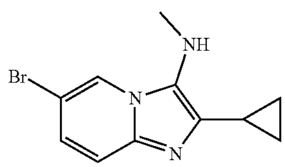 | (6-Bromo-2-cyclopropyl-imidazo[1,2-a]pyridin-3-yl)-methyl-amine | Gen-3-f D1 | 265 ($^{79}$Br), 267 ($^{81}$Br) | 266 ($^{79}$Br M + 1), 268 ($^{81}$Br M + 1) |
| Gen-4-f | 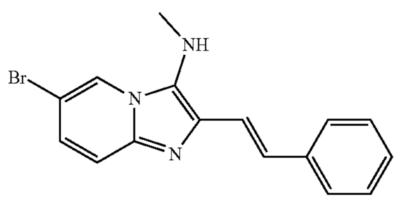 [SMILES: CNc1c(/C=C/c2ccccc2)nc2ccc(Br)cn12] | (E)-6-bromo-N-methyl-2-styrylimidazo[1,2-a]pyridin-3-amine | Gen-3-g D1 | 327 ($^{79}$Br), 329($^{81}$Br) | 328 ($^{79}$Br M + 1), 330 ($^{81}$Br M + 1) |
| Gen-4-g | 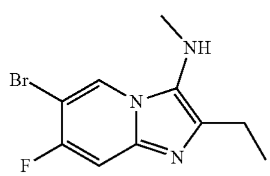 | (6-Bromo-2-ethyl-7-fluoro-imidazo[1,2-a]pyridin-3-yl)-methyl-amine | Gen-3-j D2 | 271 ($^{79}$Br), 273 ($^{81}$Br) | N.A. |
| Gen-4-h | 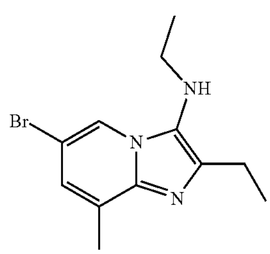 [SMILES: CCNc1c(CC)nc2c(C)cc(Br)cn12] | (6-Bromo-2-ethyl-8-methyl-imidazo[1,2-a]pyridin-3-yl)-ethyl-amine | Gen-3-h D1 | 281 ($^{79}$Br), 283 ($^{81}$Br) | 282 ($^{79}$Br M + 1), 284 ($^{81}$Br M + 1) |
| Gen-4-i | 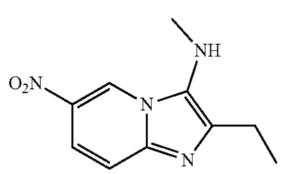 [SMILES: CCc1nc2ccc([N+](=O)[O-])cn2c1NC] | (2-Ethyl-6-nitro-imidazo[1,2-a]pyridin-3-yl)-methyl-amine | Gen-3-k D1 | 220 | 221 (M + 1) |

TABLE I-continued

Intermediates used towards the compounds of the invention.

| Int | Structures | Name | Int-Mtd | MW | MS Ms'd |
|---|---|---|---|---|---|
| Gen-4-j | 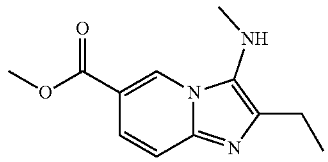 [SMILES: CCc1nc2ccc(C(=O)OC)cn2c1NC] | 2-Ethyl-3-methylamino-imidazo[1,2-a]pyridine-6-carboxylic acid methyl ester | Gen-3-1 D1 | 233 | 234 (M + 1) |
| Gen-5-a | 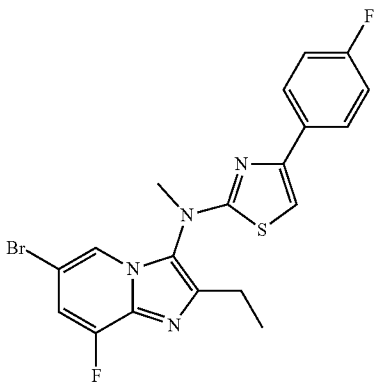 [SMILES: CCc1nc2c(F)cc(Br)cn2c1N(C)c1nc(-c2ccc(F)cc2)cs1] | (6-Bromo-2-ethyl-8-fluoro-imidazo[1,2-a]pyridin-3-yl)-[4-(4-fluoro-phenyl)-thiazol-2-yl]-methyl-amine | Gen-4-a E1 | 448 ($^{79}$Br), 450 ($^{81}$Br) | 449 ($^{79}$Br M + 1), 451 ($^{81}$Br M + 1) |
| Gen-5-b | 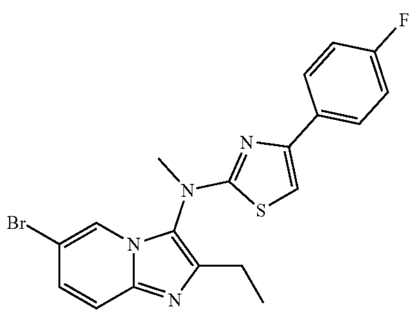 [SMILES: CCc1nc2ccc(Br)cn2c1N(C)c1nc(-c2ccc(F)cc2)cs1] | (6-Bromo-2-ethyl-imidazo[1,2-a]pyridin-3-yl)-[4-(4-fluoro-phenyl)-thiazol-2-yl]-methyl-amine | Gen-4-b E1 | 430 ($^{79}$Br), 431 ($^{81}$Br) | 431 ($^{79}$Br M + 1), 433 ($^{81}$Br M + 1) |
| Gen-5-c | 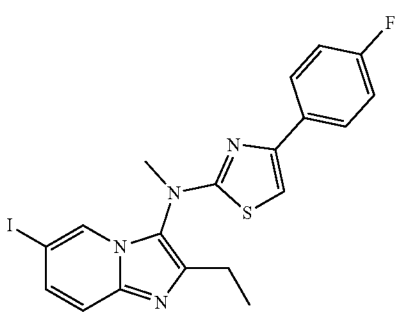 [SMILES: CCc1nc2ccc(I)cn2c1N(C)c1nc(-c2ccc(F)cc2)cs1] | (2-Ethyl-6-iodo-imidazo[1,2-a]pyridin-3-yl)-[4-(4-fluoro-phenyl)-thiazol-2-yl]-methyl-amine | Gen-4-c E1 | 478 | 479 (M + 1) |
| Gen-5d | 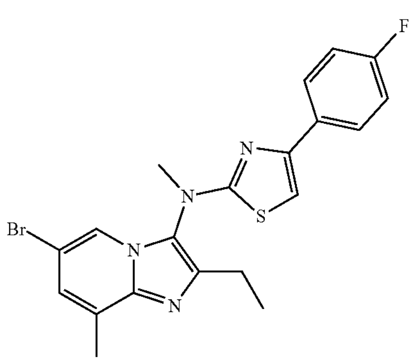 [SMILES: CCc1nc2c(C)cc(Br)cn2c1N(C)c1nc(-c2ccc(F)cc2)cs1] | (6-Bromo-2-ethyl-8-methyl-imidazo[1,2-a]pyridin-3-yl)-[4-(4-fluoro-phenyl)-thiazol-2-yl]-methyl-amine | Gen-4-d E1 | 444 ($^{79}$Br), 446 ($^{81}$Br) | 445 ($^{79}$Br M + 1), 447 ($^{81}$Br M + 1) |

TABLE I-continued

Intermediates used towards the compounds of the invention.

| Int | Structures | Name | Int-Mtd | MW | MS Ms'd |
|---|---|---|---|---|---|
| Gen-5-e | 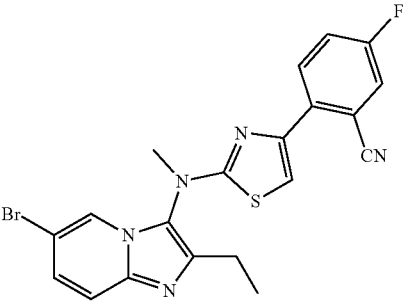 [SMILES: CCc1nc2ccc(Br)cn2c1N(C)c1nc(-c2ccc(F)cc2C#N)cs1] | 2-{2-[(6-Bromo-2-ethyl-imidazo[1,2-a]pyridin-3-yl)-methyl-amino]-thiazol-4-yl}-5-fluoro-benzonitrile | Gen-4-b E1 | 455 ($^{79}$Br), 457 ($^{81}$Br) | 456 ($^{79}$Br M + 1), 458 ($^{81}$Br M + 1) |
| Gen-5-f | 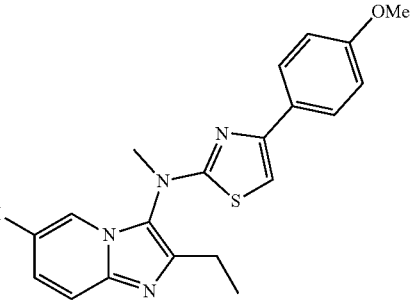 | (2-Ethyl-6-iodo-imidazo[1,2-a]pyridin-3-yl)-[4-(4-methoxy-phenyl)-thiazol-2-yl]-methyl-amine | Gen-4-c E1 | 490 | 491 (M + 1) |
| Gen-5-g | 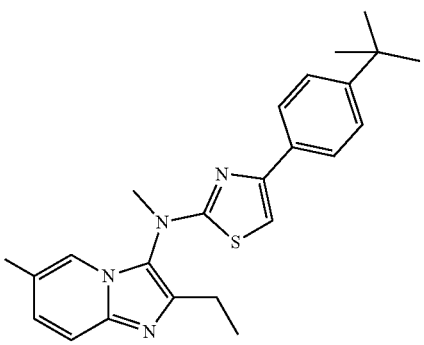 | [4-(4-tert-Butyl-phenyl)-thiazol-2-yl]-(2-ethyl-6-iodo-imidazo[1,2-a]pyridin-3-yl)-methyl-amine | Gen-4-c E1 | 516 | 517 (M + 1) |
| Gen-5-h | 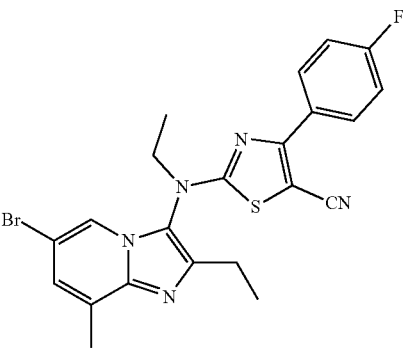 [SMILES: CCc1nc2c(C)cc(Br)cn2c1N(CC)c1nc(-c2ccc(F)cc2)c(C#N)s1] | 2-[(6-Bromo-2-ethyl-8-methyl-imidazo[1,2-a]pyridin-3-yl)-ethyl-amino]-4-(4-fluoro-phenyl)-thiazole-5-carbonitrile | Gen-4-h E2 | 483 ($^{79}$Br), 485 ($^{81}$Br) | 484 ($^{79}$Br M + 1), 486 ($^{81}$Br M + 1) |

TABLE I-continued

Intermediates used towards the compounds of the invention.

| Int | Structures | Name | Int-Mtd | MW | MS Ms'd |
|---|---|---|---|---|---|
| Gen-5-i | 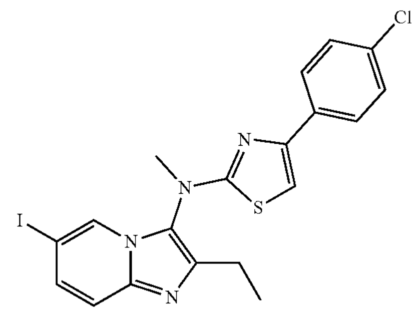 [SMILES: CCc1nc2ccc(I)cn2c1N(C)c1nc(-c2ccc(Cl)cc2)cs1] | 4-(4-Chloro-phenyl)-thiazol-2-yl]-(2-ethyl-6-iodo-imidazo[1,2-a]pyridin-3-yl)-methyl-amine | Gen-4-c E1 | 494 ($^{35}$Cl), 496 ($^{37}$Cl) | 495 ($^{35}$Cl M + 1) 497 ($^{37}$Cl M + 1) |
| Gen-5-j | 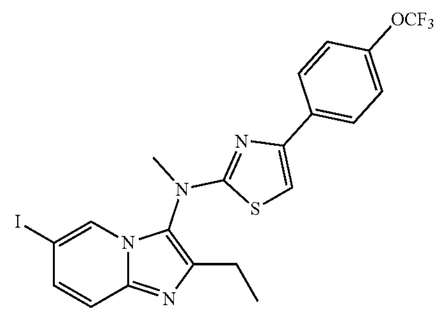 [SMILES: CCc1nc2ccc(I)cn2c1N(C)c1nc(-c2ccc(OC(F)(F)F)cc2)cs1] | (2-Ethyl-6-iodo-imidazo[1,2-a]pyridin-3-yl)-methyl-[4-(4-trifluoromethoxy-phenyl)-thiazol-2-yl]-amine | Gen-4-c E1 | 544 | 545 (M + 1) |
| Gen-5-k | 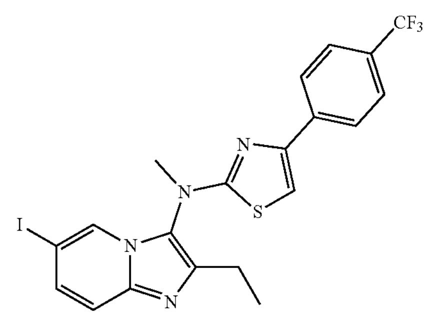 [SMILES: CCc1nc2ccc(I)cn2c1N(C)c1nc(-c2ccc(C(F)(F)F)cc2)cs1] | (2-Ethyl-6-iodo-imidazo[1,2-a]pyridin-3-yl)-methyl-[4-(4-trifluoromethyl-phenyl)-thiazol-2-yl]-amine | Gen-4-c E1 | 528 | 529 (M + 1) |
| Gen-5-l | 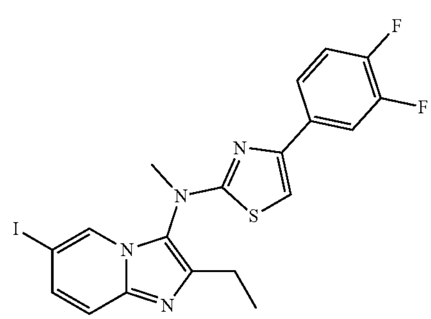 [SMILES: CCc1nc2ccc(I)cn2c1N(C)c1nc(-c2ccc(F)c(F)c2)cs1] | [4-(3,4-Difluoro-phenyl)-thiazol-2-yl]-(2-ethyl-6-iodo-imidazo[1,2-a]pyridin-3-yl)-methyl-amine | Gen-4-c E1 | 496 | 497 (M + 1) |
| Gen-5-m | 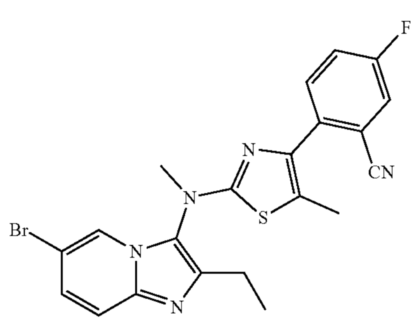 [SMILES: CCc1nc2ccc(Br)cn2c1N(C)c1nc(-c2ccc(F)cc2C#N)c(C)s1] | 2-{2-[(6-Bromo-2-ethyl-imidazo[1,2-a]pyridin-3-yl)-methyl-amino]-5-methyl-thiazol-4-yl}-5-fluoro-benzonitrile | Gen-4-b E1 | 469 ($^{79}$Br), 471 ($^{81}$Br) | 470 ($^{79}$Br M + 1), 472 ($^{81}$Br M + 1) |

TABLE I-continued

Intermediates used towards the compounds of the invention.

| Int | Structures | Name | Int-Mtd | MW | MS Ms'd |
|---|---|---|---|---|---|
| Gen-5-n | 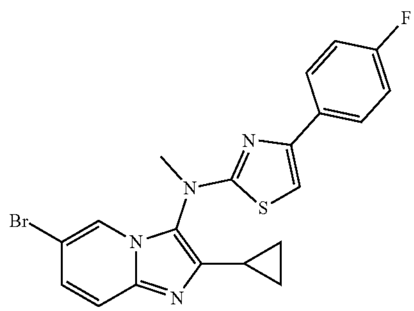 [SMILES: CN(c1nc(-c2ccc(F)cc2)cs1)c1c(C2CC2)nc2ccc(Br)cn12] | (6-Bromo-2-cyclopropyl-imidazo[1,2-a]pyridin-3-yl)-[4-(4-fluoro-phenyl)-thiazol-2-yl]-methyl-amine | Gen-4-e E1 | 442 ($^{79}$Br), 444 ($^{81}$Br) | 443 ($^{79}$Br M + 1), 445 ($^{81}$Br M + 1) |
| Gen-5-o | 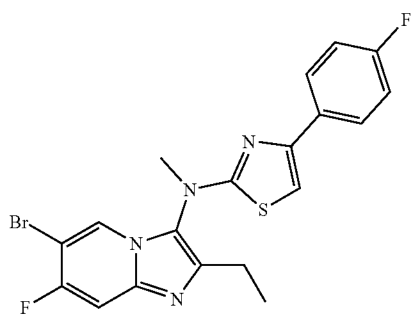 [SMILES: CCc1nc2cc(F)c(Br)cn2c1N(C)c1nc(-c2ccc(F)cc2)cs1] | (6-Bromo-2-ethyl-7-fluoro-imidazo[1,2-a]pyridin-3-yl)-[4-(4-fluoro-phenyl)-thiazol-2-yl]-methyl-amine | Gen-4-g E1 | 448 ($^{79}$Br), 450 ($^{81}$Br) | 449 ($^{79}$Br M + 1), 451 ($^{81}$Br M + 1) |
| Gen-5-p | 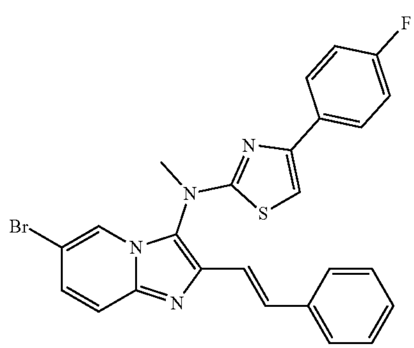 [SMILES: CN(c1nc(-c2ccc(F)cc2)cs1)c1c(/C=C/c2ccccc2)nc2ccc(Br)cn12] | (E)-N-(6-bromo-2-styrylimidazo[1,2-a]pyridin-3-yl)-4-(4-fluorophenyl)-N-methylthiazol-2-amine | Gen-4-f E1 | 504 ($^{79}$Br), 506 ($^{81}$Br) | 505 ($^{79}$Br M + 1), 507 ($^{81}$Br M + 1) |
| Gen-5q | 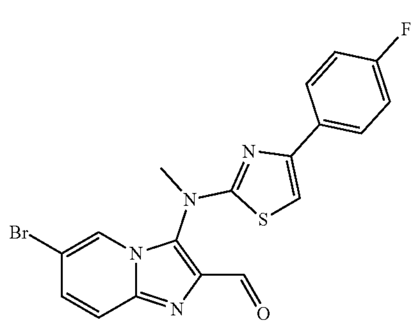 [SMILES: CN(c1nc(-c2ccc(F)cc2)cs1)c1c(C=O)nc2ccc(Br)cn12] | 6-bromo-3-((4-(4-fluorophenyl)thiazol-2-yl)(methyl)amino)imidazo[1,2-a]pyridine-2-carbaldehyde | Gen-5-ab See cpd 174 | 430 ($^{79}$Br), 432 ($^{81}$Br) | 431 ($^{79}$Br M + 1), 433 ($^{81}$Br M + 1) |

TABLE I-continued

Intermediates used towards the compounds of the invention.

| Int | Structures | Name | Int-Mtd | MW | MS Ms'd |
|---|---|---|---|---|---|
| Gen-5-r | 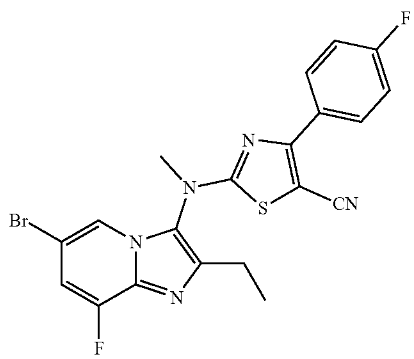 [SMILES: CCc1nc2c(F)cc(Br)cn2c1N(C)c1nc(-c2ccc(F)cc2)c(C#N)s1] | 2-[(6-Bromo-2-ethyl-8-fluoro-imidazo[1,2-a]pyridin-3-yl)-methyl-amino]-4-(4-fluoro-phenyl)-thiazole-5-carbonitrile | Gen-4-a E2 | 473 ($^{79}$Br), 475 ($^{81}$Br) | 474 ($^{79}$Br M + 1), 476 ($^{81}$Br M + 1) |
| Gen-5-s | 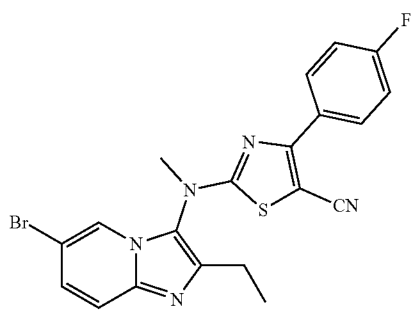 [SMILES: CCc1nc2ccc(Br)cn2c1N(C)c1nc(-c2ccc(F)cc2)c(C#N)s1] | 2-[(6-Bromo-2-ethyl-imidazo[1,2-a]pyridin-3-yl)-methyl-amino]-4-(4-fluoro-phenyl)-thiazole-5-carbonitrile | Gen-4-b E2 | 456 ($^{79}$Br), 457 ($^{81}$Br) | 457 ($^{79}$Br M + 1), 459 ($^{81}$Br M + 1) |
| Gen-5-t | 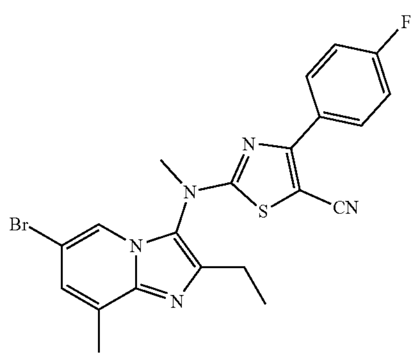 [SMILES: CCc1nc2c(C)cc(Br)cn2c1N(C)c1nc(-c2ccc(F)cc2)c(C#N)s1] | 2-[(6-Bromo-2-ethyl-8-methyl-imidazo[1,2-a]pyridin-3-yl)-methyl-amino]-4-(4-fluoro-phenyl)-thiazole-5-carbonitrile | Gen-4-d E2 | 469 ($^{79}$Br), 471 ($^{81}$Br) | 470 ($^{79}$Br M + 1), 472 ($^{81}$Br M + 1) |
| Gen-5-u | 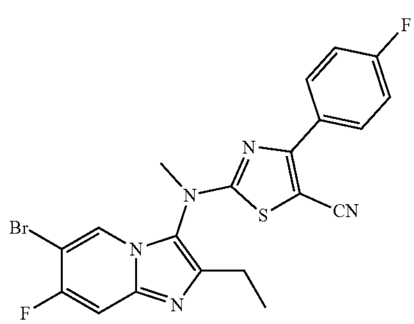 [SMILES: CCc1nc2cc(F)c(Br)cn2c1N(C)c1nc(-c2ccc(F)cc2)c(C#N)s1] | 2-[(6-Bromo-2-ethyl-7-fluoro-imidazo[1,2-a]pyridin-3-yl)-methyl-amino]-4-(4-fluoro-phenyl)-thiazole-5-carbonitrile | Gen-4-g E2 | 473 ($^{79}$Br), 475 ($^{81}$Br) | 474 ($^{79}$Br M + 1), 476 ($^{81}$Br M + 1) |

TABLE I-continued

Intermediates used towards the compounds of the invention.

| Int | Structures | Name | Int-Mtd | MW | MS Ms'd |
|---|---|---|---|---|---|
| Gen-5-v | 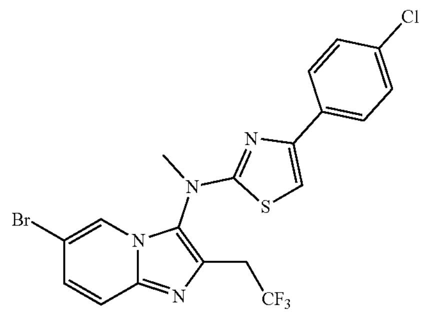 [SMILES: CN(c1nc(-c2ccc(Cl)cc2)cs1)c1c(CC(F)(F)F)nc2ccc(Br)cn12] | [6-Bromo-2-(2,2,2-trifluoro-ethyl)-imidazo[1,2-a]pyridin-3-yl]-[4-(4-chloro-phenyl)-thiazol-2-yl]-methyl-amine | Gen-7-b C1 | 499 ($^{79}$Br $^{35}$Cl), 501 $^{35}$Cl, $^{79}$Br $^{37}$Cl), 503 ($^{81}$Br $^{37}$Cl) | 500 ($^{79}$Br $^{35}$Cl M + 1), 502 ($^{81}$Br $^{35}$Cl, $^{79}$Br $^{37}$Cl M + 1), 504 ($^{81}$Br $^{37}$Cl M + 1) |
| Gen-5-w | 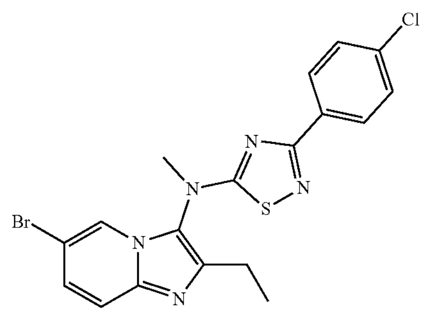 [SMILES: CCc1nc2ccc(Br)cn2c1N(C)c1nc(-c2ccc(Cl)cc2)ns1] | (6-Bromo-2-ethyl-imidazo[1,2-a]pyridin-3-yl)-[3-(4-chloro-phenyl)-[1,2,4]thiadiazol-5-yl]-methyl-amine | Gen-7-a C1 | 447 ($^{79}$Br $^{35}$Cl), 449 ($^{81}$Br $^{35}$Cl, $^{79}$Br $^{37}$Cl), 451 ($^{81}$Br $^{37}$Cl) | 448 ($^{79}$Br $^{35}$Cl M + 1), 450 ($^{81}$Br $^{35}$Cl, $^{79}$Br $^{37}$Cl M + 1), 452 ($^{81}$Br $^{37}$Cl M + 1) |
| Gen-5-x | 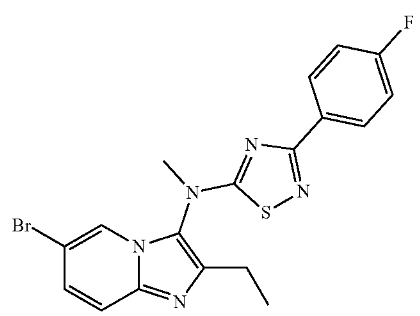 [SMILES: CCc1nc2ccc(Br)cn2c1N(C)c1nc(-c2ccc(F)cc2)ns1] | (6-Bromo-2-ethyl-imidazo[1,2-a]pyridin-3-yl)-[3-(4-fluoro-phenyl)-[1,2,4]thiadiazol-5-yl]-methyl-amine | Gen-7-c C1 | 431 ($^{79}$Br), 433 ($^{81}$Br) | 432 ($^{79}$Br M + 1), 434 ($^{81}$Br M + 1) |
| Gen-5-y | 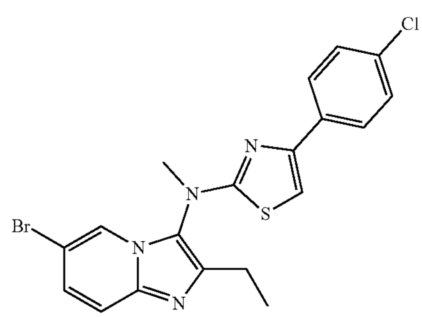 [SMILES: CCc1nc2ccc(Br)cn2c1N(C)c1nc(-c2ccc(Cl)cc2)cs1] | (6-Bromo-2-ethyl-imidazo[1,2-a]pyridin-3-yl)-[4-(4-chloro-phenyl)-thiazol-2-yl]-methyl-amine | Gen-4-b E1 | 446 ($^{79}$Br $^{35}$Cl), 448 ($^{81}$Br $^{35}$Cl, $^{79}$Br $^{37}$Cl), 450 ($^{81}$Br $^{37}$Cl) | 447 ($^{79}$Br $^{35}$Cl M + 1), 449 ($^{81}$Br $^{35}$Cl, $^{79}$Br $^{37}$Cl M + 1), 451 ($^{81}$Br $^{37}$Cl M + 1) |

TABLE I-continued

Intermediates used towards the compounds of the invention.

| Int | Structures | Name | Int-Mtd | MW | MS Ms'd |
|---|---|---|---|---|---|
| Gen-5-z | 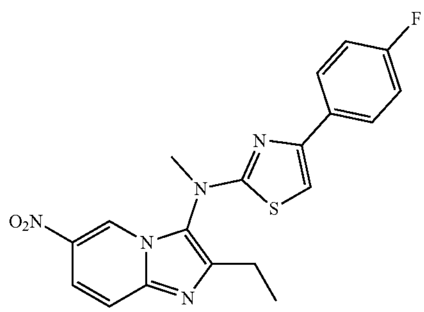 [SMILES: CCc1nc2ccc([N+](=O)[O-])cn2c1N(C)c1nc(-c2ccc(F)cc2)cs1] | (2-Ethyl-6-nitro-imidazo[1,2-a]pyridin-3-yl)-[4-(4-fluoro-phenyl)-thiazol-2-yl]-methyl-amine | Gen-4-i E1 | 397 | 398 (M + 1) |
| Gen-5-aa | 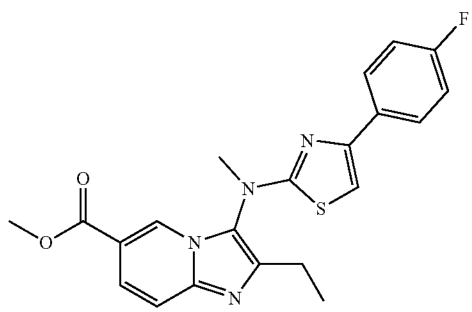 [SMILES: CCc1nc2ccc(C(=O)OC)cn2c1N(C)c1nc(-c2ccc(F)cc2)cs1] | 2-Ethyl-3-{[4-(4-fluoro-phenyl)-thiazol-2-yl]-methyl-amino}-imidazo[1,2-a]pyridine-6-carboxylic acid methyl ester | Gen-4-j E1 | 410 | 411 (M + 1) |
| Gen-5-ab | 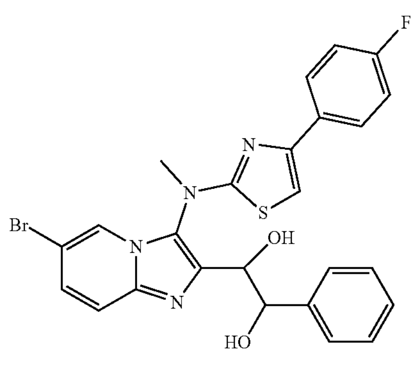 [SMILES: CN(c1nc(-c2ccc(F)cc2)cs1)c1c(C(O)C(O)c2ccccc2)nc2ccc(Br)cn12] | 1-(6-Bromo-3-{[4-(4-fluoro-phenyl)-thiazol-2-yl]-methyl-amino}-imidazo[1,2-a]pyridin-2-yl)-2-phenyl-ethane-1,2-diol | Gen-5-p see Cpd 174 | 538 ($^{79}$Br), 540 ($^{81}$Br) | 539 ($^{79}$Br M + 1), 541 ($^{81}$Br M + 1) |
| Gen-5-ac | 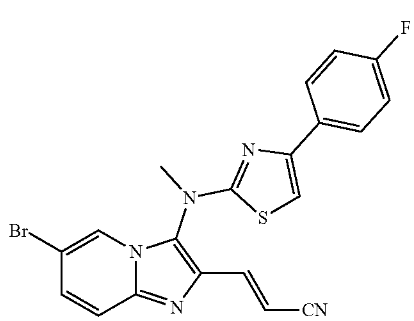 [SMILES: CN(c1nc(-c2ccc(F)cc2)cs1)c1c(/C=C/C#N)nc2ccc(Br)cn12] | 3-(6-Bromo-3-{[4-(4-fluoro-phenyl)-thiazol-2-yl]-methyl-amino}-imidazo[1,2-a]pyridin-2-yl)-acrylonitrile | Gen-5-q see Cpd 174 | 453 ($^{79}$Br), 455 ($^{81}$Br) | 454 ($^{79}$Br M + 1), 456 ($^{81}$Br M + 1) |

TABLE I-continued

Intermediates used towards the compounds of the invention.

| Int | Structures | Name | Int-Mtd | MW | MS Ms'd |
|---|---|---|---|---|---|
| Gen-5-ad | 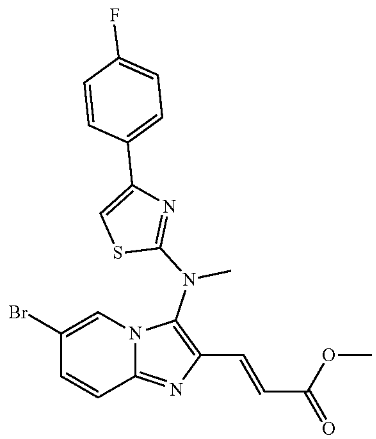 [SMILES: COC(=O)/C=C/c1nc2ccc(Br)cn2c1N(C)c1nc(-c2ccc(F)cc2)cs1] | 3-(6-Bromo-3-{[4-(4-fluoro-phenyl)-thiazol-2-yl]-methyl-amino}-imidazo[1,2-a]pyridin-2-yl)-acrylic acid methyl ester | Gen-5-q see Cpd 176 | 486 ($^{79}$Br), 488 ($^{81}$Br) | 487 ($^{79}$Br M + 1), 489 ($^{81}$Br M + 1) |
| Gen-5-ae | 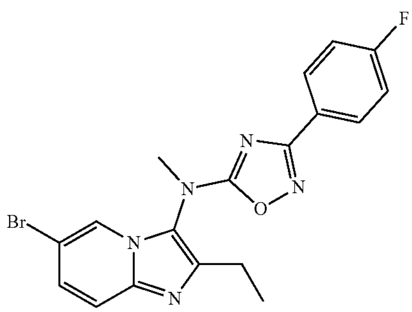 [SMILES: CCc1nc2ccc(Br)cn2c1N(C)c1nc(-c2ccc(F)cc2)no1] | (6-Bromo-2-ethyl-imidazo[1,2-a]pyridin-3-yl)[3-(4-fluoro-phenyl)-[1,2,4]oxadiazol-5-yl]-methyl-amine | Gen-4-b E3 | 415 ($^{79}$Br), 417 ($^{81}$Br) | 416 ($^{79}$Br M + 1), 418 ($^{81}$Br M + 1) |
| Gen-5-af | 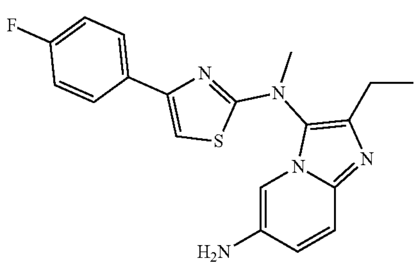 [SMILES: CCc1nc2ccc(N)cn2c1N(C)c1nc(-c2ccc(F)cc2)cs1] | 2-Ethyl-N-[4-(4-fluoro-phenyl)-thiazol-2-yl]-N-methyl-imidazo[1,2-a]pyridine-3,6-diamine | Gen-5-z See Cpd 229 | 367 | 368 (M + 1) |
| Gen-5-ag | 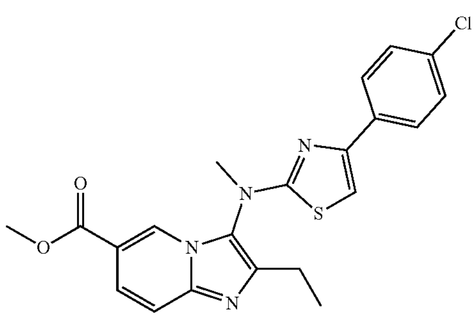 [SMILES: CCc1nc2ccc(C(=O)OC)cn2c1N(C)c1nc(-c2ccc(Cl)cc2)cs1] | 2-Ethyl-3-{[4-(4-chloro-phenyl)-thiazol-2-yl]-methyl-amino}-imidazo[1,2-a]pyridine-6-carboxylic acid methyl ester | Gen-4-j E1 | 426 ($^{35}$Cl), 428 ($^{37}$Cl) | 427 ($^{35}$Cl M + 1), 429 ($^{37}$Cl M + 1) |
| Gen-6-a | 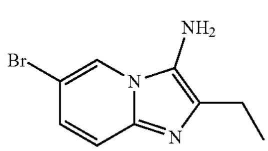 | 6-Bromo-2-ethyl-imidazo[1,2-a]pyridin-3-ylamine | Gen-2-b D1 | 239 ($^{79}$Br), 241 ($^{81}$Br) | 240 ($^{79}$Br M + 1), 242 ($^{81}$Br M + 1) |

TABLE I-continued

Intermediates used towards the compounds of the invention.

| Int | Structures | Name | Int-Mtd | MW | MS Ms'd |
|---|---|---|---|---|---|
| Gen-6-b | 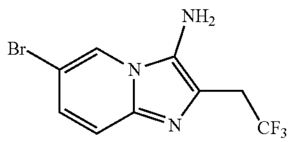 | 6-Bromo-2-(2,2,2-trifluoro-ethyl)-imidazo[1,2-a]pyridin-3-ylamine | Gen-2-f D1 | 293 ($^{79}$Br), 295 ($^{81}$Br) | 294 ($^{79}$Br M + 1), 295 ($^{81}$Br M + 1) |
| Gen-7-a | 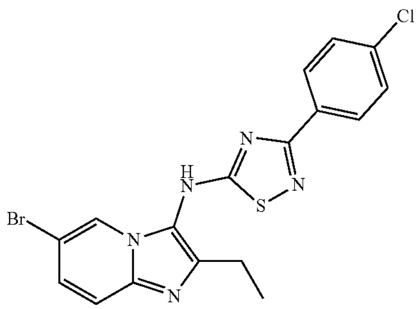 [SMILES: CCc1nc2ccc(Br)cn2c1Nc1nc(-c2ccc(Cl)cc2)ns1] | (6-Bromo-2-ethyl-imidazo[1,2-a]pyridin-3-yl)-[3-(4-chloro-phenyl)-[1,2,4]thiadiazol-5-yl]-amine | Gen-6-a H1 | 433 ($^{79}$Br $^{35}$Cl), 435 ($^{81}$Br $^{35}$Cl, $^{79}$Br $^{37}$Cl), 437 ($^{81}$Br $^{37}$Cl) | 434 ($^{79}$Br $^{35}$Cl M + 1), 436 ($^{81}$Br $^{35}$Cl, $^{79}$Br $^{37}$Cl M + 1), 438 ($^{81}$Br $^{37}$Cl M + 1) |
| Gen-7-b | 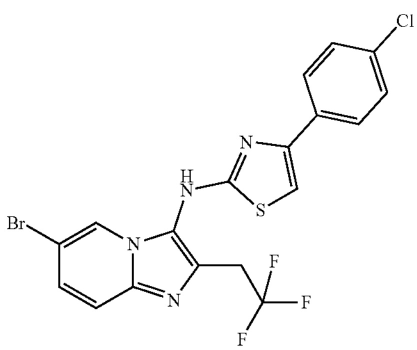 [SMILES: FC(F)(F)Cc1nc2ccc(Br)cn2c1Nc1nc(-c2ccc(Cl)cc2)cs1] | [6-Bromo-2-(2,2,2-trifluoro-ethyl)-imidazo[1,2-a]pyridin-3-yl]-[4-(4-chloro-phenyl)-thiazol-2-yl]-amine | Gen-6-b E1 | 486 ($^{79}$Br $^{35}$Cl), 488 ($^{81}$Br $^{35}$Cl, $^{79}$Br $^{37}$Cl), 490 ($^{81}$Br $^{37}$Cl) | 487 ($^{79}$Br $^{35}$Cl M + 1), 489 ($^{81}$Br $^{35}$Cl, $^{79}$Br $^{37}$Cl M + 1), 491 ($^{81}$Br $^{37}$Cl M + 1) |
| Gen-7-c | 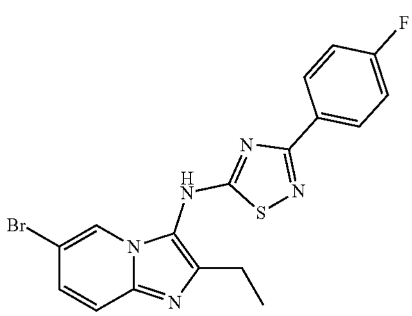 [SMILES: CCc1nc2ccc(Br)cn2c1Nc1nc(-c2ccc(F)cc2)ns1] | (6-Bromo-2-ethyl-imidazo[1,2-a]pyridin-3-yl)-[3-(4-fluoro-phenyl)-[1,2,4]thiadiazol-5-yl]-amine | Gen-6-a H1 | 417 ($^{79}$Br), 419 ($^{81}$Br) | 418 ($^{79}$Br M + 1), 420 ($^{81}$Br M + 1) |
| Gen-8-a | 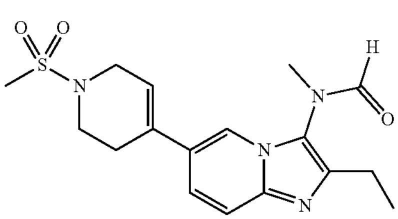 [SMILES: CCc1nc2ccc(C3=CCN(S(C)(=O)=O)CC3)cn2c1N(C)C=O] | N-[2-Ethyl-6-(1-methanesulfonyl-1,2,3,6-tetrahydro-pyridin-4-yl)-imidazo[1,2-a]pyridin-3-yl]-N-methyl-formamide | Gen-3-b F2 | 362 | 363 (M + 1) |
| Gen-8-b | 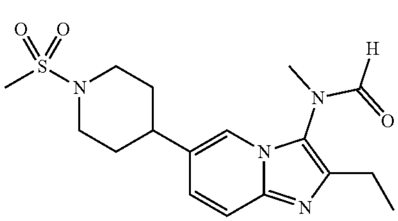 [SMILES: CCc1nc2ccc(C3CCN(S(C)(=O)=O)CC3)cn2c1N(C)C=O] | N-[2-Ethyl-6-(1-methanesulfonyl-piperidin-4-yl)-imidazo[1,2-a]pyridin-3-yl]-N-methyl-formamide | Gen-8-a F6 | 364 | 365 (M + 1) |

TABLE I-continued

Intermediates used towards the compounds of the invention.

| Int | Structures | Name | Int-Mtd | MW | MS Ms'd |
|---|---|---|---|---|---|
| Gen-8-c | 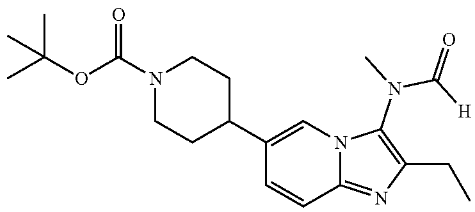 [SMILES: CCc1nc2ccc(C3CCN(C(=O)OC(C)(C)C)CC3)cn2c1N(C)C=O] | 4-[2-Ethyl-3-(formyl-methyl-amino)-imidazo[1,2-a]pyridin-6-yl]-piperidine-1-carboxylic acid tert-butyl ester | Gen-3-b F2-F6 | 386 | 387(M + 1) |
| Gen-8-d | 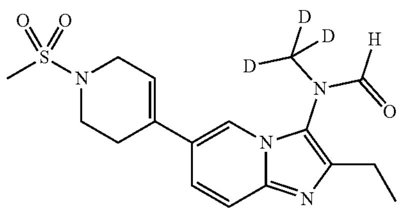 [SMILES: [2H]C([2H])([2H])N(C=O)c1c(CC)nc2ccc(C3=CCN(S(C)(=O)=O)CC3)cn12] | N-[2-Ethyl-6-(1-methanesulfonyl-1,2,3,6-tetrahydro-pyridin-4-yl)-imidazo[1,2-a]pyridin-3-yl]-N-(d$_3$-methyl)-formamide | Gen-3-c F2 | 365 | 366 (M + 1) |
| Gen-8-e | 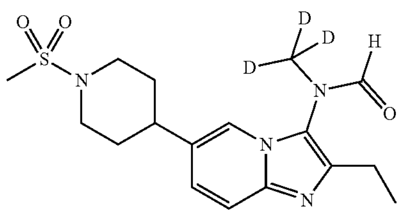 | N-[2-Ethyl-6-(1-methanesulfonyl-piperidin-4-yl)-imidazo[1,2-a]pyridin-3-yl]-N-(d$_3$-methyl)-formamide | Gen-8-d F6 | 367 | 368 (M + 1) |
| Gen-8-f | 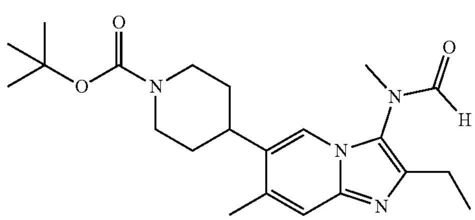 [SMILES: CCc1nc2cc(C)c(C3CCN(C(=O)OC(C)(C)C)CC3)cn2c1N(C)C=O] | 4-[2-Ethyl-3-(formyl-methyl-amino)-7-methyl-imidazo[1,2-a]pyridin-6-yl]-piperidine-1-carboxylic acid tert-butyl ester | Gen-3-i F3 | 400 | 401 (M + 1) |
| Gen-8-g | 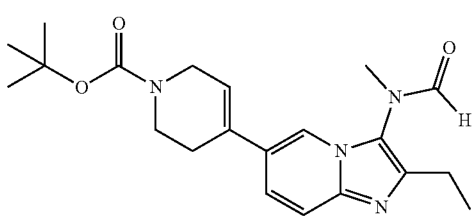 [SMILES: CCc1nc2ccc(C3=CCN(C(=O)OC(C)(C)C)CC3)cn2c1N(C)C=O] | 4-[2-Ethyl-3-(formyl-methyl-amino)-imidazo[1,2-a]pyridin-6-yl]-3,6-dihydro-2H-pyridine-1-carboxylic acid tert-butyl ester | Gen-3-b F2 | 384 | 385 (M + 1) |
| Gen-8-h | 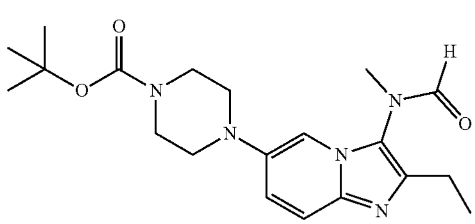 [SMILES: CCc1nc2ccc(N3CCN(C(=O)OC(C)(C)C)CC3)cn2c1N(C)C=O] | 4-[2-Ethyl-3-(formyl-methyl-amino)-imidazo[1,2-a]pyridin-6-yl]-piperazine-1-carboxylic acid tert-butyl ester | Gen-3-b F1b | 387 | 388 (M + 1) |
| Gen-9-a | 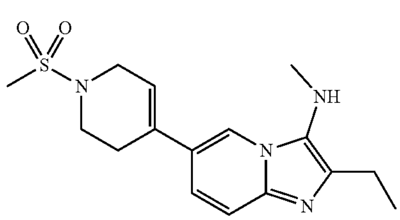 [SMILES: CCc1nc2ccc(C3=CCN(S(C)(=O)=O)CC3)cn2c1NC] | 2-Ethyl-6-(1-methanesulfonyl-1,2,3,6-tetrahydro-pyridin-4-yl)-imidazo[1,2-a]pyridin-3-yl]-methyl-amine | Gen-4-b F2 | 334 | 335 (M + 1) |

TABLE I-continued

Intermediates used towards the compounds of the invention.

| Int | Structures | Name | Int-Mtd | MW | MS Ms'd |
|---|---|---|---|---|---|
| Gen-9-b | 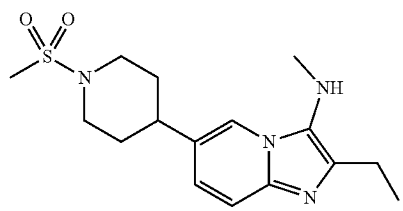 [SMILES: CCc1nc2ccc(C3CCN(S(C)(=O)=O)CC3)cn2c1NC] | [2-Ethyl-6-(1-methanesulfonyl-piperidin-4-yl)-imidazo[1,2-a]pyridin-3-yl]-methyl-amine | Gen-8-b D1 | 336 | 337 (M + 1) |
| Gen-9-c | 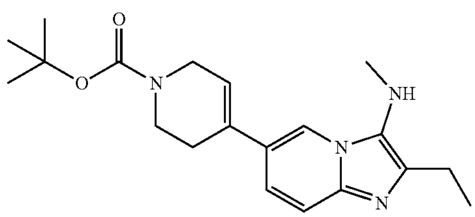 | 4-(2-Ethyl-3-methylamino-imidazo[1,2-a]pyridin-6-yl)-3,6-dihydro-2H-pyridine-1-carboxylic acid tert-butylester | Gen-4-b F2 or Gen-8-g D2 | 356 | 357 (M + 1) |
| Gen-9-d | 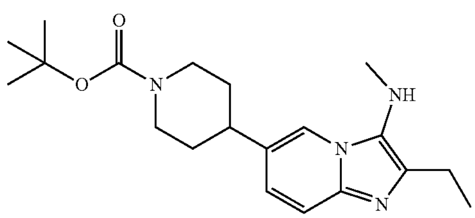 [SMILES: CCc1nc2ccc(C3CCN(C(=O)OC(C)(C)C)CC3)cn2c1NC] | 4-(2-Ethyl-3-methylamino-imidazo[1,2-a]pyridin-6-yl)-piperidine-1-carboxylic acid tert-butyl ester | Gen-8-c D1-F7 | 358 | 359 (M + 1) |
| Gen-9-e | 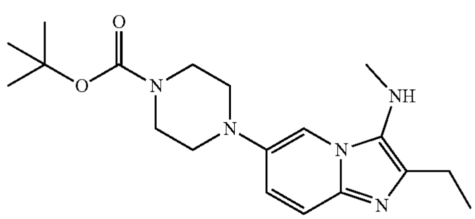 | 4-(2-Ethyl-3-methylamino-imidazo[1,2-a]pyridin-6-yl)-piperazine-1-carboxylic acid tert-butyl ester | Gen-8-h D1-F7 | 359 | 360 (M + 1) |
| Gen-9-f | 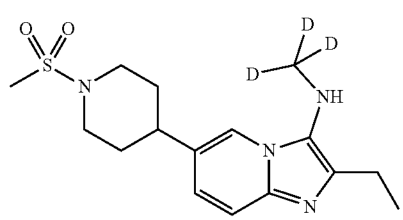 [SMILES: [2H]C([2H])([2H])Nc1c(CC)nc2ccc(C3CCN(S(C)(=O)=O)CC3)cn12] | [2-Ethyl-6-(1-methanesulfonyl-piperidin-4-yl)-imidazo[1,2-a]pyridin-3-yl]-(d$_3$-methyl)-amine | Gen-8-e D1 | 339 | 340 (M + 1) |
| Gen-9-g | 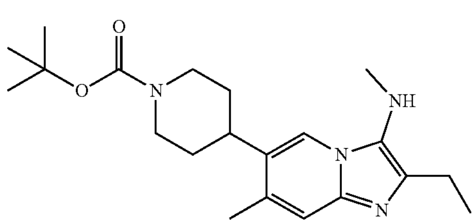 [SMILES: CCc1nc2cc(C)c(C3CCN(C(=O)OC(C)(C)C)CC3)cn2c1NC] | 4-(2-Ethyl-7-methyl-3-(d$_3$-methyl)amino-imidazo[1,2-a]pyridin-6-yl)-piperidine-1-carboxylic acid tert-butyl ester | Gen-8-f D1-F7 | 372 | 373 (M + 1) |

TABLE I-continued

Intermediates used towards the compounds of the invention.

| Int | Structures | Name | Int-Mtd | MW | MS Ms'd |
|---|---|---|---|---|---|
| Cpd 183 or Gen-10-a | 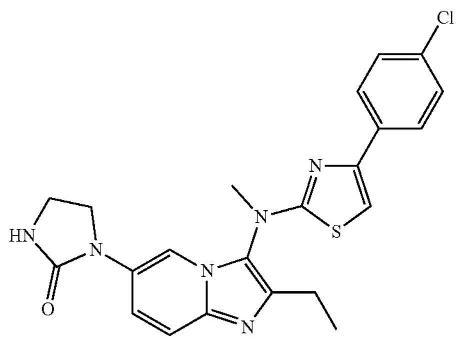 [SMILES: CCc1nc2ccc(N3CCNC3=O)cn2c1N(C)c1nc(-c2ccc(Cl)cc2)cs1] | 1-(3-{[4-(4-Chloro-phenyl)-thiazol-2-yl]-methyl-amino}-2-ethyl-imidazo[1,2-a]pyridin-6-yl)-imidazolidin-2-one | Gen-5-i F4 | 452 ($^{35}$Cl), 454 ($^{37}$Cl) | 453 ($^{35}$Cl M + 1) 455 ($^{37}$Cl M + 1) |
| Gen-10-b | 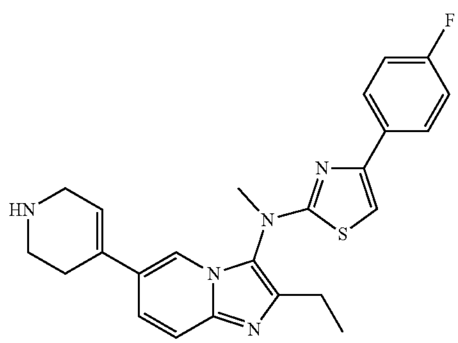 [SMILES: CCc1nc2ccc(C3=CCNCC3)cn2c1N(C)c1nc(-c2ccc(F)cc2)cs1] | [2-Ethyl-6-(1,2,3,6-tetrahydro-pyridin-4-yl)-imidazo[1,2-a]pyridin-3-yl]-[4-(4-fluoro-phenyl)-thiazol-2-yl]-methyl-amine | Gen-5-b F2-F5b | 433 | 434 (M + 1) |
| Cpd 216 or Gen-10c | 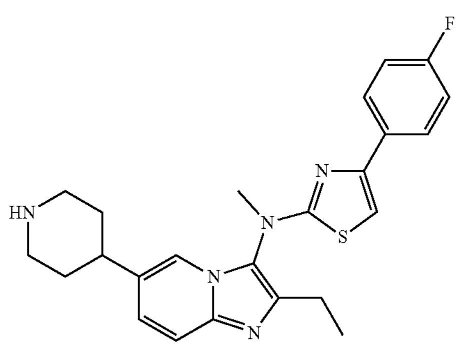 | (2-Ethyl-6-piperidin-4-yl-imidazo[1,2-a]pyridin-3-yl)-[4-(4-fluoro-phenyl)-thiazol-2-yl]-methyl-amine | Gen-5-b F2-F6-F5b or Gen-9-c E1-F6-F5b | 435 | 436 (M + 1) |
| Gen-10-d | 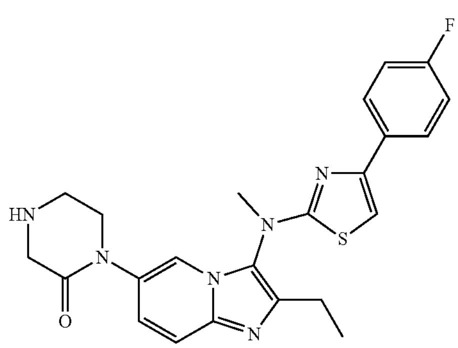 [SMILES: CCc1nc2ccc(N3CCNCC3=O)cn2c1N(C)c1nc(-c2ccc(F)cc2)cs1] | 1-(2-Ethyl-3-{[4-(4-fluoro-phenyl)-thiazol-2-yl]-methyl-amino}-imidazo[1,2-a]pyridin-6-yl)-piperazin-2-one | Gen-5-b F4-F5b | 450 | 451 (M + 1) |

TABLE I-continued

Intermediates used towards the compounds of the invention.

| Int | Structures | Name | Int-Mtd | MW | MS Ms'd |
|---|---|---|---|---|---|
| Gen-10-e | 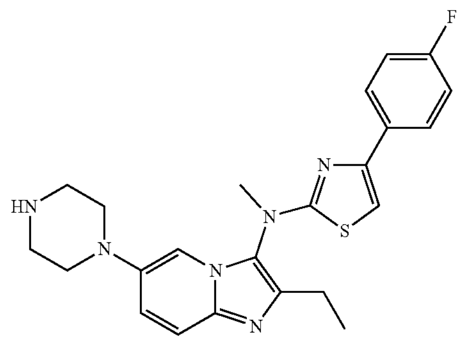 [SMILES: CCc1nc2ccc(N3CCNCC3)cn2c1N(C)c1nc(-c2ccc(F)cc2)cs1] | (2-Ethyl-6-piperazin-1-yl-imidazo[1,2-a]pyridin-3-yl)-[4-(4-fluoro-phenyl)-thiazol-2-yl]-methyl-amine | Gen-5-b F1b-F5b or F1a | 436 | 437 (M + 1) |
| Gen-10-f | 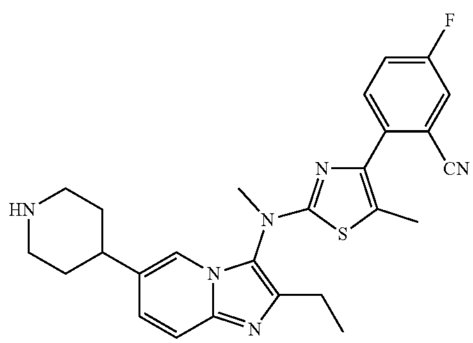 [SMILES: CCc1nc2ccc(C3CCNCC3)cn2c1N(C)c1nc(-c2ccc(F)cc2C#N)c(C)s1] | 2-{2-[(2-Ethyl-6-piperidin-4-yl-imidazo[1,2-a]pyridin-3-yl)-methyl-amino]-5-methyl-thiazol-4-yl}-5-fluoro-benzonitrile | Gen-9-d E1-F5b | 474 | 475 (M + 1) |
| Cpd 231 or Gen-10-g | 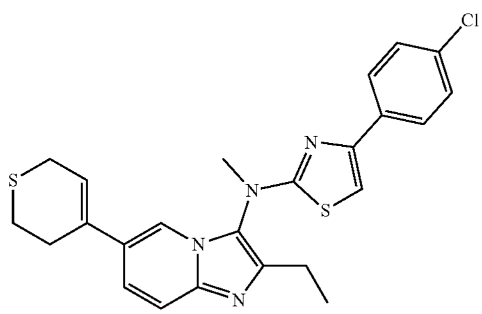 [SMILES: CCc1nc2ccc(C3=CCSCC3)cn2c1N(C)c1nc(-c2ccc(Cl)cc2)cs1] | [4-(4-Chloro-phenyl)-thiazol-2-yl]-[6-(3,6-dihydro-2H-thiopyran-4-yl)-2-ethyl-imidazo[1,2-a]pyridin-3-yl]-methyl-amine | Gen-5-i F2 | 466 ($^{35}$Cl), 468 ($^{37}$Cl) | 467 ($^{35}$Cl M + 1) 469 ($^{37}$Cl M + 1) |
| Gen-10-h | 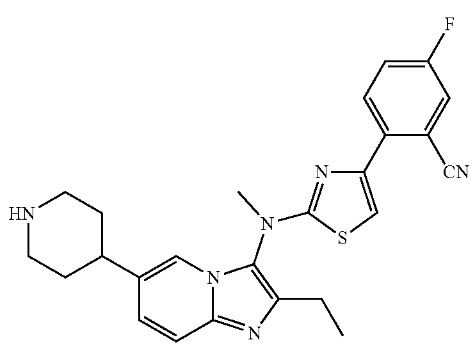 [SMILES: CCc1nc2ccc(N3CCNCC3)cn2c1N(C)c1nc(-c2ccc(F)cc2C#N)cs1] | 2-{2-[(2-Ethyl-6-piperidin-4-yl-imidazo[1,2-a]pyridin-3-yl)-methyl-amino]-thiazol-4-yl}-5-fluoro-benzonitrile | Gen-9-d E1-F5b | 460 | 461 (M + 1) |

TABLE I-continued

Intermediates used towards the compounds of the invention.

| Int | Name | Int-Mtd | MW | MS Ms'd |
|---|---|---|---|---|
| Gen-10-i | 2-{2-[(2-Ethyl-6-piperazin-1-yl-imidazo[1,2-a]pyridin-3-yl)-methyl-amino]-thiazol-4-yl}-5-fluoro-benzonitrile | Gen-5-e F1a | 461 | 462 (M + 1) |
| Gen-10-j | [4-(4-Chloro-phenyl)-thiazol-2-yl]-[6-(2,5-dihydro-1H-pyrrol-3-yl)-2-ethyl-imidazo[1,2-a]pyridin-3-yl]-methyl-amine | Gen-5-i F2-F5a | 435 ($^{35}$Cl), 437 ($^{37}$Cl) | 436 ($^{35}$Cl M + 1), 438 ($^{37}$C M + 1) |
| Gen-10-k | 2-[(2-Ethyl-6-piperazin-1-yl-imidazo[1,2-a]pyridin-3-yl)-methyl-amino]-4-(4-fluoro-phenyl)-thiazole-5-carbonitrile | Gen-5-s F1a | 461 | 462 (M + 1) |
| Gen-10-l | (2-Ethyl-8-fluoro-6-piperazin-1-yl-imidazo[1,2-a]pyridin-3-yl)-[4-(4-fluoro-phenyl)-thiazol-2-yl]-methyl-amine | Gen-5-a F1a | 454 | N.A. |

TABLE I-continued

Intermediates used towards the compounds of the invention.

| Int | Structures | Name | Int-Mtd | MW | MS Ms'd |
|---|---|---|---|---|---|
| Gen-10-m | 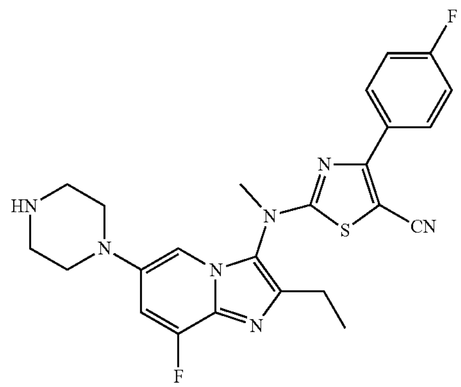 [SMILES: CCc1nc2c(F)cc(N3CCNCC3)cn2c1N(C)c1nc(-c2ccc(F)cc2)c(C#N)s1] | 2-[(2-Ethyl-8-fluoro-6-piperazin-1-yl-imidazo[1,2-a]pyridin-3-yl)-methyl-amino]-4-(4-fluoro-phenyl)-thiazole-5-carbonitrile | Gen-5-r F1a | 479 | 480 (M + 1) |
| Gen-10-n | 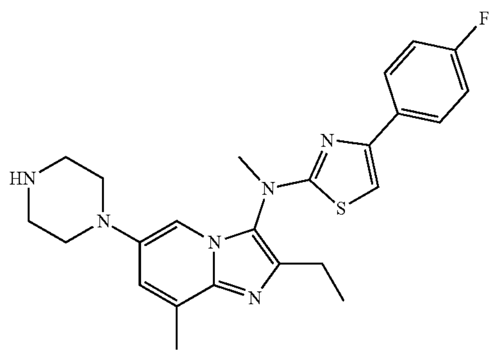 [SMILES: CCc1nc2c(C)cc(N3CCNCC3)cn2c1N(C)c1nc(-c2ccc(F)cc2)cs1] | (2-Ethyl-8-methyl-6-piperazin-1-yl-imidazo[1,2-a]pyridin-3-yl)-[4-(4-fluoro-phenyl)-thiazol-2-yl]-methyl-amine | Gen-5-d F1a | 450 | 451 (M + 1) |
| Gen-10-o | 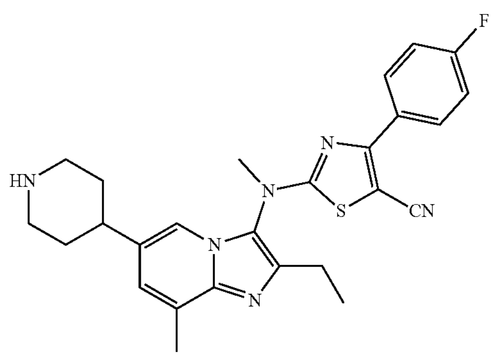 [SMILES: CCc1nc2c(C)cc(C3CCNCC3)cn2c1N(C)c1nc(-c2ccc(F)cc2)c(C#N)s1] | 2-[(2-Ethyl-8-methyl-6-piperidin-4-yl-imidazo[1,2-a]pyridin-3-yl)-methyl-amino]-4-(4-fluoro-phenyl)-thiazole-5-carbonitrile | Gen-5-t F3-F5b | 474 | 475 (M + 1) |
| Gen-10-p | 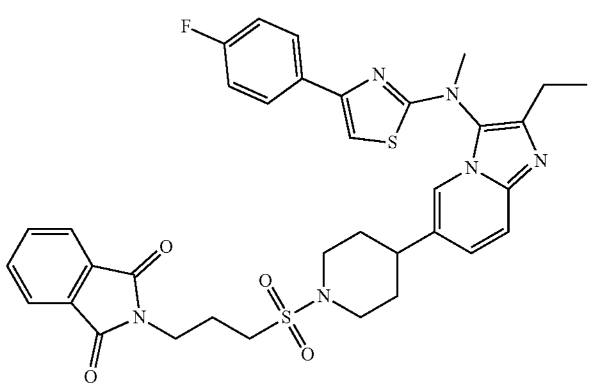 [SMILES: CCc1nc2ccc(C3CCN(S(=O)(=O)CCCN4C(=O)c5ccccc5C4=O)CC3)cn2c1N(C)c1nc(-c2ccc(F)cc2)cs1] | 2-{3-[4-(2-Ethyl-3-{[4-(4-fluoro-phenyl)-thiazol-2-yl]-methyl-amino}-imidazo[1,2-a]pyridin-6-yl)-piperidine-1-sulfonyl]-propyl}-isoindole-1,3-dione | Gen-10-c F11-F12a | 686 | 687 (M + 1) |

TABLE I-continued

Intermediates used towards the compounds of the invention.

| Int | Structures | Name | Int-Mtd | MW | MS Ms'd |
|---|---|---|---|---|---|
| Gen-10-q | 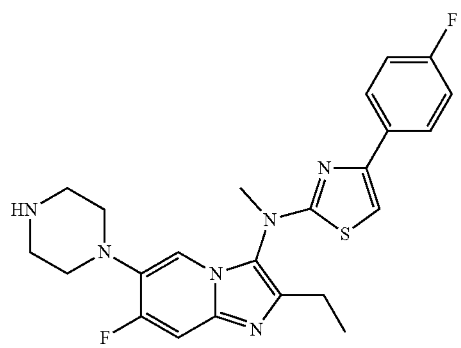 [SMILES: CCc1nc2cc(F)c(N3CCNCC3)cn2c1N(C)c1nc(-c2ccc(F)cc2)cs1] | (2-Ethyl-7-fluoro-6-piperazin-1-yl-imidazo[1,2-a]pyridin-3-yl)-[4-(4-fluoro-phenyl)-thiazol-2-yl]-methyl-amine | Gen-5-o F1a | 454 | 455 (M + 1) |
| Gen-10-r | 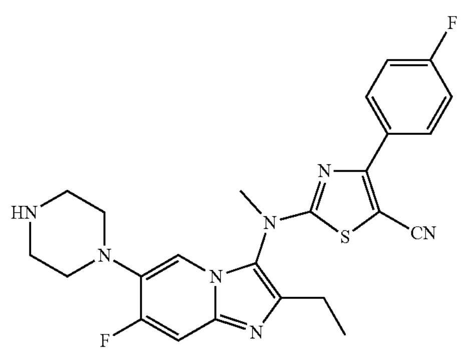 [SMILES: CCc1nc2cc(F)c(N3CCNCC3)cn2c1N(C)c1nc(-c2ccc(F)cc2)c(C#N)s1] | 2-[(2-Ethyl-7-fluoro-6-piperazin-1-yl-imidazo[1,2-a]pyridin-3-yl)-methyl-amino]-4-(4-fluoro-phenyl)-thiazole-5-carbonitrile | Gen-5-u F1a | 479 | 480 (M + 1) |
| Gen-10-s | 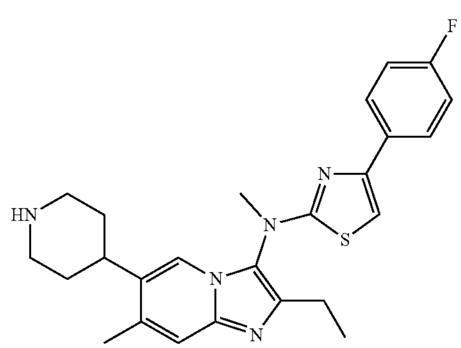 [SMILES: CCc1nc2cc(C)c(C3CCNCC3)cn2c1N(C)c1nc(-c2ccc(F)cc2)cs1] | (2-Ethyl-7-methyl-6-piperidin-4-yl-imidazo[1,2-a]pyridin-3-yl)-[4-(4-fluoro-phenyl)-thiazol-2-yl]-methyl-amine | Gen-9-g E1-F5b | 449 | 450 (M + 1) |
| Gen-10-t | 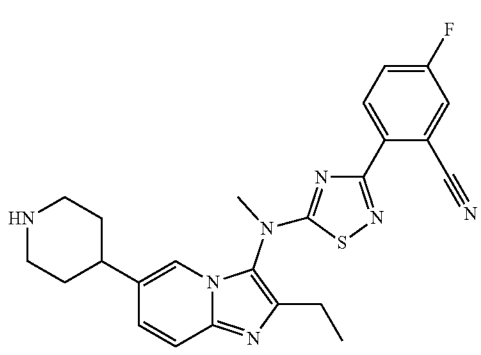 [SMILES: CCc1nc2ccc(C3CCNCC3)cn2c1N(C)c1nc(-c2ccc(F)cc2C#N)ns1] | 2-{5-[(2-Ethyl-6-piperidin-4-yl-imidazo[1,2-a]pyridin-3-yl)-methyl-amino]-[1,2,4]thiadiazol-3-yl}-5-fluoro-benzonitrile | Gen-9-d E5-F5b | 461 | 462 (M + 1) |

TABLE I-continued

Intermediates used towards the compounds of the invention.

| Int | Structures | Name | Int-Mtd | MW | MS Ms'd |
|---|---|---|---|---|---|
| Gen-10-u | 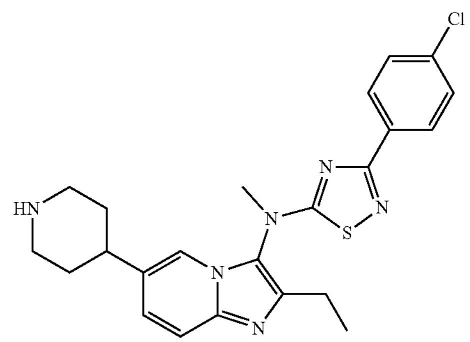 [SMILES: CCc1nc2ccc(C3CCNCC3)cn2c1N(C)c1nc(-c2ccc(Cl)cc2)ns1] | 3-(4-Chloro-phenyl)-[1,2,4]thiadiazol-5-yl]-(2-ethyl-6-piperazin-1-yl-imidazo[1,2-a]pyridin-3-yl)-methyl-amine | Gen-5-w F1b-F5b | 453 ($^{35}$Cl), 455 ($^{37}$Cl) | 454 ($^{35}$Cl M + 1), 456 ($^{37}$C M + 1) |
| Gen-10-v | 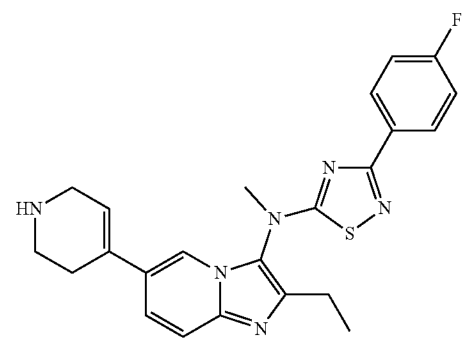 [SMILES: CCc1nc2ccc(C3=CCNCC3)cn2c1N(C)c1nc(-c2ccc(F)cc2)ns1] | [2-Ethyl-6-(1,2,3,6-tetrahydro-pyridin-4-yl)-imidazo[1,2-a]pyridin-3-yl]-[3-(4-fluoro-phenyl)-[1,2,4]thiadiazol-5-yl]-methyl-amine | Gen-9-c E4-F5b or Gen-5-x F2-F5b | 434 | 435 (M + 1) |
| Gen-10-w | 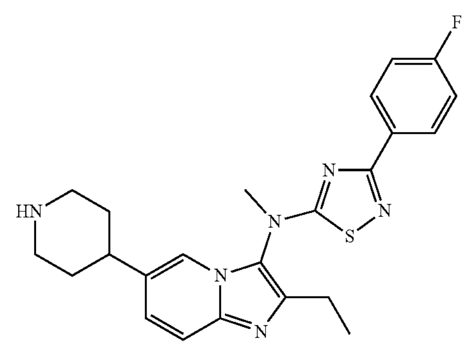 [SMILES: CCc1nc2ccc(C3CCNCC3)cn2c1N(C)c1nc(-c2ccc(F)cc2)ns1] | (2-Ethyl-6-piperidin-4-yl-imidazo[1,2-a]pyridin-3-yl)-[3-(4-fluoro-phenyl)-[1,2,4]thiadiazol-5-yl]-methyl-amine | Gen-10-v F6 | 436 | 437 (M + 1) |
| Gen-10-x | 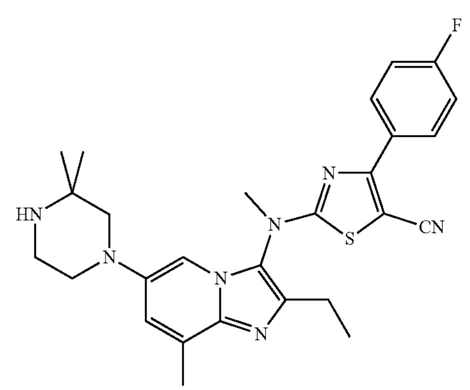 [SMILES: CCc1nc2c(C)cc(N3CCNC(C)(C)C3)cn2c1N(C)c1nc(-c2ccc(F)cc2)c(C#N)s1] | 2-{[6-(3,3-Dimethyl-piperazin-1-yl)-2-ethyl-8-methyl-imidazo[1,2-a]pyridin-3-yl]-methyl-amino}-4-(4-fluoro-phenyl)-thiazole-5-carbonitrile | Gen-5-t F1a | 503 | 504 (M + 1) |

TABLE I-continued

Intermediates used towards the compounds of the invention.

| Int | Structures | Name | Int-Mtd | MW | MS Ms'd |
|---|---|---|---|---|---|
| Gen-10-y | 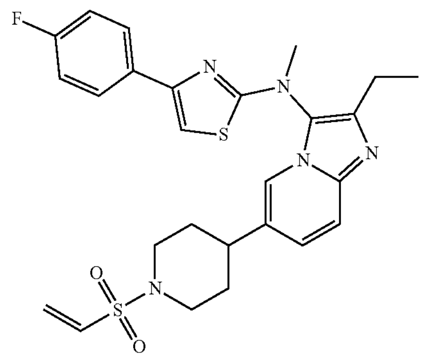 [SMILES: C=CS(=O)(=O)N1CCC(c2ccc3nc(CC)c(N(C)c4nc(-c5ccc(F)cc5)cs4)n3c2)CC1] | [6-(1-Ethenesulfonyl-piperidin-4-yl)-2-ethyl-imidazo[1,2-a]pyridin-3-yl]-[4-(4-fluoro-phenyl)-thiazol-2-yl]-methyl-amine | Gen-10-c F11 | 525 | 526 (M + 1) |
| Gen-10-z | 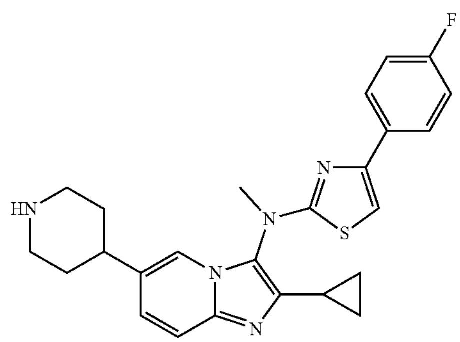 [SMILES: CN(c1nc(-c2ccc(F)cc2)cs1)c1c(C2CC2)nc2ccc(C3CCNCC3)cn12] | (2-Cyclopropyl-6-piperidin-4-yl-imidazo[1,2-a]pyridin-3-yl)-[4-(4-fluoro-phenyl)-thiazol-2-yl]-methyl-amine | Gen-5-n F2-F6-F5b | 447 | 448 (M + 1) |
| Gen-10-aa | 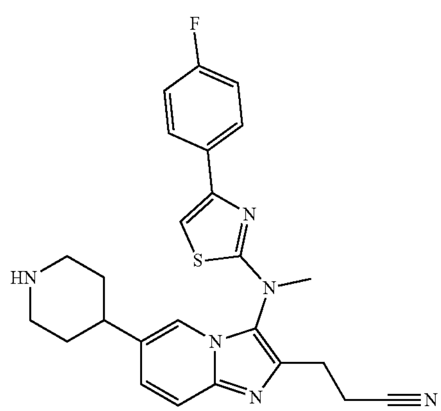 [SMILES: CN(c1nc(-c2ccc(F)cc2)cs1)c1c(CCC#N)nc2ccc(C3CCNCC3)cn12] | 3-(3-{[4-(4-Fluoro-phenyl)-thiazol-2-yl]-methyl-amino}-6-piperidin-4-yl-imidazo[1,2-a]pyridin-2-yl)-propionitrile | Gen-5-ac F2-F6-F5b See Cpd 174 | 460 | 461(M + 1) |
| Gen-10-ab | 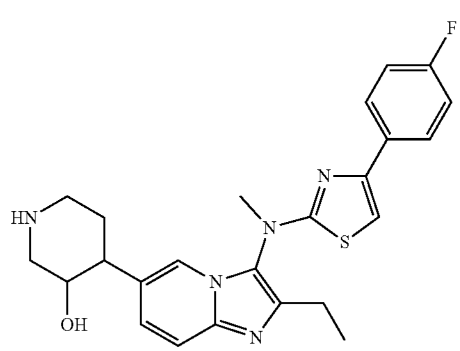 [SMILES: CCc1nc2ccc(C3CCNCC3O)cn2c1N(C)c1nc(-c2ccc(F)cc2)cs1] | 4-(2-Ethyl-3-{[4-(4-fluoro-phenyl)-thiazol-2-yl]-methyl-amino}-imidazo[1,2-a]pyridin-6-yl)-piperidin-3-ol | Cpd 78 F5b | 451 | N.A. |

TABLE I-continued

Intermediates used towards the compounds of the invention.

| Int | Structures | Name | Int-Mtd | MW | MS Ms'd |
|---|---|---|---|---|---|
| Gen-10-ac | 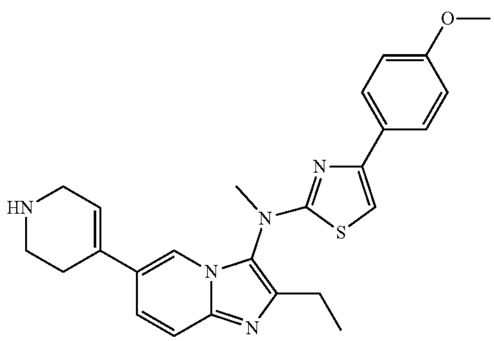 [SMILES: CCc1nc2ccc(C3=CCNCC3)cn2c1N(C)c1nc(-c2ccc(OC)cc2)cs1] | [2-Ethyl-6-(1,2,3,6-tetrahydro-pyridin-4-yl)-imidazo[1,2-a]pyridin-3-yl]-[4-(4-methoxy-phenyl)-thiazol-2-yl]-methyl-amine | Gen-5-f F2-F5b | 445 | 446 (M + 1) |
| Gen-10-ad | 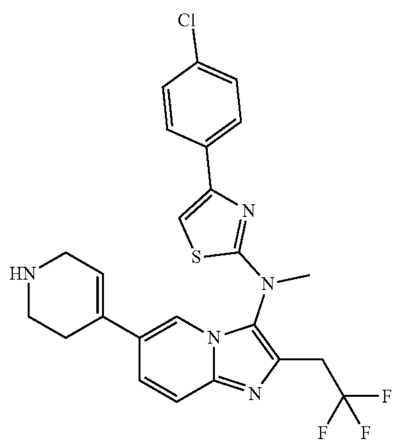 [SMILES: CN(c1nc(-c2ccc(Cl)cc2)cs1)c1c(CC(F)(F)F)nc2ccc(C3=CCNCC3)cn12] | [4-(4-Chloro-phenyl)-thiazol-2-yl]-methyl-[6-(1,2,3,6-tetrahydro-pyridin-4-yl)-2-(2,2,2-trifluoro-ethyl)-imidazo[1,2-a]pyridin-3-yl]-amine | Gen-5-v F2-F5a | 503 ($^{35}$Cl), 505 ($^{37}$Cl) | 504 ($^{35}$Cl M + 1), 506 ($^{37}$Cl M + 1). |
| Gen-10-ae | 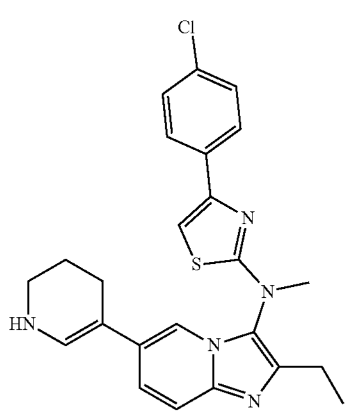 [SMILES: CCc1nc2ccc(C3=CNCCC3)cn2c1N(C)c1nc(-c2ccc(Cl)cc2)cs1] | [4-(4-Chloro-phenyl)-thiazol-2-yl]-[2-ethyl-6-(1,4,5,6-tetrahydro-pyridin-3-yl)-imidazo[1,2-a]pyridin-3-yl]-methyl-amine | Gen-5-i F2-F5a | 449 ($^{35}$Cl), 451 ($^{37}$Cl) | N.A. |

TABLE I-continued

Intermediates used towards the compounds of the invention.

| Int | Structures | Name | Int-Mtd | MW | MS Ms'd |
|---|---|---|---|---|---|
| Gen-10-af | 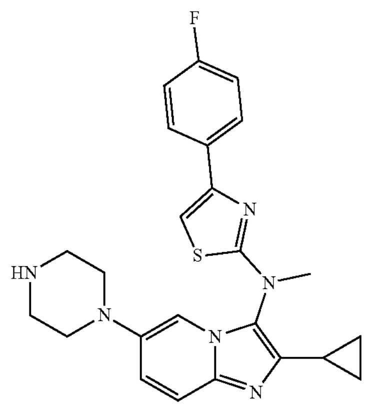 [SMILES: CN(c1nc(-c2ccc(F)cc2)cs1)c1c(C2CC2)nc2ccc(N3CCNCC3)cn12] | (2-Cyclopropyl-6-piperazin-1-yl-imidazo[1,2-a]pyridin-3-yl)-[4-(4-fluoro-phenyl)-thiazol-2-yl]-methyl-amine | Gen-5-n-F1b-F5a | 448 | 449 (M + 1) |
| Gen-10-ag | 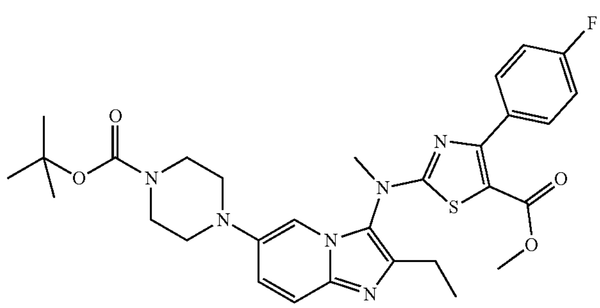 | 4-(2-Ethyl-3-{[4-(4-fluoro-phenyl)-5-methoxycarbonyl-thiazol-2-yl]-methyl-amino}-imidazo[1,2-a]pyridin-6-yl)-piperazine-1-carboxylic acid tert-butyl ester | Gen-9-e E1 | 594 | 595 (M + 1) |
| Gen-10-ah | 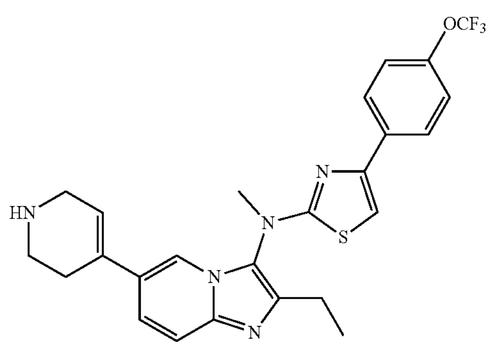 [SMILES: CCc1nc2ccc(C3=CCNCC3)cn2c1N(C)c1nc(-c2ccc(OC(F)(F)F)cc2)cs1] | [2-Ethyl-6-(1,2,3,6-tetrahydro-pyridin-4-yl)-imidazo[1,2-a]pyridin-3-yl]-methyl-[4-(4-trifluoromethoxy-phenyl)-thiazol-2-yl]-amine | Gen-5-j-F2-F5b | 499 | 500 (M + 1) |
| Gen-10-ai | 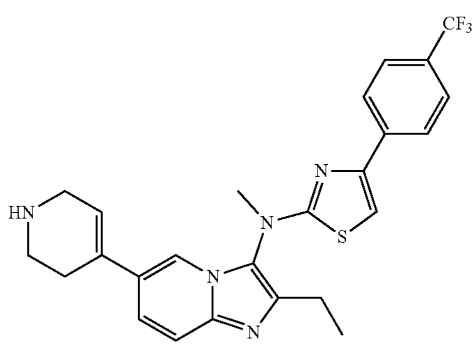 [SMILES: CCc1nc2ccc(C3=CCNCC3)cn2c1N(C)c1nc(-c2ccc(C(F)(F)F)cc2)cs1] | [2-Ethyl-6-(1,2,3,6-tetrahydro-pyridin-4-yl)-imidazo[1,2-a]pyridin-3-yl]-methyl-[4-(4-trifluoromethyl-phenyl)-thiazol-2-yl]-amine | Gen-5-k F2-F5b | 483 | N.A. |

TABLE I-continued

Intermediates used towards the compounds of the invention.

| Int | Structures | Name | Int-Mtd | MW | MS Ms'd |
|---|---|---|---|---|---|
| Gen-10-aj | 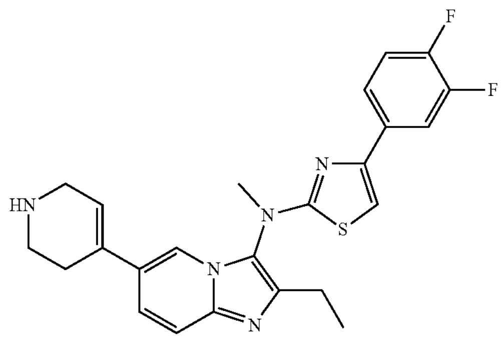 [SMILES: CCc1nc2ccc(C3=CCNCC3)cn2c1N(C)c1nc(-c2ccc(F)c(F)c2)cs1] | [4-(3,4-Difluoro-phenyl)-thiazol-2-yl]-[2-ethyl-6-(1,2,3,6-tetrahydro-pyridin-4-yl)-imidazo[1,2-a]pyridin-3-yl]-methyl-amine | Gen-5-l F2-F5b | 451 | 452 (M + 1) |
| Gen-10-ak | 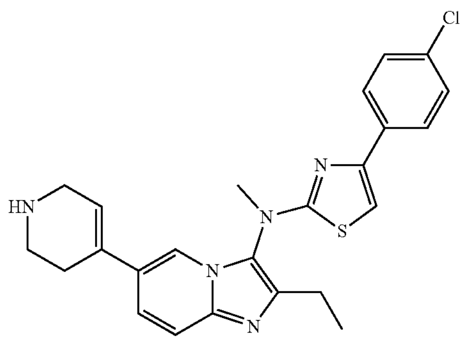 [SMILES: CCc1nc2ccc(C3=CCNCC3)cn2c1N(C)c1nc(-c2ccc(Cl)cc2)cs1] | [4-(4-Chloro-phenyl)-thiazol-2-yl]-[2-ethyl-6-(1,2,3,6-tetrahydro-pyridin-4-yl)-imidazo[1,2-a]pyridin-3-yl]-methyl-amine | Gen-5-i F2-F5b | 449 ($^{35}$Cl), 451 ($^{37}$Cl) | 450 ($^{35}$Cl M + 1), 452 ($^{37}$Cl M + 1) |
| Gen-10-al | 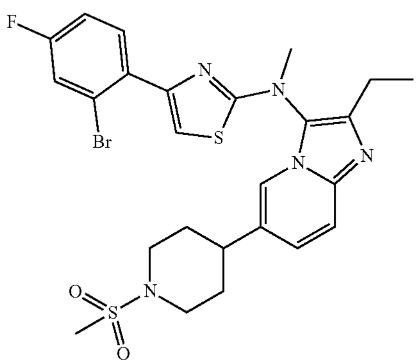 [SMILES: CCc1nc2ccc(C3CCN(S(C)(=O)=O)CC3)cn2c1N(C)c1nc(-c2ccc(F)cc2Br)cs1] | [4-(2-Bromo-4-fluoro-phenyl)-thiazol-2-yl]-[2-ethyl-6-(1-methanesulfonyl-piperidin-4-yl)-imidazo[1,2-a]pyridin-3-yl]-methyl-amine | Gen-9-b E1 | 591 ($^{79}$Br) 593 ($^{81}$Br) | 592 ($^{79}$Br M + 1), 594 ($^{81}$Br M + 1) |
| Gen-10-am | 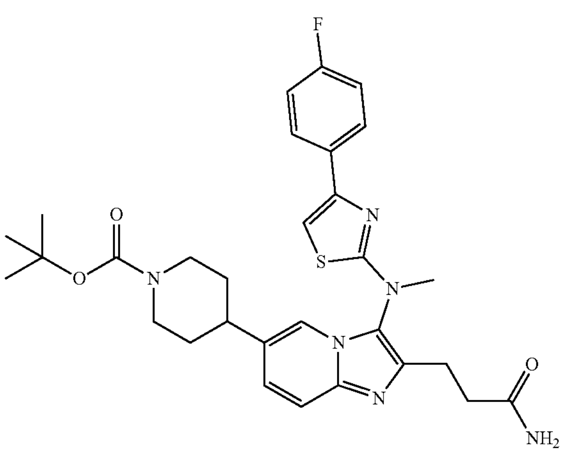 [SMILES: CN(c1nc(-c2ccc(F)cc2)cs1)c1c(CCC(N)=O)nc2ccc(C3CCN(C(=O)OC(C)(C)C)CC3)cn12] | 4-(2-(2-Carbamoyl-ethyl)-3-{[4-(4-fluoro-phenyl)-thiazol-2-yl]-methyl-amino}-imidazo[1,2-a]pyridin-6-yl)-piperidine-1-carboxylic acid tert-butyl ester | Gen-5-ad F2-F6-F13 see Cpd 176 | 578 | 579 (M + 1) |

TABLE I-continued

Intermediates used towards the compounds of the invention.

| Int | Structures | Name | Int-Mtd | MW | MS Ms'd |
|---|---|---|---|---|---|
| Gen-10-an | 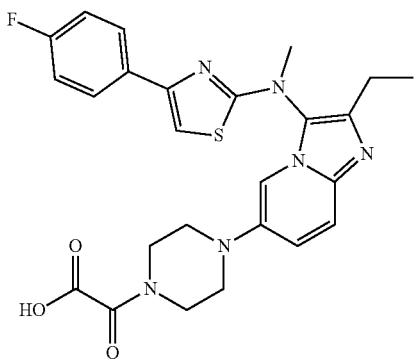 [SMILES: CCc1nc2ccc(N3CCN(C(=O)C(=O)O)CC3)cn2c1N(C)c1nc(-c2ccc(F)cc2)cs1] | [4-(2-Ethyl-3-{[4-(4-fluoro-phenyl)-thiazol-2-yl]-methyl-amino}-imidazo[1,2-a]pyridin-6-yl)-piperazin-1-yl]-oxo-acetic acid | Gen-10-e F9b-F13 | 508 | 509 (M + 1) |
| Gen-10-ao | 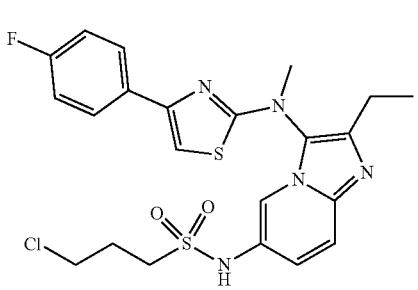 [SMILES: CCc1nc2ccc(NS(=O)(=O)CCCCl)cn2c1N(C)c1nc(-c2ccc(F)cc2)cs1] | 3-Chloro-propane-1-sulfonic acid (2-ethyl-3-{[4-(4-fluoro-phenyl)-thiazol-2-yl]-methyl-amino}-imidazo[1,2-a]pyridin-6-yl)-amide | Gen-5-af F11 | 507 ($^{35}$Cl), 509 ($^{37}$Cl); | 508 ($^{35}$Cl M + 1), 510 ($^{37}$Cl M + 1) |
| Gen-10-ap | 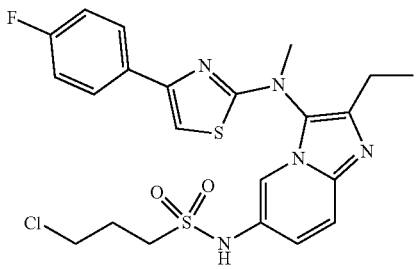 | [6-(1,4-Dioxa-8-aza-spiro[4.5]dec-8-yl)-2-ethyl-imidazo[1,2-a]pyridin-3-yl]-[4-(4-fluoro-phenyl)-thiazol-2-yl]-methyl-amine | Gen-5-c F1b | 493 | 494 (M + 1) |
| Gen-10-aq | 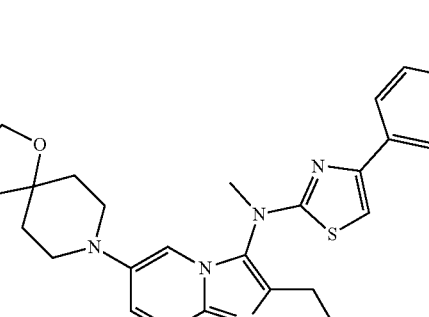 | 1-(2-Ethyl-3-{[4-(4-fluoro-phenyl)-thiazol-2-yl]-methyl-amino}-imidazo[1,2-a]pyridin-6-yl)-piperidin-4-one | Gen-10-ap See Cpd 211 | 449 | 450 (M + 1) |

TABLE I-continued

Intermediates used towards the compounds of the invention.

| Int | Structures | Name | Int-Mtd | MW | MS Ms'd |
|---|---|---|---|---|---|
| Gen-10-ar | 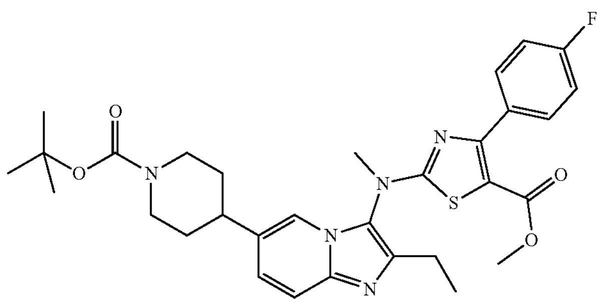 [SMILES: CCc1nc2ccc(C3CCN(C(=O)OC(C)(C)C)CC3)cn2c1N(C)c1nc(-c2ccc(F)cc2)c(C(=O)OC)s1] | 4-(2-Ethyl-3-{[4-(4-fluoro-phenyl)-5-methoxycarbonyl-thiazol-2-yl]-methyl-amino}-imidazo[1,2-a]pyridin-6-yl)-piperidine-1-carboxylic acid tert-butyl ester | Gen-9-d E1 | 593 | 594 (M + 1) |
| Cpd 1 | 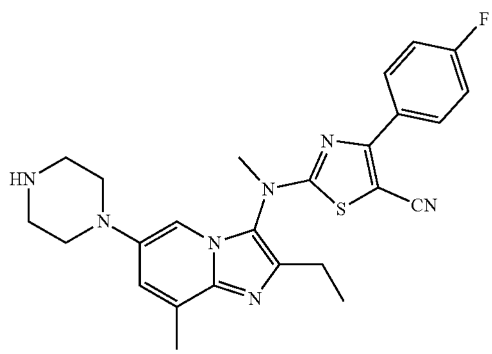 [SMILES: CCc1nc2c(C)cc(N3CCNCC3)cn2c1N(C)c1nc(-c2ccc(F)cc2)c(C#N)s1] | 2-[(2-Ethyl-8-methyl-6-piperazin-1-yl-imidazo[1,2-a]pyridin-3-yl)-methyl-amino]-4-(4-fluoro-phenyl)-thiazole-5-carbonitrile | Gen-5-t F1b-F5b | 475 | 476 (M + 1) |
| Cpd 78 | 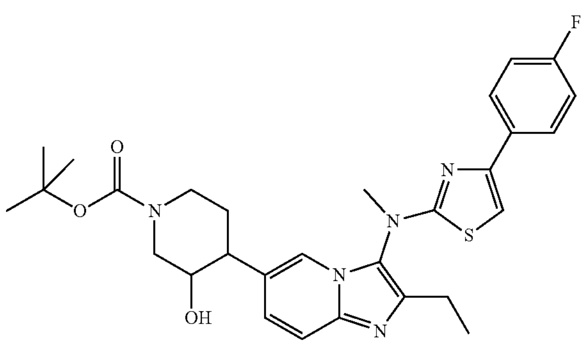 [SMILES: CCc1nc2ccc(C3CCN(C(=O)OC(C)(C)C)CC3O)cn2c1N(C)c1nc(-c2ccc(F)cc2)cs1] | 4-(2-Ethyl-3-{[4-(4-fluoro-phenyl)-thiazol-2-yl]-methyl-amino}-imidazo[1,2-a]pyridin-6-yl)-3-hydroxy-piperidine-1-carboxylic acid tert-butyl ester | Gen-5-c F2-see Cpd 78 | 551 | 552 (M + 1) |
| Cpd 161 | 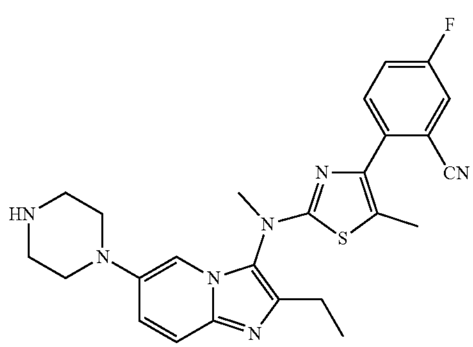 | 2-{2-[(2-Ethyl-6-piperazin-1-yl-imidazo[1,2-a]pyridin-3-yl)-methyl-amino]-5-methyl-thiazol-4-yl}-5-fluoro-benzonitrile | Gen-5-m F1a | 475 | 476 (M + 1) |

TABLE I-continued

Intermediates used towards the compounds of the invention.

| Int | Structures | Name | Int-Mtd | MW | MS Ms'd |
|---|---|---|---|---|---|
| Cpd 177 | 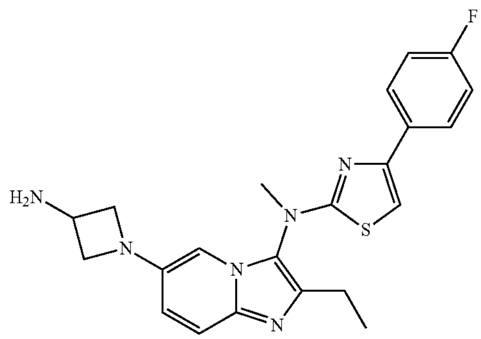 [SMILES: CCc1nc2ccc(N3CC(N)C3)cn2c1N(C)c1nc(-c2ccc(F)cc2)cs1] | [6-(3-Amino-azetidin-1-yl)-2-ethyl-imidazo[1,2-a]pyridin-3-yl]-[4-(4-fluoro-phenyl)-thiazol-2-yl]-methyl-amine | Gen-5-b F1b-F5a | 422 | 423 (M + 1) |
| Gen-11-a | 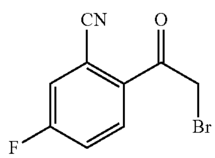 | 2-(2-Bromo-acetyl)-5-fluoro-benzonitrile | G1 | 241 ($^{79}$Br), 243 ($^{81}$Br) | 242 ($^{79}$Br M + 1), 244 ($^{81}$Br M + 1) |
| Gen-11-b | 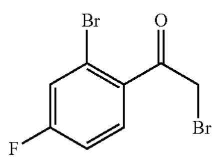 | 2-Bromo-1-(2-bromo-4-fluoro-phenyl)-ethanone | G1 | 294 ($^{79}$Br, $^{79}$Br) 296 ($^{79}$Br, $^{81}$Br) 298 ($^{81}$Br, $^{81}$Br) | N.A. |
| Gen-11-c | 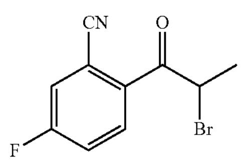 | 2-(2-Bromo-propionyl)-5-fluoro-benzonitrile | G1 | 255 ($^{79}$Br), 257 ($^{81}$Br) | N.A. |
| Gen-11-d | 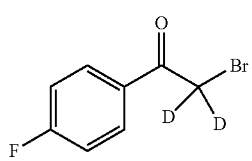 [SMILES: [2H]C([2H])(Br)C(=O)c1ccc(F)cc1] | 2-Bromo-1-(4-fluoro-phenyl)-(d$_2$-ethanone) | see example Gen-11-d | 218 ($^{79}$Br) 220 ($^{81}$Br) | N.A. |
| Gen-12-a | 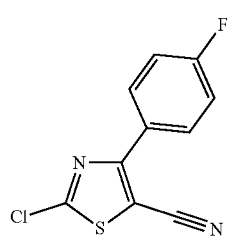 [SMILES: N#Cc1sc(Cl)nc1-c1ccc(F)cc1] | 2-Chloro-4-(4-fluoro-phenyl)-thiazole-5-carbonitrile | G2 | 238 ($^{35}$Cl), 240 ($^{37}$Cl) | 239 ($^{35}$Cl M + 1), 241 ($^{37}$Cl M + 1) |
| Gen-13-a | 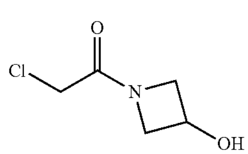 | 2-Chloro-1-(3-hydroxy-azetidin-1-yl)-ethanone | G3a | 149 ($^{35}$Cl), 151 ($^{37}$Cl) | N.A |

TABLE I-continued

Intermediates used towards the compounds of the invention.

| Int | Structures | Name | Int-Mtd | MW | MS Ms'd |
|---|---|---|---|---|---|
| Gen-13-b | 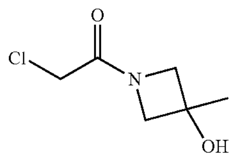 | 2-Chloro-1-(3-hydroxy-3-methyl-azetidin-1-yl)-ethanone | G3a | 163 ($^{35}$Cl), 165 ($^{37}$Cl) | 164 ($^{35}$Cl M + 1) 166 ($^{37}$Cl M + 1) |
| Gen-13-c | 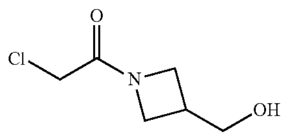 | 2-Chloro-1-(3-hydroxymethyl-azetidin-1-yl)-ethanone | G3b | 163 ($^{35}$Cl), 165 ($^{37}$Cl) | 164 ($^{35}$Cl M + 1) 166 ($^{37}$Cl M + 1) |
| Gen-13-d | 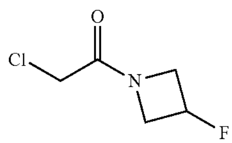 | 2-Chloro-1-(3-fluoro-azetidin-1-yl)-ethanone | G3a | 151 ($^{35}$Cl), 153 ($^{37}$Cl) | N.A |
| Gen-13-e | 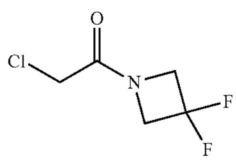 | 2-Chloro-1-(3,3-difluoro-azetidin-1-yl)-ethanone | G3a | 169 ($^{35}$Cl), 171 ($^{37}$Cl) | 170 ($^{35}$Cl M + 1) 172 ($^{37}$Cl M + 1) |
| Gen-13-f | 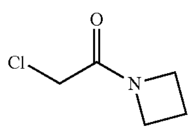 | 1-Azetidin-1-yl-2-chloro-ethanone | G3a | 133 ($^{35}$Cl), 135 ($^{37}$Cl) | N.A. |
| Gen-13-g | 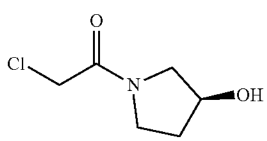 | (S)-2-Chloro-1-(3-hydroxy-pyrrolidin-1-yl)-ethanone | G3a | 163 ($^{35}$Cl), 165 ($^{37}$Cl) | 164 ($^{35}$Cl M + 1) 166 ($^{37}$Cl M + 1) |
| Gen-13-h | 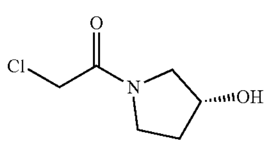 | (R)-2-Chloro-1-(3-hydroxy-pyrrolidin-1-yl)-ethanone | G3b | 163 ($^{35}$Cl), 165 ($^{37}$Cl) | 164 ($^{35}$Cl M + 1) 166 ($^{37}$Cl M + 1) |
| Gen-13-i | 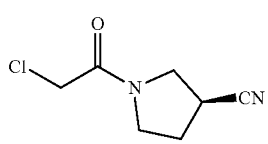 [SMILES: N#C[C@H]1CCN(C(=O)CCl)C1] | (S)-1-(2-Chloro-acetyl)-pyrrolidine-3-carbonitrile | G3b | 172 ($^{35}$Cl), 174 ($^{37}$Cl) | 173 ($^{35}$Cl M + 1), 175 ($^{37}$Cl M + 1) |
| Gen-13-j | 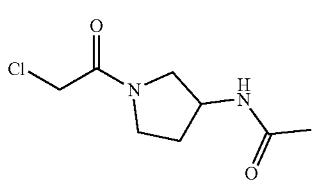 | N-[1-(2-Chloro-acetyl)-pyrrolidin-3-yl]-acetamide | see Gen-13-j | 204 ($^{35}$Cl), 206 ($^{37}$Cl) | N.A. |
| Gen-13-k | 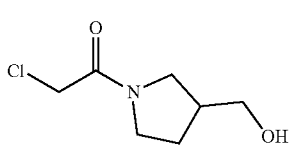 [SMILES: O=C(CCl)N1CCC(CO)C1] | 2-Chloro-1-(3-hydroxymethyl-pyrrolidin-1-yl)-ethanone | G3b | 177 ($^{35}$Cl), 179 ($^{37}$Cl) | N.A. |

TABLE I-continued

Intermediates used towards the compounds of the invention.

| Int | Structures | Name | Int-Mtd | MW | MS Ms'd |
|---|---|---|---|---|---|
| Gen-13-l | 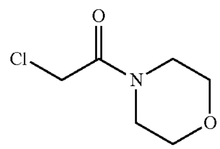 | 2-Chloro-1-morpholin-4-yl-ethanone | G3b | 163 ($^{35}$Cl), 165 ($^{37}$Cl) | N.A. |
| Gen-13-m | 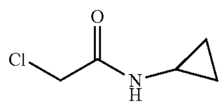 | 2-Chloro-N-cyclopropyl-acetamide | G3b | 133 ($^{35}$Cl), 135 ($^{37}$Cl) | 134 ($^{35}$Cl M + 1), 136 ($^{37}$Cl M + 1) |
| Gen-13-n | 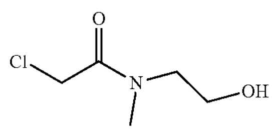 | 2-Chloro-N-(2-hydroxy-ethyl)-N-methyl-acetamide | G3b | 151 ($^{35}$Cl), 153 ($^{37}$Cl) | N.A. |
| Gen-13-o | 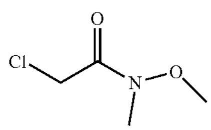 | 2-Chloro-N-methoxy-N-methyl-acetamide | G3b | 137 ($^{35}$Cl), 139 ($^{37}$Cl) | 138 ($^{35}$Cl M + 1) 140 ($^{37}$Cl M + 1) |
| Gen-13-p | 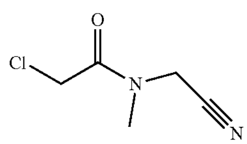 | 2-Chloro-N-cyanomethyl-N-methyl-acetamide | G3b | 146 ($^{35}$Cl), 148 ($^{37}$Cl) | N.A. |
| Gen-13-q | 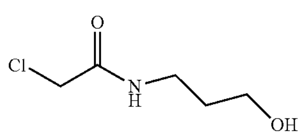 | 2-Chloro-N-(3-hydroxy-propyl)-acetamide | G3b | 151 ($^{35}$Cl), 153 ($^{37}$Cl) | N.A. |

TABLE II

NMR data of the Intermediates used towards the compounds of the invention.

| Int | NMR data (δ) |
|---|---|
| Gen-2-k | $^1$H NMR (400 MHz, CDCl$_3$) δ ppm, presence of 2 rotamers 8.71 (0.5 H, bs), 8.56 (0.5 H, s), 8.52 (0.5 H, bs), 8.16 (0.5 H, d), 8.04 (0.5 H, bs), 7.77 (0.5 H, dd), 7.71 (0.5 H, dd), 7.67 (0.5 H, bs), 7.53 (0.5 H, d), 7.49 (0.5 H, d), 3.95 (1.5 H, s), 3.92 (1.5 H, s), 2.79 (1 H, q), 2.72 (1 H, q), 1.36-1.26 (3 H, m) |
| Gen-3-c | $^1$H NMR (400 MHz, CDCl$_3$) δ ppm 8.22 (1 H, s), 7.94 (1 H, s), 7.50 (1 H, d), 7.34 (1 H, d), 2.75 (2H, q), 1.34 (3 H, t) |
| Gen-11-b | $^1$H NMR (300 MHz, CDCl$_3$) δ ppm 7.56 (1 H, dd), 7.41 (1 H, dd), 7.20-7.08 (1 H, m), 4.48 (2 H, s) |
| Gen-11-c | $^1$H NMR (400 MHz, CDCl$_3$) δ ppm 8.03 (1 H, dd), 7.55 (1 H, dd), 7.46-7.38 (1 H, m), 5.26 (1 H, q), 1.96 (3 H, d) |
| Gen-11-d | $^1$H NMR (400 MHz, CDCl$_3$) δ ppm 8.01-7.96 (2 H, m), 7.17-7.08 (2 H, m) |
| Gen-13-a | $^1$H NMR (400 MHz, CDCl$_3$) δ ppm 4.78-4.68 (1 H, m), 4.56-4.47 (1 H, m), 4.38-4.29 (1 H, m), 4.16 (1 H, ddd), 3.97 (1 H, dd), 3.91 (2 H, s), 2.56 (1 H, d) |
| Gen-13-d | $^1$H NMR (300 MHz, CDCl$_3$) δ ppm 5.49-5.40 (0.5 H, m), 5.32-5.20 (0.5 H, m), 4.69-4.50 (1 H, m), 4.49-4.29 (2 H, m), 4.28-4.10 (1 H, m), 3.93 (2 H, s) |
| Gen-13-f | $^1$H NMR (300 MHz, CDCl$_3$) δ ppm 4.18 (2 H, t), 3.96 (2 H, t), 3.73 (2 H, s), 2.27-2.14 (2 H, m) |
| Gen-13-j | $^1$H NMR (400 MHz, CDCl$_3$) δ ppm 5.33-5.01 (2 H, m), 4.60-4.41 (1 H, m), 3.79-3.65 (2 H, m), 3.63-3.44 (2 H, m), 1.97 (3 H, d), 1.90-1.80 (2 H, m) |

TABLE III

Illustrative compounds of the invention.

| Cpd | Structures | Name | Mtd (Int) | MW | MS Ms'd |
|---|---|---|---|---|---|
| 1 | 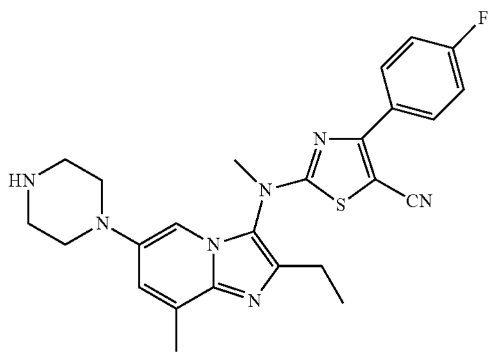 [SMILES: CCc1nc2c(C)cc(N3CCNCC3)cn2c1N(C)c1nc(-c2ccc(F)cc2)c(C#N)s1] | 2-((2-ethyl-8-methyl-6-(piperazin-1-yl)imidazo[1,2-a]pyridin-3-yl)(methyl)amino)-4-(4-fluorophenyl)thiazole-5-carbonitrile | F1b-F5b (Gen-5-t) | 475 | 476 (M + 1) |
| 2 | 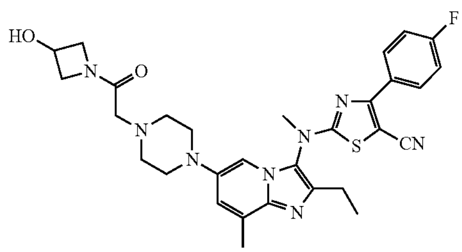 [SMILES: CCc1nc2c(C)cc(N3CCN(CC(=O)N4CC(O)C4)CC3)cn2c1N(C)c1nc(-c2ccc(F)cc2)c(C#N)s1] | 2-((2-ethyl-6-(4-(2-(3-hydroxyazetidin-1-yl)-2-oxoethyl)piperazin-1-yl)-8-methylimidazo[1,2-a]pyridin-3-yl)(methyl)amino)-4-(4-fluorophenyl)thiazole-5-carbonitrile | F8 (Cpd 1) | 588 | 589 (M + 1) |
| 3 | 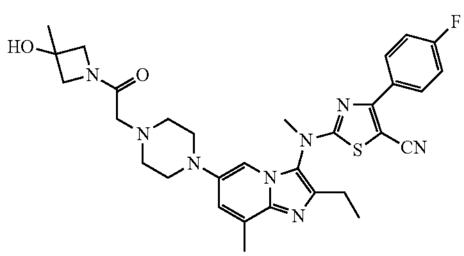 [SMILES: CCc1nc2c(C)cc(N3CCN(CC(=O)N4CC(C)(O)C4)CC3)cn2c1N(C)c1nc(-c2ccc(F)cc2)c(C#N)s1] | 2-((2-ethyl-6-(4-(2-(3-hydroxy-3-methylazetidin-1-yl)-2-oxoethyl)piperazin-1-yl)-8-methylimidazo[1,2-a]pyridin-3-yl)(methyl)amino)-4-(4-fluorophenyl)thiazole-5-carbonitrile | F8 (Cpd 1) | 602 | 603 (M + 1) |
| 4 | 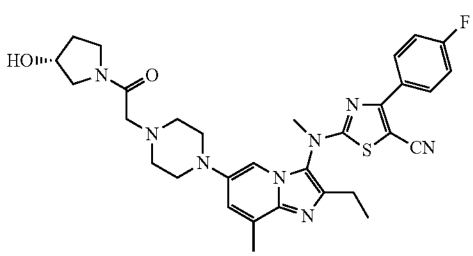 [SMILES: CCc1nc2c(C)cc(N3CCN(CC(=O)N4CC[C@@H](O)C4)CC3)cn2c1N(C)c1nc(-c2ccc(F)cc2)c(C#N)s1] | (R)-2-((2-ethyl-6-(4-(2-(3-hydroxypyrrolidin-1-yl)-2-oxoethyl)piperazin-1-yl)-8-methylimidazo[1,2-a]pyridin-3-yl)(methyl)amino)-4-(4-fluorophenyl)thiazole-5-carbonitrile | F8 (Cpd 1) | 602 | 603 (M + 1) |
| 5 | 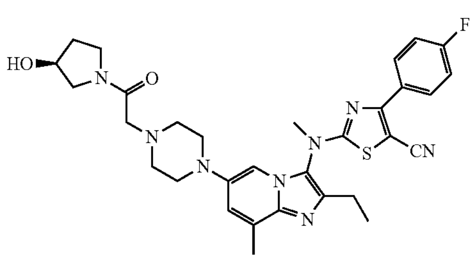 [SMILES: CCc1nc2c(C)cc(N3CCN(CC(=O)N4CC[C@H](O)C4)CC3)cn2c1N(C)c1nc(-c2ccc(F)cc2)c(C#N)s1] | (S)-2-((2-ethyl-6-(4-(2-(3-hydroxypyrrolidin-1-yl)-2-oxoethyl)piperazin-1-yl)-8-methylimidazo[1,2-a]pyridin-3-yl)(methyl)amino)-4-(4-fluorophenyl)thiazole-5-carbonitrile | B1/B2-C1-D1-E2-F1b-F5b-F8 (Cpd 1) | 602 | 603 (M + 1) |

TABLE III-continued

Illustrative compounds of the invention.

| Cpd | Structures | Name | Mtd (Int) | MW | MS Ms'd |
|---|---|---|---|---|---|
| 6 | 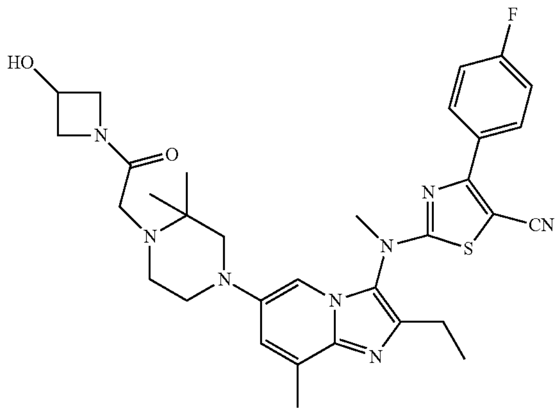 [SMILES: CCc1nc2c(C)cc(N3CCN(CC(=O)N4CC(O)C4)C(C)(C)C3)cn2c1N(C)c1nc(-c2ccc(F)cc2)c(C#N)s1] | 2-((2-ethyl-6-(4-(2-(3-hydroxyazetidin-1-yl)-2-oxoethyl)-3,3-dimethylpiperazin-1-yl)-8-methylimidazo[1,2-a]pyridin-3-yl)(methyl)amino)-4-(4-fluorophenyl)thiazole-5-carbonitrile | F8 (Gen-10-x) | 616 | 617 (M + 1) |
| 7 | 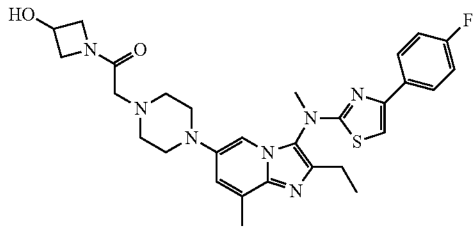 [SMILES: CCc1nc2c(C)cc(N3CCN(CC(=O)N4CC(O)C4)CC3)cn2c1N(C)c1nc(-c2ccc(F)cc2)cs1] | 2-(4-(2-ethyl-3-((4-(4-fluorophenyl)thiazol-2-yl)(methyl)amino)-8-methylimidazo[1,2-a]pyridin-6-yl)piperazin-1-yl)-1-(3-hydroxyazetidin-1-yl)ethanone | F8 (Gen-10n) | 563 | 564 (M + 1) |
| 8 | 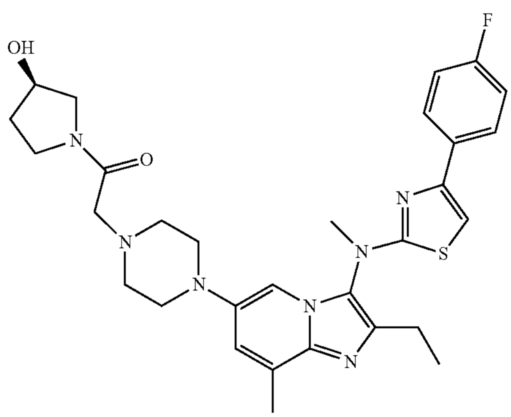 [SMILES: CCc1nc2c(C)cc(N3CCN(CC(=O)N4CC[C@@H](O)C4)CC3)cn2c1N(C)c1nc(-c2ccc(F)cc2)cs1] | (R)-2-(4-(2-ethyl-3-((4-(4-fluorophenyl)thiazol-2-yl)(methyl)amino)-8-methylimidazo[1,2-a]pyridin-6-yl)piperazin-1-yl)-1-(3-hydroxypyrrolidin-1-yl)ethanone | F8 (Gen-10n) | 577 | 578 (M + 1) |
| 9 | 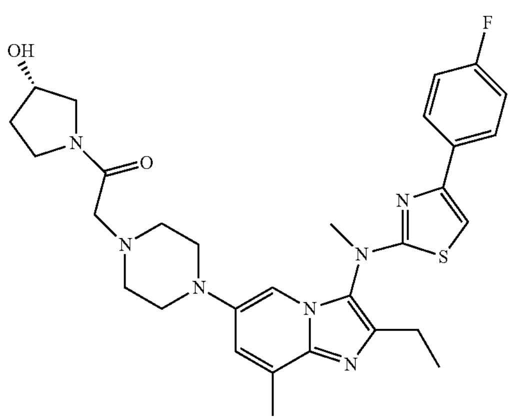 [SMILES: CCc1nc2c(C)cc(N3CCN(CC(=O)N4CC[C@H](O)C4)CC3)cn2c1N(C)c1nc(-c2ccc(F)cc2)cs1] | (S)-2-(4-(2-ethyl-3-((4-(4-fluorophenyl)thiazol-2-yl)(methyl)amino)-8-methylimidazo[1,2-a]pyridin-6-yl)piperazin-1-yl)-1-(3-hydroxypyrrolidin-1-yl)ethanone | F8 (Gen-10n) | 577 | 578 (M + 1) |

TABLE III-continued

Illustrative compounds of the invention.

| Cpd | Structures | Name | Mtd (Int) | MW | MS Ms'd |
|---|---|---|---|---|---|
| 10 | 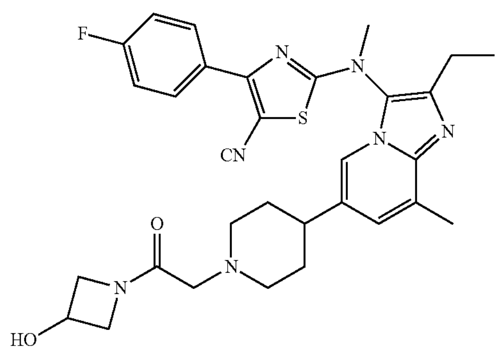 | 2-((2-ethyl-6-(1-(2-(3-hydroxyazetidin-1-yl)-2-oxoethyl)piperidin-4-yl)-8-methylimidazo[1,2-a]pyridin-3-yl)(methyl)amino)-4-(4-fluorophenyl)thiazole-5-carbonitrile | F8 (Gen-10-o) | 587 | 588 (M + 1) |
| 11 | 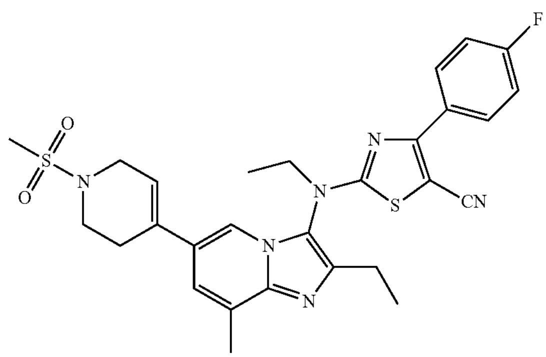 [SMILES: CCc1nc2c(C)cc(C3=CCN(S(C)(=O)=O)CC3)cn2c1N(CC)c1nc(-c2ccc(F)cc2)c(C#N)s1] | 2-(ethyl(2-ethyl-8-methyl-6-(1-(methylsulfonyl)-1,2,3,6-tetrahydropyridin-4-yl)imidazo[1,2-a]pyridin-3-yl)amino)-4-(4-fluorophenyl)thiazole-5-carbonitrile | F2 (Gen-5-h) | 564 | 565 (M + 1) |
| 12 | 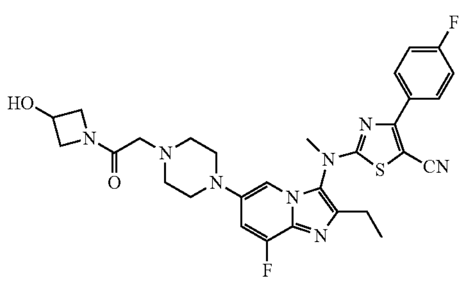 [SMILES: CCc1nc2c(F)cc(N3CCN(CC(=O)N4CC(O)C4)CC3)cn2c1N(C)c1nc(-c2ccc(F)cc2)c(C#N)s1] | 2-((2-ethyl-8-fluoro-6-(4-(2-(3-hydroxyazetidin-1-yl)-2-oxoethyl)piperazin-1-yl)imidazo[1,2-a]pyridin-3-yl)(methyl)amino)-4-(4-fluorophenyl)thiazole-5-carbonitrile | F8 (Gen-10-m) | 592 | 593 (M + 1) |
| 13 | 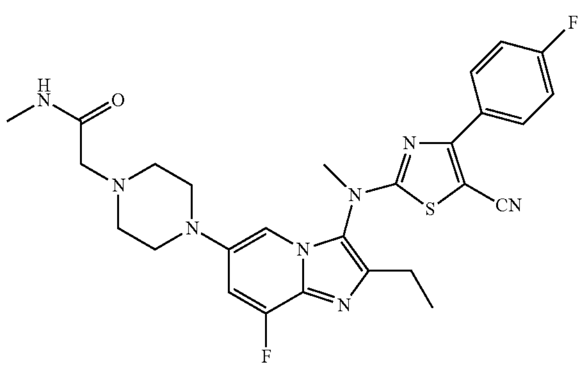 [SMILES: CCc1nc2c(F)cc(N3CCN(CC(=O)NC)CC3)cn2c1N(C)c1nc(-c2ccc(F)cc2)c(C#N)s1] | 2-(4-(3-((5-cyano-4-(4-fluorophenyl)thiazol-2-yl)(methyl)amino)-2-ethyl-8-fluoroimidazo[1,2-a]pyridin-6-yl)piperazin-1-yl)-N-methylacetamide | F8 (Gen-10-m) | 550 | 551 (M + 1) |

TABLE III-continued

Illustrative compounds of the invention.

| Cpd | Structures | Name | Mtd (Int) | MW | MS Ms'd |
|---|---|---|---|---|---|
| 14 | 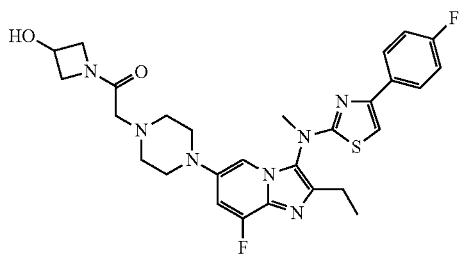 [SMILES: CCc1nc2c(F)cc(N3CCN(CC(=O)N4CC(O)C4)CC3)cn2c1N(C)c1nc(-c2ccc(F)cc2)cs1] | 2-(4-(2-ethyl-8-fluoro-3-((4-(4-fluorophenyl)thiazol-2-yl)(methyl)amino)imidazo[1,2-a]pyridin-6-yl)piperazin-1-yl)-1-(3-hydroxyazetidin-1-yl)ethanone | F8 (Gen-10-l) | 567 | 568 (M + 1) |
| 15 | 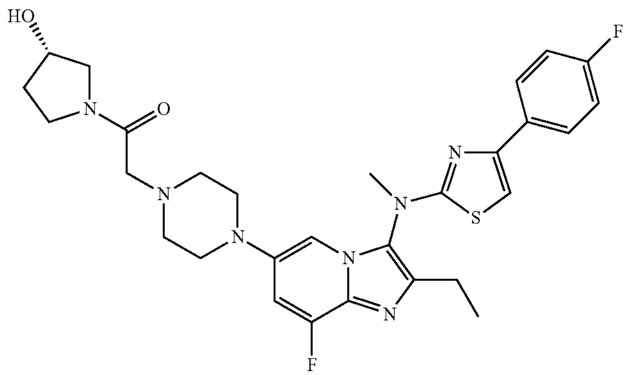 [SMILES: CCc1nc2c(F)cc(N3CCN(CC(=O)N4CC[C@H](O)C4)CC3)cn2c1N(C)c1nc(-c2ccc(F)cc2)cs1] | (S)-2-(4-(2-ethyl-8-fluoro-3-((4-(4-fluorophenyl)thiazol-2-yl)(methyl)amino)imidazo[1,2-a]pyridin-6-yl)piperazin-1-yl)-1-(3-hydroxypyrrolidin-1-yl)ethanone | F8 (Gen-10-l) | 581 | 582 (M + 1) |
| 16 | 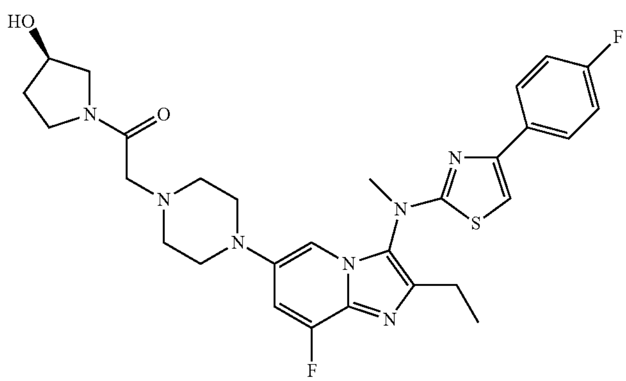 [SMILES: CCc1nc2c(F)cc(N3CCN(CC(=O)N4CC[C@@H](O)C4)CC3)cn2c1N(C)c1nc(-c2ccc(F)cc2)cs1] | (R)-2-(4-(2-ethyl-8-fluoro-3-((4-(4-fluorophenyl)thiazol-2-yl)(methyl)amino)imidazo[1,2-a]pyridin-6-yl)piperazin-1-yl)-1-(3-hydroxypyrrolidin-1-yl)ethanone | F8 (Gen-10-l) | 581 | 582 (M + 1) |
| 17 | 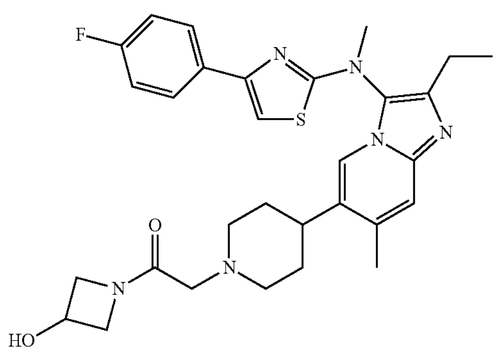 [SMILES: CCc1nc2cc(C)c(C3CCN(CC(=O)N4CC(O)C4)CC3)cn2c1N(C)c1nc(-c2ccc(F)cc2)cs1] | 2-(4-(2-ethyl-3-((4-(4-fluorophenyl)thiazol-2-yl)(methyl)amino)-7-methylimidazo[1,2-a]pyridin-6-yl)piperidin-1-yl)-1-(3-hydroxyazetidin-1-yl)ethanone | F8 (Gen-10-s) | 562 | 563 (M + 1) |

TABLE III-continued

Illustrative compounds of the invention.

| Cpd | Structures | Name | Mtd (Int) | MW | MS Ms'd |
|---|---|---|---|---|---|
| 18 | 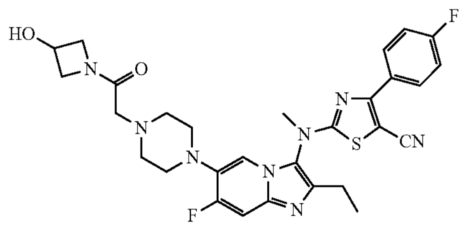 [SMILES: CCc1nc2cc(F)c(N3CCN(CC(=O)N4CC(O)C4)CC3)cn2c1N(C)c1nc(-c2ccc(F)cc2)c(C#N)s1] | 2-[(2-Ethyl-7-fluoro-6-{4-[2-(3-hydroxy-azetidin-1-yl)-2-oxo-ethyl]-piperazin-1-yl}-imidazo[1,2-a]pyridin-3-yl)-methyl-amino]-4-(4-fluoro-phenyl)-thiazole-5-carbonitrile | F8 (Gen-10-r) | 592 | 593 (M + 1) |
| 19 | 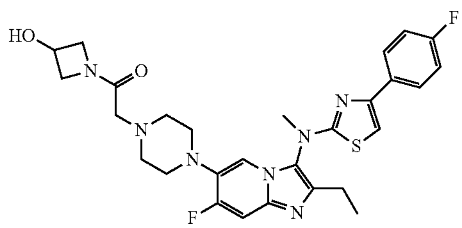 [SMILES: CCc1nc2cc(F)c(N3CCN(CC(=O)N4CC(O)C4)CC3)cn2c1N(C)c1nc(-c2ccc(F)cc2)cs1] | 2-[4-(2-Ethyl-7-fluoro-3-{[4-(4-fluoro-phenyl)-thiazol-2-yl]-methyl-amino}-imidazo[1,2-a]pyridin-6-yl)-piperazin-1-yl]-1-(3-hydroxy-azetidin-1-yl)-ethanone | F8 (Gen-10-q) | 567 | 568 (M + 1) |
| 20 | 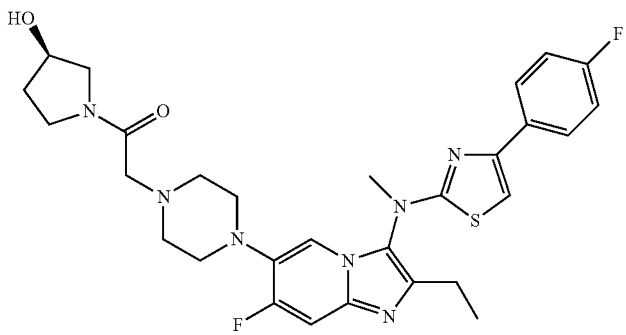 [SMILES: CCc1nc2cc(F)c(N3CCN(CC(=O)N4CC[C@@H](O)C4)CC3)cn2c1N(C)c1nc(-c2ccc(F)cc2)cs1] | (R)-2-[4-(2-Ethyl-7-fluoro-3-{[4-(4-fluoro-phenyl)-thiazol-2-yl]-methyl-amino}-imidazo[1,2-a]pyridin-6-yl)-piperazin-1-yl]-1-(3-hydroxy-pyrrolidin-1-yl)-ethanone | A-B1-C1-D2-E1-F1a-F8 (Gen-10-q) | 581 | 594 (M + Na) |
| 21 | 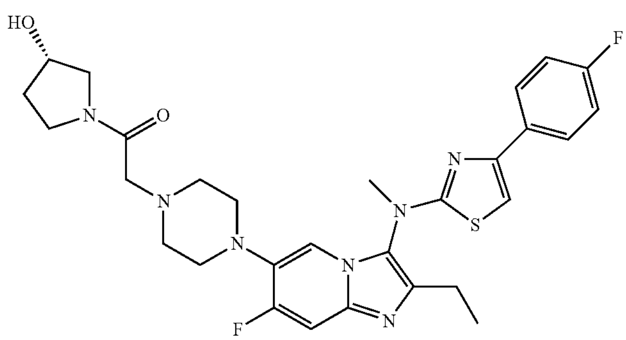 [SMILES: CCc1nc2cc(F)c(N3CCN(CC(=O)N4CC[C@H](O)C4)CC3)cn2c1N(C)c1nc(-c2ccc(F)cc2)cs1] | (S)-2-[4-(2-Ethyl-7-fluoro-3-{[4-(4-fluoro-phenyl)-thiazol-2-yl]-methyl-amino}-imidazo[1,2-a]pyridin-6-yl)-piperazin-1-yl]-1-(3-hydroxy-pyrrolidin-1-yl)-ethanone | F8 (Gen-10-q) | 581 | 594 (M + Na) |
| 22 | 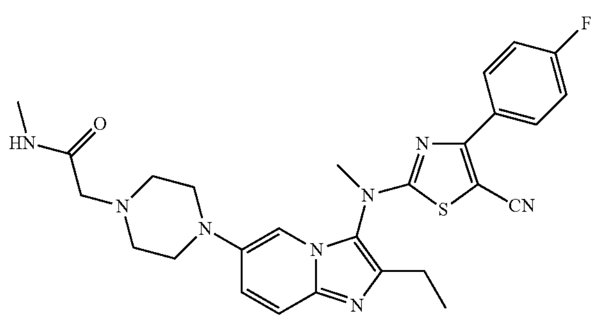 | 2-(4-(3-((5-cyano-4-(4-fluorophenyl)thiazol-2-yl)(methyl)amino)-2-ethylimidazo[1,2-a]pyridin-6-yl)piperazin-1-yl)-N-methylacetamide | F8 (Gen-10-k) | 587 | 588 (M + 1) |

TABLE III-continued

Illustrative compounds of the invention.

| Cpd | Structures | Name | Mtd (Int) | MW | MS Ms'd |
|---|---|---|---|---|---|
| 23 | 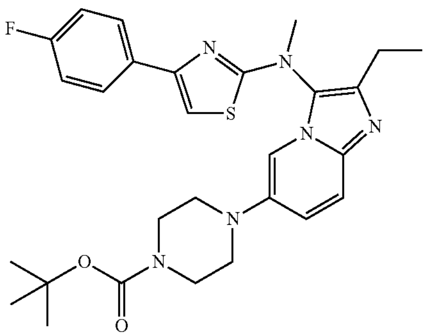 [SMILES: CCc1nc2ccc(N3CCN(C(=O)OC(C)(C)C)CC3)cn2c1N(C)c1nc(-c2ccc(F)cc2)cs1] | tert-butyl 4-(2-ethyl-3-((4-(4-fluorophenyl)thiazol-2-yl)(methyl)amino)imidazo[1,2-a]pyridin-6-yl)piperazine-1-carboxylate | F1b (Gen-5-c) | 536 | 537 (M + 1) |
| 24 | 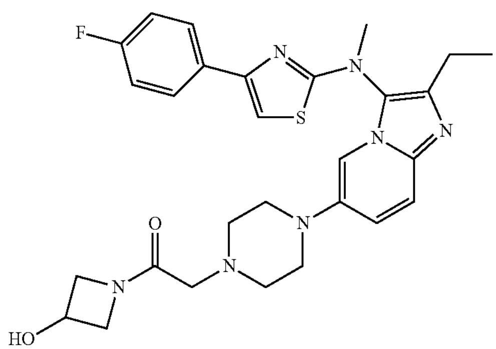 [SMILES: CCc1nc2ccc(N3CCN(CC(=O)N4CC(O)C4)CC3)cn2c1N(C)c1nc(-c2ccc(F)cc2)cs1] | 2-(4-(2-ethyl-3-((4-(4-fluorophenyl)thiazol-2-yl)(methyl)amino)imidazo[1,2-a]pyridin-6-yl)piperazin-1-yl)-1-(3-hydroxyazetidin-1-yl)ethanone | F8 (Gen-10-e) | 549 | 550 (M + 1) |
| 25 | 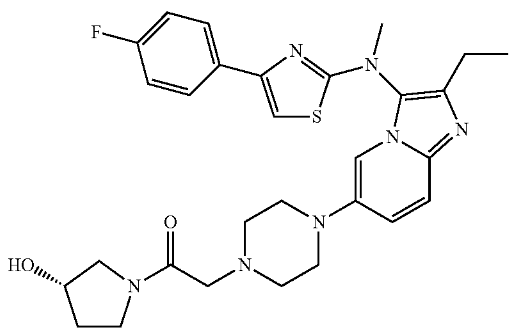 [SMILES: CCc1nc2ccc(N3CCN(CC(=O)N4CC[C@H](O)C4)CC3)cn2c1N(C)c1nc(-c2ccc(F)cc2)cs1] | (S)-2-(4-(2-ethyl-3-((4-4-fluorophenyl)thiazol-2-yl)(methyl)amino)imidazo[1,2-a]pyridin-6-yl)piperazin-1-yl)-1-(3-hydroxypyrrolidin-1-yl)ethanone | F8 (Gen-10-e) | 563 | 564 (M + 1) |
| 26 | 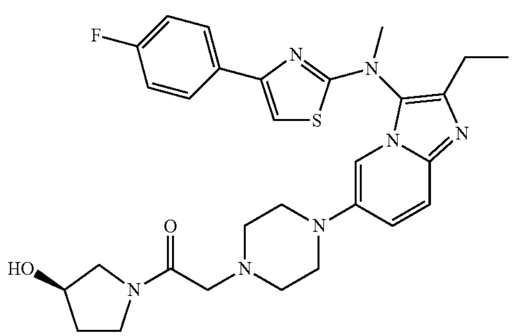 [SMILES: CCc1nc2ccc(N3CCN(CC(=O)N4CC[C@@H](O)C4)CC3)cn2c1N(C)c1nc(-c2ccc(F)cc2)cs1] | (R)-2-(4-(2-ethyl-3-((4-(4-fluorophenyl)thiazol-2-yl)(methyl)amino)imidazo[1,2-a]pyridin-6-yl)piperazin-1-yl)-1-(3-hydroxypyrrolidin-1-yl)ethanone | F8 (Gen-10-e) | 563 | 564 (M + 1) |

TABLE III-continued

Illustrative compounds of the invention.

| Cpd | Structures | Name | Mtd (Int) | MW | MS Ms'd |
|---|---|---|---|---|---|
| 27 | 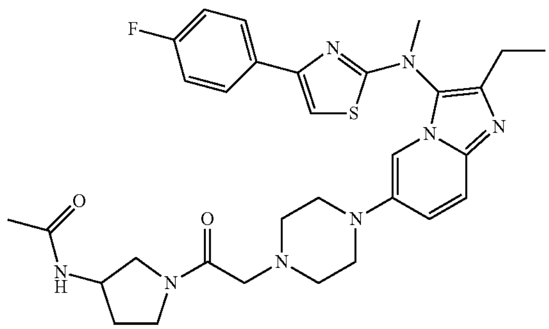 [SMILES: CCc1nc2ccc(N3CCN(CC(=O)N4CCC(NC(C)=O)C4)CC3)cn2c1N(C)c1nc(-c2ccc(F)cc2)cs1] | N-(1-(2-(4-(2-ethyl-3-((4-(4-fluorophenyl)thiazol-2-yl)(methyl)amino)imidazo[1,2-a]pyridin-6-yl)piperazin-1-yl)acetoyl)pyrrolidin-3-yl)acetamide | F8 (Gen-10-e) | 604 | 605 (M + 1) |
| 28 | 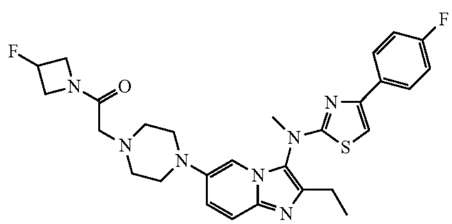 [SMILES: CCc1nc2ccc(N3CCN(CC(=O)N4CC(F)C4)CC3)cn2c1N(C)c1nc(-c2ccc(F)cc2)cs1] | 2-(4-(2-ethyl-3-((4-(4-fluorophenyl)thiazol-2-yl)(methyl)amino)imidazo[1,2-a]pyridin-6-yl)piperazin-1-yl)-1-(3-fluoroazetidin-1-yl)ethanone | F8 (Gen-10-e) | 551 | 552 (M + 1) |
| 29 | 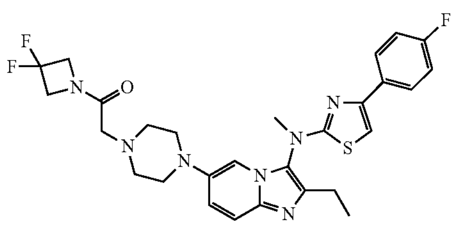 [SMILES: CCc1nc2ccc(N3CCN(CC(=O)N4CC(F)(F)C4)CC3)cn2c1N(C)c1nc(-c2ccc(F)cc2)cs1] | 1-(3,3-difluoroazetidin-1-yl)-2-(4-(2-ethyl-3-((4-(4-fluorophenyl)thiazol-2-yl)(methyl)amino)imidazo[1,2-a]pyridin-6-yl)piperazin-1-yl)ethanone | F8 (Gen-10-e) | 569 | 570 (M + 1) |
| 30 | 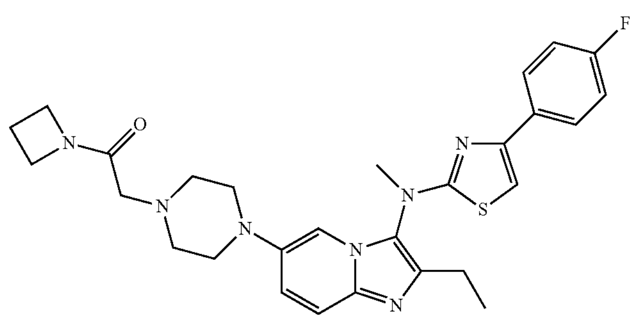 [SMILES: CCc1nc2ccc(N3CCN(CC(=O)N4CCC4)CC3)cn2c1N(C)c1nc(-c2ccc(F)cc2)cs1] | 1-(azetidin-1-yl)-2-(4-(2-ethyl-3-((4-(4-fluorophenyl)thiazol-2-yl)(methyl)amino)imidazo[1,2-a]pyridin-6-yl)piperazin-1-yl)ethanone | F8 (Gen-10-e) | 533 | 534 (M + 1) |
| 31 | 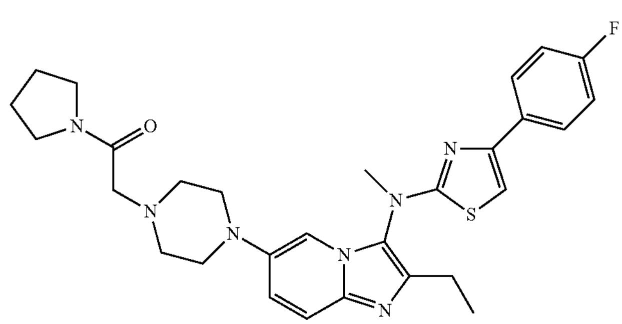 [SMILES: CCc1nc2ccc(N3CCN(CC(=O)N4CCCC4)CC3)cn2c1N(C)c1nc(-c2ccc(F)cc2)cs1] | 2-(4-(2-ethyl-3-((4-(4-fluorophenyl)thiazol-2-yl)(methyl)amino)imidazo[1,2-a]pyridin-6-yl)piperazin-1-yl)-1-(pyrrolidin-1-yl)ethanone | F8 (Gen-10-e) | 547 | 548 (M + 1) |

TABLE III-continued

Illustrative compounds of the invention.

| Cpd | Structures | Name | Mtd (Int) | MW | MS Ms'd |
|---|---|---|---|---|---|
| 32 | 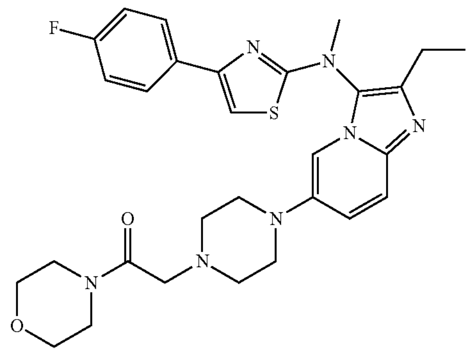 [SMILES: CCc1nc2ccc(N3CCN(CC(=O)N4CCOCC4)CC3)cn2c1N(C)c1nc(-c2ccc(F)cc2)cs1] | 2-(4-(2-ethyl-3-((4-(4-fluorophenyl)thiazol-2-yl)(methyl)amino)imidazo[1,2-a]pyridin-6-yl)piperazin-1-yl)-1-morpholinoethanone | F8 (Gen-10-e) | 563 | 564 (M + 1) |
| 33 | 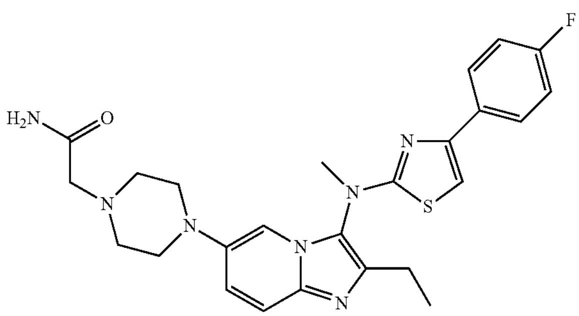 [SMILES: CCc1nc2ccc(N3CCN(CC(N)=O)CC3)cn2c1N(C)c1nc(-c2ccc(F)cc2)cs1] | 2-(4-(2-ethyl-3-((4-(4-fluorophenyl)thiazol-2-yl)(methyl)amino)imidazo[1,2-a]pyridin-6-yl)piperazin-1-yl)acetamide | F8 (Gen-10-e) | 493 | 494 (M + 1) |
| 34 | 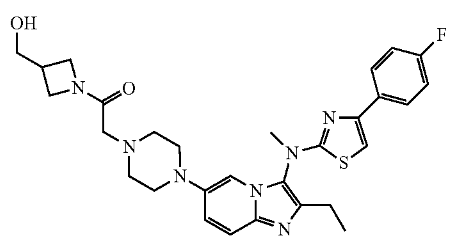 [SMILES: CCc1nc2ccc(N3CCN(CC(=O)N4CC(CO)C4)CC3)cn2c1N(C)c1nc(-c2ccc(F)cc2)cs1] | 2-(4-(2-ethyl-3-((4-(4-fluorophenyl)thiazol-2-yl)(methyl)amino)imidazo[1,2-a]pyridin-6-yl)piperazin-1-yl)-1-(3-(hydroxymethyl)azetidin-1-yl)ethanone | F8 (Gen-10-e) | 563 | 564 (M + 1) |
| 35 | 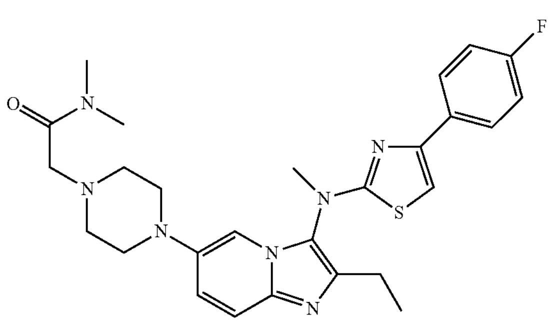 [SMILES: CCc1nc2ccc(N3CCN(CC(=O)N(C)C)CC3)cn2c1N(C)c1nc(-c2ccc(F)cc2)cs1] | 2-(4-(2-ethyl-3-((4-(4-fluorophenyl)thiazol-2-yl)(methyl)amino)imidazo[1,2-a]pyridin-6-yl)piperazin-1-yl)-N,N-dimethylacetamide | F8 (Gen-10-e) | 521 | 522 (M + 1) |
| 36 | 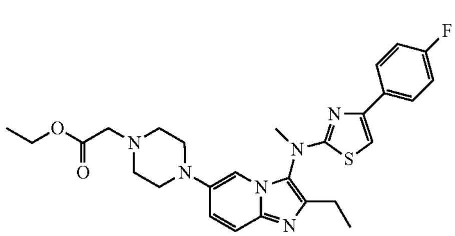 [SMILES: CCOC(=O)CN1CCN(c2ccc3nc(CC)c(N(C)c4nc(-c5ccc(F)cc5)cs4)n3c2)CC1] | ethyl 2-(4-(2-ethyl-3-((4-(4-fluorophenyl)thiazol-2-yl)(methyl)amino)imidazo[1,2-a]pyridin-6-yl)piperazin-1-yl)acetate | F8 (Gen-10-e) | 522 | 523 (M + 1) |

TABLE III-continued

Illustrative compounds of the invention.

| Cpd | Structures | Name | Mtd (Int) | MW | MS Ms'd |
|---|---|---|---|---|---|
| 37 | 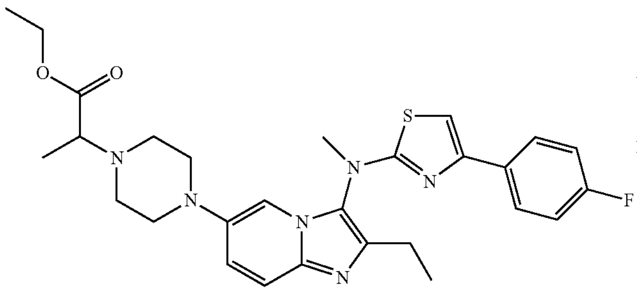 [SMILES: CCOC(=O)C(C)N1CCN(c2ccc3nc(CC)c(N(C)c4nc(-c5ccc(F)cc5)cs4)n3c2)CC1] | ethyl 2-(4-(2-ethyl-3-((4-(4-fluorophenyl)thiazol-2-yl)(methyl)amino) imidazo[1,2-a]pyridin-6-yl)piperazin-1-yl) propanoate | F8 (Gen-10-e) | 536 | 537 (M + 1) |
| 38 | 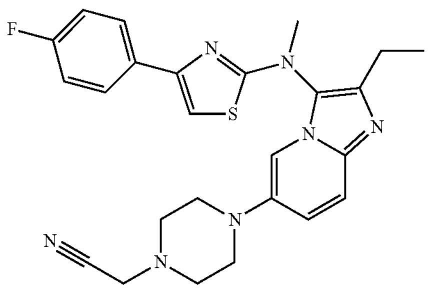 [SMILES: CCc1nc2ccc(N3CCN(CC#N)CC3)cn2c1N(C)c1nc(-c2ccc(F)cc2)cs1] | 2-(4-(2-ethyl-3-((4-(4-fluorophenyl)thiazol-2-yl)(methyl)amino) imidazo[1,2-a]pyridin-6-yl)piperazin-1-yl)acetonitrile | F8 (Gen-10-e) | 475 | 476 (M + 1) |
| 39 | 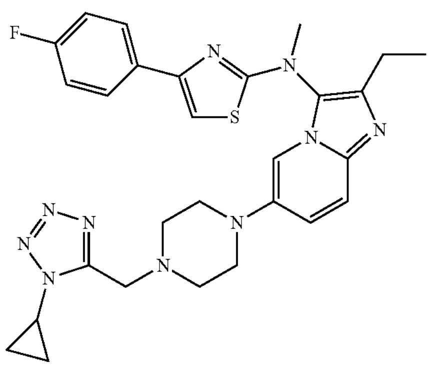 [SMILES: CCc1nc2ccc(N3CCN(Cc4nnnn4C4CC4)CC3)cn2c1N(C)c1nc(-c2ccc(F)cc2)cs1] | N-(6-(4-((1-cyclopropyl-1H-tetrazol-5-yl)methyl)piperazin-1-yl)-2-ethylimidazo[1,2-a]pyridin-3-yl)-4-(4-fluorophenyl)-N-methylthiazol-2-amine | F8 (Gen-10-e) | 558 | 559 (M + 1) |
| 40 | 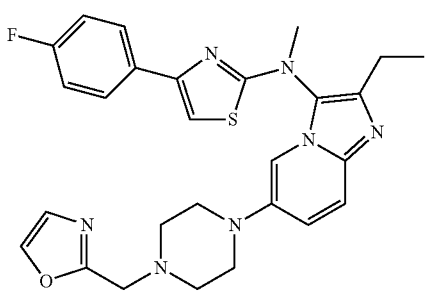 [SMILES: CCc1nc2ccc(N3CCN(Cc4ncco4)CC3)cn2c1N(C)c1nc(-c2ccc(F)cc2)cs1] | N-(2-ethyl-6-(4-(oxazol-2-ylmethyl)piperazin-1-yl)imidazo[1,2-a]pyridin-3-yl)-4-(4-fluorophenyl)-N-methylthiazol-2-amine | F8 (Gen-10-e) | 517 | 518 (M + 1) |
| 41 | 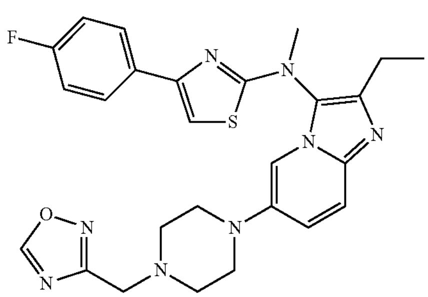 [SMILES: CCc1nc2ccc(N3CCN(Cc4ncon4)CC3)cn2c1N(C)c1nc(-c2ccc(F)cc2)cs1] | N-(6-(4-((1,2,4-oxadiazol-3-yl)methyl)piperazin-1-yl)-2-ethylimidazo[1,2-a]pyridin-3-yl)-4-(4-fluorophenyl)-N-methylthiazol-2-amine | F8 (Gen-10-e) | 518 | 519 (M + 1) |

TABLE III-continued

Illustrative compounds of the invention.

| Cpd | Structures | Name | Mtd (Int) | MW | MS Ms'd |
|---|---|---|---|---|---|
| 42 | 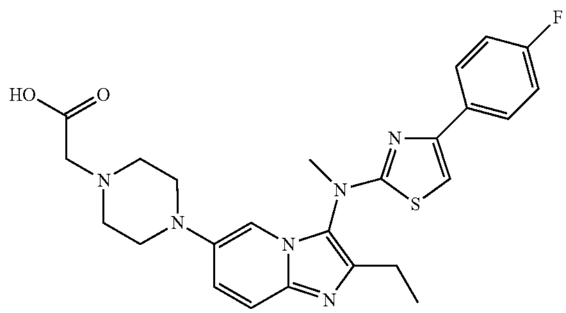 [SMILES: CCc1nc2ccc(N3CCN(CC(=O)O)CC3)cn2c1N(C)c1nc(-c2ccc(F)cc2)cs1] | 2-(4-(2-ethyl-3-((4-(4-fluorophenyl)thiazol-2-yl)(methyl)amino)imidazo[1,2-a]pyridin-6-yl)piperazin-1-yl)acetic acid | F13 (Cpd 36) | 494 | 495 (M + 1) |
| 43 | 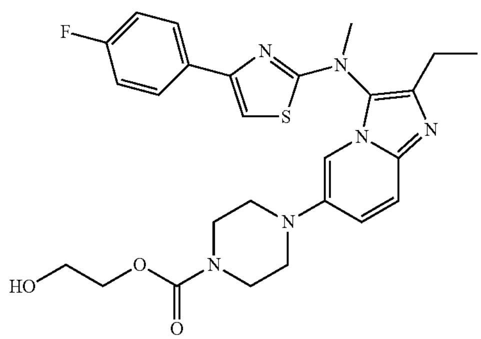 [SMILES: CCc1nc2ccc(N3CCN(C(=O)OCCO)CC3)cn2c1N(C)c1nc(-c2ccc(F)cc2)cs1] | 2-hydroxyethyl 4-(2-ethyl-3-((4-(4-fluorophenyl)thiazol-2-yl)(methyl)amino)imidazo[1,2-a]pyridin-6-yl)piperazine-1-carboxylate | see Cpd 43 (Gen-10-e) | 524 | 525 (M + 1) |
| 44 | 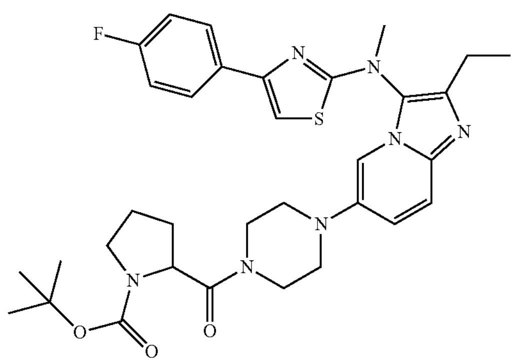 [SMILES: CCc1nc2ccc(N3CCN(C(=O)C4CCCN4C(=O)OC(C)(C)C)CC3)cn2c1N(C)c1nc(-c2ccc(F)cc2)cs1] | tert-butyl 2-(4-(2-ethyl-3-((4-(4-fluorophenyl)thiazol-2-yl)(methyl)amino)imidazo[1,2-a]pyridin-6-yl)piperazine-1-carbonyl)pyrrolidine-1-carboxylate | F9a (Gen-10-e) | 633 | 634 (M + 1) |
| 45 | 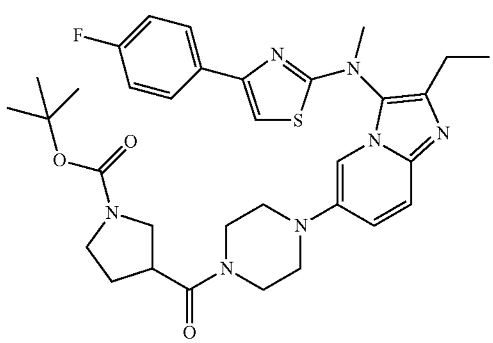 [SMILES: CCc1nc2ccc(N3CCN(C(=O)C4CCN(C(=O)OC(C)(C)C)C4)CC3)cn2c1N(C)c1nc(-c2ccc(F)cc2)cs1] | tert-butyl 3-(4-(2-ethyl-3-((4-(4-fluorophenyl)thiazol-2-yl)(methyl)amino)imidazo[1,2-a]pyridin-6-yl)piperazine-1-carbonyl)pyrrolidine-1-carboxylate | F9a (Gen-10-e) | 633 | 634 (M + 1) |

TABLE III-continued

Illustrative compounds of the invention.

| Cpd | Structures | Name | Mtd (Int) | MW | MS Ms'd |
|---|---|---|---|---|---|
| 46 | 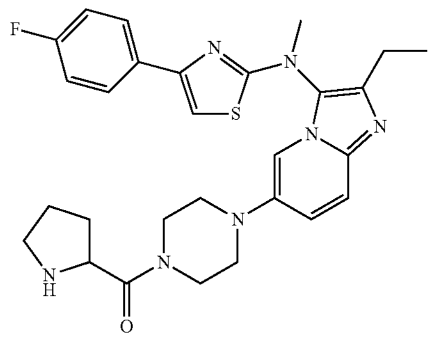 [SMILES: CCc1nc2ccc(N3CCN(C(=O)C4CCCN4)CC3)cn2c1N(C)c1nc(-c2ccc(F)cc2)cs1] | (4-(2-ethyl-3-((4-(4-fluorophenyl)thiazol-2-yl)(methyl)amino) imidazo[1,2-a]pyridin-6-yl)piperazin-1-yl)(pyrrolidin-2-yl)methanone | F5b (Cpd 44) | 533 | 534 (M + 1) |
| 47 | 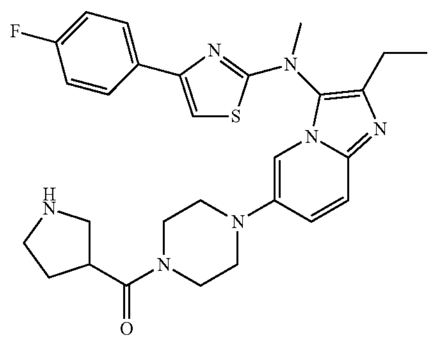 [SMILES: CCc1nc2ccc(N3CCN(C(=O)C4CCNC4)CC3)cn2c1N(C)c1nc(-c2ccc(F)cc2)cs1] | (4-(2-ethyl-3-((4-(4-fluorophenyl)thiazol-2-yl)(methyl)amino) imidazo[1,2-a]pyridin-6-yl)piperazin-1-yl)(pyrrolidin-3-yl)methanone | F5b (Cpd 45) | 533 | 534 (M + 1) |
| 48 | 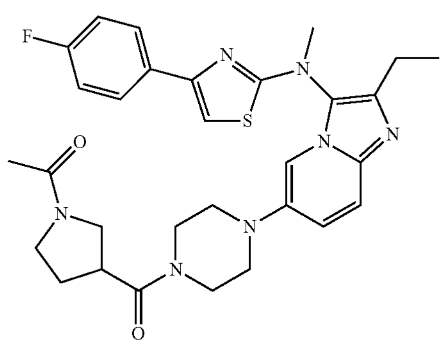 [SMILES: CCc1nc2ccc(N3CCN(C(=O)C4CCN(C(C)=O)C4)CC3)cn2c1N(C)c1nc(-c2ccc(F)cc2)cs1] | 1-(3-(4-(2-ethyl-3-((4-(4-fluorophenyl)thiazol-2-yl)(methyl)amino) imidazo[1,2-a]pyridin-6-yl)piperazine-1-carbonyl)pyrrolidin-1-yl)ethanone | F9b (Cpd 47) | 575 | 576 (M + 1) |
| 49 | 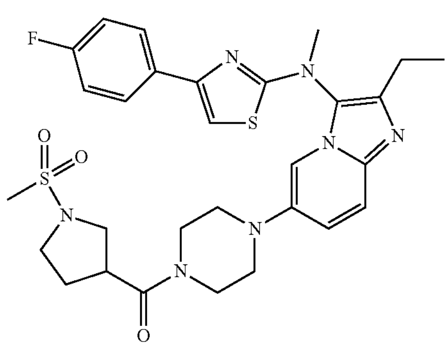 [SMILES: CCc1nc2ccc(N3CCN(C(=O)C4CCN(S(C)(=O)=O)C4)CC3)cn2c1N(C)c1nc(-c2ccc(F)cc2)cs1] | (4-(2-ethyl-3-((4-(4-fluorophenyl)thiazol-2-yl)(methyl)amino) imidazo[1,2-a]pyridin-6-yl)piperazin-1-yl)(1-(methylsulfonyl) pyrrolidin-3-yl) methanone | F11 (Cpd 47) | 611 | 612 (M + 1) |

TABLE III-continued

Illustrative compounds of the invention.

| Cpd | Structures | Name | Mtd (Int) | MW | MS Ms'd |
|---|---|---|---|---|---|
| 50 | 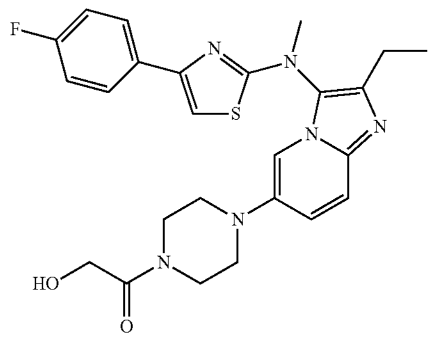 [SMILES: CCc1nc2ccc(N3CCN(C(=O)CO)CC3)cn2c1N(C)c1nc(-c2ccc(F)cc2)cs1] | 1-(4-(2-ethyl-3-((4-(4-fluorophenyl)thiazol-2-yl)(methyl)amino) imidazo[1,2-a]pyridin-6-yl)piperazin-1-yl)-2-hydroxyethanone | F9a (Gen-10-e) | 494 | 495 (M + 1) |
| 51 | 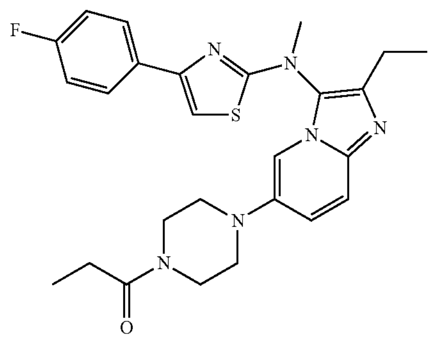 [SMILES: CCC(=O)N1CCN(c2ccc3nc(CC)c(N(C)c4nc(-c5ccc(F)cc5)cs4)n3c2)CC1] | 1-(4-(2-ethyl-3-((4-(4-fluorophenyl)thiazol-2-yl)(methyl)amino) imidazo[1,2-a]pyridin-6-yl)piperazin-1-yl)propan-1-one | F9b (Gen-10-e) | 492 | 493 (M + 1) |
| 52 | 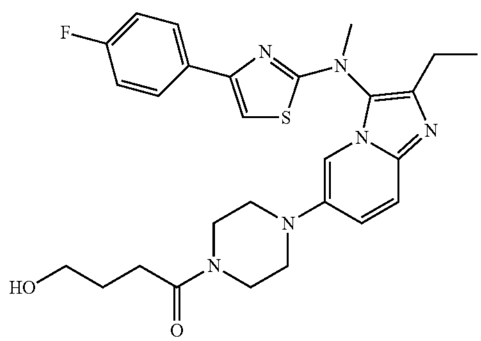 [SMILES: CCc1nc2ccc(N3CCN(C(=O)CCCO)CC3)cn2c1N(C)c1nc(-c2ccc(F)cc2)cs1] | 1-(4-(2-ethyl-3-((4-(4-fluorophenyl)thiazol-2-yl)(methyl)amino) imidazo[1,2-a]pyridin-6-yl)piperazin-1-yl)-4-hydroxybutan-1-one | F9b (Gen-10-e) | 522 | 523 (M + 1) |
| 53 | 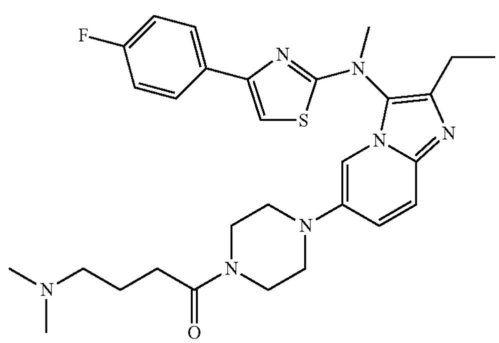 [SMILES: CCc1nc2ccc(N3CCN(C(=O)CCCN(C)C)CC3)cn2c1N(C)c1nc(-c2ccc(F)cc2)cs1] | 4-(dimethylamino)-1-(4-(2-ethyl-3-((4-(4-fluorophenyl)thiazol-2-yl)(methyl)amino) imidazo[1,2-a]pyridin-6-yl)piperazin-1-yl) butan-1-one | F9b-F12a (Gen-10-e) | 549 | 550 (M + 1) |

TABLE III-continued

Illustrative compounds of the invention.

| Cpd | Structures | Name | Mtd (Int) | MW | MS Ms'd |
|---|---|---|---|---|---|
| 54 | 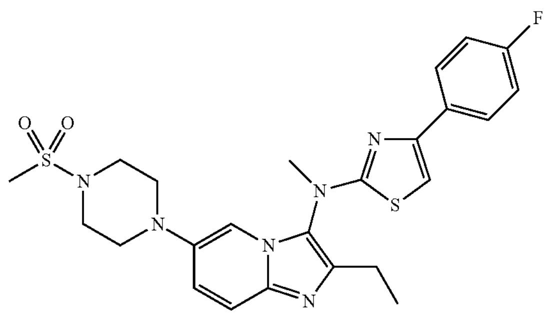 [SMILES: CCc1nc2ccc(N3CCN(S(C)(=O)=O)CC3)cn2c1N(C)c1nc(-c2ccc(F)cc2)cs1] | N-(2-ethyl-6-(4-(methylsulfonyl)piperazin-1-yl)imidazo[1,2-a]pyridin-3-yl)-4-(4-fluorophenyl)-N-methylthiazol-2-amine | F11 (Gen-10-e) | 514 | 515 (M + 1) |
| 55 | 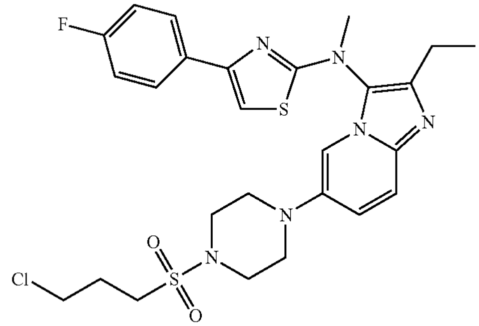 [SMILES: CCc1nc2ccc(N3CCN(S(=O)(=O)CCCCl)CC3)cn2c1N(C)c1nc(-c2ccc(F)cc2)cs1] | N-(6-(4-(3-chloropropylsulfonyl)piperazin-1-yl)-2-ethylimidazo[1,2-a]pyridin-3-yl)-4-(4-fluorophenyl)-N-methylthiazol-2-amine | F11 (Gen-10-e) | 576 | 577 (M + 1) |
| 56 | 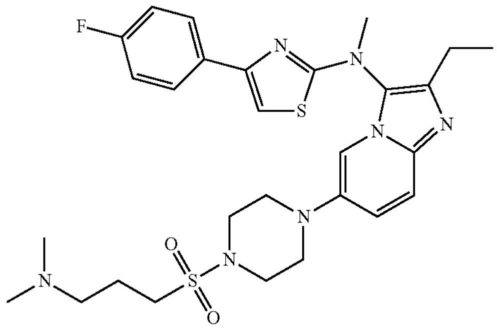 [SMILES: CCc1nc2ccc(N3CCN(S(=O)(=O)CCCN(C)C)CC3)cn2c1N(C)c1nc(-c2ccc(F)cc2)cs1] | N-(6-(4-(3-(dimethylamino)propylsulfonyl)piperazin-1-yl)-2-ethylimidazo[1,2-a]pyridin-3-yl)-4-(4-fluorophenyl)-N-methylthiazol-2-amine | F12a (Cpd 55) | 585 | 586 (M + 1) |
| 57 | 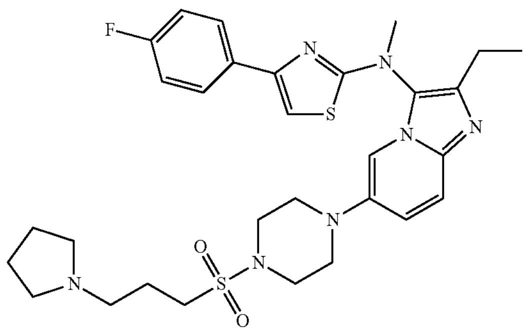 [SMILES: CCc1nc2ccc(N3CCN(S(=O)(=O)CCCN4CCCC4)CC3)cn2c1N(C)c1nc(-c2ccc(F)cc2)cs1] | N-(2-ethyl-6-(4-(3-(pyrrolidin-1-yl)propylsulfonyl)piperazin-1-yl)imidazo[1,2-a]pyridin-3-yl)-4-(4-fluorophenyl)-N-methylthiazol-2-amine | F12a (Cpd 55) | 611 | 612 (M + 1) |

TABLE III-continued

Illustrative compounds of the invention.

| Cpd | Structures | Name | Mtd (Int) | MW | MS Ms'd |
|---|---|---|---|---|---|
| 58 | 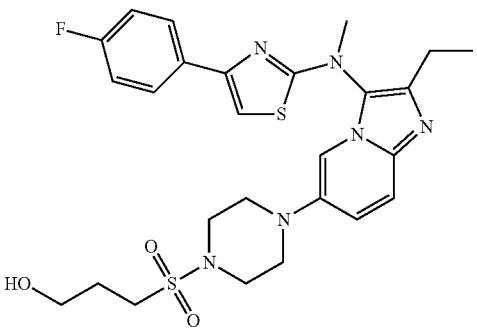 | 3-(4-(2-ethyl-3-((4-(4-fluorophenyl)thiazol-2-yl)(methyl)amino)imidazo[1,2-a]pyridin-6-yl)piperazin-1-ylsulfonyl)propan-1-ol | F12b-F13 (Cpd 55) | 558 | 559 (M + 1) |
| 59 | 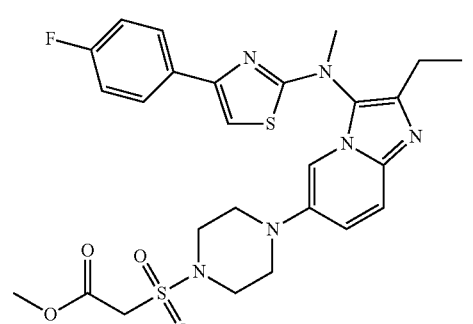 | methyl 2-(4-(2-ethyl-3-((4-(4-fluorophenyl)thiazol-2-yl)(methyl)amino)imidazo[1,2-a]pyridin-6-yl)piperazin-1-ylsulfonyl)acetate | F11 (Gen-10-e) | 572 | 573 (M + 1) |
| 60 | 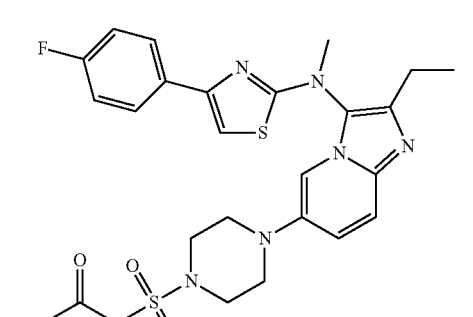 | 2-(4-(2-ethyl-3-((4-(4-fluorophenyl)thiazol-2-yl)(methyl)amino)imidazo[1,2-a]pyridin-6-yl)piperazin-1-ylsulfonyl)acetic acid | F13 (Cpd 59) | 558 | 559 (M + 1) |
| 61 | 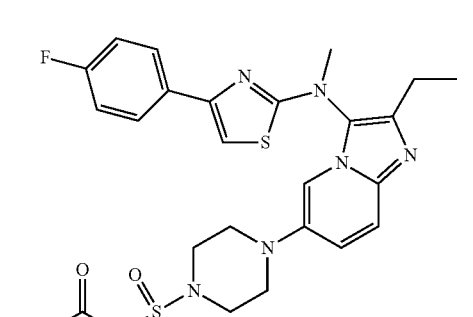 | 2-(4-(2-ethyl-3-((4-(4-fluorophenyl)thiazol-2-yl)(methyl)amino)imidazo[1,2-a]pyridin-6-yl)piperazin-1-ylsulfonyl)acetamide | see Cpd 61 (Cpd 60) | 557 | 558 (M + 1) |

TABLE III-continued

Illustrative compounds of the invention.

| Cpd | Structures | Name | Mtd (Int) | MW | MS Ms'd |
|---|---|---|---|---|---|
| 62 | 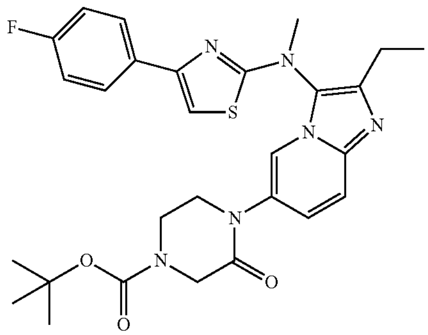 [SMILES: CCc1nc2ccc(N3CCN(C(=O)OC(C)(C)C)CC3=O)cn2c1N(C)c1nc(-c2ccc(F)cc2)cs1] | tert-butyl 4-(2-ethyl-3-((4-(4-fluorophenyl)thiazol-2-yl)(methyl)amino)imidazo[1,2-a]pyridin-6-yl)-3-oxopiperazine-1-carboxylate | F4 (Gen-5-b) | 550 | 551 (M + 1) |
| 63 | 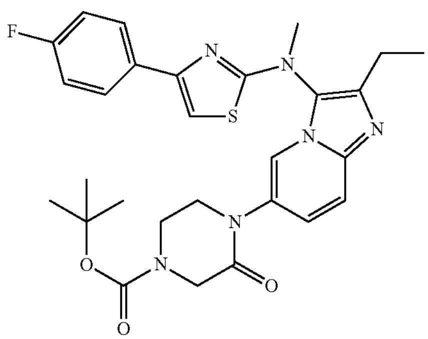 [SMILES: CCc1nc2ccc(N3CCN(C(=O)OC(C)(C)C)CC3=O)cn2c1N(C)c1nc(-c2ccc(F)cc2)cs1] | tert-butyl 4-(3-((4-(4-chlorophenyl)thiazol-2-yl)(methyl)amino)-2-ethylimidazo[1,2-a]pyridin-6-yl)-3-oxopiperazine-1-carboxylate | F4 (Gen-5-i) | 566 ($^{35}$Cl), 568 ($^{37}$Cl) | 567 ($^{35}$Cl M + 1) |
| 64 | 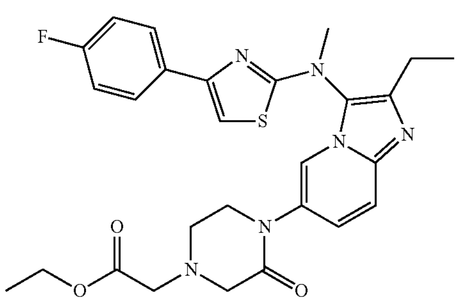 [SMILES: CCOC(=O)CN1CCN(c2ccc3nc(CC)c(N(C)c4nc(-c5ccc(F)cc5)cs4)n3c2)C(=O)C1] | ethyl 2-(4-(2-ethyl-3-((4-(4-fluorophenyl)thiazol-2-yl)(methyl)amino)imidazo[1,2-a]pyridin-6-yl)-3-oxopiperazin-1-yl)acetate | see Cpd64 (Gen-10-d) | 536 | 537 (M + 1) |
| 65 | 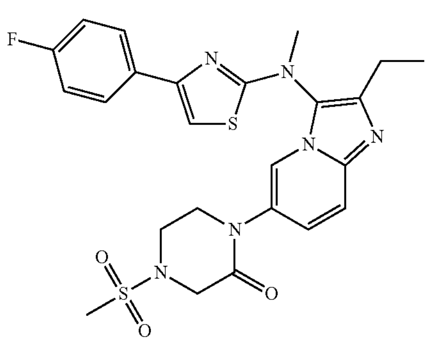 [SMILES: CCc1nc2ccc(N3CCN(S(C)(=O)=O)CC3=O)cn2c1N(C)c1nc(-c2ccc(F)cc2)cs1] | 1-(2-ethyl-3-((4-(4-fluorophenyl)thiazol-2-yl)(methyl)amino)imidazo[1,2-a]pyridin-6-yl)-4-(methylsulfonyl)piperazin-2-one | F11 (Gen-10-d) | 528 | 529 (M + 1) |

TABLE III-continued

Illustrative compounds of the invention.

| Cpd | Structures | Name | Mtd (Int) | MW | MS Ms'd |
|---|---|---|---|---|---|
| 66 | 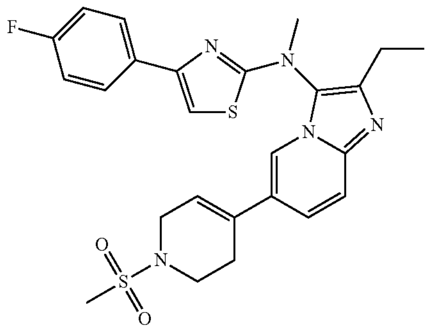 | N-(2-ethyl-6-(1-(methylsulfonyl)-1,2,3,6-tetrahydropyridin-4-yl)imidazo[1,2-a]pyridin-3-yl)-4-(4-fluorophenyl)-N-methylthiazol-2-amine | F11 (Gen-10-b) | 511 | 512 (M + 1) |
| 67 | 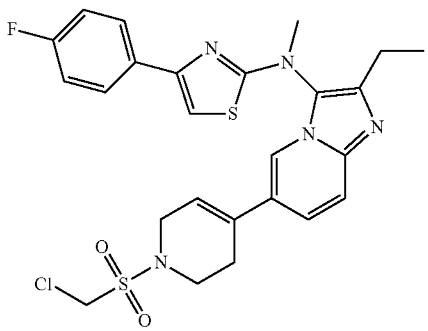 [SMILES: CCc1nc2ccc(C3=CCN(S(=O)(=O)CCl)CC3)cn2c1N(C)c1nc(-c2ccc(F)cc2)cs1] | N-(6-(1-(chloromethylsulfonyl)-1,2,3,6-tetrahydropyridin-4-yl)-2-ethylimidazo[1,2-a]pyridin-3-yl)-4-(4-fluorophenyl)-N-methylthiazol-2-amine | F11 (Gen-10-b) | 545 | 546 (M + 1) |
| 68 | 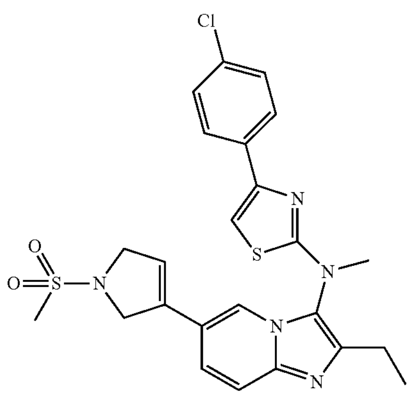 [SMILES: CCc1nc2ccc(C3=CCN(S(C)(=O)=O)C3)cn2c1N(C)c1nc(-c2ccc(Cl)cc2)cs1] | 4-(4-chlorophenyl)-N-(2-ethyl-6-(1-(methylsulfonyl)-2,5-dihydro-1H-pyrrol-3-yl)imidazo[1,2-a]pyridin-3-yl)-N-methylthiazol-2-amine | F11 (Gen-10-j) | 513 ($^{35}$Cl), 515 ($^{37}$Cl) | 514 ($^{35}$Cl M + 1) 516 ($^{37}$Cl M + 1) |
| 69 | 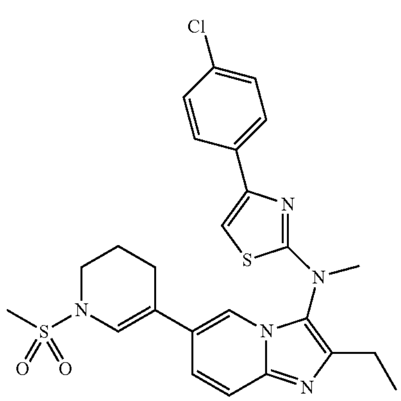 [SMILES: CCc1nc2ccc(C3=CN(S(C)(=O)=O)CCC3)cn2c1N(C)c1nc(-c2ccc(Cl)cc2)cs1] | 4-(4-chlorophenyl)-N-(2-ethyl-6-(1-(methylsulfonyl)-1,4,5,6-tetrahydropyridin-3-yl)imidazo[1,2-a]pyridin-3-yl)-N-methylthiazol-2-amine | F11 (Gen-10-ae) | 527 ($^{35}$Cl), 529 ($^{37}$Cl) | 528 ($^{35}$Cl M + 1) 530 ($^{37}$Cl M + 1) |

TABLE III-continued

Illustrative compounds of the invention.

| Cpd | Structures | Name | Mtd (Int) | MW | MS Ms'd |
|---|---|---|---|---|---|
| 70 | 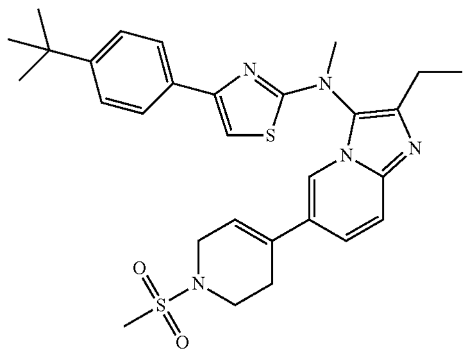 [SMILES: CCc1nc2ccc(C3=CCN(S(C)(=O)=O)CC3)cn2c1N(C)c1nc(-c2ccc(C(C)(C)C)cc2)cs1] | 4-(4-tert-butylphenyl)-N-(2-ethyl-6-(1-(methylsulfonyl)-1,2,3,6-tetrahydropyridin-4-yl)imidazo[1,2-a]pyridin-3-yl)-N-methylthiazol-2-amine | F2 (Gen-5-g)- | 549 | 550 (M + 1) |
| 71 | 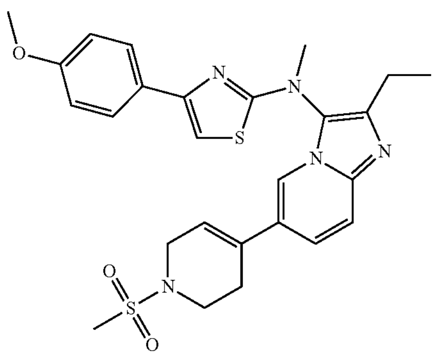 [SMILES: CCc1nc2ccc(C3=CCN(S(C)(=O)=O)CC3)cn2c1N(C)c1nc(-c2ccc(OC)cc2)cs1] | N-(2-ethyl-6-(1-(methylsulfonyl)-1,2,3,6-tetrahydropyridin-4-yl)imidazo[1,2-a]pyridin-3-yl)-4-(4-methoxyphenyl)-N-methylthiazol-2-amine | F11 (Gen-10-ac) | 523 | 524 (M + 1) |
| 72 | 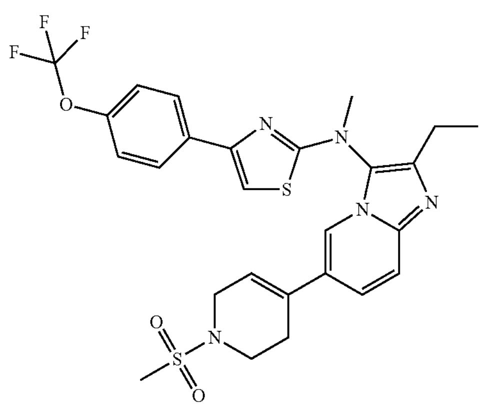 [SMILES: CCc1nc2ccc(C3=CCN(S(C)(=O)=O)CC3)cn2c1N(C)c1nc(-c2ccc(OC(F)(F)F)cc2)cs1] | N-(2-ethyl-6-(1-(methylsulfonyl)-1,2,3,6-tetrahydropyridin-4-yl)imidazo[1,2-a]pyridin-3-yl)-N-methyl-4-(4-(trifluoromethoxy)phenyl)thiazol-2-amine | F11 (Gen-10-ah) | 577 | 578 (M + 1) |
| 73 | 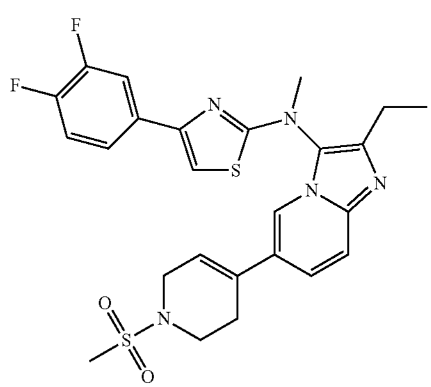 [SMILES: CCc1nc2ccc(C3=CCN(S(C)(=O)=O)CC3)cn2c1N(C)c1nc(-c2ccc(F)c(F)c2)cs1] | 4-(3,4-difluorophenyl)-N-(2-ethyl-6-(1-(methylsulfonyl)-1,2,3,6-tetrahydropyridin-4-yl)imidazo[1,2-a]pyridin-3-yl)-N-methylthiazol-2-amine | F11 (Gen-10-aj) | 529 | 530 (M + 1) |

TABLE III-continued

Illustrative compounds of the invention.

| Cpd | Structures | Name | Mtd (Int) | MW | MS Ms'd |
|---|---|---|---|---|---|
| 74 | 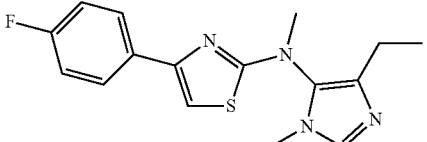 | 3-(4-(2-ethyl-3-((4-(4-fluorophenyl)thiazol-2-yl)(methyl)amino)imidazo[1,2-a]pyridin-6-yl)-5,6-dihydropyridin-1(2H)-ylsulfonyl)propyl acetate | F11-F12b (Gen-10-b)- | 597 | 598 (M + 1) |
| 75 | 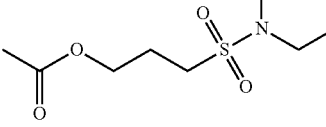 | 3-(4-(2-ethyl-3-((4-(4-fluorophenyl)thiazol-2-yl)(methyl)amino)imidazo[1,2-a]pyridin-6-yl)-5,6-dihydropyridin-1(2H)-ylsulfonyl)propan-1-ol | F13 (Cpd 74) | 555 | 556 (M + 1) |
| 76 | 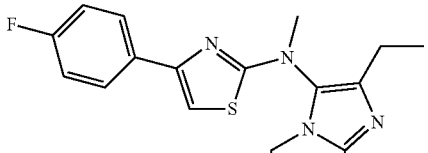 | 4-(2-ethyl-3-((4-(4-chlorophenyl)thiazol-2-yl)(methyl)amino)imidazo[1,2-a]pyridin-6-yl)-3,6-dihydro-2H-thiopyran 1,1-dioxide | see Cpd76 (Gen-10-g or cpd 231) | 498 ($^{35}$Cl), 500 ($^{37}$Cl) | 499 ($^{35}$Cl M + 1) 501 ($^{37}$Cl M + 1) |
| 77 | 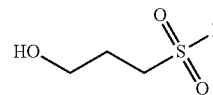 | N-(2-ethyl-6-(1-(methylsulfonyl)-1,2,3,6-tetrahydropyridin-4-yl)imidazo[1,2-a]pyridin-3-yl)-5-fluoro-4-(4-fluorophenyl)-N-methylthiazol-2-amine | F16b (Cpd 66) | 529 | 530 (M + 1) |

TABLE III-continued

Illustrative compounds of the invention.

| Cpd | Structures | Name | Mtd (Int) | MW | MS Ms'd |
|---|---|---|---|---|---|
| 78 | 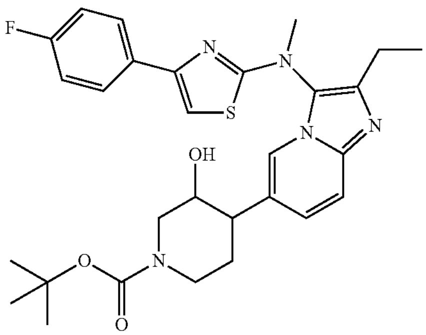 [SMILES: CCc1nc2ccc(C3CCN(C(=O)OC(C)(C)C)CC3O)cn2c1N(C)c1nc(-c2ccc(F)cc2)cs1] | tert-butyl 4-(2-ethyl-3-((4-(4-fluorophenyl)thiazol-2-yl)(methyl)amino)imidazo[1,2-a]pyridin-6-yl)-3-hydroxypiperidine-1-carboxylate | F2-see Cpd 78 (Gen-5-c) | 551 | 552 (M + 1) |
| 79 | 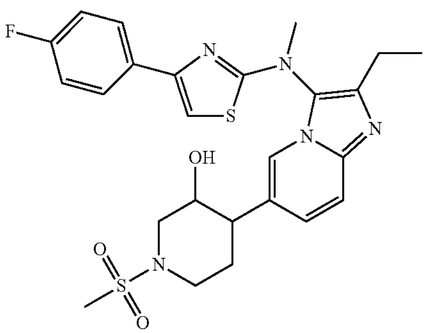 [SMILES: CCc1nc2ccc(C3CCN(S(C)(=O)=O)CC3O)cn2c1N(C)c1nc(-c2ccc(F)cc2)cs1] | 4-(2-ethyl-3-((4-(4-fluorophenyl)thiazol-2-yl)(methyl)amino)imidazo[1,2-a]pyridin-6-yl)-1-(methylsulfonyl)piperidin-3-ol | F11 (Gen-10-ab) | 529 | 530 (M + 1) |
| 80 | 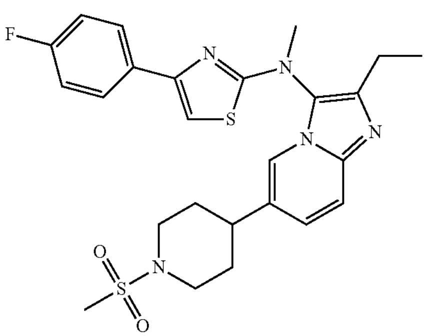 [SMILES: CCc1nc2ccc(C3CCN(S(C)(=O)=O)CC3)cn2c1N(C)c1nc(-c2ccc(F)cc2)cs1] | N-(2-ethyl-6-(1-(methylsulfonyl)piperidin-4-yl)imidazo[1,2-a]pyridin-3-yl)-4-(4-fluorophenyl)-N-methylthiazol-2-amine | F11-F6 (Gen-10-b) | 513 | 514 (M + 1) |
| 81 | 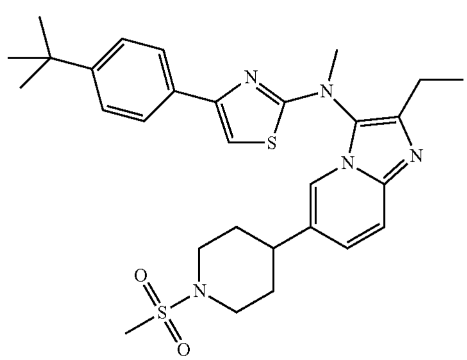 [SMILES: CCc1nc2ccc(C3CCN(S(C)(=O)=O)CC3)cn2c1N(C)c1nc(-c2ccc(C(C)(C)C)cc2)cs1] | 4-(4-tert-butylphenyl)-N-(2-ethyl-6-(1-(methylsulfonyl)piperidin-4-yl)imidazo[1,2-a]pyridin-3-yl)-N-methylthiazol-2-amine | F2-F6 (Gen-5-g)- | 551 | 552 (M + 1) |

TABLE III-continued

Illustrative compounds of the invention.

| Cpd | Structures | Name | Mtd (Int) | MW | MS Ms'd |
|---|---|---|---|---|---|
| 82 | 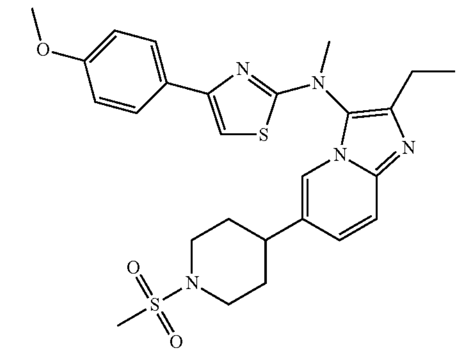 [SMILES: CCc1nc2ccc(C3CCN(S(C)(=O)=O)CC3)cn2c1N(C)c1nc(-c2ccc(OC)cc2)cs1] | N-(2-ethyl-6-(1-(methylsulfonyl)piperidin-4-yl)imidazo[1,2-a]pyridin-3-yl)-4-(4-methoxyphenyl)-N-methylthiazol-2-amine | F11-F6 (Gen-10-ac) | 525 | 526 (M + 1) |
| 83 | 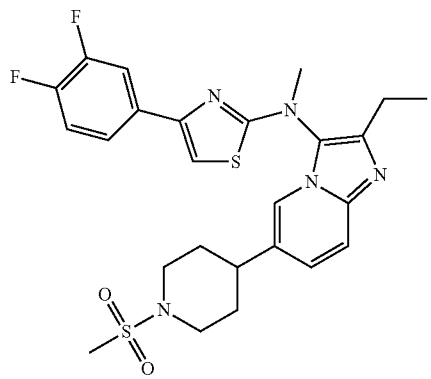 [SMILES: CCc1nc2ccc(C3CCN(S(C)(=O)=O)CC3)cn2c1N(C)c1nc(-c2ccc(F)c(F)c2)cs1] | 4-(3,4-difluorophenyl)-N-(2-ethyl-6-(1-(methylsulfonyl)piperidin-4-yl)imidazo[1,2-a]pyridin-3-yl)-N-methylthiazol-2-amine | F11-F6 (Gen-10-aj) | 531 | 532 (M + 1) |
| 84 | 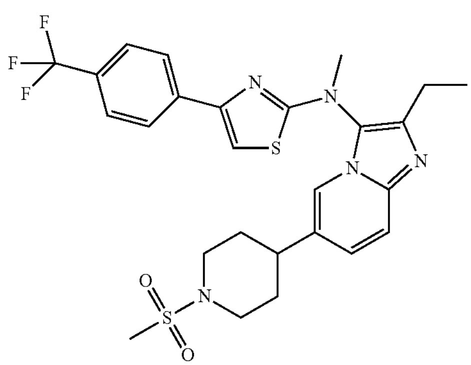 [SMILES: CCc1nc2ccc(C3CCN(S(C)(=O)=O)CC3)cn2c1N(C)c1nc(-c2ccc(C(F)(F)F)cc2)cs1] | N-(2-ethyl-6-(1-(methylsulfonyl)piperidin-4-yl)imidazo[1,2-a]pyridin-3-yl)-N-methyl-4-(4-(trifluoromethyl)phenyl)thiazol-2-amine | F11-F6 (Gen-10-ai) | 563 | 564 (M + 1) |
| 85 | 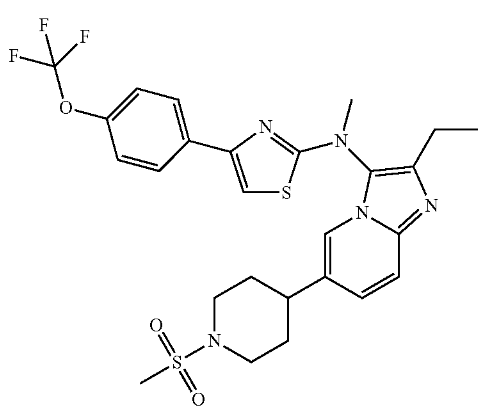 [SMILES: CCc1nc2ccc(C3CCN(S(C)(=O)=O)CC3)cn2c1N(C)c1nc(-c2ccc(OC(F)(F)F)cc2)cs1] | N-(2-ethyl-6-(1-(methylsulfonyl)piperidin-4-yl)imidazo[1,2-a]pyridin-3-yl)-N-methyl-4-(4-(trifluoromethoxy)phenyl)thiazol-2-amine | F6-F11 (Gen-10-ah) | 579 | 580 (M + 1) |

TABLE III-continued

Illustrative compounds of the invention.

| Cpd | Structures | Name | Mtd (Int) | MW | MS Ms'd |
|---|---|---|---|---|---|
| 86 | 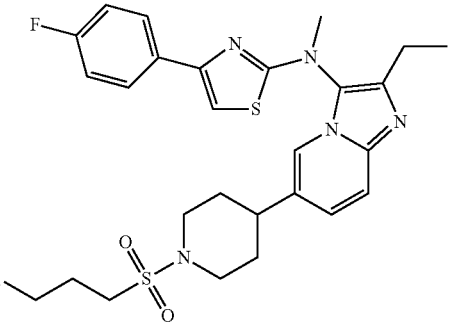 | N-(6-(1-(3-chloropropylsulfonyl)piperidin-4-yl)-2-ethylimidazo[1,2-a]pyridin-3-yl)-4-(4-fluorophenyl)-N-methylthiazol-2-amine | F11 (Gen-10-c) | 575 ($^{35}$Cl), 577 ($^{37}$Cl) | 576 ($^{35}$Cl M + 1) 578 ($^{37}$Cl M + 1) |
| 87 | 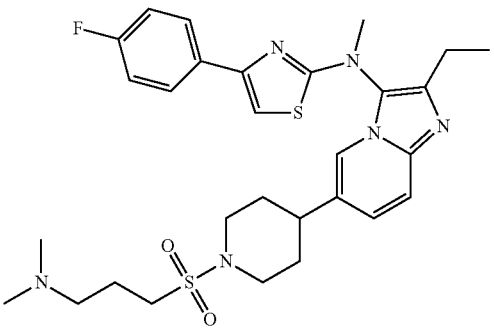 | N-(6-(1-(3-(dimethylamino)propylsulfonyl)piperidin-4-yl)-2-ethylimidazo[1,2-a]pyridin-3-yl)-4-(4-fluorophenyl)-N-methylthiazol-2-amine | F12a (Cpd 86) | 584 | 585 (M + 1) |
| 88 | 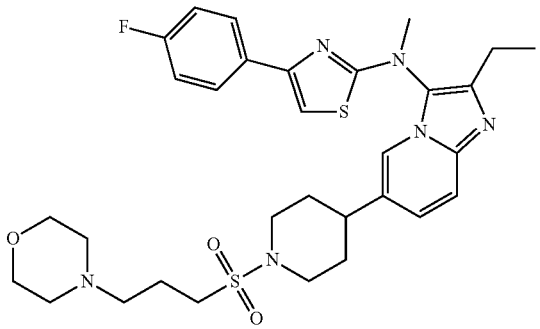 [SMILES: CCc1nc2ccc(C3CCN(S(=O)(=O)CCCN4CCOCC4)CC3)cn2c1N(C)c1nc(-c2ccc(F)cc2)cs1] | N-(2-ethyl-6-(1-(3-morpholinopropylsulfonyl)piperidin-4-yl)imidazo[1,2-a]pyridin-3-yl)-4-(4-fluorophenyl)-N-methylthiazol-2-amine | F12a (Cpd 86) | 626 | 627 (M + 1) |
| 89 | 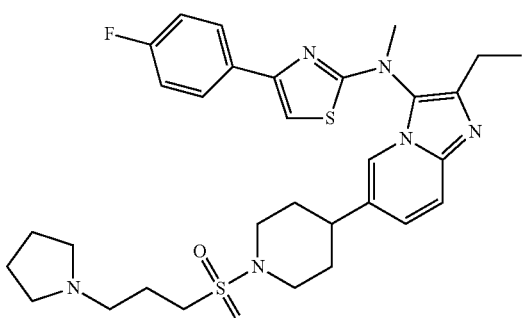 | N-(2-ethyl-6-(1-(3-(pyrrolidin-1-yl)propylsulfonyl)piperidin-4-yl)imidazo[1,2-a]pyridin-3-yl)-4-(4-fluorophenyl)-N-methylthiazol-2-amine | F12a (Cpd 86) | 610 | 611 (M + 1) |

TABLE III-continued

Illustrative compounds of the invention.

| Cpd | Structures | Name | Mtd (Int) | MW | MS Ms'd |
|---|---|---|---|---|---|
| 90 | 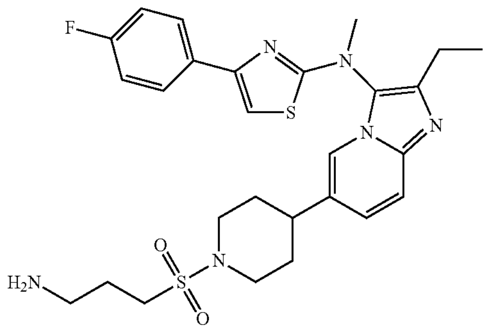 [SMILES: CCc1nc2ccc(C3CCN(S(=O)(=O)CCCN)CC3)cn2c1N(C)c1nc(-c2ccc(F)cc2)cs1] | N-(6-(1-(3-aminopropylsulfonyl)piperidin-4-yl)-2-ethylimidazo[1,2-a]pyridin-3-yl)-4-(4-fluorophenyl)-N-methylthiazol-2-amine | see Cpd 90 (Gen-10-p) | 556 | 557 (M + 1) |
| 91 | 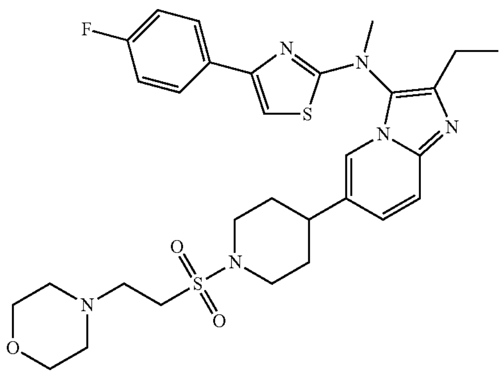 [SMILES: CCc1nc2ccc(C3CCN(S(=O)(=O)CCN4CCOCC4)CC3)cn2c1N(C)c1nc(-c2ccc(F)cc2)cs1] | N-(2-ethyl-6-(1-(2-morpholinoethylsulfonyl)piperidin-4-yl)imidazo[1,2-a]pyridin-3-yl)-4-(4-fluorophenyl)-N-methylthiazol-2-amine | see Cpd91 (Gen-10-y) | 612 | 613 (M + 1) |
| 92 | 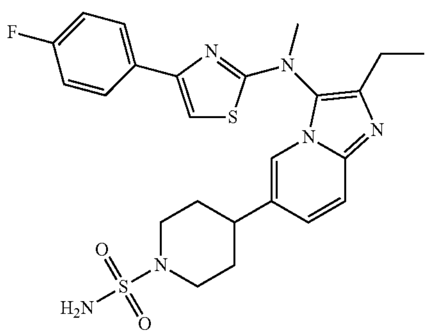 [SMILES: CCc1nc2ccc(C3CCN(S(N)(=O)=O)CC3)cn2c1N(C)c1nc(-c2ccc(F)cc2)cs1] | 4-(2-ethyl-3-((4-(4-fluorophenyl)thiazol-2-yl)(methyl)amino)imidazo[1,2-a]pyridin-6-yl)piperidine-1-sulfonamide | see Cpd92 (Gen-10-c) | 514 | 515 (M + 1) |
| 93 | 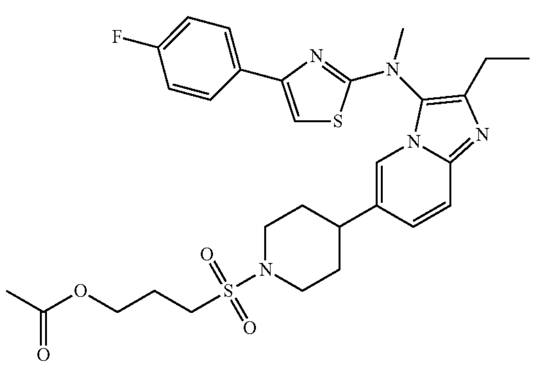 [SMILES: CCc1nc2ccc(C3CCN(S(=O)(=O)CCCOC(C)=O)CC3)cn2c1N(C)c1nc(-c2ccc(F)cc2)cs1] | 3-(4-(2-ethyl-3-((4-(4-fluorophenyl)thiazol-2-yl)(methyl)amino)imidazo[1,2-a]pyridin-6-yl)piperidin-1-ylsulfonyl)propyl acetate | F12b (Cpd 86) | 599 | 600 (M + 1) |

TABLE III-continued

Illustrative compounds of the invention.

| Cpd | Structures | Name | Mtd (Int) | MW | MS Ms'd |
|---|---|---|---|---|---|
| 94 | 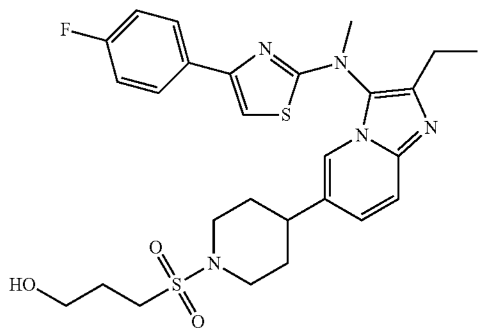 [SMILES: CCc1nc2ccc(C3CCN(S(=O)(=O)CCCO)CC3)cn2c1N(C)c1nc(-c2ccc(F)cc2)cs1] | 3-(4-(2-ethyl-3-((4-(4-fluorophenyl)thiazol-2-yl)(methyl)amino)imidazo[1,2-a]pyridin-6-yl)piperidin-1-ylsulfonyl)propan-1-ol | F13 (Cpd 93) | 557 | 558 (M + 1) |
| 95 | 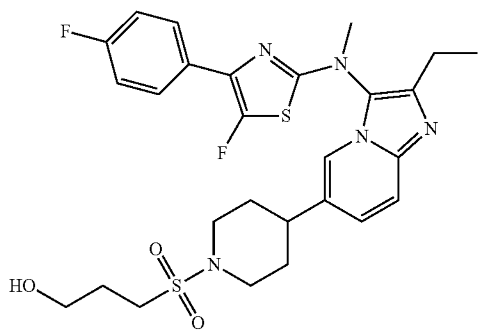 [SMILES: CCc1nc2ccc(C3CCN(S(=O)(=O)CCCO)CC3)cn2c1N(C)c1nc(-c2ccc(F)cc2)c(F)s1] | 3-(4-(2-ethyl-3-((5-fluoro-4-(4-fluorophenyl)thiazol-2-yl)(methyl)amino)imidazo[1,2-a]pyridin-6-yl)piperidin-1-ylsulfonyl)propan-1-ol | F16b (Cpd 94) | 575 | 576 (M + 1) |
| 96 | 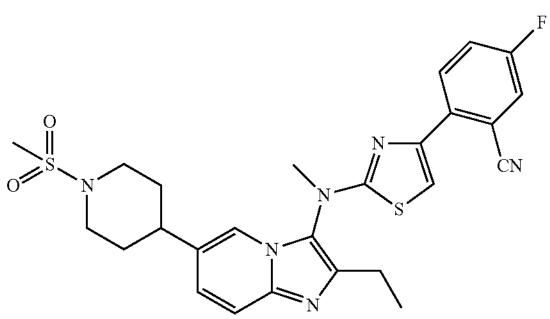 [SMILES: CCc1nc2ccc(C3CCN(S(C)(=O)=O)CC3)cn2c1N(C)c1nc(-c2ccc(F)cc2C#N)cs1] | 2-(2-((2-ethyl-6-(1-(methylsulfonyl)piperidin-4-yl)imidazo[1,2-a]pyridin-3-yl)(methyl)amino)thiazol-4-yl)-5-fluorobenzonitrile | E1 (Gen-9-b) | 538 | 539 (M + 1) |
| 97 | 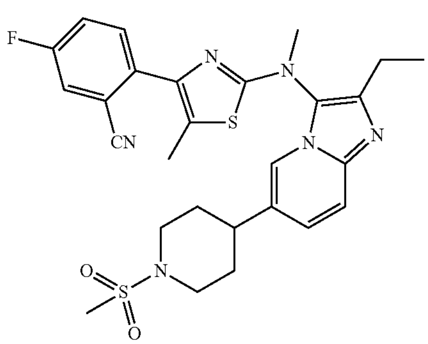 [SMILES: CCc1nc2ccc(C3CCN(S(C)(=O)=O)CC3)cn2c1N(C)c1nc(-c2ccc(F)cc2C#N)c(C)s1] | 2-(2-((2-ethyl-6-(1-(methylsulfonyl)piperidin-4-yl)imidazo[1,2-a]pyridin-3-yl)(methyl)amino)-5-methylthiazol-4-yl)-5-fluorobenzonitrile | E1 (Gen-9-b) | 552 | 553 (M + 1) |

TABLE III-continued

Illustrative compounds of the invention.

| Cpd | Structures | Name | Mtd (Int) | MW | MS Ms'd |
|---|---|---|---|---|---|
| 98 | 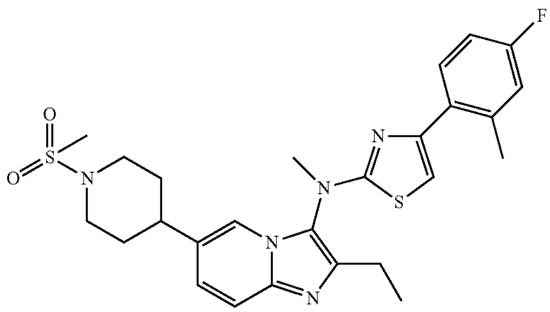 [SMILES: CCc1nc2ccc(C3CCN(S(C)(=O)=O)CC3)cn2c1N(C)c1nc(-c2ccc(F)cc2C)cs1] | N-(2-ethyl-6-(1-(methylsulfonyl)piperidin-4-yl)imidazo[1,2-a]pyridin-3-yl)-4-(4-fluoro-2-methylphenyl)-N-methylthiazol-2-amine | E1 (Gen-9-b) | 527 | 528 (M + 1) |
| 99 | 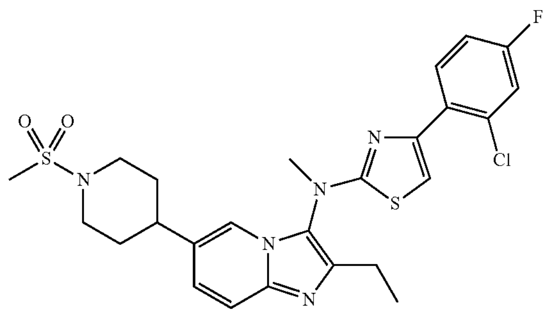 [SMILES: CCc1nc2ccc(C3CCN(S(C)(=O)=O)CC3)cn2c1N(C)c1nc(-c2ccc(F)cc2Cl)cs1] | 4-(2-chloro-4-fluorophenyl)-N-(2-ethyl-6-(1-(methylsulfonyl)piperidin-4-yl)imidazo[1,2-a]pyridin-3-yl)-N-methylthiazol-2-amine | E1 (Gen-9-b) | 547 ($^{35}$Cl) 549 ($^{37}$Cl) | 548 ($^{35}$Cl M + 1) |
| 100 | 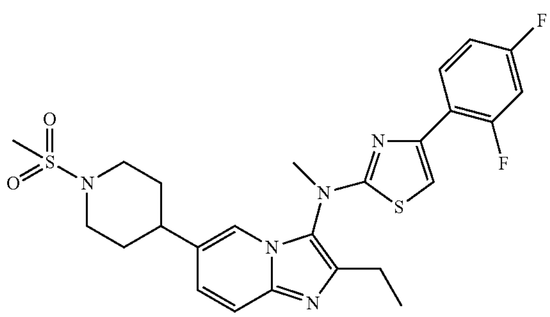 [SMILES: CCc1nc2ccc(C3CCN(S(C)(=O)=O)CC3)cn2c1N(C)c1nc(-c2ccc(F)cc2F)cs1] | 4-(2,4-difluorophenyl)-N-(2-ethyl-6-(1-(methylsulfonyl)piperidin-4-yl)imidazo[1,2-a]pyridin-3-yl)-N-methylthiazol-2-amine | E1 (Gen-9-b) | 531 | 532 (M + 1) |
| 101 | 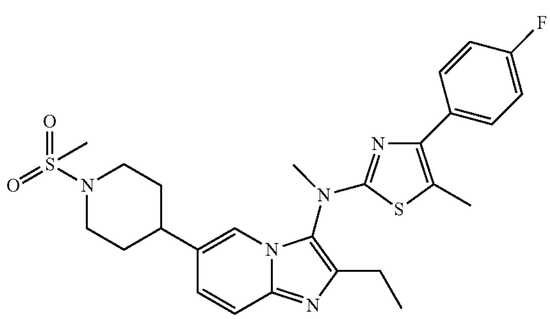 [SMILES: CCc1nc2ccc(C3CCN(S(C)(=O)=O)CC3)cn2c1N(C)c1nc(-c2ccc(F)cc2)c(C)s1] | N-(2-ethyl-6-(1-(methylsulfonyl)piperidin-4-yl)imidazo[1,2-a]pyridin-3-yl)-4-(4-fluorophenyl)-N,5-dimethylthiazol-2-amine | E1 (Gen-9b) | 527 | 528 (M + 1) |

TABLE III-continued

Illustrative compounds of the invention.

| Cpd | Structures | Name | Mtd (Int) | MW | MS Ms'd |
|---|---|---|---|---|---|
| 102 | 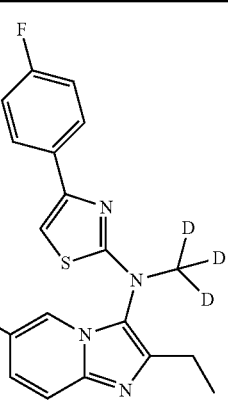 | 4-(4-fluorophenyl)-N-(2-ethyl-6-(1-(methylsulfonyl)piperidin-4-yl)imidazo[1,2-a]pyridin-3-yl)-N-(d₃-methypthiazol-2-amine | E1 (Gen-9-f) | 516 | 517 (M + 1) |
| 103 | 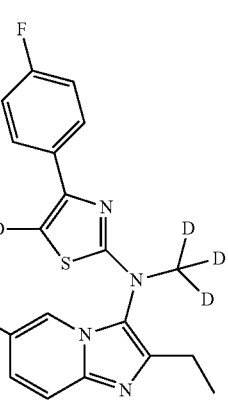 | 4-(4-fluorophenyl)-N-(2-ethyl-6-(1-(methylsulfonyl)piperidin-4-yl)imidazo[1,2-a]pyridin-3-yl)-N-(d₃-methyl)-(d-thiazol-2-)-amine | B1-C1-F2-F6-D1-E1 (Gen-9-f) | 517 | 518 (M + 1) |
| 104 | 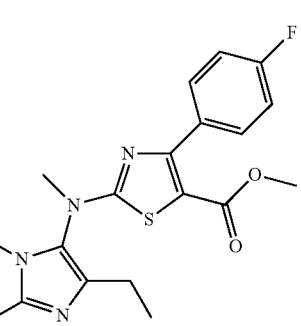 | methyl 2-((2-ethyl-6-(1-(methylsulfonyl)piperidin-4-yl)imidazo[1,2-a]pyridin-3-yl)(methyl)amino)-4-(4-fluorophenyl)thiazole-5-carboxylate | E1 (Gen-9-b) | 571 | 572 (M + 1) |
| 105 | 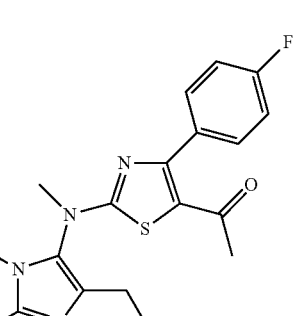 | 1-(2-((2-ethyl-6-(1-(methylsulfonyl)piperidin-4-yl)imidazo[1,2-a]pyridin-3-yl)(methyl)amino)-4-(4-fluorophenyl)thiazol-5-yl)ethanone | see Cpd 105 (Cpd 104) | 555 | 556 (M + 1) |

TABLE III-continued

Illustrative compounds of the invention.

| Cpd | Structures | Name | Mtd (Int) | MW | MS Ms'd |
|---|---|---|---|---|---|
| 106 | 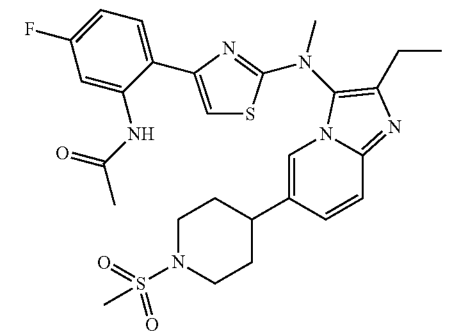 [SMILES: CCc1nc2ccc(C3CCN(S(C)(=O)=O)CC3)cn2c1N(C)c1nc(-c2ccc(F)cc2NC(C)=O)cs1] | N-(2-(2-((2-ethyl-6-(1-(methylsulfonyl)piperidin-4-yl)imidazo[1,2-a]pyridin-3-yl)(methyl)amino)thiazol-4-yl)-5-fluorophenyl)acetamide | see Cpd 106 (Gen-10-al) | 570 | 571 (M + 1) |
| 107 | 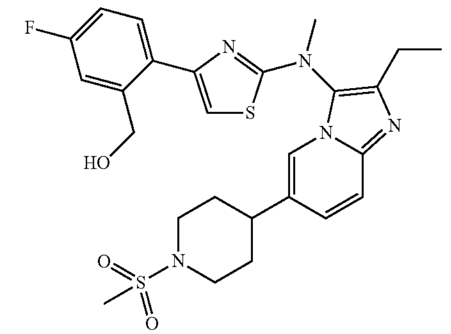 [SMILES: CCc1nc2ccc(C3CCN(S(C)(=O)=O)CC3)cn2c1N(C)c1nc(-c2ccc(F)cc2CO)cs1] | (2-(2-((2-ethyl-6-(1-(methylsulfonyl)piperidin-4-yl)imidazo[1,2-a]pyridin-3-yl)(methyl)amino)thiazol-4-yl)-5-fluorophenyl)methanol | see cpd 107 (Gen-10-al) | 543 | 544 (M + 1) |
| 108 | 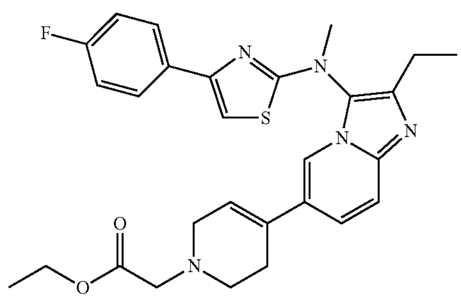 [SMILES: CCOC(=O)CN1CC=C(c2ccc3nc(CC)c(N(C)c4nc(-c5ccc(F)cc5)cs4)n3c2)CC1] | ethyl 2-(4-(2-ethyl-3-((4-(4-fluorophenyl)thiazol-2-yl)(methyl)amino)imidazo[1,2-a]pyridin-6-yl)-5,6-dihydropyridin-1(2H)-yl)acetate | F8 (Gen-10-b)- | 519 | 520 (M + 1) |
| 109 | 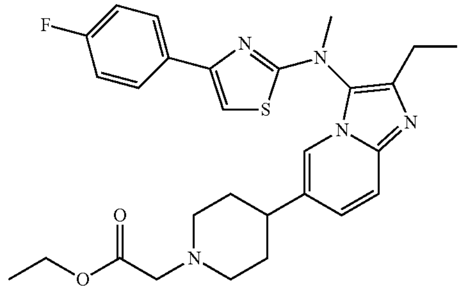 [SMILES: CCOC(=O)CN1CCC(c2ccc3nc(CC)c(N(C)c4nc(-c5ccc(F)cc5)cs4)n3c2)CC1] | ethyl 2-(4-(2-ethyl-3-((4-(4-fluorophenyl)thiazol-2-yl)(methyl)amino)imidazo[1,2-a]pyridin-6-yl)piperidin-1-yl)acetate | F8 (Gen-10-c) | 521 | 522 (M + 1) |

TABLE III-continued

Illustrative compounds of the invention.

| Cpd | Structures | Name | Mtd (Int) | MW | MS Ms'd |
|---|---|---|---|---|---|
| 110 | 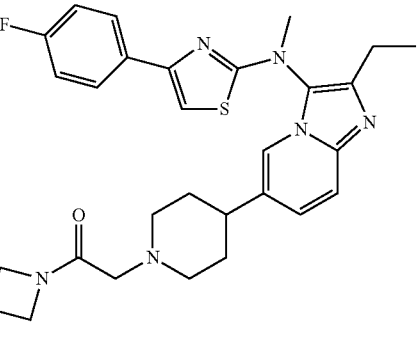 | 2-(4-(2-ethyl-3-((4-(4-fluorophenyl)thiazol-2-yl)(methyl)amino)imidazo[1,2-a]pyridin-6-yl)piperidin-1-yl)-1-(3-hydroxyazetidin-1-yl)ethanone | F8 (Gen-10-c) | 548 | 549 (M + 1) |
| 111 | 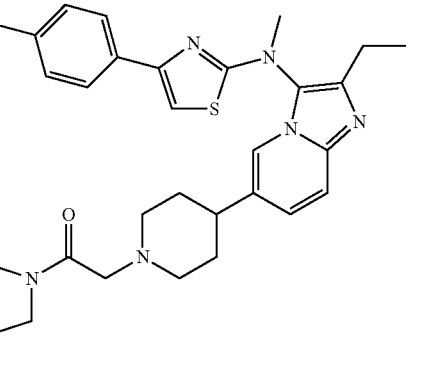 | (R)-2-(4-(2-ethyl-3-((4-(4-fluorophenyl)thiazol-2-yl)(methyl)amino)imidazo[1,2-a]pyridin-6-yl)piperidin-1-yl)-1-(3-hydroxypyrrolidin-1-yl)ethanone | F8 (Gen-10-c) | 562 | 563 (M + 1) |
| 112 | 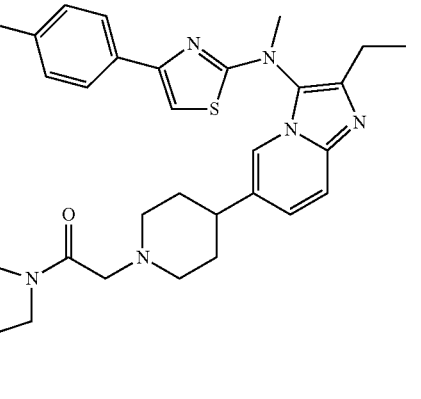 | (S)-2-(4-(2-ethyl-3-((4-(4-fluorophenyl)thiazol-2-yl)(methyl)amino)imidazo[1,2-a]pyridin-6-yl)piperidin-1-yl)-1-(3-hydroxypyrrolidin-1-yl)ethanone | F8 (Gen-10-c) | 562 | 563 (M + 1) |
| 113 | 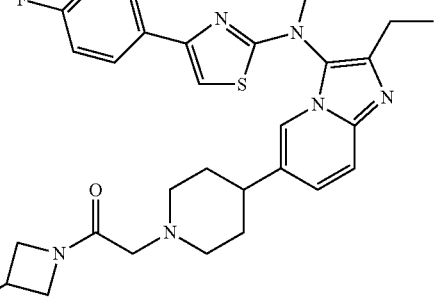 | 2-(4-(2-ethyl-3-((4-(4-fluorophenyl)thiazol-2-yl)(methyl)amino)imidazo[1,2-a]pyridin-6-yl)piperidin-1-yl)-1-(3-(hydroxymethyl)azetidin-1-yl)ethanone | F8 (Gen-10-c) | 562 | 563 (M + 1) |

TABLE III-continued

Illustrative compounds of the invention.

| Cpd | Structures | Name | Mtd (Int) | MW | MS Ms'd |
|---|---|---|---|---|---|
| 114 | 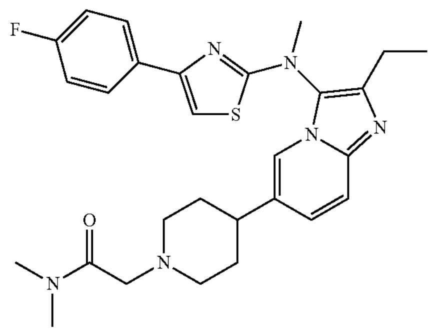 [SMILES: CCc1nc2ccc(C3CCN(CC(=O)N(C)C)CC3)cn2c1N(C)c1nc(-c2ccc(F)cc2)cs1] | 2-(4-(2-ethyl-3-((4-(4-fluorophenyl)thiazol-2-yl)(methyl)amino)imidazo[1,2-a]pyridin-6-yl)piperidin-1-yl)-N,N-dimethylacetamide | F8 (Gen-10-c) | 520 | 521 (M + 1) |
| 115 | 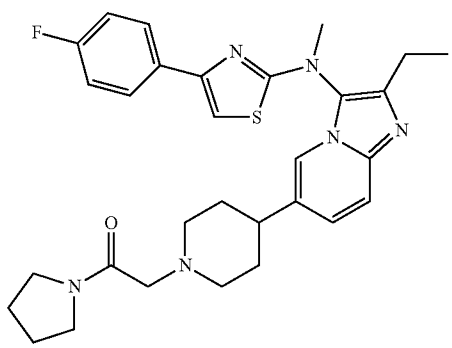 [SMILES: CCc1nc2ccc(C3CCN(CC(=O)N4CCCC4)CC3)cn2c1N(C)c1nc(-c2ccc(F)cc2)cs1] | 2-(4-(2-ethyl-3-((4-(4-fluorophenyl)thiazol-2-yl)(methyl)amino)imidazo[1,2-a]pyridin-6-yl)piperidin-1-yl)-1-(pyrrolidin-1-yl)ethanone | F8 (Gen-10-c) | 546 | 547 (M + 1) |
| 116 | 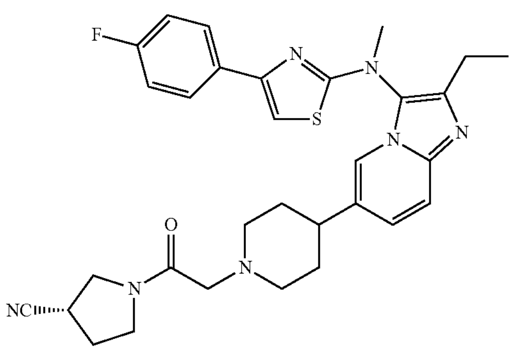 [SMILES: CCc1nc2ccc(C3CCN(CC(=O)N4CC[C@H](C#N)C4)CC3)cn2c1N(C)c1nc(-c2ccc(F)cc2)cs1] | (S)-1-(2-(4-(2-ethyl-3-((4-(4-fluorophenyl)thiazol-2-yl)(methyl)amino)imidazo[1,2-a]pyridin-6-yl)piperidin-1-yl)acetyl)pyrrolidine-3-carbonitrile | F8 (Gen-10-c) | 571 | 572 (M + 1) |
| 117 | 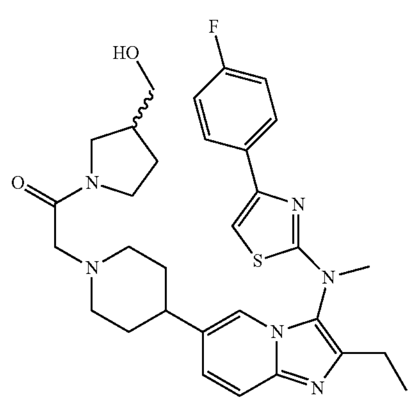 [SMILES: CCc1nc2ccc(C3CCN(CC(=O)N4CCC(CO)C4)CC3)cn2c1N(C)c1nc(-c2ccc(F)cc2)cs1] | 2-(4-(2-ethyl-3-((4-(4-fluorophenyl)thiazol-2-yl)(methyl)amino)imidazo[1,2-a]pyridin-6-yl)piperidin-1-yl)-1-(3-(hydroxymethyl)pyrrolidin-1-yl)ethanone | F8 (Gen-10-c) | 576 | 577 (M + 1) |

TABLE III-continued

Illustrative compounds of the invention.

| Cpd | Structures | Name | Mtd (Int) | MW | MS Ms'd |
|---|---|---|---|---|---|
| 118 | 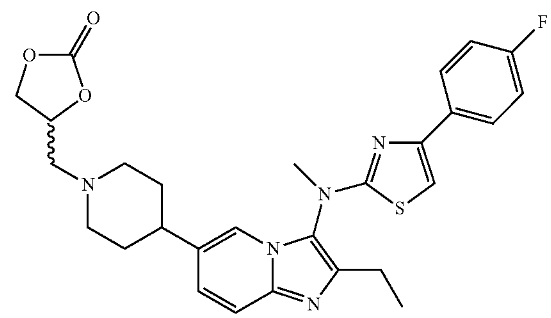 [SMILES: CCc1nc2ccc(C3CCN(CC4COC(=O)O4)CC3)cn2c1N(C)c1nc(-c2ccc(F)cc2)cs1] | 4-((4-(2-ethyl-3-((4-(4-fluorophenyl)thiazol-2-yl)(methyl)amino)imidazo[1,2-a]pyridin-6-yl)piperidin-1-yl)methyl)-1,3-dioxolan-2-one | F8 (Gen-10-c) | 535 | 536 (M + 1) |
| 119 | 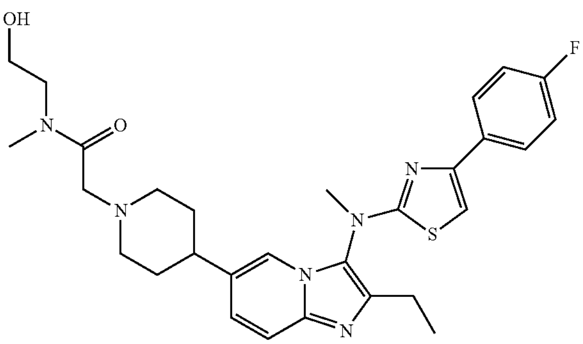 [SMILES: CCc1nc2ccc(C3CCN(CC(=O)N(C)CCO)CC3)cn2c1N(C)c1nc(-c2ccc(F)cc2)cs1] | 2-(4-(2-ethyl-3-((4-(4-fluorophenyl)thiazol-2-yl)(methyl)amino)imidazo[1,2-a]pyridin-6-yl)piperidin-1-yl)-N-(2-hydroxyethyl)-N-methylacetamide | F8 (Gen-10-c) | 550 | 551 (M + 1) |
| 120 | 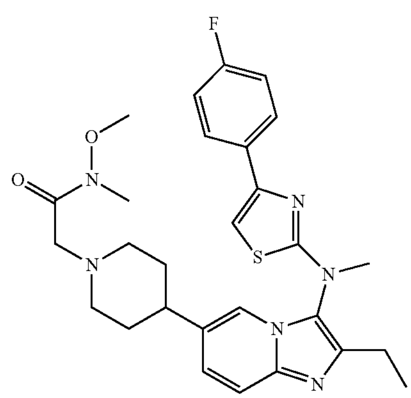 [SMILES: CCc1nc2ccc(C3CCN(CC(=O)N(C)OC)CC3)cn2c1N(C)c1nc(-c2ccc(F)cc2)cs1] | 2-(4-(2-ethyl-3-((4-(4-fluorophenyl)thiazol-2-yl)(methyl)amino)imidazo[1,2-a]pyridin-6-yl)piperidin-1-yl)-N-methoxy-N-methylacetamide | F8 (Gen-10-c) | 536 | 537 (M + 1) |
| 121 | 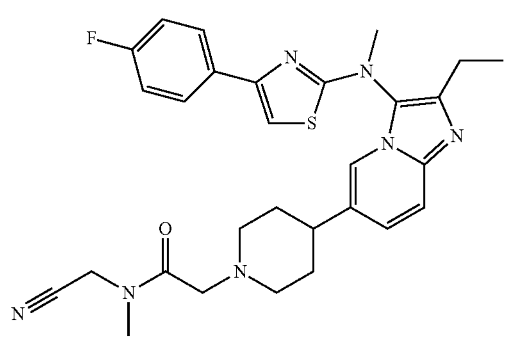 [SMILES: CCc1nc2ccc(C3CCN(CC(=O)N(C)CC#N)CC3)cn2c1N(C)c1nc(-c2ccc(F)cc2)cs1] | N-(cyanomethyl)-2-(4-(2-ethyl-3-((4-(4-fluorophenyl)thiazol-2-yl)(methyl)amino)imidazo[1,2-a]pyridin-6-yl)piperidin-1-yl)-N-methylacetamide | F8 (Gen-10-c) | 545 | 546 (M + 1) |

TABLE III-continued

Illustrative compounds of the invention.

| Cpd | Structures | Name | Mtd (Int) | MW | MS Ms'd |
|---|---|---|---|---|---|
| 122 | 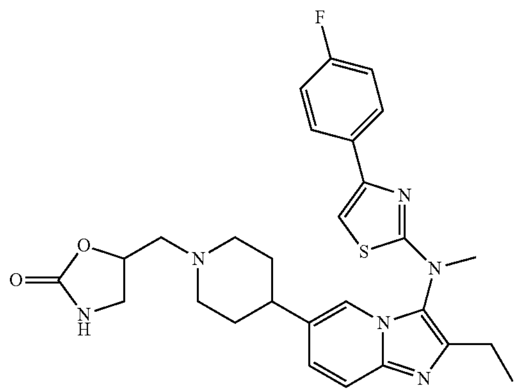 [SMILES: CCc1nc2ccc(C3CCN(CC4CNC(=O)O4)CC3)cn2c1N(C)c1nc(-c2ccc(F)cc2)cs1] | 5-((4-(2-ethyl-3-((4-(4-fluorophenyl)thiazol-2-yl)(methyl)amino)imidazo[1,2-a]pyridin-6-yl)piperidin-1-yl)methyl)oxazolidin-2-one | F8 (Gen-10-c) | 534 | 536 (M + 1) |
| 123 | 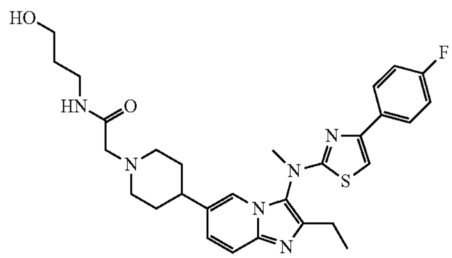 [SMILES: CCc1nc2ccc(C3CCN(CC(=O)NCCCO)CC3)cn2c1N(C)c1nc(-c2ccc(F)cc2)cs1] | 2-(4-(2-ethyl-3-((4-(4-fluorophenyl)thiazol-2-yl)(methyl)amino)imidazo[1,2-a]pyridin-6-yl)piperidin-1-yl)-N-(3-hydroxypropyl)acetamide | F8 (Gen-10-c) | 550 | 551 (M + 1) |
| 124 | 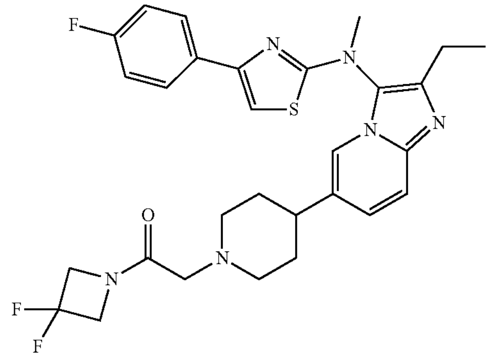 [SMILES: CCc1nc2ccc(C3CCN(CC(=O)N4CC(F)(F)C4)CC3)cn2c1N(C)c1nc(-c2ccc(F)cc2)cs1] | 1-(3,3-difluoroazetidin-1-yl)-2-(4-(2-ethyl-3-((4-(4-fluorophenyl)thiazol-2-yl)(methyl)amino)imidazo[1,2-a]pyridin-6-yl)piperidin-1-yl)ethanone | F8 (Gen-10-c) | 568 | 569 (M + 1) |
| 125 | 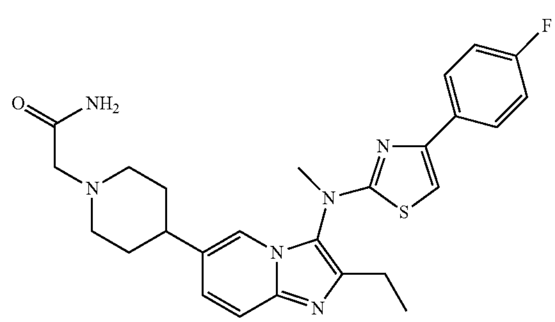 [SMILES: CCc1nc2ccc(C3CCN(CC(N)=O)CC3)cn2c1N(C)c1nc(-c2ccc(F)cc2)cs1] | 2-(4-(2-ethyl-3-((4-(4-fluorophenyl)thiazol-2-yl)(methyl)amino)imidazo[1,2-a]pyridin-6-yl)piperidin-1-yl)acetamide | F8 (Gen-10-c) | 492 | 493 (M + 1) |
| 126 | 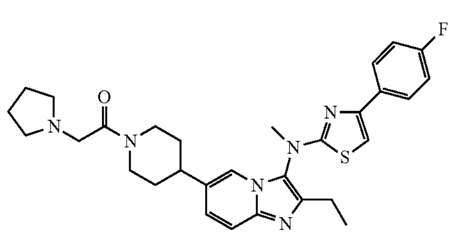 [SMILES: CCc1nc2ccc(C3CCN(C(=O)CN4CCCC4)CC3)cn2c1N(C)c1nc(-c2ccc(F)cc2)cs1] | 1-(4-(2-ethyl-3-((4-(4-fluorophenyl)thiazol-2-yl)(methyl)amino)imidazo[1,2-a]pyridin-6-yl)piperidin-1-yl)-2-(pyrrolidin-1-yl)ethanone | F9b-F12a (Gen-10-c) | 546 | 547 (M + 1) |

TABLE III-continued

Illustrative compounds of the invention.

| Cpd | Structures | Name | Mtd (Int) | MW | MS Ms'd |
|---|---|---|---|---|---|
| 127 | 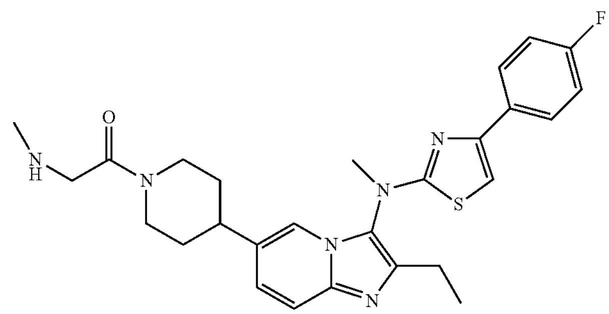 [SMILES: CCc1nc2ccc(C3CCN(C(=O)CNC)CC3)cn2c1N(C)c1nc(-c2ccc(F)cc2)cs1] | 1-(4-(2-ethyl-3-((4-(4-fluorophenyl)thiazol-2-yl)(methyl)amino) imidazo[1,2-a]pyridin-6-yl)piperidin-1-yl)-2-(methylamino)ethanone | F9b-F12a (Gen-10-c) | 506 | 507 (M + 1) |
| 128 | 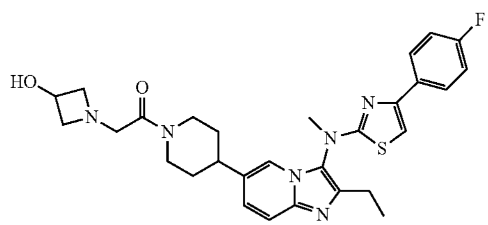 [SMILES: CCc1nc2ccc(C3CCN(C(=O)CN4CC(O)C4)CC3)cn2c1N(C)c1nc(-c2ccc(F)cc2)cs1] | 1-(4-(2-ethyl-3-((4-(4-fluorophenyl)thiazol-2-yl)(methyl)amino) imidazo[1,2-a]pyridin-6-yl)piperidin-1-yl)-2-(3-hydroxyazetidin-1-yl)ethanone | F9b-F12a (Gen-10c) | 548 | 549 (M + 1) |
| 129 | 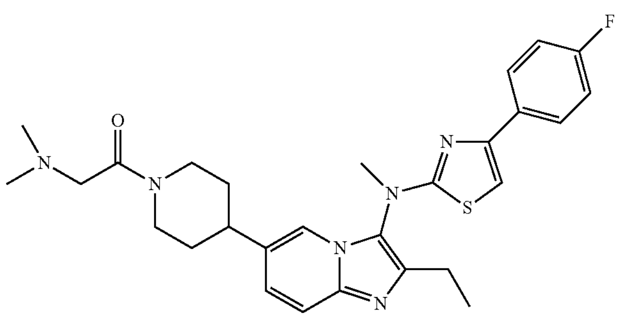 [SMILES: CCc1nc2ccc(C3CCN(C(=O)CN(C)C)CC3)cn2c1N(C)c1nc(-c2ccc(F)cc2)cs1] | 2-(dimethylamino)-1-(4-(2-ethyl-3-((4-(4-fluorophenyl)thiazol-2-yl)(methyl)amino) imidazo[1,2-a]pyridin-6-yl)piperidin-1-yl) ethanone | F9b-F12a (Gen-10-c) | 520 | 521 (M + 1) |
| 130 | 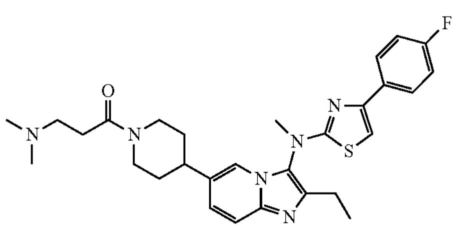 | 3-(dimethylamino)-1-(4-(2-ethyl-3-((4-(4-fluorophenyl)thiazol-2-yl)(methyl)amino) imidazo[1,2-a]pyridin-6-yl)piperidin-1-yl)propan-1-one | F9b-F12a (Gen-10-c) | 534 | 535 (M + 1) |
| 131 | 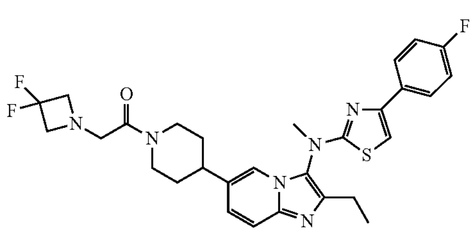 [SMILES: CCc1nc2ccc(C3CCN(C(=O)CN4CC(F)(F)C4)CC3)cn2c1N(C)c1nc(-c2ccc(F)cc2)cs1] | 2-(3,3-difluoroazetidin-1-yl)-1-(4-(2-ethyl-3-((4-(4-fluorophenyl) thiazol-2-yl)(methyl) amino)imidazo [1,2-a]pyridin-6-yl) piperidin-1-yl) ethanone | F9b-F12a (Gen-10-c) | 568 | 569 (M + 1) |
| 132 | 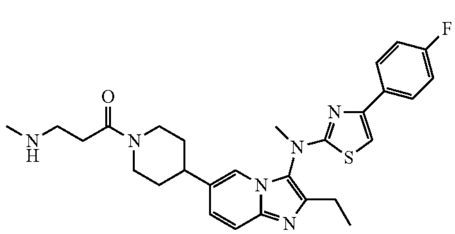 [SMILES: CCc1nc2ccc(C3CCN(C(=O)CCNC)CC3)cn2c1N(C)c1nc(-c2ccc(F)cc2)cs1] | 1-(4-(2-ethyl-3-((4-(4-fluorophenyl)thiazol-2-yl)(methyl)amino) imidazo[1,2-a]pyridin-6-yl)piperidin-1-yl)-3-(methylamino)propan-1-one | F9b-F12a (Gen-10-c) | 520 | 521 (M + 1) |

TABLE III-continued

Illustrative compounds of the invention.

| Cpd | Structures | Name | Mtd (Int) | MW | MS Ms'd |
|---|---|---|---|---|---|
| 133 | 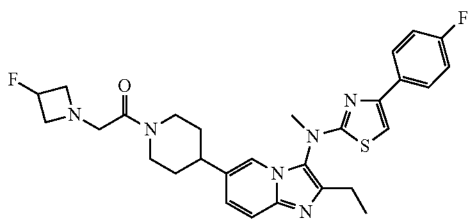 [SMILES: CCc1nc2ccc(C3CCN(C(=O)CN4CC(F)C4)CC3)cn2c1N(C)c1nc(-c2ccc(F)cc2)cs1] | 1-(4-(2-ethyl-3-((4-(4-fluorophenyl)thiazol-2-yl)(methyl)amino)imidazo[1,2-a]pyridin-6-yl)piperidin-1-yl)-2-(3-fluoroazetidin-1-yl)ethanone | F9b-F12a (Gen-10-c) | 550 | 551 (M + 1) |
| 134 | 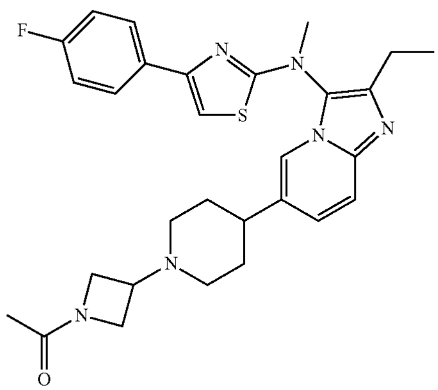 [SMILES: CCc1nc2ccc(C3CCN(C4CN(C(C)=O)C4)CC3)cn2c1N(C)c1nc(-c2ccc(F)cc2)cs1] | 1-(3-(4-(2-ethyl-3-((4-(4-fluorophenyl)thiazol-2-yl)(methyl)amino)imidazo[1,2-a]pyridin-6-yl)piperidin-1-yl)azetidin-1-yl)ethanone | F10-F5b-F9 (Gen-10-c) | 532 | 533 (M + 1) |
| 135 | 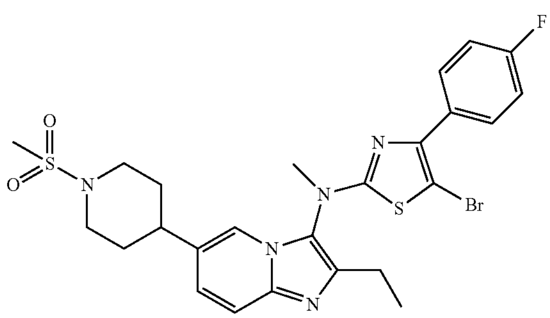 [SMILES: CCc1nc2ccc(C3CCN(S(C)(=O)=O)CC3)cn2c1N(C)c1nc(-c2ccc(F)cc2)c(Br)s1] | 5-bromo-N-(2-ethyl-6-(1-(methylsulfonyl)piperidin-4-yl)imidazo[1,2-a]pyridin-3-yl)-4-(4-fluorophenyl)-N-methylthiazol-2-amine | F16a (Cpd 80) | 592 | 593 (M + 1) |
| 136 | 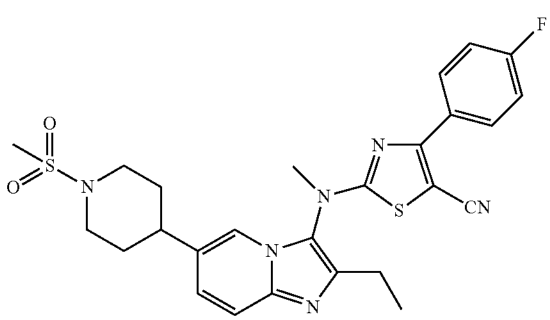 [SMILES: CCc1nc2ccc(C3CCN(S(C)(=O)=O)CC3)cn2c1N(C)c1nc(-c2ccc(F)cc2)c(C#N)s1] | 2-((2-ethyl-6-(1-(methylsulfonyl)piperidin-4-yl)imidazo[1,2-a]pyridin-3-yl)(methyl)amino)-4-(4-fluorophenyl)thiazole-5-carbonitrile | F17 (Cpd 135) | 538 | 539 (M + 1) |

TABLE III-continued

Illustrative compounds of the invention.

| Cpd | Structures | Name | Mtd (Int) | MW | MS Ms'd |
|---|---|---|---|---|---|
| 137 | 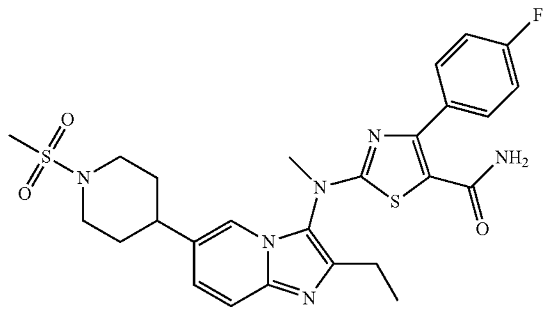 [SMILES: CCc1nc2ccc(C3CCN(S(C)(=O)=O)CC3)cn2c1N(C)c1nc(-c2ccc(F)cc2)c(C(N)=O)s1] | 2-((2-ethyl-6-(1-(methylsulfonyl)piperidin-4-yl)imidazo[1,2-a]pyridin-3-yl)(methyl)amino)-4-(4-fluorophenyl)thiazole-5-carboxamide | see Cpd 137 (Cpd 136) | 556 | 557 (M + 1) |
| 138 | 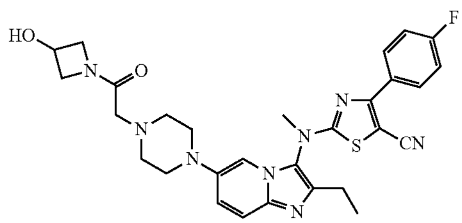 [SMILES: CCc1nc2ccc(N3CCN(CC(=O)N4CC(O)C4)CC3)cn2c1N(C)c1nc(-c2ccc(F)cc2)c(C#N)s1] | 2-((2-ethyl-6-(4-(2-(3-hydroxyazetidin-1-yl)-2-oxoethyl)piperazin-1-yl)imidazo[1,2-a]pyridin-3-yl)(methyl)amino)-4-(4-fluorophenyl)thiazole-5-carbonitrile | F16a-F17 (Cpd 24) | 574 | 575 (M + 1) |
| 139 | 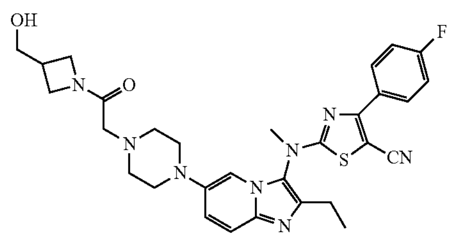 [SMILES: CCc1nc2ccc(N3CCN(CC(=O)N4CC(CO)C4)CC3)cn2c1N(C)c1nc(-c2ccc(F)cc2)c(C#N)s1] | 2-((2-ethyl-6-(4-(2-(3-(hydroxymethyl)azetidin-1-yl)-2-oxoethyl)piperazin-1-yl)imidazo[1,2-a]pyridin-3-yl)(methyl)amino)-4-(4-fluorophenyl)thiazole-5-carbonitrile | F16a-F17 (Cpd 34) | 588 | 589 (M + 1) |
| 140 | 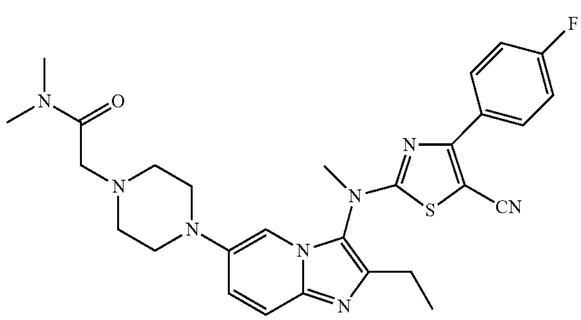 [SMILES: CCc1nc2ccc(N3CCN(CC(=O)N(C)C)CC3)cn2c1N(C)c1nc(-c2ccc(F)cc2)c(C#N)s1] | 2-(4-(3-((5-cyano-4-(4-fluorophenyl)thiazol-2-yl)(methyl)amino)-2-ethylimidazo[1,2-a]pyridin-6-yl)piperazin-1-yl)-N,N-dimethylacetamide | F16a-F17 (Cpd 35) | 546 | 547 (M + 1) |
| 141 | 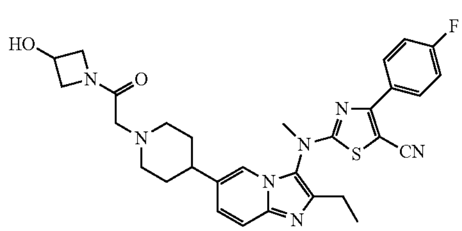 [SMILES: CCc1nc2ccc(C3CCN(CC(=O)N4CC(O)C4)CC3)cn2c1N(C)c1nc(-c2ccc(F)cc2)c(C#N)s1] | 2-((2-ethyl-6-(1-(2-(3-hydroxyazetidin-1-yl)-2-oxoethyl)piperidin-4-yl)imidazo[1,2-a]pyridin-3-yl)(methyl)amino)-4-(4-fluorophenyl)thiazole-5-carbonitrile | F16a-F17 (Cpd 110) | 573 | 574 (M + 1) |

TABLE III-continued

Illustrative compounds of the invention.

| Cpd | Structures | Name | Mtd (Int) | MW | MS Ms'd |
|---|---|---|---|---|---|
| 142 | 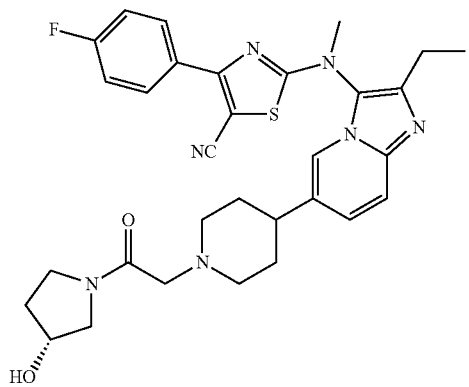 [SMILES: CCc1nc2ccc(C3CCN(CC(=O)N4CC[C@@H](O)C4)CC3)cn2c1N(C)c1nc(-c2ccc(F)cc2)c(C#N)s1] | (R)-2-((2-ethyl-6-(1-(2-(3-hydroxypyrrolidin-1-yl)-2-oxoethyl)piperidin-4-yl)imidazo[1,2-a]pyridin-3-yl)(methyl)amino)-4-(4-fluorophenyl)thiazole-5-carbonitrile | F16a-F17 (Cpd 111) | 587 | 588 (M + 1) |
| 143 | 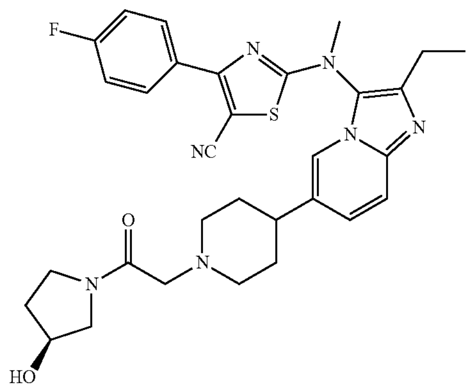 [SMILES: CCc1nc2ccc(C3CCN(CC(=O)N4CC[C@H](O)C4)CC3)cn2c1N(C)c1nc(-c2ccc(F)cc2)c(C#N)s1] | (S)-2-((2-ethyl-6-(1-(2-(3-hydroxypyrrolidin-1-yl)-2-oxoethyl)piperidin-4-yl)imidazo[1,2-a]pyridin-3-yl)(methyl)amino)-4-(4-fluorophenyl)thiazole-5-carbonitrile | F16a-F17 (Cpd 112) | 587 | 588 (M + 1) |
| 144 | 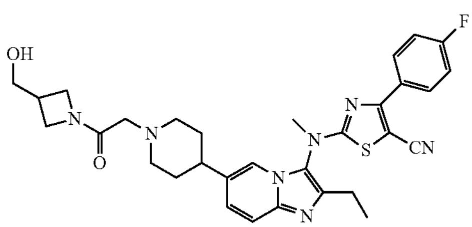 [SMILES: CCc1nc2ccc(C3CCN(CC(=O)N4CC(CO)C4)CC3)cn2c1N(C)c1nc(-c2ccc(F)cc2)c(C#N)s1] | 2-((2-ethyl-6-(1-(2-(3-(hydroxymethyl)azetidin-1-yl)-2-oxoethyl)piperidin-4-yl)imidazo[1,2-a]pyridin-3-yl)(methyl)amino)-4-(4-fluorophenyl)thiazole-5-carbonitrile | F16a-F17 (Cpd 113) | 587 | 588 (M + 1) |
| 145 | 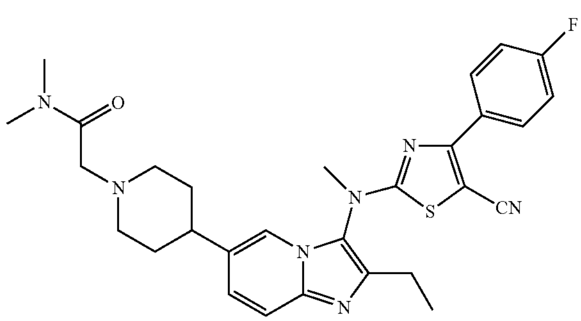 [SMILES: CCc1nc2ccc(C3CCN(CC(=O)N(C)C)CC3)cn2c1N(C)c1nc(-c2ccc(F)cc2)c(C#N)s1] | 2-(4-(3-((5-cyano-4-(4-fluorophenyl)thiazol-2-yl)(methyl)amino)-2-ethylimidazo[1,2-a]pyridin-6-yl)piperidin-1-yl)-N,N-dimethylacetamide | F16a-F17 (Cpd 114) | 545 | 546 (M + 1) |
| 146 | 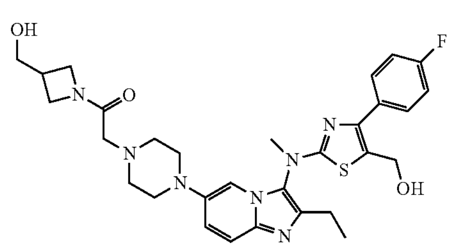 [SMILES: CCc1nc2ccc(N3CCN(CC(=O)N4CC(CO)C4)CC3)cn2c1N(C)c1nc(-c2ccc(F)cc2)c(CO)s1] | 2-(4-(2-ethyl-3-((4-(4-fluorophenyl)-5-(hydroxymethyl)thiazol-2-yl)(methyl)amino)imidazo[1,2-a]pyridin-6-yl)piperazin-1-yl)-1-(3-(hydroxymethyl)azetidin-1-yl)ethanone | F14 (Cpd 34) | 593 | 594 (M + 1) |

TABLE III-continued

Illustrative compounds of the invention.

| Cpd | Structures | Name | Mtd (Int) | MW | MS Ms'd |
|---|---|---|---|---|---|
| 147 | 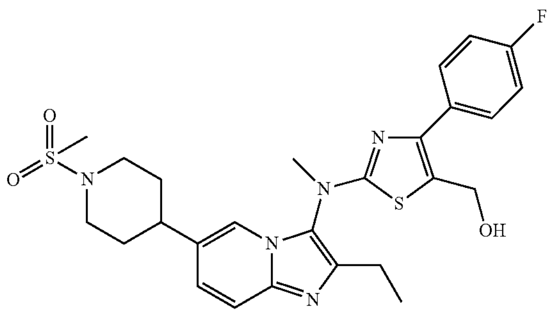 [SMILES: CCc1nc2ccc(C3CCN(S(C)(=O)=O)CC3)cn2c1N(C)c1nc(-c2ccc(F)cc2)c(CO)s1] | (2-((2-ethyl-6-(1-(methylsulfonyl)piperidin-4-yl)imidazo[1,2-a]pyridin-3-yl)(methyl)amino)-4-(4-fluorophenyl)thiazol-5-yl)methanol | F14 (Cpd 80) | 543 | 544 (M + 1) |
| 148 | 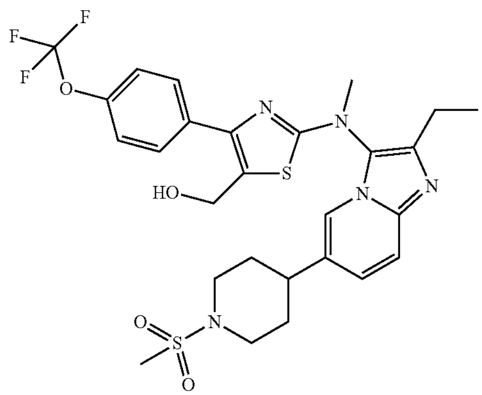 [SMILES: CCc1nc2ccc(C3CCN(S(C)(=O)=O)CC3)cn2c1N(C)c1nc(-c2ccc(OC(F)(F)F)cc2)c(CO)s1] | (2-((2-ethyl-6-(1-(methylsulfonyl)piperidin-4-yl)imidazo[1,2-a]pyridin-3-yl)(methyl)amino)-4-(4-(trifluoromethoxy)phenyl)thiazol-5-yl)methanol | F14 (Cpd 85) | 609 | 610 (M + 1) |
| 149 | 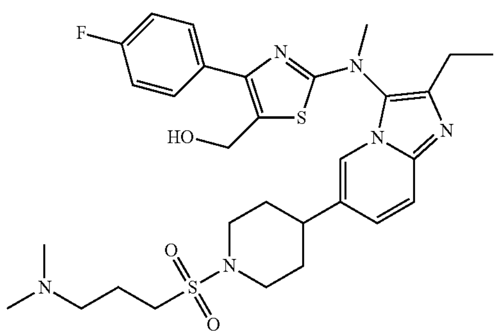 [SMILES: CCc1nc2ccc(C3CCN(S(=O)(=O)CCCN(C)C)CC3)cn2c1N(C)c1nc(-c2ccc(F)cc2)c(CO)s1] | (2-((6-(1-(3-(dimethylamino)propylsulfonyl)piperidin-4-yl)-2-ethylimidazo[1,2-a]pyridin-3-yl)(methyl)amino)-4-(4-fluorophenyl)thiazol-5-yl) | F14 (Cpd 87) | 614 | 615 (M + 1) |
| 150 | 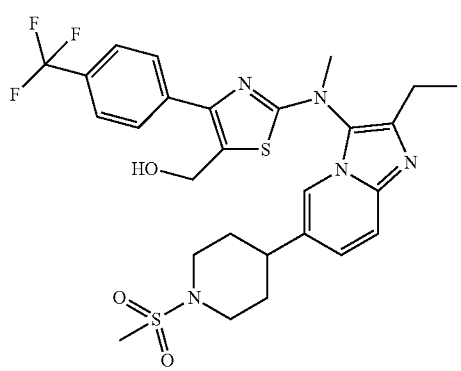 [SMILES: CCc1nc2ccc(C3CCN(S(C)(=O)=O)CC3)cn2c1N(C)c1nc(-c2ccc(C(F)(F)F)cc2)c(CO)s1] | (2-((2-ethyl-6-(1-(methylsulfonyl)piperidin-4-yl)imidazo[1,2-a]pyridin-3-yl)(methyl)amino)-4-(4-(trifluoromethyl)phenyl)thiazol-5-yl)methanol | F14 (Cpd 84) | 593 | 594 (M + 1) |

TABLE III-continued

Illustrative compounds of the invention.

| Cpd | Structures | Name | Mtd (Int) | MW | MS Ms'd |
|---|---|---|---|---|---|
| 151 | 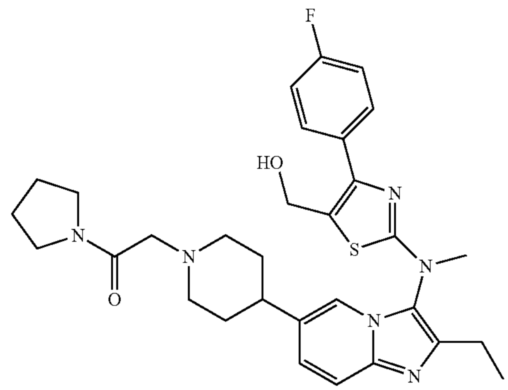 [SMILES: CCc1nc2ccc(C3CCN(CC(=O)N4CCCC4)CC3)cn2c1N(C)c1nc(-c2ccc(F)cc2)c(CO)s1] | 2-(4-(2-ethyl-3-((4-(4-fluorophenyl)-5-(hydroxymethyl)thiazol-2-yl)(methyl)amino)imidazo[1,2-a]pyridin-6-yl)piperidin-1-yl)-1-(pyrrolidin-1-yl)ethanone | F14 (Cpd 115) | 576 | 577 (M + 1) |
| 152 | 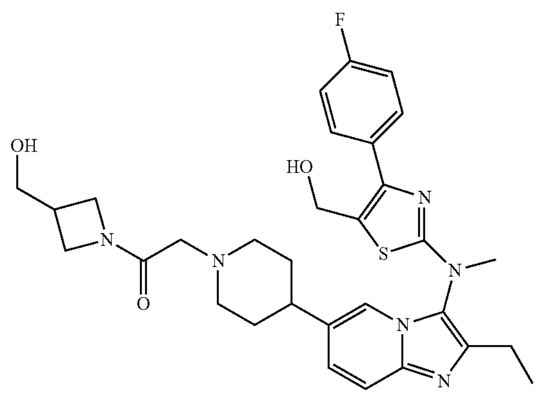 [SMILES: CCc1nc2ccc(C3CCN(CC(=O)N4CC(CO)C4)CC3)cn2c1N(C)c1nc(-c2ccc(F)cc2)c(CO)s1] | 2-(4-(2-ethyl-3-((4-(4-fluorophenyl)-5-(hydroxymethyl)thiazol-2-yl)(methyl)amino)imidazo[1,2-a]pyridin-6-yl)piperidin-1-yl)-1-(3-(hydroxymethyl)azetidin-1-yl)ethanone | F14 (Cpd 113) | 592 | 593 (M + 1) |
| 153 | 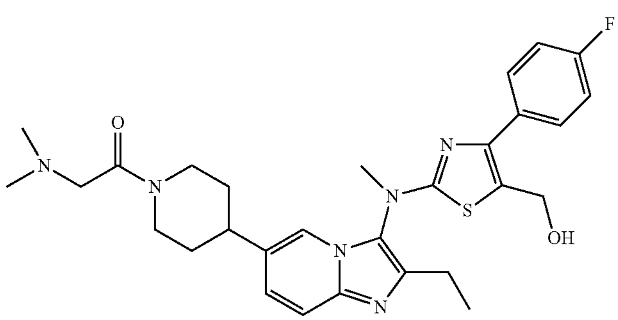 [SMILES: CCc1nc2ccc(C3CCN(C(=O)CN(C)C)CC3)cn2c1N(C)c1nc(-c2ccc(F)cc2)c(CO)s1] | 2-(dimethylamino)-1-(4-(2-ethyl-3-((4-(4-fluorophenyl)-5-(hydroxymethyl)thiazol-2-yl)(methyl)amino)imidazo[1,2-a]pyridin-6-yl)piperidin-1-yl)ethanone | F14 (Cpd 129) | 550 | 551 (M + 1) |
| 154 | 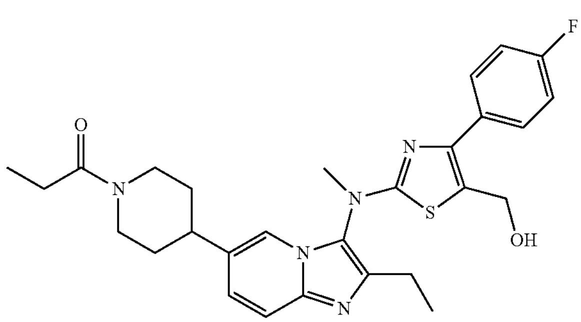 [SMILES: CCC(=O)N1CCC(c2ccc3nc(CC)c(N(C)c4nc(-c5ccc(F)cc5)c(CO)s4)n3c2)CC1] | 1-(4-(2-ethyl-3-((4-(4-fluorophenyl)-5-(hydroxymethyl)thiazol-2-yl)(methyl)amino)imidazo[1,2-a]pyridin-6-yl)piperidin-1-yl)propan-1-one | F9b-F14 (Gen-10-c) | 521 | 522 (M + 1) |

TABLE III-continued

Illustrative compounds of the invention.

| Cpd | Structures | Name | Mtd (Int) | MW | MS Ms'd |
|---|---|---|---|---|---|
| 155 | 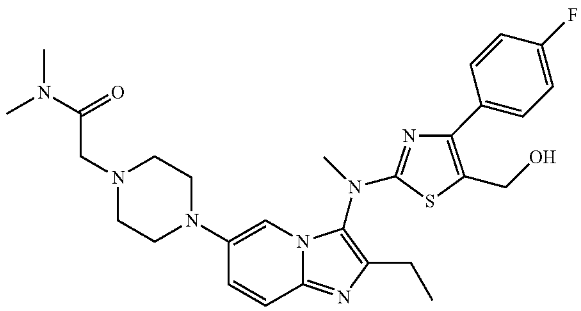 [SMILES: CCc1nc2ccc(N3CCN(CC(=O)N(C)C)CC3)cn2c1N(C)c1nc(-c2ccc(F)cc2)c(CO)s1] | 2-(4-(2-ethyl-3-((4-(4-fluorophenyl)-5-(hydroxymethyl)thiazol-2-yl)(methyl)amino)imidazo[1,2-a]pyridin-6-yl)piperazin-1-yl)-N,N-dimethylacetamide | B1-C1-F1b-D1-F7-E1-F18-F5b-F8 (Gen-10-ag) | 551 | 552 (M + 1) |
| 156 | 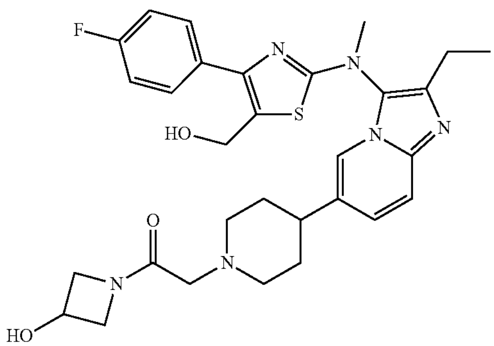 [SMILES: CCc1nc2ccc(C3CCN(CC(=O)N4CC(O)C4)CC3)cn2c1N(C)c1nc(-c2ccc(F)cc2)c(CO)s1] | 2-(4-(2-ethyl-3-((4-(4-fluorophenyl)-5-(hydroxymethyl)thiazol-2-yl)(methyl)amino)imidazo[1,2-a]pyridin-6-yl)piperidin-1-yl)-1-(3-hydroxyazetidin-1-yl)ethanone | F18-F5b-F8 (Gen-10-ar) | 578 | 579 (M + 1) |
| 157 | 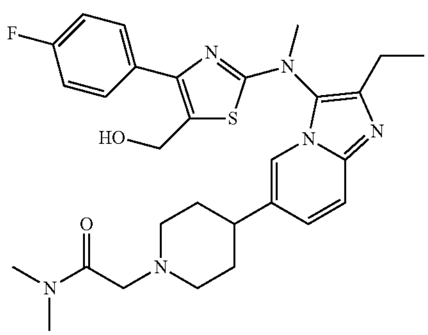 [SMILES: CCc1nc2ccc(C3CCN(CC(=O)N(C)C)CC3)cn2c1N(C)c1nc(-c2ccc(F)cc2)c(CO)s1] | 2-(4-(2-ethyl-3-((4-(4-fluorophenyl)-5-(hydroxymethyl)thiazol-2-yl)(methyl)amino)imidazo[1,2-a]pyridin-6-yl)piperidin-1-yl)-N,N-dimethylacetamide | F18-F5b-F8 (Gen-10-ar) | 550 | N.M |
| 158 | 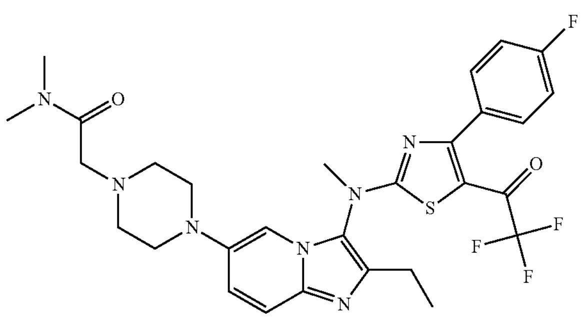 [SMILES: CCc1nc2ccc(N3CCN(CC(=O)N(C)C)CC3)cn2c1N(C)c1nc(-c2ccc(F)cc2)c(C(=O)C(F)(F)F)s1] | 2-(4-(2-ethyl-3-((4-(4-fluorophenyl)-5-(2,2,2-trifluoroacetoyl)thiazol-2-yl)(methyl)amino)imidazo[1,2-a]pyridin-6-yl)piperazin-1-yl)-N,N-dimethylacetamide | F15 (Cpd 35) | 617 | 618 (M + 1) |
| 159 | 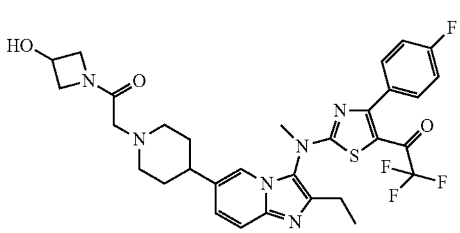 [SMILES: CCc1nc2ccc(C3CCN(CC(=O)N4CC(O)C4)CC3)cn2c1N(C)c1nc(-c2ccc(F)cc2)c(C(=O)C(F)(F)F)s1] | 1-(2-((2-ethyl-6-(1-(2-(3-hydroxyazetidin-1-yl)-2-oxoethyl)piperidin-4-yl)imidazo[1,2-a]pyridin-3-yl)(methyl)amino)-4-(4-fluorophenyl)thiazol-5-yl)-2,2,2-trifluoroethanone | F15 (Cpd 110) | 644 | 645 (M + 1) |

TABLE III-continued

Illustrative compounds of the invention.

| Cpd | Structures | Name | Mtd (Int) | MW | MS Ms'd |
|---|---|---|---|---|---|
| 160 | 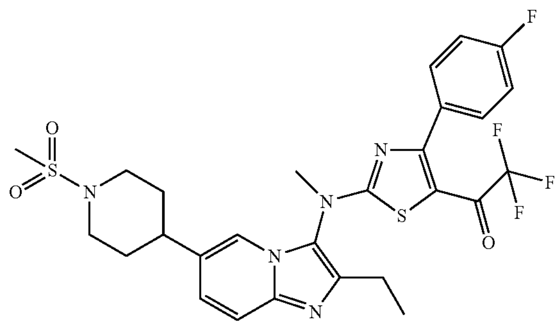 [SMILES: CCc1nc2ccc(C3CCN(S(C)(=O)=O)CC3)cn2c1N(C)c1nc(-c2ccc(F)cc2)c(C(=O)C(F)(F)F)s1] | 1-(2-((2-ethyl-6-(1-(methylsulfonyl)piperidin-4-yl)imidazo[1,2-a]pyridin-3-yl)(methyl)amino)-4-(4-fluorophenyl)thiazol-5-yl)-2,2,2-trifluoroethanone | F15 (Cpd 80) | 609 | 610 (M + 1) |
| 161 | 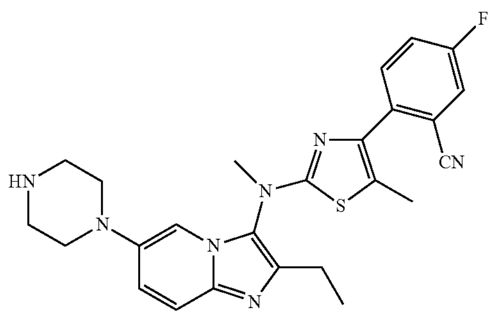 [SMILES: CCc1nc2ccc(N3CCNCC3)cn2c1N(C)c1nc(-c2ccc(F)cc2C#N)c(C)s1] | 2-(2-((2-ethyl-6-(piperazin-1-yl)imidazo[1,2-a]pyridin-3-yl)methyl)amino)-5-methylthiazol-4-yl)-5-fluorobenzonitrile | F1a (Gen-5-m) | 475 | 476 (M + 1) |
| 162 | 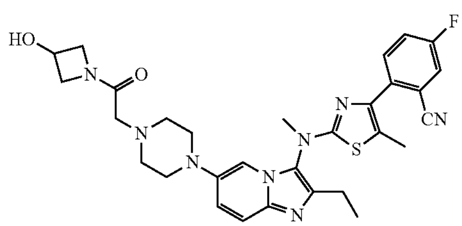 [SMILES: CCc1nc2ccc(N3CCN(CC(=O)N4CC(O)C4)CC3)cn2c1N(C)c1nc(-c2ccc(F)cc2C#N)c(C)s1] | 2-(2-((2-ethyl-6-(4-(2-(3-hydroxyazetidin-1-yl)-2-oxoethyl)piperazin-1-yl)imidazo[1,2-a]pyridin-3-yl)(methyl)amino)-5-methylthiazol-4-yl)-5-fluorobenzonitrile | F8 (Cpd 161) | 588 | 589 (M + 1) |
| 163 | 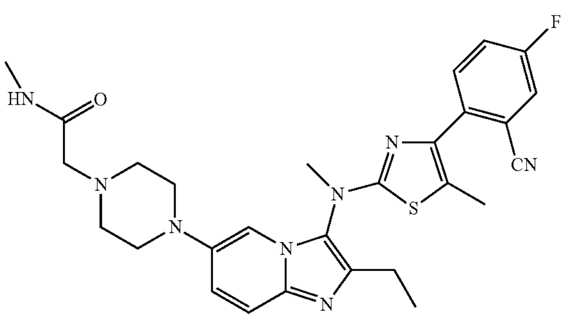 [SMILES: CCc1nc2ccc(N3CCN(CC(=O)NC)CC3)cn2c1N(C)c1nc(-c2ccc(F)cc2C#N)c(C)s1] | 2-(4-(3-((4-(2-cyano-4-fluorophenyl)-5-methylthiazol-2-yl)(methyl)amino)-2-ethylimidazo[1,2-a]pyridin-6-yl)piperazin-1-yl)-N-methylacetamide | F8 (Cpd 161) | 546 | 547 (M + 1) |
| 164 | 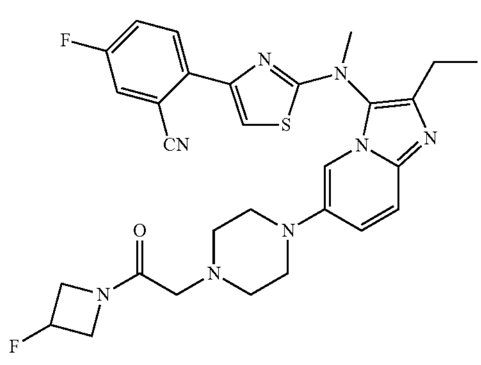 [SMILES: CCc1nc2ccc(N3CCN(CC(=O)N4CC(F)C4)CC3)cn2c1N(C)c1nc(-c2ccc(F)cc2C#N)cs1] | 2-(2-((2-ethyl-6-(4-(2-(3-fluoroazetidin-1-yl)-2-oxoethyl)piperazin-1-yl)imidazo[1,2-a]pyridin-3-yl)(methyl)amino)thiazol-4-yl)-5-fluorobenzonitrile | F8 (Gen-10-i) | 576 | 577 (M + 1) |

TABLE III-continued

Illustrative compounds of the invention.

| Cpd | Structures | Name | Mtd (Int) | MW | MS Ms'd |
|---|---|---|---|---|---|
| 165 | 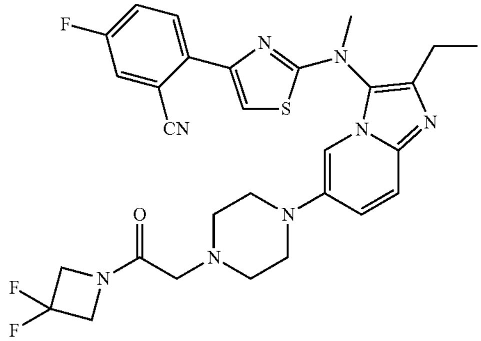 [SMILES: CCc1nc2ccc(N3CCN(CC(=O)N4CC(F)(F)C4)CC3)cn2c1N(C)c1nc(-c2ccc(F)cc2C#N)cs1] | 2-(2-((6-(4-(2-(3,3-difluoroazetidin-1-yl)-2-oxoethyl)piperazin-1-yl)-2-ethylimidazo[1,2-a]pyridin-3-yl)(methyl)amino)thiazol-4-yl)-5-fluorobenzonitrile | F8 (Gen-10-i) | 594 | 595 (M + 1) |
| 166 | 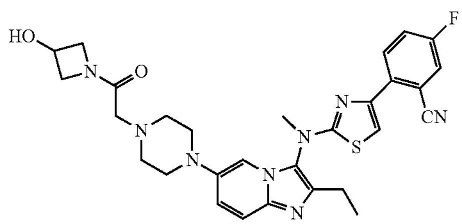 [SMILES: CCc1nc2ccc(N3CCN(CC(=O)N4CC(O)C4)CC3)cn2c1N(C)c1nc(-c2ccc(F)cc2C#N)cs1] | 2-(2-((2-ethyl-6-(4-(2-(3-hydroxyazetidin-1-yl)-2-oxoethyl)piperazin-1-yl)imidazo[1,2-a]pyridin-3-yl)(methyl)amino)thiazol-4-yl)-5-fluorobenzonitrile | F8 (Gen-10-i) | 574 | 575 (M + 1) |
| 167 | 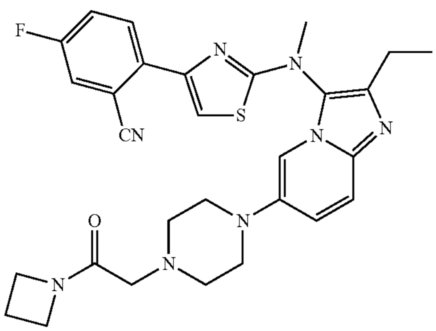 [SMILES: CCc1nc2ccc(N3CCN(CC(=O)N4CCC4)CC3)cn2c1N(C)c1nc(-c2ccc(F)cc2C#N)cs1] | 2-(2-((6-(4-(2-(azetidin-1-yl)-2-oxoethyl)piperazin-1-yl)-2-ethylimidazo[1,2-a]pyridin-3-yl)(methyl)amino)thiazol-4-yl)-5-fluorobenzonitrile | F8 (Gen-10-i) | 558 | 559 (M + 1) |
| 168 | 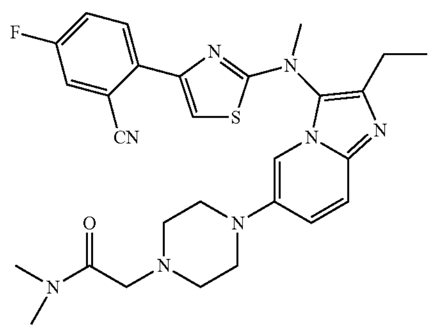 [SMILES: CCc1nc2ccc(N3CCN(CC(=O)N(C)C)CC3)cn2c1N(C)c1nc(-c2ccc(F)cc2C#N)cs1] | 2-(4-(3-((4-(2-cyano-4-fluorophenyl)thiazol-2-yl)(methyl)amino)-2-ethylimidazo[1,2-a]pyridin-6-yl)piperazin-1-yl)-N,N-dimethylacetamide | F8 (Gen-10-i) | 546 | 547 (M + 1) |
| 169 | 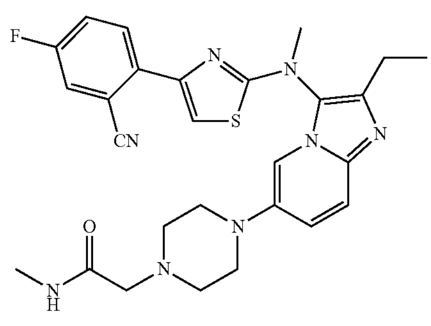 [SMILES: CCc1nc2ccc(N3CCN(CC(=O)NC)CC3)cn2c1N(C)c1nc(-c2ccc(F)cc2C#N)cs1] | 2-(4-(3-((4-(2-cyano-4-fluorophenyl)thiazol-2-yl)(methyl)amino)-2-ethylimidazo[1,2-a]pyridin-6-yl)piperazin-1-yl)-N-methylacetamide | F8 (Gen-10-i) | 532 | 533 (M + 1) |

TABLE III-continued

Illustrative compounds of the invention.

| Cpd | Structures | Name | Mtd (Int) | MW | MS Ms'd |
|---|---|---|---|---|---|
| 170 | 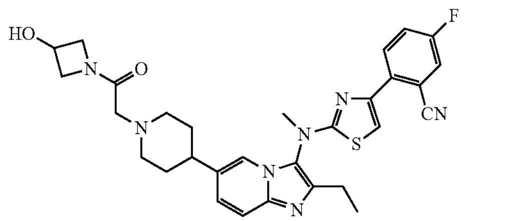 | 2-(2-((2-ethyl-6-(1-(2-(3-hydroxyazetidin-1-yl)-2-oxoethyl)piperidin-4-yl)imidazo[1,2-a]pyridin-3-yl)(methyl)amino)thiazol-4-yl)-5-fluorobenzonitrile | F8 (Gen-10-h) | 573 | 574 (M + 1) |
| 171 | 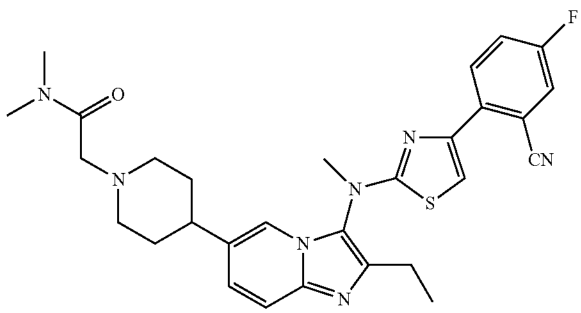 [SMILES: CCc1nc2ccc(C3CCN(CC(=O)N(C)C)CC3)cn2c1N(C)c1nc(-c2ccc(F)cc2C#N)cs1] | 2-(4-(3-((4-(2-cyano-4-fluorophenyl)thiazol-2-yl)(methyl)amino)-2-ethylimidazo[1,2-a]pyridin-6-yl)piperidin-1-yl)-N,N-dimethylacetamide | F8 (Gen-10-h) | 545 | 546 (M + 1) |
| 172 | 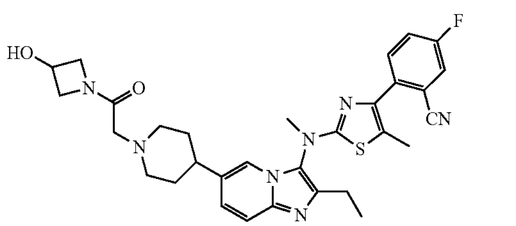 [SMILES: CCc1nc2ccc(C3CCN(CC(=O)N4CC(O)C4)CC3)cn2c1N(C)c1nc(-c2ccc(F)cc2C#N)c(C)s1] | 2-(2-((2-ethyl-6-(1-(2-(3-hydroxyazetidin-1-yl)-2-oxoethyl)piperidin-4-yl)imidazo[1,2-a]pyridin-3-yl)(methyl)amino)-5-methylthiazol-4-yl)-5-fluorobenzonitrile | F8 (Gen-10-f) | 587 | 588 (M + 1) |
| 173 | 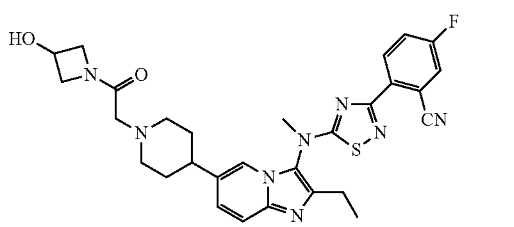 [SMILES: CCc1nc2ccc(C3CCN(CC(=O)N4CC(O)C4)CC3)cn2c1N(C)c1nc(-c2ccc(F)cc2C#N)ns1] | 2-(5-((2-ethyl-6-(1-(2-(3-hydroxyazetidin-1-yl)-2-oxoethyl)piperidin-4-yl)imidazo[1,2-a]pyridin-3-yl)(methyl)amino)-1,2,4-thiadiazol-3-yl)-5-fluorobenzonitrile | F8 (Gen-10-t) | 574 | 575 (M + 1) |
| 174 | 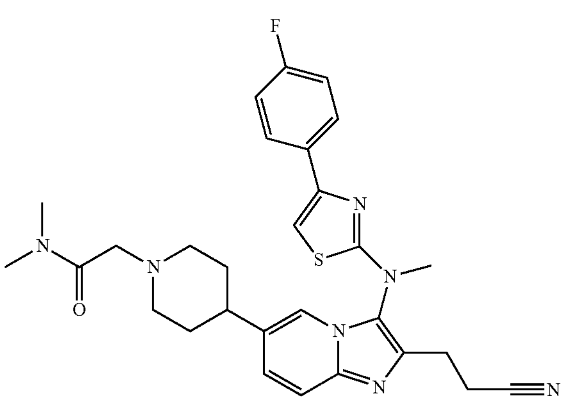 [SMILES: CN(C)C(=O)CN1CCC(c2ccc3nc(CCC#N)c(N(C)c4nc(-c5ccc(F)cc5)cs4)n3c2)CC1] | 2-(4-(2-(2-cyanoethyl)-3-((4-(4-fluorophenyl)thiazol-2-yl)(methyl)amino)imidazo[1,2-a]pyridin-6-yl)piperidin-1-yl)-N,N-dimethylacetamide | see Cpd 174-F8 (Gen-10-aa) | 545 | 546 (M + 1) |

TABLE III-continued

Illustrative compounds of the invention.

| Cpd | Structures | Name | Mtd (Int) | MW | MS Ms'd |
|---|---|---|---|---|---|
| 175 | 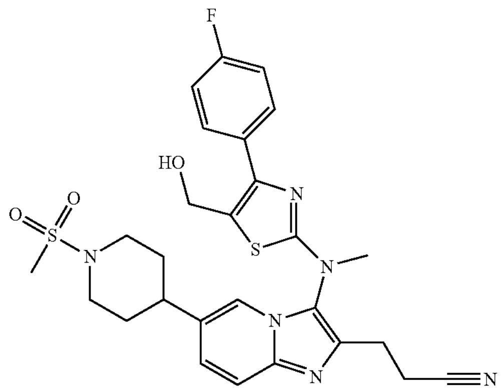 [SMILES: CN(c1nc(-c2ccc(F)cc2)c(CO)s1)c1c(CCC#N)nc2ccc(C3CCN(S(C)(=O)=O)CC3)cn12] | 3-(3-((4-(4-fluorophenyl)-5-(hydroxymethyl)thiazol-2-yl)(methyl)amino)-6-(1-(methylsulfonyl)piperidin-4-yl)imidazo[1,2-a]pyridin-2-yl)propanenitrile | F11-F14 (Gen-10-aa) | 568 | 569 (M + 1) |
| 176 | 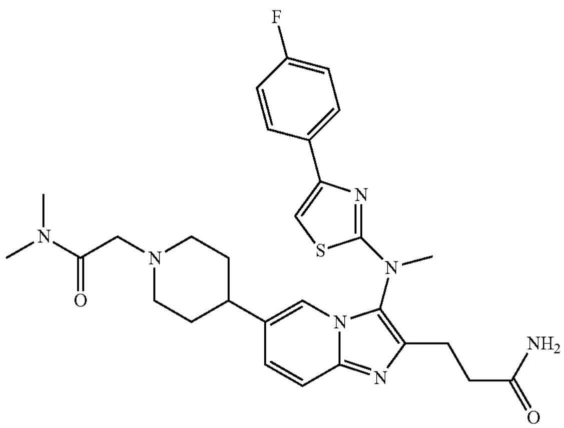 [SMILES: CN(C)C(=O)CN1CCC(c2ccc3nc(CCC(N)=O)c(N(C)c4nc(-c5ccc(F)cc5)cs4)n3c2)CC1] | 3-(6-(1-(2-(dimethylamino)-2-oxoethyl)piperidin-4-yl)-3-((4-(4-fluorophenyl)thiazol-2-yl)(methyl)amino)imidazo[1,2-a]pyridin-2-yl)propanamide | see Cpd 176-F5b-F8 (Gen-10-am) | 563 | 564 (M + 1) |
| 177 | 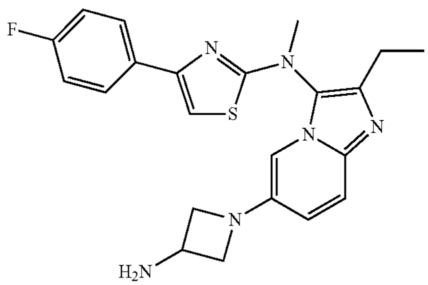 [SMILES: CCc1nc2ccc(N3CC(N)C3)cn2c1N(C)c1nc(-c2ccc(F)cc2)cs1] | N-(6-(3-aminoazetidin-1-yl)-2-ethylimidazo[1,2-a]pyridin-3-yl)-4-(4-fluorophenyl)-N-methylthiazol-2-amine | F1b-F5a (Gen-5-b) | 422 | 423 (M + 1) |
| 178 | 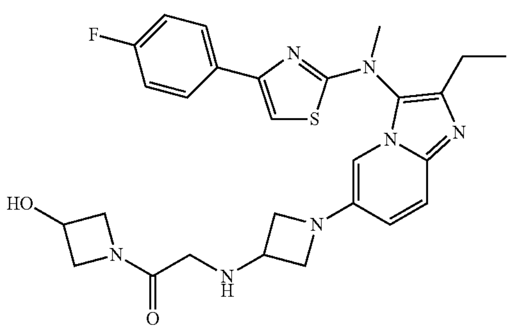 [SMILES: CCc1nc2ccc(N3CC(NCC(=O)N4CC(O)C4)C3)cn2c1N(C)c1nc(-c2ccc(F)cc2)cs1] | 2-(1-(2-ethyl-3-((4-(4-fluorophenyl)thiazol-2-yl)(methyl)amino)imidazo[1,2-a]pyridin-6-yl)azetidin-3-ylamino)-1-(3-hydroxyazetidin-1-yl)ethanone | F8 (Cpd 177) | 535 | 536 (M + 1) |

TABLE III-continued

Illustrative compounds of the invention.

| Cpd | Structures | Name | Mtd (Int) | MW | MS Ms'd |
|---|---|---|---|---|---|
| 179 | 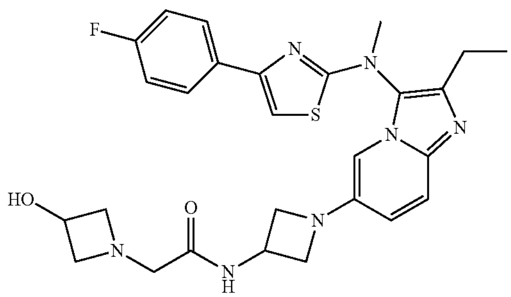 [SMILES: CCc1nc2ccc(N3CC(NC(=O)CN4CC(O)C4)C3)cn2c1N(C)c1nc(-c2ccc(F)cc2)cs1] | N-(1-(2-ethyl-3-((4-(4-fluorophenyl)thiazol-2-yl)(methyl)amino)imidazo[1,2-a]pyridin-6-yl)azetidin-3-yl)-2-(3-hydroxyazetidin-1-yl)acetamide | F9b-F8 (Cpd 177) | 535 | 536 (M + 1) |
| 180 | 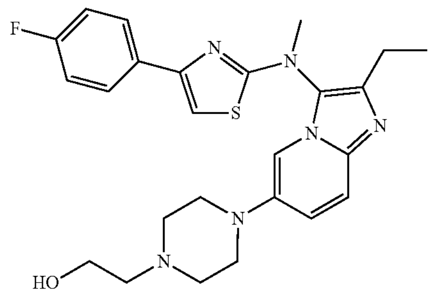 [SMILES: CCc1nc2ccc(N3CCN(CCO)CC3)cn2c1N(C)c1nc(-c2ccc(F)cc2)cs1] | 2-(4-(2-ethyl-3-((4-(4-fluorophenyl)thiazol-2-yl)(methyl)amino)imidazo[1,2-a]pyridin-6-yl)piperazin-1-yl)ethanol | F1b (Gen-5b) | 480 | 481 (M + 1) |
| 181 | 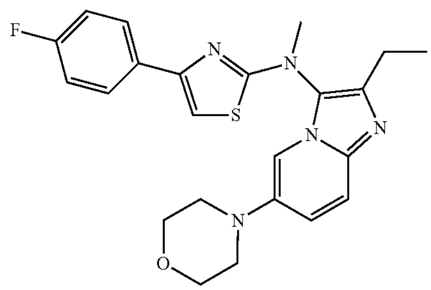 [SMILES: CCc1nc2ccc(N3CCOCC3)cn2c1N(C)c1nc(-c2ccc(F)cc2)cs1] | N-(2-ethyl-6-morpholinoimidazo[1,2-a]pyridin-3-yl)-4-(4-fluorophenyl)-N-methylthiazol-2-amine | F1b (Gen-5-b) | 437 | 438 (M + 1) |
| 182 | 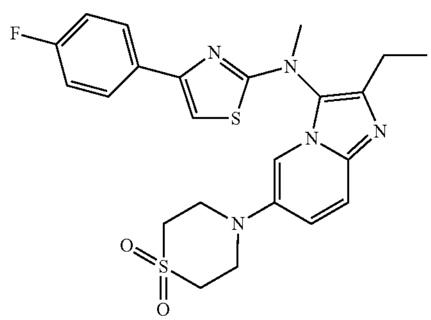 [SMILES: CCc1nc2ccc(N3CCS(=O)(=O)CC3)cn2c1N(C)c1nc(-c2ccc(F)cc2)cs1] | 4-(2-ethyl-3-((4-(4-fluorophenyl)thiazol-2-yl)(methyl)amino)imidazo[1,2-a]pyridin-6-yl)-thiomorpholine 1,1-dioxide | F1b (Gen-5-c) | 485 | 486 (M + 1) |
| 183 (or Gen-10-a) | 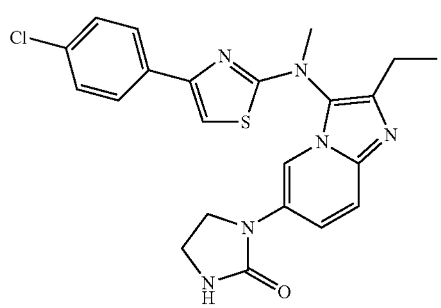 [SMILES: CCc1nc2ccc(N3CCNC3=O)cn2c1N(C)c1nc(-c2ccc(Cl)cc2)cs1] | 1-(3-((4-(4-chlorophenyl)thiazol-2-yl)(methyl)amino)-2-ethylimidazo[1,2-a]pyridin-6-yl)imidazolidin-2-one | F4 (Gen-5-i) | 452 ($^{35}$Cl), 454 ($^{37}$Cl) | 453 ($^{35}$Cl M + 1) 455 ($^{37}$Cl M + 1) |

TABLE III-continued

Illustrative compounds of the invention.

| Cpd | Structures | Name | Mtd (Int) | MW | MS Ms'd |
|---|---|---|---|---|---|
| 184 | 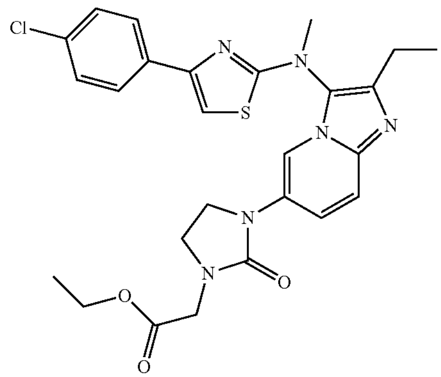 [SMILES: CCOC(=O)CN1CCN(c2ccc3nc(CC)c(N(C)c4nc(-c5ccc(Cl)cc5)cs4)n3c2)C1=O] | ethyl 2-(3-(3-((4-(4-chlorophenyl)thiazol-2-yl)(methyl)amino)-2-ethylimidazo[1,2-a]pyridin-6-yl)-2-oxoimidazolidin-1-yl)acetate | see Cpd 184-F8 (Cpd 183) | 538 ($^{35}$Cl), 540 ($^{37}$Cl) | 539 ($^{35}$Cl M + 1) 541 ($^{37}$Cl M + 1) |
| 185 | 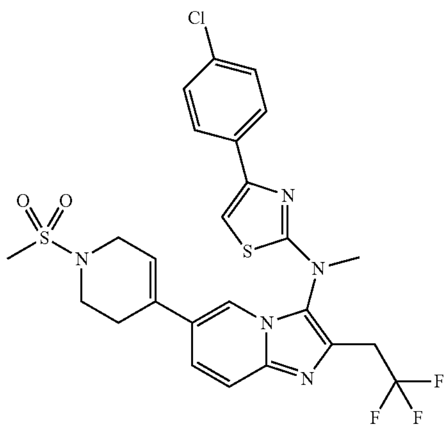 [SMILES: CN(c1nc(-c2ccc(Cl)cc2)cs1)c1c(CC(F)(F)F)nc2ccc(C3=CCN(S(C)(=O)=O)CC3)cn12] | 4-(4-chlorophenyl)-N-methyl-N-(6-(1-(methylsulfonyl)-1,2,3,6-tetrahydropyridin-4-yl)-2-(2,2,2-trifluoroethyl)imidazo[1,2-a]pyridin-3-yl)thiazol-2-amine | F11 (Gen-10-ad) | 581 ($^{35}$Cl), 583 ($^{37}$Cl) | NA |
| 186 | 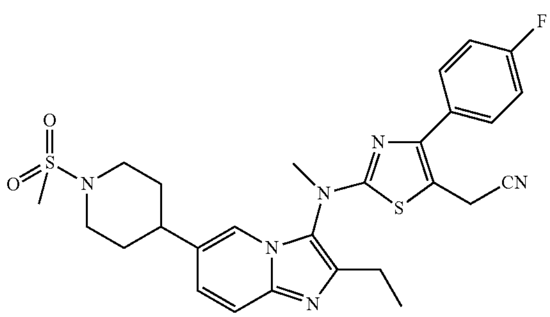 [SMILES: CCc1nc2ccc(C3CCN(S(C)(=O)=O)CC3)cn2c1N(C)c1nc(-c2ccc(F)cc2)c(CC#N)s1] | 2-(2-((2-ethyl-6-(1-(methylsulfonyl)piperidin-4-yl)imidazo[1,2-a]pyridin-3-yl)(methyl)amino)-4-(4-fluorophenyl)thiazol-5-yl)acetonitrile | see cpd 186 (Cpd 147) | 552 | 553 (M + 1) |
| 187 | 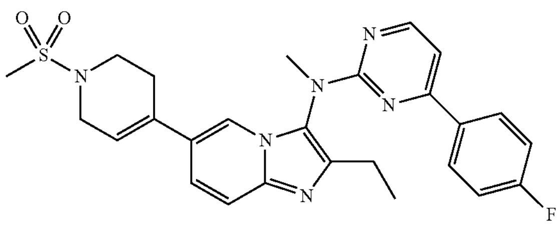 [SMILES: CCc1nc2ccc(C3=CCN(S(C)(=O)=O)CC3)cn2c1N(C)c1nccc(-c2ccc(F)cc2)n1] | 2-ethyl-N-(4-(4-fluorophenyl)pyrimidin-2-yl)-N-methyl-6-(1-(methylsulfonyl)-1,2,3,6-tetrahydropyridin-4-yl)imidazo[1,2-a]pyridin-3-amine | See Cpd 187 (Gen-9-a) | 506 | 507 (M + 1) |

TABLE III-continued

Illustrative compounds of the invention.

| Cpd | Structures | Name | Mtd (Int) | MW | MS Ms'd |
|---|---|---|---|---|---|
| 188 | 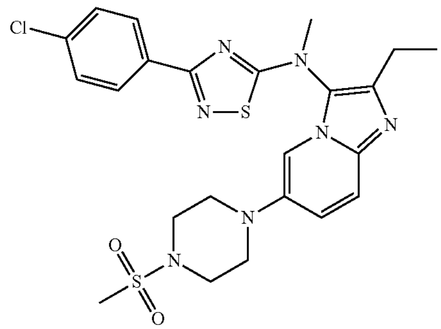 [SMILES: CCc1nc2ccc(N3CCN(S(C)(=O)=O)CC3)cn2c1N(C)c1nc(-c2ccc(Cl)cc2)ns1] | 3-(4-chlorophenyl)-N-(2-ethyl-6-(4-(methylsulfonyl)piperazin-1-yl)imidazo[1,2-a]pyridin-3-yl)-N-methyl-1,2,4-thiadiazol-5-amine | F11 (Gen-10-u) | 531 ($^{35}$Cl), 533 ($^{37}$Cl) | 532 ($^{35}$Cl M + 1) 534 ($^{37}$Cl M + 1) |
| 189 | 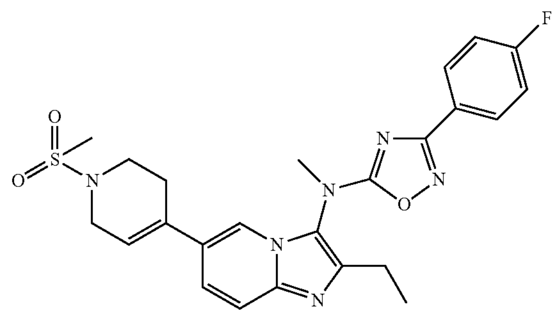 [SMILES: CCc1nc2ccc(C3=CCN(S(C)(=O)=O)CC3)cn2c1N(C)c1nc(-c2ccc(F)cc2)no1] | N-(2-ethyl-6-(1-(methylsulfonyl)-1,2,3,6-tetrahydropyridin-4-yl)imidazo[1,2-a]pyridin-3-yl)-3-(4-fluorophenyl)-N-methyl-1,2,4-oxadiazol-5-amine | F2 (Gen-5-ae) | 496 | 497 (M + 1) |
| 190 | 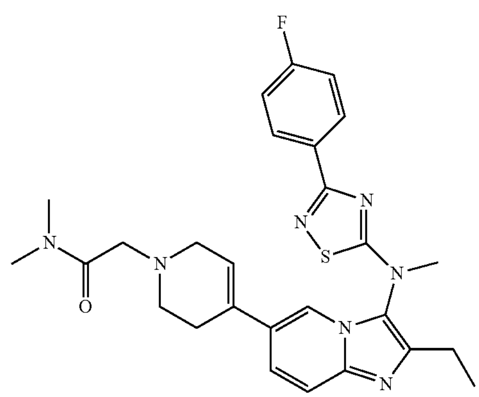 [SMILES: CCc1nc2ccc(C3=CCN(CC(=O)N(C)C)CC3)cn2c1N(C)c1nc(-c2ccc(F)cc2)ns1] | 2-(4-(2-ethyl-3-((3-(4-fluorophenyl)-1,2,4-thiadiazol-5-yl)(methyl)amino)imidazo[1,2-a]pyridin-6-yl)-5,6-dihydropyridin-1(2H)-yl)-N,N-dimethylacetamide | F8 (Gen-10-v) | 519 | 520 (M + 1) |
| 191 | 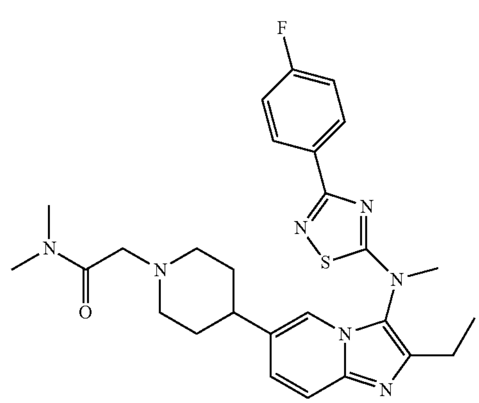 [SMILES: CCc1nc2ccc(C3CCN(CC(=O)N(C)C)CC3)cn2c1N(C)c1nc(-c2ccc(F)cc2)ns1] | 2-(4-(2-ethyl-3-((3-(4-fluorophenyl)-1,2,4-thiadiazol-5-yl)(methyl)amino)imidazo[1,2-a]pyridin-6-yl)piperidin-1-yl)-N,N-dimethylacetamide | F8 (gen-10-w) | 521 | 522 (M + 1) |

TABLE III-continued

Illustrative compounds of the invention.

| Cpd | Structures | Name | Mtd (Int) | MW | MS Ms'd |
|---|---|---|---|---|---|
| 192 | 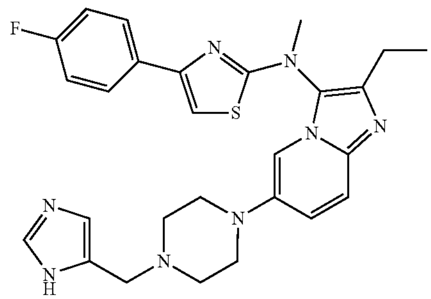 [SMILES: CCc1nc2ccc(N3CCN(Cc4cnc[nH]4)CC3)cn2c1N(C)c1nc(-c2ccc(F)cc2)cs1] | N-(6-(4-((1H-imidazol-5-yl)methyl)piperazin-1-yl)-2-ethylimidazo[1,2-a]pyridin-3-yl)-4-(4-fluorophenyl)-N-methylthiazol-2-amine | F10 (Gen-10-e) | 516 | 517 (M + 1) |
| 193 | 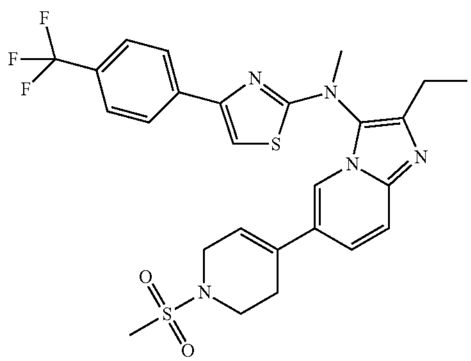 [SMILES: CCc1nc2ccc(C3=CCN(S(C)(=O)=O)CC3)cn2c1N(C)c1nc(-c2ccc(C(F)(F)F)cc2)cs1] | N-(2-ethyl-6-(1-(methylsulfonyl)-1,2,3,6-tetrahydropyridin-4-yl)imidazo[1,2-a]pyridin-3-yl)-N-methyl-4-(4-(trifluoromethyl)phenyl)thiazol-2-amine | F11 (Gen-10-ai) | 561 | 562 (M + 1) |
| 194 | 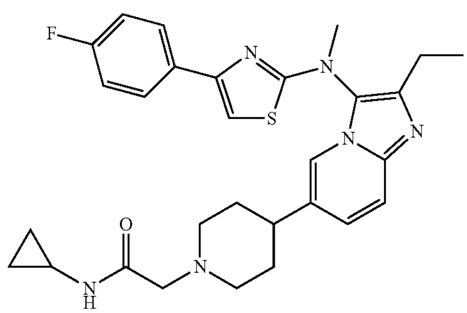 [SMILES: CCc1nc2ccc(C3CCN(CC(=O)NC4CC4)CC3)cn2c1N(C)c1nc(-c2ccc(F)cc2)cs1] | N-cyclopropyl-2-(4-(2-ethyl-3-((4-(4-fluorophenyl)thiazol-2-yl)(methyl)amino)imidazo[1,2-a]pyridin-6-yl)piperidin-1-yl)acetamide | F8 (Gen-10-c) | 532 | 533 (M + 1) |
| 195 | 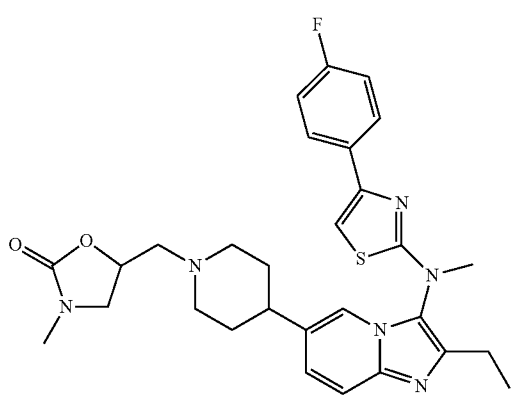 [SMILES: CCc1nc2ccc(C3CCN(CC4CN(C)C(=O)O4)CC3)cn2c1N(C)c1nc(-c2ccc(F)cc2)cs1] | 5-((4-(2-ethyl-3-((4-(4-fluorophenyl)thiazol-2-yl)(methyl)amino)imidazo[1,2-a]pyridin-6-yl)piperidin-1-yl)methyl)-3-methyloxazolidin-2-one | F8 (Gen-10-c) | 548 | 549 (M + 1) |

TABLE III-continued

Illustrative compounds of the invention.

| Cpd | Structures | Name | Mtd (Int) | MW | MS Ms'd |
|---|---|---|---|---|---|
| 196 | 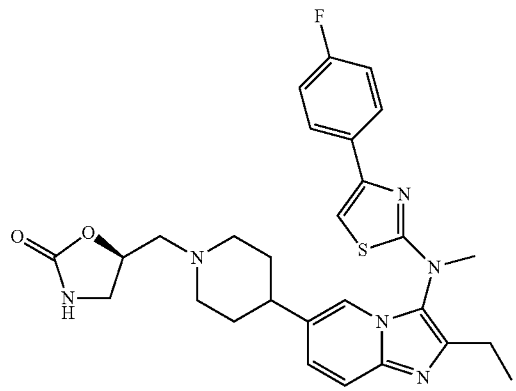 [SMILES: CCc1nc2ccc(C3CCN(C[C@H]4CNC(=O)O4)CC3)cn2c1N(C)c1nc(-c2ccc(F)cc2)cs1] | (R)-5-((4-(2-ethyl-3-((4-(4-fluorophenyl)thiazol-2-yl)(methyl)amino)imidazo[1,2-a]pyridin-6-yl)piperidin-1-yl)methyl)oxazolidin-2-one | F8 (Gen-10-c) | 534 | 535 (M + 1) |
| 197 | 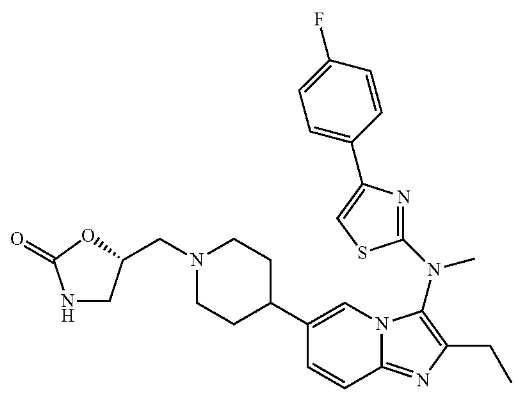 [SMILES: CCc1nc2ccc(C3CCN(C[C@@H]4CNC(=O)O4)CC3)cn2c1N(C)c1nc(-c2ccc(F)cc2)cs1] | (S)-5-((4-(2-ethyl-3-((4-(4-fluorophenyl)thiazol-2-yl)(methyl)amino)imidazo[1,2-a]pyridin-6-yl)piperidin-1-yl)methyl)oxazolidin-2-one | F8 (Gen-10-c) | 534 | 535 (M + 1) |
| 198 | 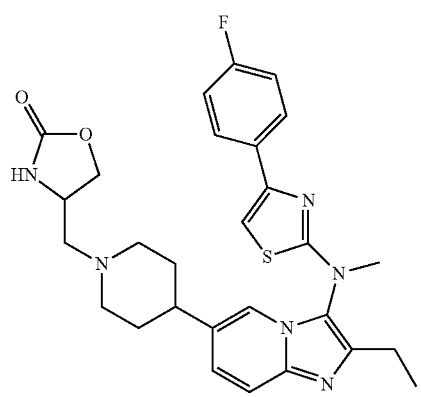 [SMILES: CCc1nc2ccc(C3CCN(CC4COC(=O)N4)CC3)cn2c1N(C)c1nc(-c2ccc(F)cc2)cs1] | 4-((4-(2-ethyl-3-((4-(4-fluorophenyl)thiazol-2-yl)(methyl)amino)imidazo[1,2-a]pyridin-6-yl)piperidin-1-yl)methyl)oxazolidin-2-one | F8 (Gen-10-c) | 534 | 535 (M + 1) |
| 199 | 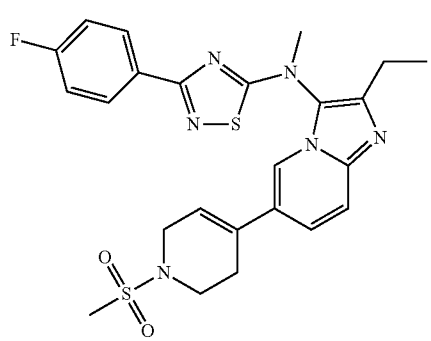 [SMILES: CCc1nc2ccc(C3=CCN(S(C)(=O)=O)CC3)cn2c1N(C)c1nc(-c2ccc(F)cc2)ns1] | N-(2-ethyl-6-(1-(methylsulfonyl)-1,2,3,6-tetrahydropyridin-4-yl)imidazo[1,2-a]pyridin-3-yl)-3-(4-fluorophenyl)-N-methyl-1,2,4-thiadiazol-5-amine | F11 (Gen-10-v) | 512 | 513 (M + 1) |

TABLE III-continued

Illustrative compounds of the invention.

| Cpd | Structures | Name | Mtd (Int) | MW | MS Ms'd |
|---|---|---|---|---|---|
| 200 | 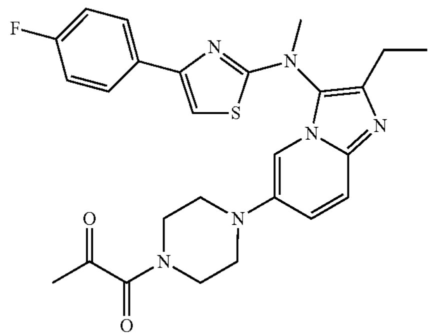 [SMILES: CCc1nc2ccc(N3CCN(C(=O)C(C)=O)CC3)cn2c1N(C)c1nc(-c2ccc(F)cc2)cs1] | 1-(4-(2-ethyl-3-((4-(4-fluorophenyl)thiazol-2-yl)(methyl)amino) imidazo[1,2-a]pyridin-6-yl)piperazin-1-yl) propane-1,2-dione | F9a (Gen-10-e) | 506 | 507 (M + 1) |
| 201 | 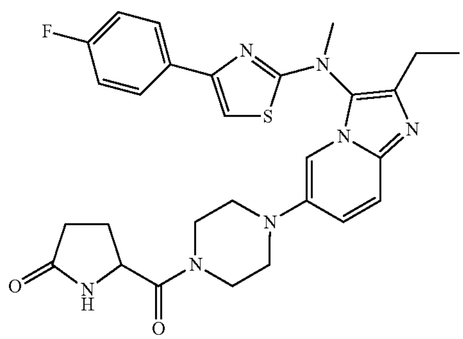 [SMILES: CCc1nc2ccc(N3CCN(C(=O)C4CCC(=O)N4)CC3)cn2c1N(C)c1nc(-c2ccc(F)cc2)cs1] | 5-(4-(2-ethyl-3-((4-(4-fluorophenyl)thiazol-2-yl)(methyl)amino) imidazo[1,2-a]pyridin-6-yl)piperazine-1-carbonyl)pyrrolidin-2-one | F9a (Gen-10-e) | 547 | 548 (M + 1) |
| 202 | 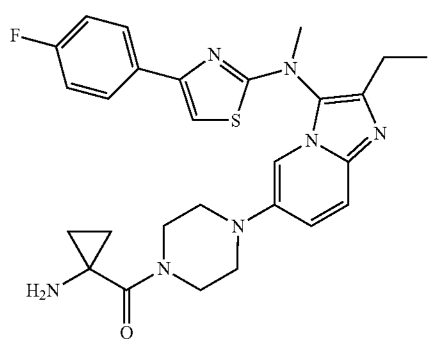 [SMILES: CCc1nc2ccc(N3CCN(C(=O)C4(N)CC4)CC3)cn2c1N(C)c1nc(-c2ccc(F)cc2)cs1] | (1-aminocyclopropyl)(4-(2-ethyl-3-((4-(4-fluorophenyl)thiazol-2-yl)(methyl)amino) imidazo[1,2-a]pyridin-6-yl)piperazin-1-yl)methanone | see Cpd 202 (Gen-10-e) | 519 | 520 (M + 1) |
| 203 | 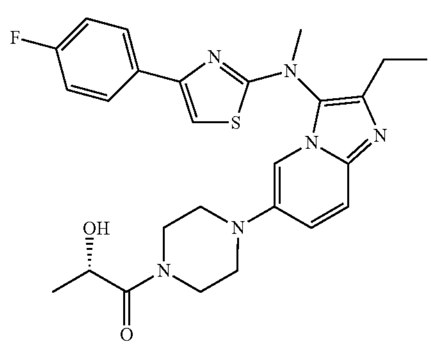 [SMILES: CCc1nc2ccc(N3CCN(C(=O)[C@H](C)O)CC3)cn2c1N(C)c1nc(-c2ccc(F)cc2)cs1] | (S)-1-(4-(2-ethyl-3-((4-(4-fluorophenyl)thiazol-2-yl) (methyl)amino)imidazo [1,2-a]pyridin-6-yl)piperazin-1-yl)-2-hydroxypropan-1-one | F9a (Gen-10-e) | 508 | 509 (M + 1) |

TABLE III-continued

Illustrative compounds of the invention.

| Cpd | Structures | Name | Mtd (Int) | MW | MS Ms'd |
|---|---|---|---|---|---|
| 204 | 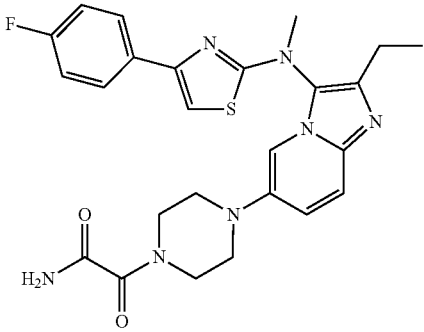 [SMILES: CCc1nc2ccc(N3CCN(C(=O)C(N)=O)CC3)cn2c1N(C)c1nc(-c2ccc(F)cc2)cs1] | 2-(4-(2-ethyl-3-((4-(4-fluorophenyl)thiazol-2-yl)(methyl)amino)imidazo[1,2-a]pyridin-6-yl)piperazin-1-yl)-2-oxoacetamide | see Cpd 204 (Gen-10-an) | 507 | 508 (M + 1) |
| 205 | 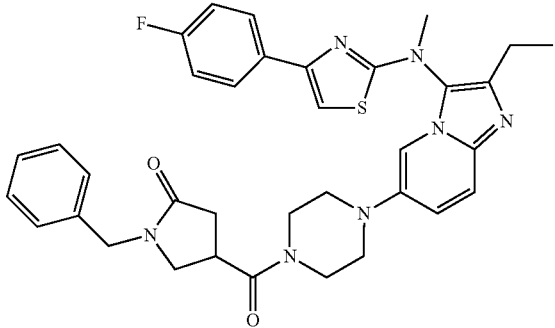 [SMILES: CCc1nc2ccc(N3CCN(C(=O)C4CC(=O)N(Cc5ccccc5)C4)CC3)cn2c1N(C)c1nc(-c2ccc(F)cc2)cs1] | 1-benzyl-4-(4-(2-ethyl-3-((4-(4-fluorophenyl)thiazol-2-yl)(methyl)amino)imidazo[1,2-a]pyridin-6-yl)piperazine-1-carbonyl)pyrrolidin-2-one | F9a (Gen-10-e) | 637 | 638 (M + 1) |
| 206 | 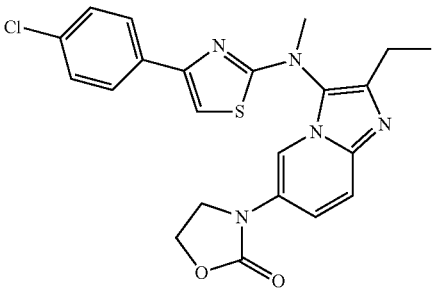 [SMILES: CCc1nc2ccc(N3CCOC3=O)cn2c1N(C)c1nc(-c2ccc(Cl)cc2)cs1] | 3-(3-((4-(4-chlorophenyl)thiazol-2-yl)(methyl)amino)-2-ethylimidazo[1,2-a]pyridin-6-yl)oxazolidin-2-one | F4 (Gen-5-i) | 453 ($^{35}$Cl), 455 ($^{37}$Cl) | 454 ($^{35}$Cl M + 1) 456 ($^{37}$Cl M + 1) |
| 207 | 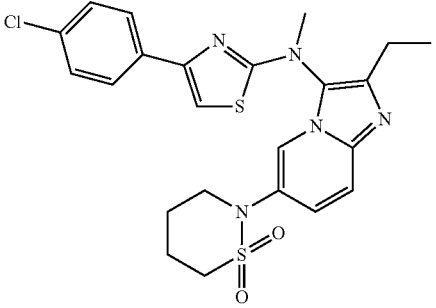 [SMILES: CCc1nc2ccc(N3CCCCS3(=O)=O)cn2c1N(C)c1nc(-c2ccc(Cl)cc2)cs1] | 2-(2-ethyl-3-((4-(4-chlorophenyl)thiazol-2-yl)(methyl)amino)imidazo[1,2-a]pyridin-6-yl)-1-[1,2]thiazinane-1,1-dioxide | F4 (Gen-5-i) | 501 ($^{35}$Cl), 503 ($^{37}$Cl) | 502 ($^{35}$Cl M + 1) 504 ($^{37}$Cl M + 1) |

TABLE III-continued

Illustrative compounds of the invention.

| Cpd | Structures | Name | Mtd (Int) | MW | MS Ms'd |
|---|---|---|---|---|---|
| 208 | 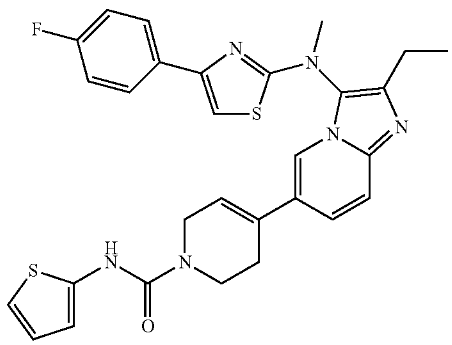 [SMILES: CCc1nc2ccc(C3=CCN(C(=O)Nc4cccs4)CC3)cn2c1N(C)c1nc(-c2ccc(F)cc2)cs1] | 4-(2-ethyl-3-((4-(4-fluorophenyl)thiazol-2-yl)(methyl)amino) imidazo[1,2-a]pyridin-6-yl)-N-(thiophen-2-yl)-5,6-dihydropyridine-1(2H)-carboxamide | F2 (Gen-5-b) | 558 | 559 (M + 1) |
| 209 | 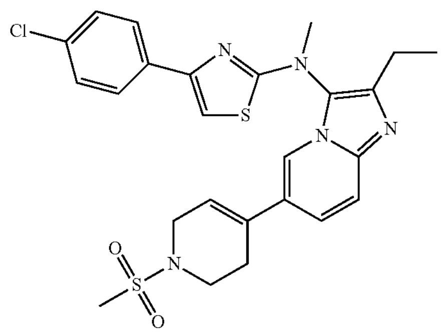 [SMILES: CCc1nc2ccc(C3=CCN(S(C)(=O)=O)CC3)cn2c1N(C)c1nc(-c2ccc(Cl)cc2)cs1] | 4-(4-chlorophenyl)-N-(2-ethyl-6-(1-(methylsulfonyl)-1,2,3,6-tetrahydropyridin-4-yl)imidazo[1,2-a]pyridin-3-yl)-N-methylthiazol-2-amine | F11 (Gen-10-ak) | 527 ($^{35}$Cl), 529 ($^{37}$Cl) | 528 ($^{35}$Cl M + 1), 530 ($^{37}$Cl M + 1) |
| 210 | 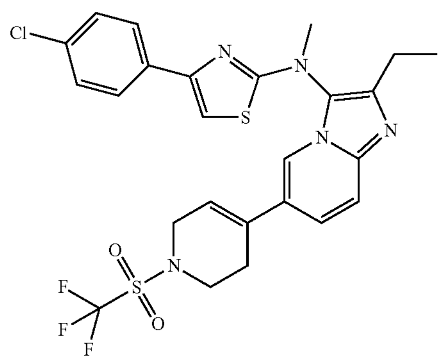 [SMILES: CCc1nc2ccc(C3=CCN(S(=O)(=O)C(F)(F)F)CC3)cn2c1N(C)c1nc(-c2ccc(Cl)cc2)cs1] | 4-(4-chlorophenyl)-N-(2-ethyl-6-(1-(trifluoromethylsulfonyl)-1,2,3,6-tetrahydropyridin-4-yl)imidazo[1,2-a]pyridin-3-yl)-N-methylthiazol-2-amine | F11 (Gen-10-ak) | 581 ($^{35}$Cl), 583 ($^{37}$Cl) | 582 ($^{35}$Cl M + 1), 584 ($^{37}$Cl M + 1) |
| 211 | 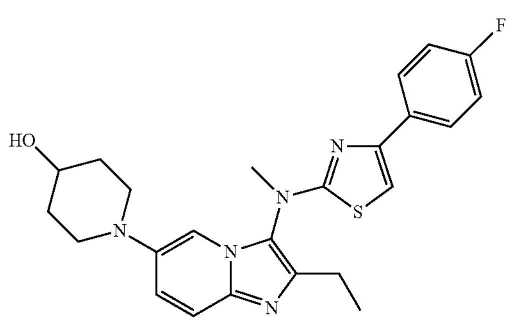 [SMILES: CCc1nc2ccc(N3CCC(O)CC3)cn2c1N(C)c1nc(-c2ccc(F)cc2)cs1] | 1-(2-ethyl-3-((4-(4-fluorophenyl)thiazol-2-yl)(methyl)amino) imidazo[1,2-a]pyridin-6-yl)piperidin-4-ol | see Cpd 211 (Gen-10-aq) | 451 | 452 (M + 1) |

| Cpd | Structures | Name | Mtd (Int) | MW | MS Ms'd |
|---|---|---|---|---|---|
| 212 | 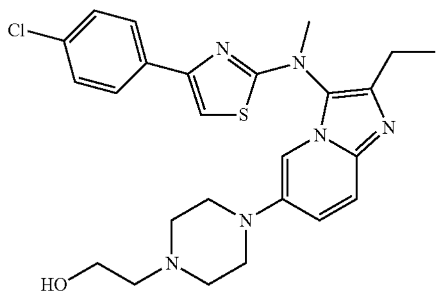 [SMILES: CCc1nc2ccc(N3CCN(CCO)CC3)cn2c1N(C)c1nc(-c2ccc(Cl)cc2)cs1] | 2-(4-(3-((4-(4-chlorophenyl)thiazol-2-yl)(methyl)amino)-2-ethylimidazo[1,2-a]pyridin-6-yl)piperazin-1-yl)ethanol | F1b (Gen-5-y) | 496 | 497 (M + 1) |
| 213 | 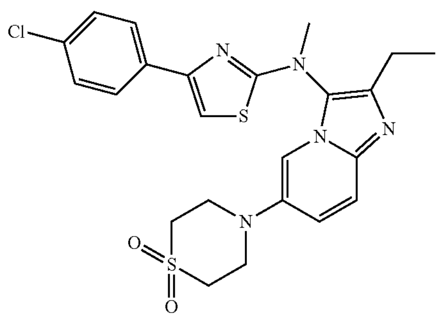 [SMILES: CCc1nc2ccc(N3CCS(=O)(=O)CC3)cn2c1N(C)c1nc(-c2ccc(Cl)cc2)cs1] | 4-(2-ethyl-3-((4-(4-chlorophenyl)thiazol-2-yl)(methyl)amino)imidazo[1,2-a]pyridin-6-yl)-thiomorpholine-1,1-dioxide | F1b (Gen-5-y) | 501 | 502 (M + 1) |
| 214 | 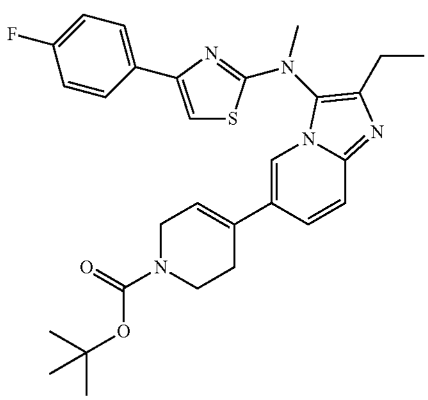 [SMILES: CCc1nc2ccc(C3=CCN(C(=O)OC(C)(C)C)CC3)cn2c1N(C)c1nc(-c2ccc(F)cc2)cs1] | tert-butyl 4-(2-ethyl-3-((4-(4-fluorophenyl)thiazol-2-yl)(methyl)amino)imidazo[1,2-a]pyridin-6-yl)-5,6-dihydropyridine-1(2H)-carboxylate | F2 (Gen-5-b) | 533 | 534 (M + 1) |
| 215 | 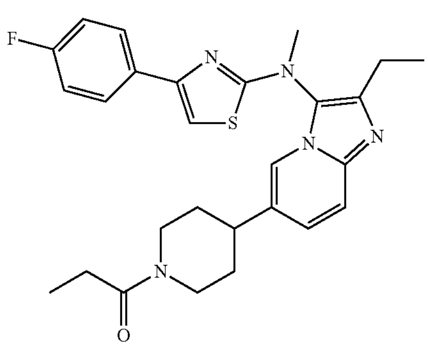 [SMILES: CCC(=O)N1CCC(c2ccc3nc(CC)c(N(C)c4nc(-c5ccc(F)cc5)cs4)n3c2)CC1] | 1-(4-(2-ethyl-3-((4-(4-fluorophenyl)thiazol-2-yl)(methyl)amino)imidazo[1,2-a]pyridin-6-yl)piperidin-1-yl)propan-1-one | F9b-F6 (Gen-10-b) | 491 | 492 (M + 1) |

TABLE III-continued

Illustrative compounds of the invention.

| Cpd | Structures | Name | Mtd (Int) | MW | MS Ms'd |
|---|---|---|---|---|---|
| 216 (Gen-10-c) | 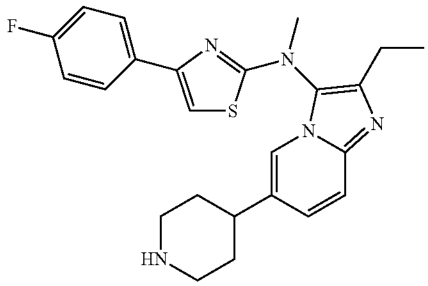 [SMILES: CCc1nc2ccc(C3CCNCC3)cn2c1N(C)c1nc(-c2ccc(F)cc2)cs1] | N-(2-ethyl-6-(piperidin-4-yl)imidazo[1,2-a]pyridin-3-yl)-4-(4-fluorophenyl)-N-methylthiazol-2-amine | E1-F6-F5a (Gen-9-c) | 435 | 436 (M + 1) |
| 217 | 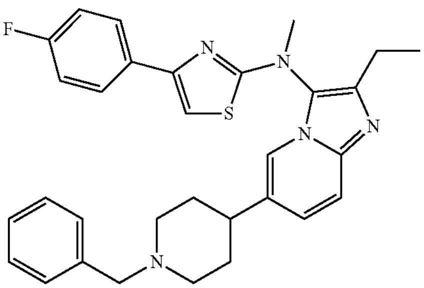 [SMILES: CCc1nc2ccc(C3CCN(Cc4ccccc4)CC3)cn2c1N(C)c1nc(-c2ccc(F)cc2)cs1] | N-(6-(1-benzylpiperidin-4-yl)-2-ethylimidazo[1,2-a]pyridin-3-yl)-4-(4-fluorophenyl)-N-methylthiazol-2-amine | F10 (Gen-10-c) | 525 | 526 (M + 1) |
| 218 | 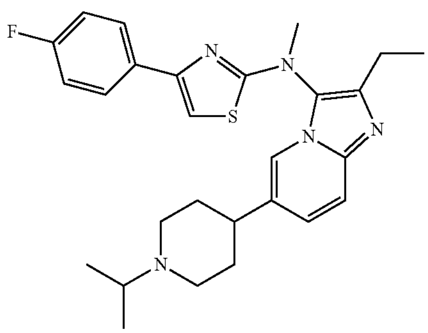 [SMILES: CCc1nc2ccc(C3CCN(C(C)C)CC3)cn2c1N(C)c1nc(-c2ccc(F)cc2)cs1] | N-(2-ethyl-6-(1-isopropylpiperidin-4-yl)imidazo[1,2-a]pyridin-3-yl)-4-(4-fluorophenyl)-N-methylthiazol-2-amine | F10 (Gen-10-c) | 477 | 478 (M + 1) |
| 219 | 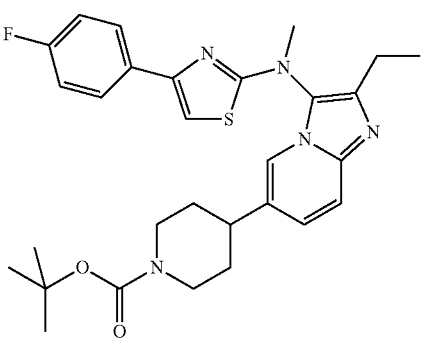 [SMILES: CCc1nc2ccc(C3CCN(C(=O)OC(C)(C)C)CC3)cn2c1N(C)c1nc(-c2ccc(F)cc2)cs1] | tert-butyl 4-(2-ethyl-3-((4-(4-fluorophenyl)thiazol-2-yl)(methyl)amino)imidazo[1,2-a]pyridin-6-yl)piperidine-1-carboxylate | F2-F6 (Gen-5-c) | 535 | 536 (M + 1) |
| 220 | 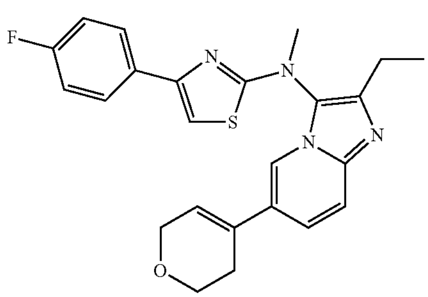 [SMILES: CCc1nc2ccc(C3=CCOCC3)cn2c1N(C)c1nc(-c2ccc(F)cc2)cs1] | N-(6-(3,6-dihydro-2H-pyran-4-yl)-2-ethylimidazo[1,2-a]pyridin-3-yl)-4-(4-fluorophenyl)-N-methylthiazol-2-amine | F2 (Gen-5-b) | 434 | 435 (M + 1) |

TABLE III-continued

Illustrative compounds of the invention.

| Cpd | Structures | Name | Mtd (Int) | MW | MS Ms'd |
|---|---|---|---|---|---|
| 221 | 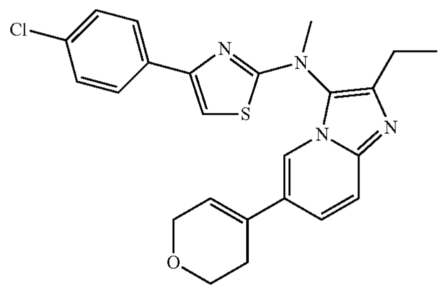 [SMILES: CCc1nc2ccc(C3=CCOCC3)cn2c1N(C)c1nc(-c2ccc(Cl)cc2)cs1] | 4-(4-chlorophenyl)-N-(6-(3,6-dihydro-2H-pyran-4-yl)-2-ethylimidazo[1,2-a]pyridin-3-yl)-N-methylthiazol-2-amine | F2 (Gen-5-i) | 450 ($^{35}$Cl), 452 ($^{37}$Cl) | 451 ($^{35}$Cl M + 1) 453 ($^{37}$Cl M + 1) |
| 222 | 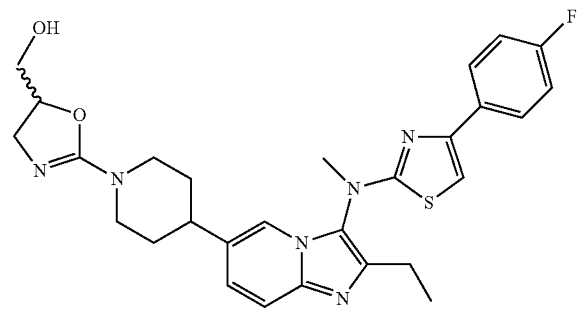 [SMILES: CCc1nc2ccc(C3CCN(C4=NCC(CO)O4)CC3)cn2c1N(C)c1nc(-c2ccc(F)cc2)cs1] | (2-(4-(2-ethyl-3-((4-(4-fluorophenyl)thiazol-2-yl)(methyl)amino)imidazo[1,2-a]pyridin-6-yl)piperidin-1-yl)-4,5-dihydrooxazol-5-yl)methanol | see Cpd 222 (Gen-10-c) | 534 | 535 (M + 1) |
| 223 | 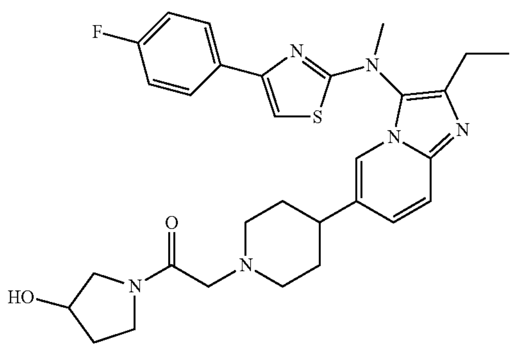 [SMILES: CCc1nc2ccc(C3CCN(CC(=O)N4CCC(O)C4)CC3)cn2c1N(C)c1nc(-c2ccc(F)cc2)cs1] | 2-(4-(2-ethyl-3-((4-(4-fluorophenyl)thiazol-2-yl)(methyl)amino)imidazo[1,2-a]pyridin-6-yl)piperidin-1-yl)-1-(3-hydroxypyrrolidin-1-yl)ethanone | F8 (Gen-10-c) | 562 | 563 (M + 1) |
| 224 | 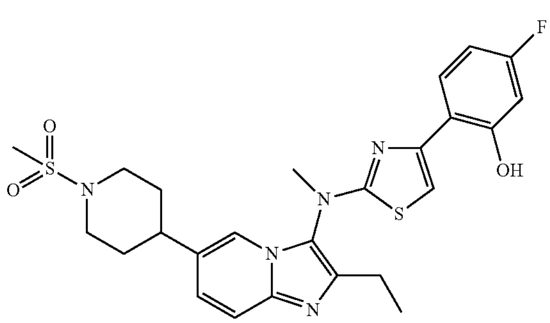 | 2-(2-((2-ethyl-6-(1-(methylsulfonyl)piperidin-4-yl)imidazo[1,2-a]pyridin-3-yl)(methyl)amino)thiazol-4-yl)-5-fluorophenol | E1 (Gen-9-b) | 529 | 530 (M + 1) |

TABLE III-continued

Illustrative compounds of the invention.

| Cpd | Structures | Name | Mtd (Int) | MW | MS Ms'd |
|---|---|---|---|---|---|
| 225 | 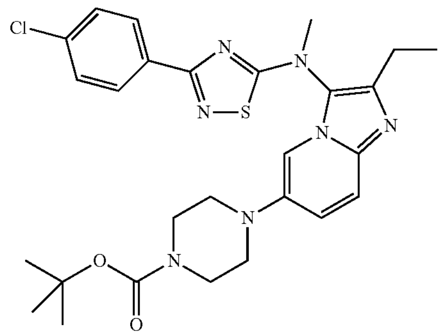 [SMILES: CCc1nc2ccc(N3CCN(C(=O)OC(C)(C)C)CC3)cn2c1N(C)c1nc(-c2ccc(Cl)cc2)ns1] | tert-butyl 4-(3-((3-(4-chlorophenyl)-1,2,4-thiadiazol-5-yl)(methyl)amino)-2-ethylimidazo[1,2-a]pyridin-6-yl)piperazine-1-carboxylate | F1b (Gen-5-w) | 553 ($^{35}$Cl), 555 ($^{37}$Cl) | 554 ($^{35}$Cl M + 1), 556 ($^{37}$Cl M + 1) |
| 226 | 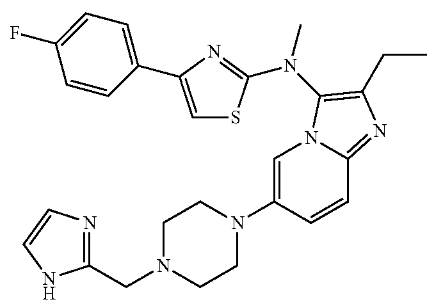 [SMILES: CCc1nc2ccc(N3CCN(Cc4ncc[nH]4)CC3)cn2c1N(C)c1nc(-c2ccc(F)cc2)cs1] | N-(6-(4-((1H-imidazol-2-yl)methyl)piperazin-1-yl)-2-ethylimidazo[1,2-a]pyridin-3-yl)-4-(4-fluorophenyl)-N-methylthiazol-2-amine | F10 (Gen-10-e) | 516 | 517 (M + 1) |
| 227 | 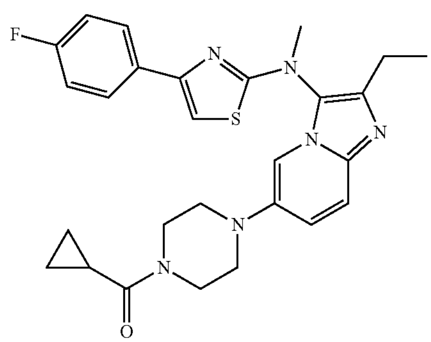 [SMILES: CCc1nc2ccc(N3CCN(C(=O)C4CC4)CC3)cn2c1N(C)c1nc(-c2ccc(F)cc2)cs1] | cyclopropyl(4-(2-ethyl-3-((4-(4-fluorophenyl)thiazol-2-yl)(methyl)amino)imidazo[1,2-a]pyridin-6-yl)piperazin-1-yl)methanone | see Cpd 227 (Gen-10-e) | 504 | 505 (M + 1) |
| 228 | 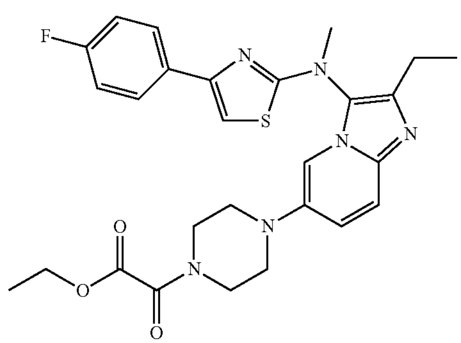 [SMILES: CCOC(=O)C(=O)N1CCN(c2ccc3nc(CC)c(N(C)c4nc(-c5ccc(F)cc5)cs4)n3c2)CC1] | ethyl 2-(4-(2-ethyl-3-((4-(4-fluorophenyl)thiazol-2-yl)(methyl)amino)imidazo[1,2-a]pyridin-6-yl)piperazin-1-yl)-2-oxoacetate | F9b (Gen-10-e) | 536 | 537 (M + 1) |

TABLE III-continued

Illustrative compounds of the invention.

| Cpd | Structures | Name | Mtd (Int) | MW | MS Ms'd |
|---|---|---|---|---|---|
| 229 | 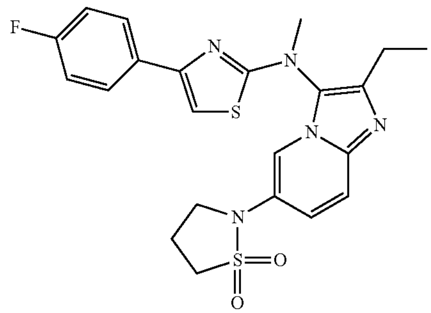 [SMILES: CCc1nc2ccc(N3CCCS3(=O)=O)cn2c1N(C)c1nc(-c2ccc(F)cc2)cs1] | [6-(1,1-Dioxo-isothiazolidin-2-yl)-2-ethyl-imidazo[1,2-a]pyridin-3-yl]-[4-(4-fluoro-phenyl)-thiazol-2-yl]-methyl-amine | see Cpd 229 (Gen-10-ao) | 471 | 472 (M + 1) |
| 230 | 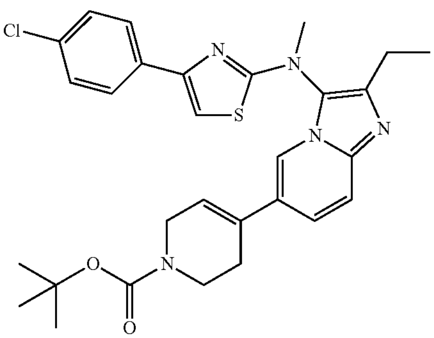 [SMILES: CCc1nc2ccc(C3=CCN(C(=O)OC(C)(C)C)CC3)cn2c1N(C)c1nc(-c2ccc(Cl)cc2)cs1] | tert-butyl 4-(3-((4-(4-chlorophenyl)thiazol-2-yl)(methyl)amino)-2-ethylimidazo[1,2-a]pyridin-6-yl)-5,6-dihydropyridine-1(2H)-carboxylate | F2 (Gen-5-i) | 549 ($^{35}$Cl) 551 ($^{37}$Cl) | 550 ($^{35}$Cl M + 1), 552 ($^{37}$Cl M + 1) |
| 231 (Gen-10-g) | 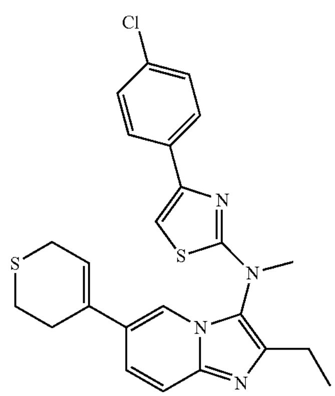 [SMILES: CCc1nc2ccc(C3=CCSCC3)cn2c1N(C)c1nc(-c2ccc(Cl)cc2)cs1] | 4-(4-chlorophenyl)-N-(6-(3,6-dihydro-2H-thiopyran-4-yl)-2-ethylimidazo[1,2-a]pyridin-3-yl)-N-methylthiazol-2-amine | F2 (Gen-5-i) | 466 ($^{35}$Cl), 468 ($^{37}$Cl) | N.M. |
| 232 | 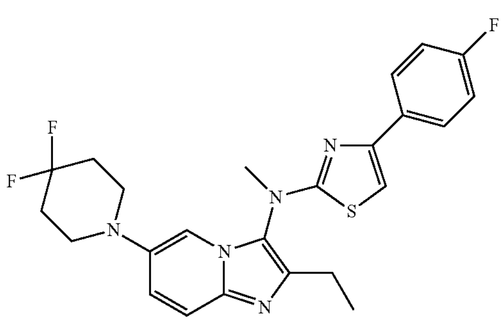 [SMILES: CCc1nc2ccc(N3CCC(F)(F)CC3)cn2c1N(C)c1nc(-c2ccc(F)cc2)cs1] | N-(6-(4,4-difluoropiperidin-1-yl)-2-ethylimidazo[1,2-a]pyridin-3-yl)-4-(4-fluorophenyl)-N-methylthiazol-2-amine | F1b (Gen-5-c) | 471 | 472 |

TABLE III-continued

Illustrative compounds of the invention.

| Cpd | Structures | Name | Mtd (Int) | MW | MS Ms'd |
|---|---|---|---|---|---|
| 233 | 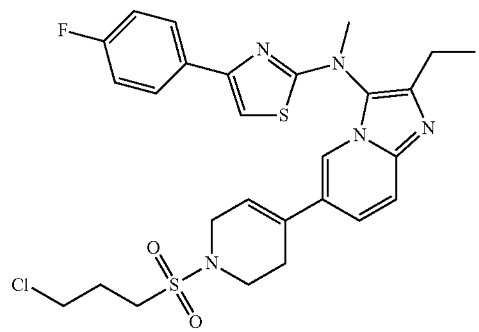 [SMILES: CCc1nc2ccc(C3=CCN(S(=O)(=O)CCCCl)CC3)cn2c1N(C)c1nc(-c2ccc(F)cc2)cs1] | N-(6-(1-(3-chloropropylsulfonyl)-1,2,3,6-tetrahydropyridin-4-yl)-2-ethylimidazo[1,2-a]pyridin-3-yl)-4-(4-fluorophenyl)-N-methylthiazol-2-amine | F11 (Gen-10-b) | 573 ($^{35}$Cl), 575 ($^{37}$Cl) | 574 ($^{35}$Cl M + 1), 576 ($^{37}$Cl M + 1) |
| 234 | 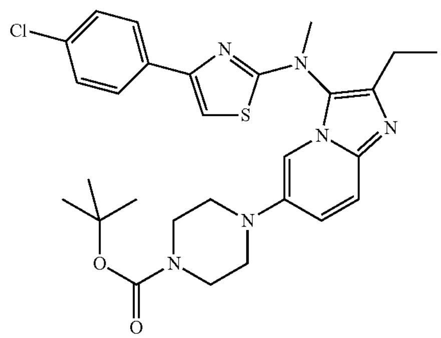 [SMILES: CCc1nc2ccc(N3CCN(C(=O)OC(C)(C)C)CC3)cn2c1N(C)c1nc(-c2ccc(Cl)cc2)cs1] | tert-butyl 4-(3-((4-(4-chlorophenyl)thiazol-2-yl)(methyl)amino)-2-ethylimidazo[1,2-a]pyridin-6-yl)piperazine-1-carboxylate | F1b (Gen-5-y) | 552 ($^{35}$Cl), 554 ($^{37}$Cl) | 553 ($^{35}$Cl M + 1), 555 ($^{37}$Cl M + 1) |
| 235 | 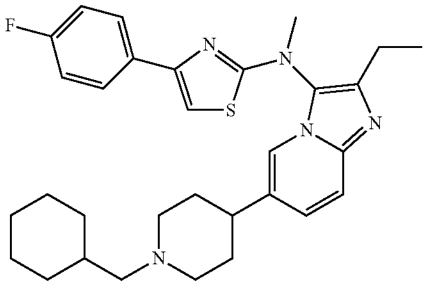 [SMILES: CCc1nc2ccc(C3CCN(CC4CCCCC4)CC3)cn2c1N(C)c1nc(-c2ccc(F)cc2)cs1] | N-(6-(1-(cyclohexylmethyl)piperidin-4-yl)-2-ethylimidazo[1,2-a]pyridin-3-yl)-4-(4-fluorophenyl)-N-methylthiazol-2-amine | F10 (Gen-10-c) | 531 | 532 (M + 1) |
| 236 | 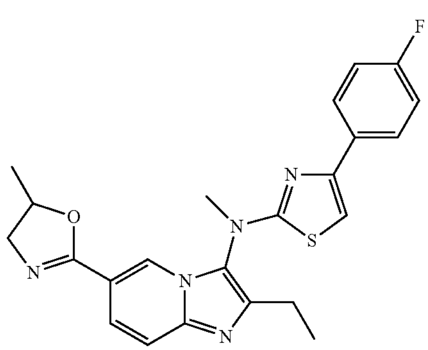 [SMILES: CCc1nc2ccc(C3=NCC(C)O3)cn2c1N(C)c1nc(-c2ccc(F)cc2)cs1] | N-(2-ethyl-6-(5-methyl-4,5-dihydrooxazol-2-yl)imidazo[1,2-a]pyridin-3-yl)-4-(4-fluorophenyl)-N-methylthiazol-2-amine | F13-F9a-F19 (Gen-5-aa) | 435 | 436 (M + 1) |

TABLE III-continued

Illustrative compounds of the invention.

| Cpd | Structures | Name | Mtd (Int) | MW | MS Ms'd |
|---|---|---|---|---|---|
| 237 | 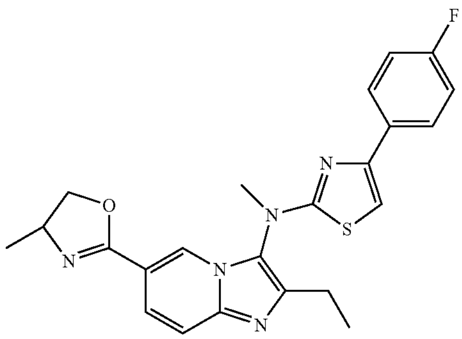 [SMILES: CCc1nc2ccc(C3=NC(C)CO3)cn2c1N(C)c1nc(-c2ccc(F)cc2)cs1] | N-(2-ethyl-6-(4-methyl-4,5-dihydrooxazol-2-yl)imidazo[1,2-a]pyridin-3-yl)-4-(4-fluorophenyl)-N-methylthiazol-2-amine | F13-F9a-F19 (Gen-5-aa) | 435 | 436 (M + 1) |
| 238 | 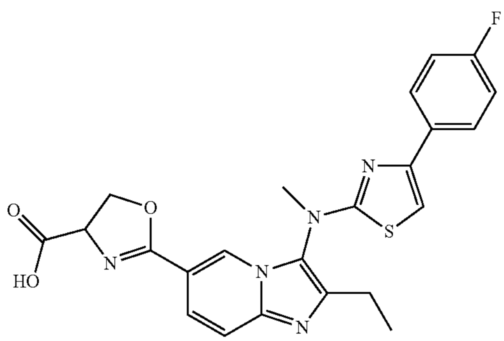 [SMILES: CCc1nc2ccc(C3=NC(C(=O)O)CO3)cn2c1N(C)c1nc(-c2ccc(F)cc2)cs1] | 2-(2-ethyl-3-((4-(4-fluorophenyl)thiazol-2-yl)(methyl)amino)imidazo[1,2-a]pyridin-6-yl)-4,5-dihydrooxazole-4-carboxylic acid | F13-F9a-F19 (Gen-5-aa) | 465 | 466 (M + 1) |
| 239 | 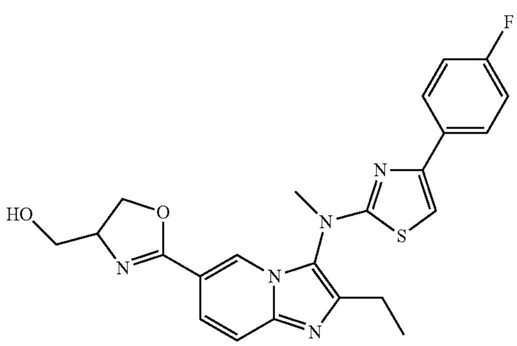 [SMILES: CCc1nc2ccc(C3=NC(CO)CO3)cn2c1N(C)c1nc(-c2ccc(F)cc2)cs1] | (2-(2-ethyl-3-((4-(4-fluorophenyl)thiazol-2-yl)(methyl)amino)imidazo[1,2-a]pyridin-6-yl)-4,5-dihydrooxazol-4-yl)methanol | F13-F9a-F19 (Gen-5-aa) | 451 | 452 (M + 1) |
| 240 | 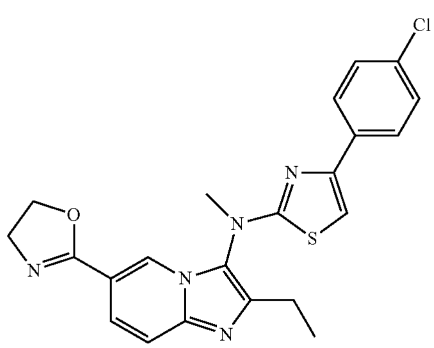 [SMILES: CCc1nc2ccc(C3=NCCO3)cn2c1N(C)c1nc(-c2ccc(Cl)cc2)cs1] | 4-(4-chlorophenyl)-N-(6-(4,5-dihydrooxazol-2-yl)-2-ethylimidazo[1,2-a]pyridin-3-yl)-N-methylthiazol-2-amine | F13-F9a-F19 (Gen-5-ag) | 437 ($^{35}$Cl), 439 ($^{37}$Cl) | 438 ($^{35}$Cl M + 1), 440 ($^{37}$Cl M + 1) |

TABLE IV

NMR data of the compounds of the invention.

| Cpd | NMR data (δ) |
|---|---|
| 1 | $^1$H NMR (400 MHz, CDCl$_3$) δ ppm 8.23-8.13 (2 H, m), 7.24-7.14 (2 H, m), 7.00 (2 H, d), 3.62 (3 H, s), 3.09 (8 H, bs), 2.77 (2 H, q), 2.62 (3 H, s), 1.35 (3 H, t) |
| 2 | $^1$H NMR (400 MHz, CDCl$_3$) δ ppm 8.20-8.12 (2 H, m), 7.22-7.13 (2 H, m), 6.99 (2 H, s), 4.68 (1 H, m), 4.43 (1 H, dd), 4.26 (1 H, dd), 4.14-4.05 (1 H, m), 3.88 (1 H, dd), 3.61 (3 H, s), 3.58-3.52 (1 H, m), 3.14-3.02 (6 H, m), 2.74 (2 H, q), 2.70-2.62 (4 H, m), 2.59 (3 H, s), 1.33 (3 H, t) |
| 3 | $^1$H NMR (300 MHz, CDCl$_3$) δ ppm 8.22-8.08 (2 H, m), 7.17 (2 H, t), 6.99 (2 H, s), 4.24-4.03 (2 H, m), 3.94 (2 H, s), 3.61 (3 H, s), 3.09 (6 H, bs.), 2.82-2.64 (6 H, m), 2.60 (3 H, s), 1.53 (3 H, s), 1.33 (3 H, t) |
| 4 | $^1$H NMR (400 MHz, CDCl$_3$) δ ppm 8.21-8.12 (2 H, m), 7.17 (2 H, t), 6.99 (2 H, s), 4.58-4.45 (1 H, m), 3.71-3.48 (7 H, m), 3.23-3.15 (2 H, m), 3.09 (4 H, bs), 2.78-2.69 (6 H, m), 2.60 (3 H, s), 2.07-2.00 (1 H, m), 2.00-1.90 (1 H, m), 1.33 (3 H, t) |
| 5 | $^1$H NMR (400 MHz, CDCl$_3$) δ ppm 8.21-8.12 (2 H, m), 7.24-7.12 (2 H, m), 6.99 (2 H, s), 4.57-4.46 (1 H, m), 3.70-3.53 (7 H, m), 3.28-3.04 (6 H, m), 2.83-2.67 (6 H, m), 2.62 (3 H, s), 2.10-2.00 (1 H, m), 1.99-1.89 (1 H, m), 1.34 (3 H, t) |
| 6 | $^1$H NMR (400 MHz, MeOD-d$_4$) δ ppm 8.25-7.99 (2 H, m), 7.33-7.06 (4 H, m), 4.62-4.49 (2 H, m), 4.19 (1 H, dd), 4.15-4.08 (1 H, m), 3.75 (1 H, dd), 3.64 (3 H, s), 3.21-3.02 (4 H, m), 2.88 (2 H, s), 2.79-2.66 (4 H, m), 2.55 (3 H, s), 1.32 (3 H, t), 1.14 (6 H, s) |
| 7 | $^1$H NMR (300 MHz, MeOD-d$_4$) δ ppm 7.95-7.84 (2 H, m), 7.22-7.16 (2 H, m), 7.11 (2 H, t), 6.94 (1 H, s), 4.61-4.51 (1 H, m), 4.50-4.41 (1 H, m), 4.20 (1 H, dd), 4.04 (1 H, dd), 3.75 (1 H, dd), 3.60 (3 H, s), 3.17-3.01 (6 H, m), 2.72 (2 H, q), 2.65 (4 H, bt), 2.55 (3 H, s), 1.31 (3 H, t) |
| 8 | $^1$H NMR (400 MHz, MeOD -d$_4$) δ ppm 7.89 (2 H, dd), 7.19 (2 H, d), 7.11 (2 H, t), 6.93 (1 H, s), 4.46-4.35 (1 H, m), 3.69-3.43 (7 H, m), 3.27-3.18 (2 H, m), 3.17-3.03 (4 H, m), 2.76-2.65 (6 H, m), 2.55 (3 H, s), 2.10-1.83 (2 H, m), 1.31 (3 H, t) |
| 9 | $^1$H NMR (300 MHz, MeOD-d$_4$) δ ppm 7.97-7.89 (2 H, m), 7.20 (2 H, bs), 7.13 (2 H, t), 6.95 (1 H, s), 4.48-4.39 (1 H, m), 3.71-3.42 (7 H, m), 3.25 (2 H, d), 3.17-3.04 (4 H, m), 2.76-2.65 (6 H, m), 2.56 (3 H, s), 2.11-1.88 (2 H, m), 1.31 (3 H, t) |
| 10 | $^1$H NMR (400 MHz, MeOD-d$_4$) δ ppm 8.27-8.04 (2 H, m), 7.78 (1 H, s), 7.33-7.16 (3 H, m), 4.61-4.54 (1 H, m), 4.50 (1 H, dd), 4.25-4.18 (1 H, m), 4.06 (1 H, dd), 3.77 (1 H, dd), 3.67 (3 H, s), 3.08 (2 H, d), 3.05-2.96 (2 H, m), 2.76 (2 H, qd), 2.59 (4 H, bs), 2.27-2.16 (2 H, m), 1.88-1.78 (4 H, m), 1.34 (3 H, t) |
| 11 | $^1$H NMR (400 MHz, MeOD- d$_4$) δ ppm 8.21-8.18 (2 H, m), 7.96 (1 H, s), 7.52 (1 H s), 7.30 (2 H, t), 6.31 (1 H, bs), 4.37-4.28 (1 H, m), 4.14-4.05 (1 H, m), 4.01-3.99 (2 H, m), 3.57-3.50 (2 H, m), 2.94 (3 H, s), 2.86-2.76 (2 H, m), 2.68 (5 H, bs), 1.43 (3 H, t), 1.38 (3 H, t) |
| 12 | $^1$H NMR (400 MHz, CDCl$_3$) δ ppm 8.21-8.13 (2 H, m), 7.22-7.15 (2 H, m), 6.97-6.89 (2 H, m), 4.74-4.65 (1 H, m), 4.48-4.40 (1 H, m), 4.33-4.24 (1 H, m), 4.14-4.07 (1 H, m), 3.90 (1 H, dd), 3.63 (3 H, bs), 3.17-3.05 (6 H, m), 2.79-2.66 (6 H, m), 1.36 (3 H, t) |
| 13 | $^1$H NMR (300 MHz, CDCl$_3$) δ ppm 8.22-8.11 (2 H, m), 7.25-7.13 (2 H, m), 7.02-6.86 (2 H, m), 3.63 (3 H, s), 3.13 (6 H, bs), 2.85 (3 H, d), 2.81-2.68 (6 H, m), 1.36 (3 H, t) |
| 14 | $^1$H NMR (400 MHz, CDCl$_3$) δ ppm 7.89-7.83 (2 H, m), 7.09 (2 H, t), 7.00 (1 H, s), 6.86 (1 H, dd), 6.69 (1 H, s), 4.68 (1 H, bs), 4.47-4.40 (1 H, m), 4.57-4.25 (1 H, m), 4.08 (1 H, dd), 3.89 (1 H, dd), 3.60 (3 H, s), 3.11-3.02 (6 H, m), 2.74 (2 H, q), 2.68-2.62 (4 H, m), 1.33 (3 H, t) |
| 15 | $^1$H NMR (400 MHz, CDCl$_3$) δ ppm 7.89-7.83 (2 H, m), 7.09 (2 H, t), 7.00 (1 H, s), 6.87 (1 H, d), 6.69 (1 H, s), 4.58-4.48 (1 H, m), 3.71-3.51 (7 H, m), 3.23-3.14 (2 H, m), 3.00-3.12 (4 H, m), 2.78-2.64 (6 H, m), 2.12-1.89 (2 H, m), 1.33 (3 H, t) |
| 16 | $^1$H NMR (300 MHz, MeOD-d$_4$) δ ppm 7.97-7.82 (2 H, m), 7.28-7.17 (2 H, m), 7.11 (2 H, t), 6.98 (1 H, s), 4.47-4.33 (1 H, m), 3.73-3.40 (7 H, m), 3.24 (2 H, d), 3.18-3.02 (4 H, m), 2.77-2.61 (6 H, m), 2.14-1.84 (2 H, m), 1.31 (3 H, t) |
| 17 | $^1$H NMR (300 MHz, CDCl$_3$) δ ppm 7.84-7.79 (2 H, m), 7.52 (1 H, s), 7.34 (1 H, s), 7.04 (2 H, t), 6.62 (1 H, s), 4.65-4.58 (1 H, m), 4.41-4.36 (1 H, m), 4.24-4.18 (1 H, m), 4.05-4.01 (1 H, m), 3.86-3.81 (1 H, m), 3.55 (3 H, s), 3.01-2.93 (4 H, m), 2.71-2.54 (3 H, m), 2.36 (3 H, s), 2.25-2.13 (2 H, m), 2.04-1.57 (4 H, m), 1.28 (3 H, t) |
| 18 | $^1$H NMR (400 MHz, CDCl$_3$) δ ppm 8.18-8.14 (2 H, m), 7.26-7.16 (4 H, m), 4.70-4.68 (1 H, m), 4.47-4.43 (1 H, m), 4.30-4.26 (1 H, m), 4.12-4.08 (1 H, m), 3.91-3.87 (1 H, m), 3.62 (3 H, s), 3.14-3.06 (6 H, m), 2.73-2.68 (6 H, m), 1.34 (3 H, t) |
| 19 | $^1$H NMR (400 MHz, DMSO) δ ppm 8.02-7.95 (2 H, m), 7.68 (1 H, d), 7.49 (1 H, d), 7.32-7.23 (3 H, m), 4.50-4.32 (2 H, m), 4.09-4.01 (1 H, m), 3.98-3.90 (1 H, m), 3.67-3.52 (4 H, m), 3.10-2.90 (6 H, m), 2.68-2.42 (6 H, m), 1.23 (3 H, t) |
| 20 | $^1$H NMR (400 MHz, CDCl$_3$) δ ppm 8.17 (1 H, s), 7.87-7.83 (2 H, m), 7.37 (1 H, d), 7.10 (2 H, t), 6.69 (1 H, s), 4.55-4.50 (1 H, m), 3.69-3.51 (7 H, m), 3.47-3.12 (2 H, m), 3.06 (4 H, bs), 2.80-2.68 (6 H, m), 1.99-2.07 (2 H, m), 1.31 (3 H, t) |
| 21 | $^1$H NMR (400 MHz, CDCl$_3$) δ ppm 7.87-7.84 (2 H, m), 7.36-7.23 (2 H, m), 7.10 (2 H, t), 6.89 (1 H, s), 4.55-4.50 (1 H, m), 3.69-3.52 (7 H, m), 3.22-3.18 (2 H, m), 3.05 (4 H, bs), 2.75-2.67 (6 H, m), 2.10-1.96 (2 H, m), 1.31 (3 H, t) |
| 22 | $^1$H NMR (400 MHz, MeOD-d$_4$) δ ppm 8.19-8.11 (2 H, m), 7.51-7.36 (3 H, m), 7.24 (2 H, t), 3.65 (3 H, s), 3.20-3.14 (4 H, m), 3.05 (2 H, s), 2.75 (3 H, s), 2.74-2.64 (6 H, m), 1.32 (3 H, t) |
| 23 | $^1$H NMR (400 MHz, MeOD-d$_4$) δ ppm 7.92-7.88 (2 H, m), 7.48-7.45 (1 H, m), 7.40-7.37 (2 H, m), 7.14-7.09 (2 H, m), 6.95 (1 H, s), 3.61 |

TABLE IV-continued

NMR data of the compounds of the invention.

| Cpd | NMR data (δ) |
|---|---|
|  | (3 H, s), 3.55 (4 H, t), 3.09-2.96 (4 H, m), 2.69 (2 H, q), 1.45 (9 H, s), 1.31 (3H, t) |
| 24 | $^1$H NMR (400 MHz, MeOD-d$_4$) δ ppm 7.94-7.84 (2 H, m), 7.44 (1 H, d), 7.40-7.29 (2 H, m), 7.11 (2 H, m), 6.94 (1 H, s), 4.58-4.51 (1 H, m), 4.50-4.42 (1 H, m), 4.23-4.16 (1 H, m), 4.04 (1 H, dd), 3.75 (1 H, dd), 3.60 (3 H, s), 3.19-3.00 (6 H, m), 2.73-2.61 (6 H, m), 1.30 (3 H, t) |
| 25 | $^1$H NMR (400 MHz, CDCl$_3$) δ ppm 7.94-7.82 (2 H, m), 7.59-7.53 (1 H, m), 7.24-7.04 (4 H, m), 6.70 (1 H, s), 4.60-4.50 (1 H, m), 3.74-3.56 (7 H, m), 3.23 (2 H, d), 3.12 (4 H, bs), 2.76 (6 H, m), 2.11-1.92 (2 H, m), 1.37 (3 H, t) |
| 26 | $^1$H NMR (300 MHz, CDCl$_3$) δ ppm 7.96-7.77 (2 H, m), 7.52 (1 H, d), 7.19-7.04 (4 H, m), 6.67 (1 H, s), 4.57-4.45 (1 H, m), 3.78-3.52 (7 H, m), 3.19 (2 H, d), 3.14-3.00 (4 H, m), 2.79-2.63 (6 H, m), 2.07-1.98 (1 H, m), 1.98-1.89 (1 H, m), 1.32 (3 H, t) |
| 27 | $^1$H NMR (400 MHz, CDCl$_3$) δ ppm 7.86 (2 H, dd), 7.49 (1 H, d), 7.22-7.04 (4 H, m), 6.67 (1 H, s), 5.89-5.75 (1 H, m)NH, 4.53-4.40 (1 H, m), 3.86-3.68 (1 H, m), 3.67-3.51(5 H, m), 3.47-3.35 (1 H, m), 3.23-3.13 (2 H, m), 3.07 (4 H, bs), 2.78-2.65 (6 H, m), 2.34-2.10 (1 H, m), 2.00-1.95 (3 H, m), 1.93-1.77 (1 H, m), 1.33 (3 H, t) |
| 28 | $^1$H NMR (400 MHz, MeOD-d$_4$) δ ppm 7.90 (2 H, dd), 7.45 (1 H, d), 7.40-7.29 (2 H, m), 7.12 (2 H, t), 6.95 (1 H, d), 5.44-5.36 (0.5 H, m), 5.31-5.22 (0.5 H, m), 4.66-4.51 (1 H, m), 4.42-4.22 (2 H, m), 4.10-3.96 (1 H, m), 3.61 (3 H, s), 3.20-3.03 (6 H, m), 2.77-2.61 (6 H, m), 1.31 (3 H, t) |
| 30 | $^1$H NMR (400 MHz, MeOD-d$_4$) δ ppm 7.97-7.84 (2 H, m), 7.44 (1 H, d), 7.39-7.30 (2 H, m), 7.15-7.07 (2 H, m), 6.93 (1 H, s), 4.27 (2 H, t), 4.00 (2 H, s), 3.60 (3 H, s), 3.16-3.03 (6 H, m), 2.74-2.60 (6 H, m), 2.28 (2 H, q), 1.30 (3 H, t) |
| 31 | $^1$H NMR (400 MHz, MeOD-d$_4$) δ ppm 8.01-7.80 (2 H, m), 7.44 (1 H, d), 7.39-7.30 (2 H, m), 7.14-7.07 (2 H, m), 6.96-6.91 (1 H, m), 3.60 (3 H, s), 3.52 (2 H, t), 3.41 (2 H, t), 3.23 (2 H, bs), 3.17-3.05 (4 H, m), 2.74-2.67 (6 H, m), 1.95 (2 H, quin), 1.85 (2 H, quin), 1.30 (3 H, t) |
| 32 | $^1$H NMR (400 MHz, CDCl$_3$) δ ppm 7.86 (2 H, dd), 7.54 (1 H, d), 7.20-7.03 (4 H, m), 6.68 (1 H, s), 3.71-3.57 (11 H, m), 3.24 (2 H, s), 3.07 (4 H, d), 2.78-2.64 (6 H, m), 1.34 (3 H, t) |
| 33 | $^1$H NMR (300 MHz, MeOD-d$_4$) δ ppm 7.96-7.83 (2 H, m), 7.51-7.28 (3 H, m), 7.19-7.05 (2 H, m), 6.95 (1 H, s), 3.61 (3 H, s), 3.13 (4 H, d), 3.05 (2 H, s), 2.76-2.64 (6 H, m), 1.31 (3 H, t) |
| 34 | $^1$H NMR (400 MHz, CDCl$_3$) δ ppm 7.92-7.79 (2 H, m), 7.56 (1 H, d), 7.22-7.15 (2 H, m), 7.10 (2 H, t), 6.69 (1 H, s), 4.29 (1 H, t), 4.13-4.01 (2 H, m), 3.85-3.72 (3 H, m), 3.61 (3 H, s), 3.08 (6 H, s), 2.85-2.63 (7 H, m), 1.34 (3 H, t) |
| 35 | $^1$H NMR (400 MHz, CDCl$_3$) δ ppm 7.87 (2 H, dd), 7.49 (1 H, d), 7.20-7.06 (4 H, m), 6.67 (1 H, s), 3.61 (3 H, s), 3.23 (2 H, s), 3.13-3.02 (7 H, m), 2.95 (3 H, s), 2.77-2.66 (6 H, m), 1.33 (3 H, t) |
| 36 | $^1$H NMR (400 MHz, CDCl$_3$) δ ppm 7.86 (2 H, dd), 7.50 (1 H, d), 7.20-7.04 (4 H, m), 6.67 (1 H, s), 4.19 (2 H, d), 3.61 (3 H, s), 3.27 (2 H, s), 3.10 (4 H, m), 2.79-2.68 (6 H, m), 1.33 (3 H, t), 1.28 (3 H, t) |
| 37 | $^1$H NMR (400 MHz, CDCl$_3$) δ ppm 7.86 (2 H, dd), 7.49 (1 H, d), 7.19-7.05 (4 H, m), 6.67 (1 H, s), 4.18 (2 H, dd), 3.60 (3 H, s), 3.33 (1 H, q), 3.12-2.96 (4 H, m), 2.83-2.66 (6 H, m), 1.37-1.24 (9 H, m) |
| 38 | $^1$H NMR (400 MHz, MeOD-d$_4$) δ ppm 7.90-7.85 (2 H, m), 7.45 (1 H, d), 7.35 (1 H, dd), 7.32 (1 H, d), 7.09 (2 H, t), 6.90 (1 H, s), 3.67 (2 H, s), 3.59 (3 H, s), 3.04-2.15 (4 H, m), 2.70 (4 H, bt), 2.67 (2 H, q), 1.29 (3 H, t) |
| 39 | $^1$H NMR (400 MHz, MeOD-d$_4$) δ ppm 7.89-7.84 (2 H, m), 7.44 (1 H, d), 7.36 (1 H, dd), 7.31 (1 H, d), 7.13-7.09 (2 H, m), 6.91 (1 H, s), 3.97 (2 H, s), 2.85 (1 H, sept), 3.59 (3 H, s), 3.33-3.29 (4 H, m), 3.14-3.03 (4 H, m), 2.70-2.65 (6 H, m), 1.29 (3 H, t) |
| 40 | $^1$H NMR (400 MHz, MeOD-d$_4$) δ ppm 7.92-7.85 (3 H, m), 7.44 (1 H, dd), 7.38-7.29 (2 H, m), 7.15 (1 H, d), 7.11 (2 H, t), 6.93 (1 H, s), 3.77 (2 H, s), 3.59 (3 H, s), 3.16-3.02 (4 H, m), 2.73-2.63 (6 H, m), 1.30 (3 H, t) |
| 41 | $^1$H NMR (400 MHz, CDCl$_3$) δ ppm 8.70 (1 H, bs), 7.86-7.81 (2 H, m), 7.67 (1 H, d), 7.23 (1 H, dd), 7.17 (1 H, d), 7.11-7.06 (2 H, m), 6.69 (1 H, s), 3.83 (2 H, s), 3.59 (3 H, s), 3.15-3.04 (4 H, m), 2.79-2.71 (6 H, m), 1.35 (3 H, t) |
| 42 | $^1$H NMR (400 MHz, MeOD-d$_4$) δ ppm 7.93-7.86 (2 H, m), 7.45 (1 H, dd), 7.41-7.35 (2 H, m), 7.11 (2 H, t), 6.95 (1 H, s), 3.61 (3 H, s), 3.25-3.13 (6 H, m), 2.96-2.89 (4 H, m), 2.70 (2 H, q), 1.31 (3 H, t) |
| 43 | $^1$H NMR (400 MHz, MeOD-d$_4$) δ ppm 7.89 (2 H, dd), 7.50-7.34 (3 H, m), 7.16-7.05 (2 H, m), 6.94 (1 H, s), 4.17-4.10 (2 H, m), 3.74-3.67 (2 H, m), 3.68-3.57 (7 H, m), 3.14-2.98 (4 H, m), 2.69 (2 H, q), 1.30 (3 H, t) |
| 44 | $^1$H NMR (400 MHz, CDCl$_3$) δ ppm (2 conformers) 7.86 (2 H, dd), 7.57-7.47 (1 H, m), 7.19 (1 H, s), 7.16-7.02 (3 H, m), 6.67 (1 H, s), 4.67 (0.5 H, dd), 4.54 (0.5 H, d), 3.77 (3 H, bs), 3.70-3.33 (6 H, m), 3.18-2.89 (4 H, m), 2.72 (2 H, q), 2.28-1.93 (2 H, m), 1.92-1.77 (2 H, m), 1.49-1.29 (12 H, m) |
| 45 | $^1$H NMR (400 MHz, CDCl$_3$) δ ppm 7.84 (2 H, dd), 7.51 (1 H, d), 7.19 (1 H, s), 7.15-7.02 (3 H, m), 6.66 (1 H, s), 3.88-3.62 (4 H, m), 3.59 (3 H, s), 3.51 (3 H, bs), 3.32 (1 H, bs), 3.18 (1 H, bs), 3.02 (4 H, bs), 2.71 (2 H, q), 2.39-2.53 (0.5 H, m), 2.18-2.33 (0.5 H, m), 2.14-1.94 (1 H, m), 1.43 (9 H, s), 1.32 (3 H, t) |
| 46 | $^1$H NMR (400 MHz, MeOD-d$_4$) δ ppm 8.08 (1 H, dd), 7.92-7.85 (3 H, m), 7.78 (1 H, s), 7.21 (1 H, s), 7.15 (2 H, t), 4.81-4.76 (1 H, m), 3.91-3.75 (4 H, m), 3.72 (3 H, s), 3.50-3.29 (6 H, m), 2.94 (2 H, q), 2.64-2.53 (1 H, m), 2.21-1.93 (3 H, m), 1.44 (3H, t) |
| 47 | $^1$H NMR (400 MHz, MeOD-d$_4$) δ ppm 8.09-8.05 (1 H, m), 7.94-7.85 (3 H, m), 7.75 (1 H, sb), 7.21 (1 H, s), 7.15 (2 H, t), 3.86-3.52 |

TABLE IV-continued

NMR data of the compounds of the invention.

| Cpd | NMR data (δ) |
|---|---|
| | (9 H, m), 3.49-3.26 (7 H, m), 2.94 (2 H, q), 2.48-2.28 (1 H, m), 2.18-2.07 (1 H, m), 1.44 (3 H, t) |
| 48 | $^1$H NMR (400 MHz, CDCl$_3$) δ ppm 7.90-7.86 (2 H, m), 7.73-7.66 (1 H, m), 7.25-7.25 (2 H, m), 7.16-7.11 (2 H, m), 6.73 (1 H, s), 3.88-3.76 (2 H, m), 3.76-3.61 (6 H, m), 3.60-3.18 (4 H, m), 3.16-3.02 (4 H, m), 2.80 (2 H, q), 2.50-2.40 (1 H, m), 2.20-2.04 (4 H, m), 1.39 (3H, t) |
| 49 | $^1$H NMR (400 MHz, CDCl$_3$) δ ppm 7.90-7.82 (2 H, m), 7.59 (1 H, d), 7.22 (1 H, d), 7.16 (1 H, dd), 7.10 (2 H, t), 6.69 (1 H, s), 3.83-3.75 (2 H, m), 3.71-3.65 (2 H, m), 3.61 (3 H, s), 3.60-3.55 (2 H, m), 3.55-3.46 (1 H, m), 3.38-3.29 (2 H, m), 3.11-3.00 (4 H, m), 2.91 (3 H, s), 2.75 (2 H, q), 2.29-2.09 (2 H, m), 1.35 (3 H, t) |
| 50 | $^1$H NMR (400 MHz, MeOD-d$_4$) δ ppm 7.88 (2 H, dd), 7.47 (1 H, dd), 7.42-7.34 (2 H, m), 7.11 (2 H, t), 6.93 (1 H, s), 4.23 (2 H, s), 3.73 (2 H, bt), 3.60 (3 H, s), 3.54 (2 H, bt), 3.14-2.99 (4 H, m), 2.69 (2 H, q), 1.30 (3 H, t) |
| 51 | $^1$H NMR (400 MHz, MeOD-d$_4$) δ ppm 7.88 (2 H, dd), 7.50-7.44 (1 H, m), 7.42-7.32 (2 H, m), 7.10 (2 H, t), 6.92 (1 H, s), 3.71 (2 H, s), 3.65 (2 H, t), 3.60 (3 H, s), 3.12-2.96 (4 H, m), 2.68 (2 H, q), 2.40 (2 H, q), 1.29 (3 H, t), 1.10 (3 H, t) |
| 52 | $^1$H NMR (400 MHz, CDCl$_3$) δ ppm 7.86-7.82 (2 H, m), 7.51 (1 H, d), 7.18 (1 H, d), 7.13-7.05 (3 H, m), 6.66 (1 H, s), 3.76 (2 H, t), 3.67 (2 H, t), 3.62 (2 H, t), 3.58 (3 H, s), 3.04-2.95 (4 H, m), 2.70 (2 H, q), 2.50 (2 H, t), 1.90 (2 H, quint), 1.31 (3 H, t) |
| 53 | $^1$H NMR (400 MHz, CDCl$_3$) δ ppm 7.92-7.82 (2 H, m), 7.52 (1 H, d), 7.20 (1 H, d), 7.15-7.04 (3 H, m), 6.67 (1 H, s), 3.77 (2 H, t), 3.67-3.58 (5 H, m), 3.06-2.94 (4 H, m), 2.73 (2 H, q), 2.40 (2 H, t), 2.33 (2 H, t), 2.22 (6 H, s), 1.82 (2 H, quin), 1.33 (3 H, t) |
| 54 | $^1$H NMR (400 MHz, CDCl$_3$) δ ppm 7.85 (2 H, dd), 7.63 (1 H, d), 7.25 (1 H, s), 7.18 (1 H, bd), 7.09 (2 H, t), 6.70 (1 H, s), 3.62 (3 H, s), 3.44-3.34 (4 H, m), 3.21-3.10 (4 H, m), 2.83 (3 H, s), 2.76 (2 H, q), 1.35 (3 H, t) |
| 55 | $^1$H NMR (400 MHz, MeOD-d$_4$) δ ppm 7.91-7.87 (2 H, m), 7.47 (1 H, d), 7.40-7.36 (2 H, m), 7.14-7.08 (2 H, m), 6.94 (1 H, s), 3.69 (2 H, t), 3.60 (3 H, s), 3.42 (4 H, bt), 3.21-3.11 (6 H, m), 2.69 (2 H, q), 2.26-2.19 (2 H, m), 1.30 (3 H, t) |
| 56 | $^1$H NMR (400 MHz, CDCl$_3$) δ ppm 7.91-7.83 (2 H, m), 7.53 (1 H, d), 7.23 (1 H, d), 7.14-7.06 (3 H, m), 6.68 (1 H, s), 3.62 (3 H, s), 3.46 (4 H, t), 3.16-3.05 (6 H, m), 2.74 (2 H, d), 2.70-2.57 (2H, m), 2.37 (6 H, bs), 2.19-2.08 (2H, m), 1.34 (3 H, t) |
| 57 | $^1$H NMR (400 MHz, CDCl$_3$) δ ppm 7.87 (2 H, dd), 7.52 (1 H, d), 7.23 (1 H, d), 7.15-7.06 (3 H, m), 6.68 (1 H, s), 3.61 (3 H, s), 3.45 (4 H, bt), 3.17-3.03 (6 H, m), 2.73 (2 H, q), 2.69-2.53 (6 H, m), 2.12-2.00 (2 H, m), 1.82 (4 H, bs), 1.34 (3 H, t) |
| 58 | $^1$H NMR (400 MHz, MeOD-d$_4$) δ ppm 7.88 (2 H, dd), 7.47 (1 H, dd), 7.42-7.31 (2 H, m), 7.10 (2 H, t), 6.92 (1 H, s), 3.64 (2 H, t), |
| | 3.60 (3 H, s), 3.40 (4 H, bt), 3.22-3.06 (6 H, m), 2.69 (2 H, q), 2.03-1.90 (2 H, m), 1.30 (3 H, t) |
| 59 | $^1$H NMR (400 MHz, MeOD-d$_4$) δ ppm 7.90 (2 H, dd), 7.48 (1 H, dd), 7.44-7.34 (2 H, m), 7.12 (2 H, t), 6.95 (1 H, s), 3.76 (3 H, s), 3.61 (3 H, s), 3.48 (4 H, bt), 3.23-3.08 (4 H, m), 2.70 (2 H, q), 1.31 (3 H, t) |
| 60 | $^1$H NMR (400 MHz, CDCl$_3$) δ ppm 7.95 (1 H, d), 7.81-7.78 (2 H, m), 7.28 (1 H, d), 7.21-7.22 (1 H, m), 7.09-7.04 (2 H, m), 6.71 (1 H, s), 4.01 (2 H, s), 3.58 (7 H, s), 3.58 (4 H, m), 2.77 (2 H, q), 1.32 (3 H, t) |
| 61 | $^1$H NMR (400 MHz, CDCl$_3$) δ ppm 7.88-7.85 (2 H, m), 7.62 (1 H, d), 7.23 (1 H, d), 7.17-7.07 (3 H, m), 6.70 (1 H, s), 6.51 (1 H, bs)NH, 5.68 (1 H, bs)NH, 2.90 (2 H, s), 3.61 (3 H, s), 3.56-3.51 (4 H, m), 3.18-3.06 (4 H, m), 2.75 (2 H, q), 1.34 (3 H, t) |
| 62 | $^1$H NMR (400 MHz, MeOD-d$_4$) δ ppm 8.27 (1 H, d), 7.91-7.81 (2 H, m), 7.59 (1 H, dd), 7.39 (1 H, dd), 7.09 (2 H, t), 6.92 (1 H, s), 4.18 (2 H, bs), 3.81-3.67 (4 H, m), 3.60 (3 H, s), 2.73 (2 H, q), 1.47 (9 H, s), 1.32 (3 H, t) |
| 63 | $^1$H NMR (400 MHz, MeOD-d$_4$) δ ppm 8.29 (1 H, dd), 7.84 (2 H, d), 7.60 (1 H, dd), 7.45-7.33 (3 H, m), 7.03 (1 H, s), 4.19 (2 H, s), 3.83-3.70 (4 H, m), 3.61 (3 H, s), 2.74 (2 H, q), 1.48 (9 H, s), 1.33 (3 H, t) |
| 64 | $^1$H NMR (400 MHz, CDCl$_3$) δ ppm 7.89-7.86 (3 H, m), 7.66 (2 H, d), 7.25-7.22 (1 H, m), 7.14-7.10 (2 H, m), 4.27-4.21 (2 H, m), 3.82-3.66 (2 H, m), 3.64 (3 H, s), 3.54 (2 H, s), 3.39 (2 H, s), 3.07-3.04 (2 H, m), 2.79 (2 H, q), 1.37 (3 H, t), 1.32 (3 H, t) |
| 65 | $^1$H NMR (400 MHz, MeOD-d$_4$) δ ppm 8.36 (1 H, dd), 7.94 (2 H, dd), 7.67 (1 H, dd), 7.46 (1 H, dd), 7.16 (2 H, t), 7.05-6.90 (1 H, m), 4.11 (2 H, s), 3.89 (2 H, dd), 3.75-3.61 (5 H, m), 3.03 (3 H, s), 2.81 (2 H, q), 1.39 (3 H, t) |
| 66 | $^1$H NMR (400 MHz, CDCl$_3$) δ ppm 7.86 (2 H, dd), 7.73 (1 H, s), 7.61 (1 H, d), 7.37 (1 H, dd), 7.10 (2 H, t), 6.69 (1 H, s), 6.10 (1 H, bs), 3.97 (2 H, bs), 3.63 (3 H, s), 3.57-3.45 (2 H, m), 2.86 (3 H, s), 2.77 (2 H, q), 2.61 (2 H, bs), 1.36 (3 H, t) |
| 67 | $^1$H NMR (400 MHz, MeOD-d$_4$) δ ppm 7.95 (1 H, s), 7.91-7.86 (2 H, m), 7.61 (1 H, dd), 7.54 (1 H, dd), 7.14-7.08 (2 H, m), 6.96 (1 H, s), 6.24-6.22 (1 H, m), 4.83 (2 H, s), 4.13-4.09 (2 H, m), 3.66 (2 H, td), 3.63 (3 H, s), 2.73 (2 H, q), 2.66-2.53 (2 H, m), 1.32 (3 H, t) |
| 68 | $^1$H NMR (300 MHz, CDCl$_3$) δ ppm 7.82 (2 H, d), 7.73 (1 H, d), 7.62 (1 H, s), 7.47 (1 H, d), 7.38 (2 H, d), 6.77 (1 H, s), 6.22 (1 H, bs), 4.55-4.31 (4 H, m), 3.63 (3 H, s), 2.90 (3 H, s), 2.79 (2 H, q), 1.37 (3 H, t) |
| 69 | $^1$H NMR (400 MHz, CDCl$_3$) δ ppm 7.81 (2 H, d), 7.77-7.72 (2 H, m), 7.45-7.34 (3 H, m), 6.79 (1 H, s), 6.30-6.20 (1 H, m), 4.12-4.04 (2 H, m), 3.64 (3 H, s), 3.50-3.36 (2 H, m), 2.87 (3 H, s), 2.80 (2 H, q), 2.53-2.45 (2 H, m), 1.39 (3 H, t) |

TABLE IV-continued

NMR data of the compounds of the invention.

| Cpd | NMR data (δ) |
|---|---|
| 70 | $^1$H NMR (300 MHz, CDCl$_3$) δ ppm 7.84-7.77 (2 H, m), 7.73 (1 H, bs), 7.58 (1 H, dd), 7.43 (2 H, d), 7.34 (1 H, dd), 6.70 (1 H, s), 6.16-6.05 (1 H, m), 3.96 (2 H, bd), 3.63 (3 H, s), 3.55-3.45 (2 H, m), 2.85 (3 H, s), 2.76 (2 H, q), 2.64-2.55 (2 H, m), 1.39-1.32 (12 H, t) |
| 71 | $^1$H NMR (400 MHz, CDCl$_3$) δ ppm 8.20 (1 H, bd), 7.87 (1 H, s), 7.78 (1 H, bd), 7.73 (2 H, d), 6.92 (2 H, d), 6.72 (1 H, s), 6.20 (1 H, bs), 3.97 (2 H, bs), 3.83 (3 H, s), 3.64 (3 H, bs), 3.54-3.46 (2 H, m), 2.92 (2 H, q), 2.84 (3 H, s), 2.60 (2 H, bs), 1.46 (3 H, t) |
| 72 | $^1$H NMR (400 MHz, CDCl$_3$) δ ppm 7.94-7.87 (2 H, m), 7.72 (1 H, bs), 7.59 (1 H, d), 7.37 (1 H, dd), 7.26 (2 H, bd), 6.76 (1 H, s), 6.10 (1 H, m), 3.97 (2 H, bs), 3.63 (3 H, s), 3.55-3.44 (2 H, m), 2.85 (3 H, s), 2.76 (2 H, q), 2.60 (2 H, bs), 1.36 (3 H, t) |
| 73 | $^1$H NMR (400 MHz, CDCl$_3$) δ ppm 7.72 (2 H, s), 7.62-7.54 (2 H, m), 7.35 (1 H, dd), 7.19 (1 H, q), 6.71 (1 H, s), 6.13-6.06 (1 H, m), 3.96 (2 H, d), 3.62 (3 H, s), 3.58-3.43 (2 H, m), 2.85 (3 H, s), 2.75 (2 H, q), 2.61 (2 H, bs), 1.35 (3 H, t) |
| 74 | $^1$H NMR (400 MHz, MeOD-d$_4$) δ ppm 7.93 (1 H, s), 7.91-7.82 (2 H, m), 7.63-7.48 (2 H, m), 7.09 (2 H, t), 6.93 (1 H, s), 6.21 (1 H, t), 4.13 (2 H, t), 4.00-3.93 (2 H, m), 3.62 (3 H, s), 3.50 (2 H, bt), 3.17-3.06 (2 H, m), 2.71 (2 H, q), 2.64-2.47 (2 H, m), 2.13-2.03 (2 H, m), 1.99 (3 H, s), 1.31 (3 H, t) |
| 75 | $^1$H NMR (400 MHz, MeOD-d$_4$) δ ppm 7.92 (1 H, s), 7.87 (2 H, dd), 7.61-7.47 (2 H, m), 7.09 (2 H, t), 6.92 (1 H, s), 6.25-6.17 (1 H, m), 3.98-3.93 (2 H, m), 3.66-3.58 (5 H, m), 3.49 (2 H, t), 3.18-3.04 (2 H, m), 2.71 (2 H, q), 2.64-2.47 (2 H, m), 2.03-1.90 (2 H, m), 1.31 (3 H, t) |
| 76 | $^1$H NMR (400 MHz, CDCl$_3$) δ ppm 7.81 (2 H, d), 7.77 (1 H, bs), 7.61 (1 H, d), 7.37 (2 H, d), 7.29 (1 H, d), 6.76 (1 H, s), 5.90 (1 H, t), 3.79 (2 H, bs), 3.63 (3 H, s), 3.26-3.20 (2 H, m), 3.15-3.07 (2 H, m), 2.77 (2 H, q), 1.35 (3 H, t) |
| 77 | $^1$H NMR (400 MHz, CDCl$_3$) δ ppm 7.93-7.84 (2 H, m), 7.74 (1 H, s), 7.67 (1 H, dd), 7.40 (1 H, dd), 7.17-7.09 (2 H, m), 6.17-6.08 (1 H, m), 3.98 (2 H, bs), 3.46-3.59 (5 H, m), 2.86 (3 H, s), 2.77 (2 H, q), 2.58-2.68 (2 H, m), 1.36 (3 H, t) |
| 78 | $^1$H NMR (400 MHz, MeOD-d$_4$) δ ppm 8.04 (1 H, d), 7.96-7.92 (2 H, m), 7.65-7.61 (1 H, m), 7.57-7.54 (1 H, m), 7.10 (2 H, t), 7.03 (1 H, s), 4.37-4.33 (1 H, m), 4.19-4.16 (1 H, m), 3.75-3.61 (4 H, m), 2.91-2.78 (3 H, m), 2.73-2.60 (2 H, m), 1.91-1.66 (2 H, m), 1.52 (9 H, d), 1.39 (3H, t) |
| 79 | $^1$H NMR (400 MHz, MeOD-d$_4$) δ ppm 8.00-7.79 (3 H, m), 7.55 (1 H, d), 7.48-7.41 (1 H, m), 7.12 (2 H, t), 6.95 (1 H, d), 3.96-3.87 (1 H, m), 3.85-3.72 (2 H, m), 3.63 (3 H, d), 2.87 (3 H, s), 2.85-2.77 (1 H, m), 2.73 (2 H, q), 2.63-2.52 (2 H, m), 1.97-1.89 (2 H, m), 1.32 (3 H, t) |
| 80 | $^1$H NMR (300 MHz, CDCl$_3$) δ ppm 7.87 (2 H, dd), 7.67-7.53 (2 H, m), 7.21-7.05 (3 H, m), 6.69 (1 H, s), 3.95 (2 H, d), 3.63 (3 H, s), 2.82-2.70 (7 H, m), 2.68-2.55 (1 H, m), 2.04-1.74 (4 H, m), 1.35 (3 H, t) |
| 81 | $^1$H NMR (400 MHz, CDCl$_3$) δ ppm 7.80 (2 H, d), 7.63 (1 H, bs), 7.58 (1 H, d), 7.43 (2 H, d), 7.15 (1 H, dd), 6.70 (1 H, s), 3.99-3.90 (2 H, m), 3.62 (3 H, s), 2.81 (3 H, s), 2.79-2.69 (4 H, m), 2.66-2.55 (1 H, m), 1.96 (2 H, d), 1.90-1.75 (2 H, m), 1.35 (9 H, s), 1.26 (3 H, t) |
| 82 | $^1$H NMR (300 MHz, CDCl$_3$) δ ppm 7.82 (2 H, d), 7.70-7.52 (2 H, m), 7.16 (1 H, dd), 6.95 (2 H, d), 6.62 (1 H, s), 3.94 (2 H, d), 3.86 (3 H, s), 3.63 (3 H, s), 2.84-2.69 (7 H, m), 2.68-2.58 (1 H, m), 2.02-1.92 (2 H, m), 1.92-1.74 (2 H, m), 1.35 (3 H, t) |
| 83 | $^1$H NMR (400 MHz, CDCl$_3$) δ ppm 7.73 (1 H, ddd), 7.63-7.53 (3 H, m), 7.24-7.11 (2 H, m), 6.70 (1 H, s), 3.95 (2 H, d), 3.62 (3 H, s), 2.81 (3 H, s), 2.79-2.69 (4 H, m), 2.68-2.56(1 H, m), 2.01-1.92 (2 H, m), 1.82 (2 H, qd), 1.35 (3 H, t) |
| 84 | $^1$H NMR (400 MHz, CDCl$_3$) δ ppm 8.00 (2 H, d), 7.71-7.56 (4 H, m), 7.17 (1 H, dd), 6.88 (1 H, s), 3.95 (2 H, d), 3.64 (3 H, s), 2.81 (3 H, s), 2.80-2.71 (4 H, m), 2.68-2.57 (1 H, m), 1.97 (2 H, d), 1.85 (2 H, qd), 1.36 (3 H, t) |
| 85 | $^1$H NMR (400 MHz, CDCl$_3$-d) δ ppm 7.91 (2 H, d), 7.62 (1 H, s), 7.59 (1 H, d), 7.26 (2 H, d), 7.16 (1 H, dd), 6.75 (1 H, s), 3.95 (2 H, d), 3.63 (3 H, s), 2.81 (3 H, s), 2.79-2.70 (4 H, m), 2.68-2.57 (1 H, m), 2.01-1.92 (2 H, m), 1.90-1.74 (2 H, m), 1.35 (3 H, t) |
| 86 | $^1$H NMR (400 MHz, MeOD-d$_4$) δ ppm 7.95-7.83 (3 H, m), 7.52 (1 H, dd), 7.39 (1 H, dd), 7.19-7.04 (2 H, m), 6.94 (1 H, s), 3.85 (2 H, bd), 3.70 (2 H, t), 3.62 (3 H, s), 3.23-3.14 (2 H, m), 2.93 (2 H, bt), 2.83-2.66 (3 H, m), 2.27-2.14 (2 H, m), 1.90 (2 H, bd), 1.77 (2 H, qd), 1.32 (3 H, t) |
| 87 | $^1$H NMR (400 MHz, CDCl$_3$) δ ppm 7.91-7.82 (2 H, m), 7.61 (1 H, s), 7.57 (1 H, d), 7.19-7.06 (3 H, m), 6.68 (1 H, s), 3.94 (2 H, d), 3.62 (3 H, s), 3.05-2.96 (2 H, m), 2.85 (2 H, t), 2.75 (2 H, q), 2.66-2.55 (1 H, m), 2.41 (2 H, t), 2.24 (6 H, s), 2.05-1.88 (4 H, m), 1.86-1.71 (2 H, m), 1.34 (3 H, t) |
| 88 | $^1$H NMR (400 MHz, MeOD-d$_4$) δ ppm 7.92-7.84 (3 H, m), 7.53 (1 H, d), 7.39 (1 H, dd), 7.11 (2 H, t), 6.93 (1 H, s), 3.84 (2 H, d), 3.68 (4 H, t), 3.62 (3 H, s), 3.08 (2 H, t), 2.91 (2 H, t), 2.81-2.66 (3 H, m), 2.52-2.38 (6 H, m), 2.01-1.85 (4 H, m), 1.75 (2 H, q), 1.31 (3 H, t) |
| 89 | $^1$H NMR (400 MHz, MeOD-d$_4$) δ ppm 7.94-7.82 (3 H, m), 7.53 (1 H, d), 7.40 (1 H, dd), 7.11 (2 H, t), 6.94 (1 H, s), 3.85 (2 H, d), 3.62 (3 H, s), 3.08 (2 H, t), 2.92 (2 H, t), 2.82-2.68 (3 H, m), 2.67-2.55 (6 H, m), 2.05-1.88 (4 H, m), 1.86-1.71 (6 H, m), 1.32 (3 H, t) |
| 90 | $^1$H NMR (300 MHz, CDCl$_3$) δ ppm 7.85 (2 H, dd), 7.61 (1 H, s), 7.57 (1 H, d), 7.19-7.02 (3 H, m), 6.67 (1 H, s), 3.92 (2 H, bd), 3.61 (3 H, s), 3.16-3.02 (1 H, m), 3.01-2.69 (7 H, m), 2.68-2.51 (1 H, m), 2.11-1.97 (2 H, m), 1.96-1.87 (2 H, m), 1.86-1.66 (2 H, m), 1.34 (3 |

TABLE IV-continued

NMR data of the compounds of the invention.

| Cpd | NMR data (δ) |
|---|---|
| 91 | $^1$H NMR (400 MHz, MeOD-d$_4$) δ ppm 7.99-7.81 (3 H, m), 7.51 (2 H, dd), 7.10 (2 H, t), 6.96 (1 H, s), 3.84 (2 H, d), 3.75-3.58 (7 H, m), 3.24 (2 H, t), 2.95 (2 H, t), 2.89-2.66 (5 H, m), 2.55 (4 H, bs), 1.92 (2 H, d), 1.85-1.67 (2 H, m), 1.32 (3 H, t) |
| 92 | $^1$H NMR (400 MHz, MeOD-d$_4$) δ ppm 7.93-7.84 (3 H, m), 7.53 (1 H, dd), 7.40 (1 H, dd), 7.11 (2 H, t), 6.94 (1 H, s), 3.75 (2 H, d), 3.62 (3 H, s), 2.76-2.66 (5 H, m), 1.90 (2 H, bd), 1.83 (2 H, qd), 1.32 (3 H, t) |
| 93 | $^1$H NMR (400 MHz, MeOD-d$_4$) δ ppm 7.91-7.82 (3 H, m), 7.52 (1 H, d), 7.38 (1 H, dd), 7.10 (2 H, t), 6.92 (1 H, s), 4.15 (2 H, t), 3.83 (2 H, d), 3.61 (3 H, s), 3.14-3.05 (2 H, m), 2.96-2.86 (2 H, m), 2.77-2.64 (3 H, m), 2.15-2.04 (2 H, m), 2.02 (3 H, s), 1.95-1.85 (2 H, m), 1.75 (2 H, dd), 1.31 (3 H, t) |
| 94 | $^1$H NMR (400 MHz, MeOD-d$_4$) δ ppm 7.96-7.81 (3 H, m), 7.53 (1 H, d), 7.41 (1 H, dd), 7.11 (2 H, t), 6.95 (1 H, s), 3.85 (2 H, d), 3.65 (2 H, t), 3.62 (3 H, s), 3.13-3.07 (2 H, m), 2.93 (2 H, bt), 2.82-2.68 (3 H, m), 2.03-1.87 (4 H, m), 1.85-1.70 (2 H, m), 1.32 (3 H, t) |
| 95 | $^1$H NMR (400 MHz, CDCl$_3$) δ ppm 7.89 (2 H, dd), 7.63 (1 H, s), 7.59 (1 H, d), 7.18 (1 H, dd), 7.13 (2 H, t), 4.00-3.92 (2 H, m), 3.80 (2 H, t), 3.52 (3 H, s), 3.12-3.06 (2 H, m), 2.93-2.84 (2 H, m), 2.75 (2 H, q), 2.71-2.60 (1 H, m), 2.14-2.03 (2 H, m), 2.00-1.89 (2 H, m), 1.88-1.74 (2 H, m), 1.36 (3 H, t) |
| 96 | $^1$H NMR (400 MHz, MeOD-d$_4$) δ ppm 8.05 (1 H, dd), 7.92 (1 H, s), 7.61 (1 H, dd), 7.56-7.47 (2 H, m), 7.43 (1 H, dd), 7.27 (1 H, s), 3.84 (2 H, d), 3.64 (3 H, s), 2.91-2.68 (8 H, m), 2.00-1.93 (2 H, m), 1.89-1.76 (2 H, m), 1.33 (3 H, t) |
| 97 | $^1$H NMR (300 MHz, CDCl$_3$) δ ppm 7.69-7.58 (3 H, m), 7.47 (1 H, dd), 7.38 (1 H, td), 7.20 (1 H, d), 3.97 (2 H, d), 3.53 (3 H, s), 2.89-2.61 (8 H, m), 2.24 (3 H, s), 2.07-1.94 (2 H, m), 1.93-1.77 (2 H, m), 1.38 (3 H, t) |
| 98 | $^1$H NMR (400 MHz, CDCl$_3$) δ ppm 7.71-7.62 (2 H, m), 7.58 (1 H, d), 7.15 (1 H, dd), 7.01-6.91 (2 H, m), 6.48 (1 H, s), 3.97 (2 H, d), 3.58 (3 H, s), 2.83 (3 H, s), 2.81-2.72 (4 H, m), 2.72-2.61 (1 H, m), 2.53 (3 H, s), 2.04-1.94 (2 H, m), 1.91-1.82 (2 H, m), 1.36 (3 H, t) |
| 99 | $^1$H NMR (400 MHz, CDCl$_3$) δ ppm 8.08 (1 H, dd), 7.63 (1 H, bs), 7.60 (1 H, d), 7.19 (2 H, ddd), 7.11 (1 H, m), 7.10-7.05 (1 H, m), 3.96 (2 H, d), 3.60 (3 H, s), 2.82 (3 H, s), 2.81-2.70 (4 H, m), 2.68-2.58 (1 H, m), 2.03-1.93 (2 H, m), 1.93-1.76 (2 H, m), 1.36 (3 H, t) |
| 100 | $^1$H NMR (400 MHz, CDCl$_3$) δ ppm 8.29-8.18 (1 H, m), 7.66-7.56 (2 H, m), 7.16 (1 H, dd), 7.03-6.95 (2 H, m), 6.89 (1 H, ddd), 3.95 (2 H, d), 3.62 (3 H, s), 2.82 (3 H, s), 2.82-2.71 (4 H, m), 2.66-2.57 (1 H, m), 2.01-1.94 (2 H, m), 1.88-1.81 (2 H, m), 1.35 (3 H, t) |
| 101 | $^1$H NMR (400 MHz, CDCl$_3$) δ ppm 7.71-7.61 (3 H, m), 7.57 (1 H, d), 7.18-7.05 (3 H, m), 3.96 (2 H, d), 3.54 (3 H, s), 2.88-2.71 (7 H, m), 2.69-2.56 (1 H, m), 2.32 (3 H, s), 2.04-1.93 (2 H, m), 1.92-1.77 (2 H, m), 1.36 (3 H, t) |
| 102 | $^1$H NMR (400 MHz, CDCl$_3$) δ ppm 7.87 (2 H, dd), 7.62 (1 H, s), 7.59 (1 H, d), 7.15 (1 H, dd), 7.11 (2 H, t), 6.68 (1 H, s), 3.95 (2 H, d), 2.82 (3 H, s), 2.80-2.70 (4 H, m), 2.68-2.55 (1 H, m), 2.03-1.91 (2 H, m), 1.91-1.76 (2 H, m), 1.35 (3 H, t) |
| 103 | $^1$H NMR (400 MHz, CDCl$_3$) δ ppm 7.89-7.76 (3 H, m), 7.66 (1 H, s), 7.28 (1 H, dd), 7.10 (2 H, t), 3.95 (2 H, d), 2.83-2.71 (7 H, m), 2.69-2.60 (1 H, m), 2.00-1.93 (2 H, m), 1.90-1.76 (2 H, m), 1.34 (3 H, t) |
| 104 | $^1$H NMR (400 MHz, CDCl$_3$) δ ppm 7.93-7.83 (2 H, m), 7.63-7.53 (2 H, m), 7.22-7.05 (3 H, m), 3.97 (2 H, bd), 3.67 (3 H, s), 3.60 (3 H, s), 2.83 (3 H, s), 2.82-2.72 (4 H, m), 2.70-2.59 (1 H, m), 2.04-1.93 (2 H, m), 1.92-1.78 (2 H, m), 1.37 (3 H, t) |
| 105 | $^1$H NMR (400 MHz, MeOD-d$_4$) δ ppm 7.96 (1 H, s), 7.69-7.60 (2 H, m), 7.55 (1 H, d), 7.44 (1 H, dd), 7.23 (2 H, t), 3.85 (2 H, d), 3.59 (3 H, s), 2.91-2.81 (5 H, m), 2.80-2.68 (3 H, m), 2.00 (3 H, s), 1.99-1.92 (2 H, m), 1.91-1.77 (2 H, m), 1.33 (3 H, t) |
| 106 | $^1$H NMR (400 MHz, CDCl$_3$) δ ppm 11.56 (1 H, bs), 8.43 (1 H, d), 7.66 (1 H, d), 7.61 (1 H, s), 7.55 (1 H, dd), 7.22 (1 H, d), 6.84-6.73 (2 H, m), 3.96 (2 H, d), 3.63 (3 H, s), 2.87-2.71 (7 H, m), 2.71-2.54 (1 H, m), 2.09 (3 H, s), 2.02-1.92 (2 H, m), 1.91-1.77 (2 H, m), 1.37 (3 H, t) |
| 107 | $^1$H NMR (300 MHz, CDCl$_3$) δ ppm 7.61 (2 H, dd), 7.53 (1 H, dd), 7.17 (2 H, td), 7.05 (1 H, td), 6.64 (1 H, s), 4.60 (2 H, d), 3.97 (2 H, d), 3.58 (3 H, s), 2.87-2.59 (8 H, m), 2.05-1.76 (4 H, m), 1.36 (3 H, t) |
| 108 | $^1$H NMR (400 MHz, MeOD-d$_4$) δ ppm 7.92-7.82 (3 H, m), 7.61 (1 H, dd), 7.51 (1 H, d), 7.10 (2 H, t), 6.94 (1 H, s), 6.20 (1 H, bs), 4.18 (2 H, q), 3.62 (3 H, s), 3.39 (2 H, s), 3.36-3.32 (2 H, m), 2.86 (2 H, bt), 2.72 (2 H, q), 2.61-2.49 (2 H, m), 1.31 (3 H, t), 1.26 (3 H, t) |
| 109 | $^1$H NMR (400 MHz, MeOD-d$_4$) δ ppm 7.88 (2 H, dd), 7.83 (1 H, s), 7.50 (1 H, dd), 7.39 (1 H, dd), 7.14-7.07 (2 H, m), 6.93 (1 H, s), 4.17 (2 H, q), 3.61 (3 H, s), 3.24 (2 H, s), 3.07-3.00 (2 H, m), 2.71 (2 H, q), 2.66-2.54 (1 H, m), 2.38-2.22 (2 H, m), 1.87-1.74 (4 H, m), 1.31 (3 H, t), 1.26 (3 H, t) |
| 110 | $^1$H NMR (400 MHz, CDCl$_3$) δ ppm 7.90-7.81 (2 H, m), 7.61 (1 H, bs), 7.55 (1 H, d), 7.20 (1 H, dd), 7.13-7.06 (2 H, m), 6.67 (1 H, s), 4.72-4.65 (1 H, m), 4.49-4.42 (1 H, m), 4.31-4.24 (1 H, m), 4.11 (1 H, dd), 3.90 (1 H, dd), 3.61 (3 H, s), 3.10-2.99 (4 H, m), 2.73 (2 H, q), 2.56-2.45 (1 H, m), 2.28-2.17 (2 H, m), 1.94-1.76 (4 H, m), 1.34 (3 H, t) |
| 111 | $^1$H NMR (400 MHz, CDCl$_3$) δ ppm 7.93-7.83 (2 H, m), 7.61 (1 H, s), 7.54 (1 H, d), 7.18 (1 H, d), 7.10 (2 H, t), 6.67 (1 H, s), 4.59-4.45 (1 H, m), 3.72-3.50 (7 H, m), 3.18 (1 H, d), 3.14 (1 H, s), 3.01-3.11 |

TABLE IV-continued

NMR data of the compounds of the invention.

| Cpd | NMR data (δ) |
|---|---|
|  | (2 H, m), 2.74 (2 H, q), 2.57-2.47 (1 H, m), 2.27-2.17 (2 H, m), 1.86-1.70 (6 H, m), 1.34 (3 H, t) |
| 112 | $^1$H NMR (400 MHz, CDCl$_3$) δ ppm 7.87 (2 H, dd), 7.61 (1 H, s), 7.54 (1 H, d), 7.18 (1 H, dt), 7.10 (2 H, t), 6.67 (1 H, s), 4.59-4.48 (1 H, m), 3.72-3.50 (7 H, m), 3.21-3.13 (2 H, m), 3.13-3.01 (2 H, m), 2.75 (2 H, q), 2.56-2.44 (1 H, m), 2.28-2.18 (2 H, m), 2.09-1.93 (2 H, m), 1.82 (4 H, m), 1.34 (3 H, t) |
| 113 | $^1$H NMR (300 MHz, CDCl$_3$) δ ppm 7.87 (2 H, dd), 7.61 (1 H, s), 7.55 (1 H, d), 7.18 (1 H, dd), 7.10 (2 H, t), 6.68 (1 H, s), 4.31 (1 H, t), 4.14-4.00 (2 H, m), 3.86-3.74 (3 H, m), 3.62 (3 H, s), 3.09-2.98 (4 H, m), 2.78 (3 H, m), 2.60-2.44 (1 H, m), 2.27-2.14 (2 H, m), 1.89-1.78 (4 H, m), 1.35 (3 H, t) |
| 114 | $^1$H NMR (300 MHz, CDCl$_3$) δ ppm 7.87 (2 H, dd), 7.61 (1 H, s), 7.54 (1 H, dd), 7.18 (1 H, dd), 7.10 (2 H, t), 6.67 (1 H, s), 3.61 (3 H, s), 3.19 (2 H, s), 3.12-2.99 (5 H, m), 2.95 (3 H, s), 2.74 (2 H, q), 2.57-2.42 (1 H, m), 2.29-2.11 (2 H, m), 1.87-1.74 (4 H, m), 1.34 (3 H, t) |
| 115 | $^1$H NMR (400 MHz, CDCl$_3$) δ ppm 7.91-7.83 (2 H, m), 7.61 (1 H, bs), 7.54 (1 H, d), 7.18 (1 H, dd), 7.10 (2 H, t), 6.67 (1 H, s), 3.61 (3 H, s), 3.49 (4 H, q), 3.15 (2 H, s), 3.07 (2 H, bd), 2.75 (2 H, q), 2.55-2.44 (1 H, m), 2.28-2.17 (2 H, m), 1.94 (2 H, q), 1.89-1.77 (6 H, m), 1.34 (3 H, t) |
| 116 | $^1$H NMR (400 MHz, CDCl$_3$) δ ppm 7.87 (2 H, dd), 7.61 (1 H, s), 7.55 (1 H, d), 7.22-7.15 (1 H, m), 7.11 (2 H, t), 6.68 (1 H, s), 3.93 (1 H, d), 3.84-3.66 (3 H, m), 3.62 (3 H, s), 3.22-3.08 (3 H, m), 3.08-2.94 (2 H, m), 2.75 (2 H, q), 2.57-2.44 (1 H, m), 2.34 (1 H, q), 2.31-2.12 (3 H, m), 1.89-1.76 (4 H, m), 1.35 (3 H, t) |
| 117 | $^1$H NMR (400 MHz, CDCl$_3$) δ ppm 7.91-7.88 (2 H, m), 7.64 (1 H, bs), 7.57 (1 H, d), 7.23-7.20 (1 H, m), 7.13 (2 H, t), 6.70 (1 H, s), 3.73-3.61 (7 H, m), 3.57-3.40 (2 H, m), 3.31-3.08 (4 H, m), 2.78 (2 H, q), 2.57-2.34 (2 H, m), 2.29-2.17 (2 H, m), 1.91-2.04 (1 H, m), 1.90-1.80 (4 H, m), 1.72-1.62 (1 H, m), 1.37 (3H, t) |
| 118 | $^1$H NMR (400 MHz, CDCl$_3$) δ ppm 7.86 (2 H, dd), 7.60 (1 H, s), 7.54 (1 H, d), 7.17 (1 H, dd), 7.09 (2 H, t), 6.67 (1 H, s), 4.85-4.77 (1 H, m), 4.52 (1 H, t), 4.23 (1 H, dd), 3.61 (3 H, s), 3.00 (2 H, t), 2.78-2.67 (4 H, m), 2.53-2.43 (1 H, m), 2.36-2.19 (2 H, m), 1.87-1.79 (2 H, m), 1.79-1.66 (2 H, m), 1.33 (3 H, t) |
| 119 | $^1$H NMR (400 MHz, CDCl$_3$) δ ppm 7.87 (2 H, dd), 7.62 (1 H, s), 7.55 (1 H, d), 7.19 (1 H, d), 7.10 (2 H, t), 6.67 (1 H, s), 3.82-3.73 (2 H, m), 3.61 (3 H, s), 3.58-3.51 (2 H, m), 3.25 (2 H, s), 3.18-3.05 (2 H, m), 2.98 (3 H, s), 2.74 (2 H, q), 2.60-2.49 (1 H, m), 2.34-2.21 (2 H, m), 1.87-1.79 (2 H, m), 1.79-1.66 (2 H, m), 1.34 (3 H, t) |
| 120 | $^1$H NMR (400 MHz, CDCl$_3$) δ ppm 7.87 (2 H, dd), 7.61 (1 H, s), 7.54 (1 H, d), 7.19 (1 H, dd), 7.10 (2 H, t), 6.67 (1 H, s), 3.71 (3 H, s), 3.61 (3 H, s), 3.35 (2 H, s), 3.19 (3 H, s), 3.11 (2 H, bd), 2.75 (2 H, q), 2.56-2.44 (1 H, m), 2.32-2.19 (2 H, m), 1.80-1.72 (4 H, m), 1.34 (3 H, t) |
| 121 | $^1$H NMR (400 MHz, CDCl$_3$) δ ppm (2 conformers) 7.87 (2 H, dd), 7.62 (1 H, s), 7.55 (1 H, d), 7.23-7.15 (1 H, m), 7.11 (2 H, t), 6.68 (1 H, s), 4.62 (0.7 H, s), 4.35 (1.3 H, s), 3.62 (3 H, s), 3.31-3.20 (4 H, m), 3.06 (1 H, s), 3.04-2.87 (2 H, m), 2.75 (2 H, q), 2.57-2.45 (1 H, m), 2.30-2.14 (2 H, m), 1.93-1.74 (4 H, m), 1.35 (3 H, t) |
| 122 | $^1$H NMR (300 MHz, CDCl$_3$) δ ppm 7.85 (2 H, dd), 7.66-7.48 (2 H, m), 7.22-6.99 (3 H, m), 6.66 (1 H, s), 6.11 (1 H, s)NH, 4.84-4.69 (1 H, m), 3.73-3.52 (4 H, m), 3.42-3.26 (1 H, m), 3.09 (1 H, d), 2.96 (1 H, d), 2.80-2.66 (3 H, m), 2.65-2.57 (1 H, m), 2.56-2.40 (1 H, m), 2.34-2.08 (2 H, m), 1.93-1.64 (4 H, m), 1.32 (3 H, t) |
| 123 | $^1$H NMR (400 MHz, CDCl$_3$) δ ppm 7.90-7.82 (2 H, m), 7.62 (1 H, s), 7.57 (1 H, d), 7.18 (1 H, dd), 7.15-7.06 (2 H, m), 6.68 (1 H, s), 3.66-3.57 (5 H, m), 3.47 (2 H, q), 3.07 (2 H, s), 2.99-2.90 (3 H, m), 2.81-2.68 (3 H, m), 2.57-2.48 (1 H, m), 2.30 (2 H, t), 1.93-1.82 (2 H, m), 1.78-1.66 (2 H, m), 1.39-1.29 (5 H, m) |
| 124 | $^1$H NMR (400 MHz, CDCl$_3$) δ ppm 7.87-7.84 (2 H, m), 7.60 (1 H, bs), 7.54 (1 H, d), 7.16 (1 H, dd), 7.09 (2 H, t), 6.66 (1 H, s), 4.58 (2 H, t), 4.33 (2 H, t), 3.60 (3 H, s), 3.12 (2 H, s), 2.97 (2 H, bd), 2.74 (2 H, q), 2.53-2.45 (1 H, m), 2.17 (2 H, bt), 1.85-1.69 (4 H, m), 1.32 (3 H, t) |
| 125 | $^1$H NMR (400 MHz, CDCl$_3$) δ ppm 7.90-7.84 (2 H, m), 7.62 (1 H, s), 7.56 (1 H, d), 7.17 (1 H, dd), 7.14-7.07 (2 H, m), 7.06-7.02 (1 H, bs)NH, 6.68 (1 H, s), 5.44-5.34 (1 H, bs)NH, 3.63 (3 H, s), 3.06-2.96 (4 H, m), 2.76 (2 H, q), 2.57-2.47 (1 H, m), 2.28 (2 H, bt), 1.92-1.84 (2 H, m), 1.81-1.69 (2 H, m), 1.35 (3 H, t) |
| 126 | $^1$H NMR (400 MHz, CDCl$_3$) δ ppm 7.87 (2 H, dd), 7.64-7.52 (2 H, m), 7.17-7.05 (3 H, m), 6.68 (1 H, s), 4.76 (1 H, d), 4.21 (1 H, d), 3.62 (3 H, s), 3.50-3.25 (2 H, m), 3.08 (1 H, t), 2.82-2.69 (3 H, m), 2.69-2.51 (5 H, m), 1.90 (2 H, d), 1.85-1.73 (4 H, m), 1.60 (2 H, quin), 1.35 (3 H, t) |
| 127 | $^1$H NMR (400 MHz, CDCl$_3$) δ ppm 7.90-7.82 (2 H, m), 7.60 (1 H, s), 7.56 (1 H, d), 7.18-7.05 (3 H, m), 6.67 (1 H, s), 4.78 (1 H, d), 3.88 (1 H, d), 3.62 (3 H, s), 3.43 (2 H, d), 3.09 (1 H, bt), 2.82-2.71 (3 H, m), 2.66 (1 H, bt), 2.46 (3 H, s), 1.91 (2 H, d), 1.71-1.54 (2 H, m), 1.34 (3 H, t) |
| 128 | $^1$H NMR (400 MHz, CDCl$_3$) δ ppm 7.93-7.78 (2 H, m), 7.67-7.51 (2 H, m), 7.20-7.03 (3 H, m), 6.68 (1 H, s), 4.72 (1 H, d), 4.55-4.36 (1 H, m), 3.94 (1 H, d), 3.85-3.70 (2 H, m), 3.62 (3 H, s), 3.49-3.28 (2 H, m), 3.22-3.00 (2 H, m), 2.85-2.68 (3 H, m), 2.67-2.25 (2 H, m), 1.89 (2 H, d), 1.76-1.46 (2 H, m), 1.34 (3 H, t) |
| 129 | $^1$H NMR (300 MHz, CDCl$_3$) δ ppm 7.85 (2 H, dd), 7.64-7.50 (2 H, m), 7.17-7.02 (3 H, m), 6.67 (1 H, s), 4.74 (1 H, d), 4.23 (1 H, d), 3.61 (3 H, s), 3.22-2.98 (3 H, m), 2.82-2.69 (3 H, m), 2.60 (1 H, t), 2.29 (6 H, s), 1.89 (2 H, d), 1.73-1.45 (2 H, m), 1.33 (3 H, t) |
| 130 | $^1$H NMR (400 MHz, CDCl$_3$) δ ppm 7.86 (2 H, dd), 7.60 (1 H, s), 7.55 (1 H, d), 7.17-7.04 (3 H, m), 6.67 (1 H, s), 4.82-4.72 (1 H, m), |

TABLE IV-continued

NMR data of the compounds of the invention.

| Cpd | NMR data (δ) |
|---|---|
| | 3.99 (1 H, d), 3.61 (3 H, s), 3.12 (1 H, t), 2.84-2.68 (5 H, m), 2.67-2.56 (3 H, m), 2.36 (6 H, s), 1.90 (2 H, t), 1.68-1.51 (2 H, m), 1.33 (3 H, t) |
| 131 | ¹H NMR (400 MHz, CDCl₃) δ ppm 7.86 (2 H, dd), 7.62-7.55 (2 H, m), 7.15-7.05 (3 H, m), 6.68 (1 H, s), 4.72 (1 H, d), 3.92 (1 H, d), 3.74 (4 H, t), 3.62 (3 H, s), 3.47 (2 H, q), 3.10 (1 H, bt), 2.75 (3 H, q), 2.62 (1 H, bt), 1.91 (2 H, d), 1.70-1.51 (2 H, m), 1.34 (3 H, t) |
| 132 | ¹H NMR (400 MHz, CDCl₃) δ ppm 7.85 (2 H, dd), 7.60 (1 H, s), 7.55 (1 H, d), 7.17-7.02 (3 H, m), 6.67 (1 H, s), 4.76 (1 H, d), 3.96 (1 H, d), 3.61 (3 H, s), 3.24 (1 H, bs)NH, 3.11 (1 H, t), 2.92 (2 H, t), 2.80-2.71 (3 H, m), 2.69-2.61 (3 H, m), 2.49 (3 H, s), 1.96-1.82 (2 H, m), 1.69-1.50 (2 H, m), 1.33 (3 H, t) |
| 133 | ¹H NMR (400 MHz, CDCl₃) δ ppm 7.90-7.82 (2 H, m), 7.62-7.56 (2 H, m), 7.17-7.06 (3 H, m), 6.68 (1 H, s), 5.24 (0.5 H, quin), 5.09 (0.5 H, quin), 4.73 (1 H, d), 4.01-3.76 (3 H, m), 3.62 (3 H, s), 3.42 (2 H, q), 3.33 (1 H, dd), 3.27 (1 H, dd), 3.10 (1 H, t), 2.82-2.69 (3 H, m), 2.61 (1 H, t), 1.90 (2 H, d), 1.74-1.50 (2 H, m), 1.35 (3 H, t) |
| 134 | ¹H NMR (400 MHz, CDCl₃) δ ppm 7.85 (2 H, dd), 7.65-7.58 (2 H, m), 7.23 (1 H, d), 7.10 (2 H, t), 6.68 (1 H, s), 4.13 (1 H, t), 4.07-3.96 (2 H, m), 3.87 (1 H, dd), 3.61 (3 H, s), 3.20-3.10 (1 H, m), 3.01-2.88 (2 H, m), 2.76 (2 H, q), 2.63-2.51 (1 H, m), 2.04-1.84 (7 H, m), 1.77 (2 H, t), 1.35 (3 H, t) |
| 135 | ¹H NMR (400 MHz, CDCl₃) δ ppm 8.50-8.43 (1 H, m), 7.93-7.87 (2 H, m), 7.85 (1 H, s), 7.83-7.76 (1 H, m), 7.12 (2 H, t), 4.00 (2 H, bd), 3.61 (3 H, s), 2.99 (2 H, q), 2.88-2.78 (6 H, m), 2.09-1.99 (2 H, m), 1.93-1.79 (2 H, m), 1.54 (3 H, t) |
| 136 | ¹H NMR (300 MHz, CDCl₃) δ ppm 8.23-8.12 (2 H, m), 7.68-7.53 (2 H, m), 7.25-7.13 (3 H, m), 3.98 (2 H, d), 3.65 (3 H, s), 2.89-2.70 (8 H, m), 2.10-1.94 (2 H, m), 1.94-1.77 (2 H, m), 1.38 (3 H, t) |
| 137 | ¹H NMR (400 MHz, DMSO-d₆) δ ppm 8.10 (1 H, s), 7.75 (2 H, t), 7.54 (1 H, d), 7.36 (1 H, d), 7.25 (2 H, t), 3.68 (2 H, d), 3.50 (3 H, s), 3.30 (2 H, s)NH2, 2.89 (3 H, s), 2.82-2.71 (3 H, m), 2.63 (2 H, q), 1.92-1.83 (2 H, m), 1.81-1.71 (2 H, m), 1.25 (3 H, t) |
| 138 | ¹H NMR (400 MHz, MeOD-d₄) δ ppm 8.16 (2 H, dd), 7.58-7.36 (3 H, m), 7.26 (2 H, t), 4.61-4.53 (1 H, m), 4.54-4.42 (1 H, m), 4.21 (1 H, dd), 4.05 (1 H, dd), 3.77 (1 H, dd), 3.66 (3 H, s), 3.20-3.09 (6 H, m), 2.76-2.62 (6 H, m), 1.33 (3 H, t) |
| 139 | ¹H NMR (400 MHz, MeOD-d₄) δ ppm 8.16 (2 H, dd), 7.51-7.38 (3 H, m), 7.26 (2 H, t), 4.37-4.28 (1 H, m), 4.09-3.99 (2 H, m), 3.81-3.72 (1 H, m), 3.70-3.63 (5 H, m), 3.15 (4 H, d), 3.11 (2 H, s), 2.83-2.64 (7 H, m), 1.33 (3 H, t) |
| 140 | ¹H NMR (300 MHz, CDCl₃) δ ppm 8.22-8.10 (2 H, m), 7.52 (1 H, d), 7.23-7.14 (3 H, m), 7.10 (1 H, d), 3.62 (3 H, s), 3.24 (2 H, d), 3.16-3.06 (7 H, m), 2.95 (3 H, s), 2.79-2.65 (6 H, m), 1.35 (3 H, t) |
| 141 | ¹H NMR (400 MHz, CDCl₃) δ ppm 8.22-8.12 (2 H, m), 7.63-7.54 (2 H, m), 7.24 (1 H, dd), 7.19 (2 H, t), 4.74-4.66 (1 H, m), 4.49-4.42 (1 H, m), 4.29 (1 H, dd), 4.11 (1 H, dd), 3.90 (1 H, dd), 3.64 (3 H, s), 3.08-2.99 (4 H, m), 2.75 (2 H, q), 2.57-2.47 (1 H, m), 2.23-2.14 (2 H, m), 1.89-1.77 (4 H, m), 1.36 (3 H, t) |
| 142 | ¹H NMR (400 MHz, CDCl₃) δ ppm 8.19-8.11 (2 H, m), 7.59-7.52 (2 H, m), 7.24 (1 H, d), 7.21-7.13 (2 H, m), 4.51 (1 H, dd), 3.71-3.57 (5 H, m), 3.56-3.46 (1 H, m), 3.19-3.00 (4 H, m), 2.73 (2 H, q), 2.57-2.46 (1 H, m), 2.28-2.08 (4 H, m), 2.09-1.94 (1 H, m), 1.87-1.76 (4 H, m), 1.34 (3 H, t) |
| 142 | ¹H NMR (400 MHz, MeOD-d₄) δ ppm 7.89 (2 H, dd), 7.48-7.42 (1 H, m), 7.40-7.28 (2 H, m), 7.11 (2 H, t), 6.94 (1 H, s), 4.66 (2 H, t), 4.33 (2 H, t), 3.61 (3 H, s), 3.19 (2 H, s), 3.17-3.03 (4 H, m), 2.74-2.61 (6 H, m), 1.30 (3 H, t) |
| 143 | ¹H NMR (400 MHz, MeOD-d₄) δ ppm 8.15 (2 H, dd), 7.95 (1 H, s), 7.52 (2 H, dd), 7.25 (2 H, t), 4.39 (1 H, d), 3.67-3.58 (4 H, m), 3.57-3.41 (3 H, m), 3.23-3.14 (2 H, m), 3.11-3.00 (2 H, m), 2.74 (2 H, q), 2.67-2.57 (1 H, m), 2.29-2.17 (2 H, m), 2.06-1.91 (2 H, m), 1.89-1.76 (4 H, m), 1.34 (3 H, t) |
| 144 | ¹H NMR (400 MHz, CDCl₃) δ ppm 8.22-8.12 (2 H, m), 7.64-7.53 (2 H, m), 7.27-7.23 (1 H, m), 7.19 (2 H, t), 4.33-4.26 (1 H, m), 4.13-4.04 (2 H, m), 3.86-3.77 (3 H, m), 3.64 (3 H, s), 3.16-3.07 (4 H, m), 2.87-2.80 (1 H, m), 2.75 (2 H, q), 2.64-2.55 (1 H, m), 2.47-2.34 (2 H, m), 1.90-1.84 (4 H, m), 1.37 (3 H, t) |
| 145 | ¹H NMR (400 MHz, CDCl₃) δ ppm 8.21-8.12 (2 H, m), 7.63-7.50 (2 H, m), 7.24 (1 H, dd), 7.18 (2 H, t), 3.63 (3 H, s), 3.23 (2 H, s), 3.11-3.03 (5 H, m), 2.95 (3 H, s), 2.75 (2 H, q), 2.60-2.49 (1 H, m), 2.34-2.22 (2 H, m), 1.90-1.80 (4 H, m), 1.36 (3 H, t) |
| 146 | ¹H NMR (400 MHz, MeOD-d₄) δ ppm 7.70 (2 H, dd), 7.47-7.41 (1 H, m), 7.40-7.30 (2 H, m), 7.17 (2 H, t), 4.56 (2 H, s), 4.32 (1 H, t), 4.09-3.98 (2 H, m), 3.76 (1 H, dd), 3.67 (2 H, d), 3.55 (3 H, s), 3.18-3.05 (6 H, m), 2.83-2.74 (1 H, m), 2.74-2.62 (6 H, m), 1.32 (3 H, t) |
| 147 | ¹H NMR (400 MHz, CDCl₃) δ ppm 7.78-7.71 (2 H, m), 7.63 (1 H, s), 7.59 (1 H, d), 7.21-7.10 (3 H, m), 4.69 (2 H, s), 3.96 (2 H, d), 3.57 (3 H, s), 2.83 (3 H, s), 2.81-2.70 (4 H, m), 2.69-2.59 (1 H, m), 2.03-1.94 (2 H, m), 1.91-1.77 (2 H, m), 1.34 (3 H, t) |
| 148 | ¹H NMR (300 MHz, CDCl₃) δ ppm 7.85-7.75 (2 H, m), 7.68-7.58 (2 H, m), 7.30 (2 H, dd), 7.20 (1 H, dd), 4.71 (2 H, s), 3.97 (2 H, d), 3.57 (3 H, s), 2.83 (3 H, s), 2.76 (4 H, m), 2.71-2.57 (1 H, m), 1.99 (2 H, d), 1.85 (2 H, bq), 1.35 (3 H, t) |
| 149 | ¹H NMR (300 MHz, CDCl₃) δ ppm 7.80-7.71 (2 H, m), 7.61 (1 H, bs), 7.54 (1 H, d), 7.19-7.09 (3 H, m), 4.68 (2 H, s), 3.93 (2 H, d), 3.56 (3 H, s), 3.06-2.97 (2 H, m), 2.94-2.81 (2 H, m), 2.77-2.58 (3 H, m), 2.44 (2 H, t), 2.25 (6 H, s), 2.08-1.98 (4 H, m), 1.89-1.71 (2 H, m), 1.32 (3 H, t) |
| 150 | ¹H NMR (300 MHz, CDCl₃) δ ppm 7.91 (2 H, d), 7.71 (2 H, d), 7.63 |

TABLE IV-continued

NMR data of the compounds of the invention.

| Cpd | NMR data (δ) |
|---|---|
|  | (1 H, s), 7.55 (1 H, d), 7.16 (1 H, dd), 4.72 (2 H, s), 3.95 (2 H, d), 3.57 (3 H, s), 2.88-2.56 (8 H, m), 2.04-1.74 (4 H, m), 1.30 (3 H, t) |
| 151 | $^1$H NMR (400 MHz, CDCl$_3$) δ ppm 7.76 (2 H, dd), 7.60 (1 H, s), 7.47 (1 H, d), 7.19-7.08 (3 H, m), 4.66 (2 H, s), 3.53 (3 H, s), 3.46 (4 H, q), 3.13 (2 H, s), 3.04 (2 H, bd), 2.71-2.60 (2 H, m), 2.54-2.44 (1 H, m), 2.27-2.14 (2 H, m), 1.99-1.89 (2 H, m), 1.88-1.75 (6 H, m), 1.28 (3 H, t) |
| 152 | $^1$H NMR (400 MHz, CDCl$_3$) δ ppm 7.74 (2 H, dd), 7.60 (1 H, s), 7.48 (1 H, d), 7.19-7.08 (3 H, m), 4.66 (2 H, s), 4.29-4.21 (1 H, m), 4.03 (2 H, bt), 3.81-3.72 (3 H, m), 3.54 (3 H, s), 3.07-2.96 (4 H, m), 2.84-2.73 (1 H, m), 2.68 (2 H, q), 2.56-2.43 (1 H, m), 2.28-2.13 (2 H, m), 1.80 (4 H, bs.), 1.29 (3 H, t) |
| 153 | $^1$H NMR (400 MHz, CDCl$_3$) δ ppm 7.79-7.72 (2 H, m), 7.60 (1 H, s), 7.53 (1 H, d), 7.19-7.08 (3 H, m), 4.75 (1 H, d), 4.68 (2 H, s), 4.25 (1 H, d), 3.56 (3 H, s), 3.24-3.03 (3 H, m), 2.81-2.58 (4 H, m), 2.32 (6 H, s), 1.91 (2 H, d), 1.71-1.52 (2 H, m), 1.33 (3 H, t) |
| 154 | $^1$H NMR (300 MHz, CDCl$_3$) δ ppm 7.76 (2 H, dd), 7.60 (1 H, s), 7.53 (1 H, d), 7.18-7.10 (3 H, m), 4.81 (1 H, d), 4.68 (2 H, s), 3.99 (1 H, d), 3.56 (3 H, s), 3.12 (1 H, t), 2.82-2.54 (4 H, m), 2.38 (2 H, q), 1.99-1.83 (2 H, m), 1.80-1.50 (2 H, m), 1.32 (3 H, t), 1.17 (3 H, t) |
| 155 | $^1$H NMR (400 MHz, MeOD-d$_4$) δ ppm 7.78-7.64 (2 H, m), 7.43 (1 H, d), 7.40-7.32 (2 H, m), 7.17 (2 H, t), 4.56 (2 H, s), 3.55 (3 H, s), 3.28 (2 H, s), 3.18-3.10 (4 H, m), 3.09 (3 H, s), 2.93 (3 H, s), 2.74-2.65 (6 H, m), 1.31 (3 H, t) |
| 156 | $^1$H NMR (400 MHz, CDCl$_3$) δ ppm 7.74 (2 H, dd), 7.60 (1 H, s), 7.52 (1 H, d), 7.21-7.09 (3 H, m), 4.73-4.65 (3 H, m), 4.50-4.43 (1 H, m), 4.27 (1 H, dd), 4.10 (1 H, dd), 3.89 (1 H, dd), 3.56 (3 H, s), 3.05 (2 H, d), 3.01 (2 H, d), 2.74 (2 H, q), 2.55-2.46 (1 H, m), 2.25-2.14 (2 H, m), 1.89-1.80 (2 H, m), 1.74-1.56 (2 H, m), 1.34 (3 H, t) |
| 157 | $^1$H NMR (400 MHz, CDCl$_3$) δ ppm 7.75 (2 H, dd), 7.61 (1 H, s), 7.53 (1 H, d), 7.22-7.11 (3 H, m), 4.67 (2 H, s), 3.56 (3 H, s), 3.21 (2 H, s), 3.09 (3 H, s), 3.08-3.00 (2 H, m), 2.96 (3 H, s), 2.74 (2 H, q), 2.58-2.46 (1 H, m), 2.27-2.17 (2 H, m), 1.89-1.79 (4 H, m), 1.35 (3 H, t) |
| 158 | $^1$H NMR (400 MHz, CDCl$_3$) δ ppm 7.79 (2 H, dd), 7.58 (1 H, d), 7.22 (1 H, dd), 7.17-7.11 (3 H, m), 3.63 (3 H, s), 3.30 (2 H, d), 3.19-3.11 (4 H, m), 3.07 (3 H, s), 2.95 (3 H, s), 2.85-2.71 (6 H, m), 1.36 (3 H, t) |
| 159 | $^1$H NMR (400 MHz, CDCl$_3$) δ ppm 7.86-7.73 (2 H, m), 7.67-7.53 (2 H, m), 7.26-7.24 (1 H, m), 7.15 (2 H, t), 4.73-4.65 (1 H, m), 4.49-4.40 (1 H, m), 4.29 (1 H, dd), 4.11 (1 H, dd), 3.92 (1 H, dd), 3.64 (3 H, s), 3.13 (4 H, bs), 2.82-2.71 (2 H, m), 2.62-2.51 (1 H, m), 2.39-2.24 (2 H, m), 1.88 (4 H, bs), 1.38 (3 H, t) |
| 160 | $^1$H NMR (300 MHz, CDCl$_3$) δ ppm 7.84-7.75 (2 H, m), 7.67-7.57 (2 H, m), 7.23 (1 H, dd), 7.15 (2 H, t), 4.03-3.93 (2 H, m), 3.65 (3 H, s), 2.85-2.72 (7 H, m), 2.73-2.59 (1 H, m), 2.07-1.95 (2 H, m), 1.88 (2 H, qd), 1.38 (3 H, t) |
| 161 | $^1$H NMR (400 MHz, CDCl$_3$) δ ppm 7.63-7.59 (1 H, m), 7.51-7.44 (2 H, m), 7.40-7.33 (1 H, m), 7.21 (1 H, d), 7.11 (1 H, dd), 3.51 (3 H, s), 3.13 (8 H, bs), 2.75 (2 H, q), 2.22 (3 H, s), 1.35 (3 H, t) |
| 162 | $^1$H NMR (300 MHz, CDCl$_3$) δ ppm 7.62 (1 H, dd), 7.54 (1 H, d), 7.46 (1 H, dd), 7.42-7.33 (1 H, m), 7.19 (2 H, s), 4.68 (1 H, bs), 4.52-4.41 (1 H, m), 4.29 (1 H, dd), 4.13 (1 H, dd), 3.91 (1 H, dd), 3.52 (3 H, s), 3.17-3.02 (6 H, m), 2.82-2.64 (6 H, m), 2.24 (3 H, s), 1.37 (3 H, t) |
| 163 | $^1$H NMR (300 MHz, CDCl$_3$) δ ppm 7.61 (2 H, dd), 7.47 (1 H, dd), 7.33-7.43 (1 H, m), 7.05-7.24 (2 H, m), 3.53 (3 H, s), 3.04-3.18 (6 H, m), 2.86 (3 H, d), 2.64-2.83 (6 H, m), 2.24 (3 H, s), 1.39 (3 H, t) |
| 164 | $^1$H NMR (300 MHz, CDCl$_3$) δ ppm 8.05 (1 H, d), 7.62 (1 H, d), 7.45 (1 H, dd), 7.38 (1 H, m), 7.16-7.25 (3 H, m), 5.36-5.45 (0.5 H, m), 5.18-5.25 (0.5 H, m), 4.45-4.61 (1 H, m), 4.24-4.44 (2 H, m), 4.05-4.23 (1 H, m), 3.62 (3 H, s), 3.05-3.17 (6 H, m), 2.64-2.82 (6 H, m), 1.37 (3 H, t) |
| 165 | $^1$H NMR (300 MHz, CDCl$_3$) δ ppm 8.04 (1 H, dd), 7.65 (1 H, d), 7.45 (1 H, dd), 7.37 (1 H, ddd), 7.26-7.16 (3 H, m), 4.58 (2 H, t), 4.36 (2 H, t), 3.62 (3 H, s), 3.19 (2 H, s), 3.16-3.07 (4 H, m), 2.78 (2 H, q), 2.72-2.63 (4 H, m), 1.38 (3 H, t) |
| 166 | $^1$H NMR (300 MHz, CDCl$_3$) δ ppm 8.07 (1 H, dd), 7.57-7.32 (3 H, m), 7.22-7.09 (3 H, m), 4.77-4.62 (1 H, m), 4.46 (1 H, t), 4.28 (1 H, dd), 4.11 (1 H, dd), 3.90 (1 H, dd), 3.61 (3 H, s), 3.18-3.03 (6 H, m), 2.82-2.61 (6 H, m), 1.34 (3 H, t) |
| 167 | $^1$H NMR (400 MHz, CDCl$_3$) δ ppm 8.06 (1 H, dd), 7.62 (1 H, d), 7.45 (1 H, dd), 7.41-7.34 (1 H, m), 7.25-7.16 (3 H, m), 4.24 (2 H, t), 4.06 (2 H, t), 3.61 (3 H, s), 3.18-3.05 (6 H, m), 2.81-2.67 (6 H, m), 2.29 (2 H, quin), 1.37 (3 H, t) |
| 168 | $^1$H NMR (400 MHz, CDCl$_3$) δ ppm 8.07 (1 H, dd), 7.59 (1 H, d), 7.44 (1 H, dd), 7.37 (1 H, dd), 7.24-7.15 (3 H, m), 3.61 (3 H, s), 3.26 (2 H, s), 3.18-3.03 (7 H, m), 2.95 (3 H, s), 2.81-2.68 (6 H, m), 1.35 (3 H, t) |
| 169 | $^1$H NMR (300 MHz, CDCl$_3$) δ ppm 8.03 (1 H, dd), 7.68 (1 H, d), 7.45 (1 H, dd), 7.38 (1 H, dd), 7.22-7.17 (2 H, m), 7.11-7.01 (1 H, m), 3.62 (3 H, s), 3.17-3.07 (6 H, m), 2.85 (3 H, d), 2.79 (2 H, q), 2.76-2.68 (4 H, m), 1.38 (3 H, t) |
| 170 | $^1$H NMR (400 MHz, CDCl$_3$) δ ppm 8.09 (1 H, dd), 7.61 (1 H, s), 7.54 (1 H, d), 7.45 (1 H, dd), 7.41-7.34 (1 H, m), 7.23-7.16 (2 H, m), 4.74-4.65 (1 H, m), 4.51-4.41 (1 H, m), 4.36-4.23 (1 H, m), 4.19-4.07 (1 H, m), 3.98-3.83 (1 H, m), 3.62 (3 H, s), 3.10-2.96 (4 H, m), 2.76 (2 H, q), 2.60-2.44 (1 H, m), 2.27-2.15 (2 H, m), 1.84 (4 H, bs), 1.35 (3 H, t) |
| 171 | $^1$H NMR (300 MHz, MeOD-d$_4$) δ ppm 8.10-8.01 (1 H, m), 7.90 (1 |

TABLE IV-continued

NMR data of the compounds of the invention.

| Cpd | NMR data (δ) |
|---|---|
| | H, s), 7.63 (1 H, dd), 7.56-7.46 (2 H, m), 7.42 (1 H, dd), 7.30 (1 H, s), 3.64 (3 H, s), 3.26 (2 H, s), 3.10 (3 H, s), 3.09-2.99 (2 H, m), 2.94 (3 H, s), 2.74 (2 H, q), 2.68-2.57 (1 H, m), 2.30-2.18 (2 H, m), 1.90-1.79 (4 H, m), 1.33 (3 H, t) |
| 172 | $^1$H NMR (400 MHz, MeOD-d$_4$) δ ppm 7.86 (1 H, s), 7.70-7.64 (2 H, m), 7.56-7.48 (2 H, m), 7.43-7.38 (1 H, m), 4.62-4.55 (1 H, m), 4.54-4.47 (1 H, m), 4.22 (1 H, dd), 4.07 (1 H, ddd), 3.78 (1 H, dd), 3.53 (3 H, s), 3.10 (2 H, s), 3.02 (2 H, bd), 2.74 (2 H, q), 2.69-2.58 (1 H, m), 2.28-2.19 (5 H, m), 1.90-1.79 (4 H, m), 1.34 (3 H, t) |
| 173 | $^1$H NMR (400 MHz, CDCl$_3$) δ ppm 8.36 (1 H, dd), 7.62-7.55 (2 H, m), 7.52 (1 H, dd), 7.43-7.35 (1 H, m), 7.23 (1 H, dd), 4.73-4.64 (1 H, m), 4.51-4.42 (1 H, m), 4.29 (1 H, dd), 4.12 (1 H, dd), 3.90 (1 H, dd), 3.71 (3 H, s), 3.11-3.01 (4 H, m), 2.75 (2 H, q), 2.58-2.48 (1 H, m), 2.29-2.18 (2 H, m), 1.92-1.78 (4 H, m), 1.35 (3 H, t) |
| 174 | $^1$H NMR (400 MHz, DMSO) δ ppm 8.04 (1 H, s), 7.96-7.90 (2 H, m), 7.61-7.55 (1 H, m), 7.37 (1 H, dd), 7.28-7.20 (3 H, m), 3.58 (3 H, s), 3.14 (2 H, s), 3.01 (3 H, s), 2.91 (6 H, bs), 2.79 (3 H, s), 2.60-2.54 (1 H, m), 2.12-2.05 (2 H, m), 1.73-1.62 (4 H, m) |
| 175 | $^1$H NMR (400 MHz, CDCl$_3$) δ ppm 7.71 (2 H, dd), 7.64 (1 H, s), 7.56 (1 H, d), 7.21 (1 H, dd), 7.14 (2 H, t), 4.68 (2 H, bd), 3.96 (2 H, bd), 3.09-3.05 (2 H, m), 2.98-2.91 (1 H, m), 2.89-2.73 (6H, m), 2.68-2.61 (1 H, m), 2.28-2.16 (1 H, bs), 2.01-1.95 (2 H, m), 1.91-1.78 (2 H, m) |
| 176 | $^1$H NMR (400 MHz, DMSO-d) δ ppm 7.99 (1 H, s), 7.96-7.91 (2 H, m), 7.50 (1 H, d), 7.36 (1 H, bs)NH, 7.32 (1 H, d), 7.27-7.21 (3 H, m), 6.78 (1 H, bs)NH, 3.55 (3 H, s), 3.10 (2 H, s), 3.01 (3 H, s), 2.90 (2 H, d), 2.87-2.65 (5 H, m), 2.60-2.42 (3 H, m), 2.12-2.04 (2 H, m), 1.75-1.60 (4H, m) |
| 177 | $^1$H NMR (300 MHz, CDCl$_3$) δ ppm 7.92-7.83 (2 H, m), 7.48 (1 H, d), 7.15-7.04 (2 H, m), 6.86 (1 H, d), 6.73 (1 H, dd), 6.68 (1 H, s), 4.12 (2 H, t), 4.01-3.90 (1 H, m), 3.60 (3 H, s), 3.41 (2 H, q), 2.72 (2 H, q), 1.78 (2 H, bs)NH2, 1.34 (3 H, t) |
| 178 | $^1$H NMR (400 MHz, CDCl$_3$) δ ppm 7.86 (2 H, dd), 7.45 (1 H, d), 7.10 (2 H, t), 6.85 (1 H, d), 6.73 (1 H, dd), 6.67 (1 H, s), 4.76-4.64 (1 H, m), 4.33-4.21 (2 H, m), 4.03 (2 H, bt), 3.98 (1 H, dd), 3.90 (1 H, dd), 3.80-3.69 (1 H, m), 3.59 (3 H, s), 3.56-3.45 (2 H, m), 3.20 (2 H, s), 2.71 (2 H, q), 1.32 (3 H, t) |
| 179 | $^1$H NMR (400 MHz, CDCl$_3$) δ ppm 7.87 (2 H, dd), 7.49 (1 H, d), 7.42 (1 H, d)NH, 7.10 (2 H, t), 6.88 (1 H, d), 6.72 (1 H, dd), 6.68 (1 H, s), 4.86 (1 H, d), 4.46 (1 H, t), 4.19 (2 H, td), 3.71 (2 H, dd), 3.66-3.54 (5 H, m), 3.17 (2 H, s), 3.14-3.04 (2 H, m), 2.73 (2 H, q), 1.34 (3 H, t) |
| 180 | $^1$H NMR (400 MHz, CDCl$_3$) δ ppm 7.86 (2 H, dd), 7.50 (1 H, d), 7.18 (1 H, s), 7.17-7.06 (3 H, m), 6.67 (1 H, s), 3.67-3.62 (2 H, m), 3.61 (3 H, s), 3.09-3.04 (4 H, m), 2.77-2.57 (8 H, m), 1.33 (3 H, t) |
| 181 | $^1$H NMR (400 MHz, MeOD-d$_4$) δ ppm 7.90 (2 H, dd), 7.47 (1 H, d), 7.42-7.29 (2 H, m), 7.12 (2 H, t), 6.95 (1 H, s), 3.81 (4 H, bt), 3.61 (3 H, s), 3.12-2.94 (4 H, m), 2.70 (2 H, q), 1.31 (3 H, t) |
| 182 | $^1$H NMR (400 MHz, MeOD-d$_4$) δ ppm 7.94-7.85 (2 H, m), 7.56 (1 H, dd), 7.49 (1 H, dd), 7.40 (1 H, dd), 7.11 (2 H, t), 6.95 (1 H, s), 3.71-3.64 (4 H, m), 3.62 (3 H, s), 3.22-3.16 (4 H, m), 2.71 (2 H, q), 1.31 (3 H, t) |
| 183 (Gen-10-a) | $^1$H NMR (400 MHz, MeOD-d$_4$) δ ppm 8.31-8.28 (1 H, m), 7.88-7.84 (2 H, m), 7.72 (1 H, dd), 7.54 (1 H, dd), 7.41-7.35 (2 H, m), 7.02 (1 H, s), 3.98-3.93 (2 H, m), 3.62 (3 H, s), 3.56-3.52 (2 H, m), 2.72 (2 H, q), 1.32 (3H, t) |
| 184 | $^1$H NMR (400 MHz, MeOD-d$_4$) δ ppm 8.39-8.28 (1 H, m), 7.84 (2 H, d), 7.71 (1 H, dd), 7.57 (1 H, dd), 7.40-7.33 (2 H, m), 7.00 (1 H, s), 4.18 (2 H, q), 4.01 (2 H, s), 3.93-3.86 (2 H, m), 3.67-3.57 (5 H, m), 2.72 (2 H, q), 1.31 (3 H, t), 1.25 (3 H, t) |
| 185 | $^1$H NMR (400 MHz, CDCl$_3$) δ ppm 7.83-7.72 (4 H, m), 7.51 (1 H, d), 7.38 (2 H, d), 6.81 (1 H, s), 6.19-6.09 (1 H, m), 3.98 (2 H, bd), 3.71-3.56 (5 H, m), 3.56-3.46 (2 H, m), 2.86 (3 H, s), 2.66-2.57 (2 H, m) |
| 186 | $^1$H NMR (400 MHz, CDCl$_3$) δ ppm 7.64-7.57 (4 H, m), 7.22-7.14 (3 H, m), 3.97 (2 H, d), 3.72 (2 H, d), 3.56 (3 H, s), 2.85-2.72 (7 H, m), 2.71-2.60 (1 H, m), 2.06-1.95 (2 H, m), 1.86 (2 H, qd), 1.37 (3 H, t) |
| 187 | $^1$H NMR (300 MHz, CDCl$_3$) δ ppm 8.41 (1 H, d), 8.05-7.90 (2 H, m), 7.65-7.42 (2 H, m), 7.28 (1 H, dd), 7.13 (3 H, d), 6.03 (1 H, t), 4.00-3.87 (2 H, m), 3.62 (3 H, s), 3.47 (2 H, t), 2.82 (3 H, s), 2.73 (2 H, q), 2.64-2.43 (2 H, m), 1.28 (3 H, t) |
| 188 | $^1$H NMR (400 MHz, CDCl$_3$) δ ppm 8.18 (2 H, d), 7.58 (1 H, d), 7.43 (2 H, d), 7.23-7.13 (2 H, m), 3.67 (3 H, s), 3.44-3.36 (4 H, m), 3.22-3.09 (4 H, m), 2.83 (3 H, s), 2.74 (2 H, q), 1.35 (3 H, t) |
| 189 | $^1$H NMR (300 MHz, CDCl$_3$) δ ppm 8.01-7.97 (2 H, m), 7.67 (1 H, s), 7.59 (1 H, d), 7.34 (1 H, dd), 7.14 (2 H, t), 6.10 (1 H, s), 3.98 (2 H, bs), 3.63 (3 H, s), 3.52 (2 H, q), 2.86 (3 H, s), 2.76 (2 H, d), 2.62 (2 H, bs), 1.35 (3 H, t) |
| 190 | $^1$H NMR (400 MHz, CDCl$_3$) δ ppm 8.24 (2 H, dd), 7.67 (1 H, s), 7.56 (1 H, d), 7.41 (1 H, dd), 7.14 (2 H, t), 6.08 (1 H, bs), 3.67 (3 H, s), 3.31 (2 H, s), 3.27 (2 H, bs), 3.08 (3 H, s), 2.95 (3 H, s), 2.83-2.49 (4 H, m), 2.54-2.45 (2 H, m), 1.35 (3 H, t) |
| 191 | $^1$H NMR (400 MHz, CDCl$_3$) δ ppm 8.28-8.20 (2 H, m), 7.61-7.53 (2 H, m), 7.21 (1 H, dd), 7.14 (2 H, t), 3.67 (3 H, s), 3.19 (2 H, s), 3.08 (3 H, s), 3.03 (2 H, bd), 2.95 (3 H, s), 2.74 (2 H, q), 2.56-2.42 (1 H, m), 2.24-2.15 (2 H, m), 1.92-1.68 (4 H, m), 1.35 (3 H, t) |
| 192 | $^1$H NMR (400 MHz, CDCl$_3$) δ ppm 7.92-7.80 (2 H, m), 7.64 (1 H, s), 7.47 (1 H, d), 7.17 (1 H, s), 7.13-7.05 (3 H, m), 7.01 (1 H, s), 6.66 (1 H, s), 3.66 (2 H, s), 3.59 (3 H, s), 3.08 (4 H, d), 2.77-2.65 (6 H, m), 1.32 (3 H, t) |

TABLE IV-continued

NMR data of the compounds of the invention.

| Cpd | NMR data (δ) |
|---|---|
| 193 | ¹H NMR (400 MHz, CDCl₃) δ ppm 7.99 (2 H, d), 7.73 (1 H, s), 7.66 dd), 7.35 (1 H, dd), 6.88 (1 H, s), 6.13-6.08 (1 H, m), 3.96 (2 H, d), 3.64 (3 H, s), 3.56-3.43 (2 H, m), 2.85 (3 H, s), 2.76 (2 H, q), 2.64-2.56 (2 H, m), 1.36 (3 H, t) |
| 194 | ¹H NMR (400 MHz, CDCl₃) δ ppm 7.87 (2 H, dd), 7.62 (1 H, s), 7.56 (1 H, d), 7.18 (1 H, dd), 7.11 (2 H, t), 6.69 (1 H, s), 3.63 (3 H, s), 2.99 (2 H, s), 2.91 (2 H, d), 2.82-2.68 (3 H, m), 2.57-2.45 (1 H, m), 2.24 (2 H, bt), 1.86 (2 H, d), 1.77-1.66 (2 H, m), 1.35 (3 H, t), 0.85-0.74 (2 H, m), 0.57-0.48 (2 H, m) |
| 195 | ¹H NMR (400 MHz, CDCl₃) δ ppm 7.90-7.84 (2 H, m), 7.61 (1 H, s), 7.57 (1 H, d), 7.18 (1 H, dd), 7.10 (2 H, t), 6.67 (1 H, s), 4.71-4.61 (1 H, m), 3.65-3.58 (4 H, m), 3.31-3.24 (1 H, t), 3.13 (1 H, bd), 3.00 (1 H, bd), 2.88 (3 H, s), 2.75 (2 H, q), 2.68 (2 H, dd), 2.55-2.46 (1 H, m), 2.36-2.18 (2 H, m), 1.86-1.70 (4 H, m), 1.34 (3 H, t) |
| 196 | ¹H NMR (400 MHz, CDCl₃) δ ppm 7.87 (2 H, dd), 7.60 (1 H, s), 7.54 (1 H, d), 7.17 (1 H, dd), 7.10 (2 H, t), 6.67 (1 H, s), 5.23-5.08 (1 H, m)NH, 4.79 (1 H, quin), 3.67 (1 H, t), 3.61 (3 H, s), 3.37 (1 H, t), 3.09 (1 H, bd), 2.99 (1 H, bd), 2.79-2.69 (3 H, m), 2.68-2.60 (1 H, m), 2.54-2.43 (1 H, m), 2.34-2.17 (2 H, m), 1.86-1.65 (4 H, m), 1.34 (3 H, t) |
| 197 | ¹H NMR (400 MHz, CDCl₃) δ ppm 7.86 (2 H, dd), 7.60 (1 H, s), 7.54 (1 H, d), 7.16 (1 H, dd), 7.10 (2 H, t), 6.67 (1 H, s), 5.10-4.86 (1 H, m)NH, 4.79 (1 H, quin), 3.67 (1 H, t), 3.61 (3 H, s), 3.37 (1 H, t), 3.09 (1 H, bs), 2.99 (1 H, bs), 2.79-2.60 (4 H, m), 2.55-2.42 (1 H, m), 2.34-2.17 (2 H, m), 1.86-1.67 (4 H, m), 1.34 (3 H, t) |
| 198 | ¹H NMR (400 MHz, DMSO-d₆) δ ppm7.95-7.90 (3 H, m), 7.66 (1 H, s), 7.51 (1 H, d), 7.31-7.20 (4 H, m), 4.34 (1 H, t), 4.01-3.97 (1 H, m), 3.96-3.88 (1 H, m), 3.54 (3 H, s), 2.96-2.88 (2 H, m), 2.63-2.38 (3 H, m), 2.38-2.35 (2 H, m), 2.09-1.93 (2 H, m), 1.72-1.56 (4 H, m), 1.21 (3 H, t) |
| 199 | ¹H NMR (400 MHz, CDCl₃) δ ppm 8.28-8.19 (2 H, m), 7.77-7.68 (2 H, m), 7.46 (1 H, dd), 7.14 (2 H, t), 6.15-6.08 (1 H, m), 4.01-3.95 (2 H, m), 3.69 (3 H, s), 3.58-3.44 (2 H, m), 2.86 (3 H, s), 2.79 (2 H, q), 2.68-2.57 (2 H, m), 1.35 (3 H, t) |
| 200 | ¹H NMR (400 MHz, CDCl₃) δ ppm 7.87-7.83 (2 H, m), 7.54 (1 H, d), 7.21 (1 H, d), 7.13-7.06 (3 H, m), 6.67 (1 H, s), 3.78 (2 H, t), 3.65 (2 H, t), 3.60 (3 H, s), 3.09-3.03 (4 H, m), 2.73 (2 H, q), 2.43 (3 H, s), 1.33 (3 H, t) |
| 201 | ¹H NMR (400 MHz, CDCl₃) δ ppm 7.85 (2 H, dd), 7.53 (1 H, d), 7.22 (1 H, d), 7.15-7.01 (3 H, m), 6.67 (1 H, s), 6.49 (1 H, d)NH, 4.48 (1 H, dd), 3.84-3.74 (2 H, m), 3.60 (5 H, bs), 3.12-2.96 (4 H, m), 2.73 (2 H, q), 2.50-2.28 (3 H, m), 2.16-2.06 (1 H, m), 1.33 (3 H, t) |
| 202 | ¹H NMR (300 MHz, CDCl₃) δ ppm 7.86 (2 H, dd), 7.54 (1 H, d), 7.24-7.04 (4 H, m), 6.68 (1 H, s), 3.84 (4 H, bt), 3.61 (3 H, s), 3.04 (4 H, bt), 2.73 (2 H, q), 1.33 (3 H, t), 1.07-0.99 (2 H, m), 0.86-0.77 (2 H, m) |
| 203 | ¹H NMR (400 MHz, CDCl₃) δ ppm 7.85 (2 H, dd), 7.56 (1 H, d), 7.22 (1 H, d), 7.17-7.03 (3 H, m), 6.68 (1 H, s), 4.52-4.43 (1 H, m), 3.93-3.70 (2 H, m), 3.66-3.51 (5 H, m), 3.13-2.97 (4 H, m), 2.74 (2 H, q), 1.40-1.28 (6 H, m) |
| 204 | ¹H NMR (400 MHz, CDCl₃) δ ppm 7.87-7.81 (2 H, m), 7.53 (1 H, dd), 7.20 (1 H, d), 7.14-7.05 (3 H, m), 7.04 (1 H, bs) NH, 6.66 (1 H, s), 5.59 (1 H, bs) NH, 4.24 (2 H, t), 3.80 (2 H, t), 3.59 (3 H, s), 2.72 (2 H, q), 3.11-3.05 (4 H, m), 1.33 (3 H, t) |
| 205 | ¹H NMR (400 MHz, CDCl₃) δ ppm 7.85 (2 H, dd), 7.54 (1 H, d), 7.35-7.18 (6 H, m), 7.14-7.02 (3 H, m), 6.68 (1 H, s), 4.56 (1 H, d), 4.35 (1 H, dd), 3.88-3.69 (2 H, m), 3.67-3.50 (6 H, m), 3.46-3.29 (2 H, m), 3.10-2.91 (4 H, m), 2.85-2.60 (4 H, m), 1.33 (3 H, t) |
| 206 | ¹H NMR (400 MHz, MeOD-d₄) δ ppm 8.33 (1 H, dd), 7.84-7.81 (2 H, m), 7.70 (1 H, dd), 7.58 (1 H, dd), 7.36-7.34 (2 H, m), 7.00 (1 H, s), 4.49-4.45 (2 H, m), 4.09-4.04 (2 H, m), 3.60 (3H, s), 2.72 (2 H, q), 1.32 (3 H, s) |
| 207 | ¹H NMR (400 MHz, MeOD-d₄) δ ppm 8.03 (1 H, dd), 7.85 (2 H, d), 7.56 (1 H, dd), 7.46 (1 H, dd), 7.37 (2 H, d), 7.03 (1 H, s), 3.71-3.65 (2 H, m), 3.61 (3 H, s), 3.29-3.23 (2 H, m), 2.73 (2 H, q), 2.30-2.21 (2 H, m), 1.92-1.83 (2 H, m), 1.32 (3 H, t) |
| 208 | ¹H NMR (400 MHz, MeOD-d₄) δ ppm 7.92-7.84 (3 H, m), 7.61 (1 H, dd), 7.52 (1 H, d), 7.14-7.07 (2 H, m), 6.93 (1 H, s), 6.81-6.75 (2 H, m), 6.64-6.62 (1 H, m), 6.28-6.18 (1 H, m), 4.16-4.14 (2 H, m), 3.70 (2 H, t), 3.62 (3 H, s), 2.72 (2 H, q), 2.64-2.44 (2 H, m), 1.29 (3 H, t) |
| 209 | ¹H NMR (400 MHz, MeOD-d₄) δ ppm 7.95 (1 H, s), 7.91-7.81 (2 H, m), 7.62 (1 H, dd), 7.54 (1 H, dd), 7.42-7.33 (2 H, m), 7.04 (1 H, s), 6.25 (1 H, t), 3.95-3.91 (2 H, m), 3.63 (3 H, s), 3.47 (2 H, td), 2.87 (3 H, s), 2.73 (2 H, q), 2.67-2.50 (2 H, m), 1.32 (3 H, t) |
| 210 | ¹H NMR (400 MHz, MeOD-d₄) δ ppm 7.95 (1 H, s), 7.90-7.80 (2 H, m), 7.62 (1 H, dd), 7.54 (1 H, dd), 7.43-7.33 (2 H, m), 7.04 (1 H, s), 6.28-6.20 (1 H, m), 4.24-4.15 (2 H, m), 3.80-3.67 (2 H, m), 3.63 (3 H, s), 2.73 (2 H, q), 2.69-2.55 (2 H, m), 1.32 (3 H, t) |
| 211 | ¹H NMR (400 MHz, MeOD-d₄) δ ppm 7.91 (2 H, dd), 7.48-7.31 (3 H, m), 7.12 (2 H, t), 6.95 (1 H, s), 3.77-3.68 (1 H, m), 3.61 (3 H, s), 3.51-3.40 (2 H, m), 2.87-2.74 (2 H, m), 2.69 (2 H, q), 2.02-1.90 (2 H, m), 1.73-1.59 (2 H, m), 1.31 (3 H, t) |
| 212 | ¹H NMR (300 MHz, MeOD-d₄) δ ppm 7.92-7.84 (2 H, m), 7.50-7.31 (5 H, m), 7.04 (1 H, s), 3.71 (2 H, t), 3.62 (3 H, s), 3.18-3.05 (4 H, m), 2.76-2.66 (6 H, m), 2.60 (2 H, t), 1.32 (3 H, t) |
| 213 | ¹H NMR (400 MHz, MeOD-d₄) δ ppm 7.87 (2 H, d), 7.57 (1 H, bd), 7.50 (1 H, d), 7.43-7.36 (3 H, m), 7.04 (1 H, s), 3.71-3.64 (4 H, m), 3.62 (3 H, s), 3.24-3.17 (4 H, m), 2.70 (2 H, q), 1.31 (3 H, t) |
| 214 | ¹H NMR (400 MHz, MeOD-d₄) δ ppm 7.90-7.86 (3 H, m), 7.60 (1 |

TABLE IV-continued

NMR data of the compounds of the invention.

| Cpd | NMR data (δ) |
|---|---|
| | H, dd), 7.51 (1 H, d), 7.12-7.07 (2 H, m), 6.93 (1 H, s), 6.18 (1 H, bs), 4.04 (2 H, bs), 3.61 (3 H, s), 3.59 (2 H, t), 2.71 (2 H, q), 2.55-2.38 (2 H, m), 1.45 (9 H, t), 1.31 (3 H, t) |
| 215 | $^1$H NMR (400 MHz, MeOD-d$_4$) δ ppm 7.94-7.82 (3 H, m), 7.52 (1 H, d), 7.38 (1 H, dd), 7.11 (2 H, t), 6.94 (1 H, s), 4.66 (1 H, d), 4.07 (1 H, d), 3.62 (3 H, s), 3.16 (1 H, t), 2.89 (1 H, t), 2.79-2.57 (3 H, m), 2.42 (2 H, q), 1.88 (2 H, t), 1.77-1.51 (2 H, m), 1.31 (3 H, t), 1.11 (3 H, t) |
| 216 (Gen-10-c) | $^1$H NMR (400 MHz, CDCl$_3$) δ ppm 7.90-7.83 (2 H, m), 7.61 (1 H, s), 7.55 (1 H, d), 7.18 (1 H, dd), 7.10 (2 H, t), 6.67 (1 H, s), 3.61 (3 H, s), 3.21-3.14 (2 H, m), 3.82-3.67 (4 H, m), 2.65-2.55 (1 H, m), 2.88-2.78 (2 H, m), 2.70-2.51 (2 H, m), 1.34 (3 H, t) |
| 217 | $^1$H NMR (400 MHz, MeOD-d$_4$) δ ppm 7.90-7.80 (2 H, m), 7.80 (1 H, bs), 7.51-7.49 (1 H, m), 7.37 (1 H, dd), 7.33 (5 H, m), 7.12-7.08 (2 H, m), 6.92 (1 H, s), 3.60 (3H, s), 3.54 (2 H, s), 2.99 (2 H, d), 2.70 (2H, q), 2.65-2.56 (1 H, m), 2.22-2.06 (2 H, m), 1.87-1.67 (4 H, m), 1.31 (3 H, t) |
| 218 | $^1$H NMR (400 MHz, MeOD-d$_4$) δ ppm 7.89-7.86 (2 H, m), 7.81 (1 H, s), 7.51 (1 H, d), 7.38 (1 H, dd), 7.13-7.08 (2 H, m), 6.93 (1 H, s), 3.61 (3 H, s), 3.02-2.97 (2 H, m), 2.81-2.57 (4 H, m), 2.32 (2 H, t), 1.90-1.84 (2 H, m), 1.79-1.62 (2 H, m), 1.31 (3 H, t), 1.11-1.05 (6 H, m) |
| 219 | $^1$H NMR (400 MHz, MeOD-d$_4$) δ ppm 7.95-7.82 (3 H, m), 7.51 (1 H, dd), 7.37 (1 H, dd), 7.11 (2 H, t), 6.93 (1 H, s), 4.18 (2 H, bd), 3.61 (3 H, s), 2.87-2.76 (1 H, m), 2.75-2.62 (4 H, m), 1.81 (2 H, d), 1.59 (2 H, qd), 1.44 (9 H, s), 1.31 (3 H, t) |
| 220 | $^1$H NMR (400 MHz, MeOD-d$_4$) δ ppm 7.86-7.91 (3 H, m), 7.60 (1 H, dd), 7.52 (1 H, dd), 7.07-7.14 (2 H, m), 6.94 (1 H, s), 6.31-6.27 (1 H, m), 4.31-4.26 (2 H, m), 3.87 (2 H, t), 3.62 (3 H, s), 2.71 (2 H, q), 2.38-2.52 (2 H, m), 1.31 (3 H, t) |
| 221 | $^1$H NMR (400 MHz, MeOD-d$_4$) δ ppm 7.90-7.80 (3 H, m), 7.60 (1 H, dd), 7.52 (1 H, dd), 7.39-7.31 (2 H, m), 7.01 (1 H, s), 6.30-6.24 (1 H, m), 4.29-4.23 (2 H, m), 3.86 (2 H, t), 3.61 (3 H, s), 2.70 (2 H, q), 2.53-2.35 (2 H, m), 1.31 (3 H, t) |

Biological Examples

Example 3

In Vitro Assays

3.1. Principle

The principle of the assay consists in quantifying the released choline with an enzymatic method using choline oxidase and peroxidase. Choline oxydation by choline oxydase releases betaine and peroxide. The latter is quantified in presence of HRP that converts the peroxide detection agent TOOS and 4-aminoantipyrine into quinoneimine dye. The appearance of quinoneimine dye is measured spectrophotometrically at 555 nm and is proportional to the amount of choline released by ENPP2. Inhibition of ENPP2 will result in a decrease of the signal.

3.2. Human ENPP2 (hENPP2) Assay

3.2.1. LPC as Substrate

Compound IC50 values are determined in a hENPP2 (UniProtKB/SwissProt Sequence ref Q13822) biochemical assay using LPC as substrate.

5 μL of a dilution series of compound, starting from 20 μM highest concentration, 1/5 dilution, is added to the wells. hENPP2 is used at a final concentration of 1 μg/mL or 3 μg/mL (it will be appreciated by the skilled person that the potency read out is independent of the enzyme concentration). The enzyme is diluted in 50 mM Tris-HCl pH 8.5, 500 mM NaCl, 5 mM KCl, 10 mM CaCl$_2$, 0.1% fatty acid free BSA in a total volume of 10 μL. the reaction is started by the addition of 10 μL of 150 μM LPC (palmitoyl 16:0) diluted in the same buffer as described above and the mixture is incubated at 37° C. for 30 min. The reaction is terminated and choline quantified by the addition of a 25 μL of a mixture containing 0.6 U/mL of choline oxidase, 0.6 U/mL of peroxydase, 1.8 mM TOOS, 1.2 mM amino-antipyrine, 20 mM EGTA (stop-developer solution) diluted in the buffer described above. Luminescence is read on the Envision after an incubation of 30 min at room temperature (Excitation 555 nm, excitation light=70%).

TABLE V

LPC hENPP2 assay IC$_{50}$ of the compounds of the invention.

| Cpd # | LPC-IC$_{50}$ |
|---|---|
| 2 | *** |
| 4 | *** |
| 5 | *** |
| 12 | **** |
| 22 | **** |
| 23 | * |
| 24 | *** |
| 25 | *** |
| 26 | *** |
| 27 | *** |
| 28 | *** |
| 29 | *** |
| 30 | **** |
| 31 | **** |
| 32 | *** |
| 33 | ** |
| 34 | *** |
| 35 | *** |
| 36 | *** |
| 37 | * |
| 38 | * |
| 39 | * |
| 40 | * |
| 41 | * |
| 42 | * |
| 43 | * |
| 44 | * |
| 45 | * |
| 46 | * |
| 47 | * |
| 48 | * |
| 49 | * |
| 50 | ** |
| 51 | * |
| 52 | * |
| 53 | * |
| 54 | ** |
| 55 | * |
| 56 | ** |
| 57 | * |
| 58 | * |
| 59 | * |

TABLE V-continued

LPC hENPP2 assay IC$_{50}$ of the compounds of the invention.

| Cpd # | LPC-IC$_{50}$ |
|---|---|
| 60 | * |
| 61 | * |
| 62 | * |
| 63 | * |
| 64 | * |
| 65 | * |
| 66 | * |
| 67 | * |
| 68 | * |
| 69 | * |
| 70 | * |
| 71 | * |
| 72 | *** |
| 73 | * |
| 74 | * |
| 75 | ** |
| 76 | * |
| 77 | * |
| 78 | * |
| 79 | * |
| 80 | ** |
| 81 | * |
| 82 | * |
| 83 | * |
| 84 | * |
| 85 | * |
| 86 | * |
| 87 | *** |
| 88 | *** |
| 89 | *** |
| 90 | ** |
| 91 | ** |
| 92 | * |
| 93 | *** |
| 94 | ** |
| 95 | * |
| 96 | *** |
| 97 | *** |
| 98 | ** |
| 99 | * |
| 100 | * |
| 101 | * |
| 102 | * |
| 103 | *** |
| 104 | * |
| 105 | *** |
| 106 | * |
| 107 | ** |
| 108 | * |
| 109 | *** |
| 110 | *** |
| 111 | *** |
| 112 | *** |
| 113 | *** |
| 114 | *** |
| 115 | **** |
| 116 | *** |
| 117 | *** |
| 118 | *** |
| 119 | ** |
| 121 | ** |
| 122 | ** |
| 123 | * |
| 124 | * |
| 125 | * |
| 126 | *** |
| 127 | ** |
| 128 | *** |
| 129 | *** |
| 130 | *** |
| 131 | *** |
| 132 | * |
| 133 | *** |
| 134 | ** |
| 135 | * |
| 136 | *** |
| 137 | * |
| 138 | **** |
| 139 | **** |
| 140 | **** |
| 141 | **** |
| 142 | **** |
| 143 | **** |
| 144 | **** |
| 145 | **** |
| 146 | ** |
| 147 | *** |
| 148 | * |
| 149 | *** |
| 150 | ** |
| 151 | ** |
| 152 | ** |
| 153 | ** |
| 154 | *** |
| 155 | ** |
| 156 | ** |
| 157 | * |
| 158 | *** |
| 159 | **** |
| 160 | *** |
| 161 | * |
| 162 | *** |
| 163 | ** |
| 164 | **** |
| 165 | *** |
| 166 | **** |
| 167 | **** |
| 168 | **** |
| 169 | **** |
| 170 | **** |
| 171 | **** |
| 172 | *** |
| 173 | **** |
| 174 | **** |
| 175 | ** |
| 176 | * |
| 177 | ** |
| 178 | *** |
| 179 | * |
| 180 | * |
| 182 | * |
| 183 | * |
| 184 | * |
| 185 | * |
| 186 | * |
| 187 | * |
| 188 | * |
| 189 | * |
| 190 | * |
| 191 | * |
| 192 | ** |
| 193 | * |
| 194 | * |
| 195 | * |
| 196 | * |
| 197 | * |
| 198 | * |
| 199 | * |
| 200 | * |
| 201 | * |
| 202 | * |
| 203 | * |
| 204 | * |
| 205 | ** |
| 206 | * |
| 207 | * |
| 208 | * |
| 209 | * |
| 210 | * |
| 211 | * |
| 212 | * |
| 213 | * |

TABLE V-continued

LPC hENPP2 assay $IC_{50}$ of the compounds of the invention.

| Cpd # | LPC-$IC_{50}$ |
|---|---|
| 214 | * |
| 215 | *** |
| 216 | * |
| 217 | * |
| 218 | * |
| 219 | * |
| 220 | * |
| 221 | * |
| 222 | ** |
| 223 | *** |
| 224 | * |
| 225 | * |
| 226 | * |
| 227 | * |
| 228 | * |
| 229 | * |
| 233 | not active |
| 239 | * |

\* >1000 nM
\*\* >500-1000 nM
\*\*\* >100-500 nM
\*\*\*\* 0.01-100 nM

3.2.2. FS-3 as Substrate

Compound $IC_{50}$ values are determined in a fluorescent hENPP2 (UniProtKB/SwissProt Sequence ref Q13822) biochemical assay using the fluorogenic autotaxin substrate FS-3 as substrate. FS-3 is a doubly labeled analog of LPC wherein the fluorophore is quenched through intramolecular energy transfer. Without hENPP2, the emission of the probe is quenched. If the substrate is hydrolyzed by hENPP2, the emission of the probe is not quenched anymore resulting in a fluorescence increase. Inhibition of hENPP2 by compounds will result in a decrease of the signal.

10 µL of a dilution series of compound, starting from 20 µM highest concentration, 1/5 dilution, is added to the wells. hENPP2 is used at a final concentration of 0.4 µg/mL or 0.64 µg/mL (it will be appreciated by the skilled person that the potency read out is independent of the enzyme concentration). The enzyme is diluted in 50 mM Tris-HCl pH 8.0, 250 mM NaCl, 5 mM KCl, 1 mM $MgCl_2$, 1 mM $CaCl_2$, 0.1% fatty acid free BSA in a total volume of 20 µL. Enzyme mixture is added to compounds and the resulting mixture is incubated for 30 min at room temperature under shaking. The reaction is started by the addition of 20 µL of 0.75 µM FS-3 diluted in the same buffer as described above and the mixture is incubated at 30° C. for 30 min. Fluorescence is read on the Envision (Excitation 485 nm, emission 520 nM).

TABLE VI

FS3 hENPP2 assay $IC_{50}$ of the compounds of the invention.

| Cpd # | FS3-$IC_{50}$ |
|---|---|
| 2 | **** |
| 4 | **** |
| 5 | **** |
| 12 | **** |
| 22 | **** |
| 23 | **** |
| 24 | **** |
| 25 | **** |
| 27 | **** |
| 35 | **** |
| 36 | **** |
| 38 | **** |
| 39 | **** |
| 40 | **** |
| 41 | **** |
| 42 | **** |
| 43 | **** |
| 46 | **** |
| 47 | **** |
| 49 | **** |
| 50 | **** |
| 51 | **** |
| 52 | **** |
| 53 | **** |
| 54 | **** |
| 55 | **** |
| 56 | **** |
| 57 | **** |
| 58 | **** |
| 59 | **** |
| 60 | **** |
| 61 | **** |
| 62 | **** |
| 63 | **** |
| 64 | **** |
| 65 | **** |
| 66 | **** |
| 67 | **** |
| 68 | **** |
| 69 | **** |
| 74 | **** |
| 75 | **** |
| 76 | **** |
| 77 | **** |
| 78 | **** |
| 79 | **** |
| 80 | **** |
| 81 | **** |
| 82 | **** |
| 86 | **** |
| 87 | **** |
| 88 | **** |
| 89 | **** |
| 90 | **** |
| 91 | **** |
| 92 | **** |
| 93 | **** |
| 94 | **** |
| 95 | **** |
| 96 | **** |
| 98 | **** |
| 99 | **** |
| 100 | **** |
| 101 | **** |
| 103 | **** |
| 105 | **** |
| 106 | **** |
| 108 | **** |
| 109 | **** |
| 110 | **** |
| 111 | **** |
| 112 | **** |
| 113 | **** |
| 114 | **** |
| 115 | **** |
| 116 | **** |
| 118 | **** |
| 124 | **** |
| 125 | **** |
| 126 | **** |
| 128 | **** |
| 133 | **** |
| 134 | **** |
| 135 | **** |
| 136 | **** |
| 137 | **** |
| 138 | **** |
| 141 | **** |

TABLE VI-continued

FS3 hENPP2 assay IC$_{50}$ of the compounds of the invention.

| Cpd # | FS3-IC$_{50}$ |
|---|---|
| 143 | **** |
| 145 | **** |
| 147 | **** |
| 155 | **** |
| 156 | **** |
| 157 | **** |
| 158 | **** |
| 159 | **** |
| 160 | **** |
| 162 | **** |
| 166 | **** |
| 167 | **** |
| 168 | **** |
| 170 | **** |
| 171 | **** |
| 172 | **** |
| 173 | **** |
| 174 | **** |
| 179 | **** |
| 180 | **** |
| 182 | **** |
| 183 | **** |
| 184 | **** |
| 185 | **** |
| 186 | **** |
| 187 | **** |
| 188 | **** |
| 189 | **** |
| 191 | **** |
| 192 | **** |
| 194 | **** |
| 199 | *** |
| 200 | **** |
| 201 | **** |
| 203 | **** |
| 204 | **** |
| 206 | **** |
| 207 | **** |
| 208 | **** |
| 209 | **** |
| 210 | **** |
| 211 | **** |
| 212 | **** |
| 213 | **** |
| 214 | **** |
| 215 | **** |
| 216 | **** |
| 217 | **** |
| 218 | **** |
| 219 | **** |
| 220 | **** |
| 221 | **** |
| 224 | **** |
| 225 | **** |
| 226 | **** |
| 227 | **** |
| 229 | *** |
| 230 | **** |
| 231 | **** |
| 232 | **** |
| 233 | **** |
| 234 | **** |
| 235 | **** |
| 236 | *** |
| 237 | **** |
| 238 | *** |
| 239 | **** |
| Gen-10-e | **** |

\* >1000 nM
\*\* >500-1000 nM
\*\*\* >100-500 nM
\*\*\*\* 0.01-100 nM 3.3. Mouse ENPP2 (mENPP2)

3.3.1. LPC as Substrate

Compound IC$_{50}$ values are determined in a mENPP2 (UniProtKB/SwissProt Sequence ref Q9R1E6) biochemical assay using LPC as substrate.

Five µL of a dilution series of compound, starting from 20 µM highest concentration, 1/5 dilution, is added to the wells. mENPP2 is used at a final concentration of 1 µg/mL. The enzyme is diluted in 50 mM Tris-HCl pH 8.5, 500 mM NaCl, 5 mM KCl, 10 mM CaC$_2$, 0.1% fatty acid free BSA in a total volume of 10 µL. the reaction is started by the addition of 10 µL of 150 µM LPC (palmitoyl 16:0) diluted in the same buffer as described above and the mixture is incubated at 37° C. for 30 min. The reaction is terminated and choline quantified by the addition of a 25 µL of a mixture containing 0.6 U/mL of choline oxidase, 0.6 U/mL of peroxydase, 1.8 mM TOOS, 1.2 mM amino-antipyrine, 20 mM EGTA (stop-developer solution) diluted in the buffer described above. Luminescence is read on the Envision after an incubation of 30 min at room temperature (Excitation 555 nm, excitation light=70%).

3.3.2. FS-3 as Substrate

Compound IC50 values are determined in a fluorescent mENPP2 (UniProtKB/SwissProt Sequence ref Q9R1E6) biochemical assay using the fluorogenic autotaxin substrate FS-3 as substrate. FS-3 is a doubly labeled analog of LPC wherein the fluorophore is quenched through intramolecular energy transfer. Without mENPP2, the emission of the probe is quenched. If the substrate is hydrolyzed by mENPP2, the emission of the probe is not quenched anymore resulting in a fluorescence increase. Inhibition of mENPP2 by compounds will result in a decrease of the signal.

10 µL of a dilution series of compound, starting from 20 µM highest concentration, 1/5 dilution, is added to the wells. mENPP2 is used at a final concentration of 0.4 µg/mL. The enzyme is diluted in 50 mM Tris-HCl pH 8.0, 250 mM NaCl, 5 mM KCl, 1 mM MgCl$_2$, 1 mM CaCl$_2$, 0.1% fatty acid free BSA in a total volume of 20 µL. Enzyme mixture is added to compounds and the resulting mixture is incubated for 30 min at room temperature under shaking. The reaction is started by the addition of 20 µL of 0.75 µM FS-3 diluted in the same buffer as described above and the mixture is incubated at 30° C. for 30 min. Fluorescence is read on the Envision (Excitation 485 nm, emission 520 nM).

Example 4

Whole Blood Assay 4.1. Human LPA Assay

Blood is collected from healthy volunteers who gave informed consent into sodium heparin tubes by venipuncture, then gently inverted several times to prevent clotting. Tubes are centrifuged at 3000 rpm for 15 min at 4° C. then plasma is stored at −80° C. Compounds are diluted in DMSO in concentration dependent manner then 0.5 µL are dispensed into 96-well plate placed in ice. Plasma is defrosted on ice then 49.5 µL of plasma are added into the well containing 0.5 µL of compound (1% DMSO final). Plates are covered with a lid in polypropylene and incubated at +37° C., 5% CO$_2$, for 2 h under gentle shaking (except controls which are stored at −20° C.).

At the end of the incubation, controls are defrosted in ice and transferred in the incubated plates for LC-MS/MS analysis with a non GLP-validated method. For the analysis, plasma proteins from a 10 µL incubated plates are precipitated with an excess of methanol containing the internal standard, LPA 17:0. After centrifugation, the corresponding supernatant is injected on a C18 column. Analytes are eluted out of the column under isocratic conditions. An API5500 QTRAP mass spectrometer (ABSciex™) is used for the detection of LPA 18:2. No calibration curve is prepared for LPA 18:2, however relative quantities are evaluated based on the peak area.

TABLE VII

Human whole blood assay $IC_{50}$ of the compounds of the invention.

| Cpd # | $IC_{50}$ |
|---|---|
| 2 | *** |
| 12 | *** |
| 13 | *** |
| 80 | * |
| 110 | * |

\* >1000 nM  
\** >500-1000 nM  
\*** >100-500 nM  
\**** 0.01-100 nM

4.2. Rat or Mouse LPA Assay

Whole blood is collected from rats or mouse by exsanguinations on sodium heparin tube, then after centrifugation at 3000 rpm for 15 min at 4° C., plasma is stored at −80° C. Compounds are diluted in DMSO in concentration dependent manner then 0.5 µL are dispensed into 96-well plate placed in ice. Plasma is defrosted on ice then 49.5 µL of plasma are added into the well containing 0.5 µL of compound (1% DMSO final). Plates are covered with a lid in polypropylene and incubated at +37° C., 5% $CO_2$, for 2 h under gentle shaking (except controls which are stored at −20° C.).

At the end of the incubation, controls are defrosted in ice and transferred in the incubated plates for LC-MS/MS analysis with a non GLP-validated method. For the analysis, plasma proteins from a 10 µL incubated plates are precipitated with an excess of methanol containing the internal standard, LPA 17:0. After centrifugation, the corresponding supernatant is injected on a C18 column. Analytes are eluted out of the column under isocratic conditions. An API5500 QTRAP mass spectrometer (ABSciex™) is used for the detection of LPA 18:2. No calibration curve is prepared for LPA 18:2, however relative quantities are evaluated based on the peak area.

TABLE VIII

Rat whole blood assay $IC_{50}$ of the compounds of the invention.

| Cpd # | $IC_{50}$ |
|---|---|
| 2 | ** |
| 3 | *** |
| 4 | *** |
| 5 | ** |
| 6 | *** |
| 10 | *** |
| 12 | **** |
| 13 | **** |
| 14 | **** |
| 15 | ** |
| 16 | ** |
| 18 | **** |
| 19 | * |
| 26 | * |
| 40 | ** |
| 46 | * |
| 48 | * |
| 53 | * |
| 54 | * |
| 56 | * |
| 58 | * |
| 66 | * |
| 72 | * |
| 75 | * |
| 80 | ** |
| 87 | *** |
| 88 | *** |
| 91 | * |
| 94 | ** |
| 95 | *** |
| 96 | **** |
| 98 | *** |
| 110 | * |
| 111 | ** |
| 112 | *** |
| 113 | *** |
| 114 | ** |
| 115 | **** |
| 136 | **** |
| 138 | **** |
| 140 | **** |
| 141 | **** |
| 142 | **** |
| 143 | **** |
| 144 | **** |
| 145 | **** |
| 147 | *** |
| 149 | * |
| 154 | ** |
| 155 | *** |
| 156 | * |
| 159 | *** |
| 160 | **** |
| 162 | *** |
| 166 | ** |
| 167 | *** |
| 170 | *** |
| 171 | *** |
| 173 | *** |
| 174 | **** |
| 175 | **** |
| 180 | * |
| 182 | * |
| 187 | *** |
| 188 | * |
| 192 | * |
| 203 | * |
| 206 | * |
| 212 | * |
| 213 | * |
| 226 | * |

\* >1000 nM  
\** >500-1000 nM  
\*** >100-500 nM  
\**** 0.01-100 nM

Example 5

In Vivo Models 5.1. Tobacco Smoke (TS) Model  
5.1.1. Lungs Inflammatory Cells Recruitment Evaluation  
5.1.1.1. Overview The aim of this experiment is to evaluate the efficacy and potency of a test compound administered p.o., once or twice daily on days 6 to 11, vs reference compounds, on pulmonary inflammation induced by 11 days of TS-exposure in female C57BL/6J mice, by assessing the effect of a test compound on the tobacco smoke induced recruitment of inflammatory cells to the lungs.

5.1.1.2. Protocol

The test compounds are formulated in PEG200/0.5% methylcellulose (25/75, v/v) and are given at a dose volume of 10 mL/kg. Roflumilast and Dexamethasone are included as positive and negative control, respectively. Each treatment group consists of 10 mice.

A first group of mice is subjected to daily TS-exposure for 5 consecutive days and sacrificed on the day 6, 24 h after the final TS-exposure.

A second group is exposed to air for 5 consecutive days (sham exposure) and sacrificed on the day 6, 24 h after the final air-exposure.

Compound and reference-treated groups are subjected to daily TS-exposure for 11 consecutive days and sacrificed on the day 12, 24 h after the final TS-exposure. Mice are dosed p.o. on days 6 to 11, twice daily, 1 h prior to and 6 h after each TS-exposure, with either vehicle, or the test compound at 3, 5, 10 or 30 mg/kg. Another group is dosed p.o. on days 6 to 11, once daily, 1 h prior to each TS-exposure, with either vehicle, or the test compound at 10 mg/kg.

An additional group is dosed p.o., once daily, on days 6 to 11, with roflumilast at 5 mg/kg, 1 h prior to each TS-exposure. Dexamethasone is dosed p.o., twice daily, on days 6 to 11, at 0.3 mg/kg, 1 h prior to and 6 h after each TS-exposure.

For each mouse, a BAL is performed using 0.4 mL of PBS. The lavage fluid is centrifuged, the supernatant removed and the resulting cell pellet re-suspended for total cell counts and cytospin slide preparation. The remaining cells are re-pelleted and frozen. The supernatants are stored at −40° C. for possible future analysis.

The lungs are dissected out and the left lobes are removed, snap-frozen and stored at −80° C. The right lobes are inflated with 10% phosphate buffered formalin (PBF) to a pressure of 18 cm PBF for 20 min and then immersed in PBF. After 24 h, the right lobe samples are transferred to 70% ethanol and stored at room temperature. Cell data are presented as individual data points for each animal and the mean value calculated for each group.

Data are subjected to an unpaired Students 't' test. Data from other groups are initially subjected to a one-way analysis of variance test (ANOVA), followed by a Bonferroni correction for multiple comparisons in order to test for differences between treatment groups. A 'p' value of <0.05 is considered to be statistically significant.

Percentage inhibitions for the cell data are calculated using the formula below:

$$\% \text{ inhibition} = \left(1 - \left(\frac{\text{treatment group result} - \text{sham group result}}{TS \text{ vehicle group result} - \text{sham group result}}\right)\right) * 100$$

5.1.1.3. Results

For example, when tested in this protocol, Compound 2 and 12 significantly inhibited the number of cells recovered in the BALF, in particular macrophage cells, epithelial cells, and neutrophils at 10 mg/kg twice daily p.o. (Compound 2 & 12) and 3 mg/kg twice daily p.o. (Compound 2).

5.1.2. Compound Efficacy and Potency Evaluation

5.1.2.1. Overview

A second tobacco smoke (TS) experiment is carried out, aimed at evaluating the efficacy and potency of a test compound administered p.o., twice daily on days 6 to 11, vs a reference compound, on pulmonary inflammation induced by 11 days of TS-exposure, reading out the effects on gene expression in the lungs. This second experiment consisted of 4 groups of mice.

5.1.2.2. Protocols

Three groups of mice are subjected to daily TS-exposure for 11 consecutive days and sacrificed on the day 12, 24 h after the final TS-exposure. Two groups are dosed, p.o., on days 6 to 11, twice daily (b.i.d.), 1 h prior to and 6 h after each TS-exposure, with either vehicle or the test compound at 10 mg/kg. The third group is dosed p.o., on days 6 to 11, once daily (q.d.) with Roflumilast at 5 mg/kg, 1 h prior to each TS-exposure. This group receives vehicle 6 h after each TS-exposure. One further group is exposed to air for 11 consecutive days and receive vehicle 1 h prior to and 6 h after exposure on days 6 to 11. This group is also sacrificed on the day 12, 24 h after the final exposure.

All groups receive a final dose, of the relevant treatment, 2 h prior to sacrifice on day 12. One final group is exposed to air for 11 consecutive days and received vehicle 1 h prior to and 6 h after exposure on days 6 to 11. This group is also sacrificed on the day 12, 24 h after the final exposure. Mice receive a dose volume of 10 mL/kg. Each group consists in 10 subjects.

Mice are euthanized, by intra-peritoneal barbiturate anaesthetic overdose, on day 12, 24 h after the final air or TS-exposure. All mice receive a final dose of the relevant treatment, 2 h prior to sacrifice. The lungs are dissected out and placed in RNAse-free 15 mL tubes containing ~5 ml of RNAlater solution, ensuring the tissue is completely submerged. The lungs are stored overnight at 4° C. Following overnight incubation, the lungs are removed from RNAlater, the left and right lobes are separated, placed in individual tubes and stored at −80° C.

RNA extractions are performed for 5 mice per group using Qiagen RNeasy Mini Kit according to the manufacturer's specifications (Animal tissue protocol). Total RNA are then eluted in RNase-free water (30 µl for four reference samples and 50 µl for the twenty-four test samples). Quality of the samples is assessed by measurement of their concentration in RNA using a NanoDrop ND-1000 spectrophotometer and by the measurement of RNA integrity using an 2100 Bioanalyzer (Agilent Technologies).

RNA preparations are of good quality (RIN value lies between 7.6 and 9.2) and subjected to quantitative real-time PCR (QrtPCR), which involved a first cDNA synthesis step. To this end, 300 ng of total RNA are reverse transcribed using the High capacity cDNA synthesis Kit (Applied Biosystems™) with random hexamers. Quantitative PCR reactions are performed using Quanti-Fast SYBR® Green PCR Master Mix (Qiagen™) and gene-specific primer pairs for β-actin (Eurogentech™) and QuantiTect primer assays for all other tested genes (Qiagen™). For the genes of interest, the following Quantitect primer pairs are used: CCL2 (QT00167832); CDK1 (QT00167734); SAA3 QT00249823), TIMP1 (QT00996282); Slc26a4 (QT00131908); LCN2 (QT00113407); CXCL5 (QT01658146), MMP 12 (QT00098945); PLA1a (QT00161448); TNFsF11 (QT00147385). Reactions are carried out with a denaturation step at 95° C. for 5 min, followed by 40 cycles (95° C. for 10 sec, 60° C. for 1 min) in a ViiATM7 Real-Time PCR System (Applied Biosystems™)

Real-time PCR data for each target gene are expressed as $2^{-\Delta\Delta Ct}$ relative quantification versus endogenous β-actin. For statistical analysis, a 2-way analysis of variance (ANOVA) followed by a Dunnett's post-hoc test versus the TS-vehicle group is performed.

The relevance of CCL2, CDK1, SAA3, TIMP1, Slc26a4, LCN2, CXCL5, MMP12, PLA1a, and TNFsF11 towards COPD is well-established through literature data based on patient specimen. A reference towards the relevant paper for each gene is provided in Table IX below.

5.1.2.3. Results

The increase in relative expression levels caused by the tobacco smoke treatment is indicated in the column 'Fold change TS+vehicle'. The pronounced increase in the expression of this relevant gene set upon tobacco smoke treatment further validates the relevance of the model applied. Treatment of mice with 10 mg/kg bid of Compound 2 strongly and significantly reduces the increase caused by the tobacco smoke treatment. The statistical significance of the compound treatment is indicated in Table VI (*p<0.05, p<0.01, *p<0.001 vs TS/vehicle). Roflumilast, an approved treatment for COPD, is taken along as positive control in the experiment.

The inhibition of ENPP2 in a therapeutic setting strongly suppresses the increase in expression of disease-relevant genes in lungs of tobacco smoke-treated mice, providing a strong support for key a role of ENPP2 in the pathogenesis of COPD.

TABLE IX

TS induced relative expression levels in selected genes

| Gene Name | Fold change TS + vehicle | Fold change TS + Compound 2 | Literature reference |
|---|---|---|---|
| CCL2 | 7.23 | 3.96 * | (Llinàs, et al., 2011) |
| SAA3 | 105.98 | 6.87 *** | (Bozinovski, et al., 2008) |
| TIMP1 | 4.76 | 1.34 *** | (Tilley, et al., 2011) |
| SLC26A4 | 4.27 | 2.17 *** | (Nakao, et al., 2008) |
| LCN2 | 7.76 | 2.54 *** | (Eagan, et al., 2010) |
| MMP12 | 14.40 | 4.99 ** | (Demedts, et al., 2006) |

5.2. CIA Model 5.2. 1. Materials

Completed Freund's adjuvant (CFA) and incomplete Freund's adjuvant (IFA) are purchased from Difco. Bovine collagen type II (CII), lipopolysaccharide (LPS), and Enbrel is obtained from Chondrex (Isle d'Abeau, France); Sigma (P4252, L'Isle d'Abeau, France), Whyett (25 mg injectable syringe, France) Acros Organics (Palo Alto, Calif.), respectively. All other reagents used are of reagent grade and all solvents are of analytical grade.

5.2.2. Animals

Dark Agouti rats (male, 7-8 weeks old) are obtained from Harlan Laboratories (Maison-Alfort, France). Rats are kept on a 12 h light/dark cycle (07:00-19:00). Temperature is maintained at 22° C., and food and water are provided ad libitum.

5.2.3. Collagen Induced Arthritis (CIA)

One day before the experiment, CII solution (2 mg/mL) is prepared with 0.05 M acetic acid and stored at 4° C. Just before the immunization, equal volumes of adjuvant (IFA) and CII are mixed by a homogenizer in a pre-cooled glass bottle in an ice water bath. Extra adjuvant and prolonged homogenization may be required if an emulsion is not formed. 0.2 mL of the emulsion is injected intradermally at the base of the tail of each rat on day 1, a second booster intradermal injection (CII solution at 2 mg/mL in CFA 0.1 mL saline) is performed on day 9. This immunization method is modified from published methods (Sims, et al., 2004) (Jou, et al., 2005).

5.2.4. Study Design

The therapeutic effects of the compounds are tested in the rat CIA model. Rats are randomly divided into equal groups and each group contains 10 rats. All rats are immunized on day 1 and boosted on day 9. Therapeutic dosing lasted from day 16 to day 30. The negative control group is treated with vehicle and the positive control group with Enbrel (10 mg/kg, 3x/week, s.c.). A compound of interest is typically tested at 4 doses, e.g. 0.3, 1, 3, and 10 mg/kg, p.o.

5.2.5. Clinical Assessment of Arthritis

Arthritis is scored according to literature-described method ((Khachigian, 2006) (Lin, et al., 2007), (Nishida, et al., 2004)). The swelling of each of the four paws is ranked with the arthritic score as follows: 0—no symptoms; 1—mild, but definite redness and swelling of one type of joint such as the ankle or wrist, or apparent redness and swelling limited to individual digits, regardless of the number of affected digits; 2—moderate redness and swelling of two or more types of joints; 3—severe redness and swelling of the entire paw including digits; 4—maximally inflamed limb with involvement of multiple joints (maximum cumulative clinical arthritis score 16 per animal) (Nishida, et al., 2004).

To permit the meta-analysis of multiple studies the clinical score values are normalised as follows:

AUC of clinical score (AUC score): The area under the curve (AUC) from day 1 to day 14 is calculated for each individual rat. The AUC of each animal is divided by the average AUC obtained for the vehicle in the study from which the data on that animal is obtained and multiplied by 100 (i.e. the AUC is expressed as a percentage of the average vehicle AUC per study).

Clinical score increase from day 1 to day 14 (End point score): The clinical score difference for each animal is divided by the average clinical score difference obtained for the vehicle in the study from which the data on that animal is obtained and multiplied by 100 (i.e. the difference is expressed as a percentage of the average clinical score difference for the vehicle per study).

5.2.6. Change in body weight (%) after onset of arthritis

Clinically, body weight loss is associated with arthritis (Shelton, Zeller, Ho, Pons, & Rosenthal, 2005); (Rall & Roubenoff, 2004); (Walsmith, Abad, Kehayias, & Roubenoff, 2004)). Hence, changes in body weight after onset of arthritis can be used as a non-specific endpoint to evaluate the effect of therapeutics in the rat model. The change in body weight (%) after onset of arthritis is calculated as follows:

$$\text{Mice:} \frac{\text{Body Weight (week 6)} - \text{Body Weight (Week 5)}}{\text{Body Weight (Week 5)}} * 100\%$$

$$\text{Rats:} \frac{\text{Body Weight (week 4)} - \text{Body Weight (Week 3)}}{\text{Body Weight (Week 5)}} * 100\%$$

5.2.7. Radiology

X-ray photos are taken of the hind paws of each individual animal. A random blind identity number is assigned to each of the photos, and the severity of bone erosion is ranked by two independent scorers with the radiological Larsen's score system as follows: 0—normal with intact bony outlines and normal joint space; 1—slight abnormality with any one or two of the exterior metatarsal bones showing slight bone erosion; 2—definite early abnormality with any three to five of the exterior metatarsal bones showing bone erosion; 3—medium destructive abnormality with all the exterior metatarsal bones as well as any one or two of the interior metatarsal bones showing definite bone erosions; 4—severe destructive abnormality with all the metatarsal bones showing definite bone erosion and at least one of the inner metatarsal joints completely eroded leaving some bony joint outlines partly preserved; 5—mutilating abnormality without bony outlines. This scoring system is a modification from literature protocols (Salvemini, et al., 2001) (Bush, Farmer, Walker, & Kirkham, 2002) (Sims, et al., 2004) (Jou, et al., 2005).

5.2.8. Histology

After radiological analysis, the hind paws of mice are fixed in 10% phosphate-buffered formalin (pH 7.4), decalcified with rapid bone decalcifiant for fine histology (Laboratories Eurobio) and embedded in paraffin. To ensure extensive evaluation of the arthritic joints, at least four serial sections (5 μm thick) are cut and each series of sections are 100 μm in between. The sections are stained with hematoxylin and eosin (H&E). Histologic examinations for synovial inflammation and bone and cartilage damage are performed double blind. In each paw, four parameters are assessed using a four-point scale. The parameters are cell infiltration, pannus severity, cartilage erosion and bone erosion. Scoring is performed according as follows: 1-normal, 2-mild, 3-moderate, 4-marked. These four scores are summed together and represented as an additional score, namely the 'RA total score'.

5.2.9. Micro-Computed Tomography (μCT) Analysis of Calcaneus (Heel Bone)

Bone degradation observed in RA occurs especially at the cortical bone and can be revealed by μCT analysis ((Sims, et al., 2004); (Oste, Salmon, & Dixon, 2007). After scanning and 3D volume reconstruction of the calcaneus bone, bone degradation is measured as the number of discrete objects present per slide, isolated in silico perpendicular to the longitudinal axis of the bone. The more the bone is degraded, the more discrete objects are measured. 1000 slices, evenly distributed along the calcaneus (spaced by about 10.8 μm), are analyzed.

5.2.10. Steady State PK

At day 7 or later, blood samples are collected at the retro-orbital sinus with lithium heparin as anti-coagulant at the following time points: predose, 1, 3 and 6 h. Whole blood samples are centrifuged and the resulting plasma samples are stored at −20° C. pending analysis. Plasma concentrations of each test compound are determined by an LC-MS/MS method in which the mass spectrometer is operated in positive electrospray mode. Pharmacokinetic parameters are calculated using Winnonlin® (Pharsight®, United States) and it is assumed that the predose plasma levels are equal to the 24 h plasma levels.

5.3. Idiopathic Pulmonary Fibrosis Assay 5.3.1. Overview

The mouse bleomycin-induced fibrosis model mimics the main characteristics of human lung fibrosis and is used to test potential new therapies for lung fibrosis (Walters & Kleeberger, 2008).

5.3.2. Protocol

In vivo efficacy of a compound of the invention is assessed in a 10-days mouse preventive bleomycin-induced pulmonary fibrosis model by oral route. Mice (20-25 g female C57BL/6; n=10-15 per group) are treated with bleomycin sulfate (1.5 U/kg) via intratracheal instillation at day 0 under isoflurane anesthesia, and then treated with the compounds accordingly to the study protocol from day 1 to day 10. Mice are kept on a 12 hr light/dark cycle (07:00-19:00). The temperature is maintained at 22° C., and food and water are provided ad libitum. At sacrifice, broncho alveolar lavage fluid (BALF; 2×0.75 mL PBS) is collected from lungs. This material is used to determine the amount of infiltrated inflammatory cells:
All the BALF cells (for example macrophage, eosinophil, neutrophil and epithelial cells) are pelleted, resuspended in PBS and counted the total amount of proteins using a Bradford dosing: this readout reflects the vascular leakage occurring, leading to the formation of an exudates in the lungs the amount of collagen using a Sircol™ dosing (Available from Biocolor Ltd., 8 Meadowbank Road, Carrickfergus, BT38 8YF, County Antrim, UK)

This readout reflects the level of extra-cellular matrix degradation and tissue remodeling occurring in the lungs.

One lung of each mouse is also collected and prepared for histological analysis using 10% neutral buffered formalin.

5.4. Septic Shock Model

Injection of lipopolysaccharide (LPS) induces a rapid release of soluble tumour necrosis factor (TNF-alpha) into the periphery. This model is used to analyse prospective blockers of TNF release in vivo.

Six BALB/cJ female mice (20 g) per group are treated at the intended dosing once, po. Thirty min later, LPS (15 μg/kg; E. Coli serotype 0111:B4) is injected ip. Ninety min later, mice are euthanized and blood is collected. Circulating TNF alpha levels are determined using commercially available ELISA kits. Dexamethasone (5 μg/kg) is used as a reference anti-inflammatory compound.

5.5. MAB Model

The MAB model allows a rapid assessment of the modulation of an RA-like inflammatory response by therapeutics (Khachigian, 2006). DBA/J mice are injected i.v. with a cocktail of mAbs directed against collagen II. One day later, compound treatment is initiated. Three days later, mice receive an i.p. LPS injection (50 μg/mouse), resulting in a fast onset of inflammation. Compound treatment is continued until 10 days after the mAb injection. Inflammation is read by measuring paw swelling and recording the clinical score of each paw. The cumulative clinical arthritis score of four limbs is presented to show the severity of inflammation. A scoring system is applied to each limb using a scale of 0-4, with 4 being the most severe inflammation.

0 Symptom free
1 Mild, but definite redness and swelling of one type of joint such as the ankle or wrist, or apparent redness and swelling limited to individual digits, regardless of the number of affected digits
2 Moderate redness and swelling of two or more types of joints
3 Severe redness and swelling of the entire paw including digits
4 Maximally inflamed limb with involvement of multiple joints 5.6. Mouse IBD Model The mouse chronic dextran sodium sulphate (DSS)-induced inflammatory bowel disease (IBD) model is a well validated disease model for inflammatory bowel disease (Sina, et al., 2009) (Wirtz, Neufert, Weigmann, & Neurath, 2007).

To induce a chronic colitis, female BALB/c mice are fed with 4% DSS dissolved in drinking water for 4 days, followed by 3 days of regular drinking water. This cycle is repeated three times. This protocol induces a strong colitis while avoiding high mortality rates. Animals are divided into several groups:

a. intact (water; vehicle alone, n=10),
 b. diseased (DSS; vehicle alone, n=10),
 c. sulfazalazine used as reference (DSS; 20 mg/kg/day sulfazalazine, p.o., n=10) and
 d. the tested compound (DSS; 1, 3, 10 and 30 mg/kg/day test compound, p.o., n=10/dose).

Clinical parameters are measured daily. The disease activity index (DAI) is a combination of the individual scores for weight loss, stool consistency and rectal bleeding. At necropsy, the complete colons are removed and rinsed with sterile PBS. Segments of the distal colon are dissected for histological analysis, gene expression and protein level measurement.

5.7. Mouse Asthma Model

In vitro and in vivo models to validate efficacy of small molecules towards asthma are described by Nials et al. (Nials & Uddin, 2008) (De Alba, et al., 2010), Park et al. (Park, et al., 2013) and Kudlacz et al. (Kudlacz, Conklyn, Andresen, Whitney-Pickett, & Changelian, 2008).

5.8. LPS Induced Lung Inflammation Model

5.8.1. Overview

The aim of the assay is to assess the effect of a test compound in a mouse model of acute lung inflammation induced by intranasal instillation of LPS. The impact on the induced cells recruitment in lung is evaluated by measurement of white cells count in broncho-alveolar lavage (BAL) fluid with VetABC device (medical solution gmbh, Hünenberg, Switzerland).

5.8.2. Protocol

The animals (BALB/c J mice, 18-20 g) are obtained from Harlan Laboratories (Maison-Alfort, France). The animals are maintained on 12 hours light/dark cycle at 22° C. with ad libitum access to tap water and food. Litters are changed twice a week. For each tested compound, a group of 10 subjects is used. In addition to the test compound-treated groups, a vehicle+LPS control group (inLPS), a non-treated group (intact), and a positive control dexamethasone treated group (DEX) are used.

LPS is dissolved in saline solution in order to obtain a final 10 µg/50 pi solution for intranasal instillation, and administered at 50 µL/mouse by intranasal instillation.

The test compounds are prepared in 15 mL PEG200 (9 mL)/H$_2$O (6 mL) to be dosed in a range of 0.3, 1, 3, 10, and 30 mg/kg, and then kept at room temperature in the dark, and are administered once (qd) or twice daily (bid) over 2 days.

Dexamethasone (10 mg/kg, bid, po) is used as a positive control.

On day 1, mice are anaesthetized by isoflurane inhalation. During breathing, LPS solution is instilled intra-nasally and mice are monitored until complete recovery from anaesthesia.

On day 2, mice are anaesthetized by intra-peritoneal injection (under a volume of 10 mL/kg) of anaesthetic solution (18 mL NaCl 0.9%+0.5 mL xylazine (5 mg/kg)+1.5 mL ketamine (75 mg/kg)).

The trachea is canulated with a catheter, and BAL is performed by 2×0.75 mL sterile PBS. The BAL fluid removed is shaked gently at room temperature before centrifugation at 1500 r.p.m. during 10 min at 4° C.

The supernatant is removed and the cell pellet is suspended in 200 µL of PBS, kept on ice and total cell count is processed with VetABC device. Finally, mice are sacrificed under anaesthesia.

5.8.3. Data Analysis

For each readout, mean and sem are calculated. A difference statistically significant between intact or treated groups and inLPS Vehicle group is evaluated with Prism® software using a one-way ANOVA (for treatment groups) followed by a Dunnett's multiple comparisons post-hoc test. *: $p<0.05$; : $p<0.01$; *: $p<0.001$ versus inLPS Vehicle group.

5.9. Pharmakokinetic Studies in Rodents and Dogs

5.9.1. Animals

Male Sprague-Dawley rats (180-200 g) and female C57BL/6Rj mice (18-22 g) are obtained from Janvier (France). Non-nave male Beagle dogs (8-13 kg) are obtained from Marshall BioResources (Italy). Two days before administration of compound, rats undergo surgery to place a catheter in the jugular vein under isoflurane anesthesia. Before oral dosing, animals are deprived of food for at least 16 h before dosing until 4 h after. Water is provided ad libitum. All in vivo experiments are carried out in a dedicated pathogen free facility (22° C.).

5.9.2. Pharmacokinetic Study

Compounds are formulated in PEG200/water for injection (25/75, v/v) for the intravenous route and in PEG200/0.5% methylcellulose (25/75, v/v) for the oral route.

5.9.2.1. Rodents

Compounds are orally dosed as a single esophageal gavage at 5 mg/kg (dosing volume of 5 mL/kg) and intravenously dosed as a bolus via the caudal vein at 1 mg/kg (dosing volume of 5 mL/kg). In the rat studies, each group consists of three rats and blood samples are collected via the jugular vein. In the mouse studies, each group consists of 21 mice (n=3/time point) and blood samples are collected by intra-cardiac puncture under isoflurane anesthesia. Li-heparin is used as anti-coagulant and blood is taken at 0.05, 0.25, 0.5, 1, 3, 5, 8 and 24 h (i.v. route) and 0.25, 0.5, 1, 3, 5, 8 and 24 h (p.o. route).

5.9.2. 2. Dogs

Compounds are dosed to three animals i.v. via a 10 min infusion in the cephalic vein with a dose level of 1 mg/kg (dose volume of 2 mL/kg) and after a washout of minimally 3 days, dosed orally as a single gavage with a dose level of 5 mg/kg (dose volume of 2 mL/kg). Blood samples are taken from the jugular vein using vacutainers and Li-heparin as anticoagulant at 0.083, 0.167, 0.5, 1, 2, 4, 6, 8, 10 and 24 h (i.v.) and at 0.25, 0.5, 1, 2, 3, 4, 6, 8, 10 and 24 h (p.o.).

5.9.3. Quantification of Compound Levels in Plasma

Whole blood samples are centrifuged at 5000 rpm for 10 min and the resulting plasma samples are stored at −20° C. pending analysis. Plasma concentrations of each test compound are determined by an LC-MS/MS method

5.9.4. Determination of Pharmacokinetic Parameters

Pharmacokinetic parameters are calculated using Winnonlin® (Pharsight®, United States).

5.9.5.5-Day Rat Toxicity Study

A 5-day oral toxicity study with test compounds is performed in Sprague-Dawley male rats to assess their toxic potential and toxicokinetics, at daily doses of 100, 300 and 600 mg/kg/day, by gavage, at the constant dosage-volume of 20 mL/kg/day.

The test compounds are formulated in PEG200/0.5% methylcellulose (25/75, v/v). Each group included 6 principal male rats as well as 3 satellite animals for toxicokinetics. A fourth group is given PEG200/0.5% methylcellulose (25/75, v/v) only, at the same frequency, dosage volume and by the same route of administration, and acted as the vehicle control group.

The goal of the study is to determine the lowest dose that resulted in no adverse events (no observable adverse effect level—NOAEL).

5.9.6. Hepatocyte Stability

Models to evaluate metabolic clearance in hepatocyte are described by McGinnity et al. Drug Metabolism and Disposition 2008, 32, 11, 1247.

5.9.7. Liability for QT Prolongation

Potential for QT prolongation is assessed in the hERG patch clamp assay.

Whole-cell patch-clamp recordings are performed using an EPC10 amplifier controlled by Pulse v8.77 software (HEKA). Series resistance is typically less than 10 MCI and compensated by greater than 60%, recordings are not leak subtracted. Electrodes are manufactured from GC150TF pipette glass (Harvard).

The external bathing solution contains: 135 mM NaCl, 5 mM KCl, 1.8 mM $CaCl_2$, 5 mM Glucose, 10 mM HEPES, pH 7.4.

The internal patch pipette solution contains: 100 mM K-gluconate, 20 mM KCl, 1 mM $CaCl_2$, 1 mM $MgCl_2$, 5 mM $Na_2ATP$, 2 mM Glutathione, 11 mM EGTA, 10 mM HEPES, pH 7.2.

Drugs are perfused using a Biologic MEV-9/EVH-9 rapid perfusion system.

All recordings are performed on HEK293 cells stably expressing hERG channels. Cells are cultured on 12 mm round coverslips (German glass, Bellco) anchored in the recording chamber using two platinum rods (Goodfellow). hERG currents are evoked using an activating pulse to +40 mV for 1000 ms followed by a tail current pulse to 50 mV for 2000 ms, holding potential is −80 mV. Pulses are applied every 20 s and all experiments are performed at r.t.

Example 6

ADME 6.1. Kinetic Solubility

Starting from a 10 mM stock in DMSO, a serial dilution of the compound is prepared in DMSO. The dilution series is transferred to a NUNC Maxisorb F-bottom 96-well plate (Cat no. 442404) and 0.1 M phosphate buffer pH 7.4 or 0.1 M citrate buffer pH 3.0 at room temperature is added.

The final concentration will range from 300 µM to 18.75 µM in 5 equal dilution steps. The final DMSO concentration does not exceed 3%. 200 µM pyrene is added to the corner points of each 96-well plate and serves as a reference point for calibration of Z-axis on the microscope.

The assay plates are sealed and incubated for 1 h at 37° C. while shaking at 230 rpm. The plates are then scanned under a white light microscope, yielding individual pictures of the precipitate per concentration. The precipitate is analyzed and converted into a number with a software tool which can be plotted onto a graph. The first concentration at which the compound appears completely dissolved is the concentration reported; however the true concentration lies somewhere between this concentration and one dilution step higher.

Solubility values measured according to this protocol are reported in µM and µg/mL.

6.2. Plasma Protein Binding (Equilibrium Dialysis)

A 10 mM stock solution of the compound in DMSO is diluted with a factor 5 in DMSO. This solution is further diluted in freshly thawed human, rat, mouse or dog plasma (BioReclamation INC) with a final concentration of 5 µM and final DMSO concentration of 0.5% (5.5 µL in 1094.5 µL plasma in a PP-Masterblock 96-well plate (Greiner, Cat no. 780285))

A Pierce Red Device plate with inserts (ThermoScientific, Cat no. 89809) is prepared and filled with 750 µL PBS in the buffer chamber and 500 µL of the spiked plasma in the plasma chamber. The plate is incubated for 4 h at 37° C. while shaking at 230 rpm. After incubation, 120 µL of both chambers is transferred to 360 µL acetonitrile in a 96-well round bottom, PP deep-well plate (Nunc, Cat no. 278743) and sealed with an aluminum foil lid. The samples are mixed and placed on ice for 30 min. This plate is then centrifuged 30 min at 1200 RCF at 4° C. and the supernatant is transferred to a 96-well V-bottom PP plate (Greiner, 651201) for analysis on LC-MS.

The plate is sealed with sealing mats (MA96RD-04S) of Kinesis, Cambs, PE19 8YX, UK and samples are measured at room temperature on LC-MS (ZQ 1525 from Waters) under optimized conditions using Quanoptimize to determine the appropriate mass of the molecule.

The samples are analyzed by LC-MS. Peak area from the compound in the buffer chamber and the plasma chamber are considered to be 100% compound. The percentage bound to plasma is derived from these results and is reported as percentage bound to plasma.

The solubility of the compound in the final test concentration in PBS is inspected by microscope to indicate whether precipitation is observed or not.

6.3. Microsomal Stability

A 10 mM stock solution of compound in DMSO is diluted to 6 µM in a 105 mM phosphate buffer, pH 7.4 in a 96 deep well plate (Greiner, Cat no. 780285) and pre-warmed at 37° C.

A Glucose-6-phosphate-dehydrogenase (G6PDH, Roche, 10127671001) working stock solution of 700 U/mL is diluted with a factor 1:700 in a 105 mM phosphate buffer, pH 7.4. A co-factor mix containing 0.528 M $MgCl_2.6H_2O$ (Sigma, M2670), 0.528 M glucose-6-phosphate (Sigma, G-7879) and 0.208 M NADP+ (Sigma, N-0505) is diluted with a factor 1:8 in a 105 mM phosphate buffer, pH 7.4.

A working solution is made containing 1 mg/mL liver microsomes (Provider, Xenotech) of the species of interest (e.g., human, mouse, rat, dog), 0.8 U/mL G6PDH and co-factor mix (6.6 mM $MgCl_2$, 6.6 mM glucose-6-phosphate, 2.6 mM NADP+). This mix is pre-incubated for 15 min, but never more than 20 min, at room temperature.

After pre-incubation, compound dilution and the mix containing the microsomes, are added together in equal amount and incubated for 30 min at 300 rpm. For the time point of 0 min, two volumes of methanol are added to the compound dilution before the microsome mix is added. The final concentration during incubation are: 3 µM test compound or control compound, 0.5 mg/mL microsomes, 0.4 U/mL G6PDH, 3.3 mM $MgCl_2$, 3.3 mM glucose-6-phosphate and 1.3 mM NaDP+.

After 30 min of incubation, the reaction is stopped with 2 volumes of methanol.

Of both time points, samples are mixed, centrifuged and the supernatant is harvested for analysis on LC-MS/MS. The instrument responses (i.e. peak heights) are referenced to the zero time-point samples (as 100%) in order to determine the percentage of compound remaining. Standard compounds Propranolol and Verapamil are included in the assay design.

The data on microsomal stability are expressed as a percentage of the total amount of compound remaining after 30 min.

6.4. CYP Inhibition

6.4.1. Direct CYP Inhibition

The in vitro direct inhibitory potential (IC50) of the compounds on cytochrome P450 isoenzymes in pooled human liver microsomes (HLM) is determined based on the draft FDA Guidance for Industry (Drug Interaction Studies—Study Design, Data Analysis, Implications for Dosing, and Labeling Recommendations), 2006, http://www.fda.gov/cder/guidance/index.htm.

The following probe substrates are used: phenacetin for CYP1A2, diclofenac for CYP2C9, S(+)-mephenytoin for CYP2C19, bufuralol for CYP2D6 and testosterone for CYP3A4. The following positive control inhibitors are used: a-naphtoflavone for CYP1A2, sulfaphenazole for CYP2C9, tranylcypromine for CYP2C19, quinidine for CYP2D6 and ketoconazole for CYP3A4.

6.4.2. Time-Dependent CYP3A4 Inhibition

Time-dependent CYP3A4 inhibition by the compounds, assessed in pooled HLM, is determined via $IC_{50}$ determination according to Grimm et al. Drug Metabolism and Disposition 2009, 37, 1355-1370 and the draft FDA Guidance for Industry (Drug Interaction Studies—Study Design, Data Analysis, Implications for Dosing, and Labeling Recommendations), 2006, http://www.fda.gov/cder/guidance/index.htm. Testosterone is used as probe substrate and troleandomycin is used as positive control.

6.5. Caco2 Permeability

Bi-directional Caco-2 assays are performed as described below. Caco-2 cells are obtained from European Collection of Cell Cultures (ECACC, cat 86010202) and used after a 21 day cell culture in 24-well Transwell plates (Fisher TKT-545-020B).

$2 \times 10^5$ cells/well are seeded in plating medium consisting of DMEM+GlutaMAXI+1% NEAA+10% FBS (FetalClone II)+1% Pen/Strep. The medium is changed every 2-3 days.

Test and reference compounds (propranolol and rhodamine 123 or vinblastine, all purchased from Sigma) are prepared in Hanks' Balanced Salt Solution containing 25 mM HEPES (pH 7.4) and added to either the apical (125 µL) or basolateral (600 µL) chambers of the Transwell plate assembly at a concentration of 10 µM with a final DMSO concentration of 0.25%.

50 µM Lucifer Yellow (Sigma) is added to the donor buffer in all wells to assess integrity of the cell layers by monitoring Lucifer Yellow permeation. As Lucifer Yellow (LY) cannot freely permeate lipophilic barriers, a high degree of LY transport indicates poor integrity of the cell layer.

After a 1 hr incubation at 37° C. while shaking at an orbital shaker at 150 rpm, 70 µL aliquots are taken from both apical (A) and basal (B) chambers and added to 100 µL 50:50 acetonitrile:water solution containing analytical internal standard (0.5 µM carbamazepine) in a 96-well plate.

Lucifer yellow is measured with a Spectramax Gemini XS (Ex 426 nm and Em 538 nm) in a clean 96-well plate containing 150 µL of liquid from basolateral and apical side.

Concentrations of compound in the samples are measured by high performance liquid-chromatography/mass spectroscopy (LC-MS/MS).

Apparent permeability (Papp) values are calculated from the relationship:

$$Papp=[\text{compound}] \text{ acceptor final} > V\text{acceptor}/([\text{compound}]\text{donor initial} \times V\text{donor})/Tinc \times V\text{donor/surface area} \times 60 \times 10^{-6} \text{ cm/s}$$

V=chamber volume
Tinc=incubation time.
Surface area=0.33 cm$^2$

The Efflux ratios, as an indication of active efflux from the apical cell surface, are calculated using the ratio of Papp B>A/Papp A>B.

The following assay acceptance criteria are used:
Propranolol: Papp (A>B) value≥20(×10$^{-6}$ cm/s)
Rhodamine 123 or Vinblastine: Papp (A>B) value<5 (×10$^{-6}$ cm/s) with Efflux ratio ≥5
Lucifer yellow permeability: ≤100 nm/s

REFERENCES

Bandoh, K., Aoki, J., Taira, A., Tsujimoto, M., Arai, H., & Inoue, K. (2000). Lysophosphatidic acid (LPA) receptors of the EDG family are differentially activated by LPA species. Structure-activity relationship of cloned LPA receptors. *FEBS Lett,* 478(1-2), 159-65.

Baumforth, K. R. (2005). Induction of autotaxin by the Epstein-Barr virus promotes the growth and survival of Hodgkin lymphoma cells. *Blood,* 106(6), 2138-2146.

Bozinovski, S., Hutchinson, A., Thompson, M., MacGregor, L., Black, J., Giannakis, E., . . . Anderson, G. P. (2008). Serum amyloid a is a biomarker of acute exacerbations of chronic obstructive pulmonary disease. *Am J Respir Crit Care Med,* 177(3), 269-78.

Braddock, D. T. (2010). Autotaxin and lipid signaling pathways as anticancer targets. *Curr Opin Investig Drugs,* 11(6), 629-37.

Bundgard, H. (1985). In *Design of Prodrugs* (pp. 7-9, 21-24). Amsterdam: Elsevier.

Bush, K. A., Farmer, K. M., Walker, J. S., & Kirkham, B. W. (2002). Reduction of Joint Inflammation and Bone Erosion in Rat Adjuvant Arthritis by Treatment With Interleukin-17 Receptor IgG1 Fc Fusion Protein. *Arthritis & Rheumatism,* 46(3), 802-805.

Castelino, F. V., Seiders, J., Bain, G., Brooks, S. F., King, C., Swaney, J. S., . . . Tager, A. M. (2011). Amelioration of dermal fibrosis by genetic deletion or pharmacologic antagonism of lysophosphatidic acid receptor 1 in a mouse model of scleroderma. *Arthritis Rheum,* 63(5), 1405-15.

Corley, E. G., Conrad, K., Murry, J. A., Savarin, C., Holko, J., & Boice, G. (2004). Direct synthesis of 4-arylpiperidines via palladium/copper(I)-cocatalyzed Negishi coupling of a 4-piperidylzinc iodide with aromatic halides and triflates. *J Org Chem,* 69(15), 5120-5123.

David, M. (2010). Cancer Cell Expression of Autotaxin Controls Bone Metastasis Formation in Mouse through Lysophosphatidic Acid-Dependent Activation of Osteoclasts. *PLoS One,* 5(3), e9741.

De Alba, J., Raemdonck, K., Dekkak, A., Collins, M., Wong, S., Nials, A. T., . . . Birrell, M. A. (2010). House dust mite induces direct airway inflammation in vivo: implications for future disease therapy? *Eur Respir J,* 1377-1387.

Demedts, I. K., Morel-Montero, A., Lebecque, S., Pacheco, Y., Cataldo, D., Joos, G. F., . . . Brusselle, G. G. (2006). Elevated MMP-12 protein levels in induced sputum from patients with COPD. *Thorax,* 61(3), 196-201.

Eagan, T. M., Damås, J. K., Ueland, T., Voll-Aanerud, M., Mollnes, T. E., Hardie, J. A., . . . Aukrust, P. (2010). Neutrophil gelatinase-associated lipocalin: a biomarker in COPD. *Chest,* 138(4), 888-95.

Emo, J., Meednu, N., Chapman, T. J., Rezaee, F., Balys, M., Randall, T., . . . Georas, S. N. (2012). Lpa2 is a negative regulator of both dendritic cell activation and murine models of allergic lung inflammation. *J Immunol*, 188(8), 3784-90.

Federico, L., Ren, H., Mueller, P. A., Wu, T., Liu, S., Popovic, J., . . . Smyth, S. S. (2012). Autotaxin and its product lysophosphatidic acid suppress brown adipose differentiation and promote diet-induced obesity in mice. *Mol Endocrinol*, 26(5), 786-97.

Ferry, G. (2003). Autotaxin is released from adipocytes, catalyzes lysophosphatidic acid synthesis, and activates preadipocyte proliferation. Up-regulated expression with adipocyte differentiation and obesity. *J Biol Chem*, 278(20), 18162-18169.

Gaetano, C. G. (2009). Inhibition of autotaxin production or activity blocks lysophosphatidylcholine-induced migration of human breast cancer and melanoma cells. *Mol Carcinog.*, 48(9), 801-809.

Ganguly, K., Stoeger, T., Wesselkamper, S. C., Reinhard, C., Sartor, M. A., Medvedovic, M., . . . Schulz, H. (2007). Candidate genes controlling pulmonary function in mice: transcript profiling and predicted protein structure. *Physiol Genomics*, 31(3), 410-21.

Gardell, S. E. (2006). Emerging medicinal roles for lysophospholipid signaling Trends Mol Med, 12(2), 65-75.

Gennero, I., Laurencin-Dalicieux, S., Conte-Auriol, F., Briand-Mésange, F., Laurencin, D., Rue, J., . . . Salles, J. (2011). Absence of the lysophosphatidic acid receptor LPA1 results in abnormal bone development and decreased bone mass. *Bone*, 49(3), 395-403.

Georas, S. N., Berdyshev, E., Hubbard, W., Gorshkova, I. A., Usatyuk, P. V., Saatian, B., . . . Natarajan, V. (2007). Lysophosphatidic acid is detectable in human bronchoalveolar lavage fluids at baseline and increased after segmental allergen challenge. *Clin Exp Allergy*, 37(3), 311-22.

Gierse, J. (2010). A Novel Autotaxin Inhibitor Reduces Lysophosphatidic Acid Levels in Plasma and the Site of Inflammation. *JPET*, 334(1), 310-317.

Greene, T W; Wuts, P G M. (1991). *Protecting Groups in Organic Synthesis, Second Edition*. New York: Wiley.

Hausmann, J. (2011). Structural basis of substrate discrimination and integrin binding by autotaxin. *Nat Struct Mol Biol*, 18(2), 198-204.

Inoue, M., Xie, W., Matsushita, Y., Chun, J., Aoki, J., & Ueda, H. (2008). Lysophosphatidylcholine induces neuropathic pain through an action of autotaxin to generate lysophosphatidic acid. *Neuroscience*, 152(2), 296-8.

Iyer, P., Lalane III, R., Morris, C., Challa, P., Vann, R., & Vasantha Rao, P. (2012). Autotaxin-lysophosphatidic acid axis is a novel molecular target for lowering intraocular pressure. *PLoS One*, 7(8)), e42627.

Jou, I., Shiau, A., Chen, S., Wang, C., Shieh, D., Tsai, C., & Wu, C. (2005). Thrombospondin 1 as an Effective Gene Therapeutic Strategy in Collagen-Induced Arthritis. *Arthritis & Rheumatism*, 52(1), 339-344.

Kanda, H. (2008). Autotaxin, a lysophosphatidic acid-producing ectozyme, promotes lymphocyte entry into secondary lymphoid organs. *Nat. Immunol.*, 9(4), 415-423.

Khachigian, L. M. (2006). Collagen antibody-induced arthritis. *Nat Protoc*, 1(5), 2512-2516.

Kishi, Y. (2006). Autotaxin is overexpressed in glioblastoma multiforme and contributes to cell motility of glioblastoma by converting lysophosphatidylcholine to lysophosphatidic acid. *J Biol Chem*, 281(25),17492-17500.

Kolonko, K. J., & Reich, H. J. (2008). Stabilization of ketone and aldehyde enols by formation of hydrogen bonds to phosphazene enolates and their aldol products. *J Am Chem Soc.*, 130(30), 9668-9669.

Kremer, A. E., Martens, J. J., Kulik, W., Kuiper, E. M., van Buuren, H. R., van Erpecum, K. J., . . . Oude Elferink, R. P. (2010). Lysophosphatidic acid is a potential mediator of cholestatic pruritus. *Gastroenterology*, 139(3), 1008-18.

Kudlacz, E., Conklyn, M., Andresen, C., Whitney-Pickett, C., & Changelian, P. (2008). The JAK-3 inhibitor CP-690550 is a potent anti-inflammatory agent in a murine model of pulmonary eosinophilia. *Eur J Pharmacol*, 154-161.

Lin, H., Hu, C., Chan, H., Liew, Y., Huang, H., Lepescheux, L., . . . Clément-Lacroix, P. (2007). Anti-rheumatic activities of histone deacetylase (HDAC) inhibitors in vivo in collagen-induced arthritis in rodents. *British Journal of Pharmacology*, 150, 862-872.

Lin, M. E. (2010). Lysophosphatidic acid (LPA) receptors: signaling properties and disease relevance. *Prostaglandins Other Lipid Mediat*, 91(3-4), 130-138.

Llinàs, L., Peinado, V. I., Goñi, J., Rabinovich, R., Pizarro, S., Rodriguez-Roisin, R., . . . Bastos, R. (2011). Similar gene expression profiles in smokers and patients with moderate COPD. *Pulm Pharmacol Ther*, 24(1), 32-41.

Matas-Rico, E., García-Diaz, B., Llebrez-Zayas, P., López-Barroso, D., Santín, L., Pedraza, C., . . . Estivill-Torrús, G. (2008). Deletion of lysophosphatidic acid receptor LPA1 reduces neurogenesis in the mouse dentate gyms. *Mol Cell Neurosci*, 39(3), 342-55.

Murph, M. M., Nguyen, G. H., Radhakrishna, H., & Mills, G. B. (2008). Sharpening the edges of understanding the structure/function of the LPA1 receptor: expression in cancer and mechanisms of regulation. *Biochim Biophys Acta*, 1781(9), 547-557.

Nakao, I., Kanaji, S., Ohta, S., Matsushita, H., Arima, K., Yuyama, N., . . . Izuhara, K. (2008). Identification of pendrin as a common mediator for mucus production in bronchial asthma and chronic obstructive pulmonary disease. *J Immunol*, 180(9), 6262-9.

Nakasaki, T., Tanaka, T., Okudaira, S., Hirosawa, M., Umemoto, E., Otani, K., . . . Miyasaka, M. (2008). Involvement of the lysophosphatidic acid-generating enzyme autotaxin in lymphocyte-endothelial cell interactions. *Am J Pathol*, 173(5), 1566-76.

Nials, A. T., & Uddin, S. (2008). Mouse models of allergic asthma: acute and chronic allergen challenge. *Dis Model Mech*, 213-220.

Nikitopoulou, I., Oikonomou, N., Karouzakis, E., Sevastou, I., Nikolaidou-Katsaridou, N., Zhao, Z., . . . Aidinis, V. (2012). Autotaxin expression from synovial fibroblasts is essential for the pathogenesis of modeled arthritis. *J Exp Med*, 209(5), 925-33.

Nishida, K., Komiyama, T., Miyazawa, S., Shen, Z., Furumatsu, T., Doi, H., . . . Asahara, H. (2004). Histone Deacetylase Inhibitor Suppression of Autoantibody-Mediated Arthritis in Mice via Regulation of p16INK4a and p21WAF1/Cip1 Expression. *Arthritis & Rheumatism*, 50(10), 3365-3376.

Nouh, M. A., Wu, X., Okazoe, H., Tsunemori, H., Haba, R., Abou-Zeid, A. M., . . . Kakehi, Y. (2009). Expression of autotaxin and acylglycerol kinase in prostate cancer: association with cancer development and progression. *Cancer Sci*, 100(9), 1631-1638.

Oikonomou, N., Mouratis, M., Tzouvelekis, A., Kaffe, E., Valavanis, C., Vilaras, G., . . . Aidinis, V. (2012). Pulmonary autotaxin expression contributes to the pathogenesis of pulmonary fibrosis. *Am J Respir Cell Mol Biol*, 47(5), 566-74.

Oste, L., Salmon, P., & Dixon, G. (2007). A High Throughput Method of Measuring Bone Archtectural Disturbance in a Murine CIA Model by Micro-CT Morphometry. *ECTC*. Montréal.

Panupinthu, N., Lee, H., & Mills, G. B. (2010). Lysophosphatidic acid production and action: critical new players in breast cancer initiation and progression. *British Journal of Cancer*, 102, 941-946.

Park, G. Y., Lee, Y. G., Berdyshev, E., Nyenhuis, S., Du, J., Fu, P., . . . Christman, J. W. (2013). Autotaxin production of lysophosphatidic acid mediates allergic asthmatic inflammation. *Am J Respir Crit Care Med*, 928-940.

Pradère, J., Klein, J., Grès, S., Guigné, C., Neau, E., Valet, P., . . . Schanstra, J. P. (2007). LPA1 receptor activation promotes renal interstitial fibrosis. *J Am Soc Nephrol*, 18(12), 3110-8.

Rall, L. C., & Roubenoff, R. (2004). Rheumatoid cachexia: metabolic abnormalities, mechanisms and interventions. *Rheumatology*, 43, 1219-1223.

Salvemini, D., Mazzon, E., Dugo, L., Serraino, I., De Sarro, A., Caputi, A. P., & Cuzzocrea, S. (2001). Amelioration of Joint Disease in a Rat Model of Collagen-Induced Arthritis by M40403, a Superoxide Dismutase Mimetic. *Arthritis & Rheumatism*, 44(12), 2909-2921.

Shelton, D. L., Zeller, J., Ho, W., Pons, J., & Rosenthal, A. (2005). Nerve growth factor mediates hyperalgesia and cachexia in auto-immune arthritis. *Pain*, 115, 8-16.

Sims, N. A., Green, J. R., Glatt, M., Schlict, S., Martin, T. J., Gillespie, M. T., & Romas, E. (2004). Targeting Osteoclasts With Zoledronic Acid Prevents Bone Destruction in Collagen-Induced Arthritis. *Arthritis & Rheumatism*, 50(7), 2338-2346.

Sina, C., Gavrilova, O., Förster, M., Till, A., Derer, S., Hildebrand, F., . . . Rosenstiel, P. (2009). G protein-coupled receptor 43 is essential for neutrophil recruitment during intestinal inflammation. *J Immunol*, 183(11), 7514-7522.

Stassar, M. J., Devitt, G., Brosius, M., Rinnab, L., Prang, J., Schradin, T., . . . Zöller, M. (2001). Identification of human renal cell carcinoma associated genes by suppression subtractive hybridization. *British Journal of Cancer*, 85(9), 1372-1382.

Sumida, H., Noguchi, K., Kihara, Y., Abe, M., Yanagida, K., Hamano, F., . . . Ishii, S. (2010). LPA4 regulates blood and lymphatic vessel formation during mouse embryogenesis. *Blood*, 116(23), 5060-70.

Tager, A. M., LaCamera, P., Shea, B. S., Campanella, G. S., Selman, M., Zhao, Z., . . . Luster, A. D. (2008). The lysophosphatidic acid receptor LPA1 links pulmonary fibrosis to lung injury by mediating fibroblast recruitment and vascular leak. *Nat Med*, 14(1), 45-54.

Tanaka, M., Okudaira, S., Kishi, Y., Ohkawa, R., Iseki, S., Ota, M., . . . Aral, H. (2006). Autotaxin stabilizes blood vessels and is required for embryonic vasculature by producing lysophosphatidic acid. *J Biol Chem*, 281(35), 25822-30.

Tania, M., Khan, A., Zhang, H., Li, J., & Song, Y. (2010). Autotaxin: A protein with two faces. *Biochemical and Biophysical Research Communications*, 401, 493-497.

Tilley, A. E., O'Connor, T. P., Hackett, N. R., Strulovici-Barel, Y., Salit, J., Amoroso, N., . . . Crystal, R. G. (2011). Biologic phenotyping of the human small airway epithelial response to cigarette smoking. *PLoS One*, 6(7), e22798.

Van Meeteren, L. A., Ruurs, P., Stortelers, C., Bouwman, P., van Rooijen, M. A., Pradere, J., . . . Jonkers, J. (2006). Autotaxin, a Secreted Lysophospholipase D, Is Essential for Blood Vessel Formation during Development. *Mol. Cell. Biol.*, 26(13), 5015-5022.

Vidot, S., Witham, J., Agarwal, R., Greenhough, S., Bamrah, H. S., Tigyi, G. J., . . . Richardson, A. (2010). Autotaxin delays apoptosis induced by carboplatin in ovarian cancer cells. *Cell Signal*, 22(6), 926-935.

Walsmith, J., Abad, L., Kehayias, J., & Roubenoff, R. (2004). Tumor Necrosis Factor-a Production Is Associated with Less Body Cell Mass in Women with Rheumatoid Arthritis. *The Journal of Rheumatology*, 31(1), 23-29.

Walters, D. M., & Kleeberger, S. R. (2008). Mouse Models of Bleomycin-Induced Pulmonary Fibrosis. *Current Protocols in Pharmacology*, 40, 5.46.1-5.46.17.

Wirtz, S., Neufert, C., Weigmann, B., & Neurath, M. F. (2007). Chemically induced mouse models of intestinal. *Nature Protocols*, 2(3), 541-546.

Wu, J., Xu, Y., Skill, N. J., Sheng, H., Zhao, Z., Yu, M., . . . Maluccio, M. A. (2010). Autotaxin expression and its connection with the TNF-alpha-NF-kappaB axis in human hepatocellular carcinoma. *Mol Cancer*, 9, 71.

Xu, M., Porte, J., Knox, A. J., Weinreb, P. H., Maher, T. M., Violette, S. M., . . . Jenkins, G. (2009). Lysophosphatidic acid induces alphavbeta6 integrin-mediated TGF-beta activation via the LPA2 receptor and the small G protein G alpha(q). *Am J Pathol*, 174(4), 1264-79.

Xu, X., & Prestwich, G. D. (2010). Inhibition of tumor growth and angiogenesis by a lysophosphatidic acid antagonist in an engineered three-dimensional lung cancer xenograft model. *Cancer*, 116(7), 1739-1750.

Ye, X., Hama, K., Contos, J. J., Anliker, B., Inoue, A., Skinner, M. K., . . . Chun, J. (2005). LPA3-mediated lysophosphatidic acid signalling in embryo implantation and spacing. *Nature*, 435(7038), 104-8.

Zhang, H., Xu, X., Gajewiak, J., Tsukahara, R., Fujiwara, Y., Liu, J., . . . Prestwich, G. D. (2009). Dual activity lysophosphatidic acid receptor pan-antagonist/autotaxin inhibitor reduces breast cancer cell migration in vitro and causes tumor regression in vivo. *Cancer Res.*, 69(13), 5441-5449.

Zhao, J., He, D., Berdyshev, E., Zhong, M., Salgia, R., Morris, A. J., . . . Zhao, Y. (2011). Autotaxin induces lung epithelial cell migration through lysoPLD activity-dependent and -independent pathways. *Biochem J*, 439(1), 45-55.

Zhao, Y., & Natarajan, V. (2013). Lysophosphatidic acid (LPA) and its receptors: Role in airway inflammation and remodeling. *Biochim Biophys Acta*, 1831(1), 86-92.

Zhao, Y., Tong, J., He, D., Pendyala, S., Evgeny, B., Chun, J., . . . Natarajan, V. (2009). Role of lysophosphatidic acid receptor LPA2 in the development of allergic airway inflammation in a murine model of asthma. *Respir Res*, 10, 114.

Final Remarks

It will be appreciated by those skilled in the art that the foregoing descriptions are exemplary and explanatory in nature, and intended to illustrate the invention and its preferred embodiments. Through routine experimentation, an artisan will recognize apparent modifications and variations that may be made without departing from the spirit of the invention. All such modifications coming within the scope of the appended claims are intended to be included therein. Thus, the invention is intended to be defined not by the above description, but by the following claims and their equivalents.

All publications, including but not limited to patents and patent applications, cited in this specification are herein incorporated by reference as if each individual publication are specifically and individually indicated to be incorporated by reference herein as though fully set forth.

It should be understood that factors such as the differential cell penetration capacity of the various compounds can contribute to discrepancies between the activity of the compounds in the in vitro biochemical and cellular assays.

At least some of the chemical names of compound of the invention as given and set forth in this application, may have been generated on an automated basis by use of a commercially available chemical naming software program, and have not been independently verified. Representative programs performing this function include the Lexichem naming tool sold by Open Eye Software, Inc. and the Autonom Software tool sold by MDL, Inc. In the instance where the indicated chemical name and the depicted structure differ, the depicted structure will control.

The invention claimed is:

1. A compound of the formula:

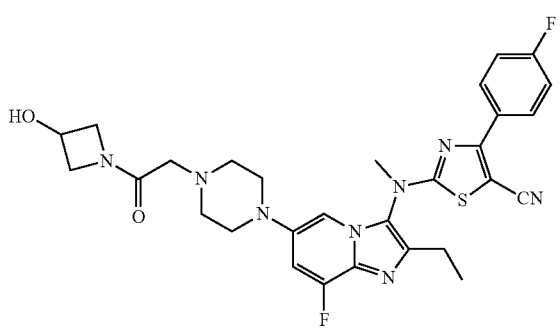 [SMILES: CCc1nc2c(F)cc(N3CCN(CC(=O)N4CC(O)C4)CC3)cn2c1N(C)c1nc(-c2ccc(F)cc2)c(C#N)s1]

or a pharmaceutically acceptable salt, or a solvate, or a pharmaceutically acceptable salt of a solvate thereof.

2. The compound according to claim 1, or a pharmaceutically acceptable salt thereof.

3. The compound according to claim 1.

4. A pharmaceutical composition comprising the compound according to claim 1, or a pharmaceutically acceptable salt, or a solvate, or a pharmaceutically acceptable salt of a solvate thereof, and a pharmaceutically acceptable carrier.

5. The pharmaceutical composition according to claim 4, comprising a further therapeutic agent.

6. The pharmaceutical composition according to claim 5, wherein the further therapeutic agent is an agent for the treatment of idiopathic pulmonary fibrosis.

7. The pharmaceutical composition according to claim 4, comprising the compound of the formula:

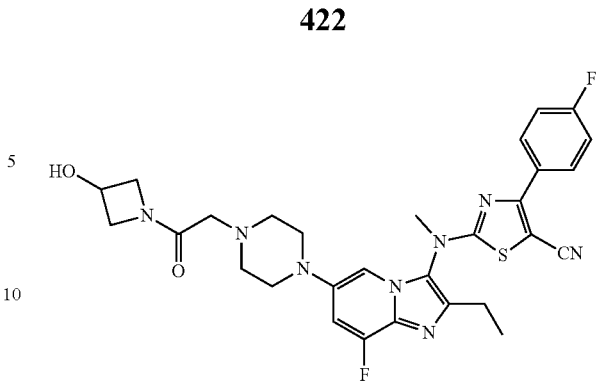

or a pharmaceutically acceptable salt thereof.

8. The pharmaceutical composition according to claim 7, comprising a further therapeutic agent.

9. The pharmaceutical composition according to claim 8, wherein the further therapeutic agent is for the treatment of idiopathic pulmonary fibrosis.

10. The pharmaceutical composition according to claim 4 comprising the compound of the formula:

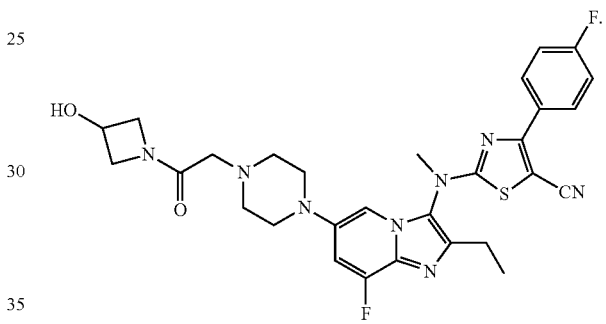

11. The pharmaceutical composition according to claim 10, comprising a further therapeutic agent.

12. The pharmaceutical composition according to claim 11, wherein the further therapeutic agent is for the treatment of idiopathic pulmonary fibrosis.

13. A method of inhibiting ectonucleotide pyrophosphatase/phosphodiesterase 2 (ENPP2), which method comprises contacting the ENPP2 with a compound according to claim 1, or a pharmaceutically acceptable salt, or a solvate, or a pharmaceutically acceptable salt of a solvate thereof.

14. The method of inhibiting ectonucleotide pyrophosphatase/phosphodiesterase 2 (ENPP2) according to claim 13, which method comprises contacting the ENPP2 with the compound of the formula:

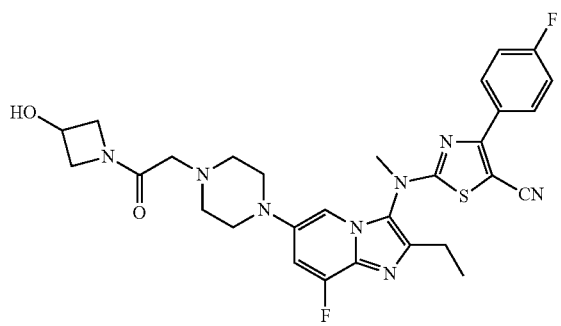 [SMILES: CCc1nc2c(F)cc(N3CCN(CC(=O)N4CC(O)C4)CC3)cn2c1N(C)c1nc(-c2ccc(F)cc2)c(C#N)s1]

or a pharmaceutically acceptable salt thereof.

15. The method of inhibiting ectonucleotide pyrophosphatase/phosphodiesterase 2 (ENPP2) according to claim 13, which method comprises contacting the ENPP2 with the compound of the formula:
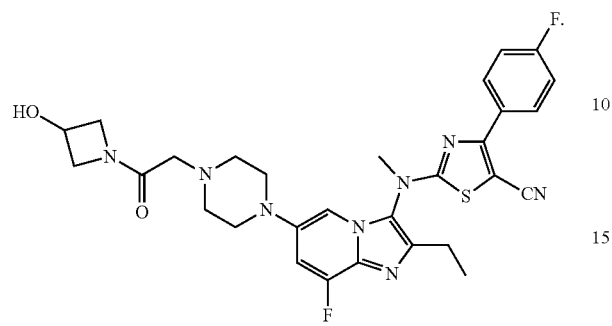
* * * * *